US009598734B2

(12) United States Patent
Knudsen

(10) Patent No.: US 9,598,734 B2
(45) Date of Patent: Mar. 21, 2017

(54) METHODS AND DEVICES FOR PREDICTING TREATMENT EFFICACY

(75) Inventor: Steen Knudsen, Birkroed (DK)

(73) Assignee: Medical Prognosis Institute A/S, Hørsholm (DK)

( * ) Notice: Subject to any disclaimer, the term of this patent is extended or adjusted under 35 U.S.C. 154(b) by 1050 days.

(21) Appl. No.: 13/695,102

(22) PCT Filed: Apr. 29, 2011

(86) PCT No.: PCT/IB2011/001405
§ 371 (c)(1),
(2), (4) Date: Oct. 29, 2012

(87) PCT Pub. No.: WO2011/135459
PCT Pub. Date: Nov. 3, 2011

(65) Prior Publication Data
US 2013/0053275 A1 Feb. 28, 2013

(30) Foreign Application Priority Data
Apr. 29, 2010 (DK) .................................. 2010 00382

(51) Int. Cl.
C12Q 1/68 (2006.01)
C07H 21/04 (2006.01)

(52) U.S. Cl.
CPC ..... C12Q 1/6886 (2013.01); C12Q 2600/106 (2013.01); C12Q 2600/178 (2013.01)

(58) Field of Classification Search
USPC ..... 424/9.1; 435/6.11, 91.1, 91.31, 375, 6.1, 435/9, 1.1; 514/1, 2, 44; 536/23.1, 24.5, 536/24.31
See application file for complete search history.

(56) References Cited

U.S. PATENT DOCUMENTS

| 6,911,306 | B1 | 6/2005 | Vertino |
| 7,239,986 | B2 | 7/2007 | Golub et al. |
| 7,709,616 | B2 | 5/2010 | Bentwich et al. |
| 8,445,198 | B2 | 5/2013 | Knudsen |
| 2002/0164663 | A1 | 11/2002 | Fuqua et al. |
| 2003/0073083 | A1 | 4/2003 | Tamayo et al. |
| 2004/0018525 | A1 | 1/2004 | Wirtz et al. |
| 2004/0072722 | A1 | 4/2004 | Kornblith et al. |
| 2005/0176669 | A1 | 8/2005 | Al-Murrani |
| 2005/0260586 | A1 | 11/2005 | Demuth et al. |
| 2005/0260646 | A1 | 11/2005 | Baker et al. |
| 2006/0105360 | A1 | 5/2006 | Croce et al. |
| 2008/0306006 | A1 | 12/2008 | Croce et al. |
| 2009/0221435 | A1 | 9/2009 | Baskerville et al. |
| 2012/0214703 | A1* | 8/2012 | Croce .................. C12N 15/111 506/9 |
| 2013/0053275 | A1 | 2/2013 | Knudsen |
| 2013/0059015 | A1* | 3/2013 | Lancaster .......... A61K 31/7088 424/649 |

FOREIGN PATENT DOCUMENTS

| CA | 2428112 A1 | 11/2003 |
| CN | 102002490 A | 4/2011 |
| EP | 1550731 A1 | 7/2005 |
| JP | 2001-017171 A | 1/2001 |
| JP | 2002-531066 A | 9/2002 |
| WO | WO-00/31930 A1 | 6/2000 |
| WO | WO-03/082078 A2 | 10/2003 |
| WO | WO-2005/005601 A2 | 1/2005 |
| WO | WO-2005/014856 A1 | 2/2005 |
| WO | WO-2005/047534 A2 | 5/2005 |
| WO | WO-2005/066371 A2 | 7/2005 |
| WO | WO-2005/087948 A2 | 9/2005 |
| WO | WO-2005/094863 A1 | 10/2005 |
| WO | WO-2005/100606 A2 | 10/2005 |
| WO | WO-2007/072225 A2 | 6/2007 |
| WO | WO 2008/112283 | 9/2008 |
| WO | WO-2008/138578 A2 | 11/2008 |
| WO | WO 2009/036332 * | 3/2009 |
| WO | WO 2009/080437 | 7/2009 |
| WO | WO-2011/135459 A2 | 11/2011 |
| WO | WO-2012/109233 A2 | 8/2012 |
| WO | WO-2012/163541 A1 | 12/2012 |

OTHER PUBLICATIONS

Yang et al., "The role of microRNA in human lung squamous cell carcinoma", Cancer Genetics and Cytogenetics, vol. 200, p. 127-133 (2010).*
Friis-Hansen et al., "1072 Mir-449 inhibits growth of gastric cancer cells partly by inhibiting the expression of met and amphiregulin," Gastroenterology 136: A-165 (2009).
Li et al., "Intronic microRNA: discovery and biological implications," DNA Cell Biol. 26: 195-207 (2007).
"NCode™ Multi-Species miRNA Microarray Probe Set. Version 2.0 (Cat.# MIRMPS2-01)," (2009). Received from http://www.invitrogen.com/site/us/en/home/Products-and-Services/Applications/epigenetics-noncoding-rna-research/miRNA-Profiling-/miRNA-Probe-Set-Files.html.
Pradervand et al., "Concordance among digital gene expression, microarrays, and qPCR when measuring differential expression of microRNAs," Biotechniques 48:219-222 (2010).
"Seq ID No. 486 of EP2112235 disclosing has-miR-766," (2009).
International Preliminary Report on Patentability for International Application No. PCT/IB2011/001405, dated Oct. 30, 2012.
International Search Report for International Application No. PCT/IB2011/001405, dated Apr. 19, 2012.
Examination Report for Australian Patent Application No. 2011246976, dated Aug. 19, 2015 (3 pages).
Liu et al., "Roles of USF, Ikaros and Sp proteins in the transcriptional regulation of the human reduced folate carrier B promoter," Biochem J. 383(Pt 2):249-57 (2004).

(Continued)

Primary Examiner — Jane Zara
(74) Attorney, Agent, or Firm — Clark & Elbing LLP; Kristina Bieker-Brady

(57) ABSTRACT

The present invention features methods, devices, and kits for predicting the sensitivity of a patient to a compound or medical treatment. The invention also features methods for identifying biomarkers, the expression of which correlates to treatment sensitivity or resistance within a patient population or subpopulation.

28 Claims, 1 Drawing Sheet

(56) References Cited

OTHER PUBLICATIONS

Office Action for Japanese Patent Application No. 2008-542865 dated Dec. 3, 2012 (12 pages).
Office Action for Chinese Patent Application No. 200680052220.2 issued Feb. 5, 2013.
Sezaki et al., "Over-expression of the dominant-negative isoform of Ikaros confers resistance to dexamethasone-induced and anti-IgM-induced apoptosis," Br J Haematol. 121(1):165-9 Abstract Only (2003).
Canadian Examination Report for Canadian Patent Application No. 2,631,236, dated Mar. 19, 2015 (6 pages).
Bild et al., "Oncogenic pathway signatures in human cancers as a guide to targeted therapies," Nature. 439(7074):353-7 (2006).
Castelli et al., "In silico analysis of microRNAS targeting the HLA-G 3' untranslated region alleles and haplotypes," Hum Immunol. 70(12):1020-5 (2009).
Dahlén et al., "Activation of the *GLI* oncogene through fusion with the beta-actin gene (*ACTB*) in a group of distinctive pericytic neoplasms: pericytoma with t(7;12)," Am J Phathol. 164(5):1645-53 (2004).
Fournier et al., "Gene expression signature in organized and growth-arrested mammary acini predicts good outcome in breast cancer," Cancer Res. 66(14):7095-7102 (2006).
Gallardo et al., "miR-34a as a prognostic marker of relapse in surgically resected non-small-cell lung cancer," Carcinogenesis. 30(11):1903-9 (2009).
Genbank Accession No. AY889152.1. Retrieved on Mar. 5, 2013 (2 pages).
Kornmann et al., "Thymidylate synthase and dihydropyrimidine dehydrogenase mRNA expression levels: predictors for survival in colorectal cancer patients receiving adjuvant 5-fluorouracil," Clinical Cancer Res. 9(11):4116-24 (2003).
Van't Veer et al., "Gene expression profiling predicts clinical outcome of breast cancer," Nature. 415(6871):530-6 (2002).
Xu et al., "[Association of miRNAs expression profiles with prognosis and relapse in childhood acute lymphoblastic leukemia]," Zhonghua Xue Ye Xue Za Zhi. 32(3):178-81 (Abstract only) (2011).
Yang et al., "The role of microRNA in human lung squamous cell carcinoma," Cancer Genet Cytogenet. 200(2):127-33 (2010).
Communication pursuant to Article 94(3) EPC in European Patent Application No. 06848658.8 dated Sep. 22, 2008 (6 pages).
International Preliminary Report on Patentability and Written Opinion of the International Searching Authority for International Application No. PCT/EP2012/002332 issued Dec. 2, 2013 (11 pages).
International Preliminary Report on Patentability and Written Opinion of the Searching Authority for International Patent Application No. PCT/EP2008/003789 issued Nov. 17, 2009 (9 pages).
International Preliminary Report on Patentability and Written Opinion of the Searching Authority for International Patent Application No. PCT/IB2006/004048 issued Jun. 4, 2008 (10 pages).
International Search Report for International Patent Application No. PCT/EP2012/002332, mailed Nov. 8, 2012 (7 pages).
International Search Report for International Patent Application No. PCT/EP2008/003789 mailed Jan. 9, 2009 (5 pages).
International Search Report for International Application No. PCT/IB2006/004048 mailed May 14, 2008 (5 pages).
Office Action in Chinese Patent Application No. 200680052220.2 issued Mar. 21, 2012 (with English Translation) (11 pages).
Office Action in Japanese Patent Application No. 2008-542865 mailed Apr. 18, 2012 (with English Translation) (17 pages).
English Translation of Office Action for Chinese Patent Application No. 200680052220.2 issued Feb. 5, 2013 (9 pages).
English translation of Office Action for Chinese Patent Application No. 201280038428.4, dated Jan. 23, 2015 (15 pages).
Yin, "Screening of laryngeal carcinoma multidrug resistance-associated genes and study on reversion by Chinese herbs" (Abstract Only), China Doctoral Dissertations Full-text Database, Division of medical and hygiene technology. 8:E072-85 (2010).
Communication pursuant to Rules 161(1) and 162 EPC for European Application No. 11741685.9, dated Dec. 6, 2012 (2 pages).
Invitation to file search results or a statement of non-availability pursuant to Rule 70b(1) EPC for European Application No. 11741685.9, dated Jul. 22, 2013 (1 page).
Communication pursuant to Article 94(3) EPC for European Application No. 11741685.9, dated May 19, 2014 (6 pages).
Communication pursuant to Rule 94(3) EPC for European Application No. 11741685.9, dated Jul. 24, 2015 (7 pages).
Decision on Rejection for Chinese Application No. 200680052220.2, dated Jun. 5, 2013 (8 pages).
Reexamination Decision for Chinese Application No. 200680052220.2, dated Nov. 24, 2014 (11 pages).
Office Action for Chinese Application No. 200680052220.2, dated Jan. 30, 2015 (8 pages).
Decision of Rejection for Japanese Application No. 2008-542865, dated Oct. 21, 2013 (11 pages).
Pre-Appeal Examination Report for Japanese Application No. 2008-542865, dated Mar. 27, 2014 (6 pages).
Notice of Reasons for Rejection for Japanese Application No. 2008-542865, dated May 28, 2015 (10 pages).
Notice of Reasons for Rejection for Japanese Application No. 2008-542865, dated Oct. 14, 2015 (8 pages).
Kuter et al., "Dose-dependent change in biomarkers during neoadjuvant endocrine therapy with fulvestrant: results from Newest, a randomized Phase II study," Breast Cancer Res Treat. 133(1):237-46 (2012).
Nikas et al., "Prognosis of treatment response (pathological complete response) in breast cancer," Biomark Insights. 7:59-70 (2012).
Juncker-Jensen et al., "Insulin-like growth factor binding protein 2 is a marker for antiestrogen resistant human breast cancer cell lines but is not a major growth regulator," Growth Horm IGF Res. 16(4):224-39 (2006).
McCune et al., "Prognosis of hormone-dependent breast cancers: implications of the presence of dysfunctional transcriptional networks activated by insulin via the immune transcription factor T-bet," Cancer Res. 70(2):685-96 (2010).
Agrawal et al., "Long-term effect of fulvestrant on hormone receptors and proliferation marker in breast cancer," EJC Supplements. 8(3):111 (2010).
International Search Report and Written Opinion for International Application No. PCT/EP2014/052236, mailed Jul. 9, 2014 (21 pages).
Zhang et al, "MicroRNA-650 targets ING4 to promote gastric cancer tumorigenicity," Biochem Biophys Res Commun. 395(2):275-280 (2010).
English translation of Second Office Action for Chinese Patent Application No. 201280038428.4, dated Sep. 15, 2015 (10 pages).
EPO Communication pursuant to Article 94(3) EPC for European Patent Application No. 12725624.6, dated Dec. 23, 2014 (6 pages).
EPO Communication pursuant to Article 94(3) EPC for European Patent Application No. 12725624.6, dated Jul. 2, 2015 (4 pages).

\* cited by examiner

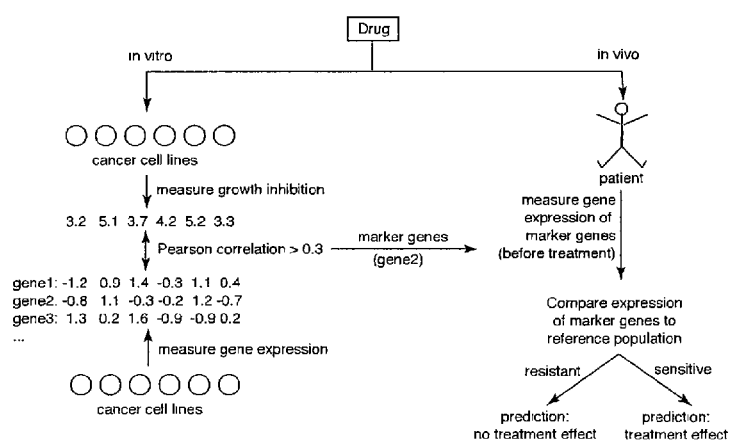

SEQUENCE LISTING

```
<160> NUMBER OF SEQ ID NOS: 687

<210> SEQ ID NO 1
<211> LENGTH: 22
<212> TYPE: DNA
<213> ORGANISM: Artificial Sequence
<220> FEATURE:
<223> OTHER INFORMATION: Synthetic Probe

<400> SEQUENCE: 1
gctgaggctg tggggctgga gt                                                  22

<210> SEQ ID NO 2
<211> LENGTH: 22
<212> TYPE: DNA
<213> ORGANISM: Artificial Sequence
<220> FEATURE:
<223> OTHER INFORMATION: Synthetic Probe

<400> SEQUENCE: 2
gcagcaagta cccacagtgc gg                                                  22

<210> SEQ ID NO 3
<211> LENGTH: 21
<212> TYPE: DNA
<213> ORGANISM: Artificial Sequence
<220> FEATURE:
<223> OTHER INFORMATION: Synthetic Probe

<400> SEQUENCE: 3
caattgccca agtctccgcc t                                                   21

<210> SEQ ID NO 4
<211> LENGTH: 25
<212> TYPE: DNA
<213> ORGANISM: Artificial Sequence
<220> FEATURE:
<223> OTHER INFORMATION: Synthetic Probe

<400> SEQUENCE: 4
gaatgttttt tttgggact catca                                                25
```

-continued

```
<210> SEQ ID NO 5
<211> LENGTH: 25
<212> TYPE: DNA
<213> ORGANISM: Artificial Sequence
<220> FEATURE:
<223> OTHER INFORMATION: Synthetic Probe

<400> SEQUENCE: 5
atggcatcag cgacacactc aagag                                          25

<210> SEQ ID NO 6
<211> LENGTH: 25
<212> TYPE: DNA
<213> ORGANISM: Artificial Sequence
<220> FEATURE:
<223> OTHER INFORMATION: Synthetic Probe

<400> SEQUENCE: 6
gcactcggga gtatgcagca ttacc                                          25

<210> SEQ ID NO 7
<211> LENGTH: 20
<212> TYPE: DNA
<213> ORGANISM: Artificial Sequence
<220> FEATURE:
<223> OTHER INFORMATION: Synthetic Probe

<400> SEQUENCE: 7
ggcattcacc gcgtgcctta                                                20

<210> SEQ ID NO 8
<211> LENGTH: 17
<212> TYPE: DNA
<213> ORGANISM: Artificial Sequence
<220> FEATURE:
<223> OTHER INFORMATION: Synthetic Probe

<400> SEQUENCE: 8
gggagaggag gaggcga                                                   17

<210> SEQ ID NO 9
<211> LENGTH: 22
<212> TYPE: DNA
<213> ORGANISM: Artificial Sequence
<220> FEATURE:
<223> OTHER INFORMATION: Synthetic Probe

<400> SEQUENCE: 9
ggtacaatca acggtcgatg gt                                             22

<210> SEQ ID NO 10
<211> LENGTH: 23
<212> TYPE: DNA
<213> ORGANISM: Artificial Sequence
<220> FEATURE:
<223> OTHER INFORMATION: Synthetic Probe

<400> SEQUENCE: 10
acccaccgac agcaatgaat gtt                                            23

<210> SEQ ID NO 11
<211> LENGTH: 23
<212> TYPE: DNA
<213> ORGANISM: Artificial Sequence
<220> FEATURE:
<223> OTHER INFORMATION: Synthetic Probe
```

```
<400> SEQUENCE: 11
acgggtgcga tttctgtgtg aga                                          23

<210> SEQ ID NO 12
<211> LENGTH: 23
<212> TYPE: DNA
<213> ORGANISM: Artificial Sequence
<220> FEATURE:
<223> OTHER INFORMATION: Synthetic Probe

<400> SEQUENCE: 12
ccacccaatg acctactcca aga                                          23

<210> SEQ ID NO 13
<211> LENGTH: 21
<212> TYPE: DNA
<213> ORGANISM: Artificial Sequence
<220> FEATURE:
<223> OTHER INFORMATION: Synthetic Probe

<400> SEQUENCE: 13
ccgtggttct accctgtggt a                                            21

<210> SEQ ID NO 14
<211> LENGTH: 22
<212> TYPE: DNA
<213> ORGANISM: Artificial Sequence
<220> FEATURE:
<223> OTHER INFORMATION: Synthetic Probe

<400> SEQUENCE: 14
ggagcagcac agccaatatt gg                                           22

<210> SEQ ID NO 15
<211> LENGTH: 22
<212> TYPE: DNA
<213> ORGANISM: Artificial Sequence
<220> FEATURE:
<223> OTHER INFORMATION: Synthetic Probe

<400> SEQUENCE: 15
ggaggccggg acgagtgcaa ta                                           22

<210> SEQ ID NO 16
<211> LENGTH: 22
<212> TYPE: DNA
<213> ORGANISM: Artificial Sequence
<220> FEATURE:
<223> OTHER INFORMATION: Synthetic Probe

<400> SEQUENCE: 16
actgggttca cctttaaggg ca                                           22

<210> SEQ ID NO 17
<211> LENGTH: 22
<212> TYPE: DNA
<213> ORGANISM: Artificial Sequence
<220> FEATURE:
<223> OTHER INFORMATION: Synthetic Probe

<400> SEQUENCE: 17
cacaagttcg gatctacggg tt                                           22

<210> SEQ ID NO 18
<211> LENGTH: 22
```

```
<212> TYPE: DNA
<213> ORGANISM: Artificial Sequence
<220> FEATURE:
<223> OTHER INFORMATION: Synthetic Probe

<400> SEQUENCE: 18
ctaccatagg gtaaaaccac tg                                              22

<210> SEQ ID NO 19
<211> LENGTH: 22
<212> TYPE: DNA
<213> ORGANISM: Artificial Sequence
<220> FEATURE:
<223> OTHER INFORMATION: Synthetic Probe

<400> SEQUENCE: 19
aacccatgga attcagttct ca                                              22

<210> SEQ ID NO 20
<211> LENGTH: 23
<212> TYPE: DNA
<213> ORGANISM: Artificial Sequence
<220> FEATURE:
<223> OTHER INFORMATION: Synthetic Probe

<400> SEQUENCE: 20
acccctatca cgattagcat taa                                             23

<210> SEQ ID NO 21
<211> LENGTH: 21
<212> TYPE: DNA
<213> ORGANISM: Artificial Sequence
<220> FEATURE:
<223> OTHER INFORMATION: Synthetic Probe

<400> SEQUENCE: 21
tctactcaga agggtgcctt a                                               21

<210> SEQ ID NO 22
<211> LENGTH: 23
<212> TYPE: DNA
<213> ORGANISM: Artificial Sequence
<220> FEATURE:
<223> OTHER INFORMATION: Synthetic Probe

<400> SEQUENCE: 22
catgagtgac gccctctgga gta                                             23

<210> SEQ ID NO 23
<211> LENGTH: 22
<212> TYPE: DNA
<213> ORGANISM: Artificial Sequence
<220> FEATURE:
<223> OTHER INFORMATION: Synthetic Probe

<400> SEQUENCE: 23
catgattgcc acgtctgcag ta                                              22

<210> SEQ ID NO 24
<211> LENGTH: 22
<212> TYPE: DNA
<213> ORGANISM: Artificial Sequence
<220> FEATURE:
<223> OTHER INFORMATION: Synthetic Probe

<400> SEQUENCE: 24
```

-continued ctacccacag acgtaccaat ca						22

<210> SEQ ID NO 25
<211> LENGTH: 22
<212> TYPE: DNA
<213> ORGANISM: Artificial Sequence
<220> FEATURE:
<223> OTHER INFORMATION: Synthetic Probe

<400> SEQUENCE: 25
gtgattgcca ctctcctgag ta						22

<210> SEQ ID NO 26
<211> LENGTH: 18
<212> TYPE: DNA
<213> ORGANISM: Artificial Sequence
<220> FEATURE:
<223> OTHER INFORMATION: Synthetic Probe

<400> SEQUENCE: 26
atgacacctc cctgtgaa						18

<210> SEQ ID NO 27
<211> LENGTH: 22
<212> TYPE: DNA
<213> ORGANISM: Artificial Sequence
<220> FEATURE:
<223> OTHER INFORMATION: Synthetic Probe

<400> SEQUENCE: 27
ataaatgaca cctccttgtg aa						22

<210> SEQ ID NO 28
<211> LENGTH: 22
<212> TYPE: DNA
<213> ORGANISM: Artificial Sequence
<220> FEATURE:
<223> OTHER INFORMATION: Synthetic Probe

<400> SEQUENCE: 28
gcggtcccgc ggcgccccgc ct						22

<210> SEQ ID NO 29
<211> LENGTH: 21
<212> TYPE: DNA
<213> ORGANISM: Artificial Sequence
<220> FEATURE:
<223> OTHER INFORMATION: Synthetic Probe

<400> SEQUENCE: 29
agtttctttt cctccgctga c						21

<210> SEQ ID NO 30
<211> LENGTH: 22
<212> TYPE: DNA
<213> ORGANISM: Artificial Sequence
<220> FEATURE:
<223> OTHER INFORMATION: Synthetic Probe

<400> SEQUENCE: 30
tgagtgcttg ctaggtgcca ag						22

<210> SEQ ID NO 31
<211> LENGTH: 21
<212> TYPE: DNA
<213> ORGANISM: Artificial Sequence

```
<220> FEATURE:
<223> OTHER INFORMATION: Synthetic Probe

<400> SEQUENCE: 31
gagctacagt gcttcatctc a                                              21

<210> SEQ ID NO 32
<211> LENGTH: 22
<212> TYPE: DNA
<213> ORGANISM: Artificial Sequence
<220> FEATURE:
<223> OTHER INFORMATION: Synthetic Probe

<400> SEQUENCE: 32
accaggttcc accccagcag gc                                             22

<210> SEQ ID NO 33
<211> LENGTH: 22
<212> TYPE: DNA
<213> ORGANISM: Artificial Sequence
<220> FEATURE:
<223> OTHER INFORMATION: Synthetic Probe

<400> SEQUENCE: 33
acaccgagga gcccatcatg at                                             22

<210> SEQ ID NO 34
<211> LENGTH: 22
<212> TYPE: DNA
<213> ORGANISM: Artificial Sequence
<220> FEATURE:
<223> OTHER INFORMATION: Synthetic Probe

<400> SEQUENCE: 34
aaggtgatgg tcagcagaca ta                                             22

<210> SEQ ID NO 35
<211> LENGTH: 22
<212> TYPE: DNA
<213> ORGANISM: Artificial Sequence
<220> FEATURE:
<223> OTHER INFORMATION: Synthetic Probe

<400> SEQUENCE: 35
ggttagtgga ccaggtcaca aa                                             22

<210> SEQ ID NO 36
<211> LENGTH: 25
<212> TYPE: DNA
<213> ORGANISM: Artificial Sequence
<220> FEATURE:
<223> OTHER INFORMATION: Synthetic Probe

<400> SEQUENCE: 36
tggcttcccc accgcgcact cggga                                          25

<210> SEQ ID NO 37
<211> LENGTH: 21
<212> TYPE: DNA
<213> ORGANISM: Artificial Sequence
<220> FEATURE:
<223> OTHER INFORMATION: Synthetic Probe

<400> SEQUENCE: 37
atctgcactg tcagcacttt a                                              21
```

<210> SEQ ID NO 38
<211> LENGTH: 22
<212> TYPE: DNA
<213> ORGANISM: Artificial Sequence
<220> FEATURE:
<223> OTHER INFORMATION: Synthetic Probe

<400> SEQUENCE: 38
tccctcacac agaattccag aa                                              22

<210> SEQ ID NO 39
<211> LENGTH: 22
<212> TYPE: DNA
<213> ORGANISM: Artificial Sequence
<220> FEATURE:
<223> OTHER INFORMATION: Synthetic Probe

<400> SEQUENCE: 39
ctaagccacc atgtgaaacc ag                                              22

<210> SEQ ID NO 40
<211> LENGTH: 22
<212> TYPE: DNA
<213> ORGANISM: Artificial Sequence
<220> FEATURE:
<223> OTHER INFORMATION: Synthetic Probe

<400> SEQUENCE: 40
gggctgcact gccgaggcac tg                                              22

<210> SEQ ID NO 41
<211> LENGTH: 22
<212> TYPE: DNA
<213> ORGANISM: Artificial Sequence
<220> FEATURE:
<223> OTHER INFORMATION: Synthetic Probe

<400> SEQUENCE: 41
gctgggctta cgttgggaga ac                                              22

<210> SEQ ID NO 42
<211> LENGTH: 21
<212> TYPE: DNA
<213> ORGANISM: Artificial Sequence
<220> FEATURE:
<223> OTHER INFORMATION: Synthetic Probe

<400> SEQUENCE: 42
cacaacccta gtggcgccat t                                               21

<210> SEQ ID NO 43
<211> LENGTH: 23
<212> TYPE: DNA
<213> ORGANISM: Artificial Sequence
<220> FEATURE:
<223> OTHER INFORMATION: Synthetic Probe

<400> SEQUENCE: 43
ctccagcccc tccagggctt cct                                             23

<210> SEQ ID NO 44
<211> LENGTH: 25
<212> TYPE: DNA
<213> ORGANISM: Artificial Sequence
<220> FEATURE:
<223> OTHER INFORMATION: Synthetic Probe

<400> SEQUENCE: 44
gtcagcagtt tgagtgtcag cattg                                         25

<210> SEQ ID NO 45
<211> LENGTH: 22
<212> TYPE: DNA
<213> ORGANISM: Artificial Sequence
<220> FEATURE:
<223> OTHER INFORMATION: Synthetic Probe

<400> SEQUENCE: 45
cgggaagtgc tagctcagca gt                                            22

<210> SEQ ID NO 46
<211> LENGTH: 23
<212> TYPE: DNA
<213> ORGANISM: Artificial Sequence
<220> FEATURE:
<223> OTHER INFORMATION: Synthetic Probe

<400> SEQUENCE: 46
ctacctgcac gaacagcact ttg                                           23

<210> SEQ ID NO 47
<211> LENGTH: 25
<212> TYPE: DNA
<213> ORGANISM: Artificial Sequence
<220> FEATURE:
<223> OTHER INFORMATION: Synthetic Probe

<400> SEQUENCE: 47
taggaacaga gaggccattc tgggc                                         25

<210> SEQ ID NO 48
<211> LENGTH: 25
<212> TYPE: DNA
<213> ORGANISM: Artificial Sequence
<220> FEATURE:
<223> OTHER INFORMATION: Synthetic Probe

<400> SEQUENCE: 48
gctacaggaa aagccccatc gggat                                         25

<210> SEQ ID NO 49
<211> LENGTH: 25
<212> TYPE: DNA
<213> ORGANISM: Artificial Sequence
<220> FEATURE:
<223> OTHER INFORMATION: Synthetic Probe

<400> SEQUENCE: 49
tggagatccc atggctatga ccagc                                         25

<210> SEQ ID NO 50
<211> LENGTH: 25
<212> TYPE: DNA
<213> ORGANISM: Artificial Sequence
<220> FEATURE:
<223> OTHER INFORMATION: Synthetic Probe

<400> SEQUENCE: 50
tacctcctct ttctatacag tcagt                                         25

<210> SEQ ID NO 51

```
<211> LENGTH: 25
<212> TYPE: DNA
<213> ORGANISM: Artificial Sequence
<220> FEATURE:
<223> OTHER INFORMATION: Synthetic Probe

<400> SEQUENCE: 51
taggccagct tcactattac ttttc                                         25

<210> SEQ ID NO 52
<211> LENGTH: 25
<212> TYPE: DNA
<213> ORGANISM: Artificial Sequence
<220> FEATURE:
<223> OTHER INFORMATION: Synthetic Probe

<400> SEQUENCE: 52
ttgatcttga gcctgcggag agcaa                                         25

<210> SEQ ID NO 53
<211> LENGTH: 25
<212> TYPE: DNA
<213> ORGANISM: Artificial Sequence
<220> FEATURE:
<223> OTHER INFORMATION: Synthetic Probe

<400> SEQUENCE: 53
ggtgttgcca tcattagcca agctt                                         25

<210> SEQ ID NO 54
<211> LENGTH: 25
<212> TYPE: DNA
<213> ORGANISM: Artificial Sequence
<220> FEATURE:
<223> OTHER INFORMATION: Synthetic Probe

<400> SEQUENCE: 54
ggcaccgtgt cctcagtggc agtcg                                         25

<210> SEQ ID NO 55
<211> LENGTH: 25
<212> TYPE: DNA
<213> ORGANISM: Artificial Sequence
<220> FEATURE:
<223> OTHER INFORMATION: Synthetic Probe

<400> SEQUENCE: 55
atcagaaggg tgacatggca gtttc                                         25

<210> SEQ ID NO 56
<211> LENGTH: 25
<212> TYPE: DNA
<213> ORGANISM: Artificial Sequence
<220> FEATURE:
<223> OTHER INFORMATION: Synthetic Probe

<400> SEQUENCE: 56
aggctcagac tccagttcgc atcac                                         25

<210> SEQ ID NO 57
<211> LENGTH: 25
<212> TYPE: DNA
<213> ORGANISM: Artificial Sequence
<220> FEATURE:
<223> OTHER INFORMATION: Synthetic Probe

<400> SEQUENCE: 57
```
gttcaagggt ggcacatctc acaca                                              25

<210> SEQ ID NO 58
<211> LENGTH: 25
<212> TYPE: DNA
<213> ORGANISM: Artificial Sequence
<220> FEATURE:
<223> OTHER INFORMATION: Synthetic Probe

<400> SEQUENCE: 58
gaggcccagc ttcatcttca acgtt                                              25

<210> SEQ ID NO 59
<211> LENGTH: 25
<212> TYPE: DNA
<213> ORGANISM: Artificial Sequence
<220> FEATURE:
<223> OTHER INFORMATION: Synthetic Probe

<400> SEQUENCE: 59
acgaggccca gcttcatctt caacg                                              25

<210> SEQ ID NO 60
<211> LENGTH: 25
<212> TYPE: DNA
<213> ORGANISM: Artificial Sequence
<220> FEATURE:
<223> OTHER INFORMATION: Synthetic Probe

<400> SEQUENCE: 60
gttcagttcg taaaatcatc cccgt                                              25

<210> SEQ ID NO 61
<211> LENGTH: 25
<212> TYPE: DNA
<213> ORGANISM: Artificial Sequence
<220> FEATURE:
<223> OTHER INFORMATION: Synthetic Probe

<400> SEQUENCE: 61
catcaatggc tgacggcagt tgcag                                              25

<210> SEQ ID NO 62
<211> LENGTH: 25
<212> TYPE: DNA
<213> ORGANISM: Artificial Sequence
<220> FEATURE:
<223> OTHER INFORMATION: Synthetic Probe

<400> SEQUENCE: 62
gacatccgca gaccatcgtg agata                                              25

<210> SEQ ID NO 63
<211> LENGTH: 25
<212> TYPE: DNA
<213> ORGANISM: Artificial Sequence
<220> FEATURE:
<223> OTHER INFORMATION: Synthetic Probe

<400> SEQUENCE: 63
aggagtagtc ttcgtcagtt atcgc                                              25

<210> SEQ ID NO 64
<211> LENGTH: 25
<212> TYPE: DNA

```
<213> ORGANISM: Artificial Sequence
<220> FEATURE:
<223> OTHER INFORMATION: Synthetic Probe

<400> SEQUENCE: 64
acaggagtag tcttcgtcag ttatc                                          25

<210> SEQ ID NO 65
<211> LENGTH: 25
<212> TYPE: DNA
<213> ORGANISM: Artificial Sequence
<220> FEATURE:
<223> OTHER INFORMATION: Synthetic Probe

<400> SEQUENCE: 65
gtcagttatc gcttctgacg gcact                                          25

<210> SEQ ID NO 66
<211> LENGTH: 25
<212> TYPE: DNA
<213> ORGANISM: Artificial Sequence
<220> FEATURE:
<223> OTHER INFORMATION: Synthetic Probe

<400> SEQUENCE: 66
atcccagttc cccaaaggcc ttagg                                          25

<210> SEQ ID NO 67
<211> LENGTH: 25
<212> TYPE: DNA
<213> ORGANISM: Artificial Sequence
<220> FEATURE:
<223> OTHER INFORMATION: Synthetic Probe

<400> SEQUENCE: 67
cgacaagatc cgcttgctgt ttgca                                          25

<210> SEQ ID NO 68
<211> LENGTH: 25
<212> TYPE: DNA
<213> ORGANISM: Artificial Sequence
<220> FEATURE:
<223> OTHER INFORMATION: Synthetic Probe

<400> SEQUENCE: 68
aaggcgacaa gatccgcttg ctgtt                                          25

<210> SEQ ID NO 69
<211> LENGTH: 25
<212> TYPE: DNA
<213> ORGANISM: Artificial Sequence
<220> FEATURE:
<223> OTHER INFORMATION: Synthetic Probe

<400> SEQUENCE: 69
cggttggcat tcatcattac tctca                                          25

<210> SEQ ID NO 70
<211> LENGTH: 17
<212> TYPE: DNA
<213> ORGANISM: Artificial Sequence
<220> FEATURE:
<223> OTHER INFORMATION: Synthetic Probe

<400> SEQUENCE: 70
gacagcctct cccccac                                                   17
```

<210> SEQ ID NO 71
<211> LENGTH: 23
<212> TYPE: DNA
<213> ORGANISM: Artificial Sequence
<220> FEATURE:
<223> OTHER INFORMATION: Synthetic Probe

<400> SEQUENCE: 71
ccagaaggag cacttagggc agt                                           23

<210> SEQ ID NO 72
<211> LENGTH: 23
<212> TYPE: DNA
<213> ORGANISM: Artificial Sequence
<220> FEATURE:
<223> OTHER INFORMATION: Synthetic Probe

<400> SEQUENCE: 72
ctatctgcac tagatgcacc tta                                           23

<210> SEQ ID NO 73
<211> LENGTH: 25
<212> TYPE: DNA
<213> ORGANISM: Artificial Sequence
<220> FEATURE:
<223> OTHER INFORMATION: Synthetic Probe

<400> SEQUENCE: 73
ccaacactca tacgccggca gttgt                                         25

<210> SEQ ID NO 74
<211> LENGTH: 25
<212> TYPE: DNA
<213> ORGANISM: Artificial Sequence
<220> FEATURE:
<223> OTHER INFORMATION: Synthetic Probe

<400> SEQUENCE: 74
tggacctcag acttccagac ctgta                                         25

<210> SEQ ID NO 75
<211> LENGTH: 25
<212> TYPE: DNA
<213> ORGANISM: Artificial Sequence
<220> FEATURE:
<223> OTHER INFORMATION: Synthetic Probe

<400> SEQUENCE: 75
tcatcgtatg tgactcatac tccac                                         25

<210> SEQ ID NO 76
<211> LENGTH: 25
<212> TYPE: DNA
<213> ORGANISM: Artificial Sequence
<220> FEATURE:
<223> OTHER INFORMATION: Synthetic Probe

<400> SEQUENCE: 76
gtgactcata ctccaccagt gctca                                         25

<210> SEQ ID NO 77
<211> LENGTH: 22
<212> TYPE: DNA
<213> ORGANISM: Artificial Sequence
<220> FEATURE:

```
<223> OTHER INFORMATION: Synthetic Probe

<400> SEQUENCE: 77
agccaagctc agacggatcc ga                                              22

<210> SEQ ID NO 78
<211> LENGTH: 23
<212> TYPE: DNA
<213> ORGANISM: Artificial Sequence
<220> FEATURE:
<223> OTHER INFORMATION: Synthetic Probe

<400> SEQUENCE: 78
actcaccgac agcgttgaat gtt                                             23

<210> SEQ ID NO 79
<211> LENGTH: 22
<212> TYPE: DNA
<213> ORGANISM: Artificial Sequence
<220> FEATURE:
<223> OTHER INFORMATION: Synthetic Probe

<400> SEQUENCE: 79
actcaccgac aggttgaatg tt                                              22

<210> SEQ ID NO 80
<211> LENGTH: 21
<212> TYPE: DNA
<213> ORGANISM: Artificial Sequence
<220> FEATURE:
<223> OTHER INFORMATION: Synthetic Probe

<400> SEQUENCE: 80
tcaatcacag atagcacccc t                                               21

<210> SEQ ID NO 81
<211> LENGTH: 22
<212> TYPE: DNA
<213> ORGANISM: Artificial Sequence
<220> FEATURE:
<223> OTHER INFORMATION: Synthetic Probe

<400> SEQUENCE: 81
aggggttcac cgagcaacat tc                                              22

<210> SEQ ID NO 82
<211> LENGTH: 22
<212> TYPE: DNA
<213> ORGANISM: Artificial Sequence
<220> FEATURE:
<223> OTHER INFORMATION: Synthetic Probe

<400> SEQUENCE: 82
aagtggatga ccctgtacga tt                                              22

<210> SEQ ID NO 83
<211> LENGTH: 25
<212> TYPE: DNA
<213> ORGANISM: Artificial Sequence
<220> FEATURE:
<223> OTHER INFORMATION: Synthetic Probe

<400> SEQUENCE: 83
atcactccgt actttcatcc tccaa                                           25
```

```
<210> SEQ ID NO 84
<211> LENGTH: 20
<212> TYPE: DNA
<213> ORGANISM: Artificial Sequence
<220> FEATURE:
<223> OTHER INFORMATION: Synthetic Probe

<400> SEQUENCE: 84 gggggggcgag gcaggtgtga                                              20

<210> SEQ ID NO 85
<211> LENGTH: 22
<212> TYPE: DNA
<213> ORGANISM: Artificial Sequence
<220> FEATURE:
<223> OTHER INFORMATION: Synthetic Probe

<400> SEQUENCE: 85
tcaggaactg cctttctctc ca                                            22

<210> SEQ ID NO 86
<211> LENGTH: 21
<212> TYPE: DNA
<213> ORGANISM: Artificial Sequence
<220> FEATURE:
<223> OTHER INFORMATION: Synthetic Probe

<400> SEQUENCE: 86
ccctccacca tgcaagggat g                                             21

<210> SEQ ID NO 87
<211> LENGTH: 23
<212> TYPE: DNA
<213> ORGANISM: Artificial Sequence
<220> FEATURE:
<223> OTHER INFORMATION: Synthetic Probe

<400> SEQUENCE: 87
ctaactgcac tagatgcacc tta                                           23

<210> SEQ ID NO 88
<211> LENGTH: 23
<212> TYPE: DNA
<213> ORGANISM: Artificial Sequence
<220> FEATURE:
<223> OTHER INFORMATION: Synthetic Probe

<400> SEQUENCE: 88
ctacctgcac tatgagcact ttg                                           23

<210> SEQ ID NO 89
<211> LENGTH: 22
<212> TYPE: DNA
<213> ORGANISM: Artificial Sequence
<220> FEATURE:
<223> OTHER INFORMATION: Synthetic Probe

<400> SEQUENCE: 89
tcagaccgag acaagtgcaa tg                                            22

<210> SEQ ID NO 90
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 90
accctctcaa cccagctttt                                              20

<210> SEQ ID NO 91
<211> LENGTH: 19
<212> TYPE: DNA
<213> ORGANISM: Artificial Sequence
<220> FEATURE:
<223> OTHER INFORMATION: Synthetic Probe

<400> SEQUENCE: 91
tcctctcaac ccagctttt                                               19

<210> SEQ ID NO 92
<211> LENGTH: 24
<212> TYPE: DNA
<213> ORGANISM: Artificial Sequence
<220> FEATURE:
<223> OTHER INFORMATION: Synthetic Probe

<400> SEQUENCE: 92
actcacacct aggttccaag gatt                                         24

<210> SEQ ID NO 93
<211> LENGTH: 22
<212> TYPE: DNA
<213> ORGANISM: Artificial Sequence
<220> FEATURE:
<223> OTHER INFORMATION: Synthetic Probe

<400> SEQUENCE: 93
cagaatcctt gcccaggtgc at                                           22

<210> SEQ ID NO 94
<211> LENGTH: 23
<212> TYPE: DNA
<213> ORGANISM: Artificial Sequence
<220> FEATURE:
<223> OTHER INFORMATION: Synthetic Probe

<400> SEQUENCE: 94
tctcacccag gtagcaagga tta                                          23

<210> SEQ ID NO 95
<211> LENGTH: 22
<212> TYPE: DNA
<213> ORGANISM: Artificial Sequence
<220> FEATURE:
<223> OTHER INFORMATION: Synthetic Probe

<400> SEQUENCE: 95
agaatccttg cccgggtgca tt                                           22

<210> SEQ ID NO 96
<211> LENGTH: 22
<212> TYPE: DNA
<213> ORGANISM: Artificial Sequence
<220> FEATURE:
<223> OTHER INFORMATION: Synthetic Probe

<400> SEQUENCE: 96
tgaatccttg cccaggtgca tt                                           22

<210> SEQ ID NO 97
<211> LENGTH: 22
```

```
<212> TYPE: DNA
<213> ORGANISM: Artificial Sequence
<220> FEATURE:
<223> OTHER INFORMATION: Synthetic Probe

<400> SEQUENCE: 97
tgcaagcctt gggtgtggga gg                                              22

<210> SEQ ID NO 98
<211> LENGTH: 22
<212> TYPE: DNA
<213> ORGANISM: Artificial Sequence
<220> FEATURE:
<223> OTHER INFORMATION: Synthetic Probe

<400> SEQUENCE: 98
acggtcctac actcaaggca tg                                              22

<210> SEQ ID NO 99
<211> LENGTH: 25
<212> TYPE: DNA
<213> ORGANISM: Artificial Sequence
<220> FEATURE:
<223> OTHER INFORMATION: Synthetic Probe

<400> SEQUENCE: 99
atctggaatg agtccctcag catcc                                           25

<210> SEQ ID NO 100
<211> LENGTH: 21
<212> TYPE: DNA
<213> ORGANISM: Artificial Sequence
<220> FEATURE:
<223> OTHER INFORMATION: Synthetic Probe

<400> SEQUENCE: 100
atagcagcgc ctcacgtttt g                                               21

<210> SEQ ID NO 101
<211> LENGTH: 23
<212> TYPE: DNA
<213> ORGANISM: Artificial Sequence
<220> FEATURE:
<223> OTHER INFORMATION: Synthetic Probe

<400> SEQUENCE: 101
ctgcagaact gttcccgctg cta                                             23

<210> SEQ ID NO 102
<211> LENGTH: 22
<212> TYPE: DNA
<213> ORGANISM: Artificial Sequence
<220> FEATURE:
<223> OTHER INFORMATION: Synthetic Probe

<400> SEQUENCE: 102
cacgaccgac gccacgccga gt                                              22

<210> SEQ ID NO 103
<211> LENGTH: 22
<212> TYPE: DNA
<213> ORGANISM: Artificial Sequence
<220> FEATURE:
<223> OTHER INFORMATION: Synthetic Probe

<400> SEQUENCE: 103
```
aggaaaccag caagtgttga cg                                              22

<210> SEQ ID NO 104
<211> LENGTH: 23
<212> TYPE: DNA
<213> ORGANISM: Artificial Sequence
<220> FEATURE:
<223> OTHER INFORMATION: Synthetic Probe

<400> SEQUENCE: 104
aaccaagacc ccggagatcc cag                                             23

<210> SEQ ID NO 105
<211> LENGTH: 22
<212> TYPE: DNA
<213> ORGANISM: Artificial Sequence
<220> FEATURE:
<223> OTHER INFORMATION: Synthetic Probe

<400> SEQUENCE: 105
agctcagaac ccagaggtct ca                                              22

<210> SEQ ID NO 106
<211> LENGTH: 25
<212> TYPE: DNA
<213> ORGANISM: Artificial Sequence
<220> FEATURE:
<223> OTHER INFORMATION: Synthetic Probe

<400> SEQUENCE: 106
tcagttatcg cttctgacgg cactt                                           25

<210> SEQ ID NO 107
<211> LENGTH: 25
<212> TYPE: DNA
<213> ORGANISM: Artificial Sequence
<220> FEATURE:
<223> OTHER INFORMATION: Synthetic Probe

<400> SEQUENCE: 107
cgtcagttat cgcttctgac ggcac                                           25

<210> SEQ ID NO 108
<211> LENGTH: 22
<212> TYPE: DNA
<213> ORGANISM: Artificial Sequence
<220> FEATURE:
<223> OTHER INFORMATION: Synthetic Probe

<400> SEQUENCE: 108
tattccccta gatacgaatt tg                                              22

<210> SEQ ID NO 109
<211> LENGTH: 21
<212> TYPE: DNA
<213> ORGANISM: Artificial Sequence
<220> FEATURE:
<223> OTHER INFORMATION: Synthetic Probe

<400> SEQUENCE: 109
cccctcccag cctccctgcc a                                               21

<210> SEQ ID NO 110
<211> LENGTH: 21
<212> TYPE: DNA
<213> ORGANISM: Artificial Sequence
<220> FEATURE:
<223> OTHER INFORMATION: Synthetic Probe

<400> SEQUENCE: 110
aaagagaccg gttcactgtg a    21

<210> SEQ ID NO 111
<211> LENGTH: 22
<212> TYPE: DNA
<213> ORGANISM: Artificial Sequence
<220> FEATURE:
<223> OTHER INFORMATION: Synthetic Probe

<400> SEQUENCE: 111
cactggtaca agggttggga ga    22

<210> SEQ ID NO 112
<211> LENGTH: 22
<212> TYPE: DNA
<213> ORGANISM: Artificial Sequence
<220> FEATURE:
<223> OTHER INFORMATION: Synthetic Probe

<400> SEQUENCE: 112
ttcaaaacat gaattgctgc tg    22

<210> SEQ ID NO 113
<211> LENGTH: 25
<212> TYPE: DNA
<213> ORGANISM: Artificial Sequence
<220> FEATURE:
<223> OTHER INFORMATION: Synthetic Probe

<400> SEQUENCE: 113
ttcatcaagg ccgtacagcg attcc    25

<210> SEQ ID NO 114
<211> LENGTH: 25
<212> TYPE: DNA
<213> ORGANISM: Artificial Sequence
<220> FEATURE:
<223> OTHER INFORMATION: Synthetic Probe

<400> SEQUENCE: 114
agcatcctca gacaattatt ctcat    25

<210> SEQ ID NO 115
<211> LENGTH: 25
<212> TYPE: DNA
<213> ORGANISM: Artificial Sequence
<220> FEATURE:
<223> OTHER INFORMATION: Synthetic Probe

<400> SEQUENCE: 115
tgttcaactt tccaaggaac ccacg    25

<210> SEQ ID NO 116
<211> LENGTH: 25
<212> TYPE: DNA
<213> ORGANISM: Artificial Sequence
<220> FEATURE:
<223> OTHER INFORMATION: Synthetic Probe

<400> SEQUENCE: 116
ggcaggctca gactccagtt cgcat    25

<210> SEQ ID NO 117
<211> LENGTH: 25
<212> TYPE: DNA
<213> ORGANISM: Artificial Sequence
<220> FEATURE:
<223> OTHER INFORMATION: Synthetic Probe

<400> SEQUENCE: 117
cgaggcccag cttcatcttc aacgt                                          25

<210> SEQ ID NO 118
<211> LENGTH: 25
<212> TYPE: DNA
<213> ORGANISM: Artificial Sequence
<220> FEATURE:
<223> OTHER INFORMATION: Synthetic Probe

<400> SEQUENCE: 118
ggtgatggca tcagcgacac actca                                          25

<210> SEQ ID NO 119
<211> LENGTH: 25
<212> TYPE: DNA
<213> ORGANISM: Artificial Sequence
<220> FEATURE:
<223> OTHER INFORMATION: Synthetic Probe

<400> SEQUENCE: 119
catgctcatt tcaggtcaga cattt                                          25

<210> SEQ ID NO 120
<211> LENGTH: 25
<212> TYPE: DNA
<213> ORGANISM: Artificial Sequence
<220> FEATURE:
<223> OTHER INFORMATION: Synthetic Probe

<400> SEQUENCE: 120
tttgtctaca tgctcatttc aggtc                                          25

<210> SEQ ID NO 121
<211> LENGTH: 25
<212> TYPE: DNA
<213> ORGANISM: Artificial Sequence
<220> FEATURE:
<223> OTHER INFORMATION: Synthetic Probe

<400> SEQUENCE: 121
gccagtggta gatgtgtcca gagac                                          25

<210> SEQ ID NO 122
<211> LENGTH: 25
<212> TYPE: DNA
<213> ORGANISM: Artificial Sequence
<220> FEATURE:
<223> OTHER INFORMATION: Synthetic Probe

<400> SEQUENCE: 122
caaggatatg ctcttccatg gctag                                          25

<210> SEQ ID NO 123
<211> LENGTH: 25
<212> TYPE: DNA
<213> ORGANISM: Artificial Sequence
<220> FEATURE:
<223> OTHER INFORMATION: Synthetic Probe

```
<400> SEQUENCE: 123
gtcatgtgtc gctggaaatg ctatt                                      25

<210> SEQ ID NO 124
<211> LENGTH: 25
<212> TYPE: DNA
<213> ORGANISM: Artificial Sequence
<220> FEATURE:
<223> OTHER INFORMATION: Synthetic Probe

<400> SEQUENCE: 124 aataccttc agtcacacat tgatc                                       25

<210> SEQ ID NO 125
<211> LENGTH: 22
<212> TYPE: DNA
<213> ORGANISM: Artificial Sequence
<220> FEATURE:
<223> OTHER INFORMATION: Synthetic Probe

<400> SEQUENCE: 125
agaaaggcag caggtcgtat ag                                         22

<210> SEQ ID NO 126
<211> LENGTH: 25
<212> TYPE: DNA
<213> ORGANISM: Artificial Sequence
<220> FEATURE:
<223> OTHER INFORMATION: Synthetic Probe

<400> SEQUENCE: 126
tgcccactct caccatcacc tacag                                      25

<210> SEQ ID NO 127
<211> LENGTH: 18
<212> TYPE: DNA
<213> ORGANISM: Artificial Sequence
<220> FEATURE:
<223> OTHER INFORMATION: Synthetic Probe

<400> SEQUENCE: 127
cccccaccac cacgcccg                                              18

<210> SEQ ID NO 128
<211> LENGTH: 22
<212> TYPE: DNA
<213> ORGANISM: Artificial Sequence
<220> FEATURE:
<223> OTHER INFORMATION: Synthetic Probe

<400> SEQUENCE: 128
cacaaaccat tatgtgctgc ta                                         22

<210> SEQ ID NO 129
<211> LENGTH: 22
<212> TYPE: DNA
<213> ORGANISM: Artificial Sequence
<220> FEATURE:
<223> OTHER INFORMATION: Synthetic Probe

<400> SEQUENCE: 129
gaacctatct ccctctgga cc                                          22

<210> SEQ ID NO 130
```

```
<211> LENGTH: 22
<212> TYPE: DNA
<213> ORGANISM: Artificial Sequence
<220> FEATURE:
<223> OTHER INFORMATION: Synthetic Probe

<400> SEQUENCE: 130
ctggaagtgc ccatactaca gt                                                  22

<210> SEQ ID NO 131
<211> LENGTH: 22
<212> TYPE: DNA
<213> ORGANISM: Artificial Sequence
<220> FEATURE:
<223> OTHER INFORMATION: Synthetic Probe

<400> SEQUENCE: 131
tggggtattt gacaaactga ca                                                  22

<210> SEQ ID NO 132
<211> LENGTH: 21
<212> TYPE: DNA
<213> ORGANISM: Artificial Sequence
<220> FEATURE:
<223> OTHER INFORMATION: Synthetic Probe

<400> SEQUENCE: 132
catgcacatg cacacataca t                                                   21

<210> SEQ ID NO 133
<211> LENGTH: 22
<212> TYPE: DNA
<213> ORGANISM: Artificial Sequence
<220> FEATURE:
<223> OTHER INFORMATION: Synthetic Probe

<400> SEQUENCE: 133
tacagatgga taccgtgcaa tt                                                  22

<210> SEQ ID NO 134
<211> LENGTH: 21
<212> TYPE: DNA
<213> ORGANISM: Artificial Sequence
<220> FEATURE:
<223> OTHER INFORMATION: Synthetic Probe

<400> SEQUENCE: 134
gttctaaccc attgtggcca a                                                   21

<210> SEQ ID NO 135
<211> LENGTH: 21
<212> TYPE: DNA
<213> ORGANISM: Artificial Sequence
<220> FEATURE:
<223> OTHER INFORMATION: Synthetic Probe

<400> SEQUENCE: 135
gctgaggtct gggccaggtc t                                                   21

<210> SEQ ID NO 136
<211> LENGTH: 22
<212> TYPE: DNA
<213> ORGANISM: Artificial Sequence
<220> FEATURE:
<223> OTHER INFORMATION: Synthetic Probe

<400> SEQUENCE: 136
```
gtaatgcaac aaatccccac cc                                        22

<210> SEQ ID NO 137
<211> LENGTH: 21
<212> TYPE: DNA
<213> ORGANISM: Artificial Sequence
<220> FEATURE:
<223> OTHER INFORMATION: Synthetic Probe

<400> SEQUENCE: 137
ggggagcggg ggccctgcct t                                         21

<210> SEQ ID NO 138
<211> LENGTH: 25
<212> TYPE: DNA
<213> ORGANISM: Artificial Sequence
<220> FEATURE:
<223> OTHER INFORMATION: Synthetic Probe

<400> SEQUENCE: 138
cactcctagg aacagagagg ccatt                                     25

<210> SEQ ID NO 139
<211> LENGTH: 25
<212> TYPE: DNA
<213> ORGANISM: Artificial Sequence
<220> FEATURE:
<223> OTHER INFORMATION: Synthetic Probe

<400> SEQUENCE: 139
gcgtttccaa cgatgtgcag gctac                                     25

<210> SEQ ID NO 140
<211> LENGTH: 25
<212> TYPE: DNA
<213> ORGANISM: Artificial Sequence
<220> FEATURE:
<223> OTHER INFORMATION: Synthetic Probe

<400> SEQUENCE: 140
tttaattgga atgtcatcac agcag                                     25

<210> SEQ ID NO 141
<211> LENGTH: 25
<212> TYPE: DNA
<213> ORGANISM: Artificial Sequence
<220> FEATURE:
<223> OTHER INFORMATION: Synthetic Probe

<400> SEQUENCE: 141
gtcatcagcc gaacgagatt ccatg                                     25

<210> SEQ ID NO 142
<211> LENGTH: 25
<212> TYPE: DNA
<213> ORGANISM: Artificial Sequence
<220> FEATURE:
<223> OTHER INFORMATION: Synthetic Probe

<400> SEQUENCE: 142
gaaaatacct ttcagtcaca cattg                                     25

<210> SEQ ID NO 143
<211> LENGTH: 25
<212> TYPE: DNA

```
<213> ORGANISM: Artificial Sequence
<220> FEATURE:
<223> OTHER INFORMATION: Synthetic Probe

<400> SEQUENCE: 143
ttcctattag tgatttcatc agagc                                               25

<210> SEQ ID NO 144
<211> LENGTH: 25
<212> TYPE: DNA
<213> ORGANISM: Artificial Sequence
<220> FEATURE:
<223> OTHER INFORMATION: Synthetic Probe

<400> SEQUENCE: 144
ggagtagtct tcgtcagtta tcgct                                               25

<210> SEQ ID NO 145
<211> LENGTH: 25
<212> TYPE: DNA
<213> ORGANISM: Artificial Sequence
<220> FEATURE:
<223> OTHER INFORMATION: Synthetic Probe

<400> SEQUENCE: 145
gttatcgctt ctgacggcac ttcct                                               25

<210> SEQ ID NO 146
<211> LENGTH: 25
<212> TYPE: DNA
<213> ORGANISM: Artificial Sequence
<220> FEATURE:
<223> OTHER INFORMATION: Synthetic Probe

<400> SEQUENCE: 146
gagtatgcag cattaccgag ttgtc                                               25

<210> SEQ ID NO 147
<211> LENGTH: 25
<212> TYPE: DNA
<213> ORGANISM: Artificial Sequence
<220> FEATURE:
<223> OTHER INFORMATION: Synthetic Probe

<400> SEQUENCE: 147
gagtctcaac actcactagg tgaac                                               25

<210> SEQ ID NO 148
<211> LENGTH: 25
<212> TYPE: DNA
<213> ORGANISM: Artificial Sequence
<220> FEATURE:
<223> OTHER INFORMATION: Synthetic Probe

<400> SEQUENCE: 148
tgagaggcac tgatgtcccc ttgga                                               25

<210> SEQ ID NO 149
<211> LENGTH: 25
<212> TYPE: DNA
<213> ORGANISM: Artificial Sequence
<220> FEATURE:
<223> OTHER INFORMATION: Synthetic Probe

<400> SEQUENCE: 149
cagttcccca aaggccttag gcatg                                               25
```

<210> SEQ ID NO 150
<211> LENGTH: 23
<212> TYPE: DNA
<213> ORGANISM: Artificial Sequence
<220> FEATURE:
<223> OTHER INFORMATION: Synthetic Probe

<400> SEQUENCE: 150
ctacctgcac tgtaagcact ttt                                          23

<210> SEQ ID NO 151
<211> LENGTH: 24
<212> TYPE: DNA
<213> ORGANISM: Artificial Sequence
<220> FEATURE:
<223> OTHER INFORMATION: Synthetic Probe

<400> SEQUENCE: 151
actgcaggct ccagcttcca ggct                                         24

<210> SEQ ID NO 152
<211> LENGTH: 23
<212> TYPE: DNA
<213> ORGANISM: Artificial Sequence
<220> FEATURE:
<223> OTHER INFORMATION: Synthetic Probe

<400> SEQUENCE: 152
ctacctgcac tgtaagcact ttg                                          23

<210> SEQ ID NO 153
<211> LENGTH: 23
<212> TYPE: DNA
<213> ORGANISM: Artificial Sequence
<220> FEATURE:
<223> OTHER INFORMATION: Synthetic Probe

<400> SEQUENCE: 153
tcagttttgc atggatttgc aca                                          23

<210> SEQ ID NO 154
<211> LENGTH: 22
<212> TYPE: DNA
<213> ORGANISM: Artificial Sequence
<220> FEATURE:
<223> OTHER INFORMATION: Synthetic Probe

<400> SEQUENCE: 154
atggcagtgg agttagtgat tg                                           22

<210> SEQ ID NO 155
<211> LENGTH: 22
<212> TYPE: DNA
<213> ORGANISM: Artificial Sequence
<220> FEATURE:
<223> OTHER INFORMATION: Synthetic Probe

<400> SEQUENCE: 155
cctcaggcac ggccgggcca cc                                           22

<210> SEQ ID NO 156
<211> LENGTH: 22
<212> TYPE: DNA
<213> ORGANISM: Artificial Sequence
<220> FEATURE:

<223> OTHER INFORMATION: Synthetic Probe

<400> SEQUENCE: 156
acaggccggg acaagtgcaa ta                                    22

<210> SEQ ID NO 157
<211> LENGTH: 25
<212> TYPE: DNA
<213> ORGANISM: Artificial Sequence
<220> FEATURE:
<223> OTHER INFORMATION: Synthetic Probe

<400> SEQUENCE: 157
acccaacact catacgccgg cagtt                                 25

<210> SEQ ID NO 158
<211> LENGTH: 25
<212> TYPE: DNA
<213> ORGANISM: Artificial Sequence
<220> FEATURE:
<223> OTHER INFORMATION: Synthetic Probe

<400> SEQUENCE: 158
atacgccggc agttgtcatc attgg                                 25

<210> SEQ ID NO 159
<211> LENGTH: 25
<212> TYPE: DNA
<213> ORGANISM: Artificial Sequence
<220> FEATURE:
<223> OTHER INFORMATION: Synthetic Probe

<400> SEQUENCE: 159
tcagacttcc agacctgtat tcacc                                 25

<210> SEQ ID NO 160
<211> LENGTH: 25
<212> TYPE: DNA
<213> ORGANISM: Artificial Sequence
<220> FEATURE:
<223> OTHER INFORMATION: Synthetic Probe

<400> SEQUENCE: 160
tgtgactcat actccaccag tgctc                                 25

<210> SEQ ID NO 161
<211> LENGTH: 25
<212> TYPE: DNA
<213> ORGANISM: Artificial Sequence
<220> FEATURE:
<223> OTHER INFORMATION: Synthetic Probe

<400> SEQUENCE: 161
atcgtatgtg actcatactc cacca                                 25

<210> SEQ ID NO 162
<211> LENGTH: 25
<212> TYPE: DNA
<213> ORGANISM: Artificial Sequence
<220> FEATURE:
<223> OTHER INFORMATION: Synthetic Probe

<400> SEQUENCE: 162
cagacacgta gtattcatcg tccat                                 25

```
<210> SEQ ID NO 163
<211> LENGTH: 22
<212> TYPE: DNA
<213> ORGANISM: Artificial Sequence
<220> FEATURE:
<223> OTHER INFORMATION: Synthetic Probe

<400> SEQUENCE: 163
agctcccaag agcctaaccc gt                                              22

<210> SEQ ID NO 164
<211> LENGTH: 22
<212> TYPE: DNA
<213> ORGANISM: Artificial Sequence
<220> FEATURE:
<223> OTHER INFORMATION: Synthetic Probe

<400> SEQUENCE: 164
cccctctggt caaccagtca ca                                              22

<210> SEQ ID NO 165
<211> LENGTH: 22
<212> TYPE: DNA
<213> ORGANISM: Artificial Sequence
<220> FEATURE:
<223> OTHER INFORMATION: Synthetic Probe

<400> SEQUENCE: 165
tcatctcgcc cgcaaagacc ca                                              22

<210> SEQ ID NO 166
<211> LENGTH: 21
<212> TYPE: DNA
<213> ORGANISM: Artificial Sequence
<220> FEATURE:
<223> OTHER INFORMATION: Synthetic Probe

<400> SEQUENCE: 166
acagcccatc gactggtgtt g                                               21

<210> SEQ ID NO 167
<211> LENGTH: 22
<212> TYPE: DNA
<213> ORGANISM: Artificial Sequence
<220> FEATURE:
<223> OTHER INFORMATION: Synthetic Probe

<400> SEQUENCE: 167
acagttcttc aactggcagc tt                                              22

<210> SEQ ID NO 168
<211> LENGTH: 22
<212> TYPE: DNA
<213> ORGANISM: Artificial Sequence
<220> FEATURE:
<223> OTHER INFORMATION: Synthetic Probe

<400> SEQUENCE: 168
aagcggttta ccatcccaca ta                                              22

<210> SEQ ID NO 169
<211> LENGTH: 21
<212> TYPE: DNA
<213> ORGANISM: Artificial Sequence
<220> FEATURE:
<223> OTHER INFORMATION: Synthetic Probe
```

```
<400> SEQUENCE: 169
aactcctgta tgaagccgtt c                                              21

<210> SEQ ID NO 170
<211> LENGTH: 21
<212> TYPE: DNA
<213> ORGANISM: Artificial Sequence
<220> FEATURE:
<223> OTHER INFORMATION: Synthetic Probe

<400> SEQUENCE: 170
acgtggaatt ccctctatgt t                                              21

<210> SEQ ID NO 171
<211> LENGTH: 22
<212> TYPE: DNA
<213> ORGANISM: Artificial Sequence
<220> FEATURE:
<223> OTHER INFORMATION: Synthetic Probe

<400> SEQUENCE: 171
gaattcacca agggcaacct ct                                             22

<210> SEQ ID NO 172
<211> LENGTH: 21
<212> TYPE: DNA
<213> ORGANISM: Artificial Sequence
<220> FEATURE:
<223> OTHER INFORMATION: Synthetic Probe

<400> SEQUENCE: 172
cctacgttcc atagtctacc a                                              21

<210> SEQ ID NO 173
<211> LENGTH: 22
<212> TYPE: DNA
<213> ORGANISM: Artificial Sequence
<220> FEATURE:
<223> OTHER INFORMATION: Synthetic Probe

<400> SEQUENCE: 173
acagagagct tgcccttgta ta                                             22

<210> SEQ ID NO 174
<211> LENGTH: 22
<212> TYPE: DNA
<213> ORGANISM: Artificial Sequence
<220> FEATURE:
<223> OTHER INFORMATION: Synthetic Probe

<400> SEQUENCE: 174
cgaatccacc acgaacaact tc                                             22

<210> SEQ ID NO 175
<211> LENGTH: 23
<212> TYPE: DNA
<213> ORGANISM: Artificial Sequence
<220> FEATURE:
<223> OTHER INFORMATION: Synthetic Probe

<400> SEQUENCE: 175
atgcaaagtt gctcgggtaa cct                                            23

<210> SEQ ID NO 176
<211> LENGTH: 21
```

```
<212> TYPE: DNA
<213> ORGANISM: Artificial Sequence
<220> FEATURE:
<223> OTHER INFORMATION: Synthetic Probe

<400> SEQUENCE: 176
cgtacgctat acggtctact a                                              21

<210> SEQ ID NO 177
<211> LENGTH: 21
<212> TYPE: DNA
<213> ORGANISM: Artificial Sequence
<220> FEATURE:
<223> OTHER INFORMATION: Synthetic Probe

<400> SEQUENCE: 177
tgcatgacgg cctgcaagac a                                              21

<210> SEQ ID NO 178
<211> LENGTH: 21
<212> TYPE: DNA
<213> ORGANISM: Artificial Sequence
<220> FEATURE:
<223> OTHER INFORMATION: Synthetic Probe

<400> SEQUENCE: 178
gtgtatatgc ccatggactg c                                              21

<210> SEQ ID NO 179
<211> LENGTH: 22
<212> TYPE: DNA
<213> ORGANISM: Artificial Sequence
<220> FEATURE:
<223> OTHER INFORMATION: Synthetic Probe

<400> SEQUENCE: 179
gaattcatca cggccagcct ct                                             22

<210> SEQ ID NO 180
<211> LENGTH: 22
<212> TYPE: DNA
<213> ORGANISM: Artificial Sequence
<220> FEATURE:
<223> OTHER INFORMATION: Synthetic Probe

<400> SEQUENCE: 180
cctggcacac agtagacctt ca                                             22

<210> SEQ ID NO 181
<211> LENGTH: 22
<212> TYPE: DNA
<213> ORGANISM: Artificial Sequence
<220> FEATURE:
<223> OTHER INFORMATION: Synthetic Probe

<400> SEQUENCE: 181
gaggtttccc gtgtatgttt ca                                             22

<210> SEQ ID NO 182
<211> LENGTH: 22
<212> TYPE: DNA
<213> ORGANISM: Artificial Sequence
<220> FEATURE:
<223> OTHER INFORMATION: Synthetic Probe

<400> SEQUENCE: 182
```
aagaagtgca ccgcgaatgt tt        22

<210> SEQ ID NO 183
<211> LENGTH: 25
<212> TYPE: DNA
<213> ORGANISM: Artificial Sequence
<220> FEATURE:
<223> OTHER INFORMATION: Synthetic Probe

<400> SEQUENCE: 183
gcgaatgttt tggaccattc atcat        25

<210> SEQ ID NO 184
<211> LENGTH: 25
<212> TYPE: DNA
<213> ORGANISM: Artificial Sequence
<220> FEATURE:
<223> OTHER INFORMATION: Synthetic Probe

<400> SEQUENCE: 184
aaggaaggtg ttgccatcat tagcc        25

<210> SEQ ID NO 185
<211> LENGTH: 25
<212> TYPE: DNA
<213> ORGANISM: Artificial Sequence
<220> FEATURE:
<223> OTHER INFORMATION: Synthetic Probe

<400> SEQUENCE: 185
aggccgtaca gcgattccgg agaat        25

<210> SEQ ID NO 186
<211> LENGTH: 25
<212> TYPE: DNA
<213> ORGANISM: Artificial Sequence
<220> FEATURE:
<223> OTHER INFORMATION: Synthetic Probe

<400> SEQUENCE: 186
gtctgtgaaa aggtcctcat catag        25

<210> SEQ ID NO 187
<211> LENGTH: 25
<212> TYPE: DNA
<213> ORGANISM: Artificial Sequence
<220> FEATURE:
<223> OTHER INFORMATION: Synthetic Probe

<400> SEQUENCE: 187
tccactaatc catcagaaag agaga        25

<210> SEQ ID NO 188
<211> LENGTH: 25
<212> TYPE: DNA
<213> ORGANISM: Artificial Sequence
<220> FEATURE:
<223> OTHER INFORMATION: Synthetic Probe

<400> SEQUENCE: 188
acttttgtac ctcacagaac atcag        25

<210> SEQ ID NO 189
<211> LENGTH: 25
<212> TYPE: DNA
<213> ORGANISM: Artificial Sequence

```
<220> FEATURE:
<223> OTHER INFORMATION: Synthetic Probe

<400> SEQUENCE: 189
ttctcaggtg ttcatgtatt ttcac                                              25

<210> SEQ ID NO 190
<211> LENGTH: 25
<212> TYPE: DNA
<213> ORGANISM: Artificial Sequence
<220> FEATURE:
<223> OTHER INFORMATION: Synthetic Probe

<400> SEQUENCE: 190
cagctcagaa aataccttc agtca                                               25

<210> SEQ ID NO 191
<211> LENGTH: 25
<212> TYPE: DNA
<213> ORGANISM: Artificial Sequence
<220> FEATURE:
<223> OTHER INFORMATION: Synthetic Probe

<400> SEQUENCE: 191
ttcatcatta ctctcagatg tccct                                              25

<210> SEQ ID NO 192
<211> LENGTH: 23
<212> TYPE: DNA
<213> ORGANISM: Artificial Sequence
<220> FEATURE:
<223> OTHER INFORMATION: Synthetic Probe

<400> SEQUENCE: 192
agcattgcaa ccgatcccaa cct                                                23

<210> SEQ ID NO 193
<211> LENGTH: 25
<212> TYPE: DNA
<213> ORGANISM: Artificial Sequence
<220> FEATURE:
<223> OTHER INFORMATION: Synthetic Probe

<400> SEQUENCE: 193
tcttgtaatt ccttcccaca gatct                                              25

<210> SEQ ID NO 194
<211> LENGTH: 25
<212> TYPE: DNA
<213> ORGANISM: Artificial Sequence
<220> FEATURE:
<223> OTHER INFORMATION: Synthetic Probe

<400> SEQUENCE: 194
tggggtaggt ttactctacc tcctc                                              25

<210> SEQ ID NO 195
<211> LENGTH: 25
<212> TYPE: DNA
<213> ORGANISM: Artificial Sequence
<220> FEATURE:
<223> OTHER INFORMATION: Synthetic Probe

<400> SEQUENCE: 195
aatgcatagg gtcaccgcag accca                                              25
```

```
<210> SEQ ID NO 196
<211> LENGTH: 25
<212> TYPE: DNA
<213> ORGANISM: Artificial Sequence
<220> FEATURE:
<223> OTHER INFORMATION: Synthetic Probe

<400> SEQUENCE: 196
atagggtcac cgcagaccca agcac                                              25

<210> SEQ ID NO 197
<211> LENGTH: 25
<212> TYPE: DNA
<213> ORGANISM: Artificial Sequence
<220> FEATURE:
<223> OTHER INFORMATION: Synthetic Probe

<400> SEQUENCE: 197
accgtgtcct cagtggcagt cggag                                              25

<210> SEQ ID NO 198
<211> LENGTH: 25
<212> TYPE: DNA
<213> ORGANISM: Artificial Sequence
<220> FEATURE:
<223> OTHER INFORMATION: Synthetic Probe

<400> SEQUENCE: 198
acagcgattc cggagaatgt catca                                              25

<210> SEQ ID NO 199
<211> LENGTH: 25
<212> TYPE: DNA
<213> ORGANISM: Artificial Sequence
<220> FEATURE:
<223> OTHER INFORMATION: Synthetic Probe

<400> SEQUENCE: 199
gtaaatcctt taatccatca cagca                                              25

<210> SEQ ID NO 200
<211> LENGTH: 25
<212> TYPE: DNA
<213> ORGANISM: Artificial Sequence
<220> FEATURE:
<223> OTHER INFORMATION: Synthetic Probe

<400> SEQUENCE: 200
gtgattgcac tcaggggatt gacag                                              25

<210> SEQ ID NO 201
<211> LENGTH: 25
<212> TYPE: DNA
<213> ORGANISM: Artificial Sequence
<220> FEATURE:
<223> OTHER INFORMATION: Synthetic Probe

<400> SEQUENCE: 201
gcgtcagcag tctaacacgt gcttt                                              25

<210> SEQ ID NO 202
<211> LENGTH: 25
<212> TYPE: DNA
<213> ORGANISM: Artificial Sequence
<220> FEATURE:
<223> OTHER INFORMATION: Synthetic Probe
```

```
<400> SEQUENCE: 202
tgtcattttg tgttcatcat ggagt                                              25

<210> SEQ ID NO 203
<211> LENGTH: 25
<212> TYPE: DNA
<213> ORGANISM: Artificial Sequence
<220> FEATURE:
<223> OTHER INFORMATION: Synthetic Probe

<400> SEQUENCE: 203
gagctagttt gattcatcat agaaa                                              25

<210> SEQ ID NO 204
<211> LENGTH: 25
<212> TYPE: DNA
<213> ORGANISM: Artificial Sequence
<220> FEATURE:
<223> OTHER INFORMATION: Synthetic Probe

<400> SEQUENCE: 204
cagccgaacg agattccatg taagt                                              25

<210> SEQ ID NO 205
<211> LENGTH: 25
<212> TYPE: DNA
<213> ORGANISM: Artificial Sequence
<220> FEATURE:
<223> OTHER INFORMATION: Synthetic Probe

<400> SEQUENCE: 205
gctcagaaaa tacctttcag tcaca                                              25

<210> SEQ ID NO 206
<211> LENGTH: 25
<212> TYPE: DNA
<213> ORGANISM: Artificial Sequence
<220> FEATURE:
<223> OTHER INFORMATION: Synthetic Probe

<400> SEQUENCE: 206
cctttcagtc acacattgat cagac                                              25

<210> SEQ ID NO 207
<211> LENGTH: 25
<212> TYPE: DNA
<213> ORGANISM: Artificial Sequence
<220> FEATURE:
<223> OTHER INFORMATION: Synthetic Probe

<400> SEQUENCE: 207
tctctctccc ttcagtagca gaact                                              25

<210> SEQ ID NO 208
<211> LENGTH: 25
<212> TYPE: DNA
<213> ORGANISM: Artificial Sequence
<220> FEATURE:
<223> OTHER INFORMATION: Synthetic Probe

<400> SEQUENCE: 208
ttccccaccg cgcactcggg agtat                                              25

<210> SEQ ID NO 209
```

```
<211> LENGTH: 25
<212> TYPE: DNA
<213> ORGANISM: Artificial Sequence
<220> FEATURE:
<223> OTHER INFORMATION: Synthetic Probe

<400> SEQUENCE: 209
ccaccgcgca ctcgggagta tgcag                                25

<210> SEQ ID NO 210
<211> LENGTH: 25
<212> TYPE: DNA
<213> ORGANISM: Artificial Sequence
<220> FEATURE:
<223> OTHER INFORMATION: Synthetic Probe

<400> SEQUENCE: 210
acccagagtc tcaacactca ctagg                                25

<210> SEQ ID NO 211
<211> LENGTH: 25
<212> TYPE: DNA
<213> ORGANISM: Artificial Sequence
<220> FEATURE:
<223> OTHER INFORMATION: Synthetic Probe

<400> SEQUENCE: 211
cactaggtga actgctgttg acgaa                                25

<210> SEQ ID NO 212
<211> LENGTH: 25
<212> TYPE: DNA
<213> ORGANISM: Artificial Sequence
<220> FEATURE:
<223> OTHER INFORMATION: Synthetic Probe

<400> SEQUENCE: 212
ttctacaagg tcaggctcag acagt                                25

<210> SEQ ID NO 213
<211> LENGTH: 25
<212> TYPE: DNA
<213> ORGANISM: Artificial Sequence
<220> FEATURE:
<223> OTHER INFORMATION: Synthetic Probe

<400> SEQUENCE: 213
tacgaggtgt cagaagtcaa agcaa                                25

<210> SEQ ID NO 214
<211> LENGTH: 19
<212> TYPE: DNA
<213> ORGANISM: Artificial Sequence
<220> FEATURE:
<223> OTHER INFORMATION: Synthetic Probe

<400> SEQUENCE: 214
cctgctccaa aaatccatt                                       19

<210> SEQ ID NO 215
<211> LENGTH: 21
<212> TYPE: DNA
<213> ORGANISM: Artificial Sequence
<220> FEATURE:
<223> OTHER INFORMATION: Synthetic Probe

<400> SEQUENCE: 215
```
agtagtgctt tctactttat g                                         21

<210> SEQ ID NO 216
<211> LENGTH: 22
<212> TYPE: DNA
<213> ORGANISM: Artificial Sequence
<220> FEATURE:
<223> OTHER INFORMATION: Synthetic Probe

<400> SEQUENCE: 216
ctacaagtgc cttcactgca gt                                        22

<210> SEQ ID NO 217
<211> LENGTH: 23
<212> TYPE: DNA
<213> ORGANISM: Artificial Sequence
<220> FEATURE:
<223> OTHER INFORMATION: Synthetic Probe

<400> SEQUENCE: 217
tcagttttgc atagatttgc aca                                       23

<210> SEQ ID NO 218
<211> LENGTH: 23
<212> TYPE: DNA
<213> ORGANISM: Artificial Sequence
<220> FEATURE:
<223> OTHER INFORMATION: Synthetic Probe

<400> SEQUENCE: 218
ctacctgcac tataagcact tta                                       23

<210> SEQ ID NO 219
<211> LENGTH: 23
<212> TYPE: DNA
<213> ORGANISM: Artificial Sequence
<220> FEATURE:
<223> OTHER INFORMATION: Synthetic Probe

<400> SEQUENCE: 219
tctctgcagg ccgtgtgctt tgc                                       23

<210> SEQ ID NO 220
<211> LENGTH: 23
<212> TYPE: DNA
<213> ORGANISM: Artificial Sequence
<220> FEATURE:
<223> OTHER INFORMATION: Synthetic Probe

<400> SEQUENCE: 220
agaggcaggc atgcgggcag aca                                       23

<210> SEQ ID NO 221
<211> LENGTH: 21
<212> TYPE: DNA
<213> ORGANISM: Artificial Sequence
<220> FEATURE:
<223> OTHER INFORMATION: Synthetic Probe

<400> SEQUENCE: 221
agacacacca cggcacactt c                                         21

<210> SEQ ID NO 222
<211> LENGTH: 21
<212> TYPE: DNA

```
<213> ORGANISM: Artificial Sequence
<220> FEATURE:
<223> OTHER INFORMATION: Synthetic Probe

<400> SEQUENCE: 222
gaaggaagtg agtgcagcca c                                          21

<210> SEQ ID NO 223
<211> LENGTH: 25
<212> TYPE: DNA
<213> ORGANISM: Artificial Sequence
<220> FEATURE:
<223> OTHER INFORMATION: Synthetic Probe

<400> SEQUENCE: 223
ttctgggcgg gtctgtcgtg catta                                      25

<210> SEQ ID NO 224
<211> LENGTH: 25
<212> TYPE: DNA
<213> ORGANISM: Artificial Sequence
<220> FEATURE:
<223> OTHER INFORMATION: Synthetic Probe

<400> SEQUENCE: 224
tcactgtcct cttcatctcc ctgct                                      25

<210> SEQ ID NO 225
<211> LENGTH: 25
<212> TYPE: DNA
<213> ORGANISM: Artificial Sequence
<220> FEATURE:
<223> OTHER INFORMATION: Synthetic Probe

<400> SEQUENCE: 225
agacgggtaa tgtgcccacg tcgta                                      25

<210> SEQ ID NO 226
<211> LENGTH: 25
<212> TYPE: DNA
<213> ORGANISM: Artificial Sequence
<220> FEATURE:
<223> OTHER INFORMATION: Synthetic Probe

<400> SEQUENCE: 226
cgcacttcaa ggttgaattc agtga                                      25

<210> SEQ ID NO 227
<211> LENGTH: 25
<212> TYPE: DNA
<213> ORGANISM: Artificial Sequence
<220> FEATURE:
<223> OTHER INFORMATION: Synthetic Probe

<400> SEQUENCE: 227
gcctcagatg caatgctgac cacat                                      25

<210> SEQ ID NO 228
<211> LENGTH: 25
<212> TYPE: DNA
<213> ORGANISM: Artificial Sequence
<220> FEATURE:
<223> OTHER INFORMATION: Synthetic Probe

<400> SEQUENCE: 228
acctttgtct acatgctcat ttcag                                      25
```

<210> SEQ ID NO 229
<211> LENGTH: 25
<212> TYPE: DNA
<213> ORGANISM: Artificial Sequence
<220> FEATURE:
<223> OTHER INFORMATION: Synthetic Probe

<400> SEQUENCE: 229
ctaatctgcc ctccggagga ggaac                                         25

<210> SEQ ID NO 230
<211> LENGTH: 22
<212> TYPE: DNA
<213> ORGANISM: Artificial Sequence
<220> FEATURE:
<223> OTHER INFORMATION: Synthetic Probe

<400> SEQUENCE: 230
cagataacag cagccccact gg                                            22

<210> SEQ ID NO 231
<211> LENGTH: 22
<212> TYPE: DNA
<213> ORGANISM: Artificial Sequence
<220> FEATURE:
<223> OTHER INFORMATION: Synthetic Probe

<400> SEQUENCE: 231
ccaaacactg ctgggtaaga cg                                            22

<210> SEQ ID NO 232
<211> LENGTH: 22
<212> TYPE: DNA
<213> ORGANISM: Artificial Sequence
<220> FEATURE:
<223> OTHER INFORMATION: Synthetic Probe

<400> SEQUENCE: 232
agcaaggcag tagcttgcgc ag                                            22

<210> SEQ ID NO 233
<211> LENGTH: 22
<212> TYPE: DNA
<213> ORGANISM: Artificial Sequence
<220> FEATURE:
<223> OTHER INFORMATION: Synthetic Probe

<400> SEQUENCE: 233
caacaaaatc actgatgctg ga                                            22

<210> SEQ ID NO 234
<211> LENGTH: 22
<212> TYPE: DNA
<213> ORGANISM: Artificial Sequence
<220> FEATURE:
<223> OTHER INFORMATION: Synthetic Probe

<400> SEQUENCE: 234
acaaccagct aagacactgc ca                                            22

<210> SEQ ID NO 235
<211> LENGTH: 20
<212> TYPE: DNA
<213> ORGANISM: Artificial Sequence
<220> FEATURE:

<223> OTHER INFORMATION: Synthetic Probe

<400> SEQUENCE: 235
ccagcagcac ctggggcagt                                            20

<210> SEQ ID NO 236
<211> LENGTH: 20
<212> TYPE: DNA
<213> ORGANISM: Artificial Sequence
<220> FEATURE:
<223> OTHER INFORMATION: Synthetic Probe

<400> SEQUENCE: 236
agtgccccca cagtttgagt                                            20

<210> SEQ ID NO 237
<211> LENGTH: 25
<212> TYPE: DNA
<213> ORGANISM: Artificial Sequence
<220> FEATURE:
<223> OTHER INFORMATION: Synthetic Probe

<400> SEQUENCE: 237
atacccactt tctgttttgc taaga                                      25

<210> SEQ ID NO 238
<211> LENGTH: 25
<212> TYPE: DNA
<213> ORGANISM: Artificial Sequence
<220> FEATURE:
<223> OTHER INFORMATION: Synthetic Probe

<400> SEQUENCE: 238
gggcacggat caaaagccaa gctgg                                      25

<210> SEQ ID NO 239
<211> LENGTH: 25
<212> TYPE: DNA
<213> ORGANISM: Artificial Sequence
<220> FEATURE:
<223> OTHER INFORMATION: Synthetic Probe

<400> SEQUENCE: 239
gcgattccgg agaatgtcat cacgc                                      25

<210> SEQ ID NO 240
<211> LENGTH: 25
<212> TYPE: DNA
<213> ORGANISM: Artificial Sequence
<220> FEATURE:
<223> OTHER INFORMATION: Synthetic Probe

<400> SEQUENCE: 240
gagggagcca gttgtcatca tgtac                                      25

<210> SEQ ID NO 241
<211> LENGTH: 25
<212> TYPE: DNA
<213> ORGANISM: Artificial Sequence
<220> FEATURE:
<223> OTHER INFORMATION: Synthetic Probe

<400> SEQUENCE: 241
cgggagtatg cagcattacc gagtt                                      25

-continued

```
<210> SEQ ID NO 242
<211> LENGTH: 25
<212> TYPE: DNA
<213> ORGANISM: Artificial Sequence
<220> FEATURE:
<223> OTHER INFORMATION: Synthetic Probe

<400> SEQUENCE: 242
accatcagag cggttggcat tcatc                                            25

<210> SEQ ID NO 243
<211> LENGTH: 25
<212> TYPE: DNA
<213> ORGANISM: Artificial Sequence
<220> FEATURE:
<223> OTHER INFORMATION: Synthetic Probe

<400> SEQUENCE: 243
atgggtgcct ctgccaggct tgctt                                            25

<210> SEQ ID NO 244
<211> LENGTH: 25
<212> TYPE: DNA
<213> ORGANISM: Artificial Sequence
<220> FEATURE:
<223> OTHER INFORMATION: Synthetic Probe

<400> SEQUENCE: 244
acatccaagg aaggtgttgc catca                                            25

<210> SEQ ID NO 245
<211> LENGTH: 25
<212> TYPE: DNA
<213> ORGANISM: Artificial Sequence
<220> FEATURE:
<223> OTHER INFORMATION: Synthetic Probe

<400> SEQUENCE: 245
tgcctacaca ggcagggcag gcacc                                            25

<210> SEQ ID NO 246
<211> LENGTH: 25
<212> TYPE: DNA
<213> ORGANISM: Artificial Sequence
<220> FEATURE:
<223> OTHER INFORMATION: Synthetic Probe

<400> SEQUENCE: 246
gtttcctcat ggcagttcag tagag                                            25

<210> SEQ ID NO 247
<211> LENGTH: 25
<212> TYPE: DNA
<213> ORGANISM: Artificial Sequence
<220> FEATURE:
<223> OTHER INFORMATION: Synthetic Probe

<400> SEQUENCE: 247
atcctcagac aattattctc atcat                                            25

<210> SEQ ID NO 248
<211> LENGTH: 25
<212> TYPE: DNA
<213> ORGANISM: Artificial Sequence
<220> FEATURE:
<223> OTHER INFORMATION: Synthetic Probe
```

<400> SEQUENCE: 248
tgcactcagg ggattgacag atttg                                25

<210> SEQ ID NO 249
<211> LENGTH: 25
<212> TYPE: DNA
<213> ORGANISM: Artificial Sequence
<220> FEATURE:
<223> OTHER INFORMATION: Synthetic Probe

<400> SEQUENCE: 249
tccaaggaac ccacgtatgg aagtc                                25

<210> SEQ ID NO 250
<211> LENGTH: 25
<212> TYPE: DNA
<213> ORGANISM: Artificial Sequence
<220> FEATURE:
<223> OTHER INFORMATION: Synthetic Probe

<400> SEQUENCE: 250
aaggaatgca tgtattgagg tcatc                                25

<210> SEQ ID NO 251
<211> LENGTH: 25
<212> TYPE: DNA
<213> ORGANISM: Artificial Sequence
<220> FEATURE:
<223> OTHER INFORMATION: Synthetic Probe

<400> SEQUENCE: 251
tccatttttt ttatagtcat catcg                                25

<210> SEQ ID NO 252
<211> LENGTH: 25
<212> TYPE: DNA
<213> ORGANISM: Artificial Sequence
<220> FEATURE:
<223> OTHER INFORMATION: Synthetic Probe

<400> SEQUENCE: 252
acctcagttc cgatgagaat gacgg                                25

<210> SEQ ID NO 253
<211> LENGTH: 25
<212> TYPE: DNA
<213> ORGANISM: Artificial Sequence
<220> FEATURE:
<223> OTHER INFORMATION: Synthetic Probe

<400> SEQUENCE: 253 tgttttttt ggaggactca tcatc                                 25

<210> SEQ ID NO 254
<211> LENGTH: 25
<212> TYPE: DNA
<213> ORGANISM: Artificial Sequence
<220> FEATURE:
<223> OTHER INFORMATION: Synthetic Probe

<400> SEQUENCE: 254
ggcccagctt catcttcaac gttgt                                25

<210> SEQ ID NO 255
<211> LENGTH: 25

```
<212> TYPE: DNA
<213> ORGANISM: Artificial Sequence
<220> FEATURE:
<223> OTHER INFORMATION: Synthetic Probe

<400> SEQUENCE: 255
gtcatctcat ggtcgggaaa ctcga                                          25

<210> SEQ ID NO 256
<211> LENGTH: 25
<212> TYPE: DNA
<213> ORGANISM: Artificial Sequence
<220> FEATURE:
<223> OTHER INFORMATION: Synthetic Probe

<400> SEQUENCE: 256
taggtagttg cggaacatca tggac                                          25

<210> SEQ ID NO 257
<211> LENGTH: 25
<212> TYPE: DNA
<213> ORGANISM: Artificial Sequence
<220> FEATURE:
<223> OTHER INFORMATION: Synthetic Probe

<400> SEQUENCE: 257
atcagttcca catcaacagt cacag                                          25

<210> SEQ ID NO 258
<211> LENGTH: 25
<212> TYPE: DNA
<213> ORGANISM: Artificial Sequence
<220> FEATURE:
<223> OTHER INFORMATION: Synthetic Probe

<400> SEQUENCE: 258
gttttgacat catgaccagc atcgg                                          25

<210> SEQ ID NO 259
<211> LENGTH: 25
<212> TYPE: DNA
<213> ORGANISM: Artificial Sequence
<220> FEATURE:
<223> OTHER INFORMATION: Synthetic Probe

<400> SEQUENCE: 259
tatgcagcat taccgagttg tcatc                                          25

<210> SEQ ID NO 260
<211> LENGTH: 25
<212> TYPE: DNA
<213> ORGANISM: Artificial Sequence
<220> FEATURE:
<223> OTHER INFORMATION: Synthetic Probe

<400> SEQUENCE: 260
gctcagctct ccaaggttgg cttcc                                          25

<210> SEQ ID NO 261
<211> LENGTH: 25
<212> TYPE: DNA
<213> ORGANISM: Artificial Sequence
<220> FEATURE:
<223> OTHER INFORMATION: Synthetic Probe

<400> SEQUENCE: 261
```
agacccagag tctcaacact cacta            25

<210> SEQ ID NO 262
<211> LENGTH: 25
<212> TYPE: DNA
<213> ORGANISM: Artificial Sequence
<220> FEATURE:
<223> OTHER INFORMATION: Synthetic Probe

<400> SEQUENCE: 262
ttttgcctcc attctacaag gtcag            25

<210> SEQ ID NO 263
<211> LENGTH: 25
<212> TYPE: DNA
<213> ORGANISM: Artificial Sequence
<220> FEATURE:
<223> OTHER INFORMATION: Synthetic Probe

<400> SEQUENCE: 263
gttgtggaac ctccaaattc acttt            25

<210> SEQ ID NO 264
<211> LENGTH: 25
<212> TYPE: DNA
<213> ORGANISM: Artificial Sequence
<220> FEATURE:
<223> OTHER INFORMATION: Synthetic Probe

<400> SEQUENCE: 264
agagcggttg gcattcatca ttact            25

<210> SEQ ID NO 265
<211> LENGTH: 25
<212> TYPE: DNA
<213> ORGANISM: Artificial Sequence
<220> FEATURE:
<223> OTHER INFORMATION: Synthetic Probe

<400> SEQUENCE: 265
atgctcattt caggtcagac atttg            25

<210> SEQ ID NO 266
<211> LENGTH: 25
<212> TYPE: DNA
<213> ORGANISM: Artificial Sequence
<220> FEATURE:
<223> OTHER INFORMATION: Synthetic Probe

<400> SEQUENCE: 266
cttcagtgtt acctttgtct acatg            25

<210> SEQ ID NO 267
<211> LENGTH: 25
<212> TYPE: DNA
<213> ORGANISM: Artificial Sequence
<220> FEATURE:
<223> OTHER INFORMATION: Synthetic Probe

<400> SEQUENCE: 267
tgaggtgctc ctgtttcaaa taaac            25

<210> SEQ ID NO 268
<211> LENGTH: 25
<212> TYPE: DNA
<213> ORGANISM: Artificial Sequence

```
<220> FEATURE:
<223> OTHER INFORMATION: Synthetic Probe

<400> SEQUENCE: 268
agcctctgga tttcagcacc gacac                                              25

<210> SEQ ID NO 269
<211> LENGTH: 25
<212> TYPE: DNA
<213> ORGANISM: Artificial Sequence
<220> FEATURE:
<223> OTHER INFORMATION: Synthetic Probe

<400> SEQUENCE: 269
agtgggaccg acagcagaat ccttt                                              25

<210> SEQ ID NO 270
<211> LENGTH: 21
<212> TYPE: DNA
<213> ORGANISM: Artificial Sequence
<220> FEATURE:
<223> OTHER INFORMATION: Synthetic Probe

<400> SEQUENCE: 270
tcccagcaca catttagctc a                                                  21

<210> SEQ ID NO 271
<211> LENGTH: 22
<212> TYPE: DNA
<213> ORGANISM: Artificial Sequence
<220> FEATURE:
<223> OTHER INFORMATION: Synthetic Probe

<400> SEQUENCE: 271
agaggcaggg tagtgtaatg ga                                                 22

<210> SEQ ID NO 272
<211> LENGTH: 23
<212> TYPE: DNA
<213> ORGANISM: Artificial Sequence
<220> FEATURE:
<223> OTHER INFORMATION: Synthetic Probe

<400> SEQUENCE: 272
cggctctgtc gtcgaggcgc tca                                                23

<210> SEQ ID NO 273
<211> LENGTH: 23
<212> TYPE: DNA
<213> ORGANISM: Artificial Sequence
<220> FEATURE:
<223> OTHER INFORMATION: Synthetic Probe

<400> SEQUENCE: 273
cgtgagctcc tggaggacag gga                                                23

<210> SEQ ID NO 274
<211> LENGTH: 18
<212> TYPE: DNA
<213> ORGANISM: Artificial Sequence
<220> FEATURE:
<223> OTHER INFORMATION: Synthetic Probe

<400> SEQUENCE: 274
ccactgaacc acccatgc                                                      18
```

<210> SEQ ID NO 275
<211> LENGTH: 22
<212> TYPE: DNA
<213> ORGANISM: Artificial Sequence
<220> FEATURE:
<223> OTHER INFORMATION: Synthetic Probe

<400> SEQUENCE: 275
acaaagttct gtagtgcact ga                                              22

<210> SEQ ID NO 276
<211> LENGTH: 21
<212> TYPE: DNA
<213> ORGANISM: Artificial Sequence
<220> FEATURE:
<223> OTHER INFORMATION: Synthetic Probe

<400> SEQUENCE: 276
ccaagttctg tcatgcactg a                                               21

<210> SEQ ID NO 277
<211> LENGTH: 22
<212> TYPE: DNA
<213> ORGANISM: Artificial Sequence
<220> FEATURE:
<223> OTHER INFORMATION: Synthetic Probe

<400> SEQUENCE: 277
agggcagtat acttgctgat tg                                              22

<210> SEQ ID NO 278
<211> LENGTH: 25
<212> TYPE: DNA
<213> ORGANISM: Artificial Sequence
<220> FEATURE:
<223> OTHER INFORMATION: Synthetic Probe

<400> SEQUENCE: 278
catggtgtct cagtggccca gacac                                           25

<210> SEQ ID NO 279
<211> LENGTH: 25
<212> TYPE: DNA
<213> ORGANISM: Artificial Sequence
<220> FEATURE:
<223> OTHER INFORMATION: Synthetic Probe

<400> SEQUENCE: 279
agttccatca tggtgtctca gtggc                                           25

<210> SEQ ID NO 280
<211> LENGTH: 25
<212> TYPE: DNA
<213> ORGANISM: Artificial Sequence
<220> FEATURE:
<223> OTHER INFORMATION: Synthetic Probe

<400> SEQUENCE: 280
gtatgcagca ttaccgagtt gtcat                                           25

<210> SEQ ID NO 281
<211> LENGTH: 21
<212> TYPE: DNA
<213> ORGANISM: Artificial Sequence
<220> FEATURE:
<223> OTHER INFORMATION: Synthetic Probe -continued

<400> SEQUENCE: 281
ctcccccact gcagctggca c                                         21

<210> SEQ ID NO 282
<211> LENGTH: 22
<212> TYPE: DNA
<213> ORGANISM: Artificial Sequence
<220> FEATURE:
<223> OTHER INFORMATION: Synthetic Probe

<400> SEQUENCE: 282
agtcggagtg tctcagaact tt                                        22

<210> SEQ ID NO 283
<211> LENGTH: 22
<212> TYPE: DNA
<213> ORGANISM: Artificial Sequence
<220> FEATURE:
<223> OTHER INFORMATION: Synthetic Probe

<400> SEQUENCE: 283
acccttatca gttctccgtc ca                                        22

<210> SEQ ID NO 284
<211> LENGTH: 23
<212> TYPE: DNA
<213> ORGANISM: Artificial Sequence
<220> FEATURE:
<223> OTHER INFORMATION: Synthetic Probe

<400> SEQUENCE: 284
cagctgcttt tgggattccg ttg                                       23

<210> SEQ ID NO 285
<211> LENGTH: 22
<212> TYPE: DNA
<213> ORGANISM: Artificial Sequence
<220> FEATURE:
<223> OTHER INFORMATION: Synthetic Probe

<400> SEQUENCE: 285
gggcggacac gacattcccg at                                        22

<210> SEQ ID NO 286
<211> LENGTH: 23
<212> TYPE: DNA
<213> ORGANISM: Artificial Sequence
<220> FEATURE:
<223> OTHER INFORMATION: Synthetic Probe

<400> SEQUENCE: 286
tcaacgggag tgatcgtgtc att                                       23

<210> SEQ ID NO 287
<211> LENGTH: 22
<212> TYPE: DNA
<213> ORGANISM: Artificial Sequence
<220> FEATURE:
<223> OTHER INFORMATION: Synthetic Probe

<400> SEQUENCE: 287
accagctaac aatacactgc ca                                        22

<210> SEQ ID NO 288

```
<211> LENGTH: 22
<212> TYPE: DNA
<213> ORGANISM: Artificial Sequence
<220> FEATURE:
<223> OTHER INFORMATION: Synthetic Probe

<400> SEQUENCE: 288
gccagctaac aatacactgc ct                                              22

<210> SEQ ID NO 289
<211> LENGTH: 21
<212> TYPE: DNA
<213> ORGANISM: Artificial Sequence
<220> FEATURE:
<223> OTHER INFORMATION: Synthetic Probe

<400> SEQUENCE: 289
ctgaaaccaa gtatgggtcg c                                               21

<210> SEQ ID NO 290
<211> LENGTH: 25
<212> TYPE: DNA
<213> ORGANISM: Artificial Sequence
<220> FEATURE:
<223> OTHER INFORMATION: Synthetic Probe

<400> SEQUENCE: 290
gctgagcaat gcctggctgg tgcct                                           25

<210> SEQ ID NO 291
<211> LENGTH: 20
<212> TYPE: DNA
<213> ORGANISM: Artificial Sequence
<220> FEATURE:
<223> OTHER INFORMATION: Synthetic Probe

<400> SEQUENCE: 291
ccctgcgcca tctcctctac                                                 20

<210> SEQ ID NO 292
<211> LENGTH: 25
<212> TYPE: DNA
<213> ORGANISM: Artificial Sequence
<220> FEATURE:
<223> OTHER INFORMATION: Synthetic Probe

<400> SEQUENCE: 292
atccaaggaa ggtagttgcc aacac                                           25

<210> SEQ ID NO 293
<211> LENGTH: 25
<212> TYPE: DNA
<213> ORGANISM: Artificial Sequence
<220> FEATURE:
<223> OTHER INFORMATION: Synthetic Probe

<400> SEQUENCE: 293
gtgtctcagt ggcccagaca cgtgg                                           25

<210> SEQ ID NO 294
<211> LENGTH: 22
<212> TYPE: DNA
<213> ORGANISM: Artificial Sequence
<220> FEATURE:
<223> OTHER INFORMATION: Synthetic Probe

<400> SEQUENCE: 294
```
cccaacaaca tgaaactacc ta                                                    22

<210> SEQ ID NO 295
<211> LENGTH: 22
<212> TYPE: DNA
<213> ORGANISM: Artificial Sequence
<220> FEATURE:
<223> OTHER INFORMATION: Synthetic Probe

<400> SEQUENCE: 295
cagactccgg tggaatgaag ga                                                    22

<210> SEQ ID NO 296
<211> LENGTH: 22
<212> TYPE: DNA
<213> ORGANISM: Artificial Sequence
<220> FEATURE:
<223> OTHER INFORMATION: Synthetic Probe

<400> SEQUENCE: 296
gaacaccagg agaaatcggt ca                                                    22

<210> SEQ ID NO 297
<211> LENGTH: 22
<212> TYPE: DNA
<213> ORGANISM: Artificial Sequence
<220> FEATURE:
<223> OTHER INFORMATION: Synthetic Probe

<400> SEQUENCE: 297
tcacgcgagc cgaacgaaca aa                                                    22

<210> SEQ ID NO 298
<211> LENGTH: 22
<212> TYPE: DNA
<213> ORGANISM: Artificial Sequence
<220> FEATURE:
<223> OTHER INFORMATION: Synthetic Probe

<400> SEQUENCE: 298
gctgccgtat atgtgatgtc ac                                                    22

<210> SEQ ID NO 299
<211> LENGTH: 22
<212> TYPE: DNA
<213> ORGANISM: Artificial Sequence
<220> FEATURE:
<223> OTHER INFORMATION: Synthetic Probe

<400> SEQUENCE: 299
cgcattatta ctcacggtac ga                                                    22

<210> SEQ ID NO 300
<211> LENGTH: 22
<212> TYPE: DNA
<213> ORGANISM: Artificial Sequence
<220> FEATURE:
<223> OTHER INFORMATION: Synthetic Probe

<400> SEQUENCE: 300
gatcactttt gtgactatgc aa                                                    22

<210> SEQ ID NO 301
<211> LENGTH: 23
<212> TYPE: DNA

```
<213> ORGANISM: Artificial Sequence
<220> FEATURE:
<223> OTHER INFORMATION: Synthetic Probe

<400> SEQUENCE: 301
gctgagagtg taggatgttt aca                                              23

<210> SEQ ID NO 302
<211> LENGTH: 22
<212> TYPE: DNA
<213> ORGANISM: Artificial Sequence
<220> FEATURE:
<223> OTHER INFORMATION: Synthetic Probe

<400> SEQUENCE: 302
cttccagtca aggatgttta ca                                               22

<210> SEQ ID NO 303
<211> LENGTH: 22
<212> TYPE: DNA
<213> ORGANISM: Artificial Sequence
<220> FEATURE:
<223> OTHER INFORMATION: Synthetic Probe

<400> SEQUENCE: 303
aaattgcatc gtgatccacc cg                                               22

<210> SEQ ID NO 304
<211> LENGTH: 22
<212> TYPE: DNA
<213> ORGANISM: Artificial Sequence
<220> FEATURE:
<223> OTHER INFORMATION: Synthetic Probe

<400> SEQUENCE: 304
tctcacccag ggacaaagga tt                                               22

<210> SEQ ID NO 305
<211> LENGTH: 22
<212> TYPE: DNA
<213> ORGANISM: Artificial Sequence
<220> FEATURE:
<223> OTHER INFORMATION: Synthetic Probe

<400> SEQUENCE: 305
caactccgat atgcaatggg ta                                               22

<210> SEQ ID NO 306
<211> LENGTH: 25
<212> TYPE: DNA
<213> ORGANISM: Artificial Sequence
<220> FEATURE:
<223> OTHER INFORMATION: Synthetic Probe

<400> SEQUENCE: 306
aggccgccac ccgcccgcga tccct                                            25

<210> SEQ ID NO 307
<211> LENGTH: 25
<212> TYPE: DNA
<213> ORGANISM: Artificial Sequence
<220> FEATURE:
<223> OTHER INFORMATION: Synthetic Probe

<400> SEQUENCE: 307
aggatcagcc agtacgaata cgcga                                            25
```

<210> SEQ ID NO 308
<211> LENGTH: 25
<212> TYPE: DNA
<213> ORGANISM: Artificial Sequence
<220> FEATURE:
<223> OTHER INFORMATION: Synthetic Probe

<400> SEQUENCE: 308
cgcgcactcg ggagtatgca gcatt                                              25

<210> SEQ ID NO 309
<211> LENGTH: 25
<212> TYPE: DNA
<213> ORGANISM: Artificial Sequence
<220> FEATURE:
<223> OTHER INFORMATION: Synthetic Probe

<400> SEQUENCE: 309
accaacacag gcttcatcag aggca                                              25

<210> SEQ ID NO 310
<211> LENGTH: 22
<212> TYPE: DNA
<213> ORGANISM: Artificial Sequence
<220> FEATURE:
<223> OTHER INFORMATION: Synthetic Probe

<400> SEQUENCE: 310
tcggtccctc gggccagggc ag                                                 22

<210> SEQ ID NO 311
<211> LENGTH: 25
<212> TYPE: DNA
<213> ORGANISM: Artificial Sequence
<220> FEATURE:
<223> OTHER INFORMATION: Synthetic Probe

<400> SEQUENCE: 311
ggcaaaaagt aatttaagtc atcat                                              25

<210> SEQ ID NO 312
<211> LENGTH: 25
<212> TYPE: DNA
<213> ORGANISM: Artificial Sequence
<220> FEATURE:
<223> OTHER INFORMATION: Synthetic Probe

<400> SEQUENCE: 312
agggcaatat caggttctca tcatt                                              25

<210> SEQ ID NO 313
<211> LENGTH: 22
<212> TYPE: DNA
<213> ORGANISM: Artificial Sequence
<220> FEATURE:
<223> OTHER INFORMATION: Synthetic Probe

<400> SEQUENCE: 313
atgccctttt aacattgcac tg                                                 22

<210> SEQ ID NO 314
<211> LENGTH: 22
<212> TYPE: DNA
<213> ORGANISM: Artificial Sequence
<220> FEATURE:

<223> OTHER INFORMATION: Synthetic Probe

<400> SEQUENCE: 314
cctggccgtg tggttagtga tt                                    22

<210> SEQ ID NO 315
<211> LENGTH: 21
<212> TYPE: DNA
<213> ORGANISM: Artificial Sequence
<220> FEATURE:
<223> OTHER INFORMATION: Synthetic Probe

<400> SEQUENCE: 315
actggctgag tcaggactag c                                     21

<210> SEQ ID NO 316
<211> LENGTH: 25
<212> TYPE: DNA
<213> ORGANISM: Artificial Sequence
<220> FEATURE:
<223> OTHER INFORMATION: Synthetic Probe

<400> SEQUENCE: 316
aacaaggttc aagggtggca catct                                 25

<210> SEQ ID NO 317
<211> LENGTH: 25
<212> TYPE: DNA
<213> ORGANISM: Artificial Sequence
<220> FEATURE:
<223> OTHER INFORMATION: Synthetic Probe

<400> SEQUENCE: 317
aggcccagct ttatttccaa cgttg                                 25

<210> SEQ ID NO 318
<211> LENGTH: 25
<212> TYPE: DNA
<213> ORGANISM: Artificial Sequence
<220> FEATURE:
<223> OTHER INFORMATION: Synthetic Probe

<400> SEQUENCE: 318
tgtgaaaagg tcctcatcat aggaa                                 25

<210> SEQ ID NO 319
<211> LENGTH: 25
<212> TYPE: DNA
<213> ORGANISM: Artificial Sequence
<220> FEATURE:
<223> OTHER INFORMATION: Synthetic Probe

<400> SEQUENCE: 319
gcagccaagc aacgccagaa agccg                                 25

<210> SEQ ID NO 320
<211> LENGTH: 25
<212> TYPE: DNA
<213> ORGANISM: Artificial Sequence
<220> FEATURE:
<223> OTHER INFORMATION: Synthetic Probe

<400> SEQUENCE: 320
atcatgacca gcatcggaga ctcta                                 25

```
<210> SEQ ID NO 321
<211> LENGTH: 23
<212> TYPE: DNA
<213> ORGANISM: Artificial Sequence
<220> FEATURE:
<223> OTHER INFORMATION: Synthetic Probe

<400> SEQUENCE: 321
acccaccgac aacaatgaat gtt                                          23

<210> SEQ ID NO 322
<211> LENGTH: 25
<212> TYPE: DNA
<213> ORGANISM: Artificial Sequence
<220> FEATURE:
<223> OTHER INFORMATION: Synthetic Probe

<400> SEQUENCE: 322
gtctggctgt gtaaactact gataa                                        25

<210> SEQ ID NO 323
<211> LENGTH: 25
<212> TYPE: DNA
<213> ORGANISM: Artificial Sequence
<220> FEATURE:
<223> OTHER INFORMATION: Synthetic Probe

<400> SEQUENCE: 323
aaaagcgatg ttttcactct cccct                                        25

<210> SEQ ID NO 324
<211> LENGTH: 25
<212> TYPE: DNA
<213> ORGANISM: Artificial Sequence
<220> FEATURE:
<223> OTHER INFORMATION: Synthetic Probe

<400> SEQUENCE: 324
gaacacagcc tgtggtaagc accag                                        25

<210> SEQ ID NO 325
<211> LENGTH: 25
<212> TYPE: DNA
<213> ORGANISM: Artificial Sequence
<220> FEATURE:
<223> OTHER INFORMATION: Synthetic Probe

<400> SEQUENCE: 325
ccaatgcatc agacaaaact ggcca                                        25

<210> SEQ ID NO 326
<211> LENGTH: 25
<212> TYPE: DNA
<213> ORGANISM: Artificial Sequence
<220> FEATURE:
<223> OTHER INFORMATION: Synthetic Probe

<400> SEQUENCE: 326
cacgtgcttt aattggaatg tcatc                                        25

<210> SEQ ID NO 327
<211> LENGTH: 25
<212> TYPE: DNA
<213> ORGANISM: Artificial Sequence
<220> FEATURE:
<223> OTHER INFORMATION: Synthetic Probe
```

<400> SEQUENCE: 327
gcccagcttc atcttcaacg ttgtg                                              25

<210> SEQ ID NO 328
<211> LENGTH: 25
<212> TYPE: DNA
<213> ORGANISM: Artificial Sequence
<220> FEATURE:
<223> OTHER INFORMATION: Synthetic Probe

<400> SEQUENCE: 328
cagcttcatc ttcaacgttg tggaa                                              25

<210> SEQ ID NO 329
<211> LENGTH: 25
<212> TYPE: DNA
<213> ORGANISM: Artificial Sequence
<220> FEATURE:
<223> OTHER INFORMATION: Synthetic Probe

<400> SEQUENCE: 329
agtacaggtc tgtgaaaagg tcctc                                              25

<210> SEQ ID NO 330
<211> LENGTH: 25
<212> TYPE: DNA
<213> ORGANISM: Artificial Sequence
<220> FEATURE:
<223> OTHER INFORMATION: Synthetic Probe

<400> SEQUENCE: 330
gatgacatca cttgaaagtt cagcc                                              25

<210> SEQ ID NO 331
<211> LENGTH: 25
<212> TYPE: DNA
<213> ORGANISM: Artificial Sequence
<220> FEATURE:
<223> OTHER INFORMATION: Synthetic Probe

<400> SEQUENCE: 331
gtttctcagg tgttcatgta ttttc                                              25

<210> SEQ ID NO 332
<211> LENGTH: 25
<212> TYPE: DNA
<213> ORGANISM: Artificial Sequence
<220> FEATURE:
<223> OTHER INFORMATION: Synthetic Probe

<400> SEQUENCE: 332
gccgaacgag attccatgta agtca                                              25

<210> SEQ ID NO 333
<211> LENGTH: 25
<212> TYPE: DNA
<213> ORGANISM: Artificial Sequence
<220> FEATURE:
<223> OTHER INFORMATION: Synthetic Probe

<400> SEQUENCE: 333
ggcggtattc aactcatcac tggtg                                              25

<210> SEQ ID NO 334
<211> LENGTH: 25

```
<212> TYPE: DNA
<213> ORGANISM: Artificial Sequence
<220> FEATURE:
<223> OTHER INFORMATION: Synthetic Probe

<400> SEQUENCE: 334
tggagtcatc tcatggtcgg gaaac                                              25

<210> SEQ ID NO 335
<211> LENGTH: 25
<212> TYPE: DNA
<213> ORGANISM: Artificial Sequence
<220> FEATURE:
<223> OTHER INFORMATION: Synthetic Probe

<400> SEQUENCE: 335
tcagatgcaa tgctgaccac atggt                                              25

<210> SEQ ID NO 336
<211> LENGTH: 25
<212> TYPE: DNA
<213> ORGANISM: Artificial Sequence
<220> FEATURE:
<223> OTHER INFORMATION: Synthetic Probe

<400> SEQUENCE: 336
agccgaatcc gtacttattt ttctt                                              25

<210> SEQ ID NO 337
<211> LENGTH: 25
<212> TYPE: DNA
<213> ORGANISM: Artificial Sequence
<220> FEATURE:
<223> OTHER INFORMATION: Synthetic Probe

<400> SEQUENCE: 337
tcagacccag agtctcaaca ctcac                                              25

<210> SEQ ID NO 338
<211> LENGTH: 25
<212> TYPE: DNA
<213> ORGANISM: Artificial Sequence
<220> FEATURE:
<223> OTHER INFORMATION: Synthetic Probe

<400> SEQUENCE: 338
ctcaacactc actaggtgaa ctgct                                              25

<210> SEQ ID NO 339
<211> LENGTH: 25
<212> TYPE: DNA
<213> ORGANISM: Artificial Sequence
<220> FEATURE:
<223> OTHER INFORMATION: Synthetic Probe

<400> SEQUENCE: 339
aaggtcaggc tcagacagtt catca                                              25

<210> SEQ ID NO 340
<211> LENGTH: 25
<212> TYPE: DNA
<213> ORGANISM: Artificial Sequence
<220> FEATURE:
<223> OTHER INFORMATION: Synthetic Probe

<400> SEQUENCE: 340
```
cgcgatttct ttccctgcac tatca                                          25

<210> SEQ ID NO 341
<211> LENGTH: 25
<212> TYPE: DNA
<213> ORGANISM: Artificial Sequence
<220> FEATURE:
<223> OTHER INFORMATION: Synthetic Probe

<400> SEQUENCE: 341
tggccatcat ctgggaccga aactt                                          25

<210> SEQ ID NO 342
<211> LENGTH: 23
<212> TYPE: DNA
<213> ORGANISM: Artificial Sequence
<220> FEATURE:
<223> OTHER INFORMATION: Synthetic Probe

<400> SEQUENCE: 342
gctttgacaa tactattgca ctg                                            23

<210> SEQ ID NO 343
<211> LENGTH: 25
<212> TYPE: DNA
<213> ORGANISM: Artificial Sequence
<220> FEATURE:
<223> OTHER INFORMATION: Synthetic Probe

<400> SEQUENCE: 343
gctccactat ttcaatactg ttctg                                          25

<210> SEQ ID NO 344
<211> LENGTH: 25
<212> TYPE: DNA
<213> ORGANISM: Artificial Sequence
<220> FEATURE:
<223> OTHER INFORMATION: Synthetic Probe

<400> SEQUENCE: 344
tcttatctgg aatggcatct agctt                                          25

<210> SEQ ID NO 345
<211> LENGTH: 25
<212> TYPE: DNA
<213> ORGANISM: Artificial Sequence
<220> FEATURE:
<223> OTHER INFORMATION: Synthetic Probe

<400> SEQUENCE: 345
gcctcaggta aatcctttaa tccat                                          25

<210> SEQ ID NO 346
<211> LENGTH: 25
<212> TYPE: DNA
<213> ORGANISM: Artificial Sequence
<220> FEATURE:
<223> OTHER INFORMATION: Synthetic Probe

<400> SEQUENCE: 346
gcatgtggag tcatctcatg gtcgg                                          25

<210> SEQ ID NO 347
<211> LENGTH: 25
<212> TYPE: DNA
<213> ORGANISM: Artificial Sequence

```
<220> FEATURE:
<223> OTHER INFORMATION: Synthetic Probe

<400> SEQUENCE: 347
aggtagttgc ggaacatcat ggacg                                        25

<210> SEQ ID NO 348
<211> LENGTH: 25
<212> TYPE: DNA
<213> ORGANISM: Artificial Sequence
<220> FEATURE:
<223> OTHER INFORMATION: Synthetic Probe

<400> SEQUENCE: 348
ggctctcatc tctctccctt cagta                                        25

<210> SEQ ID NO 349
<211> LENGTH: 25
<212> TYPE: DNA
<213> ORGANISM: Artificial Sequence
<220> FEATURE:
<223> OTHER INFORMATION: Synthetic Probe

<400> SEQUENCE: 349
gaccagcatc ggagactcta gtctg                                        25

<210> SEQ ID NO 350
<211> LENGTH: 25
<212> TYPE: DNA
<213> ORGANISM: Artificial Sequence
<220> FEATURE:
<223> OTHER INFORMATION: Synthetic Probe

<400> SEQUENCE: 350
gagcggttgg cattcatcat tactc                                        25

<210> SEQ ID NO 351
<211> LENGTH: 22
<212> TYPE: DNA
<213> ORGANISM: Artificial Sequence
<220> FEATURE:
<223> OTHER INFORMATION: Synthetic Probe

<400> SEQUENCE: 351
gtagaaggga atcttgcata ag                                           22

<210> SEQ ID NO 352
<211> LENGTH: 25
<212> TYPE: DNA
<213> ORGANISM: Artificial Sequence
<220> FEATURE:
<223> OTHER INFORMATION: Synthetic Probe

<400> SEQUENCE: 352
tgtcctcagt ggcagtcgga gccca                                        25

<210> SEQ ID NO 353
<211> LENGTH: 25
<212> TYPE: DNA
<213> ORGANISM: Artificial Sequence
<220> FEATURE:
<223> OTHER INFORMATION: Synthetic Probe

<400> SEQUENCE: 353
agttcgcatc acccgcgtca gcagt                                        25
```

<210> SEQ ID NO 354
<211> LENGTH: 25
<212> TYPE: DNA
<213> ORGANISM: Artificial Sequence
<220> FEATURE:
<223> OTHER INFORMATION: Synthetic Probe

<400> SEQUENCE: 354
tcgaatgtga gtgggagaag ttctc                                    25

<210> SEQ ID NO 355
<211> LENGTH: 25
<212> TYPE: DNA
<213> ORGANISM: Artificial Sequence
<220> FEATURE:
<223> OTHER INFORMATION: Synthetic Probe

<400> SEQUENCE: 355
gctgctttca tgaggatcaa acaat                                    25

<210> SEQ ID NO 356
<211> LENGTH: 25
<212> TYPE: DNA
<213> ORGANISM: Artificial Sequence
<220> FEATURE:
<223> OTHER INFORMATION: Synthetic Probe

<400> SEQUENCE: 356
aatcagcaca cagtttctgt ccgcc                                    25

<210> SEQ ID NO 357
<211> LENGTH: 25
<212> TYPE: DNA
<213> ORGANISM: Artificial Sequence
<220> FEATURE:
<223> OTHER INFORMATION: Synthetic Probe

<400> SEQUENCE: 357
aaagcaaatc catcacgaac tcagc                                    25

<210> SEQ ID NO 358
<211> LENGTH: 21
<212> TYPE: DNA
<213> ORGANISM: Artificial Sequence
<220> FEATURE:
<223> OTHER INFORMATION: Synthetic Probe

<400> SEQUENCE: 358
cacacacctg ccccgccca c                                         21

<210> SEQ ID NO 359
<211> LENGTH: 21
<212> TYPE: DNA
<213> ORGANISM: Artificial Sequence
<220> FEATURE:
<223> OTHER INFORMATION: Synthetic Probe

<400> SEQUENCE: 359
gcacagcccc cgtccctccc t                                        21

<210> SEQ ID NO 360
<211> LENGTH: 22
<212> TYPE: DNA
<213> ORGANISM: Artificial Sequence
<220> FEATURE:
<223> OTHER INFORMATION: Synthetic Probe

```
<400> SEQUENCE: 360
cgccaatatt tacgtgctgc ta                                          22

<210> SEQ ID NO 361
<211> LENGTH: 25
<212> TYPE: DNA
<213> ORGANISM: Artificial Sequence
<220> FEATURE:
<223> OTHER INFORMATION: Synthetic Probe

<400> SEQUENCE: 361
atccattttt tttatagtca tcatc                                       25

<210> SEQ ID NO 362
<211> LENGTH: 25
<212> TYPE: DNA
<213> ORGANISM: Artificial Sequence
<220> FEATURE:
<223> OTHER INFORMATION: Synthetic Probe

<400> SEQUENCE: 362
tttttttggg aggactcatc atcga                                       25

<210> SEQ ID NO 363
<211> LENGTH: 22
<212> TYPE: DNA
<213> ORGANISM: Artificial Sequence
<220> FEATURE:
<223> OTHER INFORMATION: Synthetic Probe

<400> SEQUENCE: 363
gtaagaagtg cttacattgc ag                                          22

<210> SEQ ID NO 364
<211> LENGTH: 21
<212> TYPE: DNA
<213> ORGANISM: Artificial Sequence
<220> FEATURE:
<223> OTHER INFORMATION: Synthetic Probe

<400> SEQUENCE: 364
ctgggaggag ggagaagagg a                                           21

<210> SEQ ID NO 365
<211> LENGTH: 22
<212> TYPE: DNA
<213> ORGANISM: Artificial Sequence
<220> FEATURE:
<223> OTHER INFORMATION: Synthetic Probe

<400> SEQUENCE: 365
ctagggaaca cagggctggt ga                                          22

<210> SEQ ID NO 366
<211> LENGTH: 22
<212> TYPE: DNA
<213> ORGANISM: Artificial Sequence
<220> FEATURE:
<223> OTHER INFORMATION: Synthetic Probe

<400> SEQUENCE: 366
actgggactt tgtaggccag tt                                          22

<210> SEQ ID NO 367
```

```
<211> LENGTH: 22
<212> TYPE: DNA
<213> ORGANISM: Artificial Sequence
<220> FEATURE:
<223> OTHER INFORMATION: Synthetic Probe

<400> SEQUENCE: 367
gcctaagaca caggcccaga ga                                              22

<210> SEQ ID NO 368
<211> LENGTH: 21
<212> TYPE: DNA
<213> ORGANISM: Artificial Sequence
<220> FEATURE:
<223> OTHER INFORMATION: Synthetic Probe

<400> SEQUENCE: 368
ccttctgact ccaagtccag t                                               21

<210> SEQ ID NO 369
<211> LENGTH: 22
<212> TYPE: DNA
<213> ORGANISM: Artificial Sequence
<220> FEATURE:
<223> OTHER INFORMATION: Synthetic Probe

<400> SEQUENCE: 369
ggacctaaaa atacaatgca ta                                              22

<210> SEQ ID NO 370
<211> LENGTH: 25
<212> TYPE: DNA
<213> ORGANISM: Artificial Sequence
<220> FEATURE:
<223> OTHER INFORMATION: Synthetic Probe

<400> SEQUENCE: 370
gccttttttg acaccacatt cacta                                           25

<210> SEQ ID NO 371
<211> LENGTH: 25
<212> TYPE: DNA
<213> ORGANISM: Artificial Sequence
<220> FEATURE:
<223> OTHER INFORMATION: Synthetic Probe

<400> SEQUENCE: 371
atgggcatca ccaaccagat gccac                                           25

<210> SEQ ID NO 372
<211> LENGTH: 25
<212> TYPE: DNA
<213> ORGANISM: Artificial Sequence
<220> FEATURE:
<223> OTHER INFORMATION: Synthetic Probe

<400> SEQUENCE: 372
gaatgggtgc ctctgccagg cttgc                                           25

<210> SEQ ID NO 373
<211> LENGTH: 25
<212> TYPE: DNA
<213> ORGANISM: Artificial Sequence
<220> FEATURE:
<223> OTHER INFORMATION: Synthetic Probe

<400> SEQUENCE: 373
```
ctgttctagc aagcactgaa ggaat 25

<210> SEQ ID NO 374
<211> LENGTH: 25
<212> TYPE: DNA
<213> ORGANISM: Artificial Sequence
<220> FEATURE:
<223> OTHER INFORMATION: Synthetic Probe

<400> SEQUENCE: 374
tgtcagcagt ttgagtgtca gcatt 25

<210> SEQ ID NO 375
<211> LENGTH: 25
<212> TYPE: DNA
<213> ORGANISM: Artificial Sequence
<220> FEATURE:
<223> OTHER INFORMATION: Synthetic Probe

<400> SEQUENCE: 375
tgagtgggag aagttctcat caccg 25

<210> SEQ ID NO 376
<211> LENGTH: 25
<212> TYPE: DNA
<213> ORGANISM: Artificial Sequence
<220> FEATURE:
<223> OTHER INFORMATION: Synthetic Probe

<400> SEQUENCE: 376
agtgctgctt tcatgaggat caaac 25

<210> SEQ ID NO 377
<211> LENGTH: 25
<212> TYPE: DNA
<213> ORGANISM: Artificial Sequence
<220> FEATURE:
<223> OTHER INFORMATION: Synthetic Probe

<400> SEQUENCE: 377
cagagcggtt ggcattcatc attac 25

<210> SEQ ID NO 378
<211> LENGTH: 25
<212> TYPE: DNA
<213> ORGANISM: Artificial Sequence
<220> FEATURE:
<223> OTHER INFORMATION: Synthetic Probe

<400> SEQUENCE: 378
ttctgtccac tactcttaaa gcatc 25

<210> SEQ ID NO 379
<211> LENGTH: 25
<212> TYPE: DNA
<213> ORGANISM: Artificial Sequence
<220> FEATURE:
<223> OTHER INFORMATION: Synthetic Probe

<400> SEQUENCE: 379
cgacactcag atggcatgtt ggggt 25

<210> SEQ ID NO 380
<211> LENGTH: 22
<212> TYPE: DNA

```
<213> ORGANISM: Artificial Sequence
<220> FEATURE:
<223> OTHER INFORMATION: Synthetic Probe

<400> SEQUENCE: 380
ggatccctgg gaccatacct ag                                         22

<210> SEQ ID NO 381
<211> LENGTH: 22
<212> TYPE: DNA
<213> ORGANISM: Artificial Sequence
<220> FEATURE:
<223> OTHER INFORMATION: Synthetic Probe

<400> SEQUENCE: 381
ggagagcctc cacccaaccc tc                                         22

<210> SEQ ID NO 382
<211> LENGTH: 25
<212> TYPE: DNA
<213> ORGANISM: Artificial Sequence
<220> FEATURE:
<223> OTHER INFORMATION: Synthetic Probe

<400> SEQUENCE: 382
tgaaaacacg ccaagcacac actgg                                      25

<210> SEQ ID NO 383
<211> LENGTH: 25
<212> TYPE: DNA
<213> ORGANISM: Artificial Sequence
<220> FEATURE:
<223> OTHER INFORMATION: Synthetic Probe

<400> SEQUENCE: 383
caggttgctc ttgcatgcag ttgga                                      25

<210> SEQ ID NO 384
<211> LENGTH: 25
<212> TYPE: DNA
<213> ORGANISM: Artificial Sequence
<220> FEATURE:
<223> OTHER INFORMATION: Synthetic Probe

<400> SEQUENCE: 384
ggagccctgc tcactcctcg ggtga                                      25

<210> SEQ ID NO 385
<211> LENGTH: 25
<212> TYPE: DNA
<213> ORGANISM: Artificial Sequence
<220> FEATURE:
<223> OTHER INFORMATION: Synthetic Probe

<400> SEQUENCE: 385
accaagacca gtgttcagat ccgat                                      25

<210> SEQ ID NO 386
<211> LENGTH: 25
<212> TYPE: DNA
<213> ORGANISM: Artificial Sequence
<220> FEATURE:
<223> OTHER INFORMATION: Synthetic Probe

<400> SEQUENCE: 386
agtgctggac atcatggagg ccccg                                      25
```

<210> SEQ ID NO 387
<211> LENGTH: 25
<212> TYPE: DNA
<213> ORGANISM: Artificial Sequence
<220> FEATURE:
<223> OTHER INFORMATION: Synthetic Probe

<400> SEQUENCE: 387
aatcgcctcg ataatcagtg gccgg                                            25

<210> SEQ ID NO 388
<211> LENGTH: 25
<212> TYPE: DNA
<213> ORGANISM: Artificial Sequence
<220> FEATURE:
<223> OTHER INFORMATION: Synthetic Probe

<400> SEQUENCE: 388
ggagccagtt gtcatcatgt acagc                                            25

<210> SEQ ID NO 389
<211> LENGTH: 25
<212> TYPE: DNA
<213> ORGANISM: Artificial Sequence
<220> FEATURE:
<223> OTHER INFORMATION: Synthetic Probe

<400> SEQUENCE: 389
ggtcagacgg gtaatgtgcc cacgt                                            25

<210> SEQ ID NO 390
<211> LENGTH: 25
<212> TYPE: DNA
<213> ORGANISM: Artificial Sequence
<220> FEATURE:
<223> OTHER INFORMATION: Synthetic Probe

<400> SEQUENCE: 390
acctcccggg tgtatccacg ttgga                                            25

<210> SEQ ID NO 391
<211> LENGTH: 25
<212> TYPE: DNA
<213> ORGANISM: Artificial Sequence
<220> FEATURE:
<223> OTHER INFORMATION: Synthetic Probe

<400> SEQUENCE: 391
aggcgcagac acgaggccca gcttt                                            25

<210> SEQ ID NO 392
<211> LENGTH: 25
<212> TYPE: DNA
<213> ORGANISM: Artificial Sequence
<220> FEATURE:
<223> OTHER INFORMATION: Synthetic Probe

<400> SEQUENCE: 392
agcttcatct tcaacgttgt ggaaa                                            25

<210> SEQ ID NO 393
<211> LENGTH: 25
<212> TYPE: DNA
<213> ORGANISM: Artificial Sequence
<220> FEATURE:

```
<223> OTHER INFORMATION: Synthetic Probe

<400> SEQUENCE: 393
tcctcagcct aaaaggctct catct                                          25

<210> SEQ ID NO 394
<211> LENGTH: 25
<212> TYPE: DNA
<213> ORGANISM: Artificial Sequence
<220> FEATURE:
<223> OTHER INFORMATION: Synthetic Probe

<400> SEQUENCE: 394
ggatcagcca gtacgaatac gcgat                                          25

<210> SEQ ID NO 395
<211> LENGTH: 25
<212> TYPE: DNA
<213> ORGANISM: Artificial Sequence
<220> FEATURE:
<223> OTHER INFORMATION: Synthetic Probe

<400> SEQUENCE: 395
ggtcagagcg ctgcggtgat ggcat                                          25

<210> SEQ ID NO 396
<211> LENGTH: 25
<212> TYPE: DNA
<213> ORGANISM: Artificial Sequence
<220> FEATURE:
<223> OTHER INFORMATION: Synthetic Probe

<400> SEQUENCE: 396
catgaccagc atcggagact ctagt                                          25

<210> SEQ ID NO 397
<211> LENGTH: 25
<212> TYPE: DNA
<213> ORGANISM: Artificial Sequence
<220> FEATURE:
<223> OTHER INFORMATION: Synthetic Probe

<400> SEQUENCE: 397
ttcctgagag gcactgatgt cccct                                          25

<210> SEQ ID NO 398
<211> LENGTH: 25
<212> TYPE: DNA
<213> ORGANISM: Artificial Sequence
<220> FEATURE:
<223> OTHER INFORMATION: Synthetic Probe

<400> SEQUENCE: 398
acccatacaa ccaacaggct gcgta                                          25

<210> SEQ ID NO 399
<211> LENGTH: 25
<212> TYPE: DNA
<213> ORGANISM: Artificial Sequence
<220> FEATURE:
<223> OTHER INFORMATION: Synthetic Probe

<400> SEQUENCE: 399
ttactctcag atgtccctac caaca                                          25
```

```
<210> SEQ ID NO 400
<211> LENGTH: 25
<212> TYPE: DNA
<213> ORGANISM: Artificial Sequence
<220> FEATURE:
<223> OTHER INFORMATION: Synthetic Probe

<400> SEQUENCE: 400
acattccagg cctcatcact gaaca                                              25

<210> SEQ ID NO 401
<211> LENGTH: 18
<212> TYPE: DNA
<213> ORGANISM: Artificial Sequence
<220> FEATURE:
<223> OTHER INFORMATION: Synthetic Probe

<400> SEQUENCE: 401
tggcgcctga acagggac                                                      18

<210> SEQ ID NO 402
<211> LENGTH: 17
<212> TYPE: DNA
<213> ORGANISM: Artificial Sequence
<220> FEATURE:
<223> OTHER INFORMATION: Synthetic Probe

<400> SEQUENCE: 402
gggtggcagc ggtggga                                                       17

<210> SEQ ID NO 403
<211> LENGTH: 22
<212> TYPE: DNA
<213> ORGANISM: Artificial Sequence
<220> FEATURE:
<223> OTHER INFORMATION: Synthetic Probe

<400> SEQUENCE: 403
atgccctttc atcattgcac tg                                                 22

<210> SEQ ID NO 404
<211> LENGTH: 22
<212> TYPE: DNA
<213> ORGANISM: Artificial Sequence
<220> FEATURE:
<223> OTHER INFORMATION: Synthetic Probe

<400> SEQUENCE: 404
ccagaactga gtccacaggg ca                                                 22

<210> SEQ ID NO 405
<211> LENGTH: 22
<212> TYPE: DNA
<213> ORGANISM: Artificial Sequence
<220> FEATURE:
<223> OTHER INFORMATION: Synthetic Probe

<400> SEQUENCE: 405
agcctatgga attcagttct ca                                                 22

<210> SEQ ID NO 406
<211> LENGTH: 22
<212> TYPE: DNA
<213> ORGANISM: Artificial Sequence
<220> FEATURE:
<223> OTHER INFORMATION: Synthetic Probe
```

<400> SEQUENCE: 406
gaccagagga aagccagccc ct					22

<210> SEQ ID NO 407
<211> LENGTH: 20
<212> TYPE: DNA
<213> ORGANISM: Artificial Sequence
<220> FEATURE:
<223> OTHER INFORMATION: Synthetic Probe

<400> SEQUENCE: 407
ttcccatgcc ctatacctct					20

<210> SEQ ID NO 408
<211> LENGTH: 23
<212> TYPE: DNA
<213> ORGANISM: Artificial Sequence
<220> FEATURE:
<223> OTHER INFORMATION: Synthetic Probe

<400> SEQUENCE: 408
acaccccaaa atcgaagcac ttc					23

<210> SEQ ID NO 409
<211> LENGTH: 22
<212> TYPE: DNA
<213> ORGANISM: Artificial Sequence
<220> FEATURE:
<223> OTHER INFORMATION: Synthetic Probe

<400> SEQUENCE: 409
acacaggacc tggagtcagg ag					22

<210> SEQ ID NO 410
<211> LENGTH: 22
<212> TYPE: DNA
<213> ORGANISM: Artificial Sequence
<220> FEATURE:
<223> OTHER INFORMATION: Synthetic Probe

<400> SEQUENCE: 410
gccttctgac cctaagtcca gt					22

<210> SEQ ID NO 411
<211> LENGTH: 23
<212> TYPE: DNA
<213> ORGANISM: Artificial Sequence
<220> FEATURE:
<223> OTHER INFORMATION: Synthetic Probe

<400> SEQUENCE: 411
aaagtctcgc tctctgcccc tca					23

<210> SEQ ID NO 412
<211> LENGTH: 22
<212> TYPE: DNA
<213> ORGANISM: Artificial Sequence
<220> FEATURE:
<223> OTHER INFORMATION: Synthetic Probe

<400> SEQUENCE: 412
aactcagtaa tggtaacggt tt					22

<210> SEQ ID NO 413
<211> LENGTH: 21

```
<212> TYPE: DNA
<213> ORGANISM: Artificial Sequence
<220> FEATURE:
<223> OTHER INFORMATION: Synthetic Probe

<400> SEQUENCE: 413
atcctgtact gagctgcccc g                                              21

<210> SEQ ID NO 414
<211> LENGTH: 22
<212> TYPE: DNA
<213> ORGANISM: Artificial Sequence
<220> FEATURE:
<223> OTHER INFORMATION: Synthetic Probe

<400> SEQUENCE: 414
ctcggggcag ctcagtacag ga                                             22

<210> SEQ ID NO 415
<211> LENGTH: 22
<212> TYPE: DNA
<213> ORGANISM: Artificial Sequence
<220> FEATURE:
<223> OTHER INFORMATION: Synthetic Probe

<400> SEQUENCE: 415
gatagagtgc agaccagggt ct                                             22

<210> SEQ ID NO 416
<211> LENGTH: 23
<212> TYPE: DNA
<213> ORGANISM: Artificial Sequence
<220> FEATURE:
<223> OTHER INFORMATION: Synthetic Probe

<400> SEQUENCE: 416
gggctcttac tccctcaggc act                                            23

<210> SEQ ID NO 417
<211> LENGTH: 22
<212> TYPE: DNA
<213> ORGANISM: Artificial Sequence
<220> FEATURE:
<223> OTHER INFORMATION: Synthetic Probe

<400> SEQUENCE: 417
ctgctcaaac cctccaatga ct                                             22

<210> SEQ ID NO 418
<211> LENGTH: 21
<212> TYPE: DNA
<213> ORGANISM: Artificial Sequence
<220> FEATURE:
<223> OTHER INFORMATION: Synthetic Probe

<400> SEQUENCE: 418
ggtggagccc tgagaaccgg a                                              21

<210> SEQ ID NO 419
<211> LENGTH: 22
<212> TYPE: DNA
<213> ORGANISM: Artificial Sequence
<220> FEATURE:
<223> OTHER INFORMATION: Synthetic Probe

<400> SEQUENCE: 419
```
aagagggaga cccaggctcg ga                                          22

<210> SEQ ID NO 420
<211> LENGTH: 25
<212> TYPE: DNA
<213> ORGANISM: Artificial Sequence
<220> FEATURE:
<223> OTHER INFORMATION: Synthetic Probe

<400> SEQUENCE: 420
aggccataaa ccattctcag tgccc                                       25

<210> SEQ ID NO 421
<211> LENGTH: 25
<212> TYPE: DNA
<213> ORGANISM: Artificial Sequence
<220> FEATURE:
<223> OTHER INFORMATION: Synthetic Probe

<400> SEQUENCE: 421
aagagccagc cctattctta ggacg                                       25

<210> SEQ ID NO 422
<211> LENGTH: 25
<212> TYPE: DNA
<213> ORGANISM: Artificial Sequence
<220> FEATURE:
<223> OTHER INFORMATION: Synthetic Probe

<400> SEQUENCE: 422
ttcatctccc tgctattgag tccac                                       25

<210> SEQ ID NO 423
<211> LENGTH: 25
<212> TYPE: DNA
<213> ORGANISM: Artificial Sequence
<220> FEATURE:
<223> OTHER INFORMATION: Synthetic Probe

<400> SEQUENCE: 423
tgttttggac cattcatcat tgtga                                       25

<210> SEQ ID NO 424
<211> LENGTH: 25
<212> TYPE: DNA
<213> ORGANISM: Artificial Sequence
<220> FEATURE:
<223> OTHER INFORMATION: Synthetic Probe

<400> SEQUENCE: 424
gccaagcttt tggtggaaac tacga                                       25

<210> SEQ ID NO 425
<211> LENGTH: 25
<212> TYPE: DNA
<213> ORGANISM: Artificial Sequence
<220> FEATURE:
<223> OTHER INFORMATION: Synthetic Probe

<400> SEQUENCE: 425
tcagatcctc agttccatca tggtg                                       25

<210> SEQ ID NO 426
<211> LENGTH: 25
<212> TYPE: DNA
<213> ORGANISM: Artificial Sequence
<220> FEATURE:
<223> OTHER INFORMATION: Synthetic Probe

<400> SEQUENCE: 426
tgtgctttca tcaaggccgt acagc 25

<210> SEQ ID NO 427
<211> LENGTH: 25
<212> TYPE: DNA
<213> ORGANISM: Artificial Sequence
<220> FEATURE:
<223> OTHER INFORMATION: Synthetic Probe

<400> SEQUENCE: 427
ctcatggcag ttcagtagag ggagc 25

<210> SEQ ID NO 428
<211> LENGTH: 25
<212> TYPE: DNA
<213> ORGANISM: Artificial Sequence
<220> FEATURE:
<223> OTHER INFORMATION: Synthetic Probe

<400> SEQUENCE: 428
gtgcccacgt cgtaacaagg ttcaa 25

<210> SEQ ID NO 429
<211> LENGTH: 25
<212> TYPE: DNA
<213> ORGANISM: Artificial Sequence
<220> FEATURE:
<223> OTHER INFORMATION: Synthetic Probe

<400> SEQUENCE: 429
tcctcagagt tatttatcct cacgg 25

<210> SEQ ID NO 430
<211> LENGTH: 25
<212> TYPE: DNA
<213> ORGANISM: Artificial Sequence
<220> FEATURE:
<223> OTHER INFORMATION: Synthetic Probe

<400> SEQUENCE: 430
atgtattttc actgtcggtc atagt 25

<210> SEQ ID NO 431
<211> LENGTH: 25
<212> TYPE: DNA
<213> ORGANISM: Artificial Sequence
<220> FEATURE:
<223> OTHER INFORMATION: Synthetic Probe

<400> SEQUENCE: 431
gatttcagag tctcaacagc aagtc 25

<210> SEQ ID NO 432
<211> LENGTH: 25
<212> TYPE: DNA
<213> ORGANISM: Artificial Sequence
<220> FEATURE:
<223> OTHER INFORMATION: Synthetic Probe

<400> SEQUENCE: 432
ctctctccct tcagtagcag aactg 25

<210> SEQ ID NO 433
<211> LENGTH: 25
<212> TYPE: DNA
<213> ORGANISM: Artificial Sequence
<220> FEATURE:
<223> OTHER INFORMATION: Synthetic Probe

<400> SEQUENCE: 433
ccgcgcactc gggagtatgc agcat                                        25

<210> SEQ ID NO 434
<211> LENGTH: 25
<212> TYPE: DNA
<213> ORGANISM: Artificial Sequence
<220> FEATURE:
<223> OTHER INFORMATION: Synthetic Probe

<400> SEQUENCE: 434
gtcagaacgt actcatcagt gagga                                        25

<210> SEQ ID NO 435
<211> LENGTH: 25
<212> TYPE: DNA
<213> ORGANISM: Artificial Sequence
<220> FEATURE:
<223> OTHER INFORMATION: Synthetic Probe

<400> SEQUENCE: 435
agagtcgtcc ttgcactgag gtgct                                        25

<210> SEQ ID NO 436
<211> LENGTH: 25
<212> TYPE: DNA
<213> ORGANISM: Artificial Sequence
<220> FEATURE:
<223> OTHER INFORMATION: Synthetic Probe

<400> SEQUENCE: 436
gagttgcttt gtccctggct gatat                                        25

<210> SEQ ID NO 437
<211> LENGTH: 25
<212> TYPE: DNA
<213> ORGANISM: Artificial Sequence
<220> FEATURE:
<223> OTHER INFORMATION: Synthetic Probe

<400> SEQUENCE: 437
aatgggtgcc tctgccaggc ttgct                                        25

<210> SEQ ID NO 438
<211> LENGTH: 25
<212> TYPE: DNA
<213> ORGANISM: Artificial Sequence
<220> FEATURE:
<223> OTHER INFORMATION: Synthetic Probe

<400> SEQUENCE: 438
ccgtactttc atcctccaac acaca                                        25

<210> SEQ ID NO 439
<211> LENGTH: 25
<212> TYPE: DNA
<213> ORGANISM: Artificial Sequence
<220> FEATURE:
<223> OTHER INFORMATION: Synthetic Probe

```
<400> SEQUENCE: 439
agatccattt tttttatagt catca                                               25

<210> SEQ ID NO 440
<211> LENGTH: 21
<212> TYPE: DNA
<213> ORGANISM: Artificial Sequence
<220> FEATURE:
<223> OTHER INFORMATION: Synthetic Probe

<400> SEQUENCE: 440
agttctccca acgtaaaccc a                                                   21

<210> SEQ ID NO 441
<211> LENGTH: 25
<212> TYPE: DNA
<213> ORGANISM: Artificial Sequence
<220> FEATURE:
<223> OTHER INFORMATION: Synthetic Probe

<400> SEQUENCE: 441
ctgcggtgat ggcatcagcg acaca                                               25

<210> SEQ ID NO 442
<211> LENGTH: 25
<212> TYPE: DNA
<213> ORGANISM: Artificial Sequence
<220> FEATURE:
<223> OTHER INFORMATION: Synthetic Probe

<400> SEQUENCE: 442
agttatcgct tctgacggca cttcc                                               25

<210> SEQ ID NO 443
<211> LENGTH: 22
<212> TYPE: DNA
<213> ORGANISM: Artificial Sequence
<220> FEATURE:
<223> OTHER INFORMATION: Synthetic Probe

<400> SEQUENCE: 443
gtccactcaa cggtcgatgg tt                                                  22

<210> SEQ ID NO 444
<211> LENGTH: 25
<212> TYPE: DNA
<213> ORGANISM: Artificial Sequence
<220> FEATURE:
<223> OTHER INFORMATION: Synthetic Probe

<400> SEQUENCE: 444
tctgcctccc tgaaaacacg ccaag                                               25

<210> SEQ ID NO 445
<211> LENGTH: 25
<212> TYPE: DNA
<213> ORGANISM: Artificial Sequence
<220> FEATURE:
<223> OTHER INFORMATION: Synthetic Probe

<400> SEQUENCE: 445
ctggctgtgt aaactactga taaaa                                               25

<210> SEQ ID NO 446
```

```
<210> SEQ ID NO 446
<211> LENGTH: 25
<212> TYPE: DNA
<213> ORGANISM: Artificial Sequence
<220> FEATURE:
<223> OTHER INFORMATION: Synthetic Probe

<400> SEQUENCE: 446
aactgtctgt ggtgccaaca ggtcc                                    25

<210> SEQ ID NO 447
<211> LENGTH: 25
<212> TYPE: DNA
<213> ORGANISM: Artificial Sequence
<220> FEATURE:
<223> OTHER INFORMATION: Synthetic Probe

<400> SEQUENCE: 447
tattgtactg acctgcgctg tcaaa                                    25

<210> SEQ ID NO 448
<211> LENGTH: 25
<212> TYPE: DNA
<213> ORGANISM: Artificial Sequence
<220> FEATURE:
<223> OTHER INFORMATION: Synthetic Probe

<400> SEQUENCE: 448
agggaattgc tgtgtgtcct gccag                                    25

<210> SEQ ID NO 449
<211> LENGTH: 25
<212> TYPE: DNA
<213> ORGANISM: Artificial Sequence
<220> FEATURE:
<223> OTHER INFORMATION: Synthetic Probe

<400> SEQUENCE: 449
atccaaggaa ggtgttgcca tcatt                                    25

<210> SEQ ID NO 450
<211> LENGTH: 25
<212> TYPE: DNA
<213> ORGANISM: Artificial Sequence
<220> FEATURE:
<223> OTHER INFORMATION: Synthetic Probe

<400> SEQUENCE: 450
tccatcatgg tgtctcagtg gccca                                    25

<210> SEQ ID NO 451
<211> LENGTH: 25
<212> TYPE: DNA
<213> ORGANISM: Artificial Sequence
<220> FEATURE:
<223> OTHER INFORMATION: Synthetic Probe

<400> SEQUENCE: 451
tgcactgtgt cctcaggggt gatca                                    25

<210> SEQ ID NO 452
<211> LENGTH: 25
<212> TYPE: DNA
<213> ORGANISM: Artificial Sequence
<220> FEATURE:
<223> OTHER INFORMATION: Synthetic Probe

<400> SEQUENCE: 452
```

```
gtcctggggt gcactgtgtc ctcag                                              25
```

<210> SEQ ID NO 453
<211> LENGTH: 25
<212> TYPE: DNA
<213> ORGANISM: Artificial Sequence
<220> FEATURE:
<223> OTHER INFORMATION: Synthetic Probe

<400> SEQUENCE: 453

```
gacatggaga catcagtgat tgcac                                              25
```

<210> SEQ ID NO 454
<211> LENGTH: 25
<212> TYPE: DNA
<213> ORGANISM: Artificial Sequence
<220> FEATURE:
<223> OTHER INFORMATION: Synthetic Probe

<400> SEQUENCE: 454

```
cgaggcccag ctttatttcc aacgt                                              25
```

<210> SEQ ID NO 455
<211> LENGTH: 25
<212> TYPE: DNA
<213> ORGANISM: Artificial Sequence
<220> FEATURE:
<223> OTHER INFORMATION: Synthetic Probe

<400> SEQUENCE: 455

```
ctacgccact tggacagagc ccggg                                              25
```

<210> SEQ ID NO 456
<211> LENGTH: 25
<212> TYPE: DNA
<213> ORGANISM: Artificial Sequence
<220> FEATURE:
<223> OTHER INFORMATION: Synthetic Probe

<400> SEQUENCE: 456

```
cccagcttca tcttcaacgt tgtgg                                              25
```

<210> SEQ ID NO 457
<211> LENGTH: 25
<212> TYPE: DNA
<213> ORGANISM: Artificial Sequence
<220> FEATURE:
<223> OTHER INFORMATION: Synthetic Probe

<400> SEQUENCE: 457

```
gacctcccag ggtatccacg ttgga                                              25
```

<210> SEQ ID NO 458
<211> LENGTH: 25
<212> TYPE: DNA
<213> ORGANISM: Artificial Sequence
<220> FEATURE:
<223> OTHER INFORMATION: Synthetic Probe

<400> SEQUENCE: 458

```
atggtgaatg ttgctcatca ctgac                                              25
```

<210> SEQ ID NO 459
<211> LENGTH: 25
<212> TYPE: DNA

```
<213> ORGANISM: Artificial Sequence
<220> FEATURE:
<223> OTHER INFORMATION: Synthetic Probe

<400> SEQUENCE: 459
tctcatggtc gggaaactcg aatgt                                              25

<210> SEQ ID NO 460
<211> LENGTH: 25
<212> TYPE: DNA
<213> ORGANISM: Artificial Sequence
<220> FEATURE:
<223> OTHER INFORMATION: Synthetic Probe

<400> SEQUENCE: 460
tcgtgagata aggacatcat ctgcc                                              25

<210> SEQ ID NO 461
<211> LENGTH: 25
<212> TYPE: DNA
<213> ORGANISM: Artificial Sequence
<220> FEATURE:
<223> OTHER INFORMATION: Synthetic Probe

<400> SEQUENCE: 461
ctggacagag ttttcatcac gagaa                                              25

<210> SEQ ID NO 462
<211> LENGTH: 25
<212> TYPE: DNA
<213> ORGANISM: Artificial Sequence
<220> FEATURE:
<223> OTHER INFORMATION: Synthetic Probe

<400> SEQUENCE: 462
acacagtttc tgtccgcccg tcaat                                              25

<210> SEQ ID NO 463
<211> LENGTH: 25
<212> TYPE: DNA
<213> ORGANISM: Artificial Sequence
<220> FEATURE:
<223> OTHER INFORMATION: Synthetic Probe

<400> SEQUENCE: 463
gtggcacaca ggtgaccaag acggc                                              25

<210> SEQ ID NO 464
<211> LENGTH: 25
<212> TYPE: DNA
<213> ORGANISM: Artificial Sequence
<220> FEATURE:
<223> OTHER INFORMATION: Synthetic Probe

<400> SEQUENCE: 464
ccagagtctc aacactcact aggtg                                              25

<210> SEQ ID NO 465
<211> LENGTH: 25
<212> TYPE: DNA
<213> ORGANISM: Artificial Sequence
<220> FEATURE:
<223> OTHER INFORMATION: Synthetic Probe

<400> SEQUENCE: 465
cgaaagtcag aacgtactca tcagt                                              25
```

<210> SEQ ID NO 466
<211> LENGTH: 25
<212> TYPE: DNA
<213> ORGANISM: Artificial Sequence
<220> FEATURE:
<223> OTHER INFORMATION: Synthetic Probe

<400> SEQUENCE: 466
aaaggcgaca agatccgctt gctgt                                          25

<210> SEQ ID NO 467
<211> LENGTH: 25
<212> TYPE: DNA
<213> ORGANISM: Artificial Sequence
<220> FEATURE:
<223> OTHER INFORMATION: Synthetic Probe

<400> SEQUENCE: 467
ttccgcgatt tctttccctg cacta                                          25

<210> SEQ ID NO 468
<211> LENGTH: 25
<212> TYPE: DNA
<213> ORGANISM: Artificial Sequence
<220> FEATURE:
<223> OTHER INFORMATION: Synthetic Probe

<400> SEQUENCE: 468
aaacacgggg aagcactttc cgcga                                          25

<210> SEQ ID NO 469
<211> LENGTH: 25
<212> TYPE: DNA
<213> ORGANISM: Artificial Sequence
<220> FEATURE:
<223> OTHER INFORMATION: Synthetic Probe

<400> SEQUENCE: 469
tgtctcgggc gctgtgccca gcgca                                          25

<210> SEQ ID NO 470
<211> LENGTH: 25
<212> TYPE: DNA
<213> ORGANISM: Artificial Sequence
<220> FEATURE:
<223> OTHER INFORMATION: Synthetic Probe

<400> SEQUENCE: 470
aaggaaccca cgtatggaag tcatc                                          25

<210> SEQ ID NO 471
<211> LENGTH: 25
<212> TYPE: DNA
<213> ORGANISM: Artificial Sequence
<220> FEATURE:
<223> OTHER INFORMATION: Synthetic Probe

<400> SEQUENCE: 471
aattggaatg tcatcacagc aggcc                                          25

<210> SEQ ID NO 472
<211> LENGTH: 25
<212> TYPE: DNA
<213> ORGANISM: Artificial Sequence
<220> FEATURE:

<223> OTHER INFORMATION: Synthetic Probe

<400> SEQUENCE: 472
gtggcacatc tcacacaagc gtatg                                    25

<210> SEQ ID NO 473
<211> LENGTH: 25
<212> TYPE: DNA
<213> ORGANISM: Artificial Sequence
<220> FEATURE:
<223> OTHER INFORMATION: Synthetic Probe

<400> SEQUENCE: 473
ggcaggaaaa ggctgcaaag cgttt                                    25

<210> SEQ ID NO 474
<211> LENGTH: 25
<212> TYPE: DNA
<213> ORGANISM: Artificial Sequence
<220> FEATURE:
<223> OTHER INFORMATION: Synthetic Probe

<400> SEQUENCE: 474
tttcatagtt attccaaagg tgtcc                                    25

<210> SEQ ID NO 475
<211> LENGTH: 25
<212> TYPE: DNA
<213> ORGANISM: Artificial Sequence
<220> FEATURE:
<223> OTHER INFORMATION: Synthetic Probe

<400> SEQUENCE: 475
gtgacatggc agtttcctca tggca                                    25

<210> SEQ ID NO 476
<211> LENGTH: 25
<212> TYPE: DNA
<213> ORGANISM: Artificial Sequence
<220> FEATURE:
<223> OTHER INFORMATION: Synthetic Probe

<400> SEQUENCE: 476
tggagacatc agtgattgca ctcag                                    25

<210> SEQ ID NO 477
<211> LENGTH: 25
<212> TYPE: DNA
<213> ORGANISM: Artificial Sequence
<220> FEATURE:
<223> OTHER INFORMATION: Synthetic Probe

<400> SEQUENCE: 477
acccaatcat cacgctcatg aacta                                    25

<210> SEQ ID NO 478
<211> LENGTH: 25
<212> TYPE: DNA
<213> ORGANISM: Artificial Sequence
<220> FEATURE:
<223> OTHER INFORMATION: Synthetic Probe

<400> SEQUENCE: 478
tctcctcaga gttatttatc ctcac                                    25

```
<210> SEQ ID NO 479
<211> LENGTH: 25
<212> TYPE: DNA
<213> ORGANISM: Artificial Sequence
<220> FEATURE:
<223> OTHER INFORMATION: Synthetic Probe

<400> SEQUENCE: 479
tcaacagcaa gtcatcagcc gaacg                                        25

<210> SEQ ID NO 480
<211> LENGTH: 25
<212> TYPE: DNA
<213> ORGANISM: Artificial Sequence
<220> FEATURE:
<223> OTHER INFORMATION: Synthetic Probe

<400> SEQUENCE: 480
gctcatggat tcgcacttca aggtt                                        25

<210> SEQ ID NO 481
<211> LENGTH: 25
<212> TYPE: DNA
<213> ORGANISM: Artificial Sequence
<220> FEATURE:
<223> OTHER INFORMATION: Synthetic Probe

<400> SEQUENCE: 481
tgaccacatg gtttattcag gtgaa                                        25

<210> SEQ ID NO 482
<211> LENGTH: 25
<212> TYPE: DNA
<213> ORGANISM: Artificial Sequence
<220> FEATURE:
<223> OTHER INFORMATION: Synthetic Probe

<400> SEQUENCE: 482
aacacaatag gtacctcctc atcgc                                        25

<210> SEQ ID NO 483
<211> LENGTH: 25
<212> TYPE: DNA
<213> ORGANISM: Artificial Sequence
<220> FEATURE:
<223> OTHER INFORMATION: Synthetic Probe

<400> SEQUENCE: 483
tcagaaatcc cttctgtcca ctact                                        25

<210> SEQ ID NO 484
<211> LENGTH: 25
<212> TYPE: DNA
<213> ORGANISM: Artificial Sequence
<220> FEATURE:
<223> OTHER INFORMATION: Synthetic Probe

<400> SEQUENCE: 484
ctacatgctc atttcaggtc agaca                                        25

<210> SEQ ID NO 485
<211> LENGTH: 25
<212> TYPE: DNA
<213> ORGANISM: Artificial Sequence
<220> FEATURE:
<223> OTHER INFORMATION: Synthetic Probe
```

<400> SEQUENCE: 485
caaggaacgg ttccgcagtc tgtct                                              25

<210> SEQ ID NO 486
<211> LENGTH: 25
<212> TYPE: DNA
<213> ORGANISM: Artificial Sequence
<220> FEATURE:
<223> OTHER INFORMATION: Synthetic Probe

<400> SEQUENCE: 486
ataagagtcg tccttgcact gaggt                                              25

<210> SEQ ID NO 487
<211> LENGTH: 25
<212> TYPE: DNA
<213> ORGANISM: Artificial Sequence
<220> FEATURE:
<223> OTHER INFORMATION: Synthetic Probe

<400> SEQUENCE: 487
tctggatttc agcaccgaca ctcag                                              25

<210> SEQ ID NO 488
<211> LENGTH: 25
<212> TYPE: DNA
<213> ORGANISM: Artificial Sequence
<220> FEATURE:
<223> OTHER INFORMATION: Synthetic Probe

<400> SEQUENCE: 488
gccatcatta gccaagcttt tggtg                                              25

<210> SEQ ID NO 489
<211> LENGTH: 25
<212> TYPE: DNA
<213> ORGANISM: Artificial Sequence
<220> FEATURE:
<223> OTHER INFORMATION: Synthetic Probe

<400> SEQUENCE: 489
tgcaccgtgt cctcaggggc agtca                                              25

<210> SEQ ID NO 490
<211> LENGTH: 25
<212> TYPE: DNA
<213> ORGANISM: Artificial Sequence
<220> FEATURE:
<223> OTHER INFORMATION: Synthetic Probe

<400> SEQUENCE: 490
gtcctcaggg gtgatcagag cccag                                              25

<210> SEQ ID NO 491
<211> LENGTH: 25
<212> TYPE: DNA
<213> ORGANISM: Artificial Sequence
<220> FEATURE:
<223> OTHER INFORMATION: Synthetic Probe

<400> SEQUENCE: 491 tcagggtga tcagagccca gtgct                                               25

<210> SEQ ID NO 492
<211> LENGTH: 25

```
<212> TYPE: DNA
<213> ORGANISM: Artificial Sequence
<220> FEATURE:
<223> OTHER INFORMATION: Synthetic Probe

<400> SEQUENCE: 492
atcagaatcg cctcgataat cagtg                                       25

<210> SEQ ID NO 493
<211> LENGTH: 25
<212> TYPE: DNA
<213> ORGANISM: Artificial Sequence
<220> FEATURE:
<223> OTHER INFORMATION: Synthetic Probe

<400> SEQUENCE: 493
gcagttgcag ccaagcaacg ccaga                                       25

<210> SEQ ID NO 494
<211> LENGTH: 25
<212> TYPE: DNA
<213> ORGANISM: Artificial Sequence
<220> FEATURE:
<223> OTHER INFORMATION: Synthetic Probe

<400> SEQUENCE: 494
ttatcttcac ttactgtcag tagca                                       25

<210> SEQ ID NO 495
<211> LENGTH: 25
<212> TYPE: DNA
<213> ORGANISM: Artificial Sequence
<220> FEATURE:
<223> OTHER INFORMATION: Synthetic Probe

<400> SEQUENCE: 495
tcgggatagg tttcatcatt gatta                                       25

<210> SEQ ID NO 496
<211> LENGTH: 25
<212> TYPE: DNA
<213> ORGANISM: Artificial Sequence
<220> FEATURE:
<223> OTHER INFORMATION: Synthetic Probe

<400> SEQUENCE: 496
tcactcagac ccagagtctc aacac                                       25

<210> SEQ ID NO 497
<211> LENGTH: 25
<212> TYPE: DNA
<213> ORGANISM: Artificial Sequence
<220> FEATURE:
<223> OTHER INFORMATION: Synthetic Probe

<400> SEQUENCE: 497
tcagaaattg catctggctt cagca                                       25

<210> SEQ ID NO 498
<211> LENGTH: 25
<212> TYPE: DNA
<213> ORGANISM: Artificial Sequence
<220> FEATURE:
<223> OTHER INFORMATION: Synthetic Probe

<400> SEQUENCE: 498
```

```
caaattcact ttgaggggca cggcc                                          25

<210> SEQ ID NO 499
<211> LENGTH: 25
<212> TYPE: DNA
<213> ORGANISM: Artificial Sequence
<220> FEATURE:
<223> OTHER INFORMATION: Synthetic Probe

<400> SEQUENCE: 499
cagcgtctgc cggaacccgt tccca                                          25

<210> SEQ ID NO 500
<211> LENGTH: 23
<212> TYPE: DNA
<213> ORGANISM: Artificial Sequence
<220> FEATURE:
<223> OTHER INFORMATION: Synthetic Probe

<400> SEQUENCE: 500
gggagtgaag acacggagcc aga                                            23

<210> SEQ ID NO 501
<211> LENGTH: 21
<212> TYPE: DNA
<213> ORGANISM: Artificial Sequence
<220> FEATURE:
<223> OTHER INFORMATION: Synthetic Probe

<400> SEQUENCE: 501
gcggaactta gccactgtga a                                              21

<210> SEQ ID NO 502
<211> LENGTH: 22
<212> TYPE: DNA
<213> ORGANISM: Artificial Sequence
<220> FEATURE:
<223> OTHER INFORMATION: Synthetic Probe

<400> SEQUENCE: 502
gctgcaaaca tccgactgaa ag                                             22

<210> SEQ ID NO 503
<211> LENGTH: 22
<212> TYPE: DNA
<213> ORGANISM: Artificial Sequence
<220> FEATURE:
<223> OTHER INFORMATION: Synthetic Probe

<400> SEQUENCE: 503
cttccagtcg aggatgttta ca                                             22

<210> SEQ ID NO 504
<211> LENGTH: 22
<212> TYPE: DNA
<213> ORGANISM: Artificial Sequence
<220> FEATURE:
<223> OTHER INFORMATION: Synthetic Probe

<400> SEQUENCE: 504
agagtaaaca gccttctccc ag                                             22

<210> SEQ ID NO 505
<211> LENGTH: 22
<212> TYPE: DNA
<213> ORGANISM: Artificial Sequence
```

```
<220> FEATURE:
<223> OTHER INFORMATION: Synthetic Probe

<400> SEQUENCE: 505
gctgtaaaca tccgactgaa ag                                        22

<210> SEQ ID NO 506
<211> LENGTH: 23
<212> TYPE: DNA
<213> ORGANISM: Artificial Sequence
<220> FEATURE:
<223> OTHER INFORMATION: Synthetic Probe

<400> SEQUENCE: 506
gcaatcagct aactacactg cct                                       23

<210> SEQ ID NO 507
<211> LENGTH: 25
<212> TYPE: DNA
<213> ORGANISM: Artificial Sequence
<220> FEATURE:
<223> OTHER INFORMATION: Synthetic Probe

<400> SEQUENCE: 507
ctatgttccc ccattcacaa tacag                                     25

<210> SEQ ID NO 508
<211> LENGTH: 25
<212> TYPE: DNA
<213> ORGANISM: Artificial Sequence
<220> FEATURE:
<223> OTHER INFORMATION: Synthetic Probe

<400> SEQUENCE: 508
tggtgtctca gtggcccaga cacgt                                     25

<210> SEQ ID NO 509
<211> LENGTH: 25
<212> TYPE: DNA
<213> ORGANISM: Artificial Sequence
<220> FEATURE:
<223> OTHER INFORMATION: Synthetic Probe

<400> SEQUENCE: 509
gtgcagccat cgcacactgg gtccc                                     25

<210> SEQ ID NO 510
<211> LENGTH: 22
<212> TYPE: DNA
<213> ORGANISM: Artificial Sequence
<220> FEATURE:
<223> OTHER INFORMATION: Synthetic Probe

<400> SEQUENCE: 510
tgtaaaccat gatgtgctgc ta                                        22

<210> SEQ ID NO 511
<211> LENGTH: 22
<212> TYPE: DNA
<213> ORGANISM: Artificial Sequence
<220> FEATURE:
<223> OTHER INFORMATION: Synthetic Probe

<400> SEQUENCE: 511
ctagtggtcc taaacatttc ac                                        22
```

```
<210> SEQ ID NO 512
<211> LENGTH: 23
<212> TYPE: DNA
<213> ORGANISM: Artificial Sequence
<220> FEATURE:
<223> OTHER INFORMATION: Synthetic Probe

<400> SEQUENCE: 512
gcgcccaatt aatgtctgtt gat                                              23

<210> SEQ ID NO 513
<211> LENGTH: 23
<212> TYPE: DNA
<213> ORGANISM: Artificial Sequence
<220> FEATURE:
<223> OTHER INFORMATION: Synthetic Probe

<400> SEQUENCE: 513
aagaatcttg tcccgcaggt cct                                              23

<210> SEQ ID NO 514
<211> LENGTH: 21
<212> TYPE: DNA
<213> ORGANISM: Artificial Sequence
<220> FEATURE:
<223> OTHER INFORMATION: Synthetic Probe

<400> SEQUENCE: 514
gctccaacct cagcagactg t                                                21

<210> SEQ ID NO 515
<211> LENGTH: 25
<212> TYPE: DNA
<213> ORGANISM: Artificial Sequence
<220> FEATURE:
<223> OTHER INFORMATION: Synthetic Probe

<400> SEQUENCE: 515
attgcgttcg aagtgtcgat gatca                                            25

<210> SEQ ID NO 516
<211> LENGTH: 23
<212> TYPE: DNA
<213> ORGANISM: Artificial Sequence
<220> FEATURE:
<223> OTHER INFORMATION: Synthetic Probe

<400> SEQUENCE: 516
cactgtgggc cctctccgca cca                                              23

<210> SEQ ID NO 517
<211> LENGTH: 22
<212> TYPE: DNA
<213> ORGANISM: Artificial Sequence
<220> FEATURE:
<223> OTHER INFORMATION: Synthetic Probe

<400> SEQUENCE: 517
ccagtgtctc cagtagtaga ca                                               22

<210> SEQ ID NO 518
<211> LENGTH: 22
<212> TYPE: DNA
<213> ORGANISM: Artificial Sequence
<220> FEATURE:
<223> OTHER INFORMATION: Synthetic Probe
```

```
<400> SEQUENCE: 518
agaaaatgcc cctcagtttt ga                                          22

<210> SEQ ID NO 519
<211> LENGTH: 22
<212> TYPE: DNA
<213> ORGANISM: Artificial Sequence
<220> FEATURE:
<223> OTHER INFORMATION: Synthetic Probe

<400> SEQUENCE: 519
ccggctgcaa cacaagacac ga                                          22

<210> SEQ ID NO 520
<211> LENGTH: 22
<212> TYPE: DNA
<213> ORGANISM: Artificial Sequence
<220> FEATURE:
<223> OTHER INFORMATION: Synthetic Probe

<400> SEQUENCE: 520
gctgggtgga gaaggtggtg aa                                          22

<210> SEQ ID NO 521
<211> LENGTH: 23
<212> TYPE: DNA
<213> ORGANISM: Artificial Sequence
<220> FEATURE:
<223> OTHER INFORMATION: Synthetic Probe

<400> SEQUENCE: 521
gaaaaacgcc ccctggcttg aaa                                         23

<210> SEQ ID NO 522
<211> LENGTH: 21
<212> TYPE: DNA
<213> ORGANISM: Artificial Sequence
<220> FEATURE:
<223> OTHER INFORMATION: Synthetic Probe

<400> SEQUENCE: 522
tgattgccac tgtctgcagt a                                           21

<210> SEQ ID NO 523
<211> LENGTH: 22
<212> TYPE: DNA
<213> ORGANISM: Artificial Sequence
<220> FEATURE:
<223> OTHER INFORMATION: Synthetic Probe

<400> SEQUENCE: 523
gacctcagct atgacagcac tt                                          22

<210> SEQ ID NO 524
<211> LENGTH: 22
<212> TYPE: DNA
<213> ORGANISM: Artificial Sequence
<220> FEATURE:
<223> OTHER INFORMATION: Synthetic Probe

<400> SEQUENCE: 524
ataaacgaca cctccttgag aa                                          22

<210> SEQ ID NO 525
```

```
<211> LENGTH: 22
<212> TYPE: DNA
<213> ORGANISM: Artificial Sequence
<220> FEATURE:
<223> OTHER INFORMATION: Synthetic Probe

<400> SEQUENCE: 525
aaagtgcttc ttacctccag at                                              22

<210> SEQ ID NO 526
<211> LENGTH: 22
<212> TYPE: DNA
<213> ORGANISM: Artificial Sequence
<220> FEATURE:
<223> OTHER INFORMATION: Synthetic Probe

<400> SEQUENCE: 526
acactctaaa gggatgcacg at                                              22

<210> SEQ ID NO 527
<211> LENGTH: 22
<212> TYPE: DNA
<213> ORGANISM: Artificial Sequence
<220> FEATURE:
<223> OTHER INFORMATION: Synthetic Probe

<400> SEQUENCE: 527
aacactctaa agggatgcac ga                                              22

<210> SEQ ID NO 528
<211> LENGTH: 21
<212> TYPE: DNA
<213> ORGANISM: Artificial Sequence
<220> FEATURE:
<223> OTHER INFORMATION: Synthetic Probe

<400> SEQUENCE: 528
agaaagtgca tccctctgga g                                               21

<210> SEQ ID NO 529
<211> LENGTH: 23
<212> TYPE: DNA
<213> ORGANISM: Artificial Sequence
<220> FEATURE:
<223> OTHER INFORMATION: Synthetic Probe

<400> SEQUENCE: 529
acagaaagtg cttccctcaa gag                                             23

<210> SEQ ID NO 530
<211> LENGTH: 21
<212> TYPE: DNA
<213> ORGANISM: Artificial Sequence
<220> FEATURE:
<223> OTHER INFORMATION: Synthetic Probe

<400> SEQUENCE: 530
tggaaaccaa gagtgggtcg c                                               21

<210> SEQ ID NO 531
<211> LENGTH: 21
<212> TYPE: DNA
<213> ORGANISM: Artificial Sequence
<220> FEATURE:
<223> OTHER INFORMATION: Synthetic Probe

<400> SEQUENCE: 531
```
aggagactca caagttcctg c                                                    21

<210> SEQ ID NO 532
<211> LENGTH: 22
<212> TYPE: DNA
<213> ORGANISM: Artificial Sequence
<220> FEATURE:
<223> OTHER INFORMATION: Synthetic Probe

<400> SEQUENCE: 532
tcagtggctc aggttcgttg ca                                                   22

<210> SEQ ID NO 533
<211> LENGTH: 22
<212> TYPE: DNA
<213> ORGANISM: Artificial Sequence
<220> FEATURE:
<223> OTHER INFORMATION: Synthetic Probe

<400> SEQUENCE: 533
gtacccctgg agattctgat aa                                                   22

<210> SEQ ID NO 534
<211> LENGTH: 23
<212> TYPE: DNA
<213> ORGANISM: Artificial Sequence
<220> FEATURE:
<223> OTHER INFORMATION: Synthetic Probe

<400> SEQUENCE: 534
caatcagcta atgacactgc cta                                                  23

<210> SEQ ID NO 535
<211> LENGTH: 25
<212> TYPE: DNA
<213> ORGANISM: Artificial Sequence
<220> FEATURE:
<223> OTHER INFORMATION: Synthetic Probe

<400> SEQUENCE: 535
ttcagatttc caaggtttcc atttt                                                25

<210> SEQ ID NO 536
<211> LENGTH: 22
<212> TYPE: DNA
<213> ORGANISM: Artificial Sequence
<220> FEATURE:
<223> OTHER INFORMATION: Synthetic Probe

<400> SEQUENCE: 536
acaaagttct gtgatgcact ga                                                   22

<210> SEQ ID NO 537
<211> LENGTH: 22
<212> TYPE: DNA
<213> ORGANISM: Artificial Sequence
<220> FEATURE:
<223> OTHER INFORMATION: Synthetic Probe

<400> SEQUENCE: 537
agcctatcct ggattacttg aa                                                   22

<210> SEQ ID NO 538
<211> LENGTH: 23
<212> TYPE: DNA

```
<213> ORGANISM: Artificial Sequence
<220> FEATURE:
<223> OTHER INFORMATION: Synthetic Probe

<400> SEQUENCE: 538
cacaaattcg gatctacagg gta                                          23

<210> SEQ ID NO 539
<211> LENGTH: 21
<212> TYPE: DNA
<213> ORGANISM: Artificial Sequence
<220> FEATURE:
<223> OTHER INFORMATION: Synthetic Probe

<400> SEQUENCE: 539
cctcaaggag cttcagtcta g                                            21

<210> SEQ ID NO 540
<211> LENGTH: 21
<212> TYPE: DNA
<213> ORGANISM: Artificial Sequence
<220> FEATURE:
<223> OTHER INFORMATION: Synthetic Probe

<400> SEQUENCE: 540
actagactgt gagctcctcg a                                            21

<210> SEQ ID NO 541
<211> LENGTH: 22
<212> TYPE: DNA
<213> ORGANISM: Artificial Sequence
<220> FEATURE:
<223> OTHER INFORMATION: Synthetic Probe

<400> SEQUENCE: 541
ctgtgaccta tggaattggc ag                                           22

<210> SEQ ID NO 542
<211> LENGTH: 21
<212> TYPE: DNA
<213> ORGANISM: Artificial Sequence
<220> FEATURE:
<223> OTHER INFORMATION: Synthetic Probe

<400> SEQUENCE: 542
ggctgtcaat tcataggtca g                                            21

<210> SEQ ID NO 543
<211> LENGTH: 22
<212> TYPE: DNA
<213> ORGANISM: Artificial Sequence
<220> FEATURE:
<223> OTHER INFORMATION: Synthetic Probe

<400> SEQUENCE: 543
tccacatgga gttgctgtta ca                                           22

<210> SEQ ID NO 544
<211> LENGTH: 22
<212> TYPE: DNA
<213> ORGANISM: Artificial Sequence
<220> FEATURE:
<223> OTHER INFORMATION: Synthetic Probe

<400> SEQUENCE: 544
tcatcattac caggcagtat ta                                           22
```

<210> SEQ ID NO 545
<211> LENGTH: 23
<212> TYPE: DNA
<213> ORGANISM: Artificial Sequence
<220> FEATURE:
<223> OTHER INFORMATION: Synthetic Probe

<400> SEQUENCE: 545
aacactgatt tcaaatggtg cta                                           23

<210> SEQ ID NO 546
<211> LENGTH: 22
<212> TYPE: DNA
<213> ORGANISM: Artificial Sequence
<220> FEATURE:
<223> OTHER INFORMATION: Synthetic Probe

<400> SEQUENCE: 546
agctgagtgt aggatgttta ca                                            22

<210> SEQ ID NO 547
<211> LENGTH: 22
<212> TYPE: DNA
<213> ORGANISM: Artificial Sequence
<220> FEATURE:
<223> OTHER INFORMATION: Synthetic Probe

<400> SEQUENCE: 547
cttccagtcg gggatgttta ca                                            22

<210> SEQ ID NO 548
<211> LENGTH: 21
<212> TYPE: DNA
<213> ORGANISM: Artificial Sequence
<220> FEATURE:
<223> OTHER INFORMATION: Synthetic Probe

<400> SEQUENCE: 548
ggactataga actttccccc t                                             21

<210> SEQ ID NO 549
<211> LENGTH: 22
<212> TYPE: DNA
<213> ORGANISM: Artificial Sequence
<220> FEATURE:
<223> OTHER INFORMATION: Synthetic Probe

<400> SEQUENCE: 549
aactatacaa cctcctacct ca                                            22

<210> SEQ ID NO 550
<211> LENGTH: 23
<212> TYPE: DNA
<213> ORGANISM: Artificial Sequence
<220> FEATURE:
<223> OTHER INFORMATION: Synthetic Probe

<400> SEQUENCE: 550
cacaaattcg gttctacagg gta                                           23

<210> SEQ ID NO 551
<211> LENGTH: 24
<212> TYPE: DNA
<213> ORGANISM: Artificial Sequence
<220> FEATURE:

<223> OTHER INFORMATION: Synthetic Probe

<400> SEQUENCE: 551
tcacaggtta aagggtctca ggga                                          24

<210> SEQ ID NO 552
<211> LENGTH: 22
<212> TYPE: DNA
<213> ORGANISM: Artificial Sequence
<220> FEATURE:
<223> OTHER INFORMATION: Synthetic Probe

<400> SEQUENCE: 552
ccatctttac cagacagtgt ta                                            22

<210> SEQ ID NO 553
<211> LENGTH: 22
<212> TYPE: DNA
<213> ORGANISM: Artificial Sequence
<220> FEATURE:
<223> OTHER INFORMATION: Synthetic Probe

<400> SEQUENCE: 553
tccagcactg tccggtaaga tg                                            22

<210> SEQ ID NO 554
<211> LENGTH: 22
<212> TYPE: DNA
<213> ORGANISM: Artificial Sequence
<220> FEATURE:
<223> OTHER INFORMATION: Synthetic Probe

<400> SEQUENCE: 554
acatcgttac cagacagtgt ta                                            22

<210> SEQ ID NO 555
<211> LENGTH: 22
<212> TYPE: DNA
<213> ORGANISM: Artificial Sequence
<220> FEATURE:
<223> OTHER INFORMATION: Synthetic Probe

<400> SEQUENCE: 555
tccaatgctg cccagtaaga tg                                            22

<210> SEQ ID NO 556
<211> LENGTH: 23
<212> TYPE: DNA
<213> ORGANISM: Artificial Sequence
<220> FEATURE:
<223> OTHER INFORMATION: Synthetic Probe

<400> SEQUENCE: 556
tccatcatta cccggcagta tta                                           23

<210> SEQ ID NO 557
<211> LENGTH: 22
<212> TYPE: DNA
<213> ORGANISM: Artificial Sequence
<220> FEATURE:
<223> OTHER INFORMATION: Synthetic Probe

<400> SEQUENCE: 557
acggttttac cagacagtat ta                                            22

```
<210> SEQ ID NO 558
<211> LENGTH: 23
<212> TYPE: DNA
<213> ORGANISM: Artificial Sequence
<220> FEATURE:
<223> OTHER INFORMATION: Synthetic Probe

<400> SEQUENCE: 558
gaaagtgctt ctttcctcga gaa                                           23

<210> SEQ ID NO 559
<211> LENGTH: 22
<212> TYPE: DNA
<213> ORGANISM: Artificial Sequence
<220> FEATURE:
<223> OTHER INFORMATION: Synthetic Probe

<400> SEQUENCE: 559
cgcaaggtcg gttctacggg tg                                            22

<210> SEQ ID NO 560
<211> LENGTH: 25
<212> TYPE: DNA
<213> ORGANISM: Artificial Sequence
<220> FEATURE:
<223> OTHER INFORMATION: Synthetic Probe

<400> SEQUENCE: 560
aaccatctca tacaaaccaa ctact                                         25

<210> SEQ ID NO 561
<211> LENGTH: 22
<212> TYPE: DNA
<213> ORGANISM: Artificial Sequence
<220> FEATURE:
<223> OTHER INFORMATION: Synthetic Probe

<400> SEQUENCE: 561
agagcaagac cccgtctcta aa                                            22

<210> SEQ ID NO 562
<211> LENGTH: 22
<212> TYPE: DNA
<213> ORGANISM: Artificial Sequence
<220> FEATURE:
<223> OTHER INFORMATION: Synthetic Probe

<400> SEQUENCE: 562
tccaacactg tactggaaga tg                                            22

<210> SEQ ID NO 563
<211> LENGTH: 24
<212> TYPE: DNA
<213> ORGANISM: Artificial Sequence
<220> FEATURE:
<223> OTHER INFORMATION: Synthetic Probe

<400> SEQUENCE: 563
agtgtgagtt ctaccattgc caaa                                          24

<210> SEQ ID NO 564
<211> LENGTH: 22
<212> TYPE: DNA
<213> ORGANISM: Artificial Sequence
<220> FEATURE:
<223> OTHER INFORMATION: Synthetic Probe
```

```
<400> SEQUENCE: 564
ttatggccct tcggtaattc ac                                              22

<210> SEQ ID NO 565
<211> LENGTH: 22
<212> TYPE: DNA
<213> ORGANISM: Artificial Sequence
<220> FEATURE:
<223> OTHER INFORMATION: Synthetic Probe

<400> SEQUENCE: 565
agtgaattct accagtgcca ta                                              22

<210> SEQ ID NO 566
<211> LENGTH: 21
<212> TYPE: DNA
<213> ORGANISM: Artificial Sequence
<220> FEATURE:
<223> OTHER INFORMATION: Synthetic Probe

<400> SEQUENCE: 566
gtctgtcaat tcataggtca t                                               21

<210> SEQ ID NO 567
<211> LENGTH: 21
<212> TYPE: DNA
<213> ORGANISM: Artificial Sequence
<220> FEATURE:
<223> OTHER INFORMATION: Synthetic Probe

<400> SEQUENCE: 567
gcagaactta gccactgtga a                                               21

<210> SEQ ID NO 568
<211> LENGTH: 21
<212> TYPE: DNA
<213> ORGANISM: Artificial Sequence
<220> FEATURE:
<223> OTHER INFORMATION: Synthetic Probe

<400> SEQUENCE: 568
ttctaggata ggcccagggg c                                               21

<210> SEQ ID NO 569
<211> LENGTH: 22
<212> TYPE: DNA
<213> ORGANISM: Artificial Sequence
<220> FEATURE:
<223> OTHER INFORMATION: Synthetic Probe

<400> SEQUENCE: 569
cggacccaca gacacgagct tg                                              22

<210> SEQ ID NO 570
<211> LENGTH: 23
<212> TYPE: DNA
<213> ORGANISM: Artificial Sequence
<220> FEATURE:
<223> OTHER INFORMATION: Synthetic Probe

<400> SEQUENCE: 570
acaacaaaat cactagtctt cca                                             23

<210> SEQ ID NO 571
<211> LENGTH: 21
```

```
<212> TYPE: DNA
<213> ORGANISM: Artificial Sequence
<220> FEATURE:
<223> OTHER INFORMATION: Synthetic Probe

<400> SEQUENCE: 571
ggaaatccct ggcaatgtga t                                          21

<210> SEQ ID NO 572
<211> LENGTH: 22
<212> TYPE: DNA
<213> ORGANISM: Artificial Sequence
<220> FEATURE:
<223> OTHER INFORMATION: Synthetic Probe

<400> SEQUENCE: 572
cagaaagtgc ttccctctag ag                                         22

<210> SEQ ID NO 573
<211> LENGTH: 22
<212> TYPE: DNA
<213> ORGANISM: Artificial Sequence
<220> FEATURE:
<223> OTHER INFORMATION: Synthetic Probe

<400> SEQUENCE: 573
cagaaagcgc ttccctctag ag                                         22

<210> SEQ ID NO 574
<211> LENGTH: 22
<212> TYPE: DNA
<213> ORGANISM: Artificial Sequence
<220> FEATURE:
<223> OTHER INFORMATION: Synthetic Probe

<400> SEQUENCE: 574
acactctaaa aggatgcact tt                                         22

<210> SEQ ID NO 575
<211> LENGTH: 22
<212> TYPE: DNA
<213> ORGANISM: Artificial Sequence
<220> FEATURE:
<223> OTHER INFORMATION: Synthetic Probe

<400> SEQUENCE: 575
aactatacaa cctactacct ca                                         22

<210> SEQ ID NO 576
<211> LENGTH: 22
<212> TYPE: DNA
<213> ORGANISM: Artificial Sequence
<220> FEATURE:
<223> OTHER INFORMATION: Synthetic Probe

<400> SEQUENCE: 576
aaccatacaa cctactacct ca                                         22

<210> SEQ ID NO 577
<211> LENGTH: 22
<212> TYPE: DNA
<213> ORGANISM: Artificial Sequence
<220> FEATURE:
<223> OTHER INFORMATION: Synthetic Probe

<400> SEQUENCE: 577
```
aactatacaa tctactacct ca 22

<210> SEQ ID NO 578
<211> LENGTH: 22
<212> TYPE: DNA
<213> ORGANISM: Artificial Sequence
<220> FEATURE:
<223> OTHER INFORMATION: Synthetic Probe

<400> SEQUENCE: 578
taaagcttgc cactgaagaa ct 22

<210> SEQ ID NO 579
<211> LENGTH: 22
<212> TYPE: DNA
<213> ORGANISM: Artificial Sequence
<220> FEATURE:
<223> OTHER INFORMATION: Synthetic Probe

<400> SEQUENCE: 579
ctgtgtttca gctcagtagg ca 22

<210> SEQ ID NO 580
<211> LENGTH: 22
<212> TYPE: DNA
<213> ORGANISM: Artificial Sequence
<220> FEATURE:
<223> OTHER INFORMATION: Synthetic Probe

<400> SEQUENCE: 580
ctgttcctgc tgaactgagc ca 22

<210> SEQ ID NO 581
<211> LENGTH: 22
<212> TYPE: DNA
<213> ORGANISM: Artificial Sequence
<220> FEATURE:
<223> OTHER INFORMATION: Synthetic Probe

<400> SEQUENCE: 581
ctcagtccca ggcaaaccat aa 22

<210> SEQ ID NO 582
<211> LENGTH: 22
<212> TYPE: DNA
<213> ORGANISM: Artificial Sequence
<220> FEATURE:
<223> OTHER INFORMATION: Synthetic Probe

<400> SEQUENCE: 582
tatccactac accccgctgc ct 22

<210> SEQ ID NO 583
<211> LENGTH: 22
<212> TYPE: DNA
<213> ORGANISM: Artificial Sequence
<220> FEATURE:
<223> OTHER INFORMATION: Synthetic Probe

<400> SEQUENCE: 583
agcgggactt tgagggccag tt 22

<210> SEQ ID NO 584
<211> LENGTH: 22
<212> TYPE: DNA
<213> ORGANISM: Artificial Sequence

```
<220> FEATURE:
<223> OTHER INFORMATION: Synthetic Probe

<400> SEQUENCE: 584
taaccgattt cagatggtgc ta                                              22

<210> SEQ ID NO 585
<211> LENGTH: 25
<212> TYPE: DNA
<213> ORGANISM: Artificial Sequence
<220> FEATURE:
<223> OTHER INFORMATION: Synthetic Probe

<400> SEQUENCE: 585
tgacatctgg aatgagtccc tcagc                                           25

<210> SEQ ID NO 586
<211> LENGTH: 25
<212> TYPE: DNA
<213> ORGANISM: Artificial Sequence
<220> FEATURE:
<223> OTHER INFORMATION: Synthetic Probe

<400> SEQUENCE: 586
tgtatatatg gaagtcatca tcgat                                           25

<210> SEQ ID NO 587
<211> LENGTH: 25
<212> TYPE: DNA
<213> ORGANISM: Artificial Sequence
<220> FEATURE:
<223> OTHER INFORMATION: Synthetic Probe

<400> SEQUENCE: 587
catgtattga ggtcatcatc gatcc                                           25

<210> SEQ ID NO 588
<211> LENGTH: 25
<212> TYPE: DNA
<213> ORGANISM: Artificial Sequence
<220> FEATURE:
<223> OTHER INFORMATION: Synthetic Probe

<400> SEQUENCE: 588
gttcagattt ccaaggtttc cattt                                           25

<210> SEQ ID NO 589
<211> LENGTH: 25
<212> TYPE: DNA
<213> ORGANISM: Artificial Sequence
<220> FEATURE:
<223> OTHER INFORMATION: Synthetic Probe

<400> SEQUENCE: 589
gctcacagaa gtgtcttggt cactc                                           25

<210> SEQ ID NO 590
<211> LENGTH: 21
<212> TYPE: DNA
<213> ORGANISM: Artificial Sequence
<220> FEATURE:
<223> OTHER INFORMATION: Synthetic Probe

<400> SEQUENCE: 590
ggtaatccct ggcaatgtga t                                               21
```

<210> SEQ ID NO 591
<211> LENGTH: 22
<212> TYPE: DNA
<213> ORGANISM: Artificial Sequence
<220> FEATURE:
<223> OTHER INFORMATION: Synthetic Probe

<400> SEQUENCE: 591
aaatcagcat gccaggaacc ca                                              22

<210> SEQ ID NO 592
<211> LENGTH: 22
<212> TYPE: DNA
<213> ORGANISM: Artificial Sequence
<220> FEATURE:
<223> OTHER INFORMATION: Synthetic Probe

<400> SEQUENCE: 592
tcaacatcag tctgataagc ta                                              22

<210> SEQ ID NO 593
<211> LENGTH: 22
<212> TYPE: DNA
<213> ORGANISM: Artificial Sequence
<220> FEATURE:
<223> OTHER INFORMATION: Synthetic Probe

<400> SEQUENCE: 593
tgctcacaag cagctaagcc ct                                              22

<210> SEQ ID NO 594
<211> LENGTH: 22
<212> TYPE: DNA
<213> ORGANISM: Artificial Sequence
<220> FEATURE:
<223> OTHER INFORMATION: Synthetic Probe

<400> SEQUENCE: 594
ctcaatagac tgtgagctcc tt                                              22

<210> SEQ ID NO 595
<211> LENGTH: 23
<212> TYPE: DNA
<213> ORGANISM: Artificial Sequence
<220> FEATURE:
<223> OTHER INFORMATION: Synthetic Probe

<400> SEQUENCE: 595
gcacatgtgc acacagccgg gtg                                             23

<210> SEQ ID NO 596
<211> LENGTH: 22
<212> TYPE: DNA
<213> ORGANISM: Artificial Sequence
<220> FEATURE:
<223> OTHER INFORMATION: Synthetic Probe

<400> SEQUENCE: 596
aacagcacaa actactacct ca                                              22

<210> SEQ ID NO 597
<211> LENGTH: 24
<212> TYPE: DNA
<213> ORGANISM: Artificial Sequence
<220> FEATURE:
<223> OTHER INFORMATION: Synthetic Probe

<400> SEQUENCE: 597
gaagtcactc ccaggcagct gcaa                                          24

<210> SEQ ID NO 598
<211> LENGTH: 25
<212> TYPE: DNA
<213> ORGANISM: Artificial Sequence
<220> FEATURE:
<223> OTHER INFORMATION: Synthetic Probe

<400> SEQUENCE: 598
tcacccaaca ctcatacgcc ggcag                                         25

<210> SEQ ID NO 599
<211> LENGTH: 25
<212> TYPE: DNA
<213> ORGANISM: Artificial Sequence
<220> FEATURE:
<223> OTHER INFORMATION: Synthetic Probe

<400> SEQUENCE: 599
ggacctcaga cttccagacc tgtat                                         25

<210> SEQ ID NO 600
<211> LENGTH: 22
<212> TYPE: DNA
<213> ORGANISM: Artificial Sequence
<220> FEATURE:
<223> OTHER INFORMATION: Synthetic Probe

<400> SEQUENCE: 600
aaccacacaa cctactacct ca                                            22

<210> SEQ ID NO 601
<211> LENGTH: 22
<212> TYPE: DNA
<213> ORGANISM: Artificial Sequence
<220> FEATURE:
<223> OTHER INFORMATION: Synthetic Probe

<400> SEQUENCE: 601
ggctcccaag aacctcacct gt                                            22

<210> SEQ ID NO 602
<211> LENGTH: 22
<212> TYPE: DNA
<213> ORGANISM: Artificial Sequence
<220> FEATURE:
<223> OTHER INFORMATION: Synthetic Probe

<400> SEQUENCE: 602
tcacaagtta gggtctcagg ga                                            22

<210> SEQ ID NO 603
<211> LENGTH: 22
<212> TYPE: DNA
<213> ORGANISM: Artificial Sequence
<220> FEATURE:
<223> OTHER INFORMATION: Synthetic Probe

<400> SEQUENCE: 603
gactcgaacc actgatccag ca                                            22

<210> SEQ ID NO 604

```
<211> LENGTH: 22
<212> TYPE: DNA
<213> ORGANISM: Artificial Sequence
<220> FEATURE:
<223> OTHER INFORMATION: Synthetic Probe

<400> SEQUENCE: 604
aaatcccatc cccaggaacc cc                                             22

<210> SEQ ID NO 605
<211> LENGTH: 22
<212> TYPE: DNA
<213> ORGANISM: Artificial Sequence
<220> FEATURE:
<223> OTHER INFORMATION: Synthetic Probe

<400> SEQUENCE: 605
tccaggagct cacaatctag tg                                             22

<210> SEQ ID NO 606
<211> LENGTH: 22
<212> TYPE: DNA
<213> ORGANISM: Artificial Sequence
<220> FEATURE:
<223> OTHER INFORMATION: Synthetic Probe

<400> SEQUENCE: 606
atgtatgtgg gacggtaaac ca                                             22

<210> SEQ ID NO 607
<211> LENGTH: 21
<212> TYPE: DNA
<213> ORGANISM: Artificial Sequence
<220> FEATURE:
<223> OTHER INFORMATION: Synthetic Probe

<400> SEQUENCE: 607
acgtggattt tcctctatga t                                              21

<210> SEQ ID NO 608
<211> LENGTH: 22
<212> TYPE: DNA
<213> ORGANISM: Artificial Sequence
<220> FEATURE:
<223> OTHER INFORMATION: Synthetic Probe

<400> SEQUENCE: 608
tcagtttcct ctgcaaacag tt                                             22

<210> SEQ ID NO 609
<211> LENGTH: 22
<212> TYPE: DNA
<213> ORGANISM: Artificial Sequence
<220> FEATURE:
<223> OTHER INFORMATION: Synthetic Probe

<400> SEQUENCE: 609
aactggatgt ccctgtatga tt                                             22

<210> SEQ ID NO 610
<211> LENGTH: 22
<212> TYPE: DNA
<213> ORGANISM: Artificial Sequence
<220> FEATURE:
<223> OTHER INFORMATION: Synthetic Probe

<400> SEQUENCE: 610
```
aagaagtgca ccatgtttgt tt                                            22

<210> SEQ ID NO 611
<211> LENGTH: 22
<212> TYPE: DNA
<213> ORGANISM: Artificial Sequence
<220> FEATURE:
<223> OTHER INFORMATION: Synthetic Probe

<400> SEQUENCE: 611
gcacatgttc tgcggcccac ca                                            22

<210> SEQ ID NO 612
<211> LENGTH: 22
<212> TYPE: DNA
<213> ORGANISM: Artificial Sequence
<220> FEATURE:
<223> OTHER INFORMATION: Synthetic Probe

<400> SEQUENCE: 612
ggtacagtca acggtcagtg gt                                            22

<210> SEQ ID NO 613
<211> LENGTH: 22
<212> TYPE: DNA
<213> ORGANISM: Artificial Sequence
<220> FEATURE:
<223> OTHER INFORMATION: Synthetic Probe

<400> SEQUENCE: 613
aaatctacat tgtatgccag gt                                            22

<210> SEQ ID NO 614
<211> LENGTH: 22
<212> TYPE: DNA
<213> ORGANISM: Artificial Sequence
<220> FEATURE:
<223> OTHER INFORMATION: Synthetic Probe

<400> SEQUENCE: 614
atggcaatat gttggcatag ca                                            22

<210> SEQ ID NO 615
<211> LENGTH: 21
<212> TYPE: DNA
<213> ORGANISM: Artificial Sequence
<220> FEATURE:
<223> OTHER INFORMATION: Synthetic Probe

<400> SEQUENCE: 615
agctatgcca gcatcttgcc t                                             21

<210> SEQ ID NO 616
<211> LENGTH: 25
<212> TYPE: DNA
<213> ORGANISM: Artificial Sequence
<220> FEATURE:
<223> OTHER INFORMATION: Synthetic Probe

<400> SEQUENCE: 616 gtttttttg gaggactcat catcg                                          25

<210> SEQ ID NO 617
<211> LENGTH: 22
<212> TYPE: DNA

```
<213> ORGANISM: Artificial Sequence
<220> FEATURE:
<223> OTHER INFORMATION: Synthetic Probe

<400> SEQUENCE: 617
cctcatggaa gggttcccca ct                                              22

<210> SEQ ID NO 618
<211> LENGTH: 24
<212> TYPE: DNA
<213> ORGANISM: Artificial Sequence
<220> FEATURE:
<223> OTHER INFORMATION: Synthetic Probe

<400> SEQUENCE: 618
tctgggaacc ggcatttgtt ctga                                            24

<210> SEQ ID NO 619
<211> LENGTH: 22
<212> TYPE: DNA
<213> ORGANISM: Artificial Sequence
<220> FEATURE:
<223> OTHER INFORMATION: Synthetic Probe

<400> SEQUENCE: 619
tgctgttagc cctagccccg ca                                              22

<210> SEQ ID NO 620
<211> LENGTH: 23
<212> TYPE: DNA
<213> ORGANISM: Artificial Sequence
<220> FEATURE:
<223> OTHER INFORMATION: Synthetic Probe

<400> SEQUENCE: 620
gaaacccagc agacaatgta gct                                             23

<210> SEQ ID NO 621
<211> LENGTH: 21
<212> TYPE: DNA
<213> ORGANISM: Artificial Sequence
<220> FEATURE:
<223> OTHER INFORMATION: Synthetic Probe

<400> SEQUENCE: 621
acccagtagc cagatgtagc t                                               21

<210> SEQ ID NO 622
<211> LENGTH: 24
<212> TYPE: DNA
<213> ORGANISM: Artificial Sequence
<220> FEATURE:
<223> OTHER INFORMATION: Synthetic Probe

<400> SEQUENCE: 622
tctaaaccac catatgaaac cagc                                            24

<210> SEQ ID NO 623
<211> LENGTH: 22
<212> TYPE: DNA
<213> ORGANISM: Artificial Sequence
<220> FEATURE:
<223> OTHER INFORMATION: Synthetic Probe

<400> SEQUENCE: 623
aactatgcaa cctactacct ct                                              22
```

<210> SEQ ID NO 624
<211> LENGTH: 22
<212> TYPE: DNA
<213> ORGANISM: Artificial Sequence
<220> FEATURE:
<223> OTHER INFORMATION: Synthetic Probe

<400> SEQUENCE: 624
aactgtacaa actactacct ca                                            22

<210> SEQ ID NO 625
<211> LENGTH: 23
<212> TYPE: DNA
<213> ORGANISM: Artificial Sequence
<220> FEATURE:
<223> OTHER INFORMATION: Synthetic Probe

<400> SEQUENCE: 625
cggcctgatt cacaacacca gct                                           23

<210> SEQ ID NO 626
<211> LENGTH: 25
<212> TYPE: DNA
<213> ORGANISM: Artificial Sequence
<220> FEATURE:
<223> OTHER INFORMATION: Synthetic Probe

<400> SEQUENCE: 626
aggtcagact agtggttcgc ttcag                                         25

<210> SEQ ID NO 627
<211> LENGTH: 25
<212> TYPE: DNA
<213> ORGANISM: Artificial Sequence
<220> FEATURE:
<223> OTHER INFORMATION: Synthetic Probe

<400> SEQUENCE: 627
atcacccaac actcatacgc cggca                                         25

<210> SEQ ID NO 628
<211> LENGTH: 25
<212> TYPE: DNA
<213> ORGANISM: Artificial Sequence
<220> FEATURE:
<223> OTHER INFORMATION: Synthetic Probe

<400> SEQUENCE: 628
ttcaccgtca atgactcata cgcca                                         25

<210> SEQ ID NO 629
<211> LENGTH: 25
<212> TYPE: DNA
<213> ORGANISM: Artificial Sequence
<220> FEATURE:
<223> OTHER INFORMATION: Synthetic Probe

<400> SEQUENCE: 629
atgtgactca tactccacca gtgct                                         25

<210> SEQ ID NO 630
<211> LENGTH: 25
<212> TYPE: DNA
<213> ORGANISM: Artificial Sequence
<220> FEATURE:

-continued

```
<223> OTHER INFORMATION: Synthetic Probe

<400> SEQUENCE: 630
atactccacc agtgctcatc atcga                                           25

<210> SEQ ID NO 631
<211> LENGTH: 22
<212> TYPE: DNA
<213> ORGANISM: Artificial Sequence
<220> FEATURE:
<223> OTHER INFORMATION: Synthetic Probe

<400> SEQUENCE: 631
atcagagccc tctgagcttc ag                                              22

<210> SEQ ID NO 632
<211> LENGTH: 22
<212> TYPE: DNA
<213> ORGANISM: Artificial Sequence
<220> FEATURE:
<223> OTHER INFORMATION: Synthetic Probe

<400> SEQUENCE: 632
accagagatg cagcactgca cc                                              22

<210> SEQ ID NO 633
<211> LENGTH: 22
<212> TYPE: DNA
<213> ORGANISM: Artificial Sequence
<220> FEATURE:
<223> OTHER INFORMATION: Synthetic Probe

<400> SEQUENCE: 633
tcatctcgcc ctcaaaaccc cg                                              22

<210> SEQ ID NO 634
<211> LENGTH: 23
<212> TYPE: DNA
<213> ORGANISM: Artificial Sequence
<220> FEATURE:
<223> OTHER INFORMATION: Synthetic Probe

<400> SEQUENCE: 634
gaacaggtag tctgaacact ggg                                             23

<210> SEQ ID NO 635
<211> LENGTH: 22
<212> TYPE: DNA
<213> ORGANISM: Artificial Sequence
<220> FEATURE:
<223> OTHER INFORMATION: Synthetic Probe

<400> SEQUENCE: 635
tcagccgctg tcacacgcac ag                                              22

<210> SEQ ID NO 636
<211> LENGTH: 22
<212> TYPE: DNA
<213> ORGANISM: Artificial Sequence
<220> FEATURE:
<223> OTHER INFORMATION: Synthetic Probe

<400> SEQUENCE: 636
actgcctgtc tgtgcctgct gt                                              22
```

```
<210> SEQ ID NO 637
<211> LENGTH: 21
<212> TYPE: DNA
<213> ORGANISM: Artificial Sequence
<220> FEATURE:
<223> OTHER INFORMATION: Synthetic Probe

<400> SEQUENCE: 637
acaggccatc tgtgttatat t                                        21

<210> SEQ ID NO 638
<211> LENGTH: 23
<212> TYPE: DNA
<213> ORGANISM: Artificial Sequence
<220> FEATURE:
<223> OTHER INFORMATION: Synthetic Probe

<400> SEQUENCE: 638
tctcgtgaca tgatgatccc cga                                      23

<210> SEQ ID NO 639
<211> LENGTH: 23
<212> TYPE: DNA
<213> ORGANISM: Artificial Sequence
<220> FEATURE:
<223> OTHER INFORMATION: Synthetic Probe

<400> SEQUENCE: 639
gcggtagcgg aagcggtaac tgg                                      23

<210> SEQ ID NO 640
<211> LENGTH: 25
<212> TYPE: DNA
<213> ORGANISM: Artificial Sequence
<220> FEATURE:
<223> OTHER INFORMATION: Synthetic Probe

<400> SEQUENCE: 640
agcttttcca aggaatgttt ttata                                    25

<210> SEQ ID NO 641
<211> LENGTH: 25
<212> TYPE: DNA
<213> ORGANISM: Artificial Sequence
<220> FEATURE:
<223> OTHER INFORMATION: Synthetic Probe

<400> SEQUENCE: 641
atgcatgtat tgaggtcatc atcga                                    25

<210> SEQ ID NO 642
<211> LENGTH: 25
<212> TYPE: DNA
<213> ORGANISM: Artificial Sequence
<220> FEATURE:
<223> OTHER INFORMATION: Synthetic Probe

<400> SEQUENCE: 642
ttgttcagat ttccaaggtt tccat                                    25

<210> SEQ ID NO 643
<211> LENGTH: 25
<212> TYPE: DNA
<213> ORGANISM: Artificial Sequence
<220> FEATURE:
<223> OTHER INFORMATION: Synthetic Probe
```

```
<400> SEQUENCE: 643
tgccatcaga actctaacat gctat                                        25

<210> SEQ ID NO 644
<211> LENGTH: 22
<212> TYPE: DNA
<213> ORGANISM: Artificial Sequence
<220> FEATURE:
<223> OTHER INFORMATION: Synthetic Probe

<400> SEQUENCE: 644
cccaacaaca ggaaactacc ta                                           22

<210> SEQ ID NO 645
<211> LENGTH: 23
<212> TYPE: DNA
<213> ORGANISM: Artificial Sequence
<220> FEATURE:
<223> OTHER INFORMATION: Synthetic Probe

<400> SEQUENCE: 645
acactcaaaa gatggcggca ctt                                          23

<210> SEQ ID NO 646
<211> LENGTH: 23
<212> TYPE: DNA
<213> ORGANISM: Artificial Sequence
<220> FEATURE:
<223> OTHER INFORMATION: Synthetic Probe

<400> SEQUENCE: 646
acgctcaaat gtcgcagcac ttt                                          23

<210> SEQ ID NO 647
<211> LENGTH: 21
<212> TYPE: DNA
<213> ORGANISM: Artificial Sequence
<220> FEATURE:
<223> OTHER INFORMATION: Synthetic Probe

<400> SEQUENCE: 647
aagggtcagt aagcacccgc g                                            21

<210> SEQ ID NO 648
<211> LENGTH: 25
<212> TYPE: DNA
<213> ORGANISM: Artificial Sequence
<220> FEATURE:
<223> OTHER INFORMATION: Synthetic Probe

<400> SEQUENCE: 648
gaatgagtcc ctcagcatcc tcaga                                        25

<210> SEQ ID NO 649
<211> LENGTH: 25
<212> TYPE: DNA
<213> ORGANISM: Artificial Sequence
<220> FEATURE:
<223> OTHER INFORMATION: Synthetic Probe

<400> SEQUENCE: 649
gggcaatatc aggttctcat cattg                                        25

<210> SEQ ID NO 650
<211> LENGTH: 25
```

<212> TYPE: DNA
<213> ORGANISM: Artificial Sequence
<220> FEATURE:
<223> OTHER INFORMATION: Synthetic Probe

<400> SEQUENCE: 650
aatgcatgta ttgaggtcat catcg                                          25

<210> SEQ ID NO 651
<211> LENGTH: 22
<212> TYPE: DNA
<213> ORGANISM: Artificial Sequence
<220> FEATURE:
<223> OTHER INFORMATION: Synthetic Probe

<400> SEQUENCE: 651
actttcggtt atctagcttt at                                             22

<210> SEQ ID NO 652
<211> LENGTH: 22
<212> TYPE: DNA
<213> ORGANISM: Artificial Sequence
<220> FEATURE:
<223> OTHER INFORMATION: Synthetic Probe

<400> SEQUENCE: 652
aacaatacaa cttactacct ca                                             22

<210> SEQ ID NO 653
<211> LENGTH: 25
<212> TYPE: DNA
<213> ORGANISM: Artificial Sequence
<220> FEATURE:
<223> OTHER INFORMATION: Synthetic Probe

<400> SEQUENCE: 653
atactccatc acctggttcc cagaa                                          25

<210> SEQ ID NO 654
<211> LENGTH: 22
<212> TYPE: DNA
<213> ORGANISM: Artificial Sequence
<220> FEATURE:
<223> OTHER INFORMATION: Synthetic Probe

<400> SEQUENCE: 654
gttcaccaat cagctaagct ct                                             22

<210> SEQ ID NO 655
<211> LENGTH: 22
<212> TYPE: DNA
<213> ORGANISM: Artificial Sequence
<220> FEATURE:
<223> OTHER INFORMATION: Synthetic Probe

<400> SEQUENCE: 655
tcgccctctc aacccagctt tt                                             22

<210> SEQ ID NO 656
<211> LENGTH: 22
<212> TYPE: DNA
<213> ORGANISM: Artificial Sequence
<220> FEATURE:
<223> OTHER INFORMATION: Synthetic Probe

<400> SEQUENCE: 656

```
ttgccctctc aacccagctt tt                                                  22
```

<210> SEQ ID NO 657
<211> LENGTH: 25
<212> TYPE: DNA
<213> ORGANISM: Artificial Sequence
<220> FEATURE:
<223> OTHER INFORMATION: Synthetic Probe

<400> SEQUENCE: 657

```
acctcagttc cgatgagaat gacgt                                               25
```

<210> SEQ ID NO 658
<211> LENGTH: 22
<212> TYPE: DNA
<213> ORGANISM: Artificial Sequence
<220> FEATURE:
<223> OTHER INFORMATION: Synthetic Probe

<400> SEQUENCE: 658

```
ctggagacac gtgcactgta ga                                                  22
```

<210> SEQ ID NO 659
<211> LENGTH: 22
<212> TYPE: DNA
<213> ORGANISM: Artificial Sequence
<220> FEATURE:
<223> OTHER INFORMATION: Synthetic Probe

<400> SEQUENCE: 659

```
actgatatca gctcagtagg ca                                                  22
```

<210> SEQ ID NO 660
<211> LENGTH: 23
<212> TYPE: DNA
<213> ORGANISM: Artificial Sequence
<220> FEATURE:
<223> OTHER INFORMATION: Synthetic Probe

<400> SEQUENCE: 660

```
tcatagccct gtacaatgct gct                                                 23
```

<210> SEQ ID NO 661
<211> LENGTH: 23
<212> TYPE: DNA
<213> ORGANISM: Artificial Sequence
<220> FEATURE:
<223> OTHER INFORMATION: Synthetic Probe

<400> SEQUENCE: 661

```
tgatagccct gtacaatgct gct                                                 23
```

<210> SEQ ID NO 662
<211> LENGTH: 22
<212> TYPE: DNA
<213> ORGANISM: Artificial Sequence
<220> FEATURE:
<223> OTHER INFORMATION: Synthetic Probe

<400> SEQUENCE: 662

```
acacacccac gcgagccgga aa                                                  22
```

<210> SEQ ID NO 663
<211> LENGTH: 20
<212> TYPE: DNA
<213> ORGANISM: Artificial Sequence

```
<220> FEATURE:
<223> OTHER INFORMATION: Synthetic Probe

<400> SEQUENCE: 663
gcagctgtcc gcccagacac                                                    20

<210> SEQ ID NO 664
<211> LENGTH: 22
<212> TYPE: DNA
<213> ORGANISM: Artificial Sequence
<220> FEATURE:
<223> OTHER INFORMATION: Synthetic Probe

<400> SEQUENCE: 664
cgaccatggc tgtagactgt ta                                                 22

<210> SEQ ID NO 665
<211> LENGTH: 23
<212> TYPE: DNA
<213> ORGANISM: Artificial Sequence
<220> FEATURE:
<223> OTHER INFORMATION: Synthetic Probe

<400> SEQUENCE: 665
acaccaatgc cctaggggat gcg                                                23

<210> SEQ ID NO 666
<211> LENGTH: 22
<212> TYPE: DNA
<213> ORGANISM: Artificial Sequence
<220> FEATURE:
<223> OTHER INFORMATION: Synthetic Probe

<400> SEQUENCE: 666
ctcagagcag acgtggttct ca                                                 22

<210> SEQ ID NO 667
<211> LENGTH: 22
<212> TYPE: DNA
<213> ORGANISM: Artificial Sequence
<220> FEATURE:
<223> OTHER INFORMATION: Synthetic Probe

<400> SEQUENCE: 667
ccagtagcac ggctcagtcc ag                                                 22

<210> SEQ ID NO 668
<211> LENGTH: 23
<212> TYPE: DNA
<213> ORGANISM: Artificial Sequence
<220> FEATURE:
<223> OTHER INFORMATION: Synthetic Probe

<400> SEQUENCE: 668
acacagctct tccatatctc cag                                                23

<210> SEQ ID NO 669
<211> LENGTH: 23
<212> TYPE: DNA
<213> ORGANISM: Artificial Sequence
<220> FEATURE:
<223> OTHER INFORMATION: Synthetic Probe

<400> SEQUENCE: 669
agggattcct gggaaaactg gac                                                23
```

-continued

```
<210> SEQ ID NO 670
<211> LENGTH: 23
<212> TYPE: DNA
<213> ORGANISM: Artificial Sequence
<220> FEATURE:
<223> OTHER INFORMATION: Synthetic Probe

<400> SEQUENCE: 670
tccaatcagt tcctgatgca gta                                              23

<210> SEQ ID NO 671
<211> LENGTH: 22
<212> TYPE: DNA
<213> ORGANISM: Artificial Sequence
<220> FEATURE:
<223> OTHER INFORMATION: Synthetic Probe

<400> SEQUENCE: 671
tgtgggtgtg tgcatgagcg tg                                               22

<210> SEQ ID NO 672
<211> LENGTH: 21
<212> TYPE: DNA
<213> ORGANISM: Artificial Sequence
<220> FEATURE:
<223> OTHER INFORMATION: Synthetic Probe

<400> SEQUENCE: 672
gccaatattt ctgtgctgct a                                                21

<210> SEQ ID NO 673
<211> LENGTH: 22
<212> TYPE: DNA
<213> ORGANISM: Artificial Sequence
<220> FEATURE:
<223> OTHER INFORMATION: Synthetic Probe

<400> SEQUENCE: 673
gaagtaaaca tccacctccc ag                                               22

<210> SEQ ID NO 674
<211> LENGTH: 25
<212> TYPE: DNA
<213> ORGANISM: Artificial Sequence
<220> FEATURE:
<223> OTHER INFORMATION: Synthetic Probe

<400> SEQUENCE: 674
acactcatac gccggcagtt gtcat                                            25

<210> SEQ ID NO 675
<211> LENGTH: 25
<212> TYPE: DNA
<213> ORGANISM: Artificial Sequence
<220> FEATURE:
<223> OTHER INFORMATION: Synthetic Probe

<400> SEQUENCE: 675
acttccagac ctgtattcac cgtca                                            25

<210> SEQ ID NO 676
<211> LENGTH: 25
<212> TYPE: DNA
<213> ORGANISM: Artificial Sequence
<220> FEATURE:
<223> OTHER INFORMATION: Synthetic Probe
```

<400> SEQUENCE: 676
cgtatgtgac tcatactcca ccagt                                          25

<210> SEQ ID NO 677
<211> LENGTH: 22
<212> TYPE: DNA
<213> ORGANISM: Artificial Sequence
<220> FEATURE:
<223> OTHER INFORMATION: Synthetic Probe

<400> SEQUENCE: 677
aggatctaca ctggctactg ag                                             22

<210> SEQ ID NO 678
<211> LENGTH: 25
<212> TYPE: DNA
<213> ORGANISM: Artificial Sequence
<220> FEATURE:
<223> OTHER INFORMATION: Synthetic Probe

<400> SEQUENCE: 678
gtgcactgtg tcctcagggg tgatc                                          25

<210> SEQ ID NO 679
<211> LENGTH: 18
<212> TYPE: DNA
<213> ORGANISM: Artificial Sequence
<220> FEATURE:
<223> OTHER INFORMATION: Synthetic Probe

<400> SEQUENCE: 679
caccaccaga gccaacgt                                                  18

<210> SEQ ID NO 680
<211> LENGTH: 17
<212> TYPE: DNA
<213> ORGANISM: Artificial Sequence
<220> FEATURE:
<223> OTHER INFORMATION: Synthetic Probe

<400> SEQUENCE: 680
tggaggcccc agcgaga                                                   17

<210> SEQ ID NO 681
<211> LENGTH: 22
<212> TYPE: DNA
<213> ORGANISM: Artificial Sequence
<220> FEATURE:
<223> OTHER INFORMATION: Synthetic Probe

<400> SEQUENCE: 681
cccatggctt ttagccctac at                                             22

<210> SEQ ID NO 682
<211> LENGTH: 21
<212> TYPE: DNA
<213> ORGANISM: Artificial Sequence
<220> FEATURE:
<223> OTHER INFORMATION: Synthetic Probe

<400> SEQUENCE: 682
ttgtctaacc agtcacctgt t                                              21

```
<210> SEQ ID NO 683
<211> LENGTH: 22
<212> TYPE: DNA
<213> ORGANISM: Artificial Sequence
<220> FEATURE:
<223> OTHER INFORMATION: Synthetic Probe

<400> SEQUENCE: 683
acatcatcgc atattgacac aa                                              22

<210> SEQ ID NO 684
<211> LENGTH: 21
<212> TYPE: DNA
<213> ORGANISM: Artificial Sequence
<220> FEATURE:
<223> OTHER INFORMATION: Synthetic Probe

<400> SEQUENCE: 684
acaaaccaca gtgtgctgct g                                               21

<210> SEQ ID NO 685
<211> LENGTH: 23
<212> TYPE: DNA
<213> ORGANISM: Artificial Sequence
<220> FEATURE:
<223> OTHER INFORMATION: Synthetic Probe

<400> SEQUENCE: 685
tcatacagct agataaccaa aga                                             23

<210> SEQ ID NO 686
<211> LENGTH: 22
<212> TYPE: DNA
<213> ORGANISM: Artificial Sequence
<220> FEATURE:
<223> OTHER INFORMATION: Synthetic Probe

<400> SEQUENCE: 686
acatcaatac ttcctggctc cc                                              22

<210> SEQ ID NO 687
<211> LENGTH: 25
<212> TYPE: DNA
<213> ORGANISM: Artificial Sequence
<220> FEATURE:
<223> OTHER INFORMATION: Synthetic Probe

<400> SEQUENCE: 687
gaaagttcag ccatatgctt gtcat                                           25
```

METHODS AND DEVICES FOR PREDICTING TREATMENT EFFICACY

CROSS-REFERENCE TO RELATED APPLICATIONS

This application is the U.S. National Stage filing under 35 U.S.C. §371 of International Application No. PCT/IB2011/001405, filed Apr. 29, 2011, which claims benefit of Danish Patent Application No. PA 2010 00382, filed on Apr. 29, 2010.

FIELD OF THE INVENTION

The invention features the use of biomarkers in methods and devices to predict the sensitivity of a patient to a medical treatment, e.g., a chemotherapeutic agent.

BACKGROUND OF THE INVENTION

DNA microarrays have been used to measure gene expression in tumor samples from patients and to facilitate diagnosis. Gene expression can reveal the presence of cancer in a patient, its type, stage, and origin, and whether genetic mutations are involved. Gene expression may even have a role in predicting the efficacy of chemotherapy. Over recent decades, the National Cancer Institute (NCI) has tested compounds, including chemotherapy agents, for their effect in limiting the growth of 60 human cancer cell lines. The NCI has also measured gene expression in those 60 cancer cell lines using DNA microarrays. Various studies have explored the relationship between gene expression and compound effect using the NCI datasets. During chemotherapy for cancers critical time is often lost due to a trial and error approach to finding an effective therapy. In addition, cancer cells often develop resistance to a previously effective therapy. In such situations, patient outcome would be greatly improved by early detection of such resistance.

There remains a need for proven methods and devices that predict the sensitivity or resistance of cancer patients to a medical treatment.

SUMMARY OF THE INVENTION

The invention features methods and devices for predicting the sensitivity or resistance of a patient, e.g., a cancer patient, to a treatment, e.g., treatment with a compound, such as a chemotherapeutic agent, or radiation. In particular, the methods and devices can be used to predict the sensitivity or resistance of a cancer patient to any medical treatment, including, e.g., treatment with a compound, drug, or radiation.

The devices and methods of the invention have been used to accurately predict treatment efficacy in cancer patients (e.g., patients with lung, lymphoma, and brain cancer) and can be used to predict treatment efficacy in patients diagnosed with any cancer.

In a first aspect, the invention features a method of predicting sensitivity of a cancer patient to a treatment for cancer by determining the expression level of at least one gene or noncoding RNA (e.g. microRNA (miRNA), such as hsa-miR-766_st (SEQ ID NO: 1)) in a cell (e.g., a cancer cell) of the patient in which the level of expression of the gene and/or RNA (e.g., miRNA) indicates the patient is sensitive or resistant to at least one treatment for cancer. In an embodiment, the method involves assaying for the level of expression of one or more (e.g., two, three, four, five, ten, twenty, thirty, forty, or fifty or more) biomarkers from one or more of Tables 1-65 and/or one or more of Tables 66-129) in a patient. For example, the method includes assaying the level of expression of hsa-miR-766_st (SEQ ID NO: 1) in a biological sample from the patient (e.g., a cell, tissue, or organ sample from a patient) or in a sample prepared from a biological sample from the patient.

In another embodiment, the method includes assaying the level of expression of at least hsa-miR-766_st (SEQ ID NO: 1) (alone or in combination with one or more (e.g., two, three, four, or more)) of the biomarkers listed in one or more of Tables 1-65 and/or one or more of the biomarkers listed in one or more of Tables 66-129). In an embodiment, the method includes determining the expression level of two of the listed biomarkers, more preferably three, four, five, six, seven, eight, nine, or ten of the listed biomarkers, and most preferably twenty, thirty, forty, fifty, sixty, seventy, eighty, ninety, or one hundred or more of the listed biomarkers. In another embodiment, the change in the level of biomarker expression (e.g., an increase or decrease) is determined relative to the level of biomarker expression in a cell or tissue known to be sensitive to the treatment, such that a similar level of biomarker expression exhibited by a cell or tissue of the patient indicates the patient is sensitive to the treatment. In another embodiment, the change in the level of biomarker expression (e.g., an increase or decrease) is determined relative to the level of biomarker expression in a cell or tissue known to be resistant to the treatment, such that a similar level of biomarker expression exhibited by a cell or tissue of the patient indicates the patient is resistant to the treatment.

A second aspect of the invention features a method for determining the development of resistance by a patient (i.e., a cell, such as a cancer cell, in the patient) to a treatment that the patient was previously sensitive to. The method includes determining the level of expression of one or more of the biomarkers set forth in the first aspect of the invention, such that the expression level of a biomarker(s) which is decreased in a cell or tissue known to be sensitive to the treatment indicates that the patient is resistant to or has a propensity to become resistant to the treatment. Alternatively, a decrease in the expression level of a biomarker(s) which is increased in a cell or tissue known to be sensitive to the treatment indicates that the patient is resistant to or has a propensity to become resistant to the treatment.

A third aspect of the invention features devices for assaying the level of expression of one or more biomarkers described herein (e.g., one or more of the biomarkers listed in Tables 1-129, e.g., at least hsa-miR-766_st (SEQ ID NO: 1) (alone or in combination with one or more (e.g., two, three, four, five, ten, twenty, thirty, forty, or fifty or more)) additional biomarkers from one or more of Tables 1-65 and/or one or more of Tables 66-129)) in a patient; the devices include probes capable of hybridizing to the biomarkers. For example, the method includes assaying the level of expression of hsa-miR-766_st (SEQ ID NO: 1) in a biological sample from the patient (e.g., a cell, tissue, or organ sample from a patient) or in a sample prepared from a biological sample from the patient. In an embodiment, the method can be used to determine the sensitivity of a patient to at least one treatment for cancer (e.g., a chemotherapy drug, such as vincristine, cisplatin, etoposide, azaguanine, carboplatin, adriamycin, aclarubicin, mitoxantrone, mitoxantrone, mitomycin, paclitaxel, gemcitabine, taxotere, dexamethasone, ara-c, methylprednisolone, methotrexate, bleomycin, methyl-gag, belinostat, carboplatin, 5-fu (5-fluorouracil), idarubicin, melphalan, IL4-PR38, valproic acid, all-trans retinoic acid (ATRA), cytoxan, topotecan, suberoylanilide hydroxamic acid (SAHA, vorinostat), depsipeptide (ER901228), bortezomib, leukeran, fludarabine, vinblastine, busulfan, dacarbazine, oxaliplatin, hydroxyurea, tegafur, daunorubicin, estramustine, mechlorethamine, streptozocin, carmustine, lomustine, mercaptopurine, teniposide, dactinomycin, tretinoin, ifosfamide, tamoxifen, irinotecan, floxuridine, thioguanine, PSC 833, erlotinib, herceptin, celecoxib, fulvestrant, iressa, anastrozole, letrozole, cetuximab, rituximab, radiation, histone deacetylase (HDAC) inhibitors, and/or 5-Aza-2'-deoxycytidine (decitabine)). In other embodiments, the method can be used to determine the sensitivity of a patient to two or more (e.g., three, four, five, ten, twenty, or more) of the treatments for cancer listed above. In yet other embodiments, the method can be used to assay the sensitivity of a patient to one or more (e.g., two or more, or even all) of the treatments for cancer listed above in a single assay.

Devices of the third aspect of the invention include probes (e.g., the device includes at least one or more probes directed to hsa-miR-766_st (SEQ ID NO: 1) having at least 85% identify (e.g., 90%, 95%, 99%, or 100% identity) to a target nucleic acid molecule with a sequence that is complementary or identical to at least 5-100 (e.g., 10-20 (e.g., 15), 20-50 (e.g., 25 and/or 40), and 25-60) consecutive nucleotides of one or more of the biomarkers of the invention (e.g., two, three, four, five, ten, twenty, thirty, forty, fifty or more, or all) of the biomarkers listed in one or more of Tables 1-65 and/or one or more (e.g., two, three, four, five, ten, twenty, thirty, forty, fifty or more, or all) of the biomarkers listed in one or more of Tables 66-129) for the chemotherapy drugs vincristine, cisplatin, etoposide, azaguanine, carboplatin, adriamycin, aclarubicin, mitoxantrone, mitoxantrone, mitomycin, paclitaxel, gemcitabine, taxotere, dexamethasone, ara-c, methylprednisolone, methotrexate, bleomycin, methyl-gag, belinostat, carboplatin, 5-fu (5-fluorouracil), idarubicin, melphalan, IL4-PR38, valproic acid, all-trans retinoic acid (ATRA), cytoxan, topotecan, suberoylanilide hydroxamic acid (SAHA, vorinostat), depsipeptide (ER901228), bortezomib, leukeran, fludarabine, vinblastine, busulfan, dacarbazine, oxaliplatin, hydroxyurea, tegafur, daunorubicin, estramustine, mechlorethamine, streptozocin, carmustine, lomustine, mercaptopurine, teniposide, dactinomycin, tretinoin, ifosfamide, tamoxifen, irinotecan, floxuridine, thioguanine, PSC 833, erlotinib, herceptin, celecoxib, fulvestrant, iressa, anastrozole, letrozole, cetuximab, rituximab, radiation, histone deacetylase (HDAC) inhibitors, and/or 5-Aza-2'-deoxycytidine (decitabine) are also provided. In other embodiments, the device includes at least one nucleic acid molecule that is complementary to or identical to at least 5 (e.g., 10, 15, 20, or 22) consecutive nucleotides of hsa-miR-766_st (SEQ ID NO: 1) (e.g., at least 5 (e.g., 10, 15, 20, or 22) consecutive nucleotides of the sequence 5'-GCTGAGGCTGTGGGGCTGGAGT-3' (SEQ ID NO: 1)). In still other embodiments, the device includes probes (e.g., the device includes at least one or more probes directed to hsa-miR-766_st (SEQ ID NO: 1)) having at least 85% identify (e.g., 90%, 95%, 99%, or 100% identity) to a target nucleic acid molecule with a sequence that is complementary or identical to at least 5-100 (e.g., 10-20 (e.g., 15), 20-50 (e.g., 25 and/or 40), and 25-60) consecutive nucleotides of those biomarkers listed in one or more (or all) of Tables 1-65 having a mean score correlation coefficient (positive correlation) of equal to or greater than 0.25, 0.30, 0.35, 0.40, 0.45, 0.50, 0.55, 0.60, 0.65, and/or 0.7 or more (preferably the devices include probes directed to those biomarkers in Tables 1-65 having a mean score correlation coefficient of 0.4 or greater and preferably the probes have a sequence that is complementary or identical to the sequences in shown Tables 1-65 for the indicated biomarkers). Other devices of the invention include probes (e.g., one or more probes directed to hsa-miR-766_st (SEQ ID NO: 1)) having at least 85% identify (e.g., 90%, 95%, 99%, or 100% identity) to a target nucleic acid molecule with a sequence that is complementary or identical to at least 5-100 (e.g., 10-20 (e.g., 15), 20-50 (e.g., 25 and/or 40), and 25-60) consecutive nucleotides of those biomarkers listed in one or more (or all) of Tables 66-129 having a mean score correlation coefficient (negative correlation) of equal to or greater than −0.7, −0.65, −0.6, −0.55, −0.5, −0.45, −0.4, −0.35, −0.3, and/or −0.25 (preferably the devices include probes directed to those biomarkers in Tables 66-129 having a mean score correlation coefficient of −0.5 or greater and preferably the probes have a sequence that is complementary or identical to the sequences in shown Tables 66-129 for the indicated biomarkers). In yet other embodiments, devices of the invention include probes having at least 85% identify (e.g., 90%, 95%, 99%, or 100% identity) to a target nucleic acid molecule with a sequence that is complementary or identical to at least 5-100 (e.g., 10-20 (e.g., 15), 20-50 (e.g., 25 and/or 40), and 25-60) consecutive nucleotides of those biomarkers listed in one or more of Tables 1-65 having a mean score correlation coefficient of greater than 0.25, 0.30, 0.35, 0.40, 0.45, 0.50, 0.55, 0.60, 0.65, and/or 0.7 or more (e.g., preferably the mean score correlation coefficient is 0.3 or greater) and probes having at least 85% identify (e.g., 90%, 95%, 99%, or 100% identity) to a target nucleic acid molecule with a sequence that is complementary or identical to at least 5-100 (e.g., 10-20 (e.g., 15), 20-50 (e.g., 25 and/or 40), and 25-60) consecutive nucleotides of those biomarkers listed in one or more of Tables 66-129 having a mean score correlation coefficient of at least −0.7, −0.65, −0.6, −0.55, −0.5, −0.45, −0.4, −0.35, −0.3, and/or −0.25 (e.g., preferably the mean score correlation coefficient is −0.3 or lower). In a preferred embodiment, the devices of the invention include probes directed to those biomarkers in Tables 1-65 having a mean score correlation coefficient of 0.4 or greater, and preferably the probes have a sequence that is complementary or identical to the sequences in shown Tables 1-65 for the indicated biomarkers, and probes directed to those biomarkers in Tables 66-129 having a mean score correlation coefficient of −0.5 or greater, preferably the probes have a sequence that is complementary or identical to the sequences in shown Tables 66-129 for the indicated biomarkers.

In another embodiment, devices of the third aspect of the invention include probes having at least 99% or 100% identity to a target nucleic acid molecule with a sequence that is complementary or identical to the biomarker sequences of Tables 1-65 and/or Tables 66-129. Another embodiment of the invention features devices that include probes having at least 99% or 100% identity to a target nucleic acid molecule with a sequence that is complementary or identical to the biomarker sequences of Tables 1-65 that have a correlation coefficient of 0.3 or greater and/or biomarker sequences of Tables 66-129 that have a correlation coefficient of −0.3 or lower.

For example, a device of the invention includes a probe for hsa-miR-766_st (SEQ ID NO: 1) (alone or in combination with one or more (e.g., two, three, four, five, ten, twenty, thirty, forty, or fifty or more) additional biomarkers from one or more of Tables 1-65 and/or one or more of Tables 66-129)) in a patient; the devices include probes capable of hybridizing to the biomarkers. For example, the method includes assaying the level of expression of hsa-miR-766_st (SEQ ID NO: 1) in a biological sample from the patient (e.g., a cell, tissue, or organ sample from a patient) or in a sample prepared from a biological sample from the patient. In an embodiment, the method can be used to determine the sensitivity of a patient to at least one treatment for cancer (e.g., a chemotherapy drug, such as vincristine, cisplatin, etoposide, azaguanine, carboplatin, adriamycin, aclarubicin, mitoxantrone, mitoxantrone, mitomycin, paclitaxel, gemcitabine, taxotere, dexamethasone, ara-c, methylprednisolone, methotrexate, bleomycin, methyl-gag, belinostat, carboplatin, 5-fu (5-fluorouracil), idarubicin, melphalan, IL4-PR38, valproic acid, all-trans retinoic acid (ATRA), cytoxan, topotecan, suberoylanilide hydroxamic acid (SAHA, vorinostat), depsipeptide (FR901228), bortezomib, leukeran, fludarabine, vinblastine, busulfan, dacarbazine, oxaliplatin, hydroxyurea, tegafur, daunorubicin, estramustine, mechlorethamine, streptozocin, carmustine, lomustine, mercaptopurine, teniposide, dactinomycin, tretinoin, ifosfamide, tamoxifen, irinotecan, floxuridine, thioguanine, PSC 833, erlotinib, herceptin, celecoxib, fulvestrant, iressa, anastrozole, letrozole, cetuximab, rituximab, radiation, histone deacetylase (HDAC) inhibitors, and/or 5-Aza-2'-deoxycytidine (decitabine)). In other embodiments, the method can be used to determine the sensitivity of a patient to two or more (e.g., three, four, five, ten, twenty, or more) of the treatments for cancer listed above. In yet other embodiments, the method can be used to assay the sensitivity of a patient to one or more (e.g., two or more, or even all) of the treatments for cancer listed above in a single assay.

For example, a device of the invention includes a probe for hsa-miR-766_st (e.g., a probe having a sequence that is complementary or identical to 5'-GCTGAGGCTGTGGGGCTGGAGT-3' (SEQ ID NO: 1)) and any one additional probe for a biomarker selected from hsa-miR-106b-star_st (SEQ ID NO: 2), hsa-miR-25-star_st (SEQ ID NO: 3), HBII-85-2_x_st (SEQ ID NOs: 4 and 252), U48_st (SEQ ID NOs: 5, 395, and 441), U55_x_st (SEQ ID NOs: 6, 36, 146, 209, 241, 260, 280, and 308), hsa-miR-124_st (SEQ ID NO: 7), hsa-miR-1281_st (SEQ ID NO: 8), hsa-miR-181a-star_st (SEQ ID NO: 9), hsa-miR-181b_st (SEQ ID NO: 10), hsa-miR-342-3p_st (SEQ ID NO: 11), hsa-miR-432_st (SEQ ID NO: 12), hsa-miR-938_st (SEQ ID NO: 16), hsa-miR-100_st (SEQ ID NO: 17), hsa-miR-140-3p_st (SEQ ID NO: 13), hsa-miR-140-5p_st (SEQ ID NO: 18), hsa-miR-146a_st (SEQ ID NO: 19), hsa-miR-155_st (SEQ ID NO: 20), hsa-miR-506_st (SEQ ID NO: 21), hsa-miR-508-5p_st (SEQ ID: 22), hsa-miR-509-3-5p_st (SEQ ID NO: 23), hsa-miR-509-3p_st (SEQ ID NO: 24), hsa-miR-510_st (SEQ ID NO: 25), hsa-miR-513a-5p_st (SEQ ID NO: 26), hsa-miR-513b_st (SEQ ID NO: 27), hsa-miR-663_st (SEQ ID NO: 28), hsa-miR-1271_st (SEQ ID NO: 30), hsa-miR-143_st (SEQ ID NO: 31), hsa-miR-370_st (SEQ ID NO: 32), hsa-miR-433_st (SEQ ID NO: 33), hsa-miR-654-3p_st (SEQ ID NO: 34), hsa-miR-758_st (SEQ ID NO: 35), U55_st (SEQ ID NOs: 6, 36, 146, 209, 241, 260, 280, and 308), hsa-miR-106b_st (SEQ ID NO: 37), hsa-miR-1299_st (SEQ ID NO: 38), hsa-miR-29b-2-star_st (SEQ ID NO: 39), hsa-miR-33b-star_st (SEQ ID NO: 40), hsa-miR-629-star_st (SEQ ID NO: 41), hsa-miR-652_st (SEQ ID NO: 42), hsa-miR-671-5p_st (SEQ ID NO: 43), hsa-miR-768-3p_st (SEQ ID NO: 44), hsa-miR-93_st (SEQ ID NO: 46), ACA10_s_st (SEQ ID NOs: 47, 138, 223, 382, and 444), ACA18_x_st (SEQ ID NOs: 48, 139, and 193), ACA44_st (SEQ ID NOs: 49, 383, and 447), ACA51_x_st (SEQ ID NOs: 50, 194, 324, and 507), ACA61_st (SEQ ID NOs: 51 and 385), ENSG00000200394_st (SEQ ID NO: 52), ENSG00000202252_st (SEQ ID NOs: 53, 184, 244, 424, 449, and 488), HBII-180A_x_st (SEQ ID NOs: 54, 197, 352, and 386), HBII-429_st (SEQ ID NOs: 55, 240, 246, 388, 427, and 475), U104_st (SEQ ID NOs: 56, 116, 140, 201, 326, 353, and 471), U13_st (SEQ ID NOs: 57, 225, 316, 389, 428, 472, and 477), U17b_st (SEQ ID NOs: 58, 117, 254, 327, and 456), U17b_x_st (SEQ ID NOs: 59, 328, 392, and 457), U26_st (SEQ ID NOs: 60 and 187), U3-2_s_st (SEQ ID NOs: 61, 319, and 493), U35A_st (SEQ ID NOs: 62 and 460), U49A_st (SEQ ID NO: 63, 64, and 143), U49A_x_st (SEQ ID NOs: 64, 106, and 144), U49B_s_st (SEQ ID NOs: 65, 145, 107, and 442), U67_st (SEQ ID NOs: 66 and 148), U68_st (SEQ ID NOs: 67, 263, and 466), U68_x_st (SEQ ID NOs: 67, 68, and 498), U74_x_st (SEQ ID NOs: 69, 191, 242, 264, 309, 350, 377, and 399), hsa-miR-1275_st (SEQ ID NO: 70), hsa-miR-18a-star_st (SEQ ID NO: 71), hsa-miR-18a_st (SEQ ID NO: 72), 14qII-14_st (SEQ ID NOs: 73, 157, 598, 627, and 674), 14qII-1_st (SEQ ID NOs: 74, 159, and 675), 14qII-26_st (SEQ ID NOs: 75, 160, 629, and 676), 14qII-26_x_st (SEQ ID NOs: 76, 161, and 630), hsa-miR-127-3p_st (SEQ ID NO: 77), hsa-miR-181a_st (SEQ ID NO: 78), hsa-miR-181c_st (SEQ ID NO: 79), hsa-miR-342-5p_st (SEQ ID NO: 80), hsa-miR-409-3p_st (SEQ ID NO: 81), hsa-miR-487b_st (SEQ ID NO: 82), hsa-miR-768-5p_st (SEQ ID NO: 83), hsa-miR-92b_st (SEQ ID NO: 15), hsa-miR-1228_st (SEQ ID NO: 84), hsa-miR-185_st (SEQ ID NO: 85), hsa-miR-188-5p_st (SEQ ID NO: 86), hsa-miR-18b_st (SEQ ID NO: 87), hsa-miR-20b_st (SEQ ID NO: 88), hsa-miR-25_st (SEQ ID NO: 89), hsa-miR-320c_st (SEQ ID NO: 90), hsa-miR-320d_st (SEQ ID NO: 91), hsa-miR-362-5p_st (SEQ ID NO: 92), hsa-miR-500-star_st (SEQ ID NO: 93), hsa-miR-500_st (SEQ ID NO: 94), hsa-miR-501-3p_st (SEQ ID NO: 95), hsa-miR-502-3p_st (SEQ ID NO: 96), hsa-miR-532-3p_st (SEQ ID NO: 97), HBII-438A_s_st (SEQ ID NOs: 99, 114, 247, 585, and 648), hsa-miR-181a-star_st (SEQ ID NO: 9), hsa-miR-503_st (SEQ ID NO: 101), hsa-miR-1307_st (SEQ ID NO: 102), hsa-miR-505_st (SEQ ID NO: 103), hsa-miR-769-3p_st (SEQ ID NO: 104), hsa-miR-769-5p_st (SEQ ID NO: 105), U49B_x_st (SEQ ID NO: 107), hsa-miR-10a-star_st (SEQ ID NO: 108), hsa-miR-1207-5p_st (SEQ ID NO: 109), hsa-miR-128_st (SEQ ID NO: 110), hsa-miR-150_st (SEQ ID NO: 111), hsa-miR-424-star_st (SEQ ID NO: 100), hsa-miR-424_st (SEQ ID NO: 112), HBII-202_st (SEQ ID NOs: 113, 185, 198, 239, and 426), HBII-85-11_st (SEQ ID NOs: 115, 249, and 470), U78_s_st (SEQ ID NOs: 119, 265, and 484), U78_x_st (SEQ ID NOs: 120, 228, and 266), ACA23_st (SEQ ID NO: 121), ACA24_x_st (SEQ ID NO: 122), ACA54_st (SEQ ID NO: 123), U31_st (SEQ ID NOs: 124, 142, and 205), hsa-let-7d-star_st (SEQ ID NO: 125), hsa-miR-1183_st (SEQ ID NO: 126), hsa-miR-1268_st (SEQ ID NO: 127), hsa-miR-15a_st (SEQ ID NO: 128), hsa-miR-198_st (SEQ ID NO: 129), hsa-miR-20b-star_st (SEQ ID NO: 130), hsa-miR-223_st (SEQ ID NO: 131), hsa-miR-297_st (SEQ ID NO: 132), hsa-miR-363_st (SEQ ID NO: 133), hsa-miR-588_st (SEQ ID NO: 134), hsa-miR-631_st (SEQ ID NO: 135), hsa-miR-92a-2-star_st (SEQ ID NO: 136), hsa-miR-940_st (SEQ ID NO: 137), U30_st (SEQ ID NOs: 141, 204, 332, 431, and 479), U31_x_st (SEQ ID NOs: 142, 190, 206, and 333), U56_st (SEQ ID NOs: 147, 210, 261, 337, 464, and 496), U67_x_st (SEQ ID NOs: 149 and 397), hsa-miR-106a_st (SEQ ID NO: 150), hsa-miR-1254_st (SEQ ID NO: 151), hsa-miR-17_st (SEQ ID NO: 152), hsa-miR-19b_st (SEQ ID NO: 153), hsa-miR-34b_st (SEQ ID NO: 154), hsa-miR-663b_st (SEQ ID NO: 155), hsa-miR-92a_st (SEQ ID NO: 156), 14qII-14_x_st (SEQ ID NOs: 73, 158, 598, 627 and 674), 14qII-1_x_st (SEQ ID NO: 74, 599, and 628), 14qII-3_st (SEQ ID NO: 162), hsa-miR-125b-1-star_st (SEQ ID NO: 163), hsa-miR-134_st (SEQ ID NO: 164), hsa-miR-193a-5p_st (SEQ ID NO: 165), hsa-miR-21-star_st (SEQ ID NO: 166), hsa-miR-22_st (SEQ ID NO: 167), hsa-miR-299-3p_st (SEQ ID NO: 168), hsa-miR-337-5p_st (SEQ ID NO: 169), hsa-miR-376c_st (SEQ ID NO: 170), hsa-miR-377-star_st (SEQ ID NO: 171), hsa-miR-379_st (SEQ ID NO: 172), hsa-miR-381_st (SEQ ID NO: 173), hsa-miR-382_st (SEQ ID NO: 174), hsa-miR-409-5p_st (SEQ ID NO: 175), hsa-miR-411_st (SEQ ID NO: 176), hsa-miR-431_st (SEQ ID NO: 177), hsa-miR-455-3p_st (SEQ ID NO: 178), hsa-miR-485-5p_st (SEQ ID NO: 179), hsa-miR-493_st (SEQ ID NO: 180), hsa-miR-494_st (SEQ ID NO: 181), hsa-miR-543_st (SEQ ID NO: 182), ENSG00000200879_st (SEQ ID NOs: 183, 292, and 423), U25_st (SEQ ID NO: 186, 318, 329, 429, and 478), U28_x_st (SEQ ID NO: 188), U29_st (SEQ ID NO: 189, 203, 331, and 430), hsa-miR-92a-1-star_st (SEQ ID NO: 192), ACA9_st (SEQ ID NOs: 195 and 373), ACA9_x_st (SEQ ID NO: 196), HBII-336_st (SEQ ID NOs: 199 and 345), HBII-55_st (SEQ ID NOs: 200, 248, 453, and 476), U27_st (SEQ ID NO: 202, 330, and 687), U38A_st (SEQ ID NOs: 207, 348, 393, 432, and 461), U56_x_st (SEQ ID NOs: 211, 210, and 338), U57_st (SEQ ID NOs: 212, 262, and 339), U60_st (SEQ ID NO: 213), hsa-miR-1246_st (SEQ ID NO: 214), hsa-miR-142-5p_st (SEQ ID NO: 215), hsa-miR-17-star_st (SEQ ID NO: 216), hsa-miR-195-star_st (SEQ ID NO: 14), hsa-miR-19a_st (SEQ ID NO: 217), hsa-miR-20a_st (SEQ ID NO: 218), hsa-miR-297_st (SEQ ID NO: 132), hsa-miR-330-3p_st (SEQ ID NO: 219), hsa-miR-346_st (SEQ ID NO: 220), hsa-miR-595_st (SEQ ID NO: 221), hsa-miR-647_st (SEQ ID NO: 222), ENSG00000199411_s_st (SEQ ID NOs: 224 and 422), U36A_x_st (SEQ ID NO: 226), U36C_st (SEQ ID NOs: 227, 335, and 481), U8_x_st (SEQ ID NOs: 229 and 481), hsa-miR-194-star_st (SEQ ID NO: 230), hsa-miR-200c-star_st (SEQ ID NO: 231), hsa-miR-324-3p_st (SEQ ID NO: 235), hsa-miR-371-5p_st (SEQ ID NO: 236), hsa-miR-93-star_st (SEQ ID NO: 45), ACA41_x_st (SEQ ID NO: 237), ACA48_x_st (SEQ ID NOs: 238, 371, and 436), ACA7_s_st (SEQ ID NOs: 243, 372, 436, and 437), ENSG00000207002_x_st (SEQ ID NO: 245), HBII-85-23_x_st (SEQ ID NOs: 250, 587, 641, and 650), HBII-85-26_st (SEQ ID NOs: 251, 361, and 439), HBII-85-6_x_st (SEQ ID NOs: 253, 362, and 616), U33_st (SEQ ID NOs: 255, 334, 346, 354, 375, and 459), U34_st (SEQ ID NOs: 256, 347, 355, and 376), U41_st (SEQ ID NOs: 257, 307, and 394), U52_st (SEQ ID NOs: 258, 320, 349, and 396), U83_st (SEQ ID NOs: 267, 435, and 486), U95_st (SEQ ID NOs: 268, 379, and 487), hsa-miR-541-star_st (SEQ ID NO: 269), hsa-miR-610_st (SEQ ID NO: 270), hsa-miR-885-5p_st (SEQ ID NO: 271), hsa-miR-339-3p_st (SEQ ID NO: 272), hsa-miR-339-5p_st (SEQ ID NO: 273), hsa-miR-1308_st (SEQ ID NO: 274), hsa-miR-148a_st (SEQ ID NO: 275), hsa-miR-152_st (SEQ ID NO: 276), hsa-miR-34a-star_st (SEQ ID NO: 277), hsa-miR-34a_st (SEQ ID NO: 234), HBII-142_st (SEQ ID NOs: 278, 293, and 450), HBII-142_x_st (SEQ ID NOs: 279, 425, and 508), hsa-miR-1202_st (SEQ ID NO: 281), hsa-miR-148a-star_st (SEQ ID NO: 282), hsa-miR-184_st (SEQ ID NO: 283), hsa-miR-191_st (SEQ ID NO: 284), hsa-miR-425-star_st (SEQ ID NO: 285), hsa-miR-425_st (SEQ ID NO: 286), hsa-miR-449a_st (SEQ ID NO: 287), hsa-miR-449b_st (SEQ ID NO: 288), hsa-miR-551b_st (SEQ ID NO: 289), hsa-miR-877_st (SEQ ID NO: 291), hsa-miR-196a_st (SEQ ID NO: 294), hsa-miR-205_st (SEQ ID NO: 295), hsa-miR-29c-star_st (SEQ ID NO: 296), hsa-miR-375_st (SEQ ID NO: 297), hsa-miR-489_st (SEQ ID NO: 298), hsa-miR-126_st (SEQ ID NO: 299), hsa-miR-153_st (SEQ ID NO: 300), hsa-miR-30c_st (SEQ ID NO: 301), hsa-miR-30e_st (SEQ ID NO: 302), hsa-miR-363-star_st (SEQ ID NO: 303), hsa-miR-532-5p_st (SEQ ID NO: 98), hsa-miR-660_st (SEQ ID NO: 305), hsa-miR-638_st (SEQ ID NO: 306), HBII-276_st (SEQ ID NO: 311), HBII-52-32_x_st (SEQ ID NOs: 312 and 649), hsa-miR-130a_st (SEQ ID NO: 313), hsa-miR-34c-3p_st (SEQ ID NO: 314), hsa-miR-554_st (SEQ ID NO: 315), hsa-miR-923_st (SEQ ID NO: 29), U17a_st (SEQ ID NOs: 317, 390, and 454), hsa-miR-181d_st (SEQ ID NO: 321), ACA15_s_st (SEQ ID NOs: 322 and 445), ACA21_st (SEQ ID NO: 323), HBII-99_st (SEQ ID NO: 325), U50B_st (SEQ ID NO: 336), U71d_x_st (SEQ ID NOs: 340 and 468), U73a_st (SEQ ID NO: 341), hsa-miR-301a_st (SEQ ID NO: 342), ENSG00000199282_st (SEQ ID NO: 343), ENSG00000201859_x_st (SEQ ID NO: 344), hsa-miR-491-3p_st (SEQ ID NO: 351), U43_x_st (SEQ ID NOs: 356 and 462), U51_st (SEQ ID NO: 357), hsa-miR-1228-star_st (SEQ ID NO: 358), hsa-miR-149-star_st (SEQ ID NO: 359), hsa-miR-16_st (SEQ ID NO: 360), hsa-miR-106a-star_st (SEQ ID NO: 363), hsa-miR-106b-star_st (SEQ ID NO: 2), hsa-miR-877-star_st (SEQ ID NO: 364), hsa-miR-1226_st (SEQ ID NO: 365), hsa-miR-193a-3p_st (SEQ ID NO: 366), hsa-miR-330-5p_st (SEQ ID NO: 367), hsa-miR-378_st (SEQ ID NO: 368), hsa-miR-586_st (SEQ ID NO: 369), ACA13_st (SEQ ID NOs: 370 and 473), HBII-239_st (SEQ ID NOs: 374 and 438), U75_st (SEQ ID NOs: 378 and 483), hsa-miR-331-5p_st (SEQ ID NO: 380), hsa-miR-296-3p_st (SEQ ID NO: 381), ACA52_st (SEQ ID NO: 384), HBII-382_s_st (SEQ ID NOs: 387 and 492), U17a_x_st (SEQ ID NOs: 391 and 455), U70_x_st (SEQ ID NOs: 398 and 509), U83B_st (SEQ ID NOs: 400, 469, and 485), hsa-miR-1274a_st (SEQ ID NO: 401), hsa-miR-1280_st (SEQ ID NO: 402), hsa-miR-130b_st (SEQ ID NO: 403), hsa-miR-146b-3p_st (SEQ ID NO: 404), hsa-miR-146b-5p_st (SEQ ID NO: 405), hsa-miR-185-star_st (SEQ ID NO: 406), hsa-miR-202_st (SEQ ID NO: 407), hsa-miR-373_st (SEQ ID NO: 408), hsa-miR-378-star_st (SEQ ID NO: 409), hsa-miR-422a_st (SEQ ID NO: 410), hsa-miR-423-5p_st (SEQ ID NO: 411), hsa-miR-451_st (SEQ ID NO: 412), hsa-miR-486-3p_st (SEQ ID NO: 413), hsa-miR-486-5p_st (SEQ ID NO: 414), hsa-miR-504_st (SEQ ID NO: 415), hsa-miR-550_st (SEQ ID NO: 416), hsa-miR-616_st (SEQ ID NO: 417), hsa-miR-671-3p_st (SEQ ID NO: 418), hsa-miR-615-3p_st (SEQ ID NO: 419), ACA43_st (SEQ ID NOs: 420 and 446), ACA57_st (SEQ ID NOs: 421 and 448), U59B_st (SEQ ID NOs: 434, 465, and 497), hsa-miR-25-star_st (SEQ ID NO: 3), hsa-miR-501-5p_st (SEQ ID NO: 304), hsa-miR-629_st (SEQ ID NO: 440), hsa-miR-181c-star_st (SEQ ID NO: 443), HBII-180C_st (SEQ ID NOs: 451, 490, and 678), HBII-180C_x_st (SEQ ID NO: 451, 452, and 491), U32A_x_st (SEQ ID NO: 458), U43_st (SEQ ID NO: 462), U46_x_st (SEQ ID NO: 463), U71d_st (SEQ ID NO: 467), hsa-miR-593-star_st (SEQ ID NO: 290), hsa-miR-874_st (SEQ ID NO: 310), ENSG00000202093_x_st (SEQ ID NO: 474), U36A_st (SEQ ID NO: 480), U54_st (SEQ ID NO: 482), HBII-180B_x_st (SEQ ID NO: 489), U38B_st (SEQ ID NO: 494), U50B_x_st (SEQ ID NO: 495), hsa-miR-1292_st (SEQ ID NO: 499), hsa-miR-149_st (SEQ ID NO: 500), hsa-miR-27a_st (SEQ ID NO: 501), hsa-miR-30a-star_st (SEQ ID NO: 502), hsa-miR-30a_st (SEQ ID NO: 503), hsa-miR-30c-2-star_st (SEQ ID NO: 504), hsa-miR-30e-star_st (SEQ ID NO: 505), hsa-miR-34c-5p_st (SEQ ID NO: 506), hsa-miR-15b_st (SEQ ID NO: 510), hsa-miR-203_st (SEQ ID NO: 511), hsa-miR-421_st (SEQ ID NO: 512), hsa-miR-492_st (SEQ ID NO: 513), hsa-miR-622_st (SEQ ID NO: 514), hsa-miR-1826_st (SEQ ID NO: 515), hsa-miR-675_st (SEQ ID NO: 516), hsa-miR-934_st (SEQ ID NO: 517), hsa-miR-1323_st (SEQ ID NO: 518), hsa-miR-187_st (SEQ ID NO: 519), hsa-miR-197_st (SEQ ID NO: 520), hsa-miR-498_st (SEQ ID NO: 521), hsa-miR-509-5p_st (SEQ ID NO: 522), hsa-miR-512-3p_st (SEQ ID NO: 523), hsa-miR-513c_st (SEQ ID NO: 524), hsa-miR-516b_st (SEQ ID NO: 525), hsa-miR-517a_st (SEQ ID NO: 526), hsa-miR-517b_st (SEQ ID NO: 527), hsa-miR-525-5p_st (SEQ ID NO: 528), hsa-miR-526b_st (SEQ ID NO: 529), hsa-miR-551a_st (SEQ ID NO: 530), hsa-miR-873_st (SEQ ID NO: 531), hsa-miR-361-5p_st (SEQ ID NO: 533), hsa-miR-498_st (SEQ ID NO: 521), hsa-let-7i-star_st (SEQ ID NO: 232), hsa-miR-338-3p_st (SEQ ID NO: 233), hsa-miR-34b-star_st (SEQ ID NO: 534), HBII-85-29_st (SEQ ID NOs: 535, 588, and 642), hsa-miR-130a_st (SEQ ID NO: 313), hsa-miR-148b_st (SEQ ID NO: 536), hsa-miR-184_st (SEQ ID NO: 283), hsa-miR-26a_st (SEQ ID NO: 537), hsa-miR-30a-star_st (SEQ ID NO: 502), hsa-miR-30a_st (SEQ ID NO: 503), hsa-miR-30c-2-star_st (SEQ ID NO: 504), hsa-miR-30c_st (SEQ ID NO: 301), hsa-miR-34a-star_st (SEQ ID NO: 277), hsa-miR-34a_st (SEQ ID NO: 234), hsa-miR-34c-5p_st (SEQ ID NO: 506), hsa-miR-449a_st (SEQ ID NO: 287), hsa-miR-449b_st (SEQ ID NO: 288), hsa-miR-10a_st (SEQ ID NO: 538), hsa-miR-151-3p_st (SEQ ID NO: 539), hsa-miR-151-5p_st (SEQ ID NO: 540), hsa-miR-192-star_st (SEQ ID NO: 541), hsa-miR-192_st (SEQ ID NO: 542), hsa-miR-194_st (SEQ ID NO: 543), hsa-miR-200b_st (SEQ ID NO: 544), hsa-miR-203_st (SEQ ID NO: 511), hsa-miR-29b_st (SEQ ID NO: 545), hsa-miR-30b_st (SEQ ID NO: 546), hsa-miR-30d_st (SEQ ID NO: 547), hsa-miR-625_st (SEQ ID NO: 548), hsa-let-7e_st (SEQ ID NO: 549), hsa-miR-10b_st (SEQ ID NO: 550), hsa-miR-125a-5p_st (SEQ ID NO: 551), hsa-miR-141_st (SEQ ID NO: 552), hsa-miR-200a-star_st (SEQ ID NO: 553), hsa-miR-200a_st (SEQ ID NO: 554), hsa-miR-200b-star_st (SEQ ID NO: 555), hsa-miR-200c_st (SEQ ID NO: 556), hsa-miR-429_st (SEQ ID NO: 557), hsa-miR-516a-5p_st (SEQ ID NO: 558), hsa-miR-934_st (SEQ ID NO: 517), hsa-miR-99b_st (SEQ ID NO: 559), hsa-miR-1244_st (SEQ ID NO: 560), hsa-miR-1303_st (SEQ ID NO: 561), hsa-miR-141-star_st (SEQ ID NO: 562), hsa-miR-182_st (SEQ ID NO: 563), hsa-miR-183-star_st (SEQ ID NO: 564), hsa-miR-183_st (SEQ ID NO: 565), hsa-miR-200c-star_st (SEQ ID NO: 231), hsa-miR-205_st (SEQ ID NO: 295), hsa-miR-215_st (SEQ ID NO: 566), hsa-miR-27b_st (SEQ ID NO: 567), hsa-miR-331-3p_st (SEQ ID NO: 568), hsa-miR-375_st (SEQ ID NO: 297), hsa-miR-622_st (SEQ ID NO: 514), hsa-miR-99b-star_st (SEQ ID NO: 569), hsa-miR-7_st (SEQ ID NO: 570), hsa-miR-23a_st (SEQ ID NO: 571), hsa-miR-518d-5p_st (SEQ ID NO: 572), hsa-miR-518e-star_st (SEQ ID NO: 573), hsa-miR-519a-star_st (SEQ ID NO: 573), hsa-miR-519a_st (SEQ ID NO: 574), hsa-miR-519b-5p_st (SEQ ID NO: 573), hsa-miR-519c-5p_st (SEQ ID NO: 573), hsa-miR-522-star_st (SEQ ID NO: 573), hsa-miR-523-star_st (SEQ ID NO: 573), hsa-miR-526a_st (SEQ ID NO: 572), hsa-let-7a_st (SEQ ID NO: 575), hsa-let-7c_st (SEQ ID NO: 576), hsa-let-7f_st (SEQ ID NO: 577), hsa-miR-193a-5p_st (SEQ ID NO: 165), hsa-miR-22-star_st (SEQ ID NO: 578), hsa-miR-22_st (SEQ ID NO: 167), hsa-miR-24-2-star_st (SEQ ID NO: 579), hsa-miR-24_st (SEQ ID NO: 580), hsa-miR-506_st (SEQ ID NO: 21), hsa-miR-508-5p_st (SEQ ID NO: 22), hsa-miR-509-3-5p_st (SEQ ID NO: 23), hsa-miR-509-3p_st (SEQ ID NO: 24), hsa-miR-509-5p_st (SEQ ID NO: 522), hsa-miR-510_st (SEQ ID NO: 25), hsa-miR-513a-5p_st (SEQ ID NO: 26), hsa-miR-513c_st (SEQ ID NO: 524), hsa-miR-584_st (SEQ ID NO: 581), hsa-miR-885-3p_st (SEQ ID NO: 582), HBII-85-29-st (SEQ ID NOs: 535, 588, and 642), hsa-miR-193b_st (SEQ ID NO: 583), hsa-miR-27a_st (SEQ ID NO: 501), hsa-miR-29a_st (SEQ ID NO: 584), hsa-miR-34b-star_st (SEQ ID NO: 534), hsa-miR-34c-3p_st (SEQ ID NO: 314), HBII-438A_s_st (SEQ ID NOs: 99, 114, 247, 585, and 648), HBII-85-11_st (SEQ ID NOs: 115, 249, and 470), HBII-85-15_x_st (SEQ ID NO: 586), HBII-85-23_x_st (SEQ ID NOs: 250, 587, 641, and 650), HBII-85-29_x_st (SEQ ID NOs: 589 and 642), hsa-miR-424-star_st (SEQ ID NO: 100), hsa-miR-23b_st (SEQ ID NO: 590), hsa-miR-23b-star_st (SEQ ID NO: 591), hsa-miR-1308_st (SEQ ID NO: 274), hsa-miR-21-star_st (SEQ ID NO: 166), hsa-miR-21_st (SEQ ID NO: 592), hsa-miR-27a-star_st (SEQ ID NO: 593), hsa-miR-339-3p_st (SEQ ID NO: 272), hsa-miR-28-5p_st (SEQ ID NO: 594), hsa-miR-516b_st (SEQ ID NO: 525), hsa-miR-517a_st (SEQ ID NO: 526), hsa-miR-525-5p_st (SEQ ID NO: 528), hsa-miR-128_st (SEQ ID NO: 110), hsa-miR-1292_st (SEQ ID NO: 499), hsa-miR-15b_st (SEQ ID NO: 510), hsa-miR-185-star_st (SEQ ID NO: 406), hsa-miR-188-5p_st (SEQ ID NO: 86), hsa-miR-18b_st (SEQ ID NO: 87), hsa-miR-20b_st (SEQ ID NO: 88), hsa-miR-215_st (SEQ ID NO: 566), hsa-miR-25_st (SEQ ID NO: 89), hsa-miR-362-5p_st (SEQ ID NO: 92), hsa-miR-378-star_st (SEQ ID NO: 409), hsa-miR-421_st (SEQ ID NO: 512), hsa-miR-425_st (SEQ ID NO: 286), hsa-miR-532-5p_st (SEQ ID NO: 98), hsa-miR-93_st (SEQ ID NO: 46), hsa-miR-941_st (SEQ ID NO: 595), hsa-let-7i_st (SEQ ID NO: 596), hsa-miR-10b_st (SEQ ID NO: 550), hsa-miR-1301_st (SEQ ID NO: 597), hsa-miR-140-5p_st (SEQ ID NO: 18), 14qII-14_st (SEQ ID NOs: 73, 157, 598, 627, and 674), 14qII-1_x_st (SEQ ID NOs: 74, 599, and 628), hsa-let-7b_st (SEQ ID NO: 600), hsa-miR-125a-3p_st (SEQ ID NO: 601), hsa-miR-125b-1-star_st (SEQ ID NO: 163), hsa-miR-125b_st (SEQ ID NO: 602), hsa-miR-1287_st (SEQ ID NO: 603), hsa-miR-134_st (SEQ ID NO: 164), hsa-miR-23a-star_st (SEQ ID NO: 604), hsa-miR-28-3p_st (SEQ ID NO: 605), hsa-miR-299-5p_st (SEQ ID NO: 606), hsa-miR-337-5p_st (SEQ ID NO: 169), hsa-miR-370_st (SEQ ID NO: 32), hsa-miR-376a_st (SEQ ID NO: 607), hsa-miR-376c_st (SEQ ID NO: 170), hsa-miR-379_st (SEQ ID NO: 172), hsa-miR-381_st (SEQ ID NO: 173), hsa-miR-382_st (SEQ ID NO: 174), hsa-miR-409-3p_st (SEQ ID NO: 81), hsa-miR-409-5p_st (SEQ ID NO: 175), hsa-miR-411_st (SEQ ID NO: 176), hsa-miR-431_st (SEQ ID NO: 177), hsa-miR-452_st (SEQ ID NO: 608), hsa-miR-485-5p_st (SEQ ID NO: 179), hsa-miR-487a_st (SEQ ID NO: 609), hsa-miR-487b_st (SEQ ID NO: 82), hsa-miR-494_st (SEQ ID NO: 181), hsa-miR-495_st (SEQ ID NO: 610), hsa-miR-543_st (SEQ ID NO: 182), hsa-miR-654-5p_st (SEQ ID NO: 611), hsa-miR-100_st (SEQ ID NO: 17), hsa-miR-181a-2-star_st (SEQ ID NO: 612), hsa-miR-197_st (SEQ ID NO: 520), hsa-miR-221-star_st (SEQ ID NO: 613), hsa-miR-525-5p_st (SEQ ID NO: 528), hsa-miR-1207-5p_st (SEQ ID NO: 109), hsa-miR-766_st (SEQ ID NO: 1), hsa-miR-31-star_st (SEQ ID NO: 614), hsa-miR-31_st (SEQ ID NO: 615), hsa-miR-320d_st (SEQ ID NO: 91), hsa-miR-146a_st (SEQ ID NO: 19), HBII-85-26_st (SEQ ID NOs: 251, 361, and 439), HBII-85-6_x_st (SEQ ID NOs: 253, 362, and 616), hsa-miR-491-5p_st (SEQ ID NO: 617), hsa-miR-589-star_st (SEQ ID NO: 618), hsa-miR-744_st (SEQ ID NO: 619), hsa-let-7b_st (SEQ ID NO: 600), hsa-miR-221_st (SEQ ID NO: 620), hsa-miR-222_st (SEQ ID NO: 621), hsa-miR-29b-1-star_st (SEQ ID NO: 622), hsa-miR-455-3p_st (SEQ ID NO: 178), hsa-let-7d_st (SEQ ID NO: 623), hsa-let-7g_st (SEQ ID NO: 624), hsa-miR-138_st (SEQ ID NO: 625), hsa-miR-503_st (SEQ ID NO: 101), HBII-289_st (SEQ ID NO: 626), hsa-miR-373_st (SEQ ID NO: 408), hsa-miR-512-3p_st (SEQ ID NO: 523), 14qII-14_x_st (SEQ ID NOs: 73, 158, 598, 627, and 674), 14qII-1_x_st (SEQ ID NOs: 74, 599, and 628), 14qII-26_st (SEQ ID NOs: 75, 160, 629, and 676), 14qII-26_x_st (SEQ ID NOs: 76, 161, and 630), hsa-miR-125b-1-star_st (SEQ ID NO: 163), hsa-miR-127-3p_st (SEQ ID NO: 77), hsa-miR-127-5p_st (SEQ ID NO: 631), hsa-miR-143-star_st (SEQ ID NO: 632), hsa-miR-143_st (SEQ ID NO: 31), hsa-miR-193a-3p_st (SEQ ID NO: 366), hsa-miR-193b-star_st (SEQ ID NO: 633), hsa-miR-199a-5p_st (SEQ ID NO: 634), hsa-miR-210_st (SEQ ID NO: 635), hsa-miR-214_st (SEQ ID NO: 636), hsa-miR-299-3p_st (SEQ ID NO: 168), hsa-miR-339-5p_st (SEQ ID NO: 273), hsa-miR-377-star_st (SEQ ID NO: 171), hsa-miR-410_st (SEQ ID NO: 637), hsa-miR-493_st (SEQ ID NO: 180), hsa-miR-542-5p_st (SEQ ID NO: 638), hsa-miR-758_st (SEQ ID NO: 35), hsa-miR-935_st (SEQ ID NO: 639), HBII-85-1_x_st (SEQ ID NOs: 640 and 657), U28_st (SEQ ID NO: 643), hsa-miR-155_st (SEQ ID NO: 20), hsa-miR-196b_st (SEQ ID NO: 644), hsa-miR-371-3p_st (SEQ ID NO: 645), hsa-miR-371-5p_st (SEQ ID NO: 236), hsa-miR-372_st (SEQ ID NO: 646), hsa-miR-886-3p_st (SEQ ID NO: 647), HBII-52-32_x_st (SEQ ID NOs: 312 and 649), hsa-miR-149_st (SEQ ID NO: 500), hsa-miR-9-star_st (SEQ ID NO: 651), hsa-miR-98_st (SEQ ID NO: 652), U91_s_st (SEQ ID NO: 653), hsa-miR-27b-star_st (SEQ ID NO: 654), hsa-miR-320a_st (SEQ ID NO: 655), hsa-miR-320b_st (SEQ ID NO: 656), hsa-miR-320c_st (SEQ ID NO: 90), hsa-miR-139-5p_st (SEQ ID NO: 658), hsa-miR-16_st (SEQ ID NO: 360), hsa-miR-675_st (SEQ ID NO: 516), hsa-miR-24-1-star_st (SEQ ID NO: 659), hsa-miR-532-3p_st (SEQ ID NO: 97), hsa-miR-103_st (SEQ ID NO: 660), hsa-miR-107_st (SEQ ID NO: 661), hsa-miR-1180_st (SEQ ID NO: 662), hsa-miR-1231_st (SEQ ID NO: 663), hsa-miR-132_st (SEQ ID NO: 664), hsa-miR-324-5p_st (SEQ ID NO: 665), hsa-miR-589_st (SEQ ID NO: 666), hsa-miR-1269_st (SEQ ID NO: 667), hsa-miR-1270_st (SEQ ID NO: 668), hsa-miR-145_st (SEQ ID NO: 669), hsa-miR-217_st (SEQ ID NO: 670), hsa-miR-574-3p_st (SEQ ID NO: 671), hsa-miR-195_st (SEQ ID NO: 672), hsa-miR-30b-star_st (SEQ ID NO: 673), hsa-miR-501-3p_st (SEQ ID NO: 95), 14qII-14_st (SEQ ID NOs: 73, 157, 598, 627, and 674), 14qII-1_st (SEQ ID NOs: 74, 159, and 675), hsa-miR-222-star_st (SEQ ID NO: 677), hsa-miR-30e-star_st (SEQ ID NO: 505), HBII-180C_st (SEQ ID NOs: 451, 490, and 678), HBII-180C_x_st (SEQ ID NOs: 451, 452, and 491), hsa-miR-106a_st (SEQ ID NO: 150), hsa-miR-106b-star_st (SEQ ID NO: 2), hsa-miR-106b_st (SEQ ID NO: 37), hsa-miR-1306_st (SEQ ID NO: 679), hsa-miR-1307_st (SEQ ID NO: 102), hsa-miR-130b_st (SEQ ID NO: 403), hsa-miR-17_st (SEQ ID NO: 152), hsa-miR-185_st (SEQ ID NO: 85), hsa-miR-18a-star_st (SEQ ID NO: 71), hsa-miR-18a_st (SEQ ID NO: 72), hsa-miR-19b_st (SEQ ID NO: 153), hsa-miR-20a_st (SEQ ID NO: 218), hsa-miR-25-star_st (SEQ ID NO: 3), hsa-miR-422a_st (SEQ ID NO: 410), hsa-miR-500-star_st (SEQ ID NO: 93), hsa-miR-500_st (SEQ ID NO: 94), hsa-miR-660_st (SEQ ID NO: 305), hsa-miR-720_st (SEQ ID NO: 680), hsa-miR-93-star_st (SEQ ID NO: 45), hsa-miR-135b-star_st (SEQ ID NO: 681), hsa-miR-194-star_st (SEQ ID NO: 230), hsa-miR-552_st (SEQ ID NO: 682), hsa-miR-592_st (SEQ ID NO: 683), hsa-miR-874_st (SEQ ID NO: 310), hsa-miR-181a_st (SEQ ID NO: 78), hsa-miR-497_st (SEQ ID NO: 684), hsa-miR-9_st (SEQ ID NO: 685), hsa-miR-502-3p_st (SEQ ID NO: 96), hsa-miR-652_st (SEQ ID NO: 42), hsa-miR-671-5p_st (SEQ ID NO: 43), hsa-miR-505-star_st (SEQ ID NO: 686), U27_st (SEQ ID NOs: 202, 330, and 687), U29_st (SEQ ID NOs: 189, 203, 331, and 430), and/or hsa-miR-191_st (SEQ ID NO: 284).

Another device of the invention includes at least a probe for hsa-miR-766_st (SEQ ID NO: 1) (e.g., a probe having a sequence that is complementary or identical to 5'-GCT-GAGGCTGTGGGGCTGGAGT-3' (SEQ ID NO: 1)) and any one additional probe for a biomarker specified in Tables 1-65. Preferably the one additional probe is for a biomarker having a correlation coefficient of equal to or greater than 0.3. In another embodiment, the one additional probe is for a biomarker having a correlation coefficient of equal to or greater than 0.4.

Another device of the invention includes at least a probe for hsa-miR-766_st (SEQ ID NO: 1) (e.g., a probe having a sequence that is complementary or identical to 5'-GCT-GAGGCTGTGGGGCTGGAGT-3' (SEQ ID NO: 1)) and any two additional probes for a biomarker specified in Tables 1-65. Preferably the two additional probes are for biomarkers having a correlation coefficient of equal to or greater than 0.3.

For example, a device of the invention may include one or more probes directed to those biomarkers in Tables 1-65 having a mean score correlation coefficient of 0.3 or greater, in which the probes have a sequence that is complementary or identical to the sequences in shown Tables 1-65 for the selected biomarkers, and can be used to predict the efficacy of treatment with one or more of vincristine, cisplatin, etoposide, azaguanine, carboplatin, adriamycin, aclarubicin, mitoxantrone, mitoxantrone, mitomycin, paclitaxel, gemcitabine, taxotere, dexamethasone, ara-c, methylprednisolone, methotrexate, bleomycin, methyl-gag, belinostat, carboplatin, 5-fu (5-fluorouracil), idarubicin, melphalan, IL4-PR38, valproic acid, all-trans retinoic acid (ATRA), cytoxan, topotecan, suberoylanilide hydroxamic acid (SAHA, vorinostat), depsipeptide (FR901228), bortezomib, leukeran, fludarabine, vinblastine, busulfan, dacarbazine, oxaliplatin, hydroxyurea, tegafur, daunorubicin, estramustine, mechlorethamine, streptozocin, carmustine, lomustine, mercaptopurine, teniposide, dactinomycin, tretinoin, ifosfamide, tamoxifen, irinotecan, floxuridine, thioguanine, PSC 833, erlotinib, herceptin, celecoxib, fulvestrant, iressa, anastrozole, letrozole, cetuximab, rituximab, radiation, histone deacetylase (HDAC) inhibitors, and/or 5-Aza-2'-deoxycytidine (decitabine) in a patient diagnosed with a cancer of the breast, prostate, lung and bronchus, colon and rectum, urinary bladder, skin, kidney, pancreas, oral cavity and pharynx, ovary, thyroid, parathyroid, stomach, brain, esophagus, liver and intrahepatic bile duct, cervix larynx, heart, testis, small and large intestine, anus, anal canal and anorectum, vulva, gallbladder, pleura, bones and joints, hypopharynx, eye and orbit, nose, nasal cavity and middle ear, nasopharynx, ureter, peritoneum, omentum and mesentery, and/or gastrointestines, as well as any form of cancer including, e.g., chronic myeloid leukemia, acute lymphocytic leukemia, non-Hodgkin lymphoma, melanoma, carcinoma, basal cell carcinoma, malignant mesothelioma, neuroblastoma, multiple myeloma, leukemia, retinoblastoma, acute myeloid leukemia, chronic lymphocytic leukemia, Hodgkin lymphoma, carcinoid tumors, acute tumor, and/or soft tissue sarcoma (e.g., preferably the cancer is a cancer of the bladder, breast, colon, rectum, uterus, kidney, lung, skin (e.g., melanoma), pancreas, prostate, blood and/or bone marrow (e.g., leukemia), lymphocytes (e.g., non-Hodgkin lymphoma), and/or thyroid). Preferably, the device also includes at least a probe for hsa-miR-766_st (SEQ ID NO:

1) (e.g., a probe having a sequence that is complementary or identical to 5'-GCTGAGGCTGTGGGGCTGGAGT-3' (SEQ ID NO: 1)).

In another example, a device of the invention may include one or more probes directed to those biomarkers in Tables 24, 28, 44-47, and/or 52 having a mean score correlation coefficient of 0.3 or greater, in which the probes have a sequence that is complementary or identical to the sequences in shown Tables 24, 28, 44-47, and/or 52 for the selected biomarkers, and can be used to predict the efficacy of treatment with an alkylating agent as correlated in Tables 24, 28, 44-47, and/or 52, such as mechlorethamine, cyclophosphamide (Cytoxan), ifosfamide, melphalan, streptozocin, lomustine, carmustine (BCNU), busulfan, and/or dacarbazine in a patient diagnosed with, e.g., chronic leukemia, lymphoma, Hodgkin disease, sarcoma, multiple myeloma, lung cancer, breast cancer, and/or ovarian cancer. The device may also include one or more probes directed to those biomarkers in Tables 2, 5, and 38 having a mean score correlation coefficient of 0.3 or greater, in which the probes have a sequence that is complementary or identical to the sequences in shown Tables 2, 5, and 38 for the selected biomarkers, and can be used to predict the efficacy of treatment with an agent as correlated in Tables 2, 5, and 38, such as cisplatin, carbonplatin, and/or oxalaplatin in a patient diagnosed with, e.g., chronic leukemia, lymphoma, Hodgkin disease, sarcoma, multiple myeloma, lung cancer, breast cancer, and/or ovarian cancer. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

In another example, a device of the invention may include all probes directed to those biomarkers in Tables 24, 28, 44-47, and/or 52 having a mean score correlation coefficient of 0.3 or greater, in which the probes have a sequence that is complementary or identical to the sequences in shown Tables 24, 28, 44-47, and/or 52 for the selected biomarkers, and can be used to predict the efficacy of treatment with an alkylating agent as correlated in Tables 24, 28, 44-47, and/or 52, such as mechlorethamine, cyclophosphamide (Cytoxan), ifosfamide, melphalan, streptozocin, lomustine, carmustine (BCNU), busulfan, and/or dacarbazine in a patient diagnosed with, e.g., chronic leukemia, lymphoma, Hodgkin disease, sarcoma, multiple myeloma, lung cancer, breast cancer, and/or ovarian cancer. The device may also include one or more probes directed to those biomarkers in Tables 2, 5, and 38 having a mean score correlation coefficient of 0.3 or greater, in which the probes have a sequence that is complementary or identical to the sequences in shown Tables 2, 5, and 38 for the selected biomarkers, and can be used to predict the efficacy of treatment with an agent as correlated in Tables 2, 5, and 38, such as cisplatin, carbonplatin, and/or oxalaplatin in a patient diagnosed with, e.g., chronic leukemia, lymphoma, Hodgkin disease, sarcoma, multiple myeloma, lung cancer, breast cancer, and/or ovarian cancer. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

Another device of the invention may include one or more probes directed to those biomarkers in Tables 11, 14, 16, 20, 34, 48, and/or 56 having a mean score correlation coefficient of 0.3 or greater, in which the probes have a sequence that is complementary or identical to the sequences in shown Tables 11, 14, 16, 20, 34, 48, and/or 56 for the selected biomarkers, and can be used to predict the efficacy of treatment with an antimetabolite as correlated in Tables 11, 14, 16, 20, 34, 48, and/or 56, such as 5-fluorouracil (5-FU), methotrexate, 6-mercaptopurine, thioguanine, cytarabine, gemcitabine, and/or fludarabine in a patient diagnosed with, e.g., chronic and/or acute leukemia, breast cancer, ovarian cancer, esophageal cancer, head and/or neck cancer, and/or cancer of the intestinal tract. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

Another device of the invention may include all probes directed to those biomarkers in Tables 11, 14, 16, 20, 34, 48, and/or 56 having a mean score correlation coefficient of 0.3 or greater, in which the probes have a sequence that is complementary or identical to the sequences in shown Tables 11, 14, 16, 20, 34, 48, and/or 56 for the selected biomarkers, and can be used to predict the efficacy of treatment with an antimetabolite selected as correlated in Tables 11, 14, 16, 20, 34, 48, and/or 56, such as 5-fluorouracil (5-FU), methotrexate, 6-mercaptopurine, thioguanine, cytarabine, gemcitabine, and/or fludarabine in a patient diagnosed with, e.g., chronic and/or acute leukemia, breast cancer, ovarian cancer, esophageal cancer, head and/or neck cancer, and/or cancer of the intestinal tract. Preferably, the device also includes at least a probe for hsa-miR-766_st (SEQ ID NO: 1) (e.g., a probe having a sequence that is complementary or identical to 5'-GCTGAGGCT-GTGGGGCTGGAGT-3' (SEQ ID NO: 1)).

Yet another device of the invention may include one or more probes directed to those biomarkers in Tables 9, 23, 41, 42, 50, and/or 59 having a mean score correlation coefficient of 0.3 or greater, in which the probes have a sequence that is complementary or identical to the sequences in shown Tables 9, 23, 41, 42, 50, and/or 59 for the selected biomarkers, and can be used to predict the efficacy of treatment with an anthracycline as correlated in Tables 9, 23, 41, 42, 50, and/or 59, such as daunorubicin, idarubicin, bleomycin, actinomycin, and/or mitomycin, in a patient diagnosed with, e.g., a leukemia, a lymphoma, breast cancer, uterine cancer, ovarian cancer, and/or lung cancer. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

Yet another device of the invention may include all probes directed to those biomarkers in Tables 9, 23, 41, 42, 50, and/or 59 having a mean score correlation coefficient of 0.3 or greater, in which the probes have a sequence that is complementary or identical to the sequences in shown Tables 9, 23, 41, 42, 50, and/or 59 for the selected biomarkers, and can be used to predict the efficacy of treatment with an anthracycline as correlated in Tables 9, 23, 41, 42, 50, and/or 59, such as daunorubicin, idarubicin, bleomycin, actinomycin, and/or mitomycin, in a patient diagnosed with, e.g., a leukemia, a lymphoma, breast cancer, uterine cancer, ovarian cancer, and/or lung cancer. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

Yet another device of the invention may include one or more probes directed to those biomarkers in Tables 3, 29, 49, 54, and/or 65 having a mean score correlation coefficient of 0.3 or greater, in which the probes have a sequence that is complementary or identical to the sequences in shown Tables 3, 29, 49, 54, and/or 65 for the selected biomarkers, and can be used to predict the efficacy of treatment with a topoisomerase inhibitor as correlated in Tables 3, 29, 49, 54, and/or 65, such as topotecan, irinotecan, etoposide, teniposide, and/or cetuximab in a patient diagnosed with, e.g., a leukemia, small cell lung cancer, colorectal cancer, ovarian cancer, and/or gastrointestinal cancer. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

Yet another device of the invention may include all probes directed to those biomarkers in Tables 3, 29, 49, 54, and/or 65 having a mean score correlation coefficient of 0.3 or greater, in which the probes have a sequence that is complementary or identical to the sequences in shown Tables 3, 29, 49, 54, and/or 65 for the selected biomarkers, and can be used to predict the efficacy of treatment with a topoisomerase inhibitor as correlated in Tables 3, 29, 49, 54, and/or 65, such as topotecan, irinotecan, etoposide, teniposide, and/or cetuximab in a patient diagnosed with, e.g., a leukemia, small cell lung cancer, colorectal cancer, ovarian cancer, and/or gastrointestinal cancer. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

Yet another device of the invention may include one or more probes directed to those biomarkers in Tables 1, 3, 10, 12, 35, 43, and/or 49 having a mean score correlation coefficient of 0.3 or greater, in which the probes have a sequence that is complementary or identical to the sequences in shown Tables 1, 3, 10, 12, 35, 43, and/or 49 for the selected biomarkers, and can be used to predict the efficacy of treatment with a plant alkaloid as correlated in Tables 1, 3, 10, 12, 35, 43, and/or 49, such as vincristine, vinblastine, paclitaxel, docetaxel, estramustine, etoposide, and/or teniposide in a patient diagnosed with, e.g., breast cancer, lung cancer, ovarian cancer, a myeloma, a lymphoma, a leukemia, and/or a mesothelioma. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

Yet another device of the invention may include all probes directed to those biomarkers in Tables 1, 3, 10, 12, 35, 43, and/or 49 having a mean score correlation coefficient of 0.3 or greater, in which the probes have a sequence that is complementary or identical to the sequences in shown Tables 1, 3, 10, 12, 35, 43, and/or 49 for the selected biomarkers, and can be used to predict the efficacy of treatment with a plant alkaloid as correlated in Tables 1, 3, 10, 12, 35, 43, and/or 49, such as vincristine, vinblastine, paclitaxel, docetaxel, estramustine, etoposide, and/or teniposide in a patient diagnosed with, e.g., breast cancer, lung cancer, ovarian cancer, a myeloma, a lymphoma, a leukemia, and/or a mesothelioma. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

Yet another device of the invention may include one or more probes directed to those biomarkers in Tables 13 and/or 15 having a mean score correlation coefficient of 0.3 or greater, in which the probes have a sequence that is complementary or identical to the sequences in shown Tables 13 and/or 15 for the selected biomarkers, and can be used to predict the efficacy of treatment with a corticosteroid as correlated in Tables 13 and/or 15, such as dexamethasone and/or methylprednisolone in a patient diagnosed with, e.g., lung cancer, breast cancer lymphoma, leukemias, and/or multiple myeloma. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3'(SEQ ID NO: 1)).

Yet another device of the invention may include all probes directed to those biomarkers in Tables 13 and/or 15 having a mean score correlation coefficient of 0.3 or greater, in which the probes have a sequence that is complementary or identical to the sequences in shown Tables 13 and/or 15 for the selected biomarkers, and can be used to predict the efficacy of treatment with a corticosteroid as correlated in Tables 13 and/or 15, such as dexamethasone and/or methylprednisolone in a patient diagnosed with, e.g., lung cancer, breast cancer lymphoma, leukemias, and/or multiple myeloma. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1).

Yet another device of the invention may include one or more probes directed to those biomarkers in Tables 2, 5, and/or 38 having a mean score correlation coefficient of 0.3 or greater, in which the probes have a sequence that is complementary or identical to the sequences in shown Tables 2, 5, and/or 38 for the selected biomarkers, and can be used to predict the efficacy of treatment with a platinum compound as correlated in Tables 2, 5, and/or 38, such as cisplatin, carbonplatin, and/or oxalaplatin in a patient diagnosed with, e.g., chronic leukemia, lymphoma, Hodgkin disease, sarcoma, multiple myeloma, mesothelioma, lung cancer, breast cancer, testicular cancer, colon cancer, and/or ovarian cancer. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

Yet another device of the invention may include all probes directed to those biomarkers in Tables 2, 5, and/or 38 having a mean score correlation coefficient of 0.3 or greater, in which the probes have a sequence that is complementary or identical to the sequences in shown Tables 2, 5, and/or 38 for the selected biomarkers, and can be used to predict the efficacy of treatment with a platinum compound as correlated in Tables 2, 5, and/or 38, such as cisplatin, carbonplatin, and/or oxalaplatin in a patient diagnosed with, e.g., chronic leukemia, lymphoma, Hodgkin disease, sarcoma, multiple myeloma, mesothelioma, lung cancer, breast cancer, testicular cancer, colon cancer, and/or ovarian cancer. Preferably, the device also includes at least a probe for hsa-miR-766_st (SEQ ID NO: 1) (e.g., a probe having a sequence that is complementary or identical to 5'-GCTGAGGCTGTGGGGCTGGAGT-3' (SEQ ID NO: 1)).

Yet another device of the invention may include one or more probes having a sequence that is complementary or identical to at least 5 (e.g., 10, 15, 20, or 22) consecutive nucleotides of hsa-miR-766_st (SEQ ID NO: 1) (e.g., preferably the probe is complementary or identical to the 22 consecutive nucleotides of the sequence 5'-GCTGAGGCTGTGGGGCTGGAGT-3' (SEQ ID NO: 1)), which can be used to predict the efficacy of treatment with a drug selected from one or more of etoposide, adriamycin, paclitaxel, dexamethasone, methylprednisolone, belinostat, aza-2'-deoxycytidine, melphalan, suberoylanilide hydroxamic acid, leukeran, fludarabine, busulfan, dacarbazine, hydroxyurea, daunorubicin, mechlorethamine, carmustine, lomustine, mercaptopurine, teniposide, dactinomycin, ifosamide, irinotecan, and/or thioguanine in a patient (e.g., a patient diagnosed with a cancer, e.g., a cancer of the breast, prostate, lung and bronchus, colon and rectum, urinary bladder, skin, kidney, pancreas, oral cavity and pharynx, ovary, thyroid, parathyroid, stomach, brain, esophagus, liver and intrahepatic bile duct, cervix larynx, heart, testis, small and large intestine, anus, anal canal and anorectum, vulva, gallbladder, pleura, bones and joints, hypopharynx, eye and orbit, nose, nasal cavity and middle ear, nasopharynx, ureter, peritoneum, omentum and mesentery, and/or gastrointestines, as well as any form of cancer including, e.g., chronic myeloid leukemia, acute lymphocytic leukemia, non-Hodgkin lymphoma, melanoma, carcinoma, basal cell carcinoma, malignant mesothelioma, neuroblastoma, multiple myeloma, leukemia, retinoblastoma, acute myeloid leukemia, chronic lymphocytic leukemia, Hodgkin lymphoma, carcinoid tumors, acute tumor, and/or soft tissue sarcoma).

In an embodiment, each of the devices described above may further include at least one probe having a sequence that is complementary to or identical to at least 5 (e.g., 10, 15, 20, or 22) consecutive nucleotides of hsa-miR-766_st (SEQ ID NO: 1) (e.g., preferably the probe has a sequence that is complementary or identical to the 22 consecutive nucleotides of the sequence 5'-GCTGAGGCTGTGGGGCTG-GAGT-3' (SEQ ID NO: 1)).

The invention also features methods of using one or more of the devices of the third aspect of the invention described above to predict the efficacy of treatment with the indicated chemotherapeutic agent in a patient having one or more of the specified cancers.

The methods and devices can be used to predict the sensitivity or resistance of a subject (e.g., a cancer patient) diagnosed with a disease condition, e.g., cancer (e.g., cancers of the breast, prostate, lung and bronchus, colon and rectum, urinary bladder, skin, kidney, pancreas, oral cavity and pharynx, ovary, thyroid, parathyroid, stomach, brain, esophagus, liver and intrahepatic bile duct, cervix larynx, heart, testis, small and large intestine, anus, anal canal and anorectum, vulva, gallbladder, pleura, bones and joints, hypopharynx, eye and orbit, nose, nasal cavity and middle ear, nasopharynx, ureter, peritoneum, omentum and mesentery, or gastrointestines, as well as any form of cancer including, e.g., chronic myeloid leukemia, acute lymphocytic leukemia, non-Hodgkin lymphoma, melanoma, carcinoma, basal cell carcinoma, malignant mesothelioma, neuroblastoma, multiple myeloma, leukemia, retinoblastoma, acute myeloid leukemia, chronic lymphocytic leukemia, Hodgkin lymphoma, carcinoid tumors, acute tumor, or soft tissue sarcoma) to a treatment, e.g., treatment with a compound or drug, e.g., a chemotherapeutic agent, or radiation, such as those treatments listed above.

A fourth aspect of the invention features a kit that includes a device having at least one or more single-stranded nucleic acid molecules (e.g., deoxyribonucleic acid (DNA) or ribonucleic acid (RNA) molecules) that are complementary to or identical to at least 5 consecutive nucleotides (more preferably at least 10, 15, 20, 25, 30, 35, 40, 45, 50, 55, 60, 65, 70, 75, 80, 85, 90, 95, 100, 150, 200, 250, 300, or more consecutive nucleotides; the nucleic acid molecule can also be 5-20, 25, 5-50, 50-100, or over 100 consecutive nucleotides long) of at least one of the biomarkers set forth in the first aspect of the invention, such that the single stranded nucleic acid molecules are sufficient for the detection of expression of the biomarkers (e.g., in a sample from a patient or prepared from a patient sample) by allowing specific hybridization between the single stranded nucleic acid molecules and one or more of the nucleic acid molecules corresponding to the biomarker, or a complement thereof. In an embodiment, the kit includes one or more of the devices of the third aspect of the invention (e.g., a device that can be used to predict the efficacy of therapy with an alkylating agent, an antimetabolite, an anthracycline, a topoisomerase inhibitor, a plant alkaloid, a corticosteroid, and/or a platinum agent). The kit further includes instructions for applying nucleic acid molecules collected from a sample from a cancer patient (e.g., from a cell, tissue, or organ of the patient), determining the level of expression of the biomarkers in the sample that hybridize to the single stranded nucleic acid molecule(s), and predicting the patient's sensitivity to at least one or more treatments for cancer when use of the kit establishes that the expression level of the biomarkers is changed (i.e., increased or decreased relative to a control sample (i.e., a cell, tissue, and/or organ) known to be sensitive or resistant to the treatment(s), as is discussed above in connection with the first aspect of the invention). In an embodiment, the instructions further indicate that an alteration in the expression level of the biomarker(s) relative to the expression of the biomarker(s) in a control sample (e.g., a cell, tissue, and/or organ known to be sensitive or resistant to the treatment(s)) indicates a change in sensitivity of the patient to the treatment(s) (i.e., a decrease in the level of expression of a biomarker (e.g., a gene and/or RNA (e.g., a miRNA)) known to be expressed in cells sensitive to the treatment(s) indicates that the patient is becoming resistant to the treatment(s) or is likely to become resistant to the treatment(s), and vice versa).

In an embodiment, the kit can be utilized to determine a patient's resistance or sensitivity to at least one or more of vincristine, cisplatin, etoposide, azaguanine, carboplatin, adriamycin, aclarubicin, mitoxantrone, mitoxantrone, mitomycin, paclitaxel, gemcitabine, taxotere, dexamethasone, ara-c, methylprednisolone, methotrexate, bleomycin, methyl-gag, belinostat, carboplatin, 5-fu (5-fluorouracil), idarubicin, melphalan, IL4-PR38, valproic acid, all-trans retinoic acid (ATRA), cytoxan, topotecan, suberoylanilide hydroxamic acid (SAHA, vorinostat), depsipeptide (FR901228), bortezomib, leukeran, fludarabine, vinblastine, busulfan, dacarbazine, oxaliplatin, hydroxyurea, tegafur, daunorubicin, estramustine, mechlorethamine, streptozocin, carmustine, lomustine, mercaptopurine, teniposide, dactinomycin, tretinoin, ifosfamide, tamoxifen, irinotecan, floxuridine, thioguanine, PSC 833, erlotinib, herceptin, celecoxib, fulvestrant, iressa, anastrozole, letrozole, cetuximab, rituximab, radiation, histone deacetylase (HDAC) inhibitors, and/or 5-Aza-2'-deoxycytidine (decitabine) by determining the expression level of one or more of the biomarkers set forth in the first aspect of the invention and known to be increased in a patient sensitive to treatment with one or more of these agents (i.e., a patient is determined to be sensitive, or is likely to be sensitive, to the indicated treatment if the level of expression of one or more of the biomarkers increases relative to the level of expression of the biomarkers in a control sample (i.e., a cell, tissue, or organ) in which increased expression of the biomarkers indicates sensitivity to the treatment, and vice versa).

In an embodiment, the nucleic acid molecules of the methods and/or devices are characterized by their ability to specifically identify nucleic acid molecules complementary to or identical to the biomarkers in a sample collected from a cancer patient.

A fifth aspect of the invention features a method of identifying biomarkers indicative of sensitivity of a cancer patient to a treatment for cancer by obtaining pluralities of measurements of the expression level of one or more gene(s) and/or RNA(s) (e.g., a miRNA)). For example, the measurements can be obtained by detecting the expression of one or more genes and/or RNAs using a single probe or by using multiple probes directed to a single gene or RNA. The methods can include assaying the expression levels of the gene(s) and/or RNA(s) in one or more different cell types and/or measuring the growth of those cell types in the presence of a treatment for cancer relative to the growth of the cell types in the absence of the treatment for cancer. The method further includes correlating each plurality of measurements of the expression level of the gene and/or RNAs in cells with the growth of the cells to obtain a correlation coefficient; selecting the median correlation coefficient calculated for the gene(s) and/or RNA(s); and identifying the gene(s) and/or RNA(s) as a biomarker for use in determining the sensitivity of a cancer patient to one or more treatments for cancer if said median correlation coefficient exceeds 0.3 (preferably the gene and/or RNA is identified as a biomarker for a patient's sensitivity to a treatment if the correlation coefficient exceeds 0.4, 0.5, 0.6, 0.7, 0.8, 0.9, 0.95, or 0.99 or more). In an embodiment, the method is performed in the presence of a second treatment.

A sixth aspect of the invention features a method of predicting sensitivity of a patient (e.g., a cancer patient) to a treatment for cancer by obtaining a measurement of the expression of a biomarker gene or RNA (e.g., a miRNA) from a sample (e.g., a cell or tissue) from the patient; applying a model predictive of sensitivity to a treatment for cancer to the measurement, in which the model is developed using an algorithm selected from the group consisting of linear sums, nearest neighbor, nearest centroid, linear discriminant analysis, support vector machines, and neural networks; and predicting whether or not the patient will be responsive to the treatment for cancer. In an embodiment, the measurement is obtained by assaying expression of the gene and/or RNA biomarker in a cell known to be sensitive or resistant to the treatment. In another embodiment, the model combines the outcomes of linear sums, linear discriminant analysis, support vector machines, neural networks, k-nearest neighbors, and nearest centroids, or the model is cross-validated using a random sample of multiple measurements. In another embodiment, treatment, e.g., a compound, has previously failed to show efficacy in a patient. In several embodiments, the linear sum is compared to a sum of a reference population with known sensitivity; the sum of a reference population is the median of the sums derived from the population members' biomarker gene and/or RNA expression. In another embodiment, the model is derived from the components of a data set obtained by independent component analysis or is derived from the components of a data set obtained by principal component analysis.

A seventh aspect of the invention features a kit, apparatus, and software used to implement the method of the sixth aspect of the invention.

In several embodiments of all aspects of the invention, the expression level of the gene(s) is determined by detecting the level of mRNA transcribed from the gene(s), by detecting the level of RNA(s) (e.g., miRNA(s)) expressed from noncoding regions, by detecting the level of a protein product of the gene(s), and/or by detecting the level of the biological activity of a protein product of the gene(s). In further embodiments of all aspects of the invention, an increase or decrease in the expression level of the gene(s) and/or RNA(s), relative to the expression level of the gene(s) and/or RNA(s) in a cell, tissue, or organ sensitive to the treatment(s), indicates increased sensitivity of the cancer patient to the treatment(s). Alternatively, an increase or decrease in the expression level of the gene(s) and/or RNA(s), relative to the expression level of the gene(s) and/or RNA(s) in a cell, tissue, or organ resistant to the treatment(s), indicates increased resistance of the cancer patient to the treatment(s). In another embodiment of all aspects of the invention, the cell is a cancer cell. In another embodiment of all aspects of the invention, the expression level of one or more of the biomarkers described herein is measured using a quantitative reverse transcription-polymerase chain reaction (qRT-PCR). In an embodiment of all aspects of the invention, the level of expression of two or more of the biomarkers described herein (e.g., two of more of the biomarkers in one or more of Tables 1-65 and/or one or more of Tables 66-129) is performed, more preferably the level of expression of three, four, five, six, seven, eight, nine, or ten of the biomarkers described herein is performed, and most preferably twenty, thirty, forty, fifty, sixty, seventy, eighty, ninety, or one hundred or more of the biomarkers described herein is performed (e.g., any combination of two or more of the biomarkers (e.g., the combination of hsa-miR-766_st (SEQ ID NO: 1) with one or more of the other biomarkers described herein). In another embodiment of all aspects of the invention, the expression level of the biomarker(s) is determined using the device of the third aspect of the invention and/or the kit of the fourth aspect of the invention.

In another embodiment of all aspects of the invention, the treatment is a compound, such as a chemotherapeutic agent selected from the group consisting of vincristine, cisplatin, etoposide, azaguanine, carboplatin, adriamycin, aclarubicin, mitoxantrone, mitoxantrone, mitomycin, paclitaxel, gemcitabine, taxotere, dexamethasone, ara-c, methylprednisolone, methotrexate, bleomycin, methyl-gag, belinostat, carboplatin, 5-fu (5-fluorouracil), idarubicin, melphalan, IL4-PR38, valproic acid, all-trans retinoic acid (ATRA), cytoxan, topotecan, suberoylanilide hydroxamic acid (SAHA, vorinostat), depsipeptide (FR901228), bortezomib, leukeran, fludarabine, vinblastine, busulfan, dacarbazine, oxaliplatin, hydroxyurea, tegafur, daunorubicin, estramustine, mechlorethamine, streptozocin, carmustine, lomustine, mercaptopurine, teniposide, dactinomycin, tretinoin, ifosfamide, tamoxifen, irinotecan, floxuridine, thioguanine, PSC 833, erlotinib, herceptin, celecoxib, fulvestrant, iressa, anastrozole, letrozole, cetuximab, rituximab, radiation, histone deacetylase (HDAC) inhibitors, and/or 5-Aza-2'-deoxycytidine (decitabine). In another embodiment of all aspects of the invention, one or more of the treatments has previously failed to show effect in a subject (e.g., a subject selected from a subpopulation predicted to be sensitive to the treatment(s), a subject selected from a subpopulation predicted to die without treatment(s), a subject selected from a subpopulation predicted to have disease symptoms without treatment(s), a subject selected from a subpopulation predicted to be cured without treatment(s)).

In another embodiment of all aspects of the invention, the treatment is, e.g., administration of a compound, a protein, an antibody, an oligonucleotide, a chemotherapeutic agent, or radiation to a patient. In an embodiment of all aspects of the invention, the treatment is, e.g., a chemotherapeutic agent, such as, e.g., Vincristine, Cisplatin, Azaguanine, Etoposide, Adriamycin, Aclarubicin, Mitoxantrone, Mitomycin, Paclitaxel, Gemcitabine, Taxotere, Dexamethasone, Ara-C, Methylprednisolone, Methotrexate, Bleomycin, Methyl-GAG, Carboplatin, 5-FU (5-Fluorouracil), MAB-THERA™ (Rituximab), histone deacetylase (HDAC) inhibitors, 5-Aza-2'-deoxycytidine (Decitabine), alpha emitters such as astatine-211, bismuth-212, bismuth-213, lead-212, radium-223, actinium-225, and thorium-227, beta emitters such as tritium, strontium-90, cesium-137, carbon-11, nitrogen-13, oxygen-15, fluorine-18, iron-52, cobalt-55, cobalt-60, copper-61, copper-62, copper-64, zinc-62, zinc-63, arsenic-70, arsenic-71, arsenic-74, bromine-76, bromine-79, rubidium-82, yttrium-86, zirconium-89, indium-110, iodine-120, iodine-124, iodine-129, iodine-131, iodine-125, xenon-122, technetium-94m, technetium-94, technetium-99m, and technetium-99, gamma emitters such as cobalt-60, cesium-137, and technetium-99m, Alemtuzumab, Daclizumab, Rituximab (MABTHERA™), Trastuzumab (HERCEPTIN™), Gemtuzumab, Ibritumomab, Edrecolomab, Tositumomab, CeaVac, Epratuzumab, Mitumomab, Bevacizumab, Cetuximab, Edrecolomab, Lintuzumab, MDX-210, IGN-101, MDX-010, MAb, AME, ABX-EGF, EMD 72 000, Apolizumab, Labetuzumab, ior-t1, MDX-220, MRA, H-11 scFv, Oregovomab, huJ591 MAb, BZL, Visilizumab, TriGem, TriAb, R3, MT-201, G-250, unconjugated, ACA-125, Onyvax-105, CDP-860, BrevaRex MAb, AR54, IMC-1C11, GlioMAb-H, ING-1, Anti-LCG MAbs, MT-103, KSB-303, Therex, KW-2871, Anti-HMI.24, Anti-PTHrP, 2C4 antibody, SGN-30, TRAIL-RI MAb, CAT, Prostate cancer antibody, H22xKi-4, ABX-MA1, Imuteran, Monopharm-C, Acivicin, Aclarubicin, Acodazole Hydrochloride, Acronine, Adozelesin, Adriamycin, Aldesleukin, Altretamine, Ambomycin, A. metantrone Acetate, Aminoglutethimide, Amsacrine, Anastrozole, Anthramycin, Asparaginase, Asperlin, Azacitidine, Azetepa, Azotomycin, Batimastat, Benzodepa, Bicalutamide, Bisantrene Hydrochloride, Bisnafide Dimesylate, Bizelesin, Bleomycin Sulfate, Brequinar Sodium, Bropirimine, Busulfan, Cactinomycin, Calusterone, Camptothecin, Caracemide, Carbetimer, Carboplatin, Carmustine, Carubicin Hydrochloride, Carzelesin, Cedefingol, Chlorambucil, Cirolemycin, Cisplatin, Cladribine, Combretestatin A-4, Crisnatol Mesylate, Cyclophosphamide, Cytarabine, Dacarbazine, DACA (N-[2-(Dimethyl-amino) ethyl] acridine-4-carboxamide), Dactinomycin, Daunorubicin Hydrochloride, Daunomycin, Decitabine, Dexormaplatin, Dezaguanine, Dezaguanine Mesylate, Diaziquone, Docetaxel, Dolasatins, Doxorubicin, Doxorubicin Hydrochloride, Droloxifene, Droloxifene Citrate, Dromostanolone Propionate, Duazomycin, Edatrexate, Eflornithine Hydrochloride, Ellipticine, Elsamitrucin, Enloplatin, Enpromate, Epipropidine, Epirubicin Hydrochloride, Erbulozole, Esorubicin Hydrochloride, Estramustine, Estramustine Phosphate Sodium, Etanidazole, Ethiodized Oil I 131, Etoposide, Etoposide Phosphate, Etoprine, Fadrozole Hydrochloride, Fazarabine, Fenretinide, Floxuridine, Fludarabine Phosphate, Fluorouracil, 5-FdUMP, Flurocitabine, Fosquidone, Fostriecin Sodium, Gemcitabine, Gemcitabine Hydrochloride, Gold Au 198, Homocamptothecin, Hydroxyurea, Idarubicin Hydrochloride, Ifosfamide, Ilmofosine, Interferon Alfa-2a, Interferon Alfa-2b, Interferon Alfa-n1, Interferon Alfa-n3, Interferon Beta-I a, Interferon Gamma-I b, Iproplatin, Irinotecan Hydrochloride, Lanreotide Acetate, Letrozole, Leuprolide Acetate, Liarozole Hydrochloride, Lometrexol Sodium, Lomustine, Losoxantrone Hydrochloride, Masoprocol, Maytansine, Mechlorethamine Hydrochloride, Megestrol Acetate, Melengestrol Acetate, Melphalan, Menogaril, Mercaptopurine, Methotrexate, Methotrexate Sodium, Metoprine, Meturedepa, Mitindomide, Mitocarcin, Mitocromin, Mitogillin, Mitomalcin, Mitomycin, Mitosper, Mitotane, Mitoxantrone Hydrochloride, Mycophenolic Acid, Nocodazole, Nogalamycin, Ormaplatin, Oxisuran, Paclitaxel, Pegaspargase, Peliomycin, Pentamustine, PeploycinSulfate, Perfosfamide, Pipobroman, Piposulfan, Piroxantrone Hydrochloride, Plicamycin, Plomestane, Porfimer Sodium, Porfiromycin, Prednimustine, Procarbazine Hydrochloride, Puromycin, Puromycin Hydrochloride, Pyrazofurin, Rhizoxin, Rhizoxin D, Riboprine, Rogletimide, Safingol, Safingol Hydrochloride, Semustine, Simtrazene, Sparfosate Sodium, Sparsomycin, Spirogermanium Hydrochloride, Spiromustine, Spiroplatin, Streptonigrin, Streptozocin, Strontium Chloride Sr 89, Sulofenur, Talisomycin, Taxane, Taxoid, Tecogalan Sodium, Tegafur, Teloxantrone Hydrochloride, Temoporfin, Teniposide, Teroxirone, Testolactone, Thiamiprine, Thioguanine, Thiotepa, Thymitaq, Tiazofurin, Tirapazamine, Tomudex, TOP53, Topotecan Hydrochloride, Toremifene Citrate, Trestolone Acetate, Triciribine Phosphate, Trimetrexate, Trimetrexate Glucuronate, Triptorelin, Tubulozole Hydrochloride, Uracil Mustard, Uredepa, Vapreotide, Verteporfin, Vinblastine, Vinblastine Sulfate, Vincristine, Vincristine Sulfate, Vindesine, Vindesine Sulfate, Vinepidine Sulfate, Vinglycinate Sulfate, Vinleurosine Sulfate, Vinorelbine Tartrate, Vinrosidine Sulfate, Vinzolidine Sulfate, Vorozole, Zeniplatin, Zinostatin, Zorubicin Hydrochloride, 2-Chlorodeoxyadenosine, 2' Deoxyformycin, 9-aminocamptothecin, raltitrexed, N-propargyl-5,8-dideazafolic acid, 2chloro-2'-arabino-fluoro-2'-deoxyadenosine, 2-chloro-2'-deoxyadenosine, anisomycin, trichostatin A, hPRL-G129R, CEP-751, linomide, sulfur mustard, nitrogen mustard (mechlor ethamine), cyclophosphamide, melphalan, chlorambucil, ifosfamide, busulfan, N-methyl-Nnitrosourea (MNU), N, N'-Bis (2-chloroethyl)-N-nitrosourea (BCNU), N-(2-chloroethyl)-N' cyclohexyl-N-nitrosourea (CCNU), N-(2-chloroethyl)-N'-(trans-4-methylcyclohexyl-N-nitrosourea (MeCCNU), N-(2-chloroethyl)-N'-(diethyl) ethylphosphonate-N-nitrosourea (fotemustine), streptozotocin, diacarbazine (DTIC), mitozolomide, temozolomide, thiotepa, mitomycin C, AZQ, adozelesin, Cisplatin, Carboplatin, Ormaplatin, Oxaliplatin, C1-973, DWA 2114R, JM216, JM335, Bis (platinum), tomudex, azacitidine, cytarabine, gemcitabine, 6-Mercaptopurine, 6-Thioguanine, Hypoxanthine, teniposide 9-amino camptothecin, Topotecan, CPT-11, Doxorubicin, Daunomycin, Epirubicin, darubicin, mitoxantrone, losoxantrone, Dactinomycin (Actinomycin D), amsacrine, pyrazoloacridine, all-trans retinol, 14-hydroxy-retroretinol, all-trans retinoic acid, N-(4-Hydroxyphenyl) retinamide, 13-cis retinoic acid, 3-Methyl TTNEB, 9-cis retinoic acid, fludarabine (2-F-ara-AMP), 2-chlorodeoxyadenosine (2-Cda), 20-pi-1,25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, ara-CDP-DL-PTBA, argininedeaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, 9-, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epirubicin, epothilones (A, R=H, B, R=Me), epithilones, episteride, estramustine analogue, estrogen agonists, estrogen antagonists, etanidazole, etoposide, etoposide 4'-phosphate (etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, homoharringtonine (HHT), hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, 4-, irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maytansine, mannostatin A, marimastat, masoprocol, maspin, matrilysin inhibitors, matrix metalloproteinase inhibitors, menogaril, merbarone, meterelin, methioninase, metoclopramide, MIF inhibitor, ifepristone, miltefosine, mirimostim, mismatched double stranded RNA, mithracin, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, 06-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, podophyllotoxin, porfimer sodium, porfiromycin, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, RII retinamide, rogletimide, rohitukine, romurtide, roquinimex, rubiginone B 1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, or zinostatin stimalamer. In another embodiment of all aspects of the invention, a second treatment is utilized to determine gene expression in a sample from the patient.

DEFINITIONS

"Resistant" or "resistance" as used herein means that a cell, a tumor, a person, or a living organism is able to withstand treatment, e.g., with a compound, such as a chemotherapeutic agent or radiation treatment, in that the treatment inhibits the growth of a cell, e.g., a cancer cell, in vitro or in a tumor, person, or living organism by less than 10%, 20%, 30%, 40%, 50%, 60%, or 70% relative to the growth of a cell not exposed to the treatment. Resistance to treatment may be determined by a cell-based assay that measures the growth of treated cells as a function of the cells' absorbance of an incident light beam as used to perform the NCI60 assays described herein. In this example, greater absorbance indicates greater cell growth, and thus, resistance to the treatment. A smaller reduction in growth indicates more resistance to a treatment. By "chemoresistant" or "chemoresistance" is meant resistance to a compound.

"Sensitive" or "sensitivity" as used herein means that a cell, a tumor, a person, or a living organism is responsive to treatment, e.g., with a compound, such as a chemotherapeutic agent or radiation treatment, in that the treatment inhibits the growth of a cell, e.g., a cancer cell, in vitro or in a tumor, person, or living organism by 70%, 80%, 90%, 95%, 99% or 100%. Sensitivity to treatment may be determined by a cell-based assay that measures the growth of treated cells as a function of the cells' absorbance of an incident light beam as used to perform the NCI60 assays described herein. In this example, lesser absorbance indicates lesser cell growth, and thus, sensitivity to the treatment. A greater reduction in growth indicates more sensitivity to the treatment. By "chemosensitive" or "chemosensitivity" is meant sensitivity to a compound.

"Complement" of a nucleic acid sequence or a "complementary" nucleic acid sequence as used herein refers to an oligonucleotide which is in "antiparallel association" when it is aligned with the nucleic acid sequence such that the 5' end of one sequence is paired with the 3' end of the other. Nucleotides and other bases may have complements and may be present in complementary nucleic acids. Bases not commonly found in natural nucleic acids that may be included in the nucleic acids of the present invention include, for example, inosine and 7-deazaguanine. "Complementarity" may not be perfect; stable duplexes of complementary nucleic acids may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

When complementary nucleic acid sequences form a stable duplex, they are said to be "hybridized" or to "hybridize" to each other or it is said that "hybridization" has occurred. Nucleic acids are referred to as being "complementary" if they contain nucleotides or nucleotide homologues that can form hydrogen bonds according to Watson-Crick base-pairing rules (e.g., G with C, A with T or A with U) or other hydrogen bonding motifs such as for example diaminopurine with T, 5-methyl C with G, 2-thiothymidine with A, inosine with C, pseudoisocytosine with G, etc. Anti-sense RNA may be complementary to other oligonucleotides, e.g., mRNA.

"Gene" as used herein indicates a coding or noncoding gene whose activity can be determined by measuring the produced RNA. Examples include protein coding genes, microRNAs, small nuclear RNAs and other RNAs with catalytic, regulatory or coding properties.

"Biomarker" as used herein indicates a gene or RNA (e.g., a miRNA) whose expression indicates sensitivity or resistance to a treatment.

"Compound" as used herein means a chemical or biological substance, e.g., a drug, a protein, an antibody, or an oligonucleotide, which may be used to treat a disease or which has biological activity in vivo or in vitro. Preferred compounds may or may not be approved by the U.S. Food and Drug Administration (FDA). Preferred compounds include, e.g., chemotherapy agents that may inhibit cancer growth. Preferred chemotherapy agents include, e.g., Vincristine, Cisplatin, Azaguanine, Etoposide, Adriamycin, Aclarubicin, Mitoxantrone, Mitomycin, Paclitaxel, Gemcitabine, Taxotere, Dexamethasone, Ara-C, Methylprednisolone, Methotrexate, Bleomycin, Methyl-GAG, Carboplatin, 5-FU (5-Fluorouracil), MABTHERA™ (Rituximab), radiation, histone deacetylase (HDAC) inhibitors, and 5-Aza-2'-deoxycytidine (Decitabine). Exemplary radioactive chemotherapeutic agents include compounds containing alpha emitters such as astatine-211, bismuth-212, bismuth-213, lead-212, radium-223, actinium-225, and thorium-227, beta emitters such as tritium, strontium-90, cesium-137, carbon-11, nitrogen-13, oxygen-15, fluorine-18, iron-52, cobalt-55, cobalt-60, copper-61, copper-62, copper-64, zinc-62, zinc-63, arsenic-70, arsenic-71, arsenic-74, bromine-76, bromine-79, rubidium-82, yttrium-86, zirconium-89, indium-110, iodine-120, iodine-124, iodine-129, iodine-131, iodine-125, xenon-122, technetium-94m, technetium-94, technetium-99m, and technetium-99, or gamma emitters such as cobalt-60, cesium-137, and technetium-99m. Exemplary chemotherapeutic agents also include antibodies such as Alemtuzumab, Daclizumab, Rituximab (MABTHERA™), Trastuzumab (HERCEPTIN™), Gemtuzumab, Ibritumomab, Edrecolomab, Tositumomab, CeaVac, Epratuzumab, Mitumomab, Bevacizumab, Cetuximab, Edrecolomab, Lintuzumab, MDX-210, IGN-101, MDX-010, MAb, AME, ABX-EGF, EMD 72 000, Apolizumab, Labetuzumab, ior-t1, MDX-220, MRA, H-11 scFv, Oregovomab, huJ591 MAb, BZL, Visilizumab, TriGem, TriAb, R3, MT-201, G-250, unconjugated, ACA-125, Onyvax-105, CDP-860, BrevaRex MAb, AR54, IMC-1C11, GlioMAb-H, ING-1, Anti-LCG MAbs, MT-103, KSB-303, Therex, KW-2871, Anti-HMI.24, Anti-PTHrP, 2C4 antibody, SGN-30, TRAIL-RI MAb, CAT, Prostate cancer antibody, H22xKi-4, ABX-MA1, Imuteran, and Monopharm-C. Exemplary chemotherapeutic agents also include Acivicin; Aclarubicin; Acodazole Hydrochloride; Acronine; Adozelesin; Adriamycin; Aldesleukin; Altretamine; Ambomycin; A. metantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Camptothecin; Caracemide; Carbetimer; Carboplatin; Carmustine; Carubicin Hydrochloride; Carzelesin; Cedefingol; Chlorambucil; Cirolemycin; Cisplatin; Cladribine; Combretestatin A-4; Crisnatol Mesylate; Cyclophosphamide; Cytarabine; Dacarbazine; DACA (N-[2-(Dimethyl-amino) ethyl] acridine-4-carboxamide); Dactinomycin; Daunorubicin Hydrochloride; Daunomycin; Decitabine; Dexormaplatin; Dezaguanine; Dezaguanine Mesylate; Diaziquone; Docetaxel; Dolasatins; Doxorubicin; Doxorubicin Hydrochloride; Droloxifene; Droloxifene Citrate; Dromostanolone Propionate; Duazomycin; Edatrexate; Eflornithine Hydrochloride; Ellipticine; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; Gemcitabine; Gemcitabine Hydrochloride; Gold Au 198; Homocamptothecin; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride;

Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; PeploycinSulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Rhizoxin; Rhizoxin D; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2' Deoxyformycin; 9-aminocamptothecin; raltitrexed; N-propargyl-5,8-dideazafolic acid; 2chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N, N'-Bis (2-chloroethyl)-N-nitrosourea (BCNU); N-(2-chloroethyl)-N' cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl) ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); or 2-chlorodeoxyadenosine (2-Cda).

Other chemotherapeutic agents include, but are not limited to, 20-pi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxycamptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; episteride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; merbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

To "inhibit growth" as used herein means causing a reduction in cell growth in vivo or in vitro by, e.g., 10%, 20%, 30%, 40%, 50%, 60%, 70%, 80%, 90%, 95%, or 99% or more, as evident by a reduction in the size or number of cells exposed to a treatment (e.g., exposure to a compound), relative to the size or number of cells in the absence of the treatment. Growth inhibition may be the result of a treatment that induces apoptosis in a cell, induces necrosis in a cell, slows cell cycle progression, disrupts cellular metabolism, induces cell lysis, or induces some other mechanism that reduces the size or number of cells.

"Marker gene" or "biomarker gene" as used herein means a gene in a cell the expression of which correlates to sensitivity or resistance of the cell (and thus the patient from which the cell was obtained) to a treatment (e.g., exposure to a compound).

"Microarray" as used herein means a device employed by any method that quantifies one or more subject oligonucleotides, e.g., DNA or RNA, or analogues thereof, at a time. One exemplary class of microarrays consists of DNA probes attached to a glass or quartz surface. For example, many microarrays, including those made by Affymetrix, use several probes for determining the expression of a single gene. The DNA microarray may contain oligonucleotide probes that may be, e.g., full-length cDNAs complementary to an RNA or cDNA fragments that hybridize to part of an RNA. Exemplary RNAs include mRNA, miRNA, and miRNA precursors. Exemplary microarrays also include a "nucleic acid microarray" having a substrate-bound plurality of nucleic acids, hybridization to each of the plurality of bound nucleic acids being separately detectable. The substrate may be solid or porous, planar or non-planar, unitary or distributed. Exemplary nucleic acid microarrays include all of the devices so called in Schena (ed.), DNA Microarrays: A Practical Approach (Practical Approach Series), Oxford University Press (1999); Nature Genet. 21(1)(suppl.):1-60 (1999); Schena (ed.), Microarray Biochip: Tools and Technology, Eaton Publishing Company/BioTechniques Books Division (2000). Additionally, exemplary nucleic acid microarrays include substrate-bound plurality of nucleic acids in which the plurality of nucleic acids are disposed on a plurality of beads, rather than on a unitary planar substrate, as is described, inter alia, in Brenner et al., Proc. Natl. Acad. Sci. USA 97(4):1665-1670 (2000). Examples of nucleic acid microarrays may be found in U.S. Pat. Nos. 6,391,623, 6,383,754, 6,383,749, 6,380,377, 6,379,897, 6,376,191, 6,372,431, 6,351,712 6,344,316, 6,316,193, 6,312,906, 6,309,828, 6,309,824, 6,306,643, 6,300,063, 6,287,850, 6,284,497, 6,284,465, 6,280,954, 6,262,216, 6,251,601, 6,245,518, 6,263,287, 6,251,601, 6,238,866, 6,228,575, 6,214,587, 6,203,989, 6,171,797, 6,103,474, 6,083,726, 6,054,274, 6,040,138, 6,083,726, 6,004,755, 6,001,309, 5,958,342, 5,952,180, 5,936,731, 5,843,655, 5,814,454, 5,837,196, 5,436,327, 5,412,087, 5,405,783, the disclosures of which are incorporated herein by reference in their entireties.

Exemplary microarrays may also include "peptide microarrays" or "protein microarrays" having a substrate-bound plurality of polypeptides, the binding of a oligonucleotide, a peptide, or a protein to each of the plurality of bound polypeptides being separately detectable. Alternatively, the peptide microarray, may have a plurality of binders, including but not limited to monoclonal antibodies, polyclonal antibodies, phage display binders, yeast 2 hybrid binders, aptamers, which can specifically detect the binding of specific oligonucleotides, peptides, or proteins. Examples of peptide arrays may be found in WO 02/31463, WO 02/25288, WO 01/94946, WO 01/88162, WO 01/68671, WO 01/57259, WO 00/61806, WO 00/54046, WO 00/47774, WO 99/40434, WO 99/39210, WO 97/42507 and U.S. Pat. Nos. 6,268,210, 5,766,960, 5,143,854, the disclosures of which are incorporated herein by reference in their entireties.

"Gene expression" as used herein means the amount of a gene product in a cell, tissue, organism, or subject, e.g., amounts of DNA, RNA, or proteins, amounts of modifications of DNA, RNA, or protein, such as splicing, phosphorylation, acetylation, or methylation, or amounts of activity of DNA, RNA, or proteins associated with a given gene.

"NCI60" as used herein means a panel of 60 cancer cell lines from lung, colon, breast, ovarian, leukemia, renal, melanoma, prostate and brain cancers including the following cancer cell lines: NSCLC_NCIH23, NSCLC_NCIH522, NSCLC_A549ATCC, NSCLC_EKVX, NSCLC_NCIH226, NSCLC_NCIH332M, NSCLC_H460, NSCLC_HOP62, NSCLC_HOP92, COLON_HT29, COLON_HCC-2998, COLON_HCT116, COLON_SW620, COLON_COLO205, COLON_HCT15, COLON_KM12, BREAST_MCF7, BREAST_MCF7ADRr, BREAST_MDAMB231, BREAST_HS578T, BREAST_MDAMB435, BREAST_MDN, BREAST_BT549, BREAST_T47D, OVAR_OVCAR3, OVAR_OVCAR4, OVAR_OVCAR5, OVAR_OVCAR8, OVAR_IGROV1, OVAR_SKOV3, LEUK_CCRFCEM, LEUK_K562, LEUK_MOLT4, LEUK_HL60, LEUK_RPMI8266, LEUK_SR, RENAL_UO31, RENAL_SN12C, RENAL_A498, RENAL_CAKI1, RENAL_RXF393, RENAL_7860, RENAL_ACHN, RENAL_TK10, MELAN_LOXIMVI, MELAN_MALME3M, MELAN_SKMEL2, MELAN_SKMEL5, MELAN_SKMEL28, MELAN_M14, MELAN_UACC62, MELAN_UACC257, PROSTATE_PC3, PROSTATE_DU145, CNS_SNB19, CNS_SNB75, CNS_U251, CNS_SF268, CNS_SF295, and CNS_SF539.

"Treatment" or "medical treatment" means administering to a subject or living organism or exposing to a cell or tumor a compound (e.g., a drug, a protein, an antibody, an oligonucleotide, a chemotherapeutic agent, and a radioactive agent) or some other form of medical intervention used to treat or prevent cancer or the symptoms of cancer (e.g., cryotherapy and radiation therapy). Radiation therapy includes the administration to a patient of radiation generated from sources such as particle accelerators and related medical devices that emit X-radiation, gamma radiation, or electron (Beta radiation) beams. A treatment may further include surgery, e.g., to remove a tumor from a subject or living organism.

Other features and advantages of the invention will be apparent from the following Detailed Description, the drawings, and the claims.

BRIEF DESCRIPTION OF THE DRAWINGS

FIG. 1 depicts an illustration of the method of identifying biomarkers and predicting patient sensitivity to a medical treatment. The method has an in vitro component where the growth inhibition of a compound or medical treatment is measured on cell lines (6 of the 60 cell lines tested are shown). The gene expression is measured on the same cell lines without compound treatment. Those genes that have a correlation above a certain cutoff (e.g., a preferred cutoff of 0.3, in which a correlation coefficient equal to or greater than the cutoff of 0.3 is deemed statistically significant by, e.g., cross-validation) to the growth inhibition are termed marker genes and the expression of those genes in vivo, e.g., may predict the sensitivity or resistance of a patient's cancer to a compound or other medical treatment. The in vivo component is applied to a patient to determine whether or not the treatment will be effective in treating disease in the patient. Here, the gene expression in cells of a sample of the suspected disease tissue (e.g., a tumor) in the patient is measured before or after treatment. The activity of the marker genes in the sample is compared to a reference population of patients known to be sensitive or resistant to the treatment. The expression of marker genes in the cells of the patient known to be expressed in the cells of reference patients sensitive to the treatment indicates that the patient to be treated is sensitive to the treatment and vice versa. Based on this comparison the patient is predicted to be sensitive or resistant to treatment with the compound.

DETAILED DESCRIPTION

The invention features methods for identifying and using one or more biomarkers of treatment sensitivity or resistance, e.g., sensitivity or resistance to one or more treatments for cancer (e.g., a chemothereutic agent), to predict treatment efficacy in a patient (e.g., a patient diagnosed with cancer), devices that include nucleic acid molecules that can detect the level of expression of the biomarkers, and kits that include the devices and instructions for use. The kits of the invention include an array (e.g., a microarray) with one or more single-stranded oligonucleotide probes that have at least 85% (e.g., at least 90%, 95%, 99%, or 100%) sequence identity to a target nucleic acid molecule having a sequence that is complementary or identical to the nucleic acid sequence of one or more biomarkers of sensitivity or resistance to treatment (e.g., treatment with a chemotherapeutic agent) described herein. For example, the probes can be used to detect one or more (e.g., two, three, four, five, ten, twenty, thirty, fifty, or all) of the biomarkers listed in one or more of Tables 1-65 and/or one or more of Tables 66-129, such as hsa-miR-766_st (SEQ ID NO: 1). The oligonucleotide probes of the array can be used detect nucleic acid molecules present in sample applied to the array (e.g., nucleic acid molecules from a sample obtained, derived, or prepared from a subject (e.g., a cell, tissue, or organ sample from a subject)). The kits can also include instructions for using the device to predict the sensitivity or resistance of the subject to the treatment.

A beneficial aspect of the invention is that the methods, devices, and kits can be used to determine the sensitivity and/or resistance of a patient to one or more treatments for cancer (e.g., two, three, four, five, ten, twenty, thirty, or more treatments for cancer, and even all of the treatments for cancer described herein) at the same time by assaying for the level of expression of one or more biomarkers, the expression of which has been correlated with a patient's sensitivity or resistance to a specific treatment for cancer. For example, the methods, devices, and kits can utilize oligonucleotide probes capable of detecting the level of expression of at least one cancer therapy-sensitive biomarker associated with each of the cancer therapies described herein (e.g., the methods, devices, and kits can utilize oligonucleotide probes to detect at least one (e.g., two, three, or more, e.g. all) of the cancer therapy-specific sensitivity biomarkers listed in one or more of Tables 1-65, or a subset thereof). Alternatively, or in addition to the cancer therapy-sensitive biomarkers, the methods, devices, and kits can utilize oligonucleotide probes capable of detecting the level of expression of at least one cancer therapy-resistant biomarker associated with each of the cancer therapies described herein (e.g., the methods, devices, and kits can utilize oligonucleotide probes to detect at least one (e.g., two, three, or more, e.g. all) of the cancer therapy-resistant sensitivity biomarkers listed in one or more of Tables 66-129, or a subset thereof).

In other examples, the methods, devices, and kits can utilize oligonucleotide probes capable of detecting the level of expression of the cancer therapy-sensitive biomarkers of one or more of Tables 1-65 (or a subset thereof) having the first and/or second and/or third highest mean score correlation coefficient (positive correlation). Alternatively, or in addition to the cancer therapy-sensitive biomarkers, the methods, devices, and kits can utilize oligonucleotide probes capable of detecting the level of expression of the cancer therapy-resistant biomarkers of one or more of Tables 66-129 (or a subset thereof) having the first and/or second and/or third highest mean score correlation coefficient (negative correlation).

The invention also features methods of using the microarrays to determine whether a subject, e.g., a cancer patient, will be sensitive or resistant to treatment with, e.g., a chemotherapy agent. Also featured are methods of identifying biomarkers of sensitivity or resistance to a medical treatment based on the correlation of biomarker expression to treatment efficacy, e.g., the growth inhibition of cancer cells. Biomarkers that identify subjects as sensitive or resistant to a treatment may also be identified within patient populations already thought to be sensitive or resistant to that treatment. Thus, the methods, devices, and kits of the invention can be used to identify patient subpopulations that are responsive to one or more treatments thought to be ineffective for treating disease (e.g., cancer) in the general population. More generally, cancer patient sensitivity to one or more compounds or other medical treatments may be predicted using biomarker expression regardless of prior knowledge about patient responsiveness to treatment. The method according to the present invention can be implemented using software that is run on an apparatus for measuring gene expression in connection with a microarray. Devices of the invention (e.g., a microarray, such as a DNA and/or RNA microarray) can be included in a kit for processing a tumor sample from a subject (e.g., a cell, tissue, or organ sample containing a tumor or a cell thereof), and the apparatus for reading the device and turning the result into a chemosensitivity profile for the subject may be used to implement the methods of the invention.

Devices Containing Oligonucleotide Probes of the Invention

The devices (e.g., microarrays) of the invention can include one or more (e.g., two, three, four, five, ten, twenty, thirty, fifty, or all) oligonucleotide probes that have nucleotide sequences that are identical (or share at least 85%, 90%, 95%, or 99% identity) to or complementary to, e.g., at least 5, 8, 12, 20, 30, 40, 60, 80, 100, 150, or 200 consecutive nucleotides (or nucleotide analogues) of one or more of the biomarkers listed in one or more of Tables 1-65 and/or one or more of Tables 66-129, such as hsa-miR-766_st (SEQ ID NO: 1). The oligonucleotide probes may be, e.g., 5-20, 25, 5-50, 50-100, or over 100 nucleotides long. The oligonucleotide probes may be deoxyribonucleic acids (DNA) or ribonucleic acids (RNA). Consecutive nucleotides within the oligonucleotide probes (e.g., 5-20, 25, 5-50, 50-100, or over 100 consecutive nucleotides), which are used as biomarkers of chemosensitivity, may also appear as consecutive nucleotides in one or more of the genes and/or RNAs (e.g., miRNA(s)) described herein beginning at or near, e.g., the first, tenth, twentieth, thirtieth, fortieth, fiftieth, sixtieth, seventieth, eightieth, ninetieth, hundredth, hundred-fiftieth, two-hundredth, five-hundredth, or one-thousandth nucleotide of one or more of the biomarkers listed in one or more of Tables 1-65 and/or one or more of Tables 66-129 below.

Probes that may be employed on devices (e.g., microarrays) of the invention include oligonucleotide probes having sequences complementary to or identical to (or sharing at least 85%, 90%, 95%, or 99% identity to) any of the target biomarker sequences described herein. Additionally, probes employed on devices (e.g., microarrays) of the invention may also include proteins, peptides, or antibodies that selectively bind any of the oligonucleotide probe sequences or their complementary sequences. Exemplary probes of treatment sensitivity are listed in Tables 1-65 and exemplary probes of treatment resistance are listed in Tables 66-129, wherein for each treatment listed, the biomarkers indicative of treatment sensitivity or resistance, respectively, the correlation of biomarker expression to growth inhibition and the sequence of an exemplary probe are shown.

Identification of Biomarkers

The gene expression measurements of the NCI60 cancer cell lines were obtained from the National Cancer Institute and the Massachusetts Institute of Technology (MIT). Each dataset was normalized so that sample expression measured by different chips could be compared. The preferred method of normalization is the logit transformation, which is performed for each gene y on each chip:

$$\text{logit}(y) = \log\left[(y-\text{background})/(\text{saturation}-y)\right],$$

where background is calculated as the minimum intensity measured on the chip minus 0.1% of the signal intensity range: min-0.001*(max-min), and saturation is calculated as the maximum intensity measured on the chip plus 0.1% of the signal intensity range: max+0.001*(max-min) The resulting logit transformed data is then z-transformed to mean zero and standard deviation 1.

Next, gene expression is correlated to cancer cell growth inhibition. Growth inhibition data (GI50) of the NCI60 cell lines in the presence of any one of thousands of tested compounds was obtained from the NCI. The correlation between the logit-transformed expression level of each gene in each cell line and the logarithm of GI50 (the concentration of a given compound that results in a 50% inhibition of growth) can be calculated, e.g., using the Pearson correlation coefficient or the Spearman Rank-Order correlation coefficient. Instead of using GI50s, any other measure of patient sensitivity to a given compound may be correlated to the patient's gene expression. Since a plurality of measurements may be available for a single gene, the most accurate determination of correlation coefficient was found to be the median of the correlation coefficients calculated for all probes measuring expression of the same gene.

The median correlation coefficient of gene expression measured on a probe to growth inhibition or patient sensitivity is calculated for all genes, and genes that have a median correlation above 0.3, 0.4, 0.5, 0.6, 0.7, 0.8, 0.9, 0.95, or 0.99 are retained as biomarker genes. Preferably, the correlation coefficient of biomarker genes will exceed 0.3. This is repeated for all the compounds to be tested. The result is a list of marker genes that correlates to sensitivity for each compound tested.

Predicting Patient Sensitivity or Resistance to Medical Treatments

For a given medical treatment (e.g., a compound or drug, such as a chemotherapy agent), the expression of one or more biomarkers has been shown to correlate to chemosensitivity and/or chemoresistance. This correlation can be used to classify a patient, e.g., a cancer patient, or a subpopulation of patients, as sensitive or resistant to one or more medical treatments, e.g., one or more of the chemotherapeutic agents or radiation therapies described herein. Using a tumor sample or a blood sample (e.g., in case of leukemia or lymphoma) from a patient, expression of the biomarkers in the cells of the patient in the presence of the treatment agent is determined (using, for example, an RNA extraction kit, a DNA microarray and a DNA microarray scanner). Measurements of biomarker expression are then logit transformed as described above. The sum of the expression measurements of the biomarkers is then compared to the median of the sums derived from a training set population of patients having the same tumor. If the sum of biomarker expression in the patient is closest to the median of the sums of expression in the surviving members of the training set, the patient is predicted to be sensitive to the compound or other medical treatment. If the sum of biomarker expression in the patient is closest to the median of the sums of expression in the non-surviving members of the training set, the patient is predicted to be resistant to the compound.

Machine learning techniques such as Neural Networks, Support Vector Machines, K Nearest Neighbor, and Nearest Centroids may also be employed to develop models that discriminate patients sensitive to treatment from those resistant to treatment using biomarker expression as model variables which assign each patient a classification as resistant or sensitive. Machine learning techniques used to classify patients using various measurements are described in U.S. Pat. No. 5,822,715; U.S. Patent Application Publication Nos. 2003/0073083, 2005/0227266, 2005/0208512, 2005/0123945, 2003/0129629, and 2002/0006613; and in Vapnik V N. Statistical Learning Theory, John Wiley & Sons, New York, 1998; Hastie et al., 2001, The Elements of Statistical Learning: Data Mining, Inference, and Prediction, Springer, N.Y.; Agresti, 1996, An Introduction to Categorical Data Analysis, John Wiley & Sons, New York; V. Tresp et al., "Neural Network Modeling of Physiological Processes", in Hanson S. J. et al. (Eds.), Computational Learning Theory and Natural Learning Systems 2, MIT Press, 1994, each of which are hereby incorporated by reference in their entirety.

A more compact microarray may be designed using only the oligonucleotide biomarker probes having measurements yielding the median correlation coefficients with cancer cell growth inhibition. Thus, in this embodiment, only one probe needs to be used to measure expression of each biomarker. For example, a microarray according to the invention includes one, two, or three (or more, e.g., all) of the biomarker probes provided in Tables 1-65 having the highest correlation coefficients (positive correlation) from among those biomarkers listed and/or one, two, or three (or more, e.g., all) of the biomarker probes provided in Tables 66-129 having the highest correlation coefficients (negative correlation) from among those biomarkers listed. The device can also include one or more probes directed to hsa-miR-766_st (SEQ ID NO: 1) along with one or more probes directed to one or more of the biomarker probes provided in one or more of Tables 1-65 and/or one or more of Tables 66-129.

As an example, Table 2 provides exemplary biomarker probes for determining a patient's sensitivity to cisplatin. A device of the invention can be prepared for assaying a patient's sensitivity to cisplatin by incorporating one or more probes directed to the biomarker hsa-miR-342-3p_st (SEQ ID NO: 11), which has the highest correlation coefficient of 0.43 for this group. In other embodiments, a device of the invention can be prepared for assaying a patient's sensitivity to cisplatin by incorporating one or more probes directed to the two biomarkers associated with cisplatin having the highest correlation coefficients (e.g., hsa-miR-342-3p_st (SEQ ID NO: 11) (0.43) and hsa-miR-124_st (SEQ ID NO: 7) (0.35)). Other devices of the invention can include one or more biomarker probes directed to those biomarkers having the first, second, and/or third, etc., highest correlation coefficients (positive correlatin) for each therapy agent of one or more of Tables 1-65 and/or one or more biomarker probes directed to those biomarkers having the first, second, and/or third, etc., highest correlation coefficients (negative correlation) for each therapy agent of one or more of Tables 66-129.

Identifying a Subpopulation of Patients Sensitive to One or More Treatments for Cancer The invention may also be used to identify a subpopulation of patients, e.g., cancer patients, that are sensitive to a compound or other medical treatment previously thought to be ineffective for the treatment of cancer. To this end, biomarkers, the expression of which correlates to sensitivity to a compound or other treatment, may be identified so that patients sensitive to a compound or other treatment may be identified. To identify such biomarkers, expression within cell lines may be correlated to the growth of those cell lines in the presence of the same compound or other treatment. Preferably, biomarkers (such as genes or RNAs) whose expression correlates to cell growth with a correlation coefficient exceeding 0.3 may be considered possible biomarkers.

Alternatively, genes or RNAs (e.g., miRNAs) may be identified as biomarkers according to their ability to discriminate patients known to be sensitive to a treatment from those known to be resistant. The significance of the differences in expression of biomarkers between the sensitive and resistant patients may be measured using, e.g., t-tests. Alternatively, naïve Bayesian classifiers may be used to identify biomarkers that discriminate sensitive and resistant patient subpopulations given the biomarker expressions of the sensitive and resistant subpopulations within a treated patient population.

The patient subpopulations considered may be further divided into patients predicted to survive without treatment, patients predicted to die without treatment, and patients predicted to have symptoms without treatment. The above methodology may be similarly applied to any of these further defined patient subpopulations to identify biomarkers able to predict a subject's sensitivity to compounds or other treatments for the treatment of cancer.

Patients with elevated expression of biomarkers correlated to sensitivity to a compound or other medical treatment would be predicted to be sensitive to that compound or other medical treatment.

The invention is particularly useful for recovering compounds or other treatments that failed in clinical trials by identifying sensitive patient subpopulations using the gene expression methodology disclosed herein to identify gene or NRA (e.g., miRNA) biomarkers that can be used to predict clinical outcome.

Kit, Apparatus, and Software for Clinical Use

This invention may also be used to predict patients who are resistant or sensitive to a particular treatment by using a kit that includes one or more of the following: a kit for RNA extraction from tumors (e.g., mirVana miRNA isolation kit from Ambion Inc), a kit for RNA labeling (e.g., FlashTag from Genisphere Inc), a microarray for measuring biomarker expression (e.g., miRNA-1.0 from Affymetrix Inc), a microarray hybridization station and scanner (e.g., GeneChip System 3000Dx from Affymetrix Inc), and/or software for analyzing the expression of biomarker genes or RNAs (e.g., miRNAs) as described in herein (e.g., implemented in R from R-Project or S-Plus from Insightful Corp.). The predicted sensitivity is either given by the meanscore or diffscore as defined in Example 2 below.

Methodology of the In Vitro Cancer Growth Inhibition Screen

The human tumor cell lines of the cancer screening panel are grown in RPMI 1640 medium containing 5% fetal bovine serum and 2 mM L-glutamine. Cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 hours prior to addition of experimental compounds.

After 24 hours, two plates of each cell line are fixed in situ with TCA, to represent a measurement of the cell population for each cell line at the time of compound addition (Tz). Experimental compounds are solubilized in dimethyl sulfoxide at 400-fold the desired final maximum test concentration and stored frozen prior to use. At the time of compound addition, an aliquot of frozen concentrate is thawed and diluted to twice the desired final maximum test concentration with complete medium containing 50 µg/ml Gentamicin. Additional four, 10-fold or ½ log serial dilutions are made to provide a total of five compound concentrations plus control. Aliquots of 100 µl of these different compound dilutions are added to the appropriate microtiter wells already containing 100 µl of medium, resulting in the required final compound concentrations.

Following compound addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air-dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air-dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of compound at the five concentration levels (Ti)], the percentage growth is calculated at each of the compound concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz

Three dose response parameters are calculated for each experimental agent. Growth inhibition of 50% (GI50) is calculated from [(Ti−Tz)/(C−Tz)]×100=50, which is the compound concentration resulting in a 50% reduction in the net protein increase (as measured by SRB staining) in control cells during the compound incubation. The compound concentration resulting in total growth inhibition (TGI) is calculated from Ti=Tz. The LC50 (concentration of compound resulting in a 50% reduction in the measured protein at the end of the compound treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested.

RNA Extraction and Biomarker Expression Measurement

Cell/tissue samples are snap frozen in liquid nitrogen until processing. RNA is extracted using e.g. Trizol Reagent from Invitrogen following manufacturer's instructions. RNA is amplified using, e.g., MessageAmp kit from Ambion following manufacturer's instructions. Amplified RNA is quantified using, e.g., HG-U133A GeneChip from Affymetrix Inc and compatible apparatus e.g. GCS3000Dx from Affymetrix, using manufacturer's instructions.

The resulting biomarker expression measurements are further processed as described in this document. The procedures described can be implemented using R software available from R-Project and supplemented with packages available from Bioconductor.

For many drugs, 1-30 (e.g., 5-30 or 10-30) biomarkers are sufficient to give an adequate response. Thus, given the relatively small number of biomarkers required, procedures, such as quantitative reverse transcriptase polymerase chain reaction (qRT-PCR), may be performed to measure, with greater precision, the amount of one or more biomarker genes or RNAs (e.g., miRNAs) expressed in a sample. This will provide an alternative to or a complement to microarrays so that a single companion test, perhaps more quantitative than microarrays alone, employing one or more of the biomarkers of the invention (e.g., hsa-miRNA-766 (SEQ ID NO: 1) alone or in combination with one or more can be used to predict sensitivity to a new drug. qRT-PCR may be performed alone or in combination with a microarray described herein. Procedures for performing qRT-PCR are described in, e.g., U.S. Pat. No. 7,101,663 and U.S. Patent Application Nos. 2006/0177837 and 2006/0088856. The methods of the invention are readily applicable to newly discovered drugs as well as drugs described herein.

The following examples are provided so that those of ordinary skill in the art can see how to use the methods and kits of the invention. The examples are not intended to limit the scope of what the inventor regards as their invention.

EXAMPLES

Example 1

Identification of Gene Biomarkers for Chemosensitivity to Common Chemotherapy Drugs DNA chip measurements of the 60 cancer cell lines of the NCI60 data set were performed using Affymetrix miRNA 1.0 arrays and logit normalized. Growth inhibition data of thousands of compounds against the same cell lines were downloaded from the National Cancer Institute. Compounds where the difference concentration to achieve 50% in growth inhibition (GI50) was less than 1 log were deemed uninformative and rejected. Each gene's expression in each cell line was correlated to its growth (−log(GI50)) in those cell lines in the presence of a given compound. The median Pearson correlation coefficient was used when multiple expression measurements were available for a given gene, and genes having a median correlation coefficient greater than 0.3 were identified as biomarkers for a given compound. Table 1-65 lists biomarkers for a number of drugs used in treating cancer.

They can be used to predict the response of a human tumor sample to treatment by the drug in question by following the procedure described in "Kit, Apparatus, and Software for Clinical Use."

Example 2

Difference Between Positive and Negative Correlated Genes

In Example 1 a procedure for identifying microRNA biomarkers with a positive correlation to drug sensitivity is described. Sensitivity to a drug can then be predicted based on the mean expression of those microRNA biomarkers. This is called mean score. But there is also information in those biomakers that correlate negatively with drug sensitivity. They could be called biomarkers of resistance.

Tables 66-129 lists the negatively correlated biomarkers for a number of drugs used to treat cancer. An even better accuracy of predicted response to a drug can be obtained when both negatively and positively correlated markers are used. One way of combining them is to subtract the mean expression of the negatively correlated biomarkers from the mean expression of the positively correlated biomarkers. This is called a difference score, or diffscore.

Table 130 shows how mean score and difference score compare in their ability to predict the GI50 values of cell lines treated with a drug. As the method would be applied to a human tumor sample in the same manner as it is here applied to a human cell line sample, the diffscore can also be used (e.g., as an alternative to the mean score, which is based on the correlation coefficient alone) to predict the response of human tumors (and thus, the patient) to treatment with one or more drugs (e.g., one or more of the chemotherapy drugs or radiation described herein).

TABLE 130 comparison of diff score and mean score in predicting
human cell line response to a number of drugs (correlation
coefficient between prediction and measurement is shown,
a higher CC means more accurate prediction)

| Drug | Diff score CC | Mean score CC |
|---|---|---|
| Vincristine | 0.56 | 0.35 |
| Herceptin | 0.50 | 0.41 |
| Iressa | 0.60 | 0.53 |
| Fulvestrant | 0.76 | 0.74 |

TABLE 130-continued comparison of diff score and mean score in predicting
human cell line response to a number of drugs (correlation
coefficient between prediction and measurement is shown,
a higher CC means more accurate prediction)

| Drug | Diff score CC | Mean score CC |
|---|---|---|
| Erlotinib (tarceva) | 0.62 | 0.59 |
| Belinostat (PXD101) | 0.61 | 0.60 |
| Cisplatin | 0.66 | 0.67 |

Example 3

Exemplary Arrays of the Invention

Exemplary arrays according to the present invention can be prepared with one or more oligonucleotide probes that are capable of detecting the level of expression of one or more of the biomarkers identified herein (e.g., one or more of the biomarkers of sensitivity described in Tables 1-65 and/or one or more of the biomarkers of resistance described in Tables 66-129). Non-limiting examples of such arrays are described in the Table 131 below. The arrays include probes capable of detecting the level of expression of the indicated biomarkers. Probes for the indicated biomarkers are selected based on the median score correlation coefficient for the biomarker. Array 1 includes one or more probes for the representative biomarker(s) selected from Tables 1-65 for each specified therapeutic. Array 2 includes one or more probes for the representative biomarkers selected from Tables 1-65 for each specific therapeutic. Array 3 includes one or more probes for the representative biomarkers from one or more of Tables 1-65 for the indicated therapeutic. Other combinations of biomarker probes can also be used to produce one or more additional arrays of the invention

TABLE 131

Examples of Arrays of the Invention with Biomarkers of Sensitivity

| Therapeutic | Array 1 Probes | Array 2 Probes | Array 3 Probes |
|---|---|---|---|
| Vincristine | hsa-miR-106b-star_st (SEQ ID NO: 2) | hsa-miR-106b-star_st (SEQ ID NO: 2) hsa-miR-25-star_st (SEQ ID NO: 3) | |
| Cisplatin | hsa-miR-342-3p_st (SEQ ID NO: 11) | hsa-miR-342-3p_st (SEQ ID NO: 11) hsa-miR-124_st (SEQ ID NO: 7) | |
| Etoposide | hsa-miR-92b_st (SEQ ID NO: 15) | hsa-miR-92b_st (SEQ ID NO: 15) hsa-miR-140-3p_st (SEQ ID NO: 13) | hsa-miR-92b_st (SEQ ID NO: 15) hsa-miR-140-3p_st (SEQ ID NO: 13) hsa-miR-766_st (SEQ ID NO: 1) |
| Azaguanine | hsa-miR-140-3p_st (SEQ ID NO: 13) | hsa-miR-140-3p_st (SEQ ID NO: 13) hsa-miR-146a_st (SEQ ID NO: 19) | |
| Carboplatin | hsa-miR-342-3p_st (SEQ ID NO: 11) | hsa-miR-342-3p_st (SEQ ID NO: 11) hsa-miR-124_st (SEQ ID NO: 7) | |
| Adriamycin | hsa-miR-106b-star_st (SEQ ID NO: 2) | hsa-miR-106b-star_st (SEQ ID NO: 2) hsa-miR-106b_st SEQ ID NO: 37) | hsa-miR-106b-star_st (SEQ ID NO: 2) hsa-miR-106b_st SEQ ID NO: 37) hsa-miR-766_st (SEQ ID NO: 1) |

TABLE 131-continued

Examples of Arrays of the Invention with Biomarkers of Sensitivity

| Therapeutic | Array 1 Probes | Array 2 Probes | Array 3 Probes |
|---|---|---|---|
| Aclarubicin | hsa-miR-1275_st (SEQ ID NO: 70) | hsa-miR-1275_st (SEQ ID NO: 70) ACA10_s_st (SEQ ID NO: 47; SEQ ID NO; 138; SEQ ID NO: 223; SEQ ID NO: 382; SEQ ID NO: 444) | |
| Mitoxantrone | hsa-miR-181a-star_st (SEQ ID NO: 9) | hsa-miR-181a-star_st (SEQ ID NO: 9) hsa-miR-432_st (SEQ ID NO: 12) | |
| Mitomycin | hsa-miR-181b_st (SEQ ID NO: 10) | hsa-miR-181b_st (SEQ ID NO: 10) hsa-miR-124_st (SEQ ID NO: 7) | |
| Paclitaxel | hsa-miR-652_st (SEQ ID NO: 42) | hsa-miR-652_st (SEQ ID NO: 42) hsa-miR-532-5p_st (SEQ ID NO: 98) | hsa-miR-652_st (SEQ ID NO: 42) hsa-miR-532-5p_st (SEQ ID NO: 98) hsa-miR-766_st (SEQ ID NO: 1) |
| Gemcitabine | hsa-miR-155_st (SEQ ID NO: 20) | hsa-miR-155_st (SEQ ID NO: 20) hsa-miR-342-3p_st (SEQ ID NO: 11) | |
| Taxotere | hsa-miR-769-5p_st (SEQ ID NO: 105) | hsa-miR-769-5p_st (SEQ ID NO: 105) hsa-miR-769-3p_st (SEQ ID NO: 104) | |
| Dexamethasone | U49B_s_st (SEQ ID NO: 65; SEQ ID NO 145; SEQ ID NO: 107; SEQ ID NO: 442) | U49B_s_st (SEQ ID NO: 65; SEQ ID NO 145; SEQ ID NO: 107; SEQ ID NO: 442) hsa-miR-424-star st (SEQ ID NO: 100) | U49B_s_st (SEQ ID NO: 65; SEQ ID NO 145; SEQ ID NO: 107; SEQ ID NO: 442) hsa-miR-424-star_st (SEQ ID NO: 100) hsa-miR-766_st (SEQ ID NO: 1) |
| Ara-C | hsa-miR-181a-star_st (SEQ ID NO: 9) | hsa-miR-181a-star_st (SEQ ID NO: 9) HBII-202_st (SEQ ID NO: 113; SEQ ID NO: 185; SEQ ID NO: 239; SEQ ID NO: 198: SEQ ID NO: 426 | |
| Methylprednisolone | hsa-miR-1207-5p_st (SEQ ID NO: 109) | hsa-miR-1207-5p_st (SEQ ID NO: 109) hsa-miR-20b-star st (SEQ ID NO: 130) | hsa-miR-1207-5p_st (SEQ ID NO: 109) hsa-miR-20b-star_st (SEQ ID NO: 130) hsa-miR-766_st (SEQ ID NO: 1) |
| Methotrexate | hsa-miR-663b_st (SEQ ID NO: 155) | hsa-miR-663b_st (SEQ ID NO: 155) U104 st (SEQ ID NO: 56; SEQ ID NO: 116: SEQ ID NO: 140; SEQ ID NO: 201; SEQ ID NO: 326; SEQ ID NO: 352) | |
| Bleomycin | 14q11-26_st (SEQ ID NO: 160; SEQ ID NO: 629; SEQ ID NO: 676) | 14qII-26_st (SEQ ID NO: 160; SEQ ID NO: 629; SEQ ID NO: 676) 14q11-14_st (SEQ ID NO: 73; SEQ ID NO: 157; SEQ ID NO: 598; SEQ ID NO: 627; SEQ ID NO: 674) hsa-miR-127-3p_st (SEQ ID NO: 77) hsa-miR-455-3p_st (SEQ ID NO: 178) | |

TABLE 131-continued

Examples of Arrays of the Invention with Biomarkers of Sensitivity

| Therapeutic | Array 1 Probes | Array 2 Probes | Array 3 Probes |
|---|---|---|---|
| Methyl-GAG | U26_st (SEQ ID NO: 60; SEQ ID NO: 187) | U26_st (SEQ ID NO: 60; SEQ ID NO: 187) ENSG00000200879_st (SEQ ID NO: 183; SEQ ID NO: 292; SEQ ID NO: 423) EN5G00000202252_st (SEQ ID NO: 53; SEQ ID NO: 184; SEQ ID NO: 244; SEQ ID NO: 424; SEQ ID NO: 449; SEQ ID NO: 488) U25_st (SEQ ID NO: 186; SEQ ID NO: 318; SEQ ID NO: 329; SEQ ID NO: 429; SEQ ID NO: 478) hsa-miR-181a-star_st (SEQ ID NO: 9) | |
| Belinostat | hsa-miR-19b_st (SEQ ID NO: 153) | hsa-miR-19b_st (SEQ ID NO: 153) hsa-miR-18a_st (SEQ ID NO: 72) | hsa-miR-19b_st (SEQ ID NO: 153) hsa-miR-18a_st (SEQ ID NO: 72) hsa-miR-766_st (SEQ ID NO: 1) |
| Fluorouracil | U74_x_st (SEQ ID NO: 69; SEQ ID NO: 191; SEQ ID NO: 242; SEQ ID NO: 264; SEQ ID NO: 309; SEQ ID NO: 350; SEQ ID NO: 377; SEQ ID NO: 399) | U74_x_st (SEQ ID NO: 69; SEQ ID NO: 191; SEQ ID NO: 242; SEQ ID NO: 264; SEQ ID NO: 309; SEQ ID NO: 350; SEQ ID NO: 377; SEQ ID NO: 399) U104_st (SEQ ID NO: 56; SEQ ID NO: 116; SEQ ID NO: 140; SEQ ID NO: 201; SEQ ID NO: 326; SEQ ID NO: 353; SEQ ID NO: 471) | |
| Radiation | hsa-let-7i-star_st (SEQ ID NO: 232) | hsa-let-7i-star_st (SEQ ID NO: 232) hsa-miR-34a_st (SEQ ID NO: 234) | |
| Aza-2'-deoxycytidine | hsa-miR-324-3p_st (SEQ ID NO: 235) | hsa-miR-324-3p_st (SEQ ID NO: 235) hsa-miR-766_st (SEQ ID NO: 1) | hsa-miR-324-3p_st (SEQ ID NO: 235) hsa-miR-195-star_st (SEQ ID NO: 14) hsa-miR-766_st (SEQ ID NO: 1) |
| Idarubicin | hsa-miR-124_st (SEQ ID NO: 7) | hsa-miR-124_st (SEQ ID NO: 7) U104_st (SEQ ID NO: 56; SEQ ID NO: 116; SEQ ID NO: 140; SEQ ID NO: 201; SEQ ID NO: 326; SEQ ID NO: 353; SEQ ID NO: 471) | |
| Melphalan | hsa-miR-181a-star_st (SEQ ID NO: 9) | hsa-miR-181a-star_st (SEQ ID NO: 9) hsa-miR-297_st (SEQ ID NO: 132) | hsa-miR-181a-star_st (SEQ ID NO: 9) hsa-miR-297_st (SEQ ID NO: 132) hsa-miR-766_st (SEQ ID NO: 1) |
| IL4-PR38 fusion protein | hsa-miR-150_st (SEQ ID NO: 111) hsa-miR-339-3p_st (SEQ ID NO: 272) | hsa-miR-150_st (SEQ ID NO: 111) hsa-miR-339-3p_st (SEQ ID NO: 272) hsa-miR-768-3p_st (SEQ ID NO: 44) | |

TABLE 131-continued

Examples of Arrays of the Invention with Biomarkers of Sensitivity

| Therapeutic | Array 1 Probes | Array 2 Probes | Array 3 Probes |
|---|---|---|---|
| Valproic acid | hsa-miR-34a_st (SEQ ID NO: 234) | hsa-miR-34a_st (SEQ ID NO: 234) hsa-miR-1308_st (SEQ ID NO: 274) hsa-miR-34a-star_st (SEQ ID NO: 277) | |
| All-trans retinoic acid | hsa-miR-449b_st (SEQ ID NO: 288) | hsa-miR-449b_st (SEQ ID NO: 288) hsa-miR-449a_st (SEQ ID NO: 287) | |
| Cytoxan | hsa-miR-449a_st (SEQ ID NO: 287) hsa-miR-449b_st (SEQ ID NO: 288) | hsa-miR-449a_st (SEQ ID NO: 287) hsa-miR-449b_st (SEQ ID NO: 288) hsa-miR-196a_st (SEQ ID NO: 294) | |
| Topotecan | hsa-miR-342-3p_st (SEQ ID NO: 11) | hsa-miR-342-3p_st (SEQ ID NO: 11) hsa-miR-342-5p_st (SEQ ID NO: 80) | |
| Suberoylanilide hydroxamic acid | hsa-miR-20b_st (SEQ ID NO: 88) | hsa-miR-20b_st (SEQ ID NO: 88) hsa-miR-18b_st (SEQ ID NO: 87) | hsa-miR-20b_st (SEQ ID NO: 88) hsa-miR-18b_st (SEQ ID NO: 87) hsa-miR-766_st (SEQ ID NO: 1) |
| Depsipeptide | hsa-miR-652_st (SEQ ID NO: 42) | hsa-miR-652_st (SEQ ID NO: 42) hsa-miR-185_st (SEQ ID NO: 85) hsa-miR-532-5p_st (SEQ ID NO: 98) | |
| Bortezomib | hsa-miR-106b_st (SEQ ID NO: 37) | hsa-miR-106b_st (SEQ ID NO: 37) hsa-miR-93_st (SEQ ID NO: 46) | |
| Leukeran | hsa-miR-181a-star_st (SEQ ID NO: 9) | hsa-miR-181a-star_st (SEQ ID NO: 9) hsa-miR-181b_st (SEQ ID NO: 10) | hsa-miR-181a-star_st (SEQ ID NO: 9) hsa-miR-181b st (SEQ ID NO: 10) hsa-miR-766_st (SEQ ID NO: 1) |
| Fludarabine | HBII-438A_s_st (SEQ ID NO: 99; SEQ ID NO: 114; SEQ ID NO: 247; SEQ ID NO: 585; SEQ ID NO: 648) | HBII-438A_s_st (SEQ ID NO: 99; SEQ ID NO: 114; SEQ ID NO: 247; SEQ ID NO: 585; SEQ ID NO: 648) hsa-miR-181b_st (SEQ ID NO: 10) hsa-miR-34c-3p_st (SEQ ID NO: 314) | HBII-438A_s_st (SEQ ID NO: 99; SEQ ID NO: 114; SEQ ID NO: 247; SEQ ID NO: 585; SEQ ID NO: 648) hsa-miR-181b_st (SEQ ID NO: 10) hsa-miR-34c-3p_st (SEQ ID NO: 314) hsa-miR-766_st (SEQ ID NO: 1) |
| Vinblastine | hsa-miR-652_st (SEQ ID NO: 42) | hsa-miR-652_st (SEQ ID NO: 42) hsa-miR-500_st (SEQ ID NO: 94) hsa-miR-532-5p_st (SEQ ID NO: 98) | |
| Busulfan | hsa-miR-1281_st (SEQ ID NO: 8) | hsa-miR-1281_st (SEQ ID NO: 8) hsa-miR-181a-star_st (SEQ ID NO: 9) | hsa-miR-1281_st (SEQ ID NO: 8) hsa-miR-181a-star_st (SEQ ID NO: 9) hsa-miR-766_st (SEQ ID NO: 1) |

TABLE 131-continued

Examples of Arrays of the Invention with Biomarkers of Sensitivity

| Therapeutic | Array 1 Probes | Array 2 Probes | Array 3 Probes |
|---|---|---|---|
| Dacarbazine | hsa-miR-223_st (SEQ ID NO: 131) hsa-miR-92a-1-star_st (SEQ ID NO: 192) | hsa-miR-223_st (SEQ ID NO: 131) hsa-miR-92a-1-star_st (SEQ ID NO: 192) U52_st (SEQ ID NO: 258; SEQ ID NO: 320; SEQ ID NO: 349; SEQ ID NO: 396) | hsa-miR-223_st (SEQ ID NO: 131) hsa-miR-92a-1-star_st (SEQ ID NO: 192) U52_st (SEQ ID NO: 258; SEQ ID NO: 320; SEQ ID NO: 349; SEQ ID NO: 396) hsa-miR-766_st (SEQ ID NO: 1) |
| Oxaliplatin | U104_st (SEQ ID NO: 56; SEQ ID NO: 116; SEQ ID NO: 140; SEQ ID NO: 201; SEQ ID NO: 326; SEQ ID NO: 353; SEQ ID NO: 471) hsa-miR-17_st (SEQ ID NO: 152) | U104_st (SEQ ID NO: 56; SEQ ID NO: 116; SEQ ID NO: 140; SEQ ID NO: 201; SEQ ID NO: 326; SEQ ID NO: 353; SEQ ID NO: 471) hsa-miR-17_st (SEQ ID NO: 152) hsa-miR-19b_st (SEQ ID NO: 153) | |
| Hydroxyurea | hsa-miR-223_st (SEQ ID NO: 131) | hsa-miR-223_st (SEQ ID NO: 131) hsa-miR-297_st (SEQ ID NO: 132) | hsa-miR-223_st (SEQ ID NO: 131) hsa-miR-297_st (SEQ ID NO: 132) hsa-miR-766_st (SEQ ID NO: 1) |
| Tegafur | U74_x_st (SEQ ID NO: 350; SEQ ID NO: 191; SEQ ID NO: 264; SEQ ID NO: 377; SEQ ID NO: 399) | U74_x_st (SEQ ID NO: 350; SEQ ID NO: 191; SEQ ID NO: 264; SEQ ID NO: 377; SEQ ID NO: 399) hsa-miR-34b_st (SEQ ID NO: 154) | |
| Daunorubicin | U55_x_st (SEQ ID NO: 6; SEQ ID NO; 260; SEQ ID NO: 280; SEQ ID NO: 308; SEQ ID NO: 146) | U55_x_st (SEQ ID NO: 6; SEQ ID NO: 260; SEQ ID NO: 280; SEQ ID NO: 308; SEQ ID NO: 146) U55_st (SEQ ID NO: 36; SEQ ID NO: 146; SEQ ID NO: 208; SEQ ID NO: 259; SEQ ID NO: 308; SEQ ID NO: 241; SEQ ID NO: 433; SEQ ID NO: 209) | U55_x_st (SEQ ID NO: 6; SEQ ID NO; 260; SEQ ID NO: 280; SEQ ID NO: 308; SEQ ID NO: 146) U55_st (SEQ ID NO: 36; SEQ ID NO: 146; SEQ ID NO: 208; SEQ ID NO: 259; SEQ ID NO: 308; SEQ ID NO: 241; SEQ ID NO: 433; SEQ ID NO: 209) hsa-miR-766_st (SEQ ID NO: 1) |
| Bleomycin | 14q11-26_st (SEQ ID NO: 160; SEQ ID NO: 629; SEQ ID NO: 676) | 14q11-26_st (SEQ ID NO: 160; SEQ ID NO: 629; SEQ ID NO: 676) 14q11-14_st (SEQ ID NO: 73; SEQ ID NO: 157; SEQ ID NO: 598; SEQ ID NO: 627; SEQ ID NO: 674) hsa-miR-127-3p_st (SEQ ID NO: 77) hsa-miR-455-3p_s (SEQ ID NO: 178) | |
| Estramustine | hsa-miR-378_st (SEQ ID NO: 368) | hsa-miR-378_st (SEQ ID NO: 368) hsa-miR-586_st (SEQ ID NO: 369) | |

TABLE 131-continued

Examples of Arrays of the Invention with Biomarkers of Sensitivity

| Therapeutic | Array 1 Probes | Array 2 Probes | Array 3 Probes |
|---|---|---|---|
| Mechlorethamine | U104_st (SEQ ID NO: 56; SEQ ID NO: 116; SEQ ID NO: 140; SEQ ID NO: 201; SEQ ID NO; 326; SEQ ID NO: 352) | U104_st (SEQ ID NO: 56; SEQ ID NO: 116: SEQ ID NO: 140; SEQ ID NO: 201; SEQ ID NO; 326; SEQ ID NO: 352) hsa-miR-768-3p_st (SEQ ID N): 44) hsa-miR-768-5p_st (SEQ ID NO: 83) | U104_st (SEQ ID NO: 56; SEQ ID NO: 116; SEQ ID NO: 140; SEQ ID NO: 201; SEQ ID NO; 326; SEQ ID NO: 352) hsa-miR-766_st (SEQ ID NO: 1) |
| Streptozocin | hsa-miR-296-3p_st (SEQ ID NO: 381) | hsa-miR-296-3p_st (SEQ ID NO: 381) hsa-miR-923_st (SEQ ID NO: 29) | |
| Carmustine | hsa-miR-146b-3p_st (SEQ ID NO: 404) | hsa-miR-146b-3p_st (SEQ ID NO: 404) hsa-miR-18a-star_st (SEQ ID NO: 71) | hsa-miR-146b-3p_st (SEQ ID NO: 404) hsa-miR-18a-star_st (SEQ ID NO: 71) hsa-miR-766_st (SEQ ID NO: 1) |
| Lomustine | hsa-miR-766_st (SEQ ID NO: 1) | hsa-miR-766_st (SEQ ID NO: 1) hsa-miR-1183_st (SEQ ID NO: 126) | hsa-miR-92a-2-star_st (SEQ ID NO: 136) hsa-miR-1183_st (SEQ ID NO: 126) hsa-miR-766_st (SEQ ID NO: 1) |
| Mercaptopurine | hsa-miR-92a-1-star_st (SEQ ID NO: 192) | hsa-miR-92a-1-star_st (SEQ ID NO: 192) U55_st (SEQ ID NO: 433; SEQ ID NO: 308; SEQ ID NO: 6; SEQ ID NO: 209; SEQ ID NO: 208) hsa-miR-17_st (SEQ ID NO: 152) | hsa-miR-92a-1-star_st (SEQ ID NO: 192) U55_st (SEQ ID NO: 433; SEQ ID NO: 308; SEQ ID NO: 6; SEQ ID NO: 209; SEQ ID NO: 208) hsa-miR-17_st (SEQ ID NO: 152) hsa-miR-766_st (SEQ ID NO: 1) |
| Teniposide | hsa-miR-181a-star_st (SEQ ID NO: 9) hsa-miR-768-3p_st (SEQ ID NO: 44) | hsa-miR-181a-star_st (SEQ ID NO: 9) hsa-miR-768-3p_st (SEQ ID NO: 44) hsa-miR-1299_st (SEQ ID NO: 38) hsa-miR-34b_st (SEQ ID NO: 154) | hsa-miR-181a-star_st (SEQ ID NO: 9) hsa-miR-768-3p_st (SEQ ID NO: 44) hsa-miR-1299_st (SEQ ID NO: 38) hsa-miR-34b_st (SEQ ID NO: 154) hsa-miR-766_st (SEQ ID NO: 1) |
| Dactinomycin | hsa-miR-652_st (SEQ ID NO: 42) | hsa-miR-652_st (SEQ ID NO: 42) hsa-miR-106b_st (SEQ ID NO: 37) | hsa-miR-652_st (SEQ ID NO: 42) hsa-miR-106b_st (SEQ ID NO; 37) hsa-miR-766_st (SEQ ID NO: 1) |
| Tretinoin | hsa-miR-449b_st (SEQ ID NO: 288) | hsa-miR-449b_st (SEQ ID NO: 288) hsa-miR-449a_st (SEQ ID NO: 287) | |
| Ifosfamide | hsa-miR-766_st (SEQ ID NO: 1) | hsa-miR-766_st (SEQ ID NO: 1) hsa-miR-181a-star_st (SEQ ID NO: 9) | hsa-miR-181a-star_st (SEQ ID NO: 9) hsa-miR-20b-star_st (SEQ ID NO: 130) hsa-miR-766_st (SEQ ID NO: 1) |
| Tamoxifen | U17b_st (SEQ ID NO: 117; SEQ ID NO: 254; SEQ ID NO: 327; SEQ ID NO: 58; SEQ ID NO: 456) | U17b_st (SEQ ID NO: 117; SEQ ID NO: 254; SEQ ID NO: 327; SEQ ID NO: 58; SEQ ID NO: 456) HBII-180A_x_st (SEQ ID NO: 54; SEQ ID NO: 352; SEQ ID NO: 386) | |

TABLE 131-continued

Examples of Arrays of the Invention with Biomarkers of Sensitivity

| Therapeutic | Array 1 Probes | Array 2 Probes | Array 3 Probes |
|---|---|---|---|
| Irinotecan | hsa-miR-181a-star_st (SEQ ID NO: 9) | hsa-miR-181a-star_st (SEQ ID NO: 9) hsa-miR-874_st (SEQ ID NO: 310) | hsa-miR-181a-star_st (SEQ ID NO: 9) hsa-miR-874_st (SEQ ID NO: 310) hsa-miR-766_st (SEQ ID NO: 1) |
| Floxuridine | HBII-202_st (SEQ ID NO: 113; SEQ ID NO: 185; SEQ ID NO: 198; SEQ ID NO: 239; SEQ ID NO: 426) | HBII-202_st (SEQ ID NO: 113; SEQ ID NO: 185; SEQ ID NO: 198; SEQ ID NO: 239; SEQ ID NO: 426) U13_st (SEQ ID NO: 57; SEQ ID NO: 225; SEQ ID NO: 316; SEQ ID NO: 389; SEQ ID NO: 428; SEQ ID NO: 472; SEQ ID NO: 477) | |
| Thioguanine | hsa-miR-17_st (SEQ ID NO: 152) | hsa-miR-17_st (SEQ ID NO: 152) U52_st (SEQ ID NO: 258; SEQ ID NO: 320; SEQ ID NO: 349; SEQ ID NO: 396) hsa-miR-106a_st (SEQ ID NO: 150) hsa-miR-17-star_st (SEQ ID NO: 216) | hsa-miR-17_st (SEQ ID NO: 152) U52_st (SEQ ID NO: 258; SEQ ID NO: 320; SEQ ID NO: 349; SEQ ID NO: 396) hsa-miR-106a_st (SEQ ID NO: 150) hsa-miR-17-star_st (SEQ ID NO: 216) hsa-miR-766_st (SEQ ID NO: 1) |
| PSC 833 | hsa-miR-378-star_st (SEQ ID NO: 409) | hsa-miR-378-star_st (SEQ ID NO: 409) hsa-miR-422a_st (SEQ ID NO: 410) | |
| Erlotinib | hsa-miR-30c_st (SEQ ID NO: 301) | hsa-miR-30c_st (SEQ ID NO: 301) hsa-miR-30c-2-star_st (SEQ ID NO: 504) | |
| Herceptin | hsa-miR-34c-3p_st (SEQ ID NO: 314) | hsa-miR-34c-3p_st (SEQ ID NO: 314) hsa-miR-34c-5p_st (SEQ ID NO: 506) | |
| Celecoxib | hsa-miR-768-3p_st (SEQ ID NO: 44) | hsa-miR-768-3p_st (SEQ ID NO: 44) HBII-142_x_st (SEQ ID NO: 279: SEQ ID NO: 425; SEQ ID NO: 508) | |
| Fulvestrant | hsa-miR-489_st (SEQ ID NO: 298) | hsa-miR-489_st (SEQ ID NO: 298) hsa-miR-425_st (SEQ ID NO: 286) | |
| Iressa | hsa-miR-934_st (SEQ ID NO: 517) | hsa-miR-934_st (SEQ ID NO: 517) hsa-miR-30c_st (SEQ ID NO: 301) | |
| Anastrozole | hsa-miR-517a_st (SEQ ID NO: 526) | hsa-miR-517a_st (SEQ ID NO: 526) hsa-miR-512-3p_st (SEQ ID NO: 523) hsa-miR-551a_st (SEQ ID NO: 530) | |
| Letrozole | hsa-miR-551a_st (SEQ ID NO: 530) | hsa-miR-551a_st (SEQ ID NO: 530) hsa-miR-517a_st (SEQ ID NO: 526) | |
| Cetuximab | hsa-miR-34c-3p_st (SEQ ID NO: 314) | hsa-miR-34c-3p_st (SEQ ID NO: 314) hsa-miR-34c-5p_st (SEQ ID NO: 506) | |

TABLE 132

Examples of Arrays of the Invention with Biomarkers of Resistance

| Therapeutic | Array 4 Probes | Array 5 Probes |
|---|---|---|
| Vincristine | hsa-miR-449a_st (SEQ ID NO: 287) | hsa-miR-449a_st (SEQ ID NO: 287) hsa-miR-130a_st (SEQ ID NO: 313) |
| Cisplatin | hsa-miR-192_st (SEQ ID NO: 542) hsa-miR-194_st (SEQ ID NO: 543) hsa-miR-30b_st (SEQ ID NO: 546) | hsa-miR-192_st (SEQ ID NO: 542) hsa-miR-194_st (SEQ ID NO: 543) hsa-miR-30b_st (SEQ ID NO: 546) hsa-miR-200b_st (SEQ ID NO: 544) |
| Etoposide | hsa-miR-151-5p_st (SEQ ID NO: 540) | hsa-miR-151-5p_st (SEQ ID NO: 540) hsa-miR-200a-star_st (SEQ ID NO: 553) |
| Azaguanine | hsa-miR-200c_st (SEQ ID NO: 556) | hsa-miR-200c_st (SEQ ID NO: 556) hsa-miR-1244_st (SEQ ID NO: 560) hsa-miR-331-3p_st (SEQ ID NO: 568) |
| Carboplatin | hsa-miR-29b_st (SEQ ID NO: 545) | hsa-miR-29b_st (SEQ ID NO: 545) hsa-miR-10a_st (SEQ ID NO: 538) hsa-miR-7_st (SEQ ID NO: 570) |
| Adriamycin | hsa-miR-516a-5p_st (SEQ ID NO: 558) | hsa-miR-516a-5p_st (SEQ ID NO: 558) hsa-miR-518d-5p_st (SEQ ID NO: 572) |
| Aclarubicin | hsa-miR-24-2-star_st (SEQ ID NO: 579) | hsa-miR-24-2-star_st (SEQ ID NO: 579) hsa-let-7f_st (SEQ ID NO: 577) |
| Mitoxantrone | hsa-miR-30d_st (SEQ ID NO: 547) | hsa-miR-30d_st (SEQ ID NO: 547) hsa-miR-513c_st (SEQ ID NO: 524) |
| Mitomycin | hsa-miR-516a-5p_st (SEQ ID NO: 558) | hsa-miR-516a-5p_st (SEQ ID NO: 558) hsa-miR-526a_st (SEQ ID NO: 572) |
| Paclitaxel | hsa-miR-30a_st (SEQ ID NO: 503) | hsa-miR-30a_st (SEQ ID NO: 503) hsa-miR-34a_st (SEQ ID NO: 234) |
| Gemcitabine | hsa-miR-141_st (SEQ ID NO: 552) | hsa-miR-141_st (SEQ ID NO: 552) hsa-miR-584_st (SEQ ID NO: 581) hsa-miR-934_st (SEQ ID NO: 517) |
| Taxotere | HBII-85-29_st (SEQ ID NO: 535; SEQ ID NO: 588; SEQ ID NO: 642) | HBII-85-29_st (SEQ ID NO: 535; SEQ ID NO: 588; SEQ ID NO: 642) hsa-miR-184_st (SEQ ID NO: 238) hsa-miR-424-star_st (SEQ ID NO: 100) |
| Dexamethasone | hsa-miR-34a_st (SEQ ID NO: 234) | hsa-miR-34a_st (SEQ ID NO: 234) hsa-miR-151-5p_st (SEQ ID NO: 540) |
| Ara-C | hsa-miR-23b_st (SEQ ID NO: 590) | hsa-miR-23b_st (SEQ ID NO: 590) hsa-miR-151-5p_st (SEQ ID NO: 540) |
| Methyl-prednisolone | hsa-miR-24_st (SEQ ID NO: 580) | hsa-miR-24_st (SEQ ID NO: 580) hsa-miR-339-3p_st (SEQ ID NO: 272) |
| Methotrexate | hsa-miR-30a_st (SEQ ID NO: 503) | hsa-miR-30a_st (SEQ ID NO: 503) hsa-miR-22_st (SEQ ID NO: 167) hsa-miR-34c-5p_st (SEQ ID NO: 506) |
| Bleomycin | hsa-miR-25_st (SEQ ID NO: 89) | hsa-miR-25_st (SEQ ID NO: 89) hsa-miR-203_st (SEQ ID NO: 511) hsa-miR-215_st (SEQ ID NO: 566) |
| Methyl-GAG | hsa-miR-10b_st (SEQ ID NO: 550) | hsa-miR-10b_st (SEQ ID NO: 550) hsa-miR-10a_st (SEQ ID NO: 538) |
| Belinostat | hsa-let-7e_st (SEQ ID NO: 549) | hsa-let-7e_st (SEQ ID NO: 549) hsa-miR-370_st (SEQ ID NO: 32) hsa-miR-452_st (SEQ ID NO: 608) hsa-miR-495_st (SEQ ID NO: 610) |
| Fluorouracil | hsa-miR-130a_st (SEQ ID NO: 313) | hsa-miR-130a_st (SEQ ID NO: 313) hsa-miR-100_st (SEQ ID NO: 17) |
| Radiation | hsa-miR-766_st (SEQ ID NO: 1) | hsa-miR-766_st (SEQ ID NO: 1) hsa-miR-1207-5p_st (SEQ ID NO: 109) hsa-miR-625_st (SEQ ID NO: 548) |
| Aza-2'-deoxycytidine | hsa-miR-30a_st (SEQ ID NO: 503) | hsa-miR-30a_st (SEQ ID NO: 503) hsa-miR-22_st (SEQ ID NO: 167) hsa-miR-99b_st (SEQ ID NO: 559) |
| Idarubicin | hsa-miR-151-5p_st (SEQ ID NO: 540) | hsa-miR-151-5p_st (SEQ ID NO: 540) hsa-miR-526a_st (SEQ ID NO: 572) |
| Melphalan | hsa-miR-151-5p_st (SEQ ID NO: 540) | hsa-miR-151-5p_st (SEQ ID NO: 540) hsa-miR-29b_st (SEQ ID NO: 545) |
| IL4-PR38 fusion protein | hsa-miR-100_st (SEQ ID NO: 17) | hsa-miR-100_st (SEQ ID NO: 17) hsa-let-7a_st (SEQ ID NO: 575) hsa-miR-146a_st (SEQ ID NO: 19) |
| Valproic acid | hsa-miR-744_st (SEQ ID NO: 619) | hsa-miR-744_st (SEQ ID NO: 619) hsa-miR-625_st (SEQ ID NO: 548) |
| All-trans retinoic acid | hsa-miR-221_st (SEQ ID NO: 620) | hsa-miR-221_st (SEQ ID NO: 620) hsa-miR-10a_st (SEQ ID NO: 538) |
| Cytoxan | hsa-miR-222_st (SEQ ID NO: 621) | hsa-miR-222_st (SEQ ID NO: 621) hsa-let-7b_st (SEQ ID NO: 600) hsa-miR-625_st (SEQ ID NO: 548) |
| Topotecan | hsa-miR-584_st (SEQ ID NO: 581) | hsa-miR-584_st (SEQ ID NO: 581) HBII-289_st (SEQ ID NO: 626) |

TABLE 132-continued

Examples of Arrays of the Invention with Biomarkers of Resistance

| Therapeutic | Array 4 Probes | Array 5 Probes |
|---|---|---|
| Suberoylanilide hydroxamic acid | hsa-miR-210_st (SEQ ID NO: 635) | hsa-miR-210_st (SEQ ID NO: 635) hsa-miR-28-3p_st (SEQ ID NO: 605) hsa-miR-455-3p_st (SEQ ID NO: 178) hsa-miR-758_st (SEQ ID NO: 35) |
| Depsipeptide | hsa-miR-516a-5p_st (SEQ ID NO: 558) | hsa-miR-516a-5p_st (SEQ ID NO: 558) HBII-85-23_x_st (SEQ ID NO: 250; SEQ ID NO: 587; SEQ ID NO: 641; SEQ ID NO: 650) HBE-85-29_x_st (SEQ ID NO: 589; SEQ ID NO:642) hsa-miR-200a-star_st (SEQ ID NO: 553) hsa-miR-203_st (SEQ ID NO: 511) hsa-miR-519a_st (SEQ ID NO: 574) hsa-miR-523-star_st (SEQ ID NO: 573) |
| Bortezomib | hsa-miR-9-star_st (SEQ ID NO: 651) | hsa-miR-9-star_st (SEQ ID NO: 651) hsa-miR-98_st (SEQ ID NO: 652) |
| Leukeran | hsa-miR-151-5p_st (SEQ ID NO: 540) | hsa-miR-151-5p_st (SEQ ID NO: 540) hsa-miR-125a-3p_st (SEQ ID NO: 601) |
| Fludarabine | hsa-miR-23b_st (SEQ ID NO: 590) | hsa-miR-23b_st (SEQ ID NO: 590) hsa-miR-203_st (SEQ ID NO: 511) hsa-miR-339-5p_st (SEQ ID NO: 273) hsa-miR-487a_st (SEQ ID NO: 609) |
| Vinblastine | hsa-miR-30c_st (SEQ ID NO: 301) | hsa-miR-30c_st (SEQ ID NO: 301) hsa-miR-34c-3p_st (SEQ ID NO: 314) |
| Busulfan | hsa-miR-125a-5p_st (SEQ ID NO: 551) | hsa-miR-125a-5p_st (SEQ ID NO: 551) hsa-miR-24-1-star_st (SEQ ID NO: 659) |
| Dacarbazine | hsa-miR-151-5p_st (SEQ ID NO: 540) | hsa-miR-151-5p_st (SEQ ID NO: 540) hsa-miR-125a-3p_st (SEQ ID NO: 601) hsa-miR-182_st (SEQ ID NO: 563) hsa-miR-215_st (SEQ ID NO: 566) hsa-miR-30a_st (SEQ ID NO: 503) hsa-miR-34a-star_st (SEQ ID NO: 277) hsa-miR-935_st (SEQ ID NO: 639) |
| Oxaliplatin | hsa-miR-28-3p_st (SEQ ID NO: 605) hsa-miR-28-5p_st (SEQ ID NO: 594) | hsa-miR-28-3p_st (SEQ ID NO: 605) hsa-miR-28-5p_st (SEQ ID NO: 594) hsa-miR-145_st (SEQ ID NO: 669) |
| Hydroxyurea | hsa-miR-151-5p_st (SEQ ID NO: 540) | hsa-miR-151-5p_st (SEQ ID NO: 540) hsa-miR-34a_st (SEQ ID NO: 234) |
| Tegafur | hsa-miR-30a-star_st (SEQ ID NO: 502) | hsa-miR-30a-star_st (SEQ ID NO: 502) hsa-miR-495_st (SEQ ID NO: 610) |
| Daunorubicin | hsa-miR-151-5p_st (SEQ ID NO: 540) | hsa-miR-151-5p_st (SEQ ID NO: 540) hsa-miR-146a_st (SEQ ID NO: 19) hsa-miR-200b-star_st (SEQ ID NO: 555) hsa-miR-221-star_st (SEQ ID NO: 613) hsa-miR-523-star_st (SEQ ID NO: 573) |
| Bleomycin | hsa-miR-25_st (SEQ ID NO: 89) | hsa-miR-25_st (SEQ ID NO: 89) HBII-180C_x_st (SEQ ID NO: 452; SEQ ID NO: 491; SEQ ID NO: 451) hsa-miR-18a-star_st (SEQ ID NO: 71) hsa-miR-192_st (SEQ ID NO: 542) hsa-miR-20a_st (SEQ ID NO: 218) hsa-miR-320d_st (SEQ ID NO: 91) hsa-miR-93-star_st (SEQ ID NO: 45) hsa-miR-934_st (SEQ ID NO: 517) |
| Estramustine | hsa-miR-552_st (SEQ ID NO: 682) | hsa-miR-552_st (SEQ ID NO: 682) hsa-miR-194-star_st (SEQ ID NO: 230) hsa-miR-21-star_st (SEQ ID NO: 166) |
| Mechlorethamine | hsa-miR-151-5p_st (SEQ ID NO: 540) | hsa-miR-151-5p_st (SEQ ID NO: 540) hsa-miR-519b-5p_st (SEQ ID NO: 573) |
| Streptozocin | hsa-miR-26a_st (SEQ ID NO: 537) | hsa-miR-26a_st (SEQ ID NO: 537) hsa-miR-526a_st (SEQ ID NO: 572) |
| Carmustine | hsa-let-7b_st (SEQ ID NO: 600) | hsa-let-7b_st (SEQ ID NO: 600) hsa-let-7f_st (SEQ ID NO: 577) hsa-miR-130a_st (SEQ ID NO: 313) hsa-miR-331-3p_st (SEQ ID NO: 568) |
| Lomustine | hsa-miR-99b_st (SEQ ID NO: 559) | hsa-miR-99b_st (SEQ ID NO: 559) hsa-miR-200c_st (SEQ ID NO: 556) hsa-miR-331-3p_st (SEQ ID NO: 568) |
| Mercaptopurine | hsa-miR-22_st (SEQ ID NO: 167) | hsa-miR-22_st (SEQ ID NO: 167) hsa-miR-23a_st (SEQ ID NO: 571) |
| Teniposide | hsa-miR-151-5p_st (SEQ ID NO: 540) | hsa-miR-151-5p_st (SEQ ID NO: 540) hsa-miR-30c-2-star_st (SEQ ID NO: 504) hsa-miR-518e-star_st (SEQ ID NO: 573) |
| Dactinomycin | hsa-miR-30a_st (SEQ ID NO: 503) | hsa-miR-30a_st (SEQ ID NO: 503) hsa-miR-27a-star_st (SEQ ID NO: 593) hsa-miR-372_st (SEQ ID NO: 646) |

TABLE 132-continued

Examples of Arrays of the Invention with Biomarkers of Resistance

| Therapeutic | Array 4 Probes | Array 5 Probes |
|---|---|---|
| Tretinoin | hsa-miR-221_st (SEQ ID NO: 620) | hsa-miR-221_st (SEQ ID NO: 620) hsa-miR-125a-5p_st (SEQ ID NO: 551) |
| Ifosfamide | hsa-miR-24_st (SEQ ID NO: 580) | hsa-miR-24_st (SEQ ID NO: 580) hsa-miR-27b_st (SEQ ID NO: 567) |
| Tamoxifen | hsa-miR-30a-star_st (SEQ ID NO: 502) | hsa-miR-30a-star_st (SEQ ID NO: 502) hsa-let-7a_st (SEQ ID NO: 575) hsa-miR-23b_st (SEQ ID NO: 590) hsa-miR-30e-star_st (SEQ ID NO: 505) |
| Irinotecan | hsa-miR-125a-5p_st (SEQ ID NO: 551) | hsa-miR-125a-5p_st (SEQ ID NO: 551) hsa-miR-320d_st (SEQ ID NO: 91) hsa-miR-584_st (SEQ ID NO: 581 |
| Floxuridine | hsa-miR-30d_st (SEQ ID NO: 547) | hsa-miR-30d_st (SEQ ID NO: 547) hsa-miR-30b_st (SEQ ID NO: 546) hsa-miR-584_st (SEQ ID NO: 581 |
| Thioguanine | hsa-miR-27b_st (SEQ ID NO: 567) | hsa-miR-27b_st (SEQ ID NO: 567) hsa-let-7b_st (SEQ ID NO: 600) hsa-miR-30a_st (SEQ ID NO: 503) |
| PSC 833 | hsa-miR-30a-star_st (SEQ ID NO: 502) hsa-miR-30a_st (SEQ ID NO: 503) | hsa-miR-30a-star_st (SEQ ID NO: 502) hsa-miR-30a_st (SEQ ID NO: 503) hsa-miR-193b-star_st (SEQ ID NO: 633) hsa-miR-22-star_st (SEQ ID NO: 578) |
| Erlotinib | hsa-miR-671-5p_st (SEQ ID NO: 43) | hsa-miR-671-5p_st (SEQ ID NO: 43) hsa-miR-500_st (SEQ ID NO: 94) hsa-miR-532-3p_st (SEQ ID NO: 97) |
| Herceptin | hsa-miR-107_st (SEQ ID NO: 661) | hsa-miR-107_st (SEQ ID NO: 661) hsa-let-7d_st (SEQ ID NO: 623) hsa-miR-103_st (SEQ ID NO: 660) |
| Celecoxib | hsa-miR-28-5p_st (SEQ ID NO: 594) | hsa-miR-28-5p_st (SEQ ID NO: 594) hsa-miR-151-3p_st hsa-miR-31-star_st |
| Fulvestrant | hsa-miR-222_st (SEQ ID NO: 621) | hsa-miR-222_st (SEQ ID NO: 621) hsa-miR-28-5p_st (SEQ ID NO: 539) |
| Iressa | hsa-miR-505-star_st (SEQ ID NO: 686) | hsa-miR-505-star_st (SEQ ID NO: 686) hsa-miR-671-5p_st (SEQ ID NO: 43) |
| Letrozole | U27_st (SEQ ID NO: 202; SEQ ID NO: 330; SEQ ID NO: 687) | U27_st (SEQ ID NO: 202; SEQ ID NO: 330; SEQ ID NO: 687) U29_st (SEQ ID NO: 203; SEQ ID NO: 189; SEQ ID NO: 331; SEQ ID NO: 430) |
| Cetuximab | hsa-miR-491-5p_st (SEQ ID NO: 617) | hsa-miR-491-5p_st (SEQ ID NO: 617) hsa-miR-191_st (SEQ ID NO: 284) |

In an embodiment, the probes of Arrays 4 and/or 5 can be included on one or more of Arrays 1, 2, and/or 3 to produce a single array that can be used to detect biomarkers of sensitivity and biomarkers of resistance.

The arrays described above and all other arrays of the invention can also include one or more probes that bind to one or more control gene products, e.g., the products of housekeeping gene (e.g., beta actin).

Other Embodiments

All publications and patent applications mentioned in this specification, including Danish Provisional Patent Application No. PA 2010 00382, WO 2007/072225, and U.S. Patent Application Publication No. 2009/0023149, are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth. For example, it is anticipated that measuring the level of proteins, metabolites, identifying genetic mutations and DNA copy number variations, all will be useful in determining chemosensitivity.

TABLE 1

Vincristine microRNA biomarkers.

| | Medianprobe | Corr | Sequence |
|---|---|---|---|
| [1,] | hsa-miR-106b-star_st | 0.35 | GCAGCAAGTACCCACAGTGCGG (SEQ ID NO: 2) |
| [2,] | hsa-miR-25-star_st | 0.3 | CAATTGCCCAAGTCTCCGCCT (SEQ ID NO: 3) |

TABLE 2

Cisplatin microRNA biomarkers.

| | Medianprobe | Corr | Sequence |
|---|---|---|---|
| [1,] | HBII-85-2_x_st | 0.31 | GAATGTTTTTTTTGGGGACTCATCA (SEQ ID NO: 4) |
| [2,] | U48_st | 0.32 | ATGGCATCAGCGACACACTCAAGAG (SEQ ID NO: 5) |
| [3,] | U55_x_st | 0.32 | GCACTCGGGAGTATGCAGCATTACC (SEQ ID NO: 6) |

TABLE 2-continued

Cisplatin microRNA biomarkers.

| | Medianprobe | Corr | Sequence |
|---|---|---|---|
| [4,] | hsa-miR-124_st | 0.35 | GGCATTCACCGCGTGCCTTA (SEQ ID NO: 7) |
| [5,] | hsa-miR-1281_st | 0.32 | GGGAGAGGAGGAGGCGA (SEQ ID NO: 8) |
| [6,] | hsa-miR-181a-star_st | 0.34 | GGTACAATCAACGGTCGATGGT (SEQ ID NO: 9) |
| [7,] | hsa-miR-181b_st | 0.33 | ACCCACCGACAGCAATGAATGTT (SEQ ID NO: 10) |
| [8,] | hsa-miR-342-3p_st | 0.43 | ACGGGTGCGATTTCTGTGTGAGA (SEQ ID NO: 11) |
| [9,] | hsa-miR-432_st | 0.33 | CCACCCAATGACCTACTCCAAGA (SEQ ID NO: 12) |

TABLE 3

Etoposide microRNA biomarkers.

| | Medianprobe | Corr | Sequence |
|---|---|---|---|
| [1,] | hsa-miR-124_st | 0.33 | GGCATTCACCGCGTGCCTTA (SEQ ID NO: 7) |
| [2,] | hsa-miR-1281_st | 0.31 | GGGAGAGGAGGAGGCGA (SEQ ID NO: 8) |
| [3,] | hsa-miR-140-3p_st | 0.36 | CCGTGGTTCTACCCTGTGGTA (SEQ ID NO: 13) |
| [4,] | hsa-miR-181a-star_st | 0.3 | GGTACAATCAACGGTCGATGGT (SEQ ID NO: 9) |
| [5,] | hsa-miR-181b_st | 0.32 | ACCCACCGACAGCAATGAATGTT (SEQ ID NO: 10) |
| [6,] | hsa-miR-195-star_st | 0.34 | GGAGCAGCACAGCCAATATTGG (SEQ ID NO: 14) |
| [7,] | hsa-miR-342-3p_st | 0.33 | ACGGGTGCGATTTCTGTGTGAGA (SEQ ID NO: 11) |
| [8,] | hsa-miR-766_st | 0.35 | GCTGAGGCTGTGGGGCTGGAGT (SEQ ID NO: 1) |
| [9,] | hsa-miR-92b_st | 0.43 | GGAGGCCGGGACGAGTGCAATA (SEQ ID NO: 15) |
| [10,] | hsa-miR-938_st | 0.33 | ACTGGGTTCACCTTTAAGGGCA (SEQ ID NO: 16) |

TABLE 4

Azaquanine microRNA biomarkers.

| | Medianprobe | Corr | Sequence |
|---|---|---|---|
| [1,] | hsa-miR-100_st | 0.37 | CACAAGTTCGGATCTACGGGTT (SEQ ID NO: 17) |
| [2,] | hsa-miR-140-3p_st | 0.45 | CCGTGGTTCTACCCTGTGGTA (SEQ ID NO: 13) |
| [3,] | hsa-miR-140-5p_st | 0.4 | CTACCATAGGGTAAAACCACTG (SEQ ID NO: 18) |
| [4,] | hsa-miR-146a_st | 0.45 | AACCCATGGAATTCAGTTCTCA (SEQ ID NO: 19) |

TABLE 4-continued

Azaquanine microRNA biomarkers.

| | Medianprobe | Corr | Sequence |
|---|---|---|---|
| [5,] | hsa-miR-155_st | 0.37 | ACCCCTATCACGATTAGCATTAA (SEQ ID NO: 20) |
| [6,] | hsa-miR-506_st | 0.35 | TCTACTCAGAAGGGTGCCTTA (SEQ ID NO: 21) |
| [7,] | hsa-miR-508-5p_st | 0.31 | CATGAGTGACGCCCTCTGGAGTA (SEQ ID NO: 22) |
| [8,] | hsa-miR-509-3-5p_st | 0.31 | CATGATTGCCACGTCTGCAGTA (SEQ ID NO: 23) |
| [9,] | hsa-miR-509-3p_st | 0.31 | CTACCCACAGACGTACCAATCA (SEQ ID NO: 24) |
| [10,] | hsa-miR-510_st | 0.32 | GTGATTGCCACTCTCCTGAGTA (SEQ ID NO: 25) |
| [11,] | hsa-miR-513a-5p_st | 0.31 | ATGACACCTCCCTGTGAA (SEQ ID NO: 26) |
| [12,] | hsa-miR-513b_st | 0.34 | ATAAATGACACCTCCTTGTGAA (SEQ ID NO: 27) |
| [13,] | hsa-miR-663_st | 0.36 | GCGGTCCCGCGGCGCCCCGCCT (SEQ ID NO: 28) |
| [14,] | hsa-miR-923_st | 0.34 | AGTTTCTTTTCCTCCGCTGAC (SEQ ID NO: 29) |

TABLE 5

Carboplatin microRNA biomarkers.

| | Medianprobe | Corr | Sequence |
|---|---|---|---|
| [1,] | U55_x_st | 0.32 | GCACTCGGGAGTATGCAGCATTACC (SEQ ID NO: 6) |
| [2,] | hsa-miR-124_st | 0.39 | GGCATTCACCGCGTGCCTTA (SEQ ID NO: 7) |
| [3,] | hsa-miR-1271_st | 0.33 | TGAGTGCTTGCTAGGTGCCAAG (SEQ ID NO: 30) |
| [4,] | hsa-miR-143_st | 0.32 | GAGCTACAGTGCTTCATCTCA (SEQ ID NO: 31) |
| [5,] | hsa-miR-342-3p_st | 0.46 | ACGGGTGCGATTTCTGTGTGAGA (SEQ ID NO: 11) |
| [6,] | hsa-miR-370_st | 0.32 | ACCAGGTTCCACCCCAGCAGGC (SEQ ID NO: 32) |
| [7,] | hsa-miR-433_st | 0.31 | ACACCGAGGAGCCCATCATGAT (SEQ ID NO: 33) |
| [8,] | hsa-miR-654-3p_st | 0.32 | AAGGTGATGGTCAGCAGACATA (SEQ ID NO: 34) |
| [9,] | hsa-miR-758_st | 0.3 | GGTTAGTGGACCAGGTCACAAA (SEQ ID NO: 35) |

TABLE 6

Adriamycin microRNA biomarkers.

| | Medianprobe | Corr | Sequence |
|---|---|---|---|
| [1,] | U55_st | 0.34 | TGGCTTCCCCACCGCGCACTCGGGA (SEQ ID NO: 36) |

TABLE 6-continued

Adriamycin microRNA biomarkers.

| Medianprobe | Corr | Sequence |
|---|---|---|
| [2,] U55_x_st | 0.34 | GCACTCGGGAGTATGCAGCATTACC (SEQ ID NO: 6) |
| [3,] hsa-miR-106b-star_st | 0.36 | GCAGCAAGTACCCACAGTGCGG (SEQ ID NO: 2) |
| [4,] hsa-miR-106b_st | 0.36 | ATCTGCACTGTCAGCACTTTA (SEQ ID NO: 37) |
| [5,] hsa-miR-124_st | 0.31 | GGCATTCACCGCGTGCCTTA (SEQ ID NO: 7) |
| [6,] hsa-miR-1299_st | 0.31 | TCCCTCACACAGAATTCCAGAA (SEQ ID NO: 38) |
| [7,] hsa-miR-29b-2-star_st | 0.33 | CTAAGCCACCATGTGAAACCAG (SEQ ID NO: 39) |
| [8,] hsa-miR-33b-star_st | 0.33 | GGGCTGCACTGCCGAGGCACTG (SEQ ID NO: 40) |
| [9,] hsa-miR-629-star_st | 0.33 | GCTGGGCTTACGTTGGGAGAAC (SEQ ID NO: 41) |
| [10,] hsa-miR-652_st | 0.35 | CACAACCCTAGTGGCGCCATT (SEQ ID NO: 42) |
| [11,] hsa-miR-671-5p_st | 0.34 | CTCCAGCCCCTCCAGGGCTTCCT (SEQ ID NO: 43) |
| [12,] hsa-miR-766_st | 0.31 | GCTGAGGCTGTGGGGCTGGAGT (SEQ ID NO: 1) |
| [13,] hsa-miR-768-3p_st | 0.33 | GTCAGCAGTTTGAGTGTCAGCATTG (SEQ ID NO: 44) |
| [14,] hsa-miR-93-star_st | 0.32 | CGGGAAGTGCTAGCTCAGCAGT (SEQ ID NO: 45) |
| [15,] hsa-miR-93_st | 0.34 | CTACCTGCACGAACAGCACTTTG (SEQ ID NO: 46) |

TABLE 7

Aclarubicin microRNA biomarkers.

| Medianprobe | Corr | Sequence |
|---|---|---|
| [1,] ACA10_s_st | 0.4 | TAGGAACAGAGAGGCCATTCTGGGC (SEQ ID NO: 47) |
| [2,] ACA18_x_st | 0.36 | GCTACAGGAAAAGCCCCATCGGGAT (SEQ ID NO: 48) |
| [3,] ACA44_st | 0.3 | TGGAGATCCCATGGCTATGACCAGC (SEQ ID NO: 49) |
| [4,] ACA51_x_st | 0.34 | TACCTCCTCTTTCTATACAGTCAGT (SEQ ID NO: 50) |
| [5,] ACA61_st | 0.39 | TAGGCCAGCTTCACTATTACTTTTC (SEQ ID NO: 51) |
| [6,] ENSG00000200394_st | 0.32 | TTGATCTTGAGCCTGCGGAGAGCAA (SEQ ID NO: 52) |

TABLE 7-continued

Aclarubicin microRNA biomarkers.

| Medianprobe | Corr | Sequence |
|---|---|---|
| [7,] ENSG00000202252_st | 0.31 | GGTGTTGCCATCATTAGCCAAGCTT (SEQ ID NO: 53) |
| [8,] HBII-180A_x_st | 0.31 | GGCACCGTGTCCTCAGTGGCAGTCG (SEQ ID NO: 54) |
| [9,] HBII-429_st | 0.32 | ATCAGAAGGGTGACATGGCAGTTTC (SEQ ID NO: 55) |
| [10,] U104_st | 0.38 | AGGCTCAGACTCCAGTTCGCATCAC (SEQ ID NO: 56) |
| [11,] U13_st | 0.33 | GTTCAAGGGTGGCACATCTCACACA (SEQ ID NO: 57) |
| [12,] U17b_st | 0.34 | GAGGCCCAGCTTCATCTTCAACGTT (SEQ ID NO: 58) |
| [13,] U17b_x_st | 0.31 | ACGAGGCCCAGCTTCATCTTCAACG (SEQ ID NO: 59) |
| [14,] U26_st | 0.35 | GTTCAGTTCGTAAAATCATCCCCGT (SEQ ID NO: 60) |
| [15,] U3-2_s_st | 0.31 | CATCAATGGCTGACGGCAGTTGCAG (SEQ ID NO: 61) |
| [16,] U35A_st | 0.3 | GACATCCGCAGACCATCGTGAGATA (SEQ ID NO: 62) |
| [17,] U49A_st | 0.31 | AGGAGTAGTCTTCGTCAGTTATCGC (SEQ ID NO: 63) |
| [18,] U49A_x_st | 0.31 | ACAGGAGTAGTCTTCGTCAGTTATC (SEQ ID NO: 64) |
| [19,] U49B_s_st | 0.36 | GTCAGTTATCGCTTCTGACGGCACT (SEQ ID NO: 65) |
| [20,] U67_st | 0.33 | ATCCCAGTTCCCCAAAGGCCTTAGG (SEQ ID NO: 66) |
| [21,] U68_st | 0.31 | CGACAAGATCCGCTTGCTGTTTGCA (SEQ ID NO: 67) |
| [22,] U68_x_st | 0.31 | AAGGCGACAAGATCCGCTTGCTGTT (SEQ ID NO: 68) |
| [23,] U74_x_st | 0.38 | CGGTTGGCATTCATCATTACTCTCA (SEQ ID NO: 69) |
| [24,] hsa-miR-1275_st | 0.45 | GACAGCCTCTCCCCCAC (SEQ ID NO: 70) |
| [25,] hsa-miR-1281_st | 0.3 | GGGAGAGGAGGAGGCGA (SEQ ID NO: 8) |

TABLE 7-continued

Aclarubicin microRNA biomarkers.

| | Medianprobe | Corr | Sequence |
|---|---|---|---|
| [26,] | hsa-miR-18a-star_st | 0.36 | CCAGAAGGAGCACTTAGGGCAGT (SEQ ID NO: 71) |
| [27,] | hsa-miR-18a_st | 0.33 | CTATCTGCACTAGATGCACCTTA (SEQ ID NO: 72) |
| [28,] | hsa-miR-25-star_st | 0.35 | CAATTGCCCAAGTCTCCGCCT (SEQ ID NO: 3) |
| [29,] | hsa-miR-33b-star_st | 0.33 | GGGCTGCACTGCCGAGGCACTG (SEQ ID NO: 40) |

TABLE 8

Mitoxantrone microRNA biomarkers.

| | Medianprobe | Corr | Sequence |
|---|---|---|---|
| [1,] | 14qII-14_st | 0.33 | CCAACACTCATACGCCGGCAGTTGT (SEQ ID NO: 73) |
| [2,] | 14qII-1_st | 0.31 | TGGACCTCAGACTTCCAGACCTGTA (SEQ ID NO: 74) |
| [3,] | 14qII-26_st | 0.33 | TCATCGTATGTGACTCATACTCCAC (SEQ ID NO: 75) |
| [4,] | 14qII-26_x_st | 0.3 | GTGACTCATACTCCACCAGTGCTCA (SEQ ID NO: 76) |
| [5,] | hsa-miR-127-3p_st | 0.36 | AGCCAAGCTCAGACGGATCCGA (SEQ ID NO: 77) |
| [6,] | hsa-miR-181a-star_st | 0.38 | GGTACAATCAACGGTCGATGGT (SEQ ID NO: 9) |
| [7,] | hsa-miR-181a_st | 0.31 | ACTCACCGACAGCGTTGAATGTT (SEQ ID NO: 78) |
| [8,] | hsa-miR-181b_st | 0.35 | ACCCACCGACAGCAATGAATGTT (SEQ ID NO: 10) |
| [9,] | hsa-miR-181c_st | 0.31 | ACTCACCGACAGGTTGAATGTT (SEQ ID NO: 79) |
| [10,] | hsa-miR-342-3p_st | 0.36 | ACGGGTGCGATTTCTGTGTGAGA (SEQ ID NO: 11) |
| [11,] | hsa-miR-342-5p_st | 0.31 | TCAATCACAGATAGCACCCCT (SEQ ID NO: 80) |
| [12,] | hsa-miR-409-3p_st | 0.34 | AGGGGTTCACCGAGCAACATTC (SEQ ID NO: 81) |
| [13,] | hsa-miR-432_st | 0.37 | CCACCCAATGACCTACTCCAAGA (SEQ ID NO: 12) |
| [14,] | hsa-miR-487b_st | 0.31 | AAGTGGATGACCCTGTACGATT (SEQ ID NO: 82) |
| [15,] | hsa-miR-654-3p_st | 0.3 | AAGGTGATGGTCAGCAGACATA (SEQ ID NO: 34) |
| [16,] | hsa-miR-768-5p_st | 0.31 | ATCACTCCGTACTTTCATCCTCCAA (SEQ ID NO: 83) |
| [17,] | hsa-miR-92b_st | 0.32 | GGAGGCCGGGACGAGTGCAATA (SEQ ID NO: 15) |

TABLE 9

Mitomycin microRNA biomarkers.

| | Medianprobe | Corr | Sequence |
|---|---|---|---|
| [1,] | hsa-miR-124_st | 0.31 | GGCATTCACCGCGTGCCTTA (SEQ ID NO: 7) |
| [2,] | hsa-miR-181a-star_st | 0.31 | GGTACAATCAACGGTCGATGGT (SEQ ID NO: 9) |
| [3,] | hsa-miR-181b_st | 0.33 | ACCCACCGACAGCAATGAATGTT (SEQ ID NO: 10) |

TABLE 10

Paclitaxel (Taxol) microRNA biomarkers.

| | Medianprobe | Corr | Sequence |
|---|---|---|---|
| [1,] | hsa-miR-106b-star_st | 0.31 | GCAGCAAGTACCCACAGTGCGG (SEQ ID NO: 2) |
| [2,] | hsa-miR-1228_st | 0.31 | GGGGGGCGAGGCAGGTGTGA (SEQ ID NO: 84) |
| [3,] | hsa-miR-185_st | 0.33 | TCAGGAACTGCCTTTCTCTCCA (SEQ ID NO: 85) |
| [4,] | hsa-miR-188-5p_st | 0.31 | CCCTCCACCATGCAAGGGATG (SEQ ID NO: 86) |
| [5,] | hsa-miR-18b_st | 0.34 | CTAACTGCACTAGATGCACCTTA (SEQ ID NO: 87) |
| [6,] | hsa-miR-20b_st | 0.32 | CTACCTGCACTATGAGCACTTTG (SEQ ID NO: 88) |
| [7,] | hsa-miR-25_st | 0.32 | TCAGACCGAGACAAGTGCAATG (SEQ ID NO: 89) |
| [8,] | hsa-miR-320c_st | 0.32 | ACCCTCTCAACCCAGCTTTT (SEQ ID NO: 90) |
| [9,] | hsa-miR-320d_st | 0.34 | TCCTCTCAACCCAGCTTTT (SEQ ID NO: 91) |
| [10,] | hsa-miR-362-5p_st | 0.4 | ACTCACACCTAGGTTCCAAGGATT (SEQ ID NO: 92) |
| [11,] | hsa-miR-500-star_st | 0.34 | CAGAATCCTTGCCCAGGTGCAT (SEQ ID NO: 93) |
| [12,] | hsa-miR-500_st | 0.34 | TCTCACCCAGGTAGCAAGGATTA (SEQ ID NO: 94) |
| [13,] | hsa-miR-501-3p_st | 0.33 | AGAATCCTTGCCCGGGTGCATT (SEQ ID NO: 95) |
| [14,] | hsa-miR-502-3p_st | 0.34 | TGAATCCTTGCCCAGGTGCATT (SEQ ID NO: 96) |
| [15,] | hsa-miR-532-3p_st | 0.35 | TGCAAGCCTTGGGTGTGGGAGG (SEQ ID NO: 97) |
| [16,] | hsa-miR-532-5p_st | 0.41 | ACGGTCCTACACTCAAGGCATG (SEQ ID NO: 98) |
| [17,] | hsa-miR-652_st | 0.47 | CACAACCCTAGTGGCGCCATT (SEQ ID NO: 42) |
| [18,] | hsa-miR-766_st | 0.31 | GCTGAGGCTGTGGGGCTGGAGT (SEQ ID NO: 1) |

TABLE 11

Gemcitabine (Gemzar) microRNA biomarkers.

| | Medianprobe | Corr | Sequence |
|---|---|---|---|
| [1,] | HBII-438A_s_st | 0.33 | ATCTGGAATGAGTCCCTCAGCATCC (SEQ ID NO: 99) |
| [2,] | hsa-miR-155_st | 0.37 | ACCCCTATCACGATTAGCATTAA (SEQ ID NO: 20) |
| [3,] | hsa-miR-181a-star_st | 0.33 | GGTACAATCAACGGTCGATGGT (SEQ ID NO: 9) |
| [4,] | hsa-miR-181b_st | 0.31 | ACCCACCGACAGCAATGAATGTT (SEQ ID NO: 10) |
| [5,] | hsa-miR-342-3p_st | 0.36 | ACGGGTGCGATTTCTGTGTGAGA (SEQ ID NO: 11) |
| [6,] | hsa-miR-424-star_st | 0.35 | ATAGCAGCGCCTCACGTTTTG (SEQ ID NO: 100) |
| [7,] | hsa-miR-503_st | 0.31 | CTGCAGAACTGTTCCCGCTGCTA (SEQ ID NO: 101) |

TABLE 12

Taxotere (docetaxel) microRNA biomarkers.

| | Medianprobe | Corr | Sequence |
|---|---|---|---|
| [1,] | hsa-miR-1307_st | 0.31 | CACGACCGACGCCACGCCGAGT (SEQ ID NO: 102) |
| [2,] | hsa-miR-505_st | 0.31 | AGGAAACCAGCAAGTGTTGACG (SEQ ID NO: 103) |
| [3,] | hsa-miR-769-3p_st | 0.35 | AACCAAGACCCCGGAGATCCCAG (SEQ ID NO: 104) |
| [4,] | hsa-miR-769-5p_st | 0.36 | AGCTCAGAACCCAGAGGTCTCA (SEQ ID NO: 105) |

TABLE 13

Dexamethasone microRNA biomarkers.

| | Medianprobe | Corr | Sequence |
|---|---|---|---|
| [1,] | U49A_st | 0.38 | ACAGGAGTAGTCTTCGTCAGTTATC (SEQ ID NO: 64) |
| [2,] | U49A_x_st | 0.41 | TCAGTTATCGCTTCTGACGGCACTT (SEQ ID NO: 106) |
| [3,] | U49B_s_st | 0.42 | GTCAGTTATCGCTTCTGACGGCACT (SEQ ID NO: 65) |
| [4,] | U49B_x_st | 0.35 | CGTCAGTTATCGCTTCTGACGGCAC (SEQ ID NO: 107) |
| [5,] | hsa-miR-10a-star_st | 0.31 | TATTCCCCTAGATACGAATTTG (SEQ ID NO: 108) |
| [6,] | hsa-miR-1207-5p_st | 0.37 | CCCCTCCCAGCCTCCCTGCCA (SEQ ID NO: 109) |
| [7,] | hsa-miR-128_st | 0.34 | AAAGAGACCGGTTCACTGTGA (SEQ ID NO: 110) |
| [8,] | hsa-miR-150_st | 0.33 | CACTGGTACAAGGGTTGGGAGA (SEQ ID NO: 111) |
| [9,] | hsa-miR-424-star_st | 0.42 | ATAGCAGCGCCTCACGTTTTG (SEQ ID NO: 100) |
| [10,] | hsa-miR-424_st | 0.38 | TTCAAAACATGAATTGCTGCTG (SEQ ID NO: 112) |
| [11,] | hsa-miR-503_st | 0.41 | CTGCAGAACTGTTCCCGCTGCTA (SEQ ID NO: 101) |
| [12,] | hsa-miR-766_st | 0.33 | GCTGAGGCTGTGGGGCTGGAGT (SEQ ID NO: 1) |
| [13,] | hsa-miR-768-5p_st | 0.31 | ATCACTCCGTACTTTCATCCTCCAA (SEQ ID NO: 83) |

TABLE 14

Ara-C (Cytarabine hydrochloride) microRNA biomarkers.

| | Medianprobe | Corr | Sequence |
|---|---|---|---|
| [1,] | HBII-202_st | 0.4 | TTCATCAAGGCCGTACAGCGATTCC (SEQ ID NO: 113) |
| [2,] | HBII-438A_s_st | 0.33 | AGCATCCTCAGACAATTATTCTCAT (SEQ ID NO: 114) |
| [3,] | HBII-85-11_st | 0.3 | TGTTCAACTTTCCAAGGAACCCACG (SEQ ID NO: 115) |
| [4,] | U104_st | 0.36 | GGCAGGCTCAGACTCCAGTTCGCAT (SEQ ID NO: 116) |
| [5,] | U17b_st | 0.31 | CGAGGCCCAGCTTCATCTTCAACGT (SEQ ID NO: 117) |
| [6,] | U17b_x_st | 0.3 | ACGAGGCCCAGCTTCATCTTCAACG (SEQ ID NO: 59) |
| [7,] | U48_st | 0.31 | GGTGATGGCATCAGCGACACACTCA (SEQ ID NO: 118) |
| [8,] | U78_s_st | 0.34 | CATGCTCATTTCAGGTCAGACATTT (SEQ ID NO: 119) |
| [9,] | U78_x_st | 0.31 | TTTGTCTACATGCTCATTTCAGGTC (SEQ ID NO: 120) |
| [10,] | hsa-miR-181a-star_st | 0.42 | GGTACAATCAACGGTCGATGGT (SEQ ID NO: 9) |
| [11,] | hsa-miR-181b_st | 0.32 | ACCCACCGACAGCAATGAATGTT (SEQ ID NO: 10) |
| [12,] | hsa-miR-342-3p_st | 0.34 | ACGGGTGCGATTTCTGTGTGAGA (SEQ ID NO: 11) |
| [13,] | hsa-miR-424-star_st | 0.3 | ATAGCAGCGCCTCACGTTTTG (SEQ ID NO: 100) |

TABLE 15

Methylprednisolone microRNA biomarkers.

| | Medianprobe | Corr | Sequence |
|---|---|---|---|
| [1,] | ACA23_st | 0.31 | GCCAGTGGTAGATGTGTCCAGAGAC (SEQ ID NO: 121) |
| [2,] | ACA24_x_st | 0.37 | CAAGGATATGCTCTTCCATGGCTAG (SEQ ID NO: 122) |

TABLE 15-continued

Methylprednisolone microRNA biomarkers.

| | Medianprobe | Corr | Sequence |
|---|---|---|---|
| [3,] | ACA54_st | 0.31 | GTCATGTGTCGCTGGAAATGCTATT (SEQ ID NO: 123) |
| [4,] | U31_st | 0.3 | AATACCTTTCAGTCACACATTGATC (SEQ ID NO: 124) |
| [5,] | hsa-let-7d-star_st | 0.34 | AGAAAGGCAGCAGGTCGTATAG (SEQ ID NO: 125) |
| [6,] | hsa-miR-106b-star_st | 0.36 | GCAGCAAGTACCCACAGTGCGG (SEQ ID NO: 2) |
| [7,] | hsa-miR-1183_st | 0.41 | TGCCCACTCTCACCATCACCTACAG (SEQ ID NO: 126) |
| [8,] | hsa-miR-1207-5p_st | 0.5 | CCCCTCCCAGCCTCCCTGCCA (SEQ ID NO: 109) |
| [9,] | hsa-miR-1268_st | 0.34 | CCCCCACCACCACGCCCG (SEQ ID NO: 127) |
| [10,] | hsa-miR-1281_st | 0.41 | GGGAGAGGAGGAGGCGA (SEQ ID NO: 8) |
| [11,] | hsa-miR-128_st | 0.45 | AAAGAGACCGGTTCACTGTGA (SEQ ID NO: 110) |
| [12,] | hsa-miR-150_st | 0.33 | CACTGGTACAAGGGTTGGGAGA (SEQ ID NO: 111) |
| [13,] | hsa-miR-15a_st | 0.38 | CACAAACCATTATGTGCTGCTA (SEQ ID NO: 128) |
| [14,] | hsa-miR-181a-star_st | 0.38 | GGTACAATCAACGGTCGATGGT (SEQ ID NO: 9) |
| [15,] | hsa-miR-181c_st | 0.37 | ACTCACCGACAGGTTGAATGTT (SEQ ID NO: 79) |
| [16,] | hsa-miR-18b_st | 0.31 | CTAACTGCACTAGATGCACCTTA (SEQ ID NO: 87) |
| [17,] | hsa-miR-198_st | 0.31 | GAACCTATCTCCCCTCTGGACC (SEQ ID NO: 129) |
| [18,] | hsa-miR-20b-star_st | 0.49 | CTGGAAGTGCCCATACTACAGT (SEQ ID NO: 130) |
| [19,] | hsa-miR-223_st | 0.38 | TGGGGTATTTGACAAACTGACA (SEQ ID NO: 131) |
| [20,] | hsa-miR-297_st | 0.34 | CATGCACATGCACACATACAT (SEQ ID NO: 132) |
| [21,] | hsa-miR-342-5p_st | 0.44 | TCAATCACAGATAGCACCCCT (SEQ ID NO: 80) |
| [22,] | hsa-miR-363_st | 0.38 | TACAGATGGATACCGTGCAATT (SEQ ID NO: 133) |
| [23,] | hsa-miR-588_st | 0.31 | GTTCTAACCCATTGTGGCCAA (SEQ ID NO: 134) |
| [24,] | hsa-miR-631_st | 0.41 | GCTGAGGTCTGGGCCAGGTCT (SEQ ID NO: 135) |
| [25,] | hsa-miR-766_st | 0.49 | GCTGAGGCTGTGGGGCTGGAGT (SEQ ID NO: 1) |
| [26,] | hsa-miR-768-5p_st | 0.32 | ATCACTCCGTACTTTCATCCTCCAA (SEQ ID NO: 83) |
| [27,] | hsa-miR-92a-2-star_st | 0.44 | GTAATGCAACAAATCCCCACCC (SEQ ID NO: 136) |
| [28,] | hsa-miR-940_st | 0.34 | GGGGAGCGGGGGCCCTGCCTT (SEQ ID NO: 137) |

TABLE 16

Methotrexate microRNA biomarkers.

| | Medianprobe | Corr | Sequence |
|---|---|---|---|
| [1,] | ACA10_s_st | 0.3 | CACTCCTAGGAACAGAGAGGCCATT (SEQ ID NO: 138) |
| [2,] | ACA18_x_st | 0.31 | GCGTTTCCAACGATGTGCAGGCTAC (SEQ ID NO: 139) |
| [3,] | HBII-202_st | 0.35 | TTCATCAAGGCCGTACAGCGATTCC (SEQ ID NO: 113) |
| [4,] | U104_st | 0.37 | TTTAATTGGAATGTCATCACAGCAG (SEQ ID NO: 140) |
| [5,] | U17b_st | 0.34 | CGAGGCCCAGCTTCATCTTCAACGT (SEQ ID NO: 117) |
| [6,] | U30_st | 0.34 | GTCATCAGCCGAACGAGATTCCATG (SEQ ID NO: 141) |
| [7,] | U31_x_st | 0.31 | GAAAATACCTTTCAGTCACACATTG (SEQ ID NO: 142) |
| [8,] | U49A_st | 0.31 | TTCCTATTAGTGATTTCATCAGAGC (SEQ ID NO: 143) |
| [9,] | U49A_x_st | 0.32 | GGAGTAGTCTTCGTCAGTTATCGCT (SEQ ID NO: 144) |
| [10,] | U49B_s_st | 0.33 | GTTATCGCTTCTGACGGCACTTCCT (SEQ ID NO: 145) |
| [11,] | U55_st | 0.34 | GAGTATGCAGCATTACCGAGTTGTC (SEQ ID NO: 146) |
| [12,] | U55_x_st | 0.33 | GAGTATGCAGCATTACCGAGTTGTC (SEQ ID NO: 146) |
| [13,] | U56_st | 0.31 | GAGTCTCAACACTCACTAGGTGAAC (SEQ ID NO: 147) |
| [14,] | U67_st | 0.36 | TGAGAGGCACTGATGTCCCCTTGGA (SEQ ID NO: 148) |
| [15,] | U67_x_st | 0.3 | CAGTTCCCCAAAGGCCTTAGGCATG (SEQ ID NO: 149) |
| [16,] | hsa-miR-106a_st | 0.33 | CTACCTGCACTGTAAGCACTTTT (SEQ ID NO: 150) |
| [17,] | hsa-miR-1254_st | 0.31 | ACTGCAGGCTCCAGCTTCCAGGCT (SEQ ID NO: 151) |
| [18,] | hsa-miR-1275_st | 0.31 | GACAGCCTCTCCCCCAC (SEQ ID NO: 70) |
| [19,] | hsa-miR-17_st | 0.35 | CTACCTGCACTGTAAGCACTTTG (SEQ ID NO: 152) |
| [20,] | hsa-miR-18a-star_st | 0.36 | CCAGAAGGAGCACTTAGGGCAGT (SEQ ID NO: 71) |

TABLE 16-continued

Methotrexate microRNA biomarkers.

| Medianprobe | Corr | Sequence |
|---|---|---|
| [21,] hsa-miR-18a_st | 0.35 | CTATCTGCACTAGATGCACCTTA (SEQ ID NO: 72) |
| [22,] hsa-miR-19b_st | 0.32 | TCAGTTTTGCATGGATTTGCACA (SEQ ID NO: 153) |
| [23,] hsa-miR-25-star_st | 0.3 | CAATTGCCCAAGTCTCCGCCT (SEQ ID NO: 3) |
| [24,] hsa-miR-297_st | 0.31 | CATGCACATGCACACATACAT (SEQ ID NO: 132) |
| [25,] hsa-miR-34b_st | 0.31 | ATGGCAGTGGAGTTAGTGATTG (SEQ ID NO: 154) |
| [26,] hsa-miR-663b_st | 0.38 | CCTCAGGCACGGCCGGGCCACC (SEQ ID NO: 155) |
| [27,] hsa-miR-92a_st | 0.33 | ACAGGCCGGGACAAGTGCAATA (SEQ ID NO: 156) |

TABLE 17

Bleomycin microRNA biomarkers.

| Medianprobe | Corr | Sequence |
|---|---|---|
| [1,] 14qII-14_st | 0.41 | ACCCAACACTCATACGCCGGCAGTT (SEQ ID NO: 157) |
| [2,] 14qII-14_x_st | 0.4 | ATACGCCGGCAGTTGTCATCATTGG (SEQ ID NO: 158) |
| [3,] 14qII-1_st | 0.38 | TCAGACTTCCAGACCTGTATTCACC (SEQ ID NO: 159) |
| [4,] 14qII-1_x_st | 0.32 | TGGACCTCAGACTTCCAGACCTGTA (SEQ ID NO: 74) |
| [5,] 14qII-26_st | 0.43 | TGTGACTCATACTCCACCAGTGCTC (SEQ ID NO: 160) |
| [6,] 14qII-26_x_st | 0.4 | ATCGTATGTGACTCATACTCCACCA (SEQ ID NO: 161) |
| [7,] 14qII-3_st | 0.33 | CAGACACGTAGTATTCATCGTCCAT (SEQ ID NO: 162) |
| [8,] hsa-miR-125b-1-star_st | 0.32 | AGCTCCCAAGAGCCTAACCCGT (SEQ ID NO: 163) |
| [9,] hsa-miR-127-3p_st | 0.41 | AGCCAAGCTCAGACGGATCCGA (SEQ ID NO: 77) |
| [10,] hsa-miR-1271_st | 0.32 | TGAGTGCTTGCTAGGTGCCAAG (SEQ ID NO: 30) |
| [11,] hsa-miR-134_st | 0.34 | CCCCTCTGGTCAACCAGTCACA (SEQ ID NO: 164) |
| [12,] hsa-miR-155_st | 0.37 | ACCCCTATCACGATTAGCATTAA (SEQ ID NO: 20) |
| [13,] hsa-miR-193a-5p_st | 0.32 | TCATCTCGCCCGCAAAGACCCA (SEQ ID NO: 165) |
| [14,] hsa-miR-21-star_st | 0.39 | ACAGCCCATCGACTGGTGTTG (SEQ ID NO: 166) |
| [15,] hsa-miR-22_st | 0.31 | ACAGTTCTTCAACTGGCAGCTT (SEQ ID NO: 167) |

TABLE 17-continued

Bleomycin microRNA biomarkers.

| Medianprobe | Corr | Sequence |
|---|---|---|
| [16,] hsa-miR-299-3p_st | 0.34 | AAGCGGTTTACCATCCCACATA (SEQ ID NO: 168) |
| [17,] hsa-miR-337-5p_st | 0.3 | AACTCCTGTATGAAGCCGTTC (SEQ ID NO: 169) |
| [18,] hsa-miR-370_st | 0.35 | ACCAGGTTCCACCCCAGCAGGC (SEQ ID NO: 32) |
| [19,] hsa-miR-376c_st | 0.3 | ACGTGGAATTTCCTCTATGTT (SEQ ID NO: 170) |
| [20,] hsa-miR-377-star_st | 0.37 | GAATTCACCAAGGGCAACCTCT (SEQ ID NO: 171) |
| [21,] hsa-miR-379_st | 0.36 | CCTACGTTCCATAGTCTACCA (SEQ ID NO: 172) |
| [22,] hsa-miR-381_st | 0.4 | ACAGAGAGCTTGCCCTTGTATA (SEQ ID NO: 173) |
| [23,] hsa-miR-382_st | 0.32 | CGAATCCACCACGAACAACTTC (SEQ ID NO: 174) |
| [24,] hsa-miR-409-3p_st | 0.36 | AGGGGTTCACCGAGCAACATTC (SEQ ID NO: 81) |
| [25,] hsa-miR-409-5p_st | 0.35 | ATGCAAAGTTCCTCGGGTAACCT (SEQ ID NO: 175) |
| [26,] hsa-miR-411_st | 0.39 | CGTACGCTATACGGTCTACTA (SEQ ID NO: 176) |
| [27,] hsa-miR-431_st | 0.32 | TGCATGACGGCCTGCAAGACA (SEQ ID NO: 177) |
| [28,] hsa-miR-455-3p_st | 0.41 | GTGTATATGCCCATGGACTGC (SEQ ID NO: 178) |
| [29,] hsa-miR-485-5p_st | 0.34 | GAATTCATCACGGCCAGCCTCT (SEQ ID NO: 179) |
| [30,] hsa-miR-487b_st | 0.37 | AAGTGGATGACCCTGTACGATT (SEQ ID NO: 82) |
| [31,] hsa-miR-493_st | 0.34 | CCTGGCACACAGTAGACCTTCA (SEQ ID NO: 180) |
| [32,] hsa-miR-494_st | 0.39 | GAGGTTTCCCGTGTATGTTTCA (SEQ ID NO: 181) |
| [33,] hsa-miR-543_st | 0.33 | AAGAAGTGCACCGCGAATGTTT (SEQ ID NO: 182) |
| [34,] hsa-miR-663_st | 0.3 | GCGGTCCCGCGGCGCCCCGCCT (SEQ ID NO: 28) |
| [35,] hsa-miR-671-5p_st | 0.32 | CTCCAGCCCCTCCAGGGCTTCCT (SEQ ID NO: 43) |
| [36,] hsa-miR-758_st | 0.33 | GGTTAGTGGACCAGGTCACAAA (SEQ ID NO: 35) |

TABLE 18

Methyl-GAG (methyl glyoxal bis amidinohydrazone dihydrochloride) microRNA biomarkers.

| Medianprobe | Corr | Sequence |
|---|---|---|
| [1,] ENSG00000200879_st | 0.34 | GCGAATGTTTTGGACCATTCATCAT (SEQ ID NO: 183) |

TABLE 18-continued

Methyl-GAG (methyl glyoxal bis amidinohydrazone dihydrochloride) microRNA biomarkers.

| | Medianprobe | Corr | Sequence |
|---|---|---|---|
| [2,] | ENSG00000202252_st | 0.34 | AAGGAAGGTGTTGCCATCATTAGCC (SEQ ID NO: 184) |
| [3,] | HBII-202_st | 0.31 | AGGCCGTACAGCGATTCCGGAGAAT (SEQ ID NO: 185) |
| [4,] | U25_st | 0.34 | GTCTGTGAAAAGGTCCTCATCATAG (SEQ ID NO: 186) |
| [5,] | U26_st | 0.35 | TCCACTAATCCATCAGAAAGAGAGA (SEQ ID NO: 187) |
| [6,] | U28_x_st | 0.3 | ACTTTTGTACCTCACAGAACATCAG (SEQ ID NO: 188) |
| [7,] | U29_st | 0.32 | TTCTCAGGTGTTCATGTATTTTCAC (SEQ ID NO: 189) |
| [8,] | U30_st | 0.31 | GTCATCAGCCGAACGAGATTCATG (SEQ ID NO: 141) |
| [9,] | U31_x_st | 0.3 | CAGCTCAGAAAATACCTTTCAGTCA (SEQ ID NO: 190) |
| [10,] | U74_x_st | 0.3 | TTCATCATTACTCTCAGATGTCCCT (SEQ ID NO: 191) |
| [11,] | hsa-miR-181a-star_st | 0.34 | GGTACAATCAACGGTCGATGGT (SEQ ID NO: 9) |
| [12,] | hsa-miR-297_st | 0.31 | CATGCACATGCACACATACAT (SEQ ID NO: 132) |
| [13,] | hsa-miR-34b_st | 0.32 | ATGGCAGTGGAGTTAGTGATTG (SEQ ID NO: 154) |
| [14,] | hsa-miR-92a-1-star_st | 0.31 | AGCATTGCAACCGATCCCAACCT (SEQ ID NO: 192) |

TABLE 19

Belinostat (PXD101) microRNA biomarkers.

| | Medianprobe | Corr | Sequence |
|---|---|---|---|
| [1,] | ACA18_x_st | 0.32 | TCTTGTAATTCCTTCCCACAGATCT (SEQ ID NO: 193) |
| [2,] | ACA51_x_st | 0.32 | TGGGGTAGGTTTACTCTACCTCCTC (SEQ ID NO: 194) |
| [3,] | ACA9_st | 0.33 | AATGCATAGGGTCACCGCAGACCCA (SEQ ID NO: 195) |
| [4,] | ACA9_x_st | 0.33 | ATAGGGTCACCGCAGACCCAAGCAC (SEQ ID NO: 196) |
| [5,] | HBII-180A_x_st | 0.32 | ACCGTGTCCTCAGTGGCAGTCGGAG (SEQ ID NO: 197) |
| [6,] | HBII-202_st | 0.33 | ACAGCGATTCCGGAGAATGTCATCA (SEQ ID NO: 198) |
| [7,] | HBII-336_st | 0.37 | GTAAATCCTTTAATCCATCACAGCA (SEQ ID NO: 199) |
| [8,] | HBII-55_st | 0.37 | GTGATTGCACTCAGGGGATTGACAG (SEQ ID NO: 200) |
| [9,] | U104_st | 0.4 | GCGTCAGCAGTCTAACACGTGCTTT (SEQ ID NO: 201) |

TABLE 19-continued

Belinostat (PXD101) microRNA biomarkers.

| | Medianprobe | Corr | Sequence |
|---|---|---|---|
| [10,] | U27_st | 0.36 | TGTCATTTTGTGTTCATCATGGAGT (SEQ ID NO: 202) |
| [11,] | U29_st | 0.34 | GAGCTAGTTTGATTCATCATAGAAA (SEQ ID NO: 203) |
| [12,] | U30_st | 0.32 | CAGCCGAACGAGATTCCATGTAAGT (SEQ ID NO: 204) |
| [13,] | U31_st | 0.32 | GCTCAGAAAATACCTTTCAGTCACA (SEQ ID NO: 205) |
| [14,] | U31_x_st | 0.31 | CCTTTCAGTCACACATTGATCAGAC (SEQ ID NO: 206) |
| [15,] | U38A_st | 0.33 | TCTCTCTCCCTTCAGTAGCAGAACT (SEQ ID NO: 207) |
| [16,] | U55_st | 0.35 | TTCCCCACCGCGCACTCGGGAGTAT (SEQ ID NO: 208) |
| [17,] | U55_x_st | 0.36 | CCACCGCGCACTCGGGAGTATGCAG (SEQ ID NO: 209) |
| [18,] | U56_st | 0.32 | ACCCAGAGTCTCAACACTCACTAGG (SEQ ID NO: 210) |
| [19,] | U56_x_st | 0.37 | CACTAGGTGAACTGCTGTTGACGAA (SEQ ID NO: 211) |
| [20,] | U57_st | 0.33 | TTCTACAAGGTCAGGCTCAGACAGT (SEQ ID NO: 212) |
| [21,] | U60_st | 0.33 | TACGAGGTGTCAGAAGTCAAAGCAA (SEQ ID NO: 213) |
| [22,] | U74_x_st | 0.35 | TTCATCATTACTCTCAGATGTCCCT (SEQ ID NO: 191) |
| [23,] | hsa-miR-106a_st | 0.48 | CTACCTGCACTGTAAGCACTTTT (SEQ ID NO: 150) |
| [24,] | hsa-miR-1183_st | 0.32 | TGCCCACTCTCACCATCACCTACAG (SEQ ID NO: 126) |
| [25,] | hsa-miR-1207-5p_st | 0.34 | CCCCTCCCAGCCTCCCTGCCA (SEQ ID NO: 109) |
| [26,] | hsa-miR-1246_st | 0.38 | CCTGCTCCAAAAATCCATT (SEQ ID NO: 214) |
| [27,] | hsa-miR-1268_st | 0.33 | CCCCCACCACCACGCCCG (SEQ ID NO: 127) |
| [28,] | hsa-miR-1299_st | 0.39 | TCCCTCACACAGAATTCCAGAA (SEQ ID NO: 38) |
| [29,] | hsa-miR-1307_st | 0.3 | CACGACCGACGCCACGCCGAGT (SEQ ID NO: 102) |
| [30,] | hsa-miR-142-5p_st | 0.31 | AGTAGTGCTTTCTACTTTATG (SEQ ID NO: 215) |
| [31,] | hsa-miR-17-star_st | 0.43 | CTACAAGTGCCTTCACTGCAGT (SEQ ID NO: 216) |
| [32,] | hsa-miR-17_st | 0.49 | CTACCTGCACTGTAAGCACTTTG (SEQ ID NO: 152) |
| [33,] | hsa-miR-18a-star_st | 0.45 | CCAGAAGGAGCACTTAGGGCAGT (SEQ ID NO: 71) |
| [34,] | hsa-miR-18a_st | 0.55 | CTATCTGCACTAGATGCACCTTA (SEQ ID NO: 72) |

TABLE 19-continued

Belinostat (PXD101) microRNA biomarkers.

| | Medianprobe | Corr | Sequence |
|---|---|---|---|
| [35,] | hsa-miR-18b_st | 0.48 | CTAACTGCACTAGATGCACCTTA (SEQ ID NO: 87) |
| [36,] | hsa-miR-195-star_st | 0.32 | GGAGCAGCACAGCCAATATTGG (SEQ ID NO: 14) |
| [37,] | hsa-miR-19a_st | 0.49 | TCAGTTTTGCATAGATTTGCACA (SEQ ID NO: 217) |
| [38,] | hsa-miR-19b_st | 0.56 | TCAGTTTTGCATGGATTTGCACA (SEQ ID NO: 153) |
| [39,] | hsa-miR-20a_st | 0.46 | CTACCTGCACTATAAGCACTTTA (SEQ ID NO: 218) |
| [40,] | hsa-miR-20b_st | 0.31 | CTACCTGCACTATGAGCACTTTG (SEQ ID NO: 88) |
| [41,] | hsa-miR-297_st | 0.38 | CATGCACATGCACACATACAT (SEQ ID NO: 132) |
| [42,] | hsa-miR-330-3p_st | 0.37 | TCTCTGCAGGCCGTGTGCTTTGC (SEQ ID NO: 219) |
| [43,] | hsa-miR-346_st | 0.33 | AGAGGCAGGCATGCGGGCAGACA (SEQ ID NO: 220) |
| [44,] | hsa-miR-34b_st | 0.41 | ATGGCAGTGGAGTTAGTGATTG (SEQ ID NO: 154) |
| [45,] | hsa-miR-595_st | 0.31 | AGACACACCACGGCACACTTC (SEQ ID NO: 221) |
| [46,] | hsa-miR-629-star_st | 0.32 | GCTGGGCTTACGTTGGGAGAAC (SEQ ID NO: 41) |
| [47,] | hsa-miR-647_st | 0.31 | GAAGGAAGTGAGTGCAGCCAC (SEQ ID NO: 222) |
| [48,] | hsa-miR-766_st | 0.41 | GCTGAGGCTGTGGGGCTGGAGT (SEQ ID NO: 1) |
| [49,] | hsa-miR-768-5p_st | 0.32 | ATCACTCCGTACTTTCATCCTCCAA (SEQ ID NO: 83) |
| [50,] | hsa-miR-92a_st | 0.48 | ACAGGCCGGGACAAGTGCAATA (SEQ ID NO: 156) |

TABLE 20

5-Fluorouracil microRNA biomarkers.

| | Medianprobe | Corr | Sequence |
|---|---|---|---|
| [1,] | ACA10_s_st | 0.34 | TTCTGGGCGGGTCTGTCGTGCATTA (SEQ ID NO: 223) |
| [2,] | ENSG00000199411_s_st | 0.31 | TCACTGTCCTCTTCATCTCCCTGCT (SEQ ID NO: 224) |
| [3,] | U104_st | 0.4 | GCGTCAGCAGTCTAACACGTGCTTT (SEQ ID NO: 201) |
| [4,] | U13_st | 0.34 | AGACGGGTAATGTGCCCACGTCGTA (SEQ ID NO: 225) |
| [5,] | U36A_x_st | 0.31 | CGCACTTCAAGGTTGAATTCAGTGA (SEQ ID NO: 226) |

TABLE 20-continued

5-Fluorouracil microRNA biomarkers.

| | Medianprobe | Corr | Sequence |
|---|---|---|---|
| [6,] | U36C_st | 0.31 | GCCTCAGATGCAATGCTGACCACAT (SEQ ID NO: 227) |
| [7,] | U74_x_st | 0.41 | CGGTTGGCATTCATCATTACTCTCA (SEQ ID NO: 69) |
| [8,] | U78_x_st | 0.31 | ACCTTTGTCTACATGCTCATTTCAG (SEQ ID NO: 228) |
| [9,] | U8_x_st | 0.34 | CTAATCTGCCCTCCGGAGGAGGAAC (SEQ ID NO: 229) |
| [10,] | hsa-miR-1246_st | 0.3 | CCTGCTCCAAAAATCCATT (SEQ ID NO: 214) |
| [11,] | hsa-miR-194-star_st | 0.32 | CAGATAACAGCAGCCCCACTGG (SEQ ID NO: 230) |
| [12,] | hsa-miR-200c-star_st | 0.33 | CCAAACACTGCTGGGTAAGACG (SEQ ID NO: 231) |
| [13,] | hsa-miR-34b_st | 0.32 | ATGGCAGTGGAGTTAGTGATTG (SEQ ID NO: 154) |
| [14,] | hsa-miR-768-3p_st | 0.32 | GTCAGCAGTTTGAGTGTCAGCATTG (SEQ ID NO: 44) |

TABLE 21

Radiation microRNA biomarkers.

| | Medianprobe | Corr | Sequence |
|---|---|---|---|
| [1,] | hsa-let-7i-star_st | 0.4 | AGCAAGGCAGTAGCTTGCGCAG (SEQ ID NO: 232) |
| [2,] | hsa-miR-338-3p_st | 0.31 | CAACAAAATCACTGATGCTGGA (SEQ ID NO: 233) |
| [3,] | hsa-miR-34a_st | 0.37 | ACAACCAGCTAAGACACTGCCA (SEQ ID NO: 234) |

TABLE 22

5-Aza-2'-deoxycytidine(decitabine) microRNA biomarkers.

| | Medianprobe | Corr | Sequence |
|---|---|---|---|
| [1,] | hsa-miR-106a_st | 0.31 | CTACCTGCACTGTAAGCACTTTT (SEQ ID NO: 150) |
| [2,] | hsa-miR-106b-star_st | 0.32 | GCAGCAAGTACCCACAGTGCGG (SEQ ID NO: 2) |
| [3,] | hsa-miR-1183_st | 0.32 | TGCCCACTCTCACCATCACCTACAG (SEQ ID NO: 126) |
| [4,] | hsa-miR-195-star_st | 0.36 | GGAGCAGCACAGCCAATATTGG (SEQ ID NO: 14) |
| [5,] | hsa-miR-297_st | 0.31 | CATGCACATGCACACATACAT (SEQ ID NO: 132) |

TABLE 22-continued

5-Aza-2'-deoxycytidine(decitabine) microRNA biomarkers.

| | Medianprobe | Corr | Sequence |
|---|---|---|---|
| [6,] | hsa-miR-324-3p_st | 0.41 | CCAGCAGCACCTGGGGCAGT (SEQ ID NO: 235) |
| [7,] | hsa-miR-34b_st | 0.34 | ATGGCAGTGGAGTTAGTGATTG (SEQ ID NO: 154) |
| [8,] | hsa-miR-371-5p_st | 0.33 | AGTGCCCCCACAGTTTGAGT (SEQ ID NO: 236) |
| [9,] | hsa-miR-766_st | 0.37 | GCTGAGGCTGTGGGGCTGGAGT (SEQ ID NO: 1) |
| [10,] | hsa-miR-92a_st | 0.33 | ACAGGCCGGGACAAGTGCAATA (SEQ ID NO: 156) |
| [11,] | hsa-miR-93-star_st | 0.31 | CGGGAAGTGCTAGCTCAGCAGT (SEQ ID NO: 45) |

TABLE 23

Idarubicin microRNA biomarkers.

| | Medianprobe | Corr | Sequence |
|---|---|---|---|
| [1,] | ACA41_x_st | 0.34 | ATACCCACTTTCTGTTTTGCTAAGA (SEQ ID NO: 237) |
| [2,] | ACA48_x_st | 0.35 | GGGCACGGATCAAAAGCCAAGCTGG (SEQ ID NO: 238) |
| [3,] | HBII-202_st | 0.32 | GCGATTCCGGAGAATGTCATCACGC (SEQ ID NO: 239) |
| [4,] | HBII-429_st | 0.3 | GAGGGAGCCAGTTGTCATCATGTAC (SEQ ID NO: 240) |
| [5,] | U104_st | 0.39 | TTTAATTGGAATGTCATCACAGCAG (SEQ ID NO: 140) |

TABLE 23-continued

Idarubicin microRNA biomarkers.

| | Medianprobe | Corr | Sequence |
|---|---|---|---|
| [6,] | U49A_st | 0.3 | AGGAGTAGTCTTCGTCAGTTATCGC (SEQ ID NO: 63) |
| [7,] | U49B_s_st | 0.32 | GTTATCGCTTCTGACGGCACTTCCT (SEQ ID NO: 145) |
| [8,] | U55_st | 0.38 | GCACTCGGGAGTATGCAGCATTACC (SEQ ID NO: 6) |
| [9,] | U55_x_st | 0.38 | CGGGAGTATGCAGCATTACCGAGTT (SEQ ID NO: 241) |
| [10,] | U74_x_st | 0.33 | ACCATCAGAGCGGTTGGCATTCATC (SEQ ID NO: 242) |
| [11,] | hsa-miR-124_st | 0.44 | GGCATTCACCGCGTGCCTTA (SEQ ID NO: 7) |
| [12,] | hsa-miR-1299_st | 0.3 | TCCCTCACACAGAATTCCAGAA (SEQ ID NO: 38) |
| [13,] | hsa-miR-181a-star_st | 0.35 | GGTACAATCAACGGTCGATGGT (SEQ ID NO: 9) |
| [14,] | hsa-miR-297_st | 0.31 | CATGCACATGCACACATACAT (SEQ ID NO: 132) |
| [15,] | hsa-miR-342-5p_st | 0.37 | TCAATCACAGATAGCACCCCT (SEQ ID NO: 80) |
| [16,] | hsa-miR-34b_st | 0.32 | ATGGCAGTGGAGTTAGTGATTG (SEQ ID NO: 154) |
| [17,] | hsa-miR-631_st | 0.3 | GCTGAGGTCTGGGCCAGGTCT (SEQ ID NO: 135) |
| [18,] | hsa-miR-768-3p_st | 0.34 | GTCAGCAGTTTGAGTGTCAGCATTG (SEQ ID NO: 44) |
| [19,] | hsa-miR-768-5p_st | 0.33 | ATCACTCCGTACTTTCATCCTCCAA (SEQ ID NO: 83) |

TABLE 24

Melphalan microRNA biomarkers.

| | Medianprobe | Corr | Sequence |
|---|---|---|---|
| [1,] | ACA7_s_st | 0.43 | ATGGGTGCCTCTGCCAGGCTTGCTT (SEQ ID NO: 243) |
| [2,] | ENSG00000202252_st | 0.35 | ACATCCAAGGAAGGTGTTGCCATCA (SEQ ID NO: 244) |
| [3,] | ENSG00000207002_x_st | 0.3 | TGCCTACACAGGCAGGGCAGGCACC (SEQ ID NO: 245) |
| [4,] | HBII-202_st | 0.35 | TTCATCAAGGCCGTACAGCGATTCC (SEQ ID NO: 113) |
| [5,] | HBII-429_st | 0.36 | GTTTCCTCATGGCAGTTCAGTAGAG (SEQ ID NO: 246) |
| [6,] | HBII-438A_s_st | 0.36 | ATCCTCAGACAATTATTCTCATCAT (SEQ ID NO: 247) |
| [7,] | HBII-55_st | 0.31 | TGCACTCAGGGGATTGACAGATTTG (SEQ ID NO: 248) |
| [8,] | HBII-85-11_st | 0.34 | TCCAAGGAACCCACGTATGGAAGTC (SEQ ID NO: 249) |

TABLE 24-continued

Melphalan microRNA biomarkers.

| | Medianprobe | Corr | Sequence |
|---|---|---|---|
| [9,] | HBII-85-23_x_st | 0.33 | AAGGAATGCATGTATTGAGGTCATC (SEQ ID NO: 250) |
| [10,] | HBII-85-26_st | 0.31 | TCCATTTTTTTATAGTCATCATCG (SEQ ID NO: 251) |
| [11,] | HBII-85-2_x_st | 0.34 | ACCTCAGTTCCGATGAGAATGACGG (SEQ ID NO: 252) |
| [12,] | HBII-85-6_x_st | 0.31 | TGTTTTTTTGGAGGACTCATCATC (SEQ ID NO: 253) |
| [13,] | U104_st | 0.41 | TTTAATTGGAATGTCATCACAGCAG (SEQ ID NO: 140) |
| [14,] | U13_st | 0.31 | AGACGGGTAATGTGCCCACGTCGTA (SEQ ID NO: 225) |
| [15,] | U17b_st | 0.38 | GGCCCAGCTTCATCTTCAACGTTGT (SEQ ID NO: 254) |
| [16,] | U17b_x_st | 0.35 | ACGAGGCCCAGCTTCATCTTCAACG (SEQ ID NO: 59) |
| [17,] | U33_st | 0.3 | GTCATCTCATGGTCGGGAAACTCGA (SEQ ID NO: 255) |
| [18,] | U34_st | 0.33 | TAGGTAGTTGCGGAACATCATGGAC (SEQ ID NO: 256) |
| [19,] | U41_st | 0.36 | ATCAGTTCCACATCAACAGTCACAG (SEQ ID NO: 257) |
| [20,] | U52_st | 0.38 | GTTTTGACATCATGACCAGCATCGG (SEQ ID NO: 258) |
| [21,] | U55_st | 0.37 | TATGCAGCATTACCGAGTTGTCATC (SEQ ID NO: 259) |
| [22,] | U55_x_st | 0.39 | GCTCAGCTCTCCAAGGTTGGCTTCC (SEQ ID NO: 260) |
| [23,] | U56_st | 0.33 | AGACCCAGAGTCTCAACACTCACTA (SEQ ID NO: 261) |
| [24,] | U57_st | 0.37 | TTTTGCCTCCATTCTACAAGGTCAG (SEQ ID NO: 262) |
| [25,] | U68_st | 0.3 | GTTGTGGAACCTCCAAATTCACTTT (SEQ ID NO: 263) |
| [26,] | U74_x_st | 0.38 | AGAGCGGTTGGCATTCATCATTACT (SEQ ID NO: 264) |
| [27,] | U78_s_st | 0.31 | ATGCTCATTTCAGGTCAGACATTTG (SEQ ID NO: 265) |
| [28,] | U78_x_st | 0.31 | CTTCAGTGTTACCTTTGTCTACATG (SEQ ID NO: 266) |
| [29,] | U83_st | 0.31 | TGAGGTGCTCCTGTTTCAAATAAAC (SEQ ID NO: 267) |
| [30,] | U95_st | 0.33 | AGCCTCTGGATTTCAGCACCGACAC (SEQ ID NO: 268) |
| [31,] | hsa-miR-1183_st | 0.35 | TGCCCACTCTCACCATCACCTACAG (SEQ ID NO: 126) |
| [32,] | hsa-miR-1207-5p_st | 0.38 | CCCCTCCCAGCCTCCCTGCCA (SEQ ID NO: 109) |
| [33,] | hsa-miR-1228_st | 0.32 | GGGGGGCGAGGCAGGTGTGA (SEQ ID NO: 84) |

TABLE 24-continued

Melphalan microRNA biomarkers.

| | Medianprobe | Corr | Sequence |
|---|---|---|---|
| [34,] | hsa-miR-124_st | 0.38 | GGCATTCACCGCGTGCCTTA (SEQ ID NO: 7) |
| [35,] | hsa-miR-1281_st | 0.44 | GGGAGAGGAGGAGGCGA (SEQ ID NO: 8) |
| [36,] | hsa-miR-1299_st | 0.45 | TCCCTCACACAGAATTCCAGAA (SEQ ID NO: 38) |
| [37,] | hsa-miR-140-3p_st | 0.3 | CCGTGGTTCTACCCTGTGGTA (SEQ ID NO: 13) |
| [38,] | hsa-miR-142-5p_st | 0.4 | AGTAGTGCTTTCTACTTTATG (SEQ ID NO: 215) |
| [39,] | hsa-miR-181a-star_st | 0.53 | GGTACAATCAACGGTCGATGGT (SEQ ID NO: 9) |
| [40,] | hsa-miR-181a_st | 0.37 | ACTCACCGACAGCGTTGAATGTT (SEQ ID NO: 78) |
| [41,] | hsa-miR-181b_st | 0.45 | ACCCACCGACAGCAATGAATGTT (SEQ ID NO: 10) |
| [42,] | hsa-miR-181c_st | 0.42 | ACTCACCGACAGGTTGAATGTT (SEQ ID NO: 79) |
| [43,] | hsa-miR-195-star_st | 0.45 | GGAGCAGCACAGCCAATATTGG (SEQ ID NO: 14) |
| [44,] | hsa-miR-223_st | 0.39 | TGGGGTATTTGACAAACTGACA (SEQ ID NO: 131) |
| [45,] | hsa-miR-297_st | 0.49 | CATGCACATGCACACATACAT (SEQ ID NO: 132) |
| [46,] | hsa-miR-29b-2-star_st | 0.32 | CTAAGCCACCATGTGAAACCAG (SEQ ID NO: 39) |
| [47,] | hsa-miR-342-3p_st | 0.45 | ACGGGTGCGATTTCTGTGTGAGA (SEQ ID NO: 11) |
| [48,] | hsa-miR-342-5p_st | 0.38 | TCAATCACAGATAGCACCCCT (SEQ ID NO: 80) |
| [49,] | hsa-miR-34b_st | 0.48 | ATGGCAGTGGAGTTAGTGATTG (SEQ ID NO: 154) |
| [50,] | hsa-miR-541-star_st | 0.35 | AGTGGGACCGACAGCAGAATCCTTT (SEQ ID NO: 269) |
| [51,] | hsa-miR-610_st | 0.31 | TCCCAGCACACATTTAGCTCA (SEQ ID NO: 270) |
| [52,] | hsa-miR-647_st | 0.32 | GAAGGAAGTGAGTGCAGCCAC (SEQ ID NO: 222) |
| [53,] | hsa-miR-766_st | 0.46 | GCTGAGGCTGTGGGGCTGGAGT (SEQ ID NO: 1) |
| [54,] | hsa-miR-768-3p_st | 0.36 | GTCAGCAGTTTGAGTGTCAGCATTG (SEQ ID NO: 44) |
| [55,] | hsa-miR-768-5p_st | 0.35 | ATCACTCCGTACTTTCATCCTCCAA (SEQ ID NO: 83) |
| [56,] | hsa-miR-885-5p_st | 0.31 | AGAGGCAGGGTAGTGTAATGGA (SEQ ID NO: 271) |

TABLE 25

IL4-PR38 fusion protein microRNA biomarkers.

| | Medianprobe | Corr | Sequence |
|---|---|---|---|
| [1,] | hsa-miR-1246_st | 0.33 | CCTGCTCCAAAAATCCATT (SEQ ID NO: 214) |
| [2,] | hsa-miR-150_st | 0.38 | CACTGGTACAAGGGTTGGGAGA (SEQ ID NO: 111) |
| [3,] | hsa-miR-339-3p_st | 0.38 | CGGCTCTGTCGTCGAGGCGCTCA (SEQ ID NO: 272) |
| [4,] | hsa-miR-339-5p_st | 0.3 | CGTGAGCTCCTGGAGGACAGGGA (SEQ ID NO: 273) |
| [5,] | hsa-miR-768-3p_st | 0.35 | GTCAGCAGTTTGAGTGTCAGCA TTG(SEQ ID NO: 44) |

TABLE 26

Valproic acid (VPA) microRNA biomarkers.

| | Medianprobe | Corr | Sequence |
|---|---|---|---|
| [1,] | hsa-miR-1308_st | 0.26 | CCACTGAACCACCCATGC (SEQ ID NO: 274) |
| [2,] | hsa-miR-148a_st | 0.25 | ACAAAGTTCTGTAGTGCACTGA (SEQ ID NO: 275) |
| [3,] | hsa-miR-152_st | 0.25 | CCAAGTTCTGTCATGCACTGA (SEQ ID NO: 276) |
| [4,] | hsa-miR-34a-star_st | 0.26 | AGGGCAGTATACTTGCTGATTG (SEQ ID NO: 277) |
| [5,] | hsa-miR-34a_st | 0.27 | ACAACCAGCTAAGACACTGCCA (SEQ ID NO: 234) |

TABLE 27

All-trans retinoic acid (ATRA) microRNA biomarkers.

| | Medianprobe | Corr | Sequence |
|---|---|---|---|
| [1,] | HBII-142_st | 0.37 | CATGGTGTCTCAGTGGCCCAGACAC (SEQ ID NO: 278) |
| [2,] | HBII-142_x_st | 0.35 | AGTTCCATCATGGTGTCTCAGTGGC (SEQ ID NO: 279) |
| [3,] | U55_st | 0.3 | GCACTCGGGAGTATGCAGCATTACC (SEQ ID NO: 6) |
| [4,] | U55_x_st | 0.3 | GTATGCAGCATTACCGAGTTGTCAT (SEQ ID NO: 280) |
| [5,] | hsa-miR-1202_st | 0.4 | CTCCCCCACTGCAGCTGGCAC (SEQ ID NO: 281) |
| [6,] | hsa-miR-124_st | 0.34 | GGCATTCACCGCGTGCCTTA (SEQ ID NO: 7) |
| [7,] | hsa-miR-148a-star_st | 0.31 | AGTCGGAGTGTCTCAGAACTTT (SEQ ID NO: 282) |
| [8,] | hsa-miR-148a_st | 0.35 | ACAAAGTTCTGTAGTGCACTGA (SEQ ID NO: 275) |
| [9,] | hsa-miR-184_st | 0.36 | ACCCTTATCAGTTCTCCGTCCA (SEQ ID NO: 283) |
| [10,] | hsa-miR-191_st | 0.32 | CAGCTGCTTTTGGGATTCCGTTG (SEQ ID NO: 284) |

TABLE 27-continued

All-trans retinoic acid (ATRA) microRNA biomarkers.

| | Medianprobe | Corr | Sequence |
|---|---|---|---|
| [11,] | hsa-miR-195-star_st | 0.31 | GGAGCAGCACAGCCAATATTGG (SEQ ID NO: 14) |
| [12,] | hsa-miR-29b-2-star_st | 0.37 | CTAAGCCACCATGTGAAACCAG (SEQ ID NO: 39) |
| [13,] | hsa-miR-425-star_st | 0.32 | GGGCGGACACGACATTCCCGAT (SEQ ID NO: 285) |
| [14,] | hsa-miR-425_st | 0.37 | TCAACGGGAGTGATCGTGTCATT (SEQ ID NO: 286) |
| [15,] | hsa-miR-449a_st | 0.43 | ACCAGCTAACAATACACTGCCA (SEQ ID NO: 287) |
| [16,] | hsa-miR-449b_st | 0.5 | GCCAGCTAACAATACACTGCCT (SEQ ID NO: 288) |
| [17,] | hsa-miR-551b_st | 0.31 | CTGAAACCAAGTATGGGTCGC (SEQ ID NO: 289) |
| [18,] | hsa-miR-593-star_st | 0.31 | GCTGAGCAATGCCTGGCTGGTGCCT (SEQ ID NO: 290) |
| [19,] | hsa-miR-768-3p_st | 0.38 | GTCAGCAGTTTGAGTGTCAGCATTG (SEQ ID NO: 44) |
| [20,] | hsa-miR-768-5p_st | 0.31 | ATCACTCCGTACTTTCATCCTCCAA (SEQ ID NO: 83) |
| [21,] | hsa-miR-877_st | 0.3 | CCCTGCGCCATCTCCTCTAC (SEQ ID NO: 291) |

TABLE 28

Cytoxan microRNA biomarkers.

| | Medianprobe | Corr | Sequence |
|---|---|---|---|
| [1,] | ENSG00000200879_st | 0.33 | ATCCAAGGAAGGTAGTTGCCAAC AC (SEQ ID NO: 292) |
| [2,] | ENSG00000202252_st | 0.34 | ACATCCAAGGAAGGTGTTGCCAT CA (SEQ ID NO: 244) |
| [3,] | HBII-142_st | 0.3 | GTGTCTCAGTGGCCCAGACACGT GG (SEQ ID NO: 293) |
| [4,] | hsa-miR-1202_st | 0.32 | CTCCCCCACTGCAGCTGGCAC (SEQ ID NO: 281) |
| [5,] | hsa-miR-184_st | 0.37 | ACCCTTATCAGTTCTCCGTCCA (SEQ ID NO: 283) |
| [6,] | hsa-miR-196a_st | 0.39 | CCCAACAACATGAAACTACCTA (SEQ ID NO: 294) |
| [7,] | hsa-miR-205_st | 0.32 | CAGACTCCGGTGGAATGAAGGA (SEQ ID NO: 295) |
| [8,] | hsa-miR-29b-2-star_st | 0.32 | CTAAGCCACCATGTGAAACCAG (SEQ ID NO: 39) |
| [9,] | hsa-miR-29c-star_st | 0.31 | GAACACCAGGAGAAATCGGTCA (SEQ ID NO: 296) |
| [10,] | hsa-miR-375_st | 0.34 | TCACGCGAGCCGAACGAACAAA (SEQ ID NO: 297) |
| [11,] | hsa-miR-449a_st | 0.73 | ACCAGCTAACAATACACTGCCA (SEQ ID NO: 287) |

TABLE 28-continued

Cytoxan microRNA biomarkers.

| Medianprobe | Corr | Sequence |
|---|---|---|
| [12,] hsa-miR-449b_st | 0.73 | GCCAGCTAACAATACACTGCCT (SEQ ID NO: 288) |
| [13,] hsa-miR-489_st | 0.32 | GCTGCCGTATATGTGATGTCAC (SEQ ID NO: 298) |
| [14,] hsa-miR-768-3p_st | 0.33 | GTCAGCAGTTTGAGTGTCAGCAT TG (SEQ ID NO: 44) |

TABLE 29

Topotecan (Hycamtin) microRNA biomarkers.

| Medianprobe | Corr | Sequence |
|---|---|---|
| [1,] hsa-miR-155_st | 0.31 | ACCCCTATCACGATTAGCATTAA (SEQ ID NO: 20) |
| [2,] hsa-miR-181b_st | 0.32 | ACCCACCGACAGCAATGAATGTT (SEQ ID NO: 10) |
| [3,] hsa-miR-342-3p_st | 0.4 | ACGGGTGCGATTTCTGTGTGAGA (SEQ ID NO: 11) |
| [4,] hsa-miR-342-5p_st | 0.39 | TCAATCACAGATAGCACCCCT (SEQ ID NO: 80) |
| [5,] hsa-miR-424-star_st | 0.34 | ATAGCAGCGCCTCACGTTTTG (SEQ ID NO: 100) |
| [6,] hsa-miR-503_st | 0.31 | CTGCAGAACTGTTCCCGCTGCTA (SEQ ID NO: 101) |

TABLE 30

Suberoylanilide hydroxamic acid (SAHA, vorinostat, Zolinza) microRNA biomarkers.

| Medianprobe | Corr | Sequence |
|---|---|---|
| [1,] U56_x_st | 0.3 | CACTAGGTGAACTGCTGTTGACGAA (SEQ ID NO: 211) |
| [2,] hsa-miR-106a_st | 0.41 | CTACCTGCACTGTAAGCACTTTT (SEQ ID NO: 150) |
| [3,] hsa-miR-126_st | 0.34 | CGCATTATTACTCACGGTACGA (SEQ ID NO: 299) |
| [4,] hsa-miR-128_st | 0.4 | AAAGAGACCGGTTCACTGTGA (SEQ ID NO: 110) |
| [5,] hsa-miR-148a-star_st | 0.3 | AGTCGGAGTGTCTCAGAACTTT (SEQ ID NO: 282) |
| [6,] hsa-miR-148a_st | 0.43 | ACAAAGTTCTGTAGTGCACTGA (SEQ ID NO: 275) |
| [7,] hsa-miR-153_st | 0.35 | GATCACTTTTGTGACTATGCAA (SEQ ID NO: 300) |
| [8,] hsa-miR-17_st | 0.44 | CTACCTGCACTGTAAGCACTTTG (SEQ ID NO: 152) |
| [9,] hsa-miR-18a-star_st | 0.31 | CCAGAAGGAGCACTTAGGGCAGT (SEQ ID NO: 71) |
| [10,] hsa-miR-18a_st | 0.34 | CTATCTGCACTAGATGCACCTTA (SEQ ID NO: 72) |

TABLE 30-continued

Suberoylanilide hydroxamic acid (SAHA, vorinostat, Zolinza) microRNA biomarkers.

| Medianprobe | Corr | Sequence |
|---|---|---|
| [11,] hsa-miR-18b_st | 0.49 | CTAACTGCACTAGATGCACCTTA (SEQ ID NO: 87) |
| [12,] hsa-miR-19a_st | 0.34 | TCAGTTTTGCATAGATTTGCACA (SEQ ID NO: 217) |
| [13,] hsa-miR-19b_st | 0.48 | TCAGTTTTGCATGGATTTGCACA (SEQ ID NO: 153) |
| [14,] hsa-miR-20a_st | 0.41 | CTACCTGCACTATAAGCACTTTA (SEQ ID NO: 218) |
| [15,] hsa-miR-20b_st | 0.56 | CTACCTGCACTATGAGCACTTTG (SEQ ID NO: 88) |
| [16,] hsa-miR-25_st | 0.35 | TCAGACCGAGACAAGTGCAATG (SEQ ID NO: 89) |
| [17,] hsa-miR-30c_st | 0.31 | GCTGAGAGTGTAGGATGTTTACA (SEQ ID NO: 301) |
| [18,] hsa-miR-30e_st | 0.35 | CTTCCAGTCAAGGATGTTTACA (SEQ ID NO: 302) |
| [19,] hsa-miR-363-star_st | 0.31 | AAATTGCATCGTGATCCACCCG (SEQ ID NO: 303) |
| [20,] hsa-miR-363_st | 0.4 | TACAGATGGATACCGTGCAATT (SEQ ID NO: 133) |
| [21,] hsa-miR-766_st | 0.31 | GCTGAGGCTGTGGGGCTGGAGT (SEQ ID NO: 1) |
| [22,] hsa-miR-92a_st | 0.43 | ACAGGCCGGGACAAGTGCAATA (SEQ ID NO: 156) |

TABLE 31

Depsipeptide (FR901228) microRNA biomarkers.

| Medianprobe | Corr | Sequence |
|---|---|---|
| [1,] hsa-miR-185_st | 0.39 | TCAGGAACTGCCTTTCTCTCCA (SEQ ID NO: 85) |
| [2,] hsa-miR-188-5p_st | 0.31 | CCCTCCACCATGCAAGGGATG (SEQ ID NO: 86) |
| [3,] hsa-miR-362-5p_st | 0.34 | ACTCACACCTAGGTTCCAAGGATT (SEQ ID NO: 92) |
| [4,] hsa-miR-500-star_st | 0.35 | CAGAATCCTTGCCCAGGTGCAT (SEQ ID NO: 93) |
| [5,] hsa-miR-500_st | 0.36 | TCTCACCCAGGTAGCAAGGATTA (SEQ ID NO: 94) |
| [6,] hsa-miR-501-3p_st | 0.31 | AGAATCCTTGCCCGGGTGCATT (SEQ ID NO: 95) |
| [7,] hsa-miR-501-5p_st | 0.33 | TCTCACCCAGGGACAAAGGATT (SEQ ID NO: 304) |
| [8,] hsa-miR-502-3p_st | 0.34 | TGAATCCTTGCCCAGGTGCATT (SEQ ID NO: 96) |
| [9,] hsa-miR-532-3p_st | 0.37 | TGCAAGCCTTGGGTGTGGGAGG (SEQ ID NO: 97) |
| [10,] hsa-miR-532-5p_st | 0.39 | ACGGTCCTACACTCAAGGCATG (SEQ ID NO: 98) |

TABLE 31-continued

Depsipeptide (FR901228) microRNA biomarkers.

| | Medianprobe | Corr | Sequence |
|---|---|---|---|
| [11,] | hsa-miR-652_st | 0.46 | CACAACCCTAGTGGCGCCATT (SEQ ID NO: 42) |
| [12,] | hsa-miR-660_st | 0.32 | CAACTCCGATATGCAATGGGTA (SEQ ID NO: 305) |
| [13,] | hsa-miR-93_st | 0.31 | CTACCTGCACGAACAGCACTTTG (SEQ ID NO: 46) |

TABLE 32

Bortezomib microRNA biomarkers.

| | Medianprobe | Corr | Sequence |
|---|---|---|---|
| [1,] | hsa-miR-106b-star_st | 0.39 | GCAGCAAGTACCCACAGTGCGG (SEQ ID NO: 2) |
| [2,] | hsa-miR-106b_st | 0.52 | ATCTGCACTGTCAGCACTTTA (SEQ ID NO: 37) |
| [3,] | hsa-miR-1307_st | 0.33 | CACGACCGACGCCACGCCGAGT (SEQ ID NO: 102) |
| [4,] | hsa-miR-188-5p_st | 0.37 | CCCTCCACCATGCAAGGGATG (SEQ ID NO: 86) |
| [5,] | hsa-miR-25-star_st | 0.31 | CAATTGCCCAAGTCTCCGCCT (SEQ ID NO: 3) |
| [6,] | hsa-miR-25_st | 0.33 | TCAGACCGAGACAAGTGCAATG (SEQ ID NO: 89) |
| [7,] | hsa-miR-320c_st | 0.31 | ACCCTCTCAACCCAGCTTTT (SEQ ID NO: 90) |
| [8,] | hsa-miR-324-3p_st | 0.32 | CCAGCAGCACCTGGGGCAGT (SEQ ID NO: 235) |
| [9,] | hsa-miR-500_st | 0.33 | TCTCACCCAGGTAGCAAGGATTA (SEQ ID NO: 94) |
| [10,] | hsa-miR-501-5p_st | 0.3 | TCTCACCCAGGGACAAAGGATT (SEQ ID NO: 304) |
| [11,] | hsa-miR-638_st | 0.3 | AGGCCGCCACCCGCCCGCGATCCCT (SEQ ID NO: 306) |
| [12,] | hsa-miR-652_st | 0.3 | CACAACCCTAGTGGCGCCATT (SEQ ID NO: 42) |
| [13,] | hsa-miR-93-star_st | 0.34 | CGGGAAGTGCTAGCTCAGCAGT (SEQ ID NO: 45) |
| [14,] | hsa-miR-93_st | 0.5 | CTACCTGCACGAACAGCACTTTG (SEQ ID NO: 46) |

TABLE 33

Leukeran microRNA biomarkers.

| | Medianprobe | Corr | Sequence |
|---|---|---|---|
| [1,] | HBII-85-2_x_st | 0.3 | ACCTCAGTTCCGATGAGAATGACGG (SEQ ID NO: 252) |
| [2,] | U104_st | 0.33 | GCGTCAGCAGTCTAACACGTGCTTT (SEQ ID NO: 201) |
| [3,] | U41_st | 0.34 | AGGATCAGCCAGTACGAATACGCGA (SEQ ID NO: 307) |

TABLE 33-continued

Leukeran microRNA biomarkers.

| | Medianprobe | Corr | Sequence |
|---|---|---|---|
| [4,] | U52_st | 0.34 | GTTTTGACATCATGACCAGCATCGG (SEQ ID NO: 258) |
| [5,] | U55_st | 0.36 | GCACTCGGGAGTATGCAGCATTACC (SEQ ID NO: 6) |
| [6,] | U55_x_st | 0.36 | CGCGCACTCGGGAGTATGCAGCATT (SEQ ID NO: 308) |
| [7,] | U57_st | 0.31 | TTTTGCCTCCATTCTACAAGGTCAG (SEQ ID NO: 262) |
| [8,] | U74_x_st | 0.32 | ACCAACACAGGCTTCATCAGAGGCA (SEQ ID NO: 309) |
| [9,] | hsa-miR-124_st | 0.35 | GGCATTCACCGCGTGCCTTA (SEQ ID NO: 7) |
| [10,] | hsa-miR-1281st | 0.37 | GGGAGAGGAGGAGGCGA (SEQ ID NO: 8) |
| [11,] | hsa-miR-1299_st | 0.32 | TCCCTCACACAGAATTCCAGAA (SEQ ID NO: 38) |
| [12,] | hsa-miR-140-3p_st | 0.3 | CCGTGGTTCTACCCTGTGGTA (SEQ ID NO: 13) |
| [13,] | hsa-miR-142-5p_st | 0.33 | AGTAGTGCTTTCTACTTTATG (SEQ ID NO: 215) |
| [14,] | hsa-miR-181a-star_st | 0.52 | GGTACAATCAACGGTCGATGGT (SEQ ID NO: 9) |
| [15,] | hsa-miR-181a_st | 0.39 | ACTCACCGACAGCGTTGAATGTT (SEQ ID NO: 78) |
| [16,] | hsa-miR-181b_st | 0.49 | ACCCACCGACAGCAATGAATGTT (SEQ ID NO: 10) |
| [17,] | hsa-miR-181c_st | 0.41 | ACTCACCGACAGGTTGAATGTT (SEQ ID NO: 79) |
| [18,] | hsa-miR-195-star_st | 0.34 | GGAGCAGCACAGCCAATATTGG (SEQ ID NO: 14) |
| [19,] | hsa-miR-223_st | 0.34 | TGGGGTATTTGACAAACTGACA (SEQ ID NO: 131) |
| [20,] | hsa-miR-297_st | 0.39 | CATGCACATGCACACATACAT (SEQ ID NO: 132) |
| [21,] | hsa-miR-342-3p_st | 0.42 | ACGGGTGCGATTTCTGTGTGAGA (SEQ ID NO: 11) |
| [22,] | hsa-miR-342-5p_st | 0.37 | TCAATCACAGATAGCACCCCT (SEQ ID NO: 80) |
| [23,] | hsa-miR-34b_st | 0.36 | ATGGCAGTGGAGTTAGTGATTG (SEQ ID NO: 154) |
| [24,] | hsa-miR-766_st | 0.43 | GCTGAGGCTGTGGGGCTGGAGT (SEQ ID NO: 1) |
| [25,] | hsa-miR-768-5p_st | 0.35 | ATCACTCCGTACTTTCATCCTCCAA (SEQ ID NO: 83) |
| [26,] | hsa-miR-874_st | 0.3 | TCGGTCCCTCGGGCCAGGGCAG (SEQ ID NO: 310) |

TABLE 34

Fludarabine microRNA biomarkers.

| | Medianprobe | Corr | Sequence |
|---|---|---|---|
| [1,] | HBII-276_st | 0.3 | GGCAAAAAGTAATTTAAGTCATCAT (SEQ ID NO: 311) |
| [2,] | HBII-438A_s_st | 0.44 | ATCCTCAGACAATTATTCTCATCAT (SEQ ID NO: 247) |
| [3,] | HBII-52-32_x_st | 0.3 | AGGGCAATATCAGGTTCTCATCATT (SEQ ID NO: 312) |
| [4,] | HBII-85-11_st | 0.39 | TGTTCAACTTTCCAAGGAACCCACG (SEQ ID NO: 115) |
| [5,] | hsa-miR-130a_st | 0.32 | ATGCCCTTTTAACATTGCACTG (SEQ ID NO: 313) |
| [6,] | hsa-miR-155_st | 0.32 | ACCCCTATCACGATTAGCATTAA (SEQ ID NO: 20) |
| [7,] | hsa-miR-181a-star_st | 0.35 | GGTACAATCAACGGTCGATGGT (SEQ ID NO: 9) |
| [8,] | hsa-miR-181a_st | 0.32 | ACTCACCGACAGCGTTGAATGTT (SEQ ID NO: 78) |
| [9,] | hsa-miR-181b_st | 0.4 | ACCCACCGACAGCAATGAATGTT (SEQ ID NO: 10) |
| [10,] | hsa-miR-20b-star_st | 0.33 | CTGGAAGTGCCCATACTACAGT (SEQ ID NO: 130) |
| [11,] | hsa-miR-20b_st | 0.3 | CTACCTGCACTATGAGCACTTTG (SEQ ID NO: 88) |
| [12,] | hsa-miR-34c-3p_st | 0.4 | CCTGGCCGTGTGGTTAGTGATT (SEQ ID NO: 314) |
| [13,] | hsa-miR-363_st | 0.33 | TACAGATGGATACCGTGCAATT (SEQ ID NO: 133) |
| [14,] | hsa-miR-424-star_st | 0.38 | ATAGCAGCGCCTCACGTTTTG (SEQ ID NO: 100) |
| [15,] | hsa-miR-503_st | 0.31 | CTGCAGAACTGTTCCCGCTGCTA (SEQ ID NO: 101) |
| [16,] | hsa-miR-554_st | 0.3 | ACTGGCTGAGTCAGGACTAGC (SEQ ID NO: 315) |
| [17,] | hsa-miR-766_st | 0.31 | GCTGAGGCTGTGGGGCTGGAGT (SEQ ID NO: 1) |

TABLE 35

Vinblastine microRNA biomarkers.

| | Medianprobe | Corr | Sequence |
|---|---|---|---|
| [1,] | hsa-miR-106b-star_st | 0.32 | GCAGCAAGTACCCACAGTGCGG (SEQ ID NO: 2) |
| [2,] | hsa-miR-25-star_st | 0.31 | CAATTGCCCAAGTCTCCGCCT (SEQ ID NO: 3) |
| [3,] | hsa-miR-362-5p_st | 0.33 | ACTCACACCTAGGTTCCAAGGATT (SEQ ID NO: 92) |
| [4,] | hsa-miR-500-star_st | 0.34 | CAGAATCCTTGCCCAGGTGCAT (SEQ ID NO: 93) |
| [5,] | hsa-miR-500_st | 0.36 | TCTCACCCAGGTAGCAAGGATTA (SEQ ID NO: 94) |
| [6,] | hsa-miR-502-3p_st | 0.35 | TGAATCCTTGCCCAGGTGCATT (SEQ ID NO: 96) |
| [7,] | hsa-miR-532-5p_st | 0.36 | ACGGTCCTACACTCAAGGCATG (SEQ ID NO: 98) |
| [8,] | hsa-miR-652_st | 0.49 | CACAACCCTAGTGGCGCCATT (SEQ ID NO: 42) |
| [9,] | hsa-miR-671-5p_st | 0.33 | CTCCAGCCCCTCCAGGGCTTCCT (SEQ ID NO: 43) |

TABLE 36

Busulfan microRNA biomarkers.

| | Medianprobe | Corr | Sequence |
|---|---|---|---|
| [1,] | U55_st | 0.34 | CGCGCACTCGGGAGTATGCAGCATT (SEQ ID NO: 308) |
| [2,] | U55_x_st | 0.31 | GCACTCGGGAGTATGCAGCATTACC (SEQ ID NO: 6) |
| [3,] | hsa-miR-1207-5p_st | 0.3 | CCCCTCCCAGCCTCCCTGCCA (SEQ ID NO: 109) |
| [4,] | hsa-miR-1246_st | 0.34 | CCTGCTCCAAAAATCCATT (SEQ ID NO: 214) |
| [5,] | hsa-miR-1281_st | 0.41 | GGGAGAGGGAGGAGGCGA (SEQ ID NO: 8) |
| [6,] | hsa-miR-181a-star_st | 0.4 | GGTACAATCAACGGTCGATGGT (SEQ ID NO: 9) |
| [7,] | hsa-miR-181b_st | 0.31 | ACCCACCGACAGCAATGAATGTT (SEQ ID NO: 10) |
| [8,] | hsa-miR-181c_st | 0.37 | ACTCACCGACAGGTTGAATGTT (SEQ ID NO: 79) |
| [9,] | hsa-miR-297_st | 0.35 | CATGCACATGCACACATACAT (SEQ ID NO: 132) |
| [10,] | hsa-miR-766_st | 0.31 | GCTGAGGCTGTGGGGCTGGAGT (SEQ ID NO: 1) |
| [11,] | hsa-miR-923_st | 0.31 | AGTTTCTTTTCCTCCGCTGAC (SEQ ID NO: 29) |

TABLE 37

Dacarbazine microRNA biomarkers.

| | Medianprobe | Corr | Sequence |
|---|---|---|---|
| [1,] | U13_st | 0.33 | AACAAGGTTCAAGGGTGGCACATCT (SEQ ID NO: 316) |
| [2,] | U17a_st | 0.31 | AGGCCCAGCTTTATTTCCAACGTTG (SEQ ID NO: 317) |
| [3,] | U25_st | 0.31 | TGTGAAAAGGTCCTCATCATAGGAA (SEQ ID NO: 318) |
| [4,] | U29_st | 0.3 | GAGCTAGTTTGATTCATCATAGAAA (SEQ ID NO: 203) |

TABLE 37-continued

Dacarbazine microRNA biomarkers.

| | Medianprobe | Corr | Sequence |
|---|---|---|---|
| [5,] | U3-2_s_st | 0.34 | GCAGCCAAGCAACGCCAGAAAGCCG (SEQ ID NO: 319) |
| [6,] | U41_st | 0.35 | AGGATCAGCCAGTACGAATACGCGA (SEQ ID NO: 307) |
| [7,] | U52_st | 0.37 | ATCATGACCAGCATCGGAGACTCTA (SEQ ID NO: 320) |
| [8,] | U55_st | 0.33 | CGGGAGTATGCAGCATTACCGAGTT (SEQ ID NO: 241) |
| [9,] | hsa-miR-1207-5p_st | 0.31 | CCCCTCCCAGCCTCCCTGCCA (SEQ ID NO: 109) |
| [10,] | hsa-miR-1299_st | 0.32 | TCCCTCACACAGAATTCCAGAA (SEQ ID NO: 38) |
| [11,] | hsa-miR-140-3p_st | 0.33 | CCGTGGTTCTACCCTGTGGTA (SEQ ID NO: 13) |
| [12,] | hsa-miR-140-5p_st | 0.31 | CTACCATAGGGTAAAACCACTG (SEQ ID NO: 18) |
| [13,] | hsa-miR-17-star_st | 0.36 | CTACAAGTGCCTTCACTGCAGT (SEQ ID NO: 216) |
| [14,] | hsa-miR-181d_st | 0.31 | ACCCACCGACAACAATGAATGTT (SEQ ID NO: 321) |
| [15,] | hsa-miR-223_st | 0.44 | TGGGGTATTTGACAAACTGACA (SEQ ID NO: 131) |
| [16,] | hsa-miR-297_st | 0.34 | CATGCACATGCACACATACAT (SEQ ID NO: 132) |
| [17,] | hsa-miR-34b_st | 0.34 | ATGGCAGTGGAGTTAGTGATTG (SEQ ID NO: 154) |
| [18,] | hsa-miR-766_st | 0.33 | GCTGAGGCTGTGGGGCTGGAGT (SEQ ID NO: 1) |
| [19,] | hsa-miR-92a-1-star_st | 0.44 | AGCATTGCAACCGATCCCAACCT (SEQ ID NO: 192) |
| [20,] | hsa-miR-92a_st | 0.33 | ACAGGCCGGGACAAGTGCAATA (SEQ ID NO: 156) |

TABLE 38

Oxaliplatin microRNA biomarkers.

| | Medianprobe | Corr | Sequence |
|---|---|---|---|
| [1,] | ACA10_s_st | 0.36 | CACTCCTAGGAACAGAGAGGCCATT (SEQ ID NO: 138) |
| [2,] | ACA15_s_st | 0.32 | GTCTGGCTGTGTAAACTACTGATAA (SEQ ID NO: 322) |
| [3,] | ACA18_x_st | 0.34 | GCGTTTCCAACGATGTGCAGGCTAC (SEQ ID NO: 139) |
| [4,] | ACA21_st | 0.33 | AAAAGCGATGTTTTCACTCTCCCCT (SEQ ID NO: 323) |
| [5,] | ACA51_x_st | 0.32 | GAACACAGCCTGTGGTAAGCACCAG (SEQ ID NO: 324) |
| [6,] | HBII-180A_x_st | 0.4 | GGCACCGTGTCCTCAGTGGCAGTCG (SEQ ID NO: 54) |

TABLE 38-continued

Oxaliplatin microRNA biomarkers.

| | Medianprobe | Corr | Sequence |
|---|---|---|---|
| [7,] | HBII-202_st | 0.34 | TTCATCAAGGCCGTACAGCGATTCC (SEQ ID NO: 113) |
| [8,] | HBII-429_st | 0.32 | ATCAGAAGGGTGACATGGCAGTTTC (SEQ ID NO: 55) |
| [9,] | HBII-55_st | 0.35 | TGCACTCAGGGGATTGACAGATTTG (SEQ ID NO: 248) |
| [10,] | HBII-99_st | 0.37 | CCAATGCATCAGACAAAACTGGCCA (SEQ ID NO: 325) |
| [11,] | U104_st | 0.45 | CACGTGCTTTAATTGGAATGTCATC (SEQ ID NO: 326) |
| [12,] | U17b_st | 0.35 | GCCCAGCTTCATCTTCAACGTTGTG (SEQ ID NO: 327) |
| [13,] | U17b_x_st | 0.33 | CAGCTTCATCTTCAACGTTGTGGAA (SEQ ID NO: 328) |
| [14,] | U25_st | 0.32 | AGTACAGGTCTGTGAAAAGGTCTC (SEQ ID NO: 329) |
| [15,] | U27_st | 0.38 | GATGACATCACTTGAAAGTTCAGCC (SEQ ID NO: 330) |
| [16,] | U29_st | 0.4 | GTTTCTCAGGTGTTCATGTATTTTC (SEQ ID NO: 331) |
| [17,] | U30_st | 0.36 | GCCGAACGAGATTCCATGTAAGTCA (SEQ ID NO: 332) |
| [18,] | U31_st | 0.34 | AATACCTTTCAGTCACACATTGATC (SEQ ID NO: 124) |
| [19,] | U31_x_st | 0.31 | GGCGGTATTCAACTCATCACTGGTG (SEQ ID NO: 333) |
| [20,] | U33_st | 0.32 | TGGAGTCATCTCATGGTCGGAAAC (SEQ ID NO: 334) |
| [21,] | U36C_st | 0.3 | TCAGATGCAATGCTGACCACATGGT (SEQ ID NO: 335) |
| [22,] | U50B_st | 0.37 | AGCCGAATCCGTACTTATTTTTCTT (SEQ ID NO: 336) |
| [23,] | U55_st | 0.34 | CGGGAGTATGCAGCATTACCGAGTT (SEQ ID NO: 241) |
| [24,] | U55_x_st | 0.32 | GCTCAGCTCTCCAAGGTTGGCTTCC (SEQ ID NO: 260) |
| [25,] | U56_st | 0.39 | TCAGACCCAGAGTCTCAACACTCAC (SEQ ID NO: 337) |
| [26,] | U56_x_st | 0.35 | CTCAACACTCACTAGGTGAACTGCT (SEQ ID NO: 338) |
| [27,] | U57_st | 0.31 | AAGGTCAGGCTCAGACAGTTCATCA (SEQ ID NO: 339) |
| [28,] | U71d_x_st | 0.31 | CGCGATTCTTTCCCTGCACTATCA (SEQ ID NO: 340) |
| [29,] | U73a_st | 0.33 | TGGCCATCATCTGGGACCGAAACTT (SEQ ID NO: 341) |
| [30,] | U74_x_st | 0.42 | CGGTTGGCATTCATCATTACTCTCA (SEQ ID NO: 69) |
| [31,] | U78_s_st | 0.36 | ATGCTCATTTCAGGTCAGACATTTG (SEQ ID NO: 265) |

TABLE 38-continued

Oxaliplatin microRNA biomarkers.

| | Medianprobe | Corr | Sequence |
|---|---|---|---|
| [32,] | U78_x_st | 0.36 | CTTCAGTGTTACCTTTGTCTACATG (SEQ ID NO: 266) |
| [33,] | U95_st | 0.34 | AGCCTCTGGATTTCAGCACCGACAC (SEQ ID NO: 268) |
| [34,] | hsa-miR-106a_st | 0.38 | CTACCTGCACTGTAAGCACTTTT (SEQ ID NO: 150) |
| [35,] | hsa-miR-106b_st | 0.36 | ATCTGCACTGTCAGCACTTTA (SEQ ID NO: 37) |
| [36,] | hsa-miR-1246_st | 0.35 | CCTGCTCCAAAAATCCATT (SEQ ID NO: 214) |
| [37,] | hsa-miR-1275_st | 0.31 | GACAGCCTCTCCCCCAC (SEQ ID NO: 70) |
| [38,] | hsa-miR-1307_st | 0.38 | CACGACCGACGCCACGCCAGT (SEQ ID NO: 102) |
| [39,] | hsa-miR-142-5p_st | 0.32 | AGTAGTGCTTTCTACTTTATG (SEQ ID NO: 215) |
| [40,] | hsa-miR-148a-star_st | 0.33 | AGTCGGAGTGTCTCAGAACTTT (SEQ ID NO: 282) |
| [41,] | hsa-miR-153_st | 0.38 | GATCACTTTTGTGACTATGCAA (SEQ ID NO: 300) |
| [42,] | hsa-miR-17-star_st | 0.35 | CTACAAGTGCCTTCACTGCAGT (SEQ ID NO: 216) |
| [43,] | hsa-miR-17_st | 0.45 | CTACCTGCACTGTAAGCACTTTG (SEQ ID NO: 152) |
| [44,] | hsa-miR-18a-star_st | 0.32 | CCAGAAGGAGCACTTAGGGCAGT (SEQ ID NO: 71) |
| [45,] | hsa-miR-18a_st | 0.38 | CTATCTGCACTAGATGCACCTTA (SEQ ID NO: 72) |
| [46,] | hsa-miR-18b_st | 0.34 | CTAACTGCACTAGATGCACCTTA (SEQ ID NO: 87) |
| [47,] | hsa-miR-19a_st | 0.37 | TCAGTTTTGCATAGATTTGCACA (SEQ ID NO: 217) |
| [48,] | hsa-miR-19b_st | 0.43 | TCAGTTTTGCATGGATTTGCACA (SEQ ID NO: 153) |
| [49,] | hsa-miR-20a_st | 0.34 | CTACCTGCACTATAAGCACTTTA (SEQ ID NO: 218) |
| [50,] | hsa-miR-297_st | 0.32 | CATGCACATGCACACATACAT (SEQ ID NO: 132) |
| [51,] | hsa-miR-301a_st | 0.32 | GCTTTGACAATACTATTGCACTG (SEQ ID NO: 342) |
| [52,] | hsa-miR-34b_st | 0.32 | ATGGCAGTGGAGTTAGTGATTG (SEQ ID NO: 154) |

TABLE 39

Hydroxyurea microRNA biomarkers.

| | Medianprobe | Corr | Sequence |
|---|---|---|---|
| [1,] | ACA7_s_st | 0.35 | ATGGGTGCCTCTGCCAGGCTTGCTT (SEQ ID NO: 243) |

TABLE 39-continued

Hydroxyurea microRNA biomarkers.

| | Medianprobe | Corr | Sequence |
|---|---|---|---|
| [2,] | ENSG-00000199282_st | 0.31 | GCTCCACTATTTCAATACTGTTCTG (SEQ ID NO: 343) |
| [3,] | ENSG-00000201859_x_st | 0.4 | TCTTATCTGGAATGGCATCTAGCTT (SEQ ID NO: 344) |
| [4,] | HBII-202_st | 0.39 | GCGATTCCGGAGAATGTCATCACGC (SEQ ID NO: 239) |
| [5,] | HBII-336_st | 0.36 | GCCTCAGGTAAATCCTTTAATCCAT (SEQ ID NO: 345) |
| [6,] | HBII-429_st | 0.31 | GTTTCCTCATGGCAGTTCAGTAGAG (SEQ ID NO: 246) |
| [7,] | U104_st | 0.38 | TTTAATTGGAATGTCATCACAGCAG (SEQ ID NO: 140) |
| [8,] | U25_st | 0.3 | AGTACAGGTCTGTGAAAGGTCCTC (SEQ ID NO: 329) |
| [9,] | U33_st | 0.33 | GCATGTGGAGTCATCTCATGGTCGG (SEQ ID NO: 346) |
| [10,] | U34_st | 0.33 | AGGTAGTTGCGGAACATCATGGACG (SEQ ID NO: 347) |
| [11,] | U38A_st | 0.3 | GGCTCTCATCTCTCTCCCTTCAGTA (SEQ ID NO: 348) |
| [12,] | U41st | 0.32 | AGGATCAGCCAGTACGAATACGCGA (SEQ ID NO: 307) |
| [13,] | U49B_s_st | 0.3 | CGTCAGTTATCGCTTCTGACGGCAC (SEQ ID NO: 107) |
| [14,] | U52_st | 0.4 | GACCAGCATCGGAGACTCTAGTCTG (SEQ ID NO: 349) |
| [15,] | U55_st | 0.43 | GCACTCGGGAGTATGCAGCATTACC (SEQ ID NO: 6) |
| [16,] | U55_x_st | 0.43 | GCTCAGCTCTCCAAGGTTGGCTTCC (SEQ ID NO: 260) |
| [17,] | U74_x_st | 0.32 | GAGCGGTTGGCATTCATCATTACTC (SEQ ID NO: 350) |
| [18,] | hsa-miR-1207-5p_st | 0.33 | CCCCTCCCAGCCTCCCTGCCA (SEQ ID NO: 109) |
| [19,] | hsa-miR-124_st | 0.45 | GGCATTCACCGCGTGCCTTA (SEQ ID NO: 7) |
| [20,] | hsa-miR-1281_st | 0.33 | GGGAGAGGAGGAGGCGA (SEQ ID NO: 8) |
| [21,] | hsa-miR-1299_st | 0.4 | TCCCTCACACAGAATTCCAGAA (SEQ ID NO: 38) |
| [22,] | hsa-miR-140-3p_st | 0.37 | CCGTGGTTCTACCCTGTGGTA (SEQ ID NO: 13) |
| [23,] | hsa-miR-155_st | 0.35 | ACCCCTATCACGATTAGCATTAA (SEQ ID NO: 20) |
| [24,] | hsa-miR-181a-star_st | 0.43 | GGTACAATCAACGGTCGATGGT (SEQ ID NO: 9) |
| [25,] | hsa-miR-181b_st | 0.35 | ACCCACCGACAGCAATGAATGTT (SEQ ID NO: 10) |
| [26,] | hsa-miR-181c_st | 0.3 | ACTCACCGACAGGTTGAATGTT (SEQ ID NO: 79) |

TABLE 39-continued

Hydroxyurea microRNA biomarkers.

| | Medianprobe | Corr | Sequence |
|---|---|---|---|
| [27,] | hsa-miR-195-star_st | 0.41 | GGAGCAGCACAGCCAATATTGG (SEQ ID NO: 14) |
| [28,] | hsa-miR-223_st | 0.49 | TGGGGTATTTGACAAACTGACA (SEQ ID NO: 131) |
| [29,] | hsa-miR-297_st | 0.47 | CATGCACATGCACACATACAT (SEQ ID NO: 132) |
| [30,] | hsa-miR-34b_st | 0.44 | ATGGCAGTGGAGTTAGTGATTG (SEQ ID NO: 154) |
| [31,] | hsa-miR-491-3p_st | 0.37 | GTAGAAGGGAATCTTGCATAAG (SEQ ID NO: 351) |
| [32,] | hsa-miR-595_st | 0.32 | AGACACACCACGGCACACTTC (SEQ ID NO: 221) |
| [33,] | hsa-miR-631_st | 0.39 | GCTGAGGTCTGGGCCAGGTCT (SEQ ID NO: 135) |
| [34,] | hsa-miR-766_st | 0.37 | GCTGAGGCTGTGGGGCTGGAGT (SEQ ID NO: 1) |
| [35,] | hsa-miR-768-5p_st | 0.35 | ATCACTCCGTACTTTCATCCTCCAA (SEQ ID NO: 83) |

TABLE 40

Tegafur microRNA biomarkers.

| | Medianprobe | Corr | Sequence |
|---|---|---|---|
| [1,] | HBII-180A_x_st | 0.34 | TGTCCTCAGTGGCAGTCGGAGCCCA (SEQ ID NO: 352) |
| [2,] | U104_st | 0.34 | AGTTCGCATCACCCGCGTCAGCAGT (SEQ ID NO: 353) |
| [3,] | U33_st | 0.33 | TCGAATGTGAGTGGGAGAAGTTCTC (SEQ ID NO: 354) |
| [4,] | U34_st | 0.32 | GCTGCTTTCATGAGGATCAAACAAT (SEQ ID NO: 355) |
| [5,] | U43_x_st | 0.31 | AATCAGCACACAGTTTCTGTCCGCC (SEQ ID NO: 356) |
| [6,] | U51_st | 0.31 | AAAGCAAATCCATCACGAACTCAGC (SEQ ID NO: 357) |
| [7,] | U55_x_st | 0.34 | TGGCTTCCCCACCGCGCACTCGGGA (SEQ ID NO: 36) |
| [8,] | U74_x_st | 0.44 | TTCATCATTACTCTCAGATGTCCCT (SEQ ID NO: 191) |
| [9,] | U78_s_st | 0.33 | CATGCTCATTTCAGGTCAGACATTT (SEQ ID NO: 119) |
| [10,] | U78_x_st | 0.32 | ACCTTTGTCTACATGCTCATTTCAG (SEQ ID NO: 228) |
| [11,] | hsa-miR-1228-star_st | 0.33 | CACACACCTGCCCCCGCCCAC (SEQ ID NO: 358) |
| [12,] | hsa-miR-1246_st | 0.38 | CCTGCTCCAAAAATCCATT (SEQ ID NO: 214) |
| [13,] | hsa-miR-124_st | 0.35 | GGCATTCACCGCGTGCCTTA (SEQ ID NO: 7) |

TABLE 40-continued

Tegafur microRNA biomarkers.

| | Medianprobe | Corr | Sequence |
|---|---|---|---|
| [14,] | hsa-miR-1299_st | 0.32 | TCCCTCACACAGAATTCCAGAA (SEQ ID NO: 38) |
| [15,] | hsa-miR-1307_st | 0.4 | CACGACCGACGCCACGCCGAGT (SEQ ID NO: 102) |
| [16,] | hsa-miR-149-star_st | 0.34 | GCACAGCCCCCGTCCCTCCCT (SEQ ID NO: 359) |
| [17,] | hsa-miR-16_st | 0.32 | CGCCAATATTTACGTGCTGCTA (SEQ ID NO: 360) |
| [18,] | hsa-miR-18a_st | 0.32 | CTATCTGCACTAGATGCACCTTA (SEQ ID NO: 72) |
| [19,] | hsa-miR-195-star_st | 0.4 | GGAGCAGCACAGCCAATATTGG (SEQ ID NO: 14) |
| [20,] | hsa-miR-297_st | 0.37 | CATGCACATGCACACATACAT (SEQ ID NO: 132) |
| [21,] | hsa-miR-330-3p_st | 0.4 | TCTCTGCAGGCCGTGTGCTTTGC (SEQ ID NO: 219) |
| [22,] | hsa-miR-346_st | 0.33 | AGAGGCAGGCATGCGGGCAGACA (SEQ ID NO: 220) |
| [23,] | hsa-miR-34b_st | 0.42 | ATGGCAGTGGAGTTAGTGATTG (SEQ ID NO: 154) |
| [24,] | hsa-miR-638_st | 0.33 | AGGCCGCCACCCGCCCGCGATCCCT (SEQ ID NO: 306) |
| [25,] | hsa-miR-923_st | 0.35 | AGTTTCTTTTCCTCCGCTGAC (SEQ ID NO: 29) |
| [26,] | hsa-miR-92a_st | 0.33 | ACAGGCCGGGACAAGTGCAATA (SEQ ID NO: 156) |

TABLE 41

Daunorubicin microRNA biomarkers.

| | Medianprobe | Corr | Sequence |
|---|---|---|---|
| [1,] | ACA48_x_st | 0.3 | GGGCACGGATCAAAAGCCAAGCTGG (SEQ ID NO: 238) |
| [2,] | HBII-85-26_st | 0.31 | ATCCATTTTTTTTATAGTCATCATC (SEQ ID NO: 361) |
| [3,] | HBII-85-6_x_st | 0.3 | TTTTTTTTGGAGGACTCATCATCGA (SEQ ID NO: 362) |
| [4,] | U104_st | 0.37 | TTTAATTGGAATGTCATCACAGCAG (SEQ ID NO: 140) |
| [5,] | U55_st | 0.41 | GTATGCAGCATTACCGAGTTGTCAT (SEQ ID NO: 280) |
| [6,] | U55_x_st | 0.42 | CGCGCACTCGGGAGTATGCAGCATT (SEQ ID NO: 308) |
| [7,] | U74_x_st | 0.32 | AGAGCGGTTGGCATTCATCATTACT (SEQ ID NO: 264) |
| [8,] | hsa-miR-106a-star_st | 0.32 | GTAAGAAGTGCTTACATTGCAG (SEQ ID NO: 363) |
| [9,] | hsa-miR-106b-star_st | 0.4 | GCAGCAAGTACCCACAGTGCGG (SEQ ID NO: 2) |

TABLE 41-continued

Daunorubicin microRNA biomarkers.

| | Medianprobe | Corr | Sequence |
|---|---|---|---|
| [10,] | hsa-miR-106b_st | 0.34 | ATCTGCACTGTCAGCACTTTA (SEQ ID NO: 37) |
| [11,] | hsa-miR-124_st | 0.38 | GGCATTCACCGCGTGCCTTA (SEQ ID NO: 7) |
| [12,] | hsa-miR-1281_st | 0.34 | GGGAGAGGAGGAGGCGA (SEQ ID NO: 8) |
| [13,] | hsa-miR-1299_st | 0.35 | TCCCTCACACAGAATTCCAGAA (SEQ ID NO: 38) |
| [14,] | hsa-miR-181a-star_st | 0.3 | GGTACAATCAACGGTCGATGGT (SEQ ID NO: 9) |
| [15,] | hsa-miR-195-star_st | 0.3 | GGAGCAGCACAGCCAATATTGG (SEQ ID NO: 14) |
| [16,] | hsa-miR-297_st | 0.33 | CATGCACATGCACACATACAT (SEQ ID NO: 132) |
| [17,] | hsa-miR-29b-2-star_st | 0.32 | CTAAGCCACCATCTGAAACCAG (SEQ ID NO: 39) |
| [18,] | hsa-miR-33b-star_st | 0.39 | GGGCTGCACTGCCGAGGCACTG (SEQ ID NO: 40) |
| [19,] | hsa-miR-342-5p_st | 0.31 | TCAATCACAGATAGCACCCCT (SEQ ID NO: 80) |
| [20,] | hsa-miR-34b_st | 0.35 | ATGGCAGTGGAGTTAGTGATTG (SEQ ID NO: 154) |
| [21,] | hsa-miR-629-star_st | 0.36 | GCTGGGCTTACGTTGGGAGAAC (SEQ ID NO: 41) |
| [22,] | hsa-miR-652_st | 0.34 | CACAACCCTAGTGGCGCCATT (SEQ ID NO: 42) |
| [23,] | hsa-miR-671-5p_st | 0.36 | CTCCAGCCCCTCCAGGGCTTCCT (SEQ ID NO: 43) |
| [24,] | hsa-miR-766_st | 0.38 | GCTGAGGCTGTGGGGCTGGAGT (SEQ ID NO: 1) |
| [25,] | hsa-miR-768-3p_st | 0.36 | GTCAGCAGTTTGAGTGTCAGCATTG (SEQ ID NO: 44) |
| [26,] | hsa-miR-768-5p_st | 0.33 | ATCACTCCGTACTTTCATCCTCCAA (SEQ ID NO: 83) |
| [27,] | hsa-miR-877-star_st | 0.34 | CTGGGAGGAGGGAGAAGAGGA (SEQ ID NO: 364) |
| [28,] | hsa-miR-93-star_st | 0.38 | CGGGAAGTGCTAGCTCAGCAGT (SEQ ID NO: 45) |
| [29,] | hsa-miR-93_st | 0.31 | CTACCTGCACGAACAGCACTTTG (SEQ ID NO: 46) |

TABLE 42

Bleomycin microRNA biomarkers.

| | Medianprobe | Corr | Sequence |
|---|---|---|---|
| [1,] | 14qII-14_st | 0.41 | ACCCAACACTCATACGCCGGCAGTT (SEQ ID NO: 157) |
| [2,] | 14qII-14_x_st | 0.4 | ATACGCCGGCAGTTGTCATCATTGG (SEQ ID NO: 158) |
| [3,] | 14qII-1_st | 0.38 | TCAGACTTCCAGACCTGTATTCACC (SEQ ID NO: 159) |
| [4,] | 14qII-1_x_st | 0.32 | TGGACCTCAGACTTCCAGACCTGTA (SEQ ID NO: 74) |
| [5,] | 14qII-26_st | 0.43 | TGTGACTCATACTCCACCAGTGCTC (SEQ ID NO: 160) |
| [6,] | 14qII-26_x_st | 0.4 | ATCGTATGTGACTCATACTCCACCA (SEQ ID NO: 161) |
| [7,] | 14qII-3_st | 0.33 | CAGACACGTAGTATTCATCGTCCAT (SEQ ID NO: 162) |
| [8,] | hsa-miR-125b-1-star_st | 0.32 | AGCTCCCAAGAGCCTAACCCGT (SEQ ID NO: 163) |
| [9,] | hsa-miR-127-3p_st | 0.41 | AGCCAAGCTCAGACGGATCCGA (SEQ ID NO: 77) |
| [10,] | hsa-miR-1271_st | 0.32 | TGAGTGCTTGCTAGGTGCCAAG (SEQ ID NO: 30) |
| [11,] | hsa-miR-134_st | 0.34 | CCCCTCTGGTCAACCAGTCACA (SEQ ID NO: 164) |
| [12,] | hsa-miR-155_st | 0.37 | ACCCCTATCACGATTAGCATTAA (SEQ ID NO: 20) |
| [13,] | hsa-miR-193a-5p_st | 0.32 | TCATCTCGCCCGCAAAGACCCA (SEQ ID NO: 165) |
| [14,] | hsa-miR-21-star_st | 0.39 | ACAGCCCATCGACTGGTGTTG (SEQ ID NO: 166) |
| [15,] | hsa-miR-22_st | 0.31 | ACAGTTCTTCAACTGGCAGCTT (SEQ ID NO: 167) |
| [16,] | hsa-miR-299-3p_st | 0.34 | AAGCGGTTTACCATCCCACATA (SEQ ID NO: 168) |
| [17,] | hsa-miR-337-5p_st | 0.3 | AACTCCTGTATGAAGCCGTTC (SEQ ID NO: 169) |
| [18,] | hsa-miR-370_st | 0.35 | ACCAGGTTCCACCCCAGCAGGC (SEQ ID NO: 32) |
| [19,] | hsa-miR-376c_st | 0.3 | ACGTGGAATTTCCTCTATGTT (SEQ ID NO: 170) |
| [20,] | hsa-miR-377-star_st | 0.37 | GAATTCACCAAGGGCAACCTCT (SEQ ID NO: 171) |
| [21,] | hsa-miR-379_st | 0.36 | CCTACGTTCCATAGTCTACCA (SEQ ID NO: 172) |
| [22,] | hsa-miR-381_st | 0.4 | ACAGAGAGCTTGCCCTTGTATA (SEQ ID NO: 173) |
| [23,] | hsa-miR-382_st | 0.32 | CGAATCCACCACGAACAACTTC (SEQ ID NO: 174) |
| [24,] | hsa-miR-409-3p_st | 0.36 | AGGGGTTCACCGAGCAACATTC (SEQ ID NO: 81) |
| [25,] | hsa-miR-409-5p_st | 0.35 | ATGCAAAGTTGCTCGGGTAACCT (SEQ ID NO: 175) |
| [26,] | hsa-miR-411_st | 0.39 | CGTACGCTATACGGTCTACTA (SEQ ID NO: 176) |
| [27,] | hsa-miR-431_st | 0.32 | TGCATGACGGCCTGCAAGACA (SEQ ID NO: 177) |

TABLE 42-continued

Bleomycin microRNA biomarkers.

| | Medianprobe | Corr | Sequence |
|---|---|---|---|
| [28,] | hsa-miR-455-3p_st | 0.41 | GTGTATATGCCCATGGACTGC (SEQ ID NO: 178) |
| [29,] | hsa-miR-485-5p_st | 0.34 | GAATTCATCACGGCCAGCCTCT (SEQ ID NO: 179) |
| [30,] | hsa-miR-487b_st | 0.37 | AAGTGGATGACCCTGTACGATT (SEQ ID NO: 82) |
| [31,] | hsa-miR-493_st | 0.34 | CCTGGCACACAGTAGACCTTCA (SEQ ID NO: 180) |
| [32,] | hsa-miR-494_st | 0.39 | GAGGTTTCCCGTGTATGTTTCA (SEQ ID NO: 181) |
| [33,] | hsa-miR-543_st | 0.33 | AAGAAGTGCACCGCGAATGTTT (SEQ ID NO: 182) |
| [34,] | hsa-miR-663_st | 0.3 | GCGGTCCCGCGGCGCCCCGCCT (SEQ ID NO: 28) |
| [35,] | hsa-miR-671-5p_st | 0.32 | CTCCAGCCCCTCCAGGGCTTCCT (SEQ ID NO: 43) |
| [36,] | hsa-miR-758_st | 0.33 | GGTTAGTGGACCAGGTCACAAA (SEQ ID NO: 35) |

TABLE 43

Estramustine microRNA biomarkers.

| | Medianprobe | Corr | Sequence |
|---|---|---|---|
| [1,] | hsa-miR-1226_st | 0.25 | CTAGGGAACACAGGGCTGGTGA (SEQ ID NO: 365) |
| [2,] | hsa-miR-193a-3p_st | 0.26 | ACTGGGACTTTGTAGGCCAGTT (SEQ ID NO: 366) |
| [3,] | hsa-miR-193a-5p_st | 0.26 | TCATCTCGCCCGCAAAGACCCA (SEQ ID NO: 165) |
| [4,] | hsa-miR-330-3p_st | 0.25 | TCTCTGCAGGCCGTGTGCTTTGC (SEQ ID NO: 219) |
| [5,] | hsa-miR-330-5p_st | 0.25 | GCCTAAGACACAGGCCCAGAGA (SEQ ID NO: 367) |
| [6,] | hsa-miR-378_st | 0.34 | CCTTCTGACTCCAAGTCCAGT (SEQ ID NO: 368) |
| [7,] | hsa-miR-586_st | 0.28 | GGACCTAAAAATACAATGCATA (SEQ ID NO: 369) |

TABLE 44

Mechlorethamine microRNA biomarkers.

| | Medianprobe | Corr | Sequence |
|---|---|---|---|
| [1,] | ACA13_st | 0.3 | GCCTTTTTTGACACCACATTCACTA (SEQ ID NO: 370) |
| [2,] | ACA21_st | 0.33 | AAAAGCGATGTTTTCACTCTCCCCT (SEQ ID NO: 323) |
| [3,] | ACA48_x_st | 0.32 | ATGGGCATCACCAACCAGATGCCAC (SEQ ID NO: 371) |
| [4,] | ACA7_s_st | 0.33 | GAATGGGTGCCTCTGCCAGGCTTGC (SEQ ID NO: 372) |
| [5,] | ACA9_st | 0.31 | CTGTTCTAGCAAGCACTGAAGGAAT (SEQ ID NO: 373) |
| [6,] | ENSG00000202252_st | 0.31 | AAGGAAGGTGTTGCCATCATTAGCC (SEQ ID NO: 184) |
| [7,] | HBII-202_st | 0.35 | ACAGCGATTCCGGAGAATGTCATCA (SEQ ID NO: 198) |
| [8,] | HBII-239_st | 0.41 | TGTCAGCAGTTTGAGTGTCAGCATT (SEQ ID NO: 374) |
| [9,] | HBII-336_st | 0.35 | GCCTCAGGTAAATCCTTTAATCCAT (SEQ ID NO: 345) |
| [10,] | HBII-429_st | 0.37 | GAGGGAGCCAGTTGTCATCATGTAC (SEQ ID NO: 240) |
| [11,] | U104_st | 0.49 | TTTAATTGGAATGTCATCACAGCAG (SEQ ID NO: 140) |
| [12,] | U33_st | 0.35 | TGAGTGGGAGAAGTTCTCATCACCG (SEQ ID NO: 375) |
| [13,] | U34_st | 0.32 | AGTGCTGCTTTCATGAGGATCAAAC (SEQ ID NO: 376) |

TABLE 44-continued

Mechlorethamine microRNA biomarkers.

| | Medianprobe | Corr | Sequence |
|---|---|---|---|
| [14,] | U52_st | 0.32 | GTTTTGACATCATGACCAGCATCGG (SEQ ID NO: 258) |
| [15,] | U55_st | 0.34 | CGCGCACTCGGGAGTATGCAGCATT (SEQ ID NO: 308) |
| [16,] | U55_x_st | 0.36 | GCTCAGCTCTCCAAGGTTGGCTTCC (SEQ ID NO: 260) |
| [17,] | U74_x_st | 0.44 | CAGAGCGGTTGGCATTCATCATTAC (SEQ ID NO: 377) |
| [18,] | U75_st | 0.37 | TTCTGTCCACTACTCTTAAAGCATC (SEQ ID NO: 378) |
| [19,] | U78_s_st | 0.32 | ATGCTCATTTCAGGTCAGACATTTG (SEQ ID NO: 265) |
| [20,] | U78_x_st | 0.33 | TTTGTCTACATGCTCATTTCAGGTC (SEQ ID NO: 120) |
| [21,] | U95_st | 0.32 | CGACACTCAGATGGCATGTTGGGGT (SEQ ID NO: 379) |
| [22,] | hsa-miR-124_st | 0.43 | GGCATTCACCGCGTGCCTTA (SEQ ID NO: 7) |
| [23,] | hsa-miR-1281_st | 0.34 | GGGAGAGGAGGAGGCGA (SEQ ID NO: 8) |
| [24,] | hsa-miR-1299_st | 0.37 | TCCCTCACACAGAATTCCAGAA (SEQ ID NO: 38) |
| [25,] | hsa-miR-142-5p_st | 0.33 | AGTAGTGCTTTCTACTTTATG (SEQ ID NO: 215) |
| [26,] | hsa-miR-181a-star_st | 0.37 | GGTACAATCAACGGTCGATGGT (SEQ ID NO: 9) |
| [27,] | hsa-miR-181a_st | 0.31 | ACTCACCGACAGCGTTGAATGTT (SEQ ID NO: 78) |
| [28,] | hsa-miR-181b_st | 0.32 | ACCCACCGACAGCAATGAATGTT (SEQ ID NO: 10) |
| [29,] | hsa-miR-195-star_st | 0.35 | GGAGCAGCACAGCCAATATTGG (SEQ ID NO: 14) |
| [30,] | hsa-miR-297_st | 0.44 | CATGCACATGCACACATACAT (SEQ ID NO: 132) |
| [31,] | hsa-miR-29b-2-star_st | 0.35 | CTAAGCCACCATGTGAAACCAG (SEQ ID NO: 39) |
| [32,] | hsa-miR-331-5p_st | 0.32 | GGATCCCTGGGACCATACCTAG (SEQ ID NO: 380) |
| [33,] | hsa-miR-34b_st | 0.42 | ATGGCAGTGGAGTTAGTGATTG (SEQ ID NO: 154) |
| [34,] | hsa-miR-425_st | 0.31 | TCAACGGGAGTGATCGTGTCATT (SEQ ID NO: 286) |
| [35,] | hsa-miR-766_st | 0.36 | GCTGAGGCTGTGGGGCTGGAGT (SEQ ID NO: 1) |
| [36,] | hsa-miR-768-3p_st | 0.46 | GTCAGCAGTTTGAGTGTCAGCATTG (SEQ ID NO: 44) |
| [37,] | hsa-miR-768-5p_st | 0.46 | ATCACTCCGTACTTTCATCCTCCAA (SEQ ID NO: 83) |

TABLE 45

Streptozocin microRNA biomarkers.

| | Medianprobe | Corr | Sequence |
|---|---|---|---|
| [1,] | hsa-miR-296-3p_st | 0.3 | GGAGAGCCTCCACCCAACCCTC (SEQ ID NO: 381) |
| [2,] | hsa-miR-923_st | 0.27 | AGTTTCTTTTCCTCCGCTGAC (SEQ ID NO: 29) |

TABLE 46

Carmustine microRNA biomarkers.

| | Medianprobe | Corr | Sequence |
|---|---|---|---|
| [1,] | ACA10_s_st | 0.34 | TGAAAACACGCCAAGCACACACTGG (SEQ ID NO: 382) |
| [2,] | ACA44_st | 0.43 | CAGGTTGCTCTTGCATGCAGTTGGA (SEQ ID NO: 383) |
| [3,] | ACA52_st | 0.32 | GGAGCCCTGCTCACTCCTCGGGTGA (SEQ ID NO: 384) |
| [4,] | ACA61_st | 0.37 | ACCAAGACCAGTGTTCAGATCCGAT (SEQ ID NO: 385) |
| [5,] | HBII-142_st | 0.3 | CATGGTGTCTCAGTGGCCCAGACAC (SEQ ID NO: 278) |
| [6,] | HBII-180A_x_st | 0.3 | AGTGCTGGACATCATGGAGGCCCCG (SEQ ID NO: 386) |
| [7,] | HBII-382_s_st | 0.33 | AATCGCCTCGATAATCAGTGGCCGG (SEQ ID NO: 387) |
| [8,] | HBII-429_st | 0.34 | GGAGCCAGTTGTCATCATGTACAGC (SEQ ID NO: 388) |
| [9,] | U13_st | 0.31 | GGTCAGACGGGTAATGTGCCCACGT (SEQ ID NO: 389) |
| [10,] | U17a_st | 0.49 | ACCTCCCGGTGTATCCACGTTGGA (SEQ ID NO: 390) |
| [11,] | U17a_x_st | 0.33 | AGGCGCAGACACGAGGCCCAGCTTT (SEQ ID NO: 391) |
| [12,] | U17b_st | 0.4 | GAGGCCCAGCTTCATCTTCAACGTT (SEQ ID NO: 58) |
| [13,] | U17b_x_st | 0.41 | AGCTTCATCTTCAACGTTGTGGAAA (SEQ ID NO: 392) |
| [14,] | U38A_st | 0.36 | TCCTCAGCCTAAAAGGCTCTCATCT (SEQ ID NO: 393) |
| [15,] | U41_st | 0.35 | GGATCAGCCAGTACGAATACGCGAT (SEQ ID NO: 394) |
| [16,] | U48_st | 0.31 | GGTCAGAGCGCTGCGGTGATGGCAT (SEQ ID NO: 395) |
| [17,] | U52_st | 0.36 | CATGACCAGCATCGGAGACTCTAGT (SEQ ID NO: 396) |
| [18,] | U55_st | 0.42 | GAGTATGCAGCATTACCGAGTTGTC (SEQ ID NO: 146) |
| [19,] | U55_x_st | 0.36 | GTATGCAGCATTACCGAGTTGTCAT (SEQ ID NO: 280) |
| [20,] | U67_st | 0.38 | ATCCCAGTTCCCCAAAGGCCTTAGG (SEQ ID NO: 66) |
| [21,] | U67_x_st | 0.31 | TTCCTGAGAGGCACTGATGTCCCCT (SEQ ID NO: 397) |
| [22,] | U70_x_st | 0.36 | ACCCATACAACCAACAGGCTGCGTA (SEQ ID NO: 398) |
| [23,] | U74_x_st | 0.33 | TTACTCTCAGATGTCCCTACCAACA (SEQ ID NO: 399) |
| [24,] | U83B_st | 0.32 | ACATTCCAGGCCTCATCACTGAACA (SEQ ID NO: 400) |
| [25,] | hsa-miR-106a_st | 0.32 | CTACCTGCACTGTAAGCACTTTT (SEQ ID NO: 150) |
| [26,] | hsa-miR-1274a_st | 0.35 | TGGCGCCTGAACAGGGAC (SEQ ID NO: 401) |
| [27,] | hsa-miR-1275_st | 0.41 | GACAGCCTCTCCCCCAC (SEQ ID NO: 70) |
| [28,] | hsa-miR-1280_st | 0.31 | GGGTGGCAGCGGTGGGA (SEQ ID NO: 402) |
| [29,] | hsa-miR-130b_st | 0.45 | ATGCCCTTTCATCATTGCACTG (SEQ ID NO: 403) |
| [30,] | hsa-miR-146b-3p_st | 0.63 | CCAGAACTGAGTCCACAGGGCA (SEQ ID NO: 404) |
| [31,] | hsa-miR-146b-5p_st | 0.54 | AGCCTATGGAATTCAGTTCTCA (SEQ ID NO: 405) |
| [32,] | hsa-miR-17-star_st | 0.43 | CTACAAGTGCCTTCACTGCAGT (SEQ ID NO: 216) |
| [33,] | hsa-miR-185-star_st | 0.31 | GACCAGAGGAAAGCCAGCCCCT (SEQ ID NO: 406) |
| [34,] | hsa-miR-18a-star_st | 0.61 | CCAGAAGGAGCACTTAGGGCAGT (SEQ ID NO: 71) |
| [35,] | hsa-miR-18a_st | 0.44 | CTATCTGCACTAGATGCACCTTA (SEQ ID NO: 72) |
| [36,] | hsa-miR-18b_st | 0.45 | CTAACTGCACTAGATGCACCTTA (SEQ ID NO: 87) |
| [37,] | hsa-miR-19a_st | 0.4 | TCAGTTTTGCATAGATTTGCACA (SEQ ID NO: 217) |
| [38,] | hsa-miR-19b_st | 0.33 | TCAGTTTTGCATGGATTTGCACA (SEQ ID NO: 153) |
| [39,] | hsa-miR-202_st | 0.35 | TTCCCATGCCCTATACCTCT (SEQ ID NO: 407) |
| [40,] | hsa-miR-20a_st | 0.33 | CTACCTGCACTATAAGCACTTTA (SEQ ID NO: 218) |
| [41,] | hsa-miR-20b_st | 0.3 | CTACCTGCACTATGAGCACTTTG (SEQ ID NO: 88) |
| [42,] | hsa-miR-223_st | 0.51 | TGGGGTATTTGACAAACTGACA (SEQ ID NO: 131) |
| [43,] | hsa-miR-25-star_st | 0.54 | CAATTGCCCAAGTCTCCGCCT (SEQ ID NO: 3) |
| [44,] | hsa-miR-373_st | 0.31 | ACACCCCAAAATCGAAGCACTTC (SEQ ID NO: 408) |
| [45,] | hsa-miR-378-star_st | 0.34 | ACACAGGACCTGGAGTCAGGAG (SEQ ID NO: 409) |

TABLE 46-continued

Carmustine microRNA biomarkers.

| | Medianprobe | Corr | Sequence |
|---|---|---|---|
| [46,] | hsa-miR-422a_st | 0.32 | GCCTTCTGACCCTAAGTCCAGT (SEQ ID NO: 410) |
| [47,] | hsa-miR-423-5p_st | 0.32 | AAAGTCTCGCTCTCTGCCCCTCA (SEQ ID NO: 411) |
| [48,] | hsa-miR-451_st | 0.44 | AACTCAGTAATGGTAACGGTTT (SEQ ID NO: 412) |
| [49,] | hsa-miR-486-3p_st | 0.55 | ATCCTGTACTGAGCTGCCCCG (SEQ ID NO: 413) |
| [50,] | hsa-miR-486-5p_st | 0.39 | CTCGGGGCAGCTCAGTACAGGA (SEQ ID NO: 414) |
| [51,] | hsa-miR-504_st | 0.31 | GATAGAGTGCAGACCAGGGTCT (SEQ ID NO: 415) |
| [52,] | hsa-miR-550_st | 0.43 | GGGCTCTTACTCCCTCAGGCACT (SEQ ID NO: 416) |
| [53,] | hsa-miR-616_st | 0.38 | CTGCTCAAACCCTCCAATGACT (SEQ ID NO: 417) |
| [54,] | hsa-miR-611-3p_st | 0.34 | GGTGGAGCCCTGAGAACCGGA (SEQ ID NO: 418) |
| [55,] | hsa-miR-671-5p_st | 0.37 | CTCCAGCCCCTCCAGGGCTTCCT (SEQ ID NO: 43) |
| [56,] | hsa-miR-766_st | 0.38 | GCTGAGGCTGTGGGGCTGGAGT (SEQ ID NO: 1) |
| [57,] | hsa-miR-92a-1-star_st | 0.51 | AGCATTGCAACCGATCCCAACCT (SEQ ID NO: 192) |
| [58,] | hsa-miR-92a_st | 0.39 | ACAGGCCGGGACAAGTGCAATA (SEQ ID NO: 156) |
| [59,] | hsa-miR-93-star_st | 0.32 | CGGGAAGTGCTAGCTCAGCAGT (SEQ ID NO: 45) |

TABLE 47

Lomustine microRNA biomarkers.

| | Medianprobe | Corr | Sequence |
|---|---|---|---|
| [1,] | U41_st | 0.31 | GGATCAGCCAGTACGAATACGCGAT (SEQ ID NO: 394) |
| [2,] | hsa-miR-106b-star_st | 0.33 | GCAGCAAGTACCCACAGTGCGG (SEQ ID NO: 2) |
| [3,] | hsa-miR-1183_st | 0.34 | TGCCCACTCTCACCATCACCTACAG (SEQ ID NO: 126) |
| [4,] | hsa-miR-1207-5p_st | 0.31 | CCCCTCCCAGCCTCCCTGCCA (SEQ ID NO: 109) |
| [5,] | hsa-miR-1281_st | 0.31 | GGGAGAGGAGGAGGCGA (SEQ ID NO: 8) |
| [6,] | hsa-miR-18b_st | 0.3 | CTAACTGCACTAGATGCACCTTA (SEQ ID NO: 87) |
| [7,] | hsa-miR-195-star_st | 0.33 | GGAGCAGCACAGCCAATATTGG (SEQ ID NO: 14) |
| [8,] | hsa-miR-615-3p_st | 0.32 | AAGAGGGAGACCCAGGCTCGGA (SEQ ID NO: 419) |
| [9,] | hsa-miR-631_st | 0.3 | GCTGAGGTCTGGGCCAGGTCT (SEQ ID NO: 135) |
| [10,] | hsa-miR-766_st | 0.46 | GCTGAGGCTGTGGGGCTGGAGT (SEQ ID NO: 1) |
| [11,] | hsa-miR-92a-2-star_st | 0.41 | GTAATGCAACAAATCCCCACCC (SEQ ID NO: 136) |

TABLE 48

Mercaptopurine microRNA biomarkers.

| | Medianprobe | Corr | Sequence |
|---|---|---|---|
| [1,] | ACA43_st | 0.31 | AGGCCATAAACCATTCTCAGTGCCC (SEQ ID NO: 420) |
| [2,] | ACA57_st | 0.32 | AAGAGCCAGCCCTATTCTTAGGACG (SEQ ID NO: 421) |
| [3,] | ENSG00000199411_s_st | 0.34 | TTCATCTCCCTGCTATTGAGTCCAC (SEQ ID NO: 422) |
| [4,] | ENSG00000200879_st | 0.31 | TGTTTTGGACCATTCATCATTGTGA (SEQ ID NO: 423) |
| [5,] | ENSG00000202252_st | 0.43 | GCCAAGCTTTTGGTGGAAACTACGA (SEQ ID NO: 424) |
| [6,] | HBII-142_st | 0.38 | GTGTCTCAGTGGCCCAGACACGTGG (SEQ ID NO: 293) |
| [7,] | HBII-142_x_st | 0.35 | TCAGATCCTCAGTTCCATCATGGTG (SEQ ID NO: 425) |
| [8,] | HBII-202_st | 0.43 | TGTGCTTTCATCAAGGCCGTACAGC (SEQ ID NO: 426) |

TABLE 48-continued

Mercaptopurine microRNA biomarkers.

| | Medianprobe | Corr | Sequence |
|---|---|---|---|
| [9,] | HBII-429_st | 0.34 | CTCATGGCAGTTCAGTAGAGGGAGC (SEQ ID NO: 427) |
| [10,] | U13_st | 0.35 | GTGCCCACGTCGTAACAAGGTTCAA (SEQ ID NO: 428) |
| [11,] | U25_st | 0.34 | TCCTCAGAGTTATTTATCCTCACGG (SEQ ID NO: 429) |
| [12,] | U27_st | 0.34 | GATGACATCACTTGAAAGTTCAGCC (SEQ ID NO: 330) |
| [13,] | U29_st | 0.34 | ATGTATTTTCACTGTCGGTCATAGT (SEQ ID NO: 430) |
| [14,] | U30_st | 0.36 | GATTTCAGAGTCTCAACAGCAAGTC (SEQ ID NO: 431) |
| [15,] | U31_x_st | 0.35 | CAGCTCAGAAAATACCTTTCAGTCA (SEQ ID NO: 190) |
| [16,] | U36C_st | 0.33 | TCAGATGCAATGCTGACCACATGGT (SEQ ID NO: 335) |
| [17,] | U38A_st | 0.37 | CTCTCTCCCTTCAGTAGCAGAACTG (SEQ ID NO: 432) |
| [18,] | U52_st | 0.4 | GACCAGCATCGGAGACTCTAGTCTG (SEQ ID NO: 349) |
| [19,] | U55_st | 0.45 | CCGCGCACTCGGGAGTATGCAGCAT (SEQ ID NO: 433) |
| [20,] | U55_x_st | 0.39 | GAGTATGCAGCATTACCGAGTTGTC (SEQ ID NO: 146) |
| [21,] | U59B_st | 0.35 | GTCAGAACGTACTCATCAGTGAGGA (SEQ ID NO: 434) |
| [22,] | U74_x_st | 0.42 | CAGAGCGGTTGGCATTCATCATTAC (SEQ ID NO: 377) |
| [23,] | U83B_st | 0.37 | ACATTCCAGGCCTCATCACTGAACA (SEQ ID NO: 400) |
| [24,] | U83_st | 0.35 | AGAGTCGTCCTTGCACTGAGGTGCT (SEQ ID NO: 435) |
| [25,] | hsa-miR-106a_st | 0.44 | CTACCTGCACTGTAAGCACTTTT (SEQ ID NO: 150) |
| [26,] | hsa-miR-1275_st | 0.3 | GACAGCCTCTCCCCCAC (SEQ ID NO: 70) |
| [27,] | hsa-miR-17-star_st | 0.42 | CTACAAGTGCCTTCACTGCAGT (SEQ ID NO: 216) |
| [28,] | hsa-miR-17_st | 0.45 | CTACCTGCACTGTAAGCACTTTG (SEQ ID NO: 152) |
| [29,] | hsa-miR-18a-star_st | 0.4 | CCAGAAGGAGCACTTAGGGCAGT (SEQ ID NO: 71) |
| [30,] | hsa-miR-18a_st | 0.42 | CTATCTGCACTAGATGCACCTTA (SEQ ID NO: 72) |
| [31,] | hsa-miR-18b_st | 0.39 | CTAACTGCACTAGATGCACCTTA (SEQ ID NO: 87) |
| [32,] | hsa-miR-19a_st | 0.35 | TCAGTTTTGCATAGATTTGCACA (SEQ ID NO: 217) |
| [33,] | hsa-miR-19b_st | 0.4 | TCAGTTTTGCATGGATTTGCACA (SEQ ID NO: 153) |

TABLE 48-continued

Mercaptopurine microRNA biomarkers.

| | Medianprobe | Corr | Sequence |
|---|---|---|---|
| [34,] | hsa-miR-20a_st | 0.41 | CTACCTGCACTATAAGCACTTTA (SEQ ID NO: 218) |
| [35,] | hsa-miR-20b_st | 0.36 | CTACCTGCACTATGAGCACTTTG (SEQ ID NO: 88) |
| [36,] | hsa-miR-25-star_st | 0.37 | CAATTGCCCAAGTCTCCGCCT (SEQ ID NO: 3) |
| [37,] | hsa-m1R-378-star_st | 0.32 | ACACAGGACCTGGAGTCAGGAG (SEQ ID NO: 409) |
| [38,] | hsa-miR-378_st | 0.36 | CCTTCTGACTCCAAGTCCAGT (SEQ ID NO: 368) |
| [39,] | hsa-miR-422a_st | 0.33 | GCCTTCTGACCCTAAGTCCAGT (SEQ ID NO: 410) |
| [40,] | hsa-miR-423-5p_st | 0.34 | AAAGTCTCGCTCTCTGCCCCTCA (SEQ ID NO: 411) |
| [41,] | hsa-miR-663b_st | 0.33 | CCTCAGGCACGGCCGGGCCACC (SEQ ID NO: 155) |
| [42,] | hsa-miR-766_st | 0.32 | GCTGAGGCTGTGGGGCTGGAGT (SEQ ID NO: 1) |
| [43,] | hsa-miR-92a-1-star_st | 0.47 | AGCATTGCAACCGATCCCAACCT (SEQ ID NO: 192) |
| [44,] | hsa-miR-92a_st | 0.44 | ACAGGCCGGGACAAGTGCAATA (SEQ ID NO: 156) |

TABLE 49

Teniposide microRNA biomarkers.

| | Medianprobe | Corr | Sequence |
|---|---|---|---|
| [1,] | ACA48_x_st | 0.33 | GAGTTGCTTTGTCCCTGGCTGATAT (SEQ ID NO: 436) |
| [2,] | ACA7_s_st | 0.31 | AATGGGTGCCTCTGCCAGGCTTGCT (SEQ ID NO: 437) |
| [3,] | HBII-239_st | 0.31 | CCGTACTTTCATCCTCCAACACACA (SEQ ID NO: 438) |
| [4,] | HBII-429_st | 0.31 | ATCAGAAGGGTGACATGGCAGTTTC (SEQ ID NO: 55) |
| [5,] | HBII-85-26_st | 0.32 | AGATCCATTTTTTTTATAGTCATCA (SEQ ID NO: 439) |
| [6,] | U104_st | 0.39 | TTTAATTGGAATGTCATCACAGCAG (SEQ ID NO: 140) |
| [7,] | U17b_st | 0.31 | GAGGCCCAGCTTCATCTTCAACGTT (SEQ ID NO: 58) |
| [8,] | U17b_x_st | 0.31 | CAGCTTCATCTTCAACGTTGTGGAA (SEQ ID NO: 328) |
| [9,] | U55_st | 0.34 | CGCGCACTCGGGAGTATGCAGCATT (SEQ ID NO: 308) |
| [10,] | U55_x_st | 0.37 | GTATGCAGCATTACCGAGTTGTCAT (SEQ ID NO: 280) |
| [11,] | hsa-miR-106b-star_st | 0.31 | GCAGCAAGTACCCACAGTGCGG (SEQ ID NO: 2) |
| [12,] | hsa-miR-124_st | 0.36 | GGCATTCACCGCGTGCCTTA (SEQ ID NO: 7) |
| [13,] | hsa-miR-1281_st | 0.33 | GGGAGAGGAGGAGGCGA (SEQ ID NO: 8) |
| [14,] | hsa-miR-1299_st | 0.41 | TCCCTCACACAGAATTCCAGAA (SEQ ID NO: 38) |
| [15,] | hsa-miR-140-3p_st | 0.34 | CCGTGGTTCTACCCTGTGGTA (SEQ ID NO: 13) |
| [16,] | hsa-miR-142-5p_st | 0.31 | AGTAGTGCTTTCTACTTTATG (SEQ ID NO: 215) |
| [17,] | hsa-miR-181a-star_st | 0.43 | GGTACAATCAACGGTCGATGGT (SEQ ID NO: 9) |
| [18,] | hsa-miR-181a_st | 0.33 | ACTCACCGACAGCGTTGAATGTT (SEQ ID NO: 78) |
| [19,] | hsa-miR-181b_st | 0.35 | ACCCACCGACAGCAATGAATGTT (SEQ ID NO: 10) |
| [20,] | hsa-miR-181c_st | 0.35 | ACTCACCGACAGGTTGAATGTT (SEQ ID NO: 79) |
| [21,] | hsa-miR-195-star_st | 0.4 | GGAGCAGCACAGCCAATATTGG (SEQ ID NO: 14) |
| [22,] | hsa-miR-297_st | 0.4 | CATGCACATGCACACATACAT (SEQ ID NO: 132) |

TABLE 49-continued

Teniposide microRNA biomarkers.

| | Medianprobe | Corr | Sequence |
|---|---|---|---|
| [23,] | hsa-miR-29b-2-star_st | 0.37 | CTAAGCCACCATGTGAAACCAG (SEQ ID NO: 39) |
| [24,] | hsa-miR-33b-star_st | 0.31 | GGGCTGCACTGCCGAGGCACTG (SEQ ID NO: 40) |
| [25,] | hsa-miR-34b_st | 0.41 | ATGGCAGTGGAGTTAGTGATTG (SEQ ID NO: 154) |
| [26,] | hsa-miR-629-star_st | 0.3 | GCTGGGCTTACGTTGGGAGAAC (SEQ ID NO: 41) |
| [27,] | hsa-miR-766_st | 0.32 | GCTGAGGCTGTGGGGCTGGAGT (SEQ ID NO: 1) |
| [28,] | hsa-miR-768-3p_st | 0.43 | GTCAGCAGTTTGAGTGTCAGCATTG (SEQ ID NO: 44) |
| [29,] | hsa-miR-768-5p_st | 0.38 | ATCACTCCGTACTTTCATCCTCCAA (SEQ ID NO: 83) |
| [30,] | hsa-miR-92b_st | 0.31 | GGAGGCCGGGACGAGTGCAATA (SEQ ID NO: 15) |

TABLE 50

Dactinomycin microRNA biomarkers.

| | Medianprobe | Corr | Sequence |
|---|---|---|---|
| [1,] | hsa-miR-106b-star_st | 0.36 | GCAGCAAGTACCCACAGTGCGG (SEQ ID NO: 2) |
| [2,] | hsa-miR-106b_st | 0.43 | ATCTGCACTGTCAGCACTTTA (SEQ ID NO: 37) |
| [3,] | hsa-miR-1275_st | 0.31 | GACAGCCTCTCCCCCAC (SEQ ID NO: 70) |
| [4,] | hsa-miR-25-star_st | 0.34 | CAATTGCCCAAGTCTCCGCCT (SEQ ID NO: 3) |
| [5,] | hsa-miR-25_st | 0.39 | TCAGACCGAGACAAGTGCAATG (SEQ ID NO: 89) |
| [6,] | hsa-miR-33b-star_st | 0.36 | GGGCTGCACTGCCGAGGCACTG (SEQ ID NO: 40) |
| [7,] | hsa-miR-362-5p_st | 0.33 | ACTCACACCTAGGTTCCAAGGATT (SEQ ID NO: 92) |
| [8,] | hsa-miR-500-star_st | 0.31 | CAGAATCCTTGCCCAGGTGCAT (SEQ ID NO: 93) |
| [9,] | hsa-miR-500_st | 0.36 | TCTCACCCAGGTAGCAAGGATTA (SEQ ID NO: 94) |
| [10,] | hsa-miR-501-5p_st | 0.35 | TCTCACCCAGGGACAAAGGATT (SEQ ID NO: 304) |
| [11,] | hsa-miR-502-3p_st | 0.31 | TGAATCCTTGCCCAGGTGCATT (SEQ ID NO: 96) |
| [12,] | hsa-miR-532-5p_st | 0.36 | ACGGTCCTACACTCAAGGCATG (SEQ ID NO: 98) |
| [13,] | hsa-miR-629-star_st | 0.41 | GCTGGGCTTACGTTGGGAGAAC (SEQ ID NO: 41) |
| [14,] | hsa-miR-629_st | 0.35 | AGTTCTCCCAACGTAAACCCA (SEQ ID NO: 440) |
| [15,] | hsa-miR-652_st | 0.51 | CACAACCCTAGTGGCGCCATT (SEQ ID NO: 42) |
| [16,] | hsa-miR-671-5p_st | 0.34 | CTCCAGCCCCTCCAGGGCTTCCT (SEQ ID NO: 43) |
| [17,] | hsa-miR-766_st | 0.35 | GCTGAGGCTGTGGGGCTGGAGT (SEQ ID NO: 1) |
| [18,] | hsa-miR-93-star_st | 0.31 | CGGGAAGTGCTAGCTCAGCAGT (SEQ ID NO: 45) |
| [19,] | hsa-miR-93_st | 0.41 | CTACCTGCACGAACAGCACTTTG (SEQ ID NO: 46) |

TABLE 51

Tretinoin microRNA biomarkers.

| | Medianprobe | Corr | Sequence |
|---|---|---|---|
| [1,] | HBII-142_st | 0.37 | CATGGTGTCTCAGTGGCCCAGACAC (SEQ ID NO: 278) |
| [2,] | HBII-142_x_st | 0.35 | AGTTCCATCATGGTGTCTCAGTGGC (SEQ ID NO: 279) |
| [3,] | U55_st | 0.3 | GCACTCGGGAGTATGCAGCATTACC (SEQ ID NO: 6) |
| [4,] | U55_x_st | 0.3 | GTATGCAGCATTACCGAGTTGTCAT (SEQ ID NO: 280) |
| [5,] | hsa-miR-1202_st | 0.4 | CTCCCCCACTGCAGCTGGCAC (SEQ ID NO: 281) |
| [6,] | hsa-miR-124_st | 0.34 | GGCATTCACCGCGTGCCTTA (SEQ ID NO: 7) |
| [7,] | hsa-miR-148a-star_st | 0.31 | AGTCGGAGTGTCTCAGAACTTT (SEQ ID NO: 282) |
| [8,] | hsa-miR-149a_st | 0.35 | ACAAAGTTCTGTAGTGCACTGA (SEQ ID NO: 275) |
| [9,] | hsa-miR-184_st | 0.36 | ACCCTTATCAGTTCTCCGTCCA (SEQ ID NO: 283) |
| [10,] | hsa-miR-191_st | 0.32 | CAGCTGCTTTTGGGATTCCGTTG (SEQ ID NO: 284) |
| [11,] | hsa-miR-195-star_st | 0.31 | GGAGCAGCACAGCCAATATTGG (SEQ ID NO: 14) |
| [12,] | hsa-miR-29b-2-star_st | 0.37 | CTAAGCCACCATGTGAAACCAG (SEQ ID NO: 39) |
| [13,] | hsa-miR-425-star_st | 0.32 | CGGCGGACACGACATTCCCGAT (SEQ ID NO: 285) |
| [14,] | hsa-miR-425_st | 0.37 | TCAACGGGAGTGATCGTGTCATT (SEQ ID NO: 286) |
| [15,] | hsa-miR-449a_st | 0.43 | ACCAGCTAACAATACACTGCCA (SEQ ID NO: 287) |
| [16,] | hsa-miR-449b_st | 0.5 | GCCAGCTAACAATACACTGCCT (SEQ ID NO: 288) |
| [17,] | hsa-miR-551b_st | 0.31 | CTGAAACCAAGTATGGGTCGC (SEQ ID NO: 289) |

TABLE 51-continued

Tretinoin microRNA biomarkers.

| | Medianprobe | Corr | Sequence |
|---|---|---|---|
| [18,] | hsa-miR-593-star_st | 0.31 | GCTGAGCAATGCCTGGCTGGTGCCT (SEQ ID NO: 290) |
| [19,] | hsa-miR-768-3p_st | 0.38 | GTCAGCAGTTTGAGTGTCAGCATTG (SEQ ID NO: 44) |
| [20,] | hsa-miR-768-5p_st | 0.31 | ATCACTCCGTACTTTCATCCTCCAA (SEQ ID NO: 83) |
| [21,] | hsa-miR-877_st | 0.3 | CCCTGCGCCATCTCCTCTAC (SEQ ID NO: 291) |

TABLE 52

Ifosfamide microRNA biomarkers.

| | Medianprobe | Corr | Sequence |
|---|---|---|---|
| [1,] | U17b_st | 0.3 | GGCCCAGCTTCATCTTCAACGTTGT (SEQ ID NO: 254) |
| [2,] | U48_st | 0.33 | CTGCGGTGATGGCATCAGCGACACA (SEQ ID NO: 441) |
| [3,] | U49B_s_st | 0.31 | AGTTATCGCTTCTGACGGCACTTCC (SEQ ID NO: 442) |
| [4,] | U55_st | 0.32 | CCACCGCGCACTCGGGAGTATGCAG (SEQ ID NO: 209) |

TABLE 52-continued

Ifosfamide microRNA biomarkers.

| | Medianprobe | Corr | Sequence |
|---|---|---|---|
| [5,] | hsa-miR-1207-5p_st | 0.32 | CCCCTCCCAGCCTCCCTGCCA (SEQ ID NO: 109) |
| [6,] | hsa-miR-128_st | 0.33 | AAAGAGACCGGTTCACTGTGA (SEQ ID NO: 110) |
| [7,] | hsa-miR-181a-star_st | 0.38 | GGTACAATCAACGGTCGATGGT (SEQ ID NO: 9) |
| [8,] | hsa-miR-181c-star_st | 0.33 | GTCCACTCAACGGTCGATGGTT (SEQ ID NO: 443) |
| [9,] | hsa-miR-181d_st | 0.34 | ACCCACCGACAACAATGAATGTT (SEQ ID NO: 321) |
| [10,] | hsa-miR-20b-star_st | 0.36 | CTGGAAGTGCCCATACTACAGT (SEQ ID NO: 130) |
| [11,] | hsa-miR-20b_st | 0.32 | CTACCTGCACTATGAGCACTTTG (SEQ ID NO: 88) |
| [12,] | hsa-miR-223_st | 0.33 | TGGGGTATTTGACAAACTGACA (SEQ ID NO: 131) |
| [13,] | hsa-miR-363_st | 0.33 | TACAGATGGATACCGTGCAATT (SEQ ID NO: 133) |
| [14,] | hsa-miR-766_st | 0.4 | GCTGAGGCTGTGGGGCTGGAGT (SEQ ID NO: 1) |

TABLE 53

Tamoxifen microRNA biomarkers.

| | Medianprobe | Corr | Sequence |
|---|---|---|---|
| [1,] | ACA10_s_st | 0.33 | TCTGCCTCCCTGAAAACACGCCAAG (SEQ ID NO: 444) |
| [2,] | ACA15_s_st | 0.37 | CTGGCTGTGTAAACTACTGATAAAA (SEQ ID NO: 445) |
| [3,] | ACA43_st | 0.34 | AACTGTCTGTGGTGCCAACAGGTCC (SEQ ID NO: 446) |
| [4,] | ACA44_st | 0.34 | TATTGTACTGACCTGCGCTGTCAAA (SEQ ID NO: 447) |
| [5,] | ACA51_x_st | 0.3 | GAACACAGCCTGTGGTAAGCACCAG (SEQ ID NO: 324) |
| [6,] | ACA57_st | 0.41 | AGGGAATTGCTGTGTGTCCTGCCAG (SEQ ID NO: 448) |
| [7,] | ENSG00000202252_st | 0.32 | ATCCAAGGAAGGTGTTGCCATCATT (SEQ ID NO: 449) |
| [8,] | HBII-142_st | 0.38 | TCCATCATGGTGTCTCAGTGGCCCA (SEQ ID NO: 450) |
| [9,] | HBII-142_x_st | 0.33 | TCAGATCCTCAGTTCCATCATGGTG (SEQ ID NO: 425) |
| [10,] | HBII-180A_x_st | 0.48 | GGCACCGTGTCCTCAGTGGCAGTCG (SEQ ID NO: 54) |
| [11,] | HBII-180C_st | 0.38 | TGCACTGTGTCCTCAGGGGTGATCA (SEQ ID NO: 451) |
| [12,] | HBII-180C_x_st | 0.4 | GTCCTGGGGTGCACTGTGTCCTCAG (SEQ ID NO: 452) |

TABLE 53-continued

Tamoxifen microRNA biomarkers.

| | Medianprobe | Corr | Sequence |
|---|---|---|---|
| [13,] | HBII-202_st | 0.31 | ACAGCGATTCCGGAGAATGTCATCA (SEQ ID NO: 198) |
| [14,] | HBII-429_st | 0.36 | GGAGCCAGTTGTCATCATGTACAGC (SEQ ID NO: 388) |
| [15,] | HBII-55_st | 0.39 | GACATGGAGACATCAGTGATTGCAC (SEQ ID NO: 453) |
| [16,] | U104_st | 0.38 | AGGCTCAGACTCCAGTTCGCATCAC (SEQ ID NO: 56) |
| [17,] | U17a_st | 0.34 | CGAGGCCCAGCTTTATTTCCAACGT (SEQ ID NO: 454) |
| [18,] | U17a_x_st | 0.31 | CTACGCCACTTGGACAGAGCCCGGG (SEQ ID NO: 455) |
| [19,] | U17b_st | 0.5 | CCCAGCTTCATCTTCAACGTTGTGG (SEQ ID NO: 456) |
| [20,] | U17b_x_st | 0.45 | GACCTCCCAGGGTATCCACGTTGGA (SEQ ID NO: 457) |
| [21,] | U32A_x_st | 0.39 | ATGGTGAATGTTGCTCATCACTGAC (SEQ ID NO: 458) |
| [22,] | U33_st | 0.44 | TCTCATGGTCGGGAAACTCGAATGT (SEQ ID NO: 459) |
| [23,] | U34_st | 0.4 | TAGGTAGTTGCGGAACATCATGGAC (SEQ ID NO: 256) |
| [24,] | U35A_st | 0.36 | TCGTGAGATAAGGACATCATCTGCC (SEQ ID NO: 460) |
| [25,] | U38A_st | 0.37 | CTGGACAGAGTTTTCATCACGAGAA (SEQ ID NO: 461) |
| [26,] | U43_st | 0.31 | ACACAGTTTCTGTCCGCCCGTCAAT (SEQ ID NO: 462) |
| [27,] | U43_x_st | 0.31 | ACACAGTTTCTGTCCGCCCGTCAAT (SEQ ID NO: 462) |
| [28,] | U46_x_st | 0.32 | GTGGCACACAGGTGACCAAGACGGC (SEQ ID NO: 463) |
| [29,] | U52_st | 0.32 | GTTTTGACATCATGACCAGCATCGG (SEQ ID NO: 258) |
| [30,] | U55_st | 0.44 | CCACCGCGCACTCGGGAGTATGCAG (SEQ ID NO: 209) |
| [31,] | U55_x_st | 0.44 | GAGTATGCAGCATTACCGAGTTGTC (SEQ ID NO: 146) |
| [32,] | U56_st | 0.35 | CCAGAGTCTCAACACTCACTAGGTG (SEQ ID NO: 464) |
| [33,] | U56_x_st | 0.3 | CACTAGGTGAACTGCTGTTGACGAA (SEQ ID NO: 211) |
| [34,] | U59B_st | 0.3 | CGAAAGTCAGAACGTACTCATCAGT (SEQ ID NO: 465) |
| [35,] | U68_st | 0.33 | AAAGGCGACAAGATCCGCTTGCTGT (SEQ ID NO: 466) |
| [36,] | U70_x_st | 0.38 | ACCCATACAACCAACAGGCTGCGTA (SEQ ID NO: 398) |
| [37,] | U71d_st | 0.35 | TTCCGCGATTTCTTTCCCTGCACTA (SEQ ID NO: 467) |

TABLE 53-continued

Tamoxifen microRNA biomarkers.

| | Medianprobe | Corr | Sequence |
|---|---|---|---|
| [38,] | U71d_x_st | 0.34 | AAACACGGGGAAGCACTTTCCGCGA (SEQ ID NO: 468) |
| [39,] | U74x_st | 0.43 | TTCATCATTACTCTCAGATGTCCCT (SEQ ID NO: 191) |
| [40,] | U83B_st | 0.4 | TGTCTCGGGCGCTGTGCCCAGCGCA (SEQ ID NO: 469) |
| [41,] | hsa-miR-106a_st | 0.31 | CTACCTGCACTGTAAGCACTTTT (SEQ ID NO: 150) |
| [42,] | hsa-miR-106b-star_st | 0.37 | GCAGCAAGTACCCACAGTGCGG (SEQ ID NO: 2) |
| [43,] | hsa-miR-106b_st | 0.31 | ATCTGCACTGTCAGCACTTTA (SEQ ID NO: 37) |
| [44,] | hsa-miR-1183_st | 0.33 | TGCCCACTCTCACCATCACCTACAG (SEQ ID NO: 126) |
| [45,] | hsa-miR-1228_st | 0.34 | GGGGGGCGAGGCAGGTGTGA (SEQ ID NO: 84) |
| [46,] | hsa-miR-1246_st | 0.35 | CCTGCTCCAAAAATCCATT (SEQ ID NO: 214) |
| [47,] | hsa-miR-1281_st | 0.38 | GGGAGAGGAGGAGGCGA (SEQ ID NO: 8) |
| [48,] | hsa-miR-149-star_st | 0.33 | GCACAGCCCCGTCCCTCCCT (SEQ ID NO: 359) |
| [49,] | hsa-miR-17-star_st | 0.44 | CTACAAGTGCCTTCACTGCAGT (SEQ ID NO: 216) |
| [50,] | hsa-miR-17_st | 0.32 | CTACCTGCACTGTAAGCACTTTG (SEQ ID NO: 152) |
| [51,] | hsa-miR-18a-star_st | 0.37 | CCAGAAGGAGCACTTAGGGCAGT (SEQ ID NO: 71) |
| [52,] | hsa-miR-18a_st | 0.37 | CTATCTGCACTAGATGCACCTTA (SEQ ID NO: 72) |
| [53,] | hsa-miR-195-star_st | 0.32 | GGAGCAGCACAGCCAATATTGG (SEQ ID NO: 14) |
| [54,] | hsa-miR-19a_st | 0.34 | TCAGTTTTGCATAGATTTGCACA (SEQ ID NO: 217) |
| [55,] | hsa-miR-19b_st | 0.41 | TCAGTTTTGCATGGATTTGCACA (SEQ ID NO: 153) |
| [56,] | hsa-miR-20a_st | 0.3 | CTACCTGCACTATAAGCACTTTA (SEQ ID NO: 218) |
| [57,] | hsa-miR-25-star_st | 0.35 | CAATTGCCCAAGTCTCCGCCT (SEQ ID NO: 3) |
| [58,] | hsa-miR-297_st | 0.38 | CATGCACATGCACACATACAT (SEQ ID NO: 132) |
| [59,] | hsa-miR-34b_st | 0.38 | ATGGCAGTGGAGTTAGTGATTG (SEQ ID NO: 154) |
| [60,] | hsa-miR-593-star_st | 0.31 | GCTGAGCAATGCCTGGCTGGTGCCT (SEQ ID NO: 290) |
| [61,] | hsa-miR-629-star_st | 0.3 | GCTGGGCTTACGTTGGGAGAAC (SEQ ID NO: 41) |
| [62,] | hsa-miR-652_st | 0.32 | CACAACCCTAGTGGCGCCATT (SEQ ID NO: 42) |

TABLE 53-continued

Tamoxifen microRNA biomarkers.

| | Medianprobe | Corr | Sequence |
|---|---|---|---|
| [63,] | hsa-miR-671-5p_st | 0.35 | CTCCAGCCCCTCCAGGGCTTCCT (SEQ ID NO: 43) |
| [64,] | hsa-miR-769-5p_st | 0.33 | AGCTCAGAACCCAGAGGTCTCA (SEQ ID NO: 105) |
| [65,] | hsa-miR-92a_st | 0.38 | ACAGGCCGGGACAAGTGCAATA (SEQ ID NO: 156) |
| [66,] | hsa-miR-93-star_st | 0.36 | CGGGAAGTGCTAGCTCAGCAGT (SEQ ID NO: 45) |
| [67,] | hsa-miR-93_st | 0.31 | CTACCTGCACGAACAGCACTTTG (SEQ ID NO: 46) |

TABLE 54

Irinotecan microRNA biomarkers.

| | Medianprobe | Corr | Sequence |
|---|---|---|---|
| [1,] | hsa-miR-181a-star_st | 0.39 | GGTACAATCAACGGTCGATGGT (SEQ ID NO: 9) |
| [2,] | hsa-miR-297_st | 0.32 | CATGCACATGCACACATACAT (SEQ ID NO: 132) |
| [3,] | hsa-miR-432_st | 0.31 | CCACCCAATGACCTACTCCAAGA (SEQ ID NO: 12) |
| [4,] | hsa-miR-766_st | 0.34 | GCTGAGGCTGTGGGGCTGGAGT (SEQ ID NO: 1) |
| [5,] | hsa-miR-874_st | 0.33 | TCGGTCCCTCGGGCCAGGGCAG (SEQ ID NO: 310) |

TABLE 55

Floxuridine microRNA biomarkers.

| | Medianprobe | Corr | Sequence |
|---|---|---|---|
| [1,] | HBII-202_st | 0.35 | GCGATTCCGGAGAATGTCATCACGC (SEQ ID NO: 239) |
| [2,] | HBII-85-11_st | 0.31 | AAGGAACCCACGTATGGAAGTCATC (SEQ ID NO: 470) |
| [3,] | U104_st | 0.3 | AATTGGAATGTCATCACAGCAGGCC (SEQ ID NO: 471) |
| [4,] | U13_st | 0.32 | GTGGCACATCTCACACAAGCGTATG (SEQ ID NO: 472) |

TABLE 56

Thioguanine microRNA biomarkers.

| | Medianprobe | Corr | Sequence |
|---|---|---|---|
| [1,] | ACA13_st | 0.3 | GGCAGGAAAAGGCTGCAAAGCGTTT (SEQ ID NO: 473) |
| [2,] | ENSG00000202093_x_st | 0.3 | TTTCATAGTTATTCCAAAGGTGTCC (SEQ ID NO: 474) |
| [3,] | ENSG00000202252_st | 0.4 | ACATCCAAGGAAGGTGTTGCCATCA (SEQ ID NO: 244) |
| [4,] | HBII-202_st | 0.4 | ACAGCGATTCCGGAGAATGTCATCA (SEQ ID NO: 198) |
| [5,] | HBII-429_st | 0.35 | GTGACATGGCAGTTTCCTCATGGCA (SEQ ID NO: 475) |
| [6,] | HBII-55_st | 0.32 | TGGAGACATCAGTGATTGCACTCAG (SEQ ID NO: 476) |
| [7,] | U104_st | 0.41 | GGCAGGCTCAGACTCCAGTTCGCAT (SEQ ID NO: 116) |
| [8,] | U13_st | 0.37 | ACCCAATCATCACGCTCATGAACTA (SEQ ID NO: 477) |
| [9,] | U17b_st | 0.35 | CCCAGCTTCATCTTCAACGTTGTGG (SEQ ID NO: 456) |
| [10,] | U17b_x_st | 0.32 | ACGAGGCCCAGCTTCATCTTCAACG (SEQ ID NO: 59) |
| [11,] | U25_st | 0.35 | TCTCCTCAGAGTTATTTATCCTCAC (SEQ ID NO: 478) |
| [12,] | U27_st | 0.33 | GATGACATCACTTGAAAGTTCAGCC (SEQ ID NO: 330) |
| [13,] | U29_st | 0.35 | GAGCTAGTTTGATTCATCATAGAAA (SEQ ID NO: 203) |
| [14,] | U30_st | 0.37 | TCAACAGCAAGTCATCAGCCGAACG (SEQ ID NO: 479) |
| [15,] | U31_st | 0.31 | GAAAATACCTTTCAGTCACACATTG (SEQ ID NO: 142) |

TABLE 56-continued

Thioguanine microRNA biomarkers.

| Medianprobe | Corr | Sequence |
|---|---|---|
| [16,] U31_x_st | 0.31 | GCTCAGAAAATACCTTTCAGTCACA (SEQ ID NO: 205) |
| [17,] U36A_st | 0.31 | GCTCATGGATTCGCACTTCAAGGTT (SEQ ID NO: 480) |
| [18,] U36C_st | 0.31 | TGACCACATGGTTTATTCAGGTGAA (SEQ ID NO: 481) |
| [19,] U38A_st | 0.37 | GGCTCTCATCTCTCTCCCTTCAGTA (SEQ ID NO: 348) |
| [20,] U52_st | 0.45 | GTTTTGACATCATGACCAGCATCGG (SEQ ID NO: 258) |
| [21,] U54_st | 0.32 | AACACAATAGGTACCTCCTCATCGC (SEQ ID NO: 482) |
| [22,] U55_st | 0.38 | TTCCCCACCGCGCACTCGGGAGTAT (SEQ ID NO: 208) |
| [23,] U55_x_st | 0.38 | GTATGCAGCATTACCGAGTTGTCAT (SEQ ID NO: 280) |
| [24,] U56_x_st | 0.3 | ACCCAGAGTCTCAACACTCACTAGG (SEQ ID NO: 210) |
| [25,] U74_x_st | 0.44 | AGAGCGGTTGGCATTCATCATTACT (SEQ ID NO: 264) |
| [26,] U75_st | 0.32 | TCAGAAATCCCTTCTGTCCACTACT (SEQ ID NO: 483) |
| [27,] U78_s_st | 0.31 | CTACATGCTCATTTCAGGTCAGACA (SEQ ID NO: 484) |
| [28,] U78_x_st | 0.32 | ACCTTTGTCTACATGCTCATTTCAG (SEQ ID NO: 228) |
| [29,] U83B_st | 0.34 | CAAGGAACGGTTCCGCAGTCTGTCT (SEQ ID NO: 485) |
| [30,] U83_st | 0.32 | ATAAGAGTCGTCCTTGCACTGAGGT (SEQ ID NO: 486) |
| [31,] U95_st | 0.32 | TCTGGATTTCAGCACCGACACTCAG (SEQ ID NO: 487) |
| [32,] hsa-miR-106a_st | 0.45 | CTACCTGCACTGTAAGCACTTTT (SEQ ID NO: 150) |
| [33,] hsa-miR-1183_st | 0.31 | TGCCCACTCTCACCATCACCTACAG (SEQ ID NO: 126) |
| [34,] hsa-miR-1246_st | 0.38 | CCTGCTCCAAAAATCCATT (SEQ ID NO: 214) |
| [35,] hsa-miR-1281_st | 0.32 | GGGAGAGGAGGAGGCGA (SEQ ID NO: 8) |
| [36,] hsa-miR-142-5p_st | 0.31 | AGTAGTGCTTTCTACTTTATG (SEQ ID NO: 215) |
| [37,] hsa-miR-17-star_st | 0.45 | CTACAAGTGCCTTCACTGCAGT (SEQ ID NO: 216) |
| [38,] hsa-miR-17_st | 0.47 | CTACCTGCACTGTAAGCACTTTG (SEQ ID NO: 152) |
| [39,] hsa-miR-18a-star_st | 0.39 | CCAGAAGGAGCACTTAGGGCAGT (SEQ ID NO: 71) |
| [40,] hsa-miR-18a_st | 0.41 | CTATCTGCACTAGATGCACCTTA (SEQ ID NO: 72) |
| [41,] hsa-miR-18b_st | 0.33 | CTAACTGCACTAGATGCACCTTA (SEQ ID NO: 87) |
| [42,] hsa-miR-19a_st | 0.36 | TCAGTTTTGCATAGATTTGCACA (SEQ ID NO: 217) |
| [43,] hsa-miR-19b_st | 0.38 | TCAGTTTTGCATGGATTTGCACA (SEQ ID NO: 153) |
| [44,] hsa-miR-20a_st | 0.43 | CTACCTGCACTATAAGCACTTTA (SEQ ID NO: 218) |
| [45,] hsa-miR-297_st | 0.33 | CATGCACATGCACACATACAT (SEQ ID NO: 132) |
| [46,] hsa-miR-34b_st | 0.34 | ATGGCAGTGGAGTTAGTGATTG (SEQ ID NO: 154) |
| [47,] hsa-miR-378-star_st | 0.32 | ACACAGGACCTGGAGTCAGGAG (SEQ ID NO: 409) |
| [48,] hsa-miR-378_st | 0.36 | CCTTCTGACTCCAAGTCCAGT (SEQ ID NO: 368) |
| [49,] hsa-miR-491-3p_st | 0.32 | GTAGAAGGGAATCTTGCATAAG (SEQ ID NO: 351) |
| [50,] hsa-miR-766_st | 0.36 | GCTGAGGCTGTGGGCTGGAGT (SEQ ID NO: 1) |
| [51,] hsa-miR-92a-1-star_st | 0.41 | AGCATTGCAACCGATCCCAACCT (SEQ ID NO: 192) |
| [52,] hsa-miR-92a_st | 0.45 | ACAGGCCGGGACAAGTGCAATA (SEQ ID NO: 156) |

TABLE 57

PSC 833 microRNA biomarkers.

| Medianprobe | Corr | Sequence |
|---|---|---|
| [1,] ACA18_x_st | 0.31 | GCTACAGGAAAAGCCCCATCGGGAT (SEQ ID NO: 48) |
| [2,] ACA9_st | 0.34 | CTGTTCTAGCAAGCACTGAAGGAAT (SEQ ID NO: 373) |
| [3,] ENSG00000202252_st | 0.31 | GCCATCATTAGCCAAGCTTTTGGTG (SEQ ID NO: 488) |
| [4,] HBII-180A_x_st | 0.4 | GGCACCGTGTCCTCAGTGGCAGTCG (SEQ ID NO: 54) |
| [5,] HBII-180B_x_st | 0.32 | TGCACCGTGTCCTCAGGGGCAGTCA (SEQ ID NO: 489) |
| [6,] HBII-180C_st | 0.34 | GTCCTCAGGGGTGATCAGAGCCCAG (SEQ ID NO: 490) |
| [7,] HBII-180C_x_st | 0.36 | TCAGGGGTGATCAGAGCCCAGTGCT (SEQ ID NO: 491) |
| [8,] HBII-382_s_st | 0.32 | ATCAGAATCGCCTCGATAATCAGTG (SEQ ID NO: 492) |
| [9,] U3-2_s_st | 0.37 | GCAGTTGCAGCCAAGCAACGCCAGA (SEQ ID NO: 493) |
| [10,] U34_st | 0.3 | GCTGCTTTCATGAGGATCAAACAAT (SEQ ID NO: 355) |
| [11,] U38B_st | 0.31 | TTATCTTCACTTACTGTCAGTAGCA (SEQ ID NO: 494) |
| [12,] U50B_x_st | 0.31 | TCGGGATAGGTTTCATCATTGATTA (SEQ ID NO: 495) |
| [13,] U56_st | 0.3 | TCACTCAGACCCAGAGTCTCAACAC (SEQ ID NO: 496) |
| [14,] U59B_st | 0.32 | TCAGAAATTGCATCTGGCTTCAGCA (SEQ ID NO: 497) |
| [15,] U68_x_st | 0.32 | CAAATTCACTTTGAGGGGCACGGCC (SEQ ID NO: 498) |
| [16,] hsa-miR-106a_st | 0.42 | CTACCTGCACTGTAAGCACTTTT (SEQ ID NO: 150) |
| [17,] hsa-miR-1281_st | 0.32 | GGGAGAGGAGGAGGCGA (SEQ ID NO: 8) |
| [18,] hsa-miR-1292_st | 0.35 | CAGCGTCTGCCGGAACCCATTCCCA (SEQ ID NO: 499) |
| [19,] hsa-miR-1307_st | 0.34 | CACGACCGACGCCACGCCGAGT (SEQ ID NO: 102) |
| [20,] hsa-miR-17-star_st | 0.32 | CTACAAGTGCCTTCACTGCAGT (SEQ ID NO: 216) |
| [21,] hsa-miR-17_st | 0.44 | CTACCTGCACTGTAAGCACTTTG (SEQ ID NO: 152) |
| [22,] hsa-miR-18a-star_st | 0.39 | CCAGAAGGAGCACTTAGGGCAGT (SEQ ID NO: 71) |
| [23,] hsa-miR-18a_st | 0.43 | CTATCTGCACTAGATGCACCTTA (SEQ ID NO: 72) |
| [24,] hsa-miR-18b_st | 0.32 | CTAACTGCACTAGATGCACCTTA (SEQ ID NO: 87) |
| [25,] hsa-miR-19b_st | 0.34 | TCAGTTTTGCATGGATTTGCACA (SEQ ID NO: 153) |
| [26,] hsa-miR-20a_st | 0.37 | CTACCTGCACTATAAGCACTTTA (SEQ ID NO: 218) |
| [27,] hsa-miR-25-star_st | 0.31 | CAATTGCCCAAGTCTCCGCCT (SEQ ID NO: 3) |
| [28,] hsa-miR-378-star_st | 0.48 | ACACAGGACCTGGAGTCAGGAG (SEQ ID NO: 409) |
| [29,] hsa-miR-378_st | 0.45 | CCTTCTGACTCCAAGTCCAGT (SEQ ID NO: 368) |
| [30,] hsa-miR-422a_st | 0.47 | GCCTTCTGACCCTAAGTCCAGT (SEQ ID NO: 410) |
| [31,] hsa-miR-92a-1-star_st | 0.34 | AGCATTGCAACCGATCCCAACCT (SEQ ID NO: 192) |
| [32,] hsa-miR-92a_st | 0.45 | ACAGGCCGGGACAAGTGCAATA (SEQ ID NO: 156) |
| [33,] hsa-miR-93-star_st | 0.31 | CGGGAAGTGCTAGCTCAGCAGT (SEQ ID NO: 45) |

TABLE 58

Erlotinib (tarceva) microRNA biomarkers.

| Medianprobe | Corr | Sequence |
|---|---|---|
| [1,] hsa-miR-130a_st | 0.36 | ATGCCCTTTTAACATTGCACTG (SEQ ID NO: 313) |
| [2,] hsa-miR-149_st | 0.34 | GGGAGTGAAGACACGGAGCCAGA (SEQ ID NO: 500) |
| [3,] hsa-miR-193a-3p_st | 0.31 | ACTGGGACTTTGTAGGCCAGTT (SEQ ID NO: 366) |

TABLE 58-continued

Erlotinib (tarceva) microRNA biomarkers.

| Medianprobe | Corr | Sequence |
|---|---|---|
| [4,] hsa-miR-27a_st | 0.3 | GCGGAACTTAGCCACTGTGAA (SEQ ID NO: 501) |
| [5,] hsa-miR-30a-star_st | 0.53 | GCTGCAAACATCCGACTGAAAG (SEQ ID NO: 502) |
| [6,] hsa-miR-30a_st | 0.51 | CTTCCAGTCGAGGATGTTTACA (SEQ ID NO: 503) |
| [7,] hsa-miR-30c-2-star_st | 0.56 | AGAGTAAACAGCCTTCTCCCAG (SEQ ID NO: 504) |
| [8,] hsa-miR-30c_st | 0.65 | GCTGAGAGTGTAGGATGTTTACA (SEQ ID NO: 301) |
| [9,] hsa-miR-30e-star_st | 0.35 | GCTGTAAACATCCGACTGAAAG (SEQ ID NO: 505) |

TABLE 59

Herceptin microRNA biomarkers.

| Medianprobe | Corr | Sequence |
|---|---|---|
| [1,] hsa-miR-34c-3p_st | 0.34 | CCTGGCCGTGTGGTTAGTGATT (SEQ ID NO: 314) |
| [2,] hsa-miR-34c-5p_st | 0.32 | GCAATCAGCTAACTACACTGCCT (SEQ ID NO: 506) |
| [3,] hsa-miR-489_st | 0.3 | GCTGCCGTATATGTGATGTCAC (SEQ ID NO: 298) |

TABLE 60

Celecoxib microRNA biomarkers.

| Medianprobe | Corr | Sequence |
|---|---|---|
| [1,] ACA18_x_st | 0.3 | GCGTTTCCAACGATGTGCAGGCTAC (SEQ ID NO: 139) |
| [2,] ACA51_x_st | 0.3 | CTATGTTCCCCCATTCACAATACAG (SEQ ID NO: 507) |
| [3,] HBII-142_st | 0.32 | GTGTCTCAGTGGCCCAGACACGTGG (SEQ ID NO: 293) |
| [4,] HBII-142_x_st | 0.35 | TGGTGTCTCAGTGGCCCAGACACGT (SEQ ID NO: 508) |
| [5,] HBII-180A_x_st | 0.31 | AGTGCTGGACATCATGGAGGCCCCG (SEQ ID NO: 386) |
| [6,] HBII-180C_x_st | 0.3 | TGCACTGTGTCCTCAGGGGTGATCA (SEQ ID NO: 451) |
| [7,] U68_x_st | 0.3 | CGACAAGATCCGCTTGCTGTTTGCA (SEQ ID NO: 67) |
| [8,] U70_x_st | 0.3 | GTGCAGCCATCGCACACTGGGTCCC (SEQ ID NO: 509) |
| [9,] hsa-miR-1207-5p_st | 0.33 | CCCCTCCCAGCCTCCCTGCCA (SEQ ID NO: 109) |
| [10,] hsa-miR-1268_st | 0.31 | CCCCCACCACCACGCCCG (SEQ ID NO: 127) |

TABLE 60-continued

Celecoxib microRNA biomarkers.

| Medianprobe | Corr | Sequence |
|---|---|---|
| [11,] hsa-miR-768-3p_st | 0.37 | GTCAGCAGTTTGAGTGTCAGCATTG (SEQ ID NO: 44) |

TABLE 61

Fulvestrant microRNA biomarkers.

| Medianprobe | Corr | Sequence |
|---|---|---|
| [1,] U104_st | 0.35 | GGCAGGCTCAGACTCCAGTTCGCAT (SEQ ID NO: 116) |
| [2,] hsa-miR-1202_st | 0.43 | CTCCCCCACTGCAGCTGGCAC (SEQ ID NO: 281) |
| [3,] hsa-miR-1226_st | 0.33 | CTAGGGAACACAGGGCTGGTGA (SEQ ID NO: 365) |
| [4,] hsa-miR-15b_st | 0.3 | TGTAAACCATGATGTGCTGCTA (SEQ ID NO: 510) |
| [5,] hsa-miR-191_st | 0.46 | CAGCTGCTTTTGGGATTCCGTTG (SEQ ID NO: 284) |
| [6,] hsa-miR-203_st | 0.32 | CTAGTGGTCCTAAACATTTCAC (SEQ ID NO: 511) |
| [7,] hsa-miR-25_st | 0.33 | TCAGACCGAGACAAGTGCAATG (SEQ ID NO: 89) |
| [8,] hsa-miR-29b-2-star_st | 0.3 | CTAAGCCACCATGTGAAACCAG (SEQ ID NO: 39) |
| [9,] hsa-miR-301a_st | 0.47 | GCTTTGACAATACTATTGCACTG (SEQ ID NO: 342) |
| [10,] hsa-miR-339-5p_st | 0.35 | CGTGAGCTCCTGGAGGACAGGGA (SEQ ID NO: 273) |
| [11,] hsa-miR-342-5p_st | 0.45 | TCAATCACAGATAGCACCCCT (SEQ ID NO: 80) |
| [12,] hsa-miR-421_st | 0.36 | GCGCCCAATTAATGTCTGTTGAT (SEQ ID NO: 512) |
| [13,] hsa-miR-425-star_st | 0.36 | GGGCGGACACGACATTCCCGAT (SEQ ID NO: 285) |
| [14,] hsa-miR-425_st | 0.49 | TCAACGGGAGTGATCGTGTCATT (SEQ ID NO: 286) |
| [15,] hsa-miR-449b_st | 0.35 | GCCAGCTAACAATACACTGCCT (SEQ ID NO: 288) |
| [16,] hsa-miR-489_st | 0.61 | GCTGCCGTATATGTGATGTCAC (SEQ ID NO: 298) |
| [17,] hsa-miR-492_st | 0.36 | AAGAATCTTGTCCCGCAGGTCCT (SEQ ID NO: 513) |
| [18,] hsa-miR-622_st | 0.37 | GCTCCAACCTCAGCAGACTGT (SEQ ID NO: 514) |
| [19,] hsa-miR-768-3p_st | 0.41 | GTCAGCAGTTTGAGTGTCAGCATTG (SEQ ID NO: 44) |
| [20,] hsa-miR-768-5p_st | 0.39 | ATCACTCCGTACTTTCATCCTCCAA (SEQ ID NO: 83) |

TABLE 62

Iressa microRNA biomarkers.

| | Medianprobe | Corr | Sequence |
|---|---|---|---|
| [1,] | hsa-miR-1826_st | 0.34 | ATTGCGTTCGAAGTGTCGATGATCA (SEQ ID NO: 515) |
| [2,] | hsa-miR-205_st | 0.3 | CAGACTCCGGTGGAATGAAGGA (SEQ ID NO: 295) |
| [3,] | hsa-miR-30c_st | 0.46 | GCTGAGAGTGTAGGATGTTTACA (SEQ ID NO: 301) |
| [4,] | hsa-miR-675_st | 0.32 | CACTGTGGGCCCTCTCCGCACCA (SEQ ID NO: 516) |
| [5,] | hsa-miR-934_st | 0.48 | CCAGTGTCTCCAGTAGTAGACA (SEQ ID NO: 517) |

TABLE 63

Anastrozole microRNA biomarkers.

| | Medianprobe | Corr | Sequence |
|---|---|---|---|
| [1,] | hsa-miR-1323_st | 0.31 | AGAAAATGCCCCTCAGTTTTGA (SEQ ID NO: 518) |
| [2,] | hsa-miR-184_st | 0.34 | ACCCTTATCAGTTCTCCGTCCA (SEQ ID NO: 283) |
| [3,] | hsa-miR-187_st | 0.38 | CCGGCTGCAACACAAGACACGA (SEQ ID NO: 519) |
| [4,] | hsa-miR-197_st | 0.32 | GCTGGGTGGAGAAGGTGGTGAA (SEQ ID NO: 520) |
| [5,] | hsa-miR-498_st | 0.45 | GAAAACGCCCCCTGGCTTGAAA (SEQ ID NO: 521) |
| [6,] | hsa-miR-504_st | 0.42 | GATAGAGTGCAGACCAGGGTCT (SEQ ID NO: 415) |
| [7,] | hsa-miR-506_st | 0.38 | TCTACTCAGAAGGGTGCCTTA (SEQ ID NO: 21) |
| [8,] | hsa-miR-508-5p_st | 0.42 | CATGAGTGACGCCCTCTGGAGTA (SEQ ID NO: 22) |
| [9,] | hsa-miR-509-3-5p_st | 0.35 | CATGATTGCCACGTCTGCAGTA (SEQ ID NO: 23) |
| [10,] | hsa-miR-509-3p_st | 0.37 | CTACCCACAGACGTACCAATCA (SEQ ID NO: 24) |
| [11,] | hsa-miR-509-5p_st | 0.38 | TGATTGCCACTGTCTGCAGTA (SEQ ID NO: 522) |
| [12,] | hsa-miR-510_st | 0.36 | GTGATTGCCACTCTCCTGAGTA (SEQ ID NO: 25) |
| [13,] | hsa-miR-512-3p_st | 0.54 | GACCTCAGCTATGACAGCACTT (SEQ ID NO: 523) |
| [14,] | hsa-miR-513a-5p_st | 0.39 | ATGACACCTCCCTGTGAA (SEQ ID NO: 26) |
| [15,] | hsa-miR-513b_st | 0.31 | ATAAATGACACCTCCTTGTGAA (SEQ ID NO: 27) |
| [16,] | hsa-miR-513c_st | 0.39 | ATAAACGACACCTCCTTGAGAA (SEQ ID NO: 524) |
| [17,] | hsa-miR-516b_st | 0.53 | AAAGTGCTTCTTACCTCCAGAT (SEQ ID NO: 525) |

TABLE 63-continued

Anastrozole microRNA biomarkers.

| | Medianprobe | Corr | Sequence |
|---|---|---|---|
| [18,] | hsa-miR-517a_st | 0.56 | ACACTCTAAAGGGATGCACGAT (SEQ ID NO: 526) |
| [19,] | hsa-miR-517b_st | 0.38 | AACACTCTAAAGGGATGCACGA (SEQ ID NO: 527) |
| [20,] | hsa-miR-525-5p_st | 0.52 | AGAAAGTGCATCCCTCTGGAG (SEQ ID NO: 528) |
| [21,] | hsa-miR-526b_st | 0.33 | ACAGAAAGTGCTTCCCTCAAGAG (SEQ ID NO: 529) |
| [22,] | hsa-miR-551a_st | 0.54 | TGGAAACCAAGAGTGGGTCGC (SEQ ID NO: 530) |
| [23,] | hsa-miR-873_st | 0.31 | AGGAGACTCACAAGTTCCTGC (SEQ ID NO: 531) |
| [24,] | hsa-miR-891a_st | 0.36 | TCAGTGGCTCAGGTTCGTTGCA (SEQ ID NO: 532) |

TABLE 64

Letrozole microRNA biomarkers.

| | Medianprobe | Corr | Sequence |
|---|---|---|---|
| [1,] | hsa-miR-1323_st | 0.31 | AGAAAATGCCCCTCAGTTTTGA (SEQ ID NO: 518) |
| [2,] | hsa-miR-361-5p_st | 0.35 | GTACCCCTGGAGATTCTGATAA (SEQ ID NO: 533) |
| [3,] | hsa-miR-498_st | 0.36 | GAAAACGCCCCCTGGCTTGAAA (SEQ ID NO: 521) |
| [4,] | hsa-miR-512-3p_st | 0.37 | GACCTCAGCTATGACAGCACTT (SEQ ID NO: 523) |
| [5,] | hsa-miR-516b_st | 0.48 | AAAGTGCTTCTTACCTCCAGAT (SEQ ID NO: 525) |
| [6,] | hsa-miR-517a_st | 0.52 | ACACTCTAAAGGGATGCACGAT (SEQ ID NO: 526) |
| [7,] | hsa-miR-525-5p_st | 0.42 | AGAAAGTGCATCCCTCTGGAG (SEQ ID NO: 528) |
| [8,] | hsa-miR-551a_st | 0.57 | TGGAAACCAAGAGTGGGTCGC (SEQ ID NO: 530) |
| [9,] | hsa-miR-873_st | 0.32 | AGGAGACTCACAAGTTCCTGC (SEQ ID NO: 531) |

TABLE 65

Cetuximab (erbitux) microRNA biomarkers.

| | Medianprobe | Corr | Sequence |
|---|---|---|---|
| [1,] | hsa-miR-1826_st | 0.31 | ATTGCGTTCGAAGTGTCGATGATCA (SEQ ID NO: 515) |
| [2,] | hsa-miR-30c-2-star_st | 0.31 | AGAGTAAACAGCCTTCTCCCAG (SEQ ID NO: 504) |
| [3,] | hsa-miR-34b-star_st | 0.37 | CAATCAGCTAATGACACTGCCTA (SEQ ID NO: 534) |
| [4,] | hsa-miR-34c-3p_st | 0.46 | CCTGGCCGTGTGGTTAGTGATT (SEQ ID NO: 314) |

TABLE 65-continued

Cetuximab (erbitux) microRNA biomarkers.

| | Medianprobe | Corr | Sequence |
|---|---|---|---|
| [5,] | hsa-miR-34c-5p_st | 0.4 | GCAATCAGCTAACTACACTGCCT (SEQ ID NO: 506) |
| [6,] | hsa-miR-489_st | 0.3 | GCTGCCGTATATGTGATGTCAC (SEQ ID NO: 298) |

TABLE 66

Vincristine microRNA biomarkers.

| | Medianprobe | Corr | Sequence |
|---|---|---|---|
| [1,] | HBII-85-29_st | -0.34 | TTCAGATTTCCAAGGTTTCCATTTT (SEQ ID NO: 535) |
| [2,] | hsa-miR-130a_st | -0.3 | ATGCCCTTTTAACATTGCACTG (SEQ ID NO: 313) |
| [3,] | hsa-miR-148b_st | -0.33 | ACAAAGTTCTGTGATGCACTGA (SEQ ID NO: 536) |
| [4,] | hsa-miR-184_st | -0.4 | ACCCTTATCAGTTCTCCGTCCA (SEQ ID NO: 283) |
| [5,] | hsa-miR-26a_st | -0.31 | AGCCTATCCTGGATTACTTGAA (SEQ ID NO: 537) |
| [6,] | hsa-miR-30a-star_st | -0.33 | GCTGCAAACATCCGACTGAAAG (SEQ ID NO: 502) |
| [7,] | hsa-miR-30a_st | -0.39 | CTTCCAGTCGAGGATGTTTACA (SEQ ID NO: 503) |
| [8,] | hsa-miR-30c-2-star_st | -0.33 | AGAGTAAACAGCCTTCTCCCAG (SEQ ID NO: 504) |
| [9,] | hsa-miR-30c_st | -0.43 | GCTGAGAGTGTAGGATGTTTACA (SEQ ID NO: 301) |
| [10,] | hsa-miR-34a-star_st | -0.33 | AGGGCAGTATACTTGCTGATTG (SEQ ID NO: 277) |
| [11,] | hsa-miR-34a_st | -0.32 | ACAACCAGCTAAGACACTGCCA (SEQ ID NO: 234) |
| [12,] | hsa-miR-34c-5p_st | -0.38 | GCAATCAGCTAACTACACTGCCT (SEQ ID NO: 506) |
| [13,] | hsa-miR-449a_st | -0.5 | ACCAGCTAACAATACACTGCCA (SEQ ID NO: 287) |
| [14,] | hsa-miR-449b_st | -0.49 | GCCAGCTAACAATACACTGCCT (SEQ ID NO: 288) |

TABLE 67

Cisplatin microRNA biomarkers.

| | Medianprobe | Corr | Sequence |
|---|---|---|---|
| [1,] | hsa-miR-10a_st | -0.34 | CACAAATTCGGATCTACAGGGTA (SEQ ID NO: 538) |
| [2,] | hsa-miR-151-3p_st | -0.38 | CCTCAAGGAGCTTCAGTCTAG (SEQ ID NO: 539) |
| [3,] | hsa-miR-151-5p_st | -0.35 | ACTAGACTGTGAGCTCCTCGA (SEQ ID NO: 540) |

TABLE 67-continued

Cisplatin microRNA biomarkers.

| | Medianprobe | Corr | Sequence |
|---|---|---|---|
| [4,] | hsa-miR-192-star_st | -0.33 | CTGTGACCTATGGAATTGGCAG (SEQ ID NO: 541) |
| [5,] | hsa-miR-192_st | -0.4 | GGCTGTCAATTCATAGGTCAG (SEQ ID NO: 542) |
| [6,] | hsa-miR-194_st | -0.4 | TCCACATGGAGTTGCTGTTACA (SEQ ID NO: 543) |
| [7,] | hsa-miR-200b_st | -0.32 | TCATCATTACCAGGCAGTATTA (SEQ ID NO: 544) |
| [8,] | hsa-miR-203_st | -0.36 | CTAGTGGTCCTAAACATTTCAC (SEQ ID NO: 511) |
| [9,] | hsa-miR-29b_st | -0.36 | AACACTGATTTCAAATGGTGCTA (SEQ ID NO: 545) |
| [10,] | hsa-miR-30b_st | -0.4 | AGCTGAGTGTAGGATGTTTACA (SEQ ID NO: 546) |
| [11,] | hsa-miR-30d_st | -0.38 | CTTCCAGTCGGGGATGTTTACA (SEQ ID NO: 547) |
| [12,] | hsa-miR-625_st | -0.34 | GGACTATAGAACTTTCCCCCT (SEQ ID NO: 548) |

TABLE 68

Etoposide microRNA biomarkers.

| | Medianprobe | Corr | Sequence |
|---|---|---|---|
| [1,] | hsa-let-7e_st | -0.34 | AACTATACAACCTCCTACCTCA (SEQ ID NO: 549) |
| [2,] | hsa-miR-10b_st | -0.37 | CACAAATTCGGTTCTACAGGGTA (SEQ ID NO: 550) |
| [3,] | hsa-miR-125a-5p_st | -0.33 | TCACAGGTTAAAGGGTCTCAGGGA (SEQ ID NO: 551) |
| [4,] | hsa-miR-141_st | -0.37 | CCATCTTTACCAGACAGTGTTA (SEQ ID NO: 552) |
| [5,] | hsa-miR-151-3p_st | -0.43 | CCTCAAGGAGCTTCAGTCTAG (SEQ ID NO: 539) |
| [6,] | hsa-miR-151-5p_st | -0.47 | ACTAGACTGTGAGCTCCTCGA (SEQ ID NO: 540) |
| [7,] | hsa-miR-200a-star_st | -0.3 | TCCAGCACTGTCCGGTAAGATG (SEQ ID NO: 553) |
| [8,] | hsa-miR-200a_st | -0.34 | ACATCGTTACCAGACAGTGTTA (SEQ ID NO: 554) |
| [9,] | hsa-miR-200b-star_st | -0.33 | TCCAATGCTGCCCAGTAAGATG (SEQ ID NO: 555) |
| [10,] | hsa-miR-200b_st | -0.38 | TCATCATTACCAGGCAGTATTA (SEQ ID NO: 544) |
| [11,] | hsa-miR-200c_st | -0.35 | TCCATCATTACCCGGCAGTATTA (SEQ ID NO: 556) |
| [12,] | hsa-miR-203_st | -0.34 | CTAGTGGTCCTAAACATTTCAC (SEQ ID NO: 511) |
| [13,] | hsa-miR-30a_st | -0.32 | CTTCCAGTCGAGGATGTTTACA (SEQ ID NO: 503) |

TABLE 68-continued

Etoposide microRNA biomarkers.

| | Medianprobe | Corr | Sequence |
|---|---|---|---|
| [14,] | hsa-miR-30b_st | -0.35 | AGCTGAGTGTAGGATGTTTACA (SEQ ID NO: 546) |
| [15,] | hsa-miR-30c_st | -0.34 | GCTGAGAGTGTAGGATGTTTACA (SEQ ID NO: 301) |
| [16,] | hsa-miR-30d_st | -0.43 | CTTCCAGTCGGGGATGTTTACA (SEQ ID NO: 547) |
| [17,] | hsa-miR-429_st | -0.31 | ACGGTTTTACCAGACAGTATTA (SEQ ID NO: 557) |
| [18,] | hsa-miR-516a-5p_st | -0.37 | GAAAGTGCTTCTTTCCTCGAGAA (SEQ ID NO: 558) |
| [19,] | hsa-miR-934_st | -0.41 | CCAGTGTCTCCAGTAGTAGACA (SEQ ID NO: 517) |
| [20,] | hsa-miR-99b_st | -0.33 | CGCAAGGTCGGTTCTACGGGTG (SEQ ID NO: 559) |

TABLE 69

Azaguanine microRNA biomarkers.

| | Medianprobe | Corr | Sequence |
|---|---|---|---|
| [1,] | hsa-miR-1244_st | -0.3 | AACCATCTCATACAAACCAACTACT (SEQ ID NO: 560) |
| [2,] | hsa-miR-1303_st | -0.32 | AGAGCAAGACCCCGTCTCTAAA (SEQ ID NO: 561) |
| [3,] | hsa-miR-141-star_st | -0.35 | TCCAACACTGTACTGGAAGATG (SEQ ID NO: 562) |
| [4,] | hsa-miR-141_st | -0.6 | CCATCTTTACCAGACAGTGTTA (SEQ ID NO: 552) |
| [5,] | hsa-miR-182_st | -0.38 | AGTGTGAGTTCTACCATTGCCAAA (SEQ ID NO: 563) |
| [6,] | hsa-miR-183-star_st | -0.38 | TTATGGCCCTTCGGTAATTCAC (SEQ ID NO: 564) |
| [7,] | hsa-miR-183_st | -0.45 | AGTGAATTCTACCAGTGCCATA (SEQ ID NO: 565) |
| [8,] | hsa-miR-192-star_st | -0.4 | CTGTGACCTATGGAATTGGCAG (SEQ ID NO: 541) |
| [9,] | hsa-miR-192_st | -0.46 | GGCTGTCAATTCATAGGTCAG (SEQ ID NO: 542) |
| [10,] | hsa-miR-194_st | -0.46 | TCCACATGGAGTTGCTGTTACA (SEQ ID NO: 543) |
| [11,] | hsa-miR-200a-star_st | -0.37 | TCCAGCACTGTCCGGTAAGATG (SEQ ID NO: 553) |
| [12,] | hsa-miR-200a_st | -0.43 | ACATCGTTACCAGACAGTGTTA (SEQ ID NO: 554) |
| [13,] | hsa-miR-200b-star_st | -0.42 | TCCAATGCTGCCCAGTAAGATG (SEQ ID NO: 555) |
| [14,] | hsa-miR-200b_st | -0.42 | TCATCATTACCAGGCAGTATTA (SEQ ID NO: 544) |
| [15,] | hsa-miR-200c-star_st | -0.5 | CCAAACACTGCTGGGTAAGACG (SEQ ID NO: 231) |

TABLE 69-continued

Azaguanine microRNA biomarkers.

| | Medianprobe | Corr | Sequence |
|---|---|---|---|
| [16,] | hsa-miR-200c_st | -0.64 | TCCATCATTACCCGGCAGTATTA (SEQ ID NO: 556) |
| [17,] | hsa-miR-203_st | -0.51 | CTAGTGGTCCTAAACATTTCAC (SEQ ID NO: 511) |
| [18,] | hsa-miR-205_st | -0.38 | CAGACTCCGGTGGAATGAAGGA (SEQ ID NO: 295) |
| [19,] | hsa-miR-215_st | -0.36 | GTCTGTCAATTCATAGGTCAT (SEQ ID NO: 566) |
| [20,] | hsa-miR-27b_st | -0.3 | GCAGAACTTAGCCACTGTGAA (SEQ ID NO: 567) |
| [21,] | hsa-miR-331-3p_st | -0.3 | TTCTAGGATAGGCCCAGGGGC (SEQ ID NO: 568) |
| [22,] | hsa-miR-375_st | -0.35 | TCACGCGAGCCGAACGAACAAA (SEQ ID NO: 297) |
| [23,] | hsa-miR-429_st | -0.4 | ACGGTTTTACCAGACAGTATTA (SEQ ID NO: 557) |
| [24,] | hsa-miR-622_st | -0.43 | GCTCCAACCTCAGCAGACTGT (SEQ ID NO: 514) |
| [25,] | hsa-miR-934_st | -0.37 | CCAGTGTCTCCAGTAGTAGACA (SEQ ID NO: 517) |
| [26,] | hsa-miR-99b-star_st | -0.31 | CGGACCCACAGACACGAGCTTG (SEQ ID NO: 569) |

TABLE 70

Carboplatin microRNA biomarkers.

| | Medianprobe | Corr | Sequence |
|---|---|---|---|
| [1,] | hsa-miR-10a_st | -0.31 | CACAAATTCGGATCTACAGGGTA (SEQ ID NO: 538) |
| [2,] | hsa-miR-183_st | -0.33 | AGTGAATTCTACCAGTGCCATA (SEQ ID NO: 565) |
| [3,] | hsa-miR-192-star_st | -0.33 | CTGTGACCTATGGAATTGGCAG (SEQ ID NO: 541) |
| [4,] | hsa-miR-192_st | -0.38 | GGCTGTCAATTCATAGGTCAG (SEQ ID NO: 542) |
| [5,] | hsa-miR-194_st | -0.4 | TCCACATGGAGTTGCTGTTACA (SEQ ID NO: 543) |
| [6,] | hsa-miR-200a-star_st | -0.31 | TCCAGCACTGTCCGGTAAGATG (SEQ ID NO: 553) |
| [7,] | hsa-miR-200a_st | -0.35 | ACATCGTTACCAGACAGTGTTA (SEQ ID NO: 554) |
| [8,] | hsa-miR-200b-star_st | -0.35 | TCCAATGCTGCCCAGTAAGATG (SEQ ID NO: 555) |
| [9,] | hsa-miR-200b_st | -0.37 | TCATCATTACCAGGCAGTATTA (SEQ ID NO: 544) |
| [10,] | hsa-miR-200c-star_st | -0.31 | CCAAACACTGCTGGGTAAGACG (SEQ ID NO: 231) |
| [11,] | hsa-miR-203_st | -0.39 | CTAGTGGTCCTAAACATTTCAC (SEQ ID NO: 511) |

TABLE 70 -continued

Carboplatin microRNA biomarkers.

| | Medianprobe | Corr | Sequence |
|---|---|---|---|
| [12,] | hsa-miR-29b_st | −0.41 | AACACTGATTTCAAATGGTGCTA (SEQ ID NO: 545) |
| [13,] | hsa-miR-30b_st | −0.39 | AGCTGAGTGTAGGATGTTTACA (SEQ ID NO: 546) |
| [14,] | hsa-miR-30d_st | −0.32 | CTTCCAGTCGGGGATGTTTACA (SEQ ID NO: 547) |
| [15,] | hsa-miR-429_st | −0.36 | ACGGTTTTACCAGACAGTATTA (SEQ ID NO: 557) |
| [16,] | hsa-miR-625_st | −0.37 | GGACTATAGAACTTTCCCCCT (SEQ ID NO: 548) |
| [17,] | hsa-miR-7_st | −0.31 | ACAACAAAATCACTAGTCTTCCA (SEQ ID NO: 570) |

TABLE 71

Adriamycin microRNA biomarkers.

| | Medianprobe | Corr | Sequence |
|---|---|---|---|
| [1,] | hsa-let-7e_st | −0.37 | AACTATACAACCTCCTACCTCA (SEQ ID NO: 549) |
| [2,] | hsa-miR-125a-5p_st | −0.36 | TCACAGGTTAAAGGGTCTCAGGGA (SEQ ID NO: 551) |
| [3,] | hsa-miR-151-3p_st | −0.41 | CCTCAAGGAGCTTCAGTCTAG (SEQ ID NO: 539) |
| [4,] | hsa-miR-151-5p_st | −0.43 | ACTAGACTGTGAGCTCCTCGA (SEQ ID NO: 540) |
| [5,] | hsa-miR-203_st | −0.31 | CTAGTGGTCCTAAACATTTCAC (SEQ ID NO: 511) |
| [6,] | hsa-miR-23a_st | −0.36 | GGAAATCCCTGGCAATGTGAT (SEQ ID NO: 571) |
| [7,] | hsa-miR-29b_st | −0.34 | AACACTGATTTCAAATGGTGCTA (SEQ ID NO: 545) |
| [8,] | hsa-miR-30a_st | −0.31 | CTTCCAGTCGAGGATGTTTACA (SEQ ID NO: 503) |
| [9,] | hsa-miR-30c_st | −0.31 | GCTGAGAGTGTAGGATGTTTACA (SEQ ID NO: 301) |
| [10,] | hsa-miR-516a-5p_st | −0.53 | GAAAGTGCTTCTTTCCTCGAGAA (SEQ ID NO: 558) |
| [11,] | hsa-miR-518d-5p_st | −0.3 | CAGAAAGTGCTTCCCTCTAGAG (SEQ ID NO: 572) |
| [12,] | hsa-miR-518e-star_st | −0.35 | CAGAAAGCGCTTCCCTCTAGAG (SEQ ID NO: 573) |
| [13,] | hsa-miR-519a-star_st | −0.36 | CAGAAAGCGCTTCCCTCTAGAG (SEQ ID NO: 573) |
| [14,] | hsa-miR-519a_st | −0.41 | ACACTCTAAAAGGATGCACTTT (SEQ ID NO: 574) |
| [15,] | hsa-miR-519b-5p_st | −0.35 | CAGAAAGCGCTTCCCTCTAGAG (SEQ ID NO: 573) |
| [16,] | hsa-miR-519c-5p_st | −0.38 | CAGAAAGCGCTTCCCTCTAGAG (SEQ ID NO: 573) |

TABLE 71 -continued

Adriamycin microRNA biomarkers.

| | Medianprobe | Corr | Sequence |
|---|---|---|---|
| [17,] | hsa-miR-522-star_st | −0.34 | CAGAAAGCGCTTCCCTCTAGAG (SEQ ID NO: 573) |
| [18,] | hsa-miR-523-star_st | −0.32 | CAGAAAGCGCTTCCCTCTAGAG (SEQ ID NO: 573) |
| [19,] | hsa-miR-526a_st | −0.36 | CAGAAAGTGCTTCCCTCTAGAG (SEQ ID NO: 572) |
| [20,] | hsa-miR-99b_st | −0.33 | CGCAAGGTCGGTTCTACGGGTG (SEQ ID NO: 559) |

TABLE 72

Aclarubicin microRNA biomarkers.

| | Medianprobe | Corr | Sequence |
|---|---|---|---|
| [1,] | hsa-let-7a_st | −0.33 | AACTATACAACCTACTACCTCA (SEQ ID NO: 575) |
| [2,] | hsa-let-7c_st | −0.32 | AACCATACAACCTACTACCTCA (SEQ ID NO: 576) |
| [3,] | hsa-let-7e_st | −0.37 | AACTATACAACCTCCTACCTCA (SEQ ID NO: 549) |
| [4,] | hsa-let-7f_st | −0.31 | AACTATACAATCTACTACCTCA (SEQ ID NO: 577) |
| [5,] | hsa-miR-125a-5p_st | −0.36 | TCACAGGTTAAAGGGTCTCAGGA (SEQ ID NO: 551) |
| [6,] | hsa-miR-193a-5p_st | −0.33 | TCATCTCGCCCGCAAAGACCCA (SEQ ID NO: 165) |
| [7,] | hsa-miR-22-star_st | −0.33 | TAAAGCTTGCCACTGAAGAACT (SEQ ID NO: 578) |
| [8,] | hsa-miR-22_st | −0.33 | ACAGTTCTTCAACTGGCAGCTT (SEQ ID NO: 167) |
| [9,] | hsa-miR-23a_st | −0.35 | GGAAATCCCTGGCAATGTGAT (SEQ ID NO: 571) |
| [10,] | hsa-miR-24-2-star_st | −0.43 | CTGTGTTTCAGCTCAGTAGGCA (SEQ ID NO: 579) |
| [11,] | hsa-miR-24_st | −0.33 | CTGTTCCTGCTGAACTGAGCCA (SEQ ID NO: 580) |
| [12,] | hsa-miR-30a_st | −0.34 | CTTCCAGTCGAGGATGTTTACA (SEQ ID NO: 503) |
| [13,] | hsa-miR-99b_st | −0.33 | CGCAAGGTCGGTTCTACGGGTG (SEQ ID NO: 559) |

TABLE 73

Mitoxantrone microRNA biomarkers.

| | Medianprobe | Corr | Sequence |
|---|---|---|---|
| [1,] | hsa-miR-151-5p_st | −0.35 | ACTAGACTGTGAGCTCCTCGA (SEQ ID NO: 540) |
| [2,] | hsa-miR-29b_st | −0.31 | AACACTGATTTCAAATGGTGCTA (SEQ ID NO: 545) |

TABLE 73-continued

Mitoxantrone microRNA biomarkers.

| | Medianprobe | Corr | Sequence |
|---|---|---|---|
| [3,] | hsa-miR-30b_st | −0.43 | AGCTGAGTGTAGGATGTTTACA (SEQ ID NO: 546) |
| [4,] | hsa-miR-30d_st | −0.48 | CTTCCAGTCGGGGATGTTTACA (SEQ ID NO: 547) |
| [5,] | hsa-miR-506_st | −0.34 | TCTACTCAGAAGGGTGCCTTA (SEQ ID NO: 21) |
| [6,] | hsa-miR-508-5p_st | −0.32 | CATGAGTGACGCCCTCTGGAGTA (SEQ ID NO: 22) |
| [7,] | hsa-miR-509-3-5p_st | −0.36 | CATGATTGCCACGTCTGCAGTA (SEQ ID NO: 23) |
| [8,] | hsa-miR-509-3p_st | −0.34 | CTACCCACAGACGTACCAATCA (SEQ ID NO: 24) |
| [9,] | hsa-miR-509-5p_st | −0.32 | TGATTGCCACTGTCTGCAGTA (SEQ ID NO: 522) |
| [10,] | hsa-miR-510_st | −0.31 | GTGATTGCCACTCTCCTGAGTA (SEQ ID NO: 25) |
| [11,] | hsa-miR-513a-5p_st | −0.34 | ATGACACCTCCCTGTGAA (SEQ ID NO: 26) |
| [12,] | hsa-miR-513c_st | −0.3 | ATAAACGACACCTCCTTGAGAA (SEQ ID NO: 524) |
| [13,] | hsa-miR-516a-5p_st | −0.33 | GAAAGTGCTTCTTTCCTCGAGAA (SEQ ID NO: 558) |
| [14,] | hsa-miR-584_st | −0.41 | CTCAGTCCCAGGCAAACCATAA (SEQ ID NO: 581) |
| [15,] | hsa-miR-885-3p_st | −0.32 | TATCCACTACACCCCGCTGCCT (SEQ ID NO: 582) |

TABLE 74

Mitomycin microRNA biomarkers.

| | Medianprobe | Corr | Sequence |
|---|---|---|---|
| [1,] | hsa-miR-516a-5p_st | −0.33 | GAAAGTGCTTCTTTCCTCGAGAA (SEQ ID NO: 558) |
| [2,] | hsa-miR-526a_st | −0.35 | CAGAAGTGCTTCCCTCTAGAG (SEQ ID NO: 572) |

TABLE 75

Paclitaxel (Taxol) microRNA biomarkers.

| | Medianprobe | Corr | Sequence |
|---|---|---|---|
| [1,] | HBII-85-29_st | −0.31 | TTCAGATTTCCAAGGTTTCCATTT (SEQ ID NO: 535) |
| [2,] | hsa-let-7e_st | −0.31 | AACTATACAACCTCCTACCTCA (SEQ ID NO: 549) |
| [3,] | hsa-miR-125a-5p_st | −0.32 | TCACAGGTTAAAGGGTCTCAGGGA (SEQ ID NO: 551) |
| [4,] | hsa-miR-130a_st | −0.31 | ATGCCCTTTTAACATTGCACTG (SEQ ID NO: 313) |
| [5,] | hsa-miR-193b_st | −0.34 | AGCGGGACTTTGAGGGCCAGTT (SEQ ID NO: 583) |

TABLE 75-continued

Paclitaxel (Taxol) microRNA biomarkers.

| | Medianprobe | Corr | Sequence |
|---|---|---|---|
| [6,] | hsa-miR-22_st | −0.46 | ACAGTTCTTCAACTGGCAGCTT (SEQ ID NO: 167) |
| [7,] | hsa-miR-27a_st | −0.34 | GCGGAACTTAGCCACTGTGAA (SEQ ID NO: 501) |
| [8,] | hsa-miR-29a_st | −0.33 | TAACCGATTTCAGATGGTGCTA (SEQ ID NO: 584) |
| [9,] | hsa-miR-29b_st | −0.43 | AACACTGATTTCAAATGGTGCTA (SEQ ID NO: 545) |
| [10,] | hsa-miR-30a-star_st | −0.42 | GCTGCAAACATCCGACTGAAAG (SEQ ID NO: 502) |
| [11,] | hsa-miR-30a_st | −0.49 | CTTCCAGTCGAGGATGTTTACA (SEQ ID NO: 503) |
| [12,] | hsa-miR-30c-2-star_st | −0.47 | AGAGTAAACAGCCTTCTCCCAG (SEQ ID NO: 504) |
| [13,] | hsa-miR-30c_st | −0.44 | GCTGAGAGTGTAGGATGTTTACA (SEQ ID NO: 301) |
| [14,] | hsa-miR-34a_st | −0.3 | ACAACCAGCTAAGACACTGCCA (SEQ ID NO: 234) |
| [15,] | hsa-miR-34b-star_st | −0.39 | CAATCAGCTAATGACACTGCCTA (SEQ ID NO: 534) |
| [16,] | hsa-miR-34c-3p_st | −0.42 | CCTGGCCGTGTGGTTAGTGATT (SEQ ID NO: 314) |
| [17,] | hsa-miR-34c-5p_st | −0.48 | GCAATCAGCTAACTACACTGCCT (SEQ ID NO: 506) |

TABLE 76

Gemcitabine (Gemzar) microRNA biomarkers.

| | Medianprobe | Corr | Sequence |
|---|---|---|---|
| [1,] | hsa-miR-141_st | −0.33 | CCATCTTTACCAGACAGTGTTA (SEQ ID NO: 552) |
| [2,] | hsa-miR-584_st | −0.31 | CTCAGTCCCAGGCAAACCATAA (SEQ ID NO: 581) |
| [3,] | hsa-miR-934_st | −0.31 | CCAGTGTCTCCAGTAGTAGACA (SEQ ID NO: 517) |

TABLE 77

Taxotere (docetaxel) microRNA biomarkers.

| | Medianprobe | Corr | Sequence |
|---|---|---|---|
| [1,] | HBII-438A_s_st | −0.42 | TGACATCTGGAATGAGTCCCTCAGC (SEQ ID NO: 585) |
| [2,] | HBII-85-11_st | −0.42 | TCCAAGGAACCCACGTATGGAAGTC (SEQ ID NO: 249) |
| [3,] | HBII-85-15_x_st | −0.33 | TGTATATATGGAAGTCATCATCGAT (SEQ ID NO: 586) |
| [4,] | HBII-85-23_x_st | −0.42 | CATGTATTGAGGTCATCATCGATCC (SEQ ID NO: 587) |
| [5,] | HBII-85-29_st | −0.47 | GTTCAGATTTCCAAGGTTTCCATTT (SEQ ID NO: 588) |

TABLE 77 -continued

Taxotere (docetaxel) microRNA biomarkers.

| | Medianprobe | Corr | Sequence |
|---|---|---|---|
| [6,] | HBII-85-29_x_st | -0.38 | GCTCACAGAAGTGTCTTGGTCACTC (SEQ ID NO: 589) |
| [7,] | hsa-miR-184_st | -0.3 | ACCCTTATCAGTTCTCCGTCCA (SEQ ID NO: 283) |
| [8,] | hsa-miR-29a_st | -0.33 | TAACCGATTTCAGATGGTGCTA (SEQ ID NO: 584) |
| [9,] | hsa-miR-29b_st | -0.34 | AACACTGATTTCAAATGGTGCTA (SEQ ID NO: 545) |
| [10,] | hsa-miR-34a_st | -0.33 | ACAACCAGCTAAGACACTGCCA (SEQ ID NO: 234) |
| [11,] | hsa-miR-34c-3p_st | -0.46 | CCTGGCCGTGTGGTTAGTGATT (SEQ ID NO: 314) |
| [12,] | hsa-miR-34c-5p_st | -0.41 | GCAATCAGCTAACTACACTGCCT (SEQ ID NO: 506) |
| [13,] | hsa-miR-424-star_st | -0.3 | ATAGCAGCGCCTCACGTTTTG (SEQ ID NO: 100) |

TABLE 78

Dexamethasone microRNA biomarkers.

| | Medianprobe | Corr | Sequence |
|---|---|---|---|
| [1,] | hsa-let-7e_st | -0.31 | AACTATACAACCTCCTACCTCA (SEQ ID NO: 549) |
| [2,] | hsa-miR-151-5p_st | -0.3 | ACTAGACTGTGAGCTCCTCGA (SEQ ID NO: 540) |
| [3,] | hsa-miR-182_st | -0.31 | AGTGTGAGTTCTACCATTGCCAAA (SEQ ID NO: 563) |
| [4,] | hsa-miR-23b_st | -0.31 | GGTAATCCCTGGCAATGTGAT (SEQ ID NO: 590) |
| [5,] | hsa-miR-24_st | -0.35 | CTGTTCCTGCTGAACTGAGCCA (SEQ ID NO: 580) |
| [6,] | hsa-miR-34_st | -0.36 | ACAACCAGCTAAGACACTGCCA (SEQ ID NO: 234) |
| [7,] | hsa-miR-99b_st | -0.32 | CGCAAGGTCGGTTCTACGGGTG (SEQ ID NO: 559) |

TABLE 79

Ara-C (Cytarabine hydrochloride) microRNA biomarkers.

| | Medianprobe | Corr | Sequence |
|---|---|---|---|
| [1,] | hsa-miR-151-5p_st | -0.3 | ACTAGACTGTGAGCTCCTCGA (SEQ ID NO: 540) |
| [2,] | hsa-miR-23b-star_st | -0.31 | AAATCAGCATGCCAGGAACCCA (SEQ ID NO: 591) |
| [3,] | hsa-miR-23b_st | -0.38 | GGTAATCCCTGGCAATGTGAT (SEQ ID NO: 590) |
| [4,] | hsa-miR-27b_st | -0.36 | GCAGAACTTAGCCACTGTGAA (SEQ ID NO: 567) |

TABLE 79 -continued

Ara-C (Cytarabine hydrochloride) microRNA biomarkers.

| | Medianprobe | Corr | Sequence |
|---|---|---|---|
| [5,] | hsa-miR-99b_st | -0.31 | CGCAAGGTCGGTTCTACGGGTG (SEQ ID NO: 559) |

TABLE 80

Methylprednisolone microRNA biomarkers.

| | Medianprobe | Corr | Sequence |
|---|---|---|---|
| [1,] | hsa-let-7e_st | -0.43 | AACTATACAACCTCCTACCTCA (SEQ ID NO: 549) |
| [2,] | hsa-miR-125a-5p_st | -0.41 | TCACAGGTTAAAGGGTCTCAGGGA (SEQ ID NO: 551) |
| [3,] | hsa-miR-1308_st | -0.39 | CCACTGAACCACCCATGC (SEQ ID NO: 274) |
| [4,] | hsa-miR-151-3p_st | -0.37 | CCTCAAGGAGCTTCAGTCTAG (SEQ ID NO: 539) |
| [5,] | hsa-miR-151-5p_st | -0.42 | ACTAGACTGTGAGCTCCTCGA (SEQ ID NO: 540) |
| [6,] | hsa-miR-182_st | -0.39 | AGTGTGAGTTCTACCATTGCCAAA (SEQ ID NO: 563) |
| [7,] | hsa-miR-193b_st | -0.33 | AGCGGGACTTTGAGGGCCAGTT (SEQ ID NO: 583) |
| [8,] | hsa-miR-21-star_st | -0.31 | ACAGCCCATCGACTGGTGTTG (SEQ ID NO: 166) |
| [9,] | hsa-miR-21_st | -0.34 | TCAACATCACTCTGATAAGCTA (SEQ ID NO: 592) |
| [10,] | hsa-miR-22_st | -0.37 | ACAGTTCTTCAACTGGCAGCTT (SEQ ID NO: 167) |
| [11,] | hsa-miR-23a_st | -0.5 | GGAAATCCCTGGCAATGTGAT (SEQ ID NO: 571) |
| [12,] | hsa-miR-23b_st | -0.4 | GGTAATCCCTGGCAATGTGAT (SEQ ID NO: 590) |
| [13,] | hsa-miR-24-2-star_st | -0.36 | CTGTGTTTCAGCTCAGTAGGCA (SEQ ID NO: 579) |
| [14,] | hsa-miR-24_st | -0.57 | CTGTTCCTGCTGAACTGAGCCA (SEQ ID NO: 580) |
| [15,] | hsa-miR-27a-star_st | -0.42 | TGCTCACAAGCAGCTAAGCCCT (SEQ ID NO: 593) |
| [16,] | hsa-miR-27a_st | -0.4 | GCGGAACTTAGCCACTGTGAA (SEQ ID NO: 501) |
| [17,] | hsa-miR-27b_st | -0.34 | GCAGAACTTAGCCACTGTGAA (SEQ ID NO: 567) |
| [18,] | hsa-miR-339-3p_st | -0.3 | CGGCTCTGTCGTCGAGGCGCTCA (SEQ ID NO: 272) |
| [19,] | hsa-miR-34a_st | -0.32 | ACAACCAGCTAAGACACTGCCA (SEQ ID NO: 234) |
| [20,] | hsa-miR-99b_st | -0.43 | CGCAAGGTCGGTTCTACGGGTG (SEQ ID NO: 559) |

TABLE 81

Methotrexate microRNA biomarkers.

| | Medianprobe | Corr | Sequence |
|---|---|---|---|
| [1,] | hsa-let-7e_st | -0.31 | AACTATACAACCTCCTACCTCA (SEQ ID NO: 549) |
| [2,] | hsa-miR-125a-5p_st | -0.32 | TCACAGGTTAAAGGGTCTCAGGGA (SEQ ID NO: 551) |
| [3,] | hsa-miR-22_st | -0.3 | ACAGTTCTTCAACTGGCAGCTT (SEQ ID NO: 167) |
| [4,] | hsa-miR-23b_st | -0.35 | GGTAATCCCTGGCAATGTGAT (SEQ ID NO: 590) |
| [5,] | hsa-miR-27b_st | -0.31 | GCAGAACTTAGCCACTGTGAA (SEQ ID NO: 567) |
| [6,] | hsa-miR-28-5p_st | -0.35 | CTCAATAGACTGTGAGCTCCTT (SEQ ID NO: 594) |
| [7,] | hsa-miR-30a-star_st | -0.32 | GCTGCAAACATCCGACTGAAAG (SEQ ID NO: 502) |
| [8,] | hsa-miR-30a_st | -0.37 | CTTCCAGTCGAGGATGTTTACA (SEQ ID NO: 503) |
| [9,] | hsa-miR-34c-5p_st | -0.3 | GCAATCAGCTAACTACACTGCCT (SEQ ID NO: 506) |
| [10,] | hsa-miR-516b_st | -0.31 | AAAGTGCTTCTTACCTCCAGAT (SEQ ID NO: 525) |
| [11,] | hsa-miR-517a_st | -0.32 | ACACTCTAAAGGGATGCACGAT (SEQ ID NO: 526) |
| [12,] | hsa-miR-525-5p_st | -0.32 | AGAAAGTGCATCCCTCTGGAG (SEQ ID NO: 528) |

TABLE 82

Bleomycin microRNA biomarkers.

| | Medianprobe | Corr | Sequence |
|---|---|---|---|
| [1,] | hsa-miR-1244_st | -0.31 | AACCATCTCATACAAACCAACTACT (SEQ ID NO: 560) |
| [2,] | hsa-miR-128_st | -0.32 | AAAGAGACCGGTTCACTGTGA (SEQ ID NO: 110) |
| [3,] | hsa-miR-1292_st | -0.32 | CAGCGTCTGCCGGAACCCGTTCCCA (SEQ ID NO: 499) |
| [4,] | hsa-miR-141_st | -0.34 | CCATCTTTACCAGACAGTGTTA (SEQ ID NO: 552) |
| [5,] | hsa-miR-15b_st | -0.33 | TGTAAACCATGATGTGCTGCTA (SEQ ID NO: 510) |
| [6,] | hsa-miR-185-star_st | -0.32 | GACCAGAGGAAAGCCAGCCCT (SEQ ID NO: 406) |
| [7,] | hsa-miR-188-5p_st | -0.32 | CCCTCCACCATGCAAGGGATG (SEQ ID NO: 86) |
| [8,] | hsa-miR-18b_st | -0.37 | CTAACTGCACTAGATGCACCTTA (SEQ ID NO: 87) |
| [9,] | hsa-miR-200c_st | -0.33 | TCCATCATTACCCGGCAGTATTA (SEQ ID NO: 556) |
| [10,] | hsa-miR-203_st | -0.3 | CTAGTGGTCCTAAACATTTCAC (SEQ ID NO: 511) |
| [11,] | hsa-miR-20b_st | -0.31 | CTACCTGCACTATGAGCACTTTG (SEQ ID NO: 88) |
| [12,] | hsa-miR-215_st | -0.3 | GTCTGTCAATTCATAGGTCAT (SEQ ID NO: 566) |
| [13,] | hsa-miR-25_st | -0.39 | TCAGACCGAGACAAGTGCAATG (SEQ ID NO: 89) |
| [14,] | hsa-miR-30b_st | -0.32 | AGCTGAGTGTAGGATGTTTACA (SEQ ID NO: 546) |
| [15,] | hsa-miR-30d_st | -0.36 | CTTCCAGTCGGGGATGTTTACA (SEQ ID NO: 547) |
| [16,] | hsa-miR-362-5p_st | -0.36 | ACTCACACCTAGGTTCCAAGGATT (SEQ ID NO: 92) |
| [17,] | hsa-miR-378-star_st | -0.31 | ACACAGGACCTGGAGTCAGGAG (SEQ ID NO: 409) |
| [18,] | hsa-miR-421_st | -0.32 | GCGCCCAATTAATGTCTGTTGAT (SEQ ID NO: 512) |
| [19,] | hsa-miR-425_st | -0.35 | TCAACGGGAGTGATCGTGTCATT (SEQ ID NO: 286) |
| [20,] | hsa-miR-532-5p_st | -0.33 | ACGGTCCTACACTCAAGGCATG (SEQ ID NO: 98) |
| [21,] | hsa-miR-93_st | -0.34 | CTACCTGCACGAACAGCACTTTG (SEQ ID NO: 46) |
| [22,] | hsa-miR-941_st | -0.34 | GCACATGTGCACACAGCCGGGTG (SEQ ID NO: 595) |

TABLE 83

Methyl-GAG (methyl glyoxal bis amidinohydrazone dihydrochloride) microRNA biomarkers.

| | Medianprobe | Corr | Sequence |
|---|---|---|---|
| [1,] | hsa-let-7e_st | -0.39 | AACTATACAACCTCCTACCTCA (SEQ ID NO: 549) |
| [2,] | hsa-let-7i_st | -0.39 | AACAGCACAAACTACTACCTCA (SEQ ID NO: 596) |
| [3,] | hsa-miR-10a_st | -0.3 | CACAAATTCGGATCTACAGGGTA (SEQ ID NO: 538) |
| [4,] | hsa-miR-10b_st | -0.41 | CACAAATTCGGTTCTACAGGGTA (SEQ ID NO: 550) |
| [5,] | hsa-miR-125a-5p_st | -0.37 | TCACAGGTTAAAGGGTCTCAGGGA (SEQ ID NO: 551) |
| [6,] | hsa-miR-1301_st | -0.35 | GAAGTCACTCCCAGGCAGCTGCAA (SEQ ID NO: 597) |
| [7,] | hsa-miR-140-5p_st | -0.32 | CTACCATAGGGTAAAACCACTG (SEQ ID NO: 18) |
| [8,] | hsa-miR-99b_st | -0.34 | CGCAAGGTCGGTTCTACGGGTG (SEQ ID NO: 559) |

TABLE 84

Belinostat (PXD101) microRNA biomarkers.

| | Medianprobe | Corr | Sequence |
|---|---|---|---|
| [1,] | 14qII-14_st | −0.32 | TCACCCAACACTCATACGCCGGCAG (SEQ ID NO: 598) |
| [2,] | 14qII-1_x_st | −0.32 | GGACCTCAGACTTCCAGACCTGTAT (SEQ ID NO: 599) |
| [3,] | hsa-let-7b_st | −0.35 | AACCACACAACCTACTACCTCA (SEQ ID NO: 600) |
| [4,] | hsa-let-7c_st | −0.4 | AACCACACAACCTACTACCTCA (SEQ ID NO: 576) |
| [5,] | hsa-let-7e_st | −0.45 | AACTATACAACCTCCTACCTCA (SEQ ID NO: 549) |
| [6,] | hsa-miR-10a_st | −0.4 | CACAAATTCGGATCTACAGGGTA (SEQ ID NO: 538) |
| [7,] | hsa-miR-10b_st | −0.31 | CACAAATTCGGTTCTACAGGGTA (SEQ ID NO: 550) |
| [8,] | hsa-miR-125a-3p_st | −0.38 | GGCTCCCAAGAACCTCACCTGT (SEQ ID NO: 601) |
| [9,] | hsa-miR-125a-5p_st | −0.43 | TCACAGGTTAAAGGGTCTCAGGGA (SEQ ID NO: 551) |
| [10,] | hsa-miR-125b-1-star_st | −0.33 | AGCTCCCAAGAGCCTAACCCGT (SEQ ID NO: 163) |
| [11,] | hsa-miR-125b_st | −0.31 | TCACAAGTTAGGGTCTCAGGGA (SEQ ID NO: 602) |
| [12,] | hsa-miR-1287_st | −0.31 | GACTCGAACCACTGATCCAGCA (SEQ ID NO: 603) |
| [13,] | hsa-miR-134_st | −0.34 | CCCCTCTGGTCAACCAGTCACA (SEQ ID NO: 164) |
| [14,] | hsa-miR-151-3p_st | −0.37 | CCTCAAGGAGCTTCAGTCTAG (SEQ ID NO: 539) |
| [15,] | hsa-miR-151-5p_st | −0.42 | ACTAGACTGTGAGCTCCTCGA (SEQ ID NO: 540) |
| [16,] | hsa-miR-22_st | −0.36 | ACAGTTCTTCAACTGGCAGCTT (SEQ ID NO: 167) |
| [17,] | hsa-miR-23a-star_st | −0.33 | AAATCCCATCCCCAGGAACCCC (SEQ ID NO: 604) |
| [18,] | hsa-miR-23a_st | −0.34 | GGAAATCCCTGGCAATGTGAT (SEQ ID NO: 571) |
| [19,] | hsa-miR-23b_st | −0.31 | GGTAATCCCTGGCAATGTGAT (SEQ ID NO: 590) |
| [20,] | hsa-miR-24-2-star_st | −0.35 | CTGTGTTTCAGCTCAGTAGGCA (SEQ ID NO: 579) |
| [21,] | hsa-miR-24_st | −0.37 | CTGTTCCTGCTGAACTGAGCCA (SEQ ID NO: 580) |
| [22,] | hsa-miR-27a_st | −0.31 | GCGGAACTTAGCCACTGTGAA (SEQ ID NO: 501) |
| [23,] | hsa-miR-27b_st | −0.33 | GCAGAACTTAGCCACTGTGAA (SEQ ID NO: 567) |
| [24,] | hsa-miR-28-3p_st | −0.39 | TCCAGGAGCTCACAATCTAGTG (SEQ ID NO: 605) |
| [25,] | hsa-miR-28-5p_st | −0.35 | CTCAATAGACTGTGAGCTCCTT (SEQ ID NO: 594) |
| [26,] | hsa-miR-299-5p_st | −0.32 | ATGTATGTGGGACGGTAAACCA (SEQ ID NO: 606) |
| [27,] | hsa-miR-337-5p_st | −0.36 | AACTCCTGTATGAAGCCGTTC (SEQ ID NO: 169) |
| [28,] | hsa-miR-370_st | −0.3 | ACCAGGTTCCACCCCAGCAGGC (SEQ ID NO: 32) |
| [29,] | hsa-miR-376a_st | −0.38 | ACGTGGATTTTCCTCTATGAT (SEQ ID NO: 607) |
| [30,] | hsa-miR-376c_st | −0.37 | ACGTGGAATTTCCTCTATGTT (SEQ ID NO: 170) |
| [31,] | hsa-miR-379_st | −0.38 | CCTACGTTCCATAGTCTACCA (SEQ ID NO: 172) |
| [32,] | hsa-miR-381_st | −0.35 | ACAGAGAGCTTGCCCTTGTATA (SEQ ID NO: 173) |
| [33,] | hsa-miR-382_st | −0.37 | CGAATCCACCACGAACAACTTC (SEQ ID NO: 174) |
| [34,] | hsa-miR-409-3p_st | −0.38 | AGGGGTTCACCGAGCAACATTC (SEQ ID NO: 81) |
| [35,] | hsa-miR-409-5p_st | −0.32 | ATGCAAAGTTGCTCGGGTAACCT (SEQ ID NO: 175) |
| [36,] | hsa-miR-411_st | −0.31 | CGTACGCTATACGGTCTACTA (SEQ ID NO: 176) |
| [37,] | hsa-miR-431_st | −0.31 | TGCATGACGGCCTGCAAGACA (SEQ ID NO: 177) |
| [38,] | hsa-miR-452_st | −0.3 | TCAGTTTCCTCTGCAAACAGTT (SEQ ID NO: 608) |
| [39,] | hsa-miR-485-5p_st | −0.31 | GAATTCATCACGGCCAGCCTCT (SEQ ID NO: 179) |
| [40,] | hsa-miR-487a_st | −0.32 | AACTGGATGTCCCTGTATGATT (SEQ ID NO: 609) |
| [41,] | hsa-miR-487b_st | −0.32 | AAGTGGATGACCCTGTACGATT (SEQ ID NO: 82) |
| [42,] | hsa-miR-494_st | −0.37 | GAGGTTTCCCGTGTATGTTTCA (SEQ ID NO: 181) |
| [43,] | hsa-miR-495_st | −0.3 | AAGAAGTGCACCATGTTTGTTT (SEQ ID NO: 610) |
| [44,] | hsa-miR-543_st | −0.34 | AAGAAGTGCACCGCGAATGTTT (SEQ ID NO: 182) |
| [45,] | hsa-miR-654-5p_st | −0.31 | GCACATGTTCTGCGGCCCACCA (SEQ ID NO: 611) |
| [46,] | hsa-miR-99b-star_st | −0.37 | CGGACCCACAGACACGAGCTTG (SEQ ID NO: 569) |
| [47,] | hsa-miR-99b_st | −0.4 | CGCAAGCTCGGTTCTACGGGTG (SEQ ID NO: 559) |

TABLE 85

5-Fluorouracil microRNA biomarkers.

| | Medianprobe | Corr | Sequence |
|---|---|---|---|
| [1,] | hsa-miR-100_st | -0.31 | CACAAGTTCGGATCTACGGGTT (SEQ ID NO: 17) |
| [2,] | hsa-miR-125b_st | -0.34 | TCACAAGTTAGGGTCTCAGGGA (SEQ ID NO: 602) |
| [3,] | hsa-miR-130a_st | -0.39 | ATGCCCTTTTAACATTGCACTG (SEQ ID NO: 313) |
| [4,] | hsa-miR-181a-2-star_st | -0.33 | GGTACAGTCAACGGTCAGTGGT (SEQ ID NO: 612) |
| [5,] | hsa-miR-184_st | -0.34 | ACCCTTATCAGTTCTCCGTCCA (SEQ ID NO: 283) |
| [6,] | hsa-miR-197_st | -0.34 | GCTGGGTGGAGAAGGTGGTGAA (SEQ ID NO: 520) |
| [7,] | hsa-miR-221-star_st | -0.34 | AAATCTACATTGTATGCCAGGT (SEQ ID NO: 613) |
| [8,] | hsa-miR-30a-star_st | -0.36 | GCTGCAAACATCCGACTGAAAG (SEQ ID NO: 502) |
| [9,] | hsa-miR-30a_st | -0.34 | CTTCCAGTCGAGGATGTTTACA (SEQ ID NO: 503) |
| [10,] | hsa-miR-30c-2-star_st | -0.33 | AGAGTAAACAGCCTTCTCCCAG (SEQ ID NO: 504) |
| [11,] | hsa-miR-525-5p_st | -0.32 | AGAAAGTGCATCCCTCTGGAG (SEQ ID NO: 528) |
| [12,] | hsa-miR-584_st | -0.32 | CTCAGTCCCAGGCAAACCATAA (SEQ ID NO: 581) |

TABLE 86

Radiation microRNA biomarkers.

| | Medianprobe | Corr | Sequence |
|---|---|---|---|
| [1,] | hsa-miR-1207-5p_st | -0.31 | CCCCTCCCAGCCTCCCTGCCA (SEQ ID NO: 109) |
| [2,] | hsa-miR-625_st | -0.31 | GGACTATAGAACTTTCCCCCT (SEQ ID NO: 548) |
| [3,] | hsa-miR-766_st | -0.33 | GCTGAGGCTGTGGGGCTGGAGT (SEQ ID NO: 1) |

TABLE 87

5-Aza-2'-deoxycytidine(decitabine) microRNA biomarkers.

| | Medianprobe | Corr | Sequence |
|---|---|---|---|
| [1,] | hsa-let-7e_st | -0.34 | AACTATACAACCTCCTACCTCA (SEQ ID NO: 549) |
| [2,] | hsa-miR-151-3p_st | -0.34 | CCTCAAGGAGCTTCAGTCTAG (SEQ ID NO: 539) |
| [3,] | hsa-miR-151-5p_st | -0.35 | ACTAGACTGTGAGCTCCTCGA (SEQ ID NO: 540) |
| [4,] | hsa-miR-21_st | -0.39 | TCAACATCAGTCTGATAAGCTA (SEQ ID NO: 592) |
| [5,] | hsa-miR-22_st | -0.31 | ACAGTTCTTCAACTGGCAGCTT (SEQ ID NO: 167) |
| [6,] | hsa-miR-30a-star_st | -0.36 | GCTGCAAACATCCGACTGAAAG (SEQ ID NO: 502) |
| [7,] | hsa-miR-30a_st | -0.42 | CTTCCAGTCGAGGATGTTTACA (SEQ ID NO: 503) |
| [8,] | hsa-miR-30c-2-star_st | -0.32 | AGAGTAAACAGCCTTCTCCCAG (SEQ ID NO: 504) |
| [9,] | hsa-miR-99b_st | -0.31 | CGCAAGGTCGGTTCTACGGGTG (SEQ ID NO: 559) |

TABLE 88

Idarubicin microRNA biomarkers.

| | Medianprobe | Corr | Sequence |
|---|---|---|---|
| [1,] | hsa-let-7e_st | -0.31 | AACTATACAACCTCCTACCTCA (SEQ ID NO: 549) |
| [2,] | hsa-miR-125a-5p_st | -0.31 | TCACAGGTTAAAGGGTCTCAGGGA (SEQ ID NO: 551) |
| [3,] | hsa-miR-151-3p_st | -0.4 | CCTCAAGGAGCTTCAGTCTAG (SEQ ID NO: 539) |
| [4,] | hsa-miR-151-5p_st | -0.44 | ACTAGACTGTGAGCTCCTCGA (SEQ ID NO: 540) |
| [5,] | hsa-miR-221-star_st | -0.35 | AAATCTACATTGTATGCCAGGT (SEQ ID NO: 613) |
| [6,] | hsa-miR-23a_st | -0.4 | GGAAATCCCTGGCAATGTGAT (SEQ ID NO: 571) |
| [7,] | hsa-miR-24-2-star_st | -0.35 | CTGTGTTTCAGCTCAGTAGGCA (SEQ ID NO: 579) |
| [8,] | hsa-miR-24_st | -0.35 | CTGTTCCTGCTGAACTGAGCCA (SEQ ID NO: 580) |
| [9,] | hsa-miR-30b_st | -0.31 | AGCTGAGTGTAGGATGTTTACA (SEQ ID NO: 546) |
| [10,] | hsa-miR-30d_st | -0.38 | CTTCCAGTCGGGGATGTTTACA (SEQ ID NO: 547) |
| [11,] | hsa-miR-526a_st | -0.3 | CAGAAAGTGCTTCCCTCTAGAG (SEQ ID NO: 572) |
| [12,] | hsa-miR-584_st | -0.43 | CTCAGTCCCAGGCAAACCATAA (SEQ ID NO: 581) |
| [13,] | hsa-miR-99b_st | -0.33 | CGCAAGGTCGGTTCTACGGGTG (SEQ ID NO: 559) |

TABLE 89

Melphalan microRNA biomarkers.

| | Medianprobe | Corr | Sequence |
|---|---|---|---|
| [1,] | hsa-let-7e_st | -0.5 | AACTATACAACCTCCTACCTCA (SEQ ID NO: 549) |

TABLE 89-continued

Melphalan microRNA biomarkers.

| | Medianprobe | Corr | Sequence |
|---|---|---|---|
| [2,] | hsa-miR-10a_st | -0.35 | CACAAATTCGGATCTACAGGGTA (SEQ ID NO: 538) |
| [3,] | hsa-miR-125a-3p_st | -0.33 | GGCTCCCAAGAACCTCACCTGT (SEQ ID NO: 601) |
| [4,] | hsa-miR-125a-5p_st | -0.5 | TCACAGGTTAAAGGGTCTCAGGGA (SEQ ID NO: 551) |
| [5,] | hsa-miR-151-3p_st | -0.58 | CCTCAAGGAGCTTCAGTCTAG (SEQ ID NO: 539) |
| [6,] | hsa-miR-151-5p_st | -0.65 | ACTAGACTGTGAGCTCCTCGA (SEQ ID NO: 540) |
| [7,] | hsa-miR-182_st | -0.34 | AGTGTGAGTTCTACCATTGCCAAA (SEQ ID NO: 563) |
| [8,] | hsa-miR-183-star_st | -0.32 | TTATGGCCCTTCGGTAATTCAC (SEQ ID NO: 564) |
| [9,] | hsa-miR-183_st | -0.35 | AGTGAATTCTACCAGTGCCATA (SEQ ID NO: 565) |
| [10,] | hsa-miR-193b_st | -0.45 | AGCGGGACTTTGAGGGCCAGTT (SEQ ID NO: 583) |
| [11,] | hsa-miR-200b-star_st | -0.31 | TCCAATGCTGCCCAGTAAGATG (SEQ ID NO: 555) |
| [12,] | hsa-miR-200b_st | -0.31 | TCATCATTACCAGGCAGTATTA (SEQ ID NO: 544) |
| [13,] | hsa-miR-21_st | -0.33 | TCAACATCAGTCTGATAAGCTA (SEQ ID NO: 592) |
| [14,] | hsa-miR-221-star_st | -0.35 | AAATCTACATTGTATGCCAGGT (SEQ ID NO: 613) |
| [15,] | hsa-miR-22_st | -0.39 | ACAGTTCTTCAACTGGCAGCTT (SEQ ID NO: 167) |
| [16,] | hsa-miR-23a_st | -0.4 | GGAAATCCCTGGCAATGTGAT (SEQ ID NO: 571) |
| [17,] | hsa-miR-23b_st | -0.38 | GGTAATCCCTGGCAATGTGAT (SEQ ID NO: 590) |
| [18,] | hsa-miR-24_st | -0.41 | CTGTTCCTGCTGAACTGAGCCA (SEQ ID NO: 580) |
| [19,] | hsa-miR-27b_st | -0.31 | GCAGAACTTAGCCACTGTGAA (SEQ ID NO: 567) |
| [20,] | hsa-miR-29b_st | -0.3 | AACACTGATTTCAAATGGTGCTA (SEQ ID NO: 545) |
| [21,] | hsa-miR-30a_st | -0.31 | CTTCCAGTCGAGGATGTTTACA (SEQ ID NO: 503) |
| [22,] | hsa-miR-30d_st | -0.37 | CTTCCAGTCGGGGATGTTTACA (SEQ ID NO: 547) |
| [23,] | hsa-miR-31-star_st | -0.34 | ATGGCAATATGTTGGCATAGCA (SEQ ID NO: 614) |
| [24,] | hsa-miR-31_st | -0.34 | AGCTATGCCAGCATCTTGCCT (SEQ ID NO: 615) |
| [25,] | hsa-miR-320d_st | -0.31 | TCCTCTCAACCCAGCTTTT (SEQ ID NO: 91) |
| [26,] | hsa-miR-584_st | -0.33 | CTCAGTCCCAGGCAAACCATAA (SEQ ID NO: 581) |

TABLE 89-continued

Melphalan microRNA biomarkers.

| | Medianprobe | Corr | Sequence |
|---|---|---|---|
| [27,] | hsa-miR-99b-star_st | -0.38 | CGGACCCACAGACACGAGCTTG (SEQ ID NO: 569) |
| [28,] | hsa-miR-99b_st | -0.5 | CGCAAGGTCGGTTCTACGGGTG (SEQ ID NO: 559) |

TABLE 90

IL4-PR38 fusion protein microRNA biomarkers.

| | Medianprobe | Corr | Sequence |
|---|---|---|---|
| [1,] | hsa-let-7a_st | -0.31 | AACTATACAACCTACTACCTCA (SEQ ID NO: 575) |
| [2,] | hsa-miR-100_st | -0.38 | CACAAGTTCGGATCTACGGGTT (SEQ ID NO: 17) |
| [3,] | hsa-miR-146a_st | -0.3 | AACCCATGGAATTCAGTTCTCA (SEQ ID NO: 19) |

TABLE 91

Valproic acid (VPA) microRNA biomarkers.

| | Medianprobe | Corr | Sequence |
|---|---|---|---|
| [1,] | HBII-85-26_st | -0.3 | AGATCCATTTTTTTTATAGTCATCA (SEQ ID NO: 439) |
| [2,] | HBII-85-6_x_st | -0.28 | GTTTTTTTTGGAGGACTCATCATCG (SEQ ID NO: 616) |
| [3,] | hsa-miR-491-5p_st | -0.28 | CCTCATGGAAGGGTTCCCCACT (SEQ ID NO: 617) |
| [4,] | hsa-miR-589-star_st | -0.32 | TCTGGGAACCGGCATTTGTTCTGA (SEQ ID NO: 618) |
| [5,] | hsa-miR-625_st | -0.27 | GGACTATAGAACTTTCCCCCT (SEQ ID NO: 548) |
| [6,] | hsa-miR-744_st | -0.33 | TGCTGTTAGCCCTAGCCCCGCA (SEQ ID NO: 619) |

TABLE 92

All-trans retinoic acid (ATRA) microRNA biomarkers.

| | Medianprobe | Corr | Sequence |
|---|---|---|---|
| [1,] | hsa-let-7b_st | -0.3 | AACCACACAACCTACTACCTCA (SEQ ID NO: 600) |
| [2,] | hsa-let-7e_st | -0.34 | AACTATACAACCTCCTACCTCA (SEQ ID NO: 549) |
| [3,] | hsa-let-7i_st | -0.32 | AACAGCACAAACTACTACCTCA (SEQ ID NO: 596) |
| [4,] | hsa-miR-10a_st | -0.25 | CACAAATTCGGATCTACAGGGTA (SEQ ID NO: 538) |
| [5,] | hsa-miR-10b_st | -0.28 | CACAAATTCGGTTCTACAGGGTA (SEQ ID NO: 550) |
| [6,] | hsa-miR-125a-3p_st | -0.26 | GGCTCCCAAGAACCTCACCTGT (SEQ ID NO: 601) |

TABLE 92-continued

All-trans retinoic acid (ATRA) microRNA biomarkers.

| | Medianprobe | Corr | Sequence |
|---|---|---|---|
| [7,] | hsa-miR-125a-5p_st | -0.31 | TCACAGGTTAAAGGGTCTCAGGGA (SEQ ID NO: 551) |
| [8,] | hsa-miR-151-3p_st | -0.37 | CCTCAAGGAGCTTCAGTCTAG (SEQ ID NO: 539) |
| [9,] | hsa-miR-151-5p_st | -0.39 | ACTAGACTGTGAGCTCCTCGA (SEQ ID NO: 540) |
| [10,] | hsa-miR-181a-2-star_st | -0.33 | GGTACAGTCAACGGTCAGTGGT (SEQ ID NO: 612) |
| [11,] | hsa-miR-21-star_st | -0.33 | ACAGCCCATCGACTGGTGTTG (SEQ ID NO: 166) |
| [12,] | hsa-miR-21_st | -0.38 | TCAACATCAGTCTGATAAGCTA (SEQ ID NO: 592) |
| [13,] | hsa-miR-221_st | -0.6 | GAAACCCAGCAGACAATGTAGCT (SEQ ID NO: 620) |
| [14,] | hsa-miR-222_st | -0.56 | ACCCAGTAGCCAGATGTAGCT (SEQ ID NO: 621) |
| [15,] | hsa-miR-22_st | -0.37 | ACAGTTCTTCAACTGGCAGCTT (SEQ ID NO: 167) |
| [16,] | hsa-miR-28-3p_st | -0.46 | TCCAGGAGCTCACAATCTAGTG (SEQ ID NO: 605) |
| [17,] | hsa-miR-28-5p_st | -0.43 | CTCAATAGACTGTGAGCTCCTT (SEQ ID NO: 594) |
| [18,] | hsa-miR-29b-1-star_st | -0.27 | TCTAAACCACCATATGAAACCAGC (SEQ ID NO: 622) |
| [19,] | hsa-miR-30a-star_st | -0.32 | GCTGCAAACATCCGACTGAAAG (SEQ ID NO: 502) |
| [20,] | hsa-miR-30a_st | -0.36 | CTTCCAGTCGAGGATGTTTACA (SEQ ID NO: 503) |
| [21,] | hsa-miR-30c-2-star_st | -0.33 | AGAGTAAACAGCCTTCTCCCAG (SEQ ID NO: 504) |
| [22,] | hsa-miR-455-3p_st | -0.32 | GTGTATATGCCCATGGACTGC (SEQ ID NO: 178) |
| [23,] | hsa-miR-99b-star_st | -0.32 | CGGACCCACAGACACGAGCTTG (SEQ ID NO: 569) |
| [24,] | hsa-miR-99b_st | -0.3 | CGCAAGGTCGGTTCTACGGGTG (SEQ ID NO: 559) |

TABLE 93

Cytoxan microRNA biomarkers.

| | Medianprobe | Corr | Sequence |
|---|---|---|---|
| [1,] | hsa-let-7b_st | -0.26 | AACCACACAACCTACTACCTCA (SEQ ID NO: 600) |
| [2,] | hsa-let-7d_st | -0.36 | AACTATGCAACCTACTACCTCT (SEQ ID NO: 623) |
| [3,] | hsa-let-7g_st | -0.29 | AACTGTACAAAACTACTACCTCA (SEQ ID NO: 624) |
| [4,] | hsa-let-7i_st | -0.46 | AACAGCACAAACTACTACCTCA (SEQ ID NO: 596) |

TABLE 93-continued

Cytoxan microRNA biomarkers.

| | Medianprobe | Corr | Sequence |
|---|---|---|---|
| [5,] | hsa-miR-100_st | -0.29 | CACAAGTTCGGATCTACGGGTT (SEQ ID NO: 17) |
| [6,] | hsa-miR-138_st | -0.31 | CGGCCTGATTCACAACACCAGCT (SEQ ID NO: 625) |
| [7,] | hsa-miR-221_st | -0.62 | GAAACCCAGCAGACAATGTAGCT (SEQ ID NO: 620) |
| [8,] | hsa-miR-222_st | -0.65 | ACCCAGTAGCCAGATGTAGCT (SEQ ID NO: 621) |
| [9,] | hsa-miR-27a-star_st | -0.28 | TGCTCACAAGCAGCTAAGCCCT (SEQ ID NO: 593) |
| [10,] | hsa-miR-29a_st | -0.34 | TAACCGATTTCAGATGGTGCTA (SEQ ID NO: 584) |
| [11,] | hsa-miR-31_st | -0.29 | AGCTATGCCAGCATCTTGCCT (SEQ ID NO: 615) |
| [12,] | hsa-miR-503_st | -0.29 | CTGCAGAACTGTTCCCGCTGCTA (SEQ ID NO: 101) |
| [13,] | hsa-miR-625_st | -0.26 | GGACTATAGAACTTTCCCCCT (SEQ ID NO: 548) |

TABLE 94

Topotecan (Hycamtin) microRNA biomarkers.

| | Medianprobe | Corr | Sequence |
|---|---|---|---|
| [1,] | HBII-289_st | -0.27 | AGGTCAGACTAGTGGTTCGCTTCAG (SEQ ID NO: 626) |
| [2,] | hsa-miR-141_st | -0.29 | CCATCTTTACCAGACAGTGTTA (SEQ ID NO: 552) |
| [3,] | hsa-miR-373_st | -0.28 | ACACCCCAAAATCGAAGCACTTC (SEQ ID NO: 408) |
| [4,] | hsa-miR-512-3p_st | -0.32 | GACCTCAGCTATGACAGCACTT (SEQ ID NO: 523) |
| [5,] | hsa-miR-517a_st | -0.32 | ACACTCTAAAGGGATGCACGAT (SEQ ID NO: 526) |
| [6,] | hsa-miR-525-5p_st | -0.29 | AGAAAGTGCATCCCTCTGGAG (SEQ ID NO: 528) |
| [7,] | hsa-miR-584_st | -0.33 | CTCAGTCCCAGGCAAACCATAA (SEQ ID NO: 581) |
| [8,] | hsa-miR-934_st | -0.31 | CCAGTGTCTCCAGTAGTAGACA (SEQ ID NO: 517) |

TABLE 95

Suberoylanilide hydroxamic acid (SAHA, vorinostat, Zolinza) microRNA biomarkers.

| | Medianprobe | Corr | Sequence |
|---|---|---|---|
| [1,] | 14qII-14_st | -0.32 | ATCACCCAACACTCATACGCCGGCA (SEQ ID NO: 627) |
| [2,] | 14qII-14_x_st | -0.29 | CCAACACTCATACGCCGGCAGTTGT (SEQ ID NO: 73) |

TABLE 95-continued

Suberoylanilide hydroxamic acid (SAHA, vorinostat, Zolinza) microRNA biomarkers.

| | Medianprobe | Corr | Sequence |
|---|---|---|---|
| [3,] | 14qII-1_x_st | -0.28 | TTCACCGTCAATGACTCATACGCCA (SEQ ID NO: 628) |
| [4,] | 14qII-26_st | -0.35 | ATGTGACTCATACTCCACCAGTGCT (SEQ ID NO: 629) |
| [5,] | 14qII-26_x_st | -0.28 | ATACTCCACCAGTGCTCATCATCGA (SEQ ID NO: 630) |
| [6,] | hsa-let-7e_st | -0.3 | AACTATACAACCTCCTACCTCA (SEQ ID NO: 549) |
| [7,] | hsa-miR-125a-3p_st | -0.34 | GGCTCCCAAGAACCTCACCTGT (SEQ ID NO: 601) |
| [8,] | hsa-miR-125a-5p_st | -0.29 | TCACAGGTTAAAGGGTCTCAGGGA (SEQ ID NO: 551) |
| [9,] | hsa-miR-125b-1-star_st | -0.33 | AGCTCCCAAGAGCCTAACCCGT (SEQ ID NO: 163) |
| [10,] | hsa-miR-127-3p_st | -0.31 | AGCCAAGCTCAGACGGATCGA (SEQ ID NO: 77) |
| [11,] | hsa-miR-127-5p_st | -0.3 | ATCAGAGCCCTCTGAGCTTCAG (SEQ ID NO: 631) |
| [12,] | hsa-miR-134_st | -0.35 | CCCCTCTGGTCAACCAGTCACA (SEQ ID NO: 164) |
| [13,] | hsa-miR-143-star_st | -0.26 | ACCAGAGATGCAGCACTGCACC (SEQ ID NO: 632) |
| [14,] | hsa-miR-143_st | -0.32 | GAGCTACAGTGCTTCATCTCA (SEQ ID NO: 31) |
| [15,] | hsa-miR-193a-3p_st | -0.27 | ACTGGGACTTTGTAGGCCAGTT (SEQ ID NO: 366) |
| [16,] | hsa-miR-193a-5p_st | -0.35 | TCATCTCGCCCGCAAAGACCCA (SEQ ID NO: 165) |
| [17,] | hsa-miR-193b-star_st | -0.26 | TCATCTCGCCCTCAAAACCCCG (SEQ ID NO: 633) |
| [18,] | hsa-miR-199a-5p_st | -0.29 | GAACAGGTAGTCTGAACACTGGG (SEQ ID NO: 634) |
| [19,] | hsa-miR-21-star_st | -0.29 | ACAGCCCATCGACTGGTGTTG (SEQ ID NO: 166) |
| [20,] | hsa-miR-210_st | -0.46 | TCAGCCGCTGTCACACGCACAG (SEQ ID NO: 635) |
| [21,] | hsa-miR-214_st | -0.3 | ACTGCCTGTCTGTGCCTGCTGT (SEQ ID NO: 636) |
| [22,] | hsa-miR-22_st | -0.39 | ACAGTTCTTCAACTGGCAGCTT (SEQ ID NO: 167) |
| [23,] | hsa-miR-23a-star_st | -0.41 | AAATCCCATCCCCAGGAACCCC (SEQ ID NO: 604) |
| [24,] | hsa-miR-23b-star_st | -0.3 | AAATCAGCATGCCAGGAACCCA (SEQ ID NO: 591) |
| [25,] | hsa-miR-23b_st | -0.32 | GGTAATCCCTGGCAATGTGAT (SEQ ID NO: 590) |
| [26,] | hsa-miR-24-2-star_st | -0.26 | CTGTGTTTCAGCTCAGTAGGCA (SEQ ID NO: 579) |
| [27,] | hsa-miR-24_st | -0.33 | CTGTTCCTGCTGAACTGAGCCA (SEQ ID NO: 580) |
| [28,] | hsa-miR-27a-star_st | -0.39 | TGCTCACAAGCAGCTAAGCCCT (SEQ ID NO: 593) |
| [29,] | hsa-miR-27a_st | -0.37 | GCGGAACTTAGCCACTGTGAA (SEQ ID NO: 501) |
| [30,] | hsa-miR-27b_st | -0.31 | GCAGAACTTAGCCACTGTGAA (SEQ ID NO: 567) |
| [31,] | hsa-miR-28-3p_st | -0.25 | ICCAGGAGCTCACAATCTAGTG (SEQ ID NO: 605) |
| [32,] | hsa-miR-299-3p_st | -0.32 | AAGCGGTTTACCATCCCACATA (SEQ ID NO: 168) |
| [33,] | hsa-miR-337-5p_st | -0.32 | AACTCCTGTATGAAGCCGTTC (SEQ ID NO: 169) |
| [34,] | hsa-miR-339-3p_st | -0.36 | CGGCTCTGTCGTCGAGGCGCTCA (SEQ ID NO: 272) |
| [35,] | hsa-miR-339-5p_st | -0.34 | CGTGAGCTCCTGGAGGACAGGGA (SEQ ID NO: 273) |
| [36,] | hsa-miR-370_st | -0.3 | ACCAGGTTCCACCCCAGCAGGC (SEQ ID NO: 32) |
| [37,] | hsa-miR-376c_st | -0.28 | ACGTGGAATTTCCTCTATGTT (SEQ ID NO: 170) |
| [38,] | hsa-miR-377-star_st | -0.3 | GAATTCACCAAGGGCAACCTCT (SEQ ID NO: 171) |
| [39,] | hsa-miR-379_st | -0.29 | CCTACGTTCCATAGTCTACCA (SEQ ID NO: 172) |
| [40,] | hsa-miR-381_st | -0.3 | ACAGAGAGCTTGCCCTTGTATA (SEQ ID NO: 173) |
| [41,] | hsa-miR-409-3p_st | -0.32 | AGGGGTTCACCGAGCAACATTC (SEQ ID NO: 81) |
| [42,] | hsa-miR-409-5p_st | -0.3 | ATGCAAAGTTGCTCGGGTAACCT (SEQ ID NO: 175) |
| [43,] | hsa-miR-410_st | -0.26 | ACAGGCCATCTGTGTTATATT (SEQ ID NO: 637) |
| [44,] | hsa-miR-411_st | -0.3 | CGTACGCTATACGGTCTACTA (SEQ ID NO: 176) |
| [45,] | hsa-miR-431_st | -0.26 | TGCATGACGGCCTGCAAGACA (SEQ ID NO: 177) |
| [46,] | hsa-miR-455-3p_st | -0.25 | GTGTATATGCCCATGGACTGC (SEQ ID NO: 178) |
| [47,] | hsa-miR-485-5p_st | -0.28 | GAATTCATCACGGCCAGCCTCT (SEQ ID NO: 179) |
| [48,] | hsa-miR-487a_st | -0.29 | AACTGGATGTCCCTGTATGATT (SEQ ID NO: 609) |
| [49,] | hsa-miR-487b_st | -0.31 | AAGTGGATGACCCTGTACGATT (SEQ ID NO: 82) |
| [50,] | hsa-miR-491-5p_st | -0.34 | CCTCATGGAAGGGTTCCCCACT (SEQ ID NO: 617) |
| [51,] | hsa-miR-493_st | -0.28 | CCTGGCACACAGTAGACCTTCA (SEQ ID NO: 180) |
| [52,] | hsa-miR-494_st | -0.38 | GAGGTTTCCCGTGTATGTTTCA (SEQ ID NO: 181) |

TABLE 95-continued

Suberoylanilide hydroxamic acid (SAHA, vorinostat, Zolinza) microRNA biomarkers.

| | Medianprobe | Corr | Sequence |
|---|---|---|---|
| [53,] | hsa-miR-542-5p_st | −0.27 | TCTCGTGACATGATGATCCCCGA (SEQ ID NO: 638) |
| [54,] | hsa-miR-744_st | −0.38 | TGCTGTTAGCCCTAGCCCCGCA (SEQ ID NO: 619) |
| [55,] | hsa-miR-758_st | −0.25 | GGTTAGTGGACCAGGTCACAAA (SEQ ID NO: 35) |
| [56,] | hsa-miR-935_st | −0.26 | GCGGTAGCGGAAGCGGTAACTGG (SEQ ID NO: 639) |
| [57,] | hsa-miR-99b-star_st | −0.41 | CGGACCCACAGACACGAGCTTG (SEQ ID NO: 569) |
| [58,] | hsa-miR-99b_st | −0.34 | CGCAAGGTCGGTTCTACGGGTG (SEQ ID NO: 559) |

TABLE 96

Depsipeptide (FR901228) microRNA biomarkers.

| | Medianprobe | Corr | Sequence |
|---|---|---|---|
| [1,] | HBII-85-11_st | −0.26 | AAGGAACCCACGTATGGAAGTCATC (SEQ ID NO: 470) |
| [2,] | HBII-85-1_x_st | −0.27 | AGCTTTTCCAAGGAATGTTTTTATA (SEQ ID NO: 640) |
| [3,] | HBII-85-23_x_st | −0.25 | ATGCATGTATTGAGGTCATCATCGA (SEQ ID NO: 641) |
| [4,] | HBII-85-29_st | −0.33 | TTGTTCAGATTTCCAAGGTTTCCAT (SEQ ID NO: 642) |
| [5,] | HBII-85-29_x_st | −0.25 | TTGTTCAGATTTCCAAGGTTTCCAT (SEQ ID NO: 642) |
| [6,] | U28_st | −0.27 | TGCCATCAGAACTCTAACATGCTAT (SEQ ID NO: 643) |
| [7,] | hsa-miR-155_st | −0.29 | ACCCTATCACGATTAGCATTAA (SEQ ID NO: 20) |
| [8,] | hsa-miR-196b_st | −0.36 | CCCAACAACAGGAAACTACCTA (SEQ ID NO: 644) |
| [9,] | hsa-miR-200a-star_st | −0.25 | TCCAGCACTGTCCGGTAAGATG (SEQ ID NO: 553) |
| [10,] | hsa-miR-200a_st | −0.31 | ACATCGTTACCAGACAGTGTTA (SEQ ID NO: 554) |
| [11,] | hsa-miR-200b-star_st | −0.3 | TCCAATGCTGCCCAGTAAGATG (SEQ ID NO: 555) |
| [12,] | hsa-miR-200b_st | −0.26 | TCATCATTACCAGGCAGTATTA (SEQ ID NO: 544) |
| [13,] | hsa-miR-203_st | −0.25 | CTAGTGGTCCTAAACATTTCAC (SEQ ID NO: 511) |
| [14,] | hsa-miR-29b_st | −0.35 | AACACTGATTTCAAATGGTGCTA (SEQ ID NO: 545) |
| [15,] | hsa-miR-30c_st | −0.31 | GCTGAGAGTGTAGGATGTTTACA (SEQ ID NO: 301) |

TABLE 96-continued

Depsipeptide (FR901228) microRNA biomarkers.

| | Medianprobe | Corr | Sequence |
|---|---|---|---|
| [16,] | hsa-miR-371-3p_st | −0.31 | ACACTCAAAAGATGGCGGCACTT (SEQ ID NO: 645) |
| [17,] | hsa-miR-371-5p_st | −0.38 | AGTGCCCCCACAGTTTGAGT (SEQ ID NO: 236) |
| [18,] | hsa-miR-372_st | −0.39 | ACGCTCAAATGTCGCAGCACTTT (SEQ ID NO: 646) |
| [19,] | hsa-miR-373_st | −0.32 | ACACCCCAAAATCGAAGCACTTC (SEQ ID NO: 408) |
| [20,] | hsa-miR-516a-5p_st | −0.46 | GAAAGTGCTTCTTTCCTCGAGAA (SEQ ID NO: 558) |
| [21,] | hsa-miR-518d-5p_st | −0.27 | CAGAAAGTGCTTCCCTCTAGAG (SEQ ID NO: 572) |
| [22,] | hsa-miR-518e-star_st | −0.28 | CAGAAAGCGCTTCCCTCTAGAG (SEQ ID NO: 573) |
| [23,] | hsa-miR-519a-star_st | −0.3 | CAGAAAGCGCTTCCCTCTAGAG (SEQ ID NO: 573) |
| [24,] | hsa-miR-519a_st | −0.25 | ACACTCTAAAAGGATGCACTTT (SEQ ID NO: 574) |
| [25,] | hsa-miR-519b-5p_st | −0.27 | CAGAAAGCGCTTCCCTCTAGAG (SEQ ID NO: 573) |
| [26,] | hsa-miR-519c-5p_st | −0.27 | CAGAAAGCGCTTCCCTCTAGAG (SEQ ID NO: 573) |
| [27,] | hsa-miR-523-star_st | −0.25 | CAGAAAGCGCTTCCCTCTAGAG (SEQ ID NO: 573) |
| [28,] | hsa-miR-886-3p_st | −0.26 | AAGGGTCAGTAAGCACCCGCG (SEQ ID NO: 647) |

TABLE 97

Bortezomib microRNA biomarkers.

| | Medianprobe | Corr | Sequence |
|---|---|---|---|
| [1,] | HBII-438A_s_st | −0.28 | GAATGAGTCCCTCAGCATCCTCAGA (SEQ ID NO: 648) |
| [2,] | HBII-52-32_x_st | −0.39 | GGGCAATATCAGGTTCTCATCATTG (SEQ ID NO: 649) |
| [3,] | HBII-85-1_x_st | −0.26 | AGCTTTCCAAGGAATGTTTTTATA (SEQ ID NO: 640) |
| [4,] | HBII-85-23_x_st | −0.28 | AATGCATGTATTGAGGTCATCATCG (SEQ ID NO: 650) |
| [5,] | hsa-let-7e_st | −0.3 | AACTATACAACCTCCTACCTCA (SEQ ID NO: 549) |
| [6,] | hsa-miR-125a-3p_st | −0.29 | GGCTCCCAAGAACCTCACCTGT (SEQ ID NO: 601) |
| [7,] | hsa-miR-125a-5p_st | −0.31 | TCACAGGTTAAAGGGTCTCAGGGA (SEQ ID NO: 551) |
| [8,] | hsa-miR-149_st | −0.28 | GGGAGTGAAGACACGGAGCCAGA (SEQ ID NO: 500) |
| [9,] | hsa-miR-151-3p_st | −0.29 | CCTCAAGGAGCTTCAGTCTAG (SEQ ID NO: 539) |

TABLE 97-continued

Bortezomib microRNA biomarkers.

| | Medianprobe | Corr | Sequence |
|---|---|---|---|
| [10,] | hsa-miR-151-5p_st | −0.27 | ACTAGACTGTGAGCTCCTCGA (SEQ ID NO: 540) |
| [11,] | hsa-miR-193b_st | −0.28 | AGCGGGACTTTGAGGGCCAGTT (SEQ ID NO: 583) |
| [12,] | hsa-miR-21-star_st | −0.29 | ACAGCCCATCGACTGGTGTTG (SEQ ID NO: 166) |
| [13,] | hsa-miR-21_st | −0.35 | TCAACATCAGTCTGATAAGCTA (SEQ ID NO: 592) |
| [14,] | hsa-miR-22_st | −0.26 | ACAGTTCTTCAACTGGCAGCTT (SEQ ID NO: 167) |
| [15,] | hsa-miR-23a-star_st | −0.4 | AAATCCCATCCCCAGGAACCCC (SEQ ID NO: 604) |
| [16,] | hsa-miR-23a_st | −0.3 | GGAAATCCCTGGCAATGTGAT (SEQ ID NO: 571) |
| [17,] | hsa-miR-24-2-star_st | −0.3 | CTGTGTTTCAGCTCAGTAGGCA (SEQ ID NO: 579) |
| [18,] | hsa-miR-24_st | −0.29 | CTGTTCCTGCTGAACTGAGCCA (SEQ ID NO: 580) |
| [19,] | hsa-miR-27a-star_st | −0.36 | IGCTCACAAGCAGCTAAGCCCT (SEQ ID NO: 593) |
| [20,] | hsa-miR-27a_st | −0.26 | GCGGAACTTAGCCACTGTGAA (SEQ ID NO: 501) |
| [21,] | hsa-miR-30a-star_st | −0.35 | GCTGCAAACATCCGACTGAAAG (SEQ ID NO: 502) |
| [22,] | hsa-miR-30a_st | −0.34 | CTTCCAGTCGAGGATGTTTACA (SEQ ID NO: 503) |
| [23,] | hsa-miR-30c-2-star_st | −0.3 | AGAGTAAACAGCCTTCTCCCAG (SEQ ID NO: 504) |
| [24,] | hsa-miR-30c_st | −0.28 | GCTGAGAGTGTAGGATGTTTACA (SEQ ID NO: 301) |
| [25,] | hsa-miR-31-star_st | −0.27 | ATGGCAATATGTTGGCATAGCA (SEQ ID NO: 614) |
| [26,] | hsa-miR-516a-5p_st | −0.35 | GAAAGTGCTTCTTTCCTCGAGAA (SEQ ID NO: 558) |
| [27,] | hsa-miR-518d-5p_st | −0.27 | CAGAAAGTGCTTCCCTCTAGAG (SEQ ID NO: 572) |
| [28,] | hsa-miR-518e-star_st | −0.26 | CAGAAAGCGCTTCCCTCTAGAG (SEQ ID NO: 573) |
| [29,] | hsa-miR-519a-star_st | −0.28 | CAGAAAGCGCTTCCCTCTAGAG (SEQ ID NO: 573) |
| [30,] | hsa-miR-519c-5p_st | −0.32 | CAGAAAGCGCTTCCCTCTAGAG (SEQ ID NO: 573) |
| [31,] | hsa-miR-522-star_st | −0.29 | CAGAAAGCGCTTCCCTCTAGAG (SEQ ID NO: 573) |
| [32,] | hsa-miR-9-star_st | −0.41 | ACTTTCGGTTATCTAGCTTTAT (SEQ ID NO: 651) |
| [33,] | hsa-miR-935_st | −0.3 | GCGGTAGCGGAAGCGGTAACTGG (SEQ ID NO: 639) |

TABLE 97-continued

Bortezomib microRNA biomarkers.

| | Medianprobe | Corr | Sequence |
|---|---|---|---|
| [34,] | hsa-miR-98_st | −0.25 | AACAATACAACTTACTACCTCA (SEQ ID NO: 652) |
| [35,] | hsa-miR-99b-star_st | −0.26 | CGGACCCACAGACACGAGCTTG (SEQ ID NO: 569) |
| [36,] | hsa-miR-99b_st | −0.27 | CGCAAGGTCGGTTCTACGGGTG (SEQ ID NO: 559) |

TABLE 98

Leukeran microRNA biomarkers.

| | Medianprobe | Corr | Sequence |
|---|---|---|---|
| [1,] | hsa-let-7e_st | −0.42 | AACTATACAACCTCCTACCTCA (SEQ ID NO: 549) |
| [2,] | hsa-miR-10a_st | −0.36 | CACAAATTCGGATCTACAGGGTA (SEQ ID NO: 538) |
| [3,] | hsa-miR-125a-3p_st | −0.25 | GGCTCCCAAGAACCTCACCTGT (SEQ ID NO: 601) |
| [4,] | hsa-miR-125a-5p_st | −0.43 | TCACAGGTTAAAGGGTCTCAGGGA (SEQ ID NO: 551) |
| [5,] | hsa-miR-1287_st | −0.26 | GACTCGAACCACTGATCCAGCA (SEQ ID NO: 603) |
| [6,] | hsa-miR-141_st | −0.31 | CCATCTTTACCAGACAGTGTTA (SEQ ID NO: 552) |
| [7,] | hsa-miR-151-3p_st | −0.53 | CCTCAAGGAGCTTCAGTCTAG (SEQ ID NO: 539) |
| [8,] | hsa-miR-151-5p_st | −0.58 | ACTAGACTGTGAGCTCCTCGA (SEQ ID NO: 540) |
| [9,] | hsa-miR-182_st | −0.26 | AGTGTGAGTTCTACCATTGCCAAA (SEQ ID NO: 563) |
| [10,] | hsa-miR-183-star_st | −0.27 | TTATGGCCCTTCGGTAATTCAC (SEQ ID NO: 564) |
| [11,] | hsa-miR-183_st | −0.31 | AGTGAATTCTACCAGTGCCATA (SEQ ID NO: 565) |
| [12,] | hsa-miR-192_st | −0.29 | GGCTGTCAATTCATAGGTCAG (SEQ ID NO: 542) |
| [13,] | hsa-miR-193b_st | −0.37 | AGCGGGACTTTGAGGGCCAGTT (SEQ ID NO: 583) |
| [14,] | hsa-miR-194_st | −0.29 | TCCACATGGAGTTGCTGTTACA (SEQ ID NO: 543) |
| [15,] | hsa-miR-200b-star_st | −0.27 | TCCAATGCTGCCCAGTAAGATG (SEQ ID NO: 555) |
| [16,] | hsa-miR-200b_st | −0.29 | TCATCATTACCAGGCAGTATTA (SEQ ID NO: 544) |
| [17,] | hsa-miR-200c_st | −0.29 | TCCATCATTACCCGGCAGTATTA (SEQ ID NO: 556) |
| [18,] | hsa-miR-203_st | −0.3 | CTAGTGGTCCTAAACATTTCAC (SEQ ID NO: 511) |
| [19,] | hsa-miR-21_st | −0.28 | TCAACATCAGTCTGATAAGCTA (SEQ ID NO: 592) |

TABLE 98-continued

Leukeran microRNA biomarkers.

| | Medianprobe | Corr | Sequence |
|---|---|---|---|
| [20,] | hsa-miR-221-star_st | -0.29 | AAATCTACATTGTATGCCAGGT (SEQ ID NO: 613) |
| [21,] | hsa-miR-22_st | -0.32 | ACAGTTCTTCAACTGGCAGCTT (SEQ ID NO: 167) |
| [22,] | hsa-miR-23a_st | -0.36 | GGAAATCCCTGGCAATGTGAT (SEQ ID NO: 571) |
| [23,] | hsa-miR-23b-star_st | -0.27 | AAATCAGCATGCCAGGAACCCA (SEQ ID NO: 591) |
| [24,] | hsa-miR-23b_st | -0.36 | GGTAATCCCTGGCAATGTGAT (SEQ ID NO: 590) |
| [25,] | hsa-miR-24_st | -0.36 | CTGTTCCTGCTGAACTGAGCCA (SEQ ID NO: 580) |
| [26,] | hsa-miR-27b_st | -0.32 | GCAGAACTTAGCCACTGTGAA (SEQ ID NO: 567) |
| [27,] | hsa-miR-29b_st | -0.28 | AACACTGATTTCAAATGGTGCTA (SEQ ID NO: 545) |
| [28,] | hsa-miR-30b_st | -0.33 | AGCTGAGTGTAGGATGTTTACA (SEQ ID NO: 546) |
| [29,] | hsa-miR-30d_st | -0.42 | CTTCCAGTCGGGGATGTTTACA (SEQ ID NO: 547) |
| [30,] | hsa-miR-320d_st | -0.33 | TCCTCTCAACCCAGCTTTT (SEQ ID NO: 91) |
| [31,] | hsa-miR-584_st | -0.38 | CTCAGTCCCAGGCAAACCATAA (SEQ ID NO: 581) |
| [32,] | hsa-miR-99b-star_st | -0.29 | CGGACCCACAGACACGAGCTTG (SEQ ID NO: 569) |
| [33,] | hsa-miR-99b_st | -0.42 | CGCAAGGTCGGTTCTACGGGTG (SEQ ID NO: 559) |

TABLE 99

Fludarabine microRNA biomarkers.

| | Medianprobe | Corr | Sequence |
|---|---|---|---|
| [1,] | U91_s_st | -0.26 | ATACTCCATCACCTGGTTCCCAGAA (SEQ ID NO: 653) |
| [2,] | hsa-miR-10a_st | -0.27 | CACAAATTCGGATCTACAGGGTA (SEQ ID NO: 538) |
| [3,] | hsa-miR-125a-5p_st | -0.26 | TCACAGGTTAAAGGGTCTCAGGGA (SEQ ID NO: 551) |
| [4,] | hsa-miR-134_st | -0.27 | CCCCTCTGGTCAACCAGTCACA (SEQ ID NO: 164) |
| [5,] | hsa-miR-141-star_st | -0.27 | TCCAACACTGTACTGGAAGATG (SEQ ID NO: 562) |
| [6,] | hsa-miR-141_st | -0.39 | CCATCTTTACCAGACAGTGTTA (SEQ ID NO: 552) |
| [7,] | hsa-miR-151-5p_st | -0.31 | ACTAGACTGTGAGCTCCTCGA (SEQ ID NO: 540) |
| [8,] | hsa-miR-192_st | -0.28 | GGCTGTCAATTCATAGGTCAG (SEQ ID NO: 542) |

TABLE 99-continued

Fludarabine microRNA biomarkers.

| | Medianprobe | Corr | Sequence |
|---|---|---|---|
| [9,] | hsa-miR-193b_st | -0.26 | AGCGGGACTTTGAGGGCCAGTT (SEQ ID NO: 583) |
| [10,] | hsa-miR-194_st | -0.28 | TCCACATGGAGTTGCTGTTACA (SEQ ID NO: 543) |
| [11,] | hsa-miR-200a-star_st | -0.28 | TCCAGCACTGTCCGGTAAGATG (SEQ ID NO: 553) |
| [12,] | hsa-miR-200a_st | -0.32 | ACATCGTTACCAGACAGTGTTA (SEQ ID NO: 554) |
| [13,] | hsa-miR-200b-star_st | -0.28 | TCCAATGCTGCCCAGTAAGATG (SEQ ID NO: 555) |
| [14,] | hsa-miR-200b_st | -0.28 | TCATCATTACCAGGCAGTATTA (SEQ ID NO: 544) |
| [15,] | hsa-miR-200c_st | -0.35 | TCCATCATTACCCGGCAGTATTA (SEQ ID NO: 556) |
| [16,] | hsa-miR-203_st | -0.25 | CTAGTGGTCCTAAACATTTCAC (SEQ ID NO: 511) |
| [17,] | hsa-miR-205_st | -0.27 | CAGACTCCGGTGGAATGAAGGA (SEQ ID NO: 295) |
| [18,] | hsa-miR-210_st | -0.4 | TCAGCCGCTGTCACACGCACAG (SEQ ID NO: 635) |
| [19,] | hsa-miR-215_st | -0.3 | GTCTGTCAATTCATAGGTCAT (SEQ ID NO: 566) |
| [20,] | hsa-miR-23b-star_st | -0.38 | AAATCAGCATGCCAGGAACCCA (SEQ ID NO: 591) |
| [21,] | hsa-miR-23b_st | -0.44 | GGTAATCCCTGGCAATGTGAT (SEQ ID NO: 590) |
| [22,] | hsa-miR-24_st | -0.3 | CTGTTCCTGCTGAACTGAGCCA (SEQ ID NO: 580) |
| [23,] | hsa-miR-27b-star_st | -0.35 | GTTCACCAATCAGCTAAGCTCT (SEQ ID NO: 654) |
| [24,] | hsa-miR-27b_st | -0.43 | GCAGAACTTAGCCACTGTGAA (SEQ ID NO: 567) |
| [25,] | hsa-miR-299-5p_st | -0.26 | ATGTATGTGGGACGGTAAACCA (SEQ ID NO: 606) |
| [26,] | hsa-miR-320a_st | -0.3 | TCGCCCTCTCAACCCAGCTTTT (SEQ ID NO: 655) |
| [27,] | hsa-miR-320b_st | -0.3 | TTGCCCTCTCAACCCAGCTTTT (SEQ ID NO: 656) |
| [28,] | hsa-miR-320c_st | -0.28 | ACCCTCTCAACCCAGCTTTT (SEQ ID NO: 90) |
| [29,] | hsa-miR-320d_st | -0.33 | TCCTCTCAACCCAGCTTTT (SEQ ID NO: 91) |
| [30,] | hsa-miR-337-5p_st | -0.26 | AACTCCTGTATGAAGCCGTTC (SEQ ID NO: 169) |
| [31,] | hsa-miR-339-3p_st | -0.31 | CGGCTCTGTCGTCGAGGCGCTCA (SEQ ID NO: 272) |
| [32,] | hsa-miR-339-5p_st | -0.25 | CGTGAGCTCCTGGAGGACAGGGA (SEQ ID NO: 273) |

TABLE 99-continued

Fludarabine microRNA biomarkers.

| | Medianprobe | Corr | Sequence |
|---|---|---|---|
| [33,] | hsa-miR-370_st | -0.26 | ACCAGGTTCCACCCCAGCAGGC (SEQ ID NO: 32) |
| [34,] | hsa-miR-375_st | -0.26 | TCACGCGAGCCGAACGAACAAA (SEQ ID NO: 297) |
| [35,] | hsa-miR-382_st | -0.29 | CGAATCCACCACGAACAACTTC (SEQ ID NO: 174) |
| [36,] | hsa-miR-429_st | -0.28 | ACGGTTTIACCAGACAGTATTA (SEQ ID NO: 557) |
| [37,] | hsa-miR-485-5p_st | -0.28 | GAATTCATCACGGCCAGCCTCT (SEQ ID NO: 179) |
| [38,] | hsa-miR-487a_st | -0.25 | AACTGGATGTCCCTGTATGATT (SEQ ID NO: 609) |
| [39,] | hsa-miR-494_st | -0.34 | GAGGTTTCCCGTGTATGTTTCA (SEQ ID NO: 181) |
| [40,] | hsa-miR-99b-star_st | -0.3 | CGGACCCACAGACACGAGCTTG (SEQ ID NO: 569) |
| [41,] | hsa-miR-99b_st | -0.32 | CGCAAGGTCGGTTCTACGGGTG (SEQ ID NO: 559) |

TABLE 100

Vinblastine microRNA biomarkers.

| | Medianprobe | Corr | Sequence |
|---|---|---|---|
| [1,] | HBII-85-1_x_st | -0.26 | ACCTCAGTTCCGATGAGAATGACGT (SEQ ID NO: 657) |
| [2,] | HBII-85-29_st | -0.26 | TTCAGATTTCCAAGGTTTCCATTTT (SEQ ID NO: 535) |
| [3,] | hsa-miR-125a-5p_st | -0.28 | TCACAGGTTAAAGGGTCTCAGGGA (SEQ ID NO: 551) |
| [4,] | hsa-miR-130a_st | -0.31 | ATGCCCTTTTAACATTGCACTG (SEQ ID NO: 313) |
| [5,] | hsa-miR-139-5p_st | -0.36 | CTGGAGACACGTGCACTGTAGA (SEQ ID NO: 658) |
| [6,] | hsa-miR-149_st | -0.29 | GGGAGTGAAGACACGGAGCCAGA (SEQ ID NO: 500) |
| [7,] | hsa-miR-16_st | -0.27 | CGCCAATATTTACGTGCTGCTA (SEQ ID NO: 360) |
| [8,] | hsa-miR-193b_st | -0.34 | AGCGGGACTTTGAGGGCCAGTT (SEQ ID NO: 583) |
| [9,] | hsa-miR-196b_st | -0.27 | CCCAACAACAGGAAAACTACCTA (SEQ ID NO: 644) |
| [10,] | hsa-miR-200a_st | -0.28 | ACATCGTTACCAGACAGTGTTA (SEQ ID NO: 554) |
| [11,] | hsa-miR-200b-star_st | -0.28 | TCCAATGCTGCCCAGTAAGATG (SEQ ID NO: 555) |
| [12,] | hsa-miR-200b_st | -0.28 | TCATCATTACCAGGCAGTATTA (SEQ ID NO: 544) |
| [13,] | hsa-miR-203_st | -0.33 | CTAGTGGTCCTAAACATTTCAC (SEQ ID NO: 511) |
| [14,] | hsa-miR-22_st | -0.27 | ACAGTTCTTCAACTGGCAGCTT (SEQ ID NO: 167) |
| [15,] | hsa-miR-26a_st | -0.27 | AGCCTATCCTGGATTACTTGAA (SEQ ID NO: 537) |
| [16,] | hsa-miR-29b_st | -0.34 | AACACTGATTTCAAATGGTGCTA (SEQ ID NO: 545) |
| [17,] | hsa-miR-30a-star_st | -0.38 | GCTGCAAACATCCGACTGAAAG (SEQ ID NO: 502) |
| [18,] | hsa-miR-30a_st | -0.41 | CTTCCAGTCGAGGATGTTTACA (SEQ ID NO: 503) |
| [19,] | hsa-miR-30c-2-star_st | -0.38 | AGAGTAAACAGCCTTCTCCCAG (SEQ ID NO: 504) |
| [20,] | hsa-miR-30c_st | -0.5 | GCTGAGAGTGTAGGATGTTTACA (SEQ ID NO: 301) |
| [21,] | hsa-miR-331-3p_st | -0.27 | TTCTAGGATAGGCCCAGGGGC (SEQ ID NO: 568) |
| [22,] | hsa-miR-34a_st | -0.26 | ACAACCAGCTAAGACACTGCCA (SEQ ID NO: 234) |
| [23,] | hsa-miR-34b-star_st | -0.29 | CAATCAGCTAATGACACTGCCTA (SEQ ID NO: 534) |
| [24,] | hsa-miR-34c-3p_st | -0.25 | CCTGGCCGTGTGGTTAGTGATT (SEQ ID NO: 314) |
| [25,] | hsa-miR-34c-5p_st | -0.34 | GCAATCAGCTAACTACACTGCCT (SEQ ID NO: 506) |
| [26,] | hsa-miR-449a_st | -0.43 | ACCAGCTAACAATACACTGCCA (SEQ ID NO: 287) |
| [27,] | hsa-miR-449b_st | -0.38 | GCCAGCTAACAATACACTGCCT (SEQ ID NO: 288) |
| [28,] | hsa-miR-516a-5p_st | -0.28 | GAAAGTGCTTCTTTCCTCGAGAA (SEQ ID NO: 558) |
| [29,] | hsa-miR-675_st | -0.26 | CACTGTGGGCCCTCTCCGCACCA (SEQ ID NO: 516) |

TABLE 101

Busulfan microRNA biomarkers.

| | Medianprobe | Corr | Sequence |
|---|---|---|---|
| [1,] | hsa-let-7b_st | -0.27 | AACCACACAACCTACTACCTCA (SEQ ID NO: 600) |
| [2,] | hsa-let-7e_st | -0.66 | AACTATACAACCTCCTACCTCA (SEQ ID NO: 549) |
| [3,] | hsa-miR-10a_st | -0.26 | CACAAATTCGGATCTACAGGGTA (SEQ ID NO: 538) |
| [4,] | hsa-miR-125a-3p_st | -0.49 | GGCTCCCAAGAACCTCACCTGT (SEQ ID NO: 601) |
| [5,] | hsa-miR-125a-5p_st | -0.69 | TCACAGGTTAAAGGGTCTCAGGGA (SEQ ID NO: 551) |
| [6,] | hsa-miR-149_st | -0.36 | GGGAGTGAAGACACGGAGCCAGA (SEQ ID NO: 500) |
| [7,] | hsa-miR-151-3p_st | -0.44 | CCTCAAGGAGCTTCAGTCTAG (SEQ ID NO: 539) |
| [8,] | hsa-miR-151-5p_st | -0.48 | ACTAGACTGTGAGCTCCTCGA (SEQ ID NO: 540) |
| [9,] | hsa-miR-182_st | -0.27 | AGTGTGAGTTCTACCATTGCCAAA (SEQ ID NO: 563) |
| [10,] | hsa-miR-183-star_st | -0.35 | TTATGGCCCTTCGGTAATTCAC (SEQ ID NO: 564) |
| [11,] | hsa-miR-183_st | -0.31 | AGTGAATTCTACCAGTGCCATA (SEQ ID NO: 565) |
| [12,] | hsa-miR-193b_st | -0.41 | AGCGGGACTTTGAGGGCCAGTT (SEQ ID NO: 583) |
| [13,] | hsa-miR-203_st | -0.27 | CTAGTGGTCCTAAACATTTCAC (SEQ ID NO: 511) |
| [14,] | hsa-miR-22_st | -0.31 | ACAGTTCTTCAACTGGCAGCTT (SEQ ID NO: 167) |
| [15,] | hsa-miR-23a_st | -0.26 | GGAAATCCCTGGCAATGTGAT (SEQ ID NO: 571) |

TABLE 101-continued

Busulfan microRNA biomarkers.

| | Medianprobe | Corr | Sequence | |
|---|---|---|---|---|
| [16,] | hsa-miR-23b_st | -0.38 | GGTAATCCCTGGCAATGTGAT | (SEQ ID NO: 590) |
| [17,] | hsa-miR-24-1-star_st | -0.25 | ACTGATATCAGCTCAGTAGGCA | (SEQ ID NO: 659) |
| [18,] | hsa-miR-24_st | -0.26 | CTGTTCCTGCTGAACTGAGCCA | (SEQ ID NO: 580) |
| [19,] | hsa-miR-27b_st | -0.36 | GCAGAACTTAGCCACTGTGAA | (SEQ ID NO: 567) |
| [20,] | hsa-miR-30b_st | -0.34 | AGCTGAGTGTAGGATGTTTACA | (SEQ ID NO: 546) |
| [21,] | hsa-miR-30d_st | -0.33 | CTTCCAGTCGGGGATGTTTACA | (SEQ ID NO: 547) |
| [22,] | hsa-miR-320d_st | -0.26 | TCCTCTCAACCCAGCTTTT | (SEQ ID NO: 91) |
| [23,] | hsa-miR-532-3p_st | -0.26 | TGCAAGCCTTGGGTGTGGGAGG | (SEQ ID NO: 97) |
| [24,] | hsa-miR-99b-star_st | -0.52 | CGGACCCACAGACACGAGCTTG | (SEQ ID NO: 569) |
| [25,] | hsa-miR-99b_st | -0.66 | CGCAAGGTCGGTTCTACGGGTG | (SEQ ID NO: 559) |

TABLE 102

Dacarbazine microRNA biomarkers.

| | Medianprobe | Corr | Sequence | |
|---|---|---|---|---|
| [1,] | hsa-let-7e_st | -0.34 | AACTATACAACCTCCTACCTCA | (SEQ ID NO: 549) |
| [2,] | hsa-miR-103_st | -0.3 | TCATAGCCCTGTACAATGCTGCT | (SEQ ID NO: 660) |
| [3,] | hsa-miR-107_st | -0.31 | TGATAGCCCTGTACAATGCTGCT | (SEQ ID NO: 661) |
| [4,] | hsa-miR-1180_st | -0.27 | ACACACCCACGCGAGCCGGAAA | (SEQ ID NO: 662) |
| [5,] | hsa-miR-1231st | -0.27 | GCAGCTGTCCGCCCAGACAC | (SEQ ID NO: 663) |
| [6,] | hsa-miR-125a-3p_st | -0.26 | GGCTCCCAAGAACCTCACCTGT | (SEQ ID NO: 601) |
| [7,] | hsa-miR-125a-5p_st | -0.35 | TCACAGGTTAAAGGGTCTCAGGGA | (SEQ ID NO: 551) |
| [8,] | hsa-miR-1301_st | -0.3 | GAAGTCACTCCCAGGCAGCTGCAA | (SEQ ID NO: 597) |
| [9,] | hsa-miR-1303_st | -0.29 | AGAGCAAGACCCCGTCTCTAAA | (SEQ ID NO: 561) |
| [10,] | hsa-miR-132_st | -0.31 | CGACCATGGCTGTAGACTGTTA | (SEQ ID NO: 664) |
| [11,] | hsa-miR-141_st | -0.3 | CCATCTTTACCAGACAGTGTTA | (SEQ ID NO: 552) |
| [12,] | hsa-miR-151-3p_st | -0.44 | CCTCAAGGAGCTTCAGTCTAG | (SEQ ID NO: 539) |
| [13,] | hsa-miR-151-5p_st | -0.49 | ACTAGACTGTGAGCTCCTCGA | (SEQ ID NO: 540) |
| [14,] | hsa-miR-182_st | -0.26 | AGTGTGAGTTCTACCATTGCCAAA | (SEQ ID NO: 563) |
| [15,] | hsa-miR-183_st | -0.29 | AGTGAATTCTACCAGTGCCATA | (SEQ ID NO: 565) |
| [16,] | hsa-miR-192_st | -0.28 | GGCTGTCAATTCATAGGTCAG | (SEQ ID NO: 542) |
| [17,] | hsa-miR-194_st | -0.27 | TCCACATGGAGTTGCTGTTACA | (SEQ ID NO: 543) |
| [18,] | hsa-miR-200b_st | -0.27 | TCATCATTACCAGGCAGTATTA | (SEQ ID NO: 544) |
| [19,] | hsa-miR-200c_st | -0.32 | TCCATCATTACCCGGCAGTATTA | (SEQ ID NO: 556) |
| [20,] | hsa-miR-215_st | -0.26 | GTCTGTCAATTCATAGGTCAT | (SEQ ID NO: 566) |
| [21,] | hsa-miR-22_st | -0.4 | ACAGTTCTTCAACTGGCAGCTT | (SEQ ID NO: 167) |
| [22,] | hsa-miR-24_st | -0.27 | CTGTTCCTGCTGAACTGAGCCA | (SEQ ID NO: 580) |
| [23,] | hsa-miR-28-3p_st | -0.38 | TCCAGGAGCTCACAATCTAGTG | (SEQ ID NO: 605) |
| [24,] | hsa-miR-28-5p_st | -0.4 | CTCAATAGACTGTGAGCTCCTT | (SEQ ID NO: 594) |
| [25,] | hsa-miR-30a_st | -0.26 | CTTCCAGTCGAGGATGTTTACA | (SEQ ID NO: 503) |
| [26,] | hsa-miR-30b_st | -0.38 | AGCTGAGTGTAGGATGTTTACA | (SEQ ID NO: 546) |
| [27,] | hsa-miR-30d_st | -0.39 | CTTCCAGTCGGGGATGTTTACA | (SEQ ID NO: 547) |
| [28,] | hsa-miR-324-5p_st | -0.34 | ACACCAATGCCCTAGGGGATGCG | (SEQ ID NO: 665) |
| [29,] | hsa-miR-339-3p_st | -0.3 | CGGCTCTGTCGTCGAGGCGCTCA | (SEQ ID NO: 272) |
| [30,] | hsa-miR-34a-star_st | -0.26 | AGGGCAGTATACTTGCTGATTG | (SEQ ID NO: 277) |
| [31,] | hsa-miR-34a_st | -0.42 | ACAACCAGCTAAGACACTGCCA | (SEQ ID NO: 234) |
| [32,] | hsa-miR-429_st | -0.31 | ACGGTTTTACCAGACAGTATTA | (SEQ ID NO: 557) |
| [33,] | hsa-miR-589_st | -0.27 | CTCAGAGCAGACGTGGTTCTCA | (SEQ ID NO: 666) |
| [34,] | hsa-miR-934_st | -0.3 | CCAGTGTCTCCAGTAGTAGACA | (SEQ ID NO: 517) |
| [35,] | hsa-miR-935_st | -0.26 | GCGGTAGCGGAAGCGGTAACTGG | (SEQ ID NO: 639) |
| [36,] | hsa-miR-99b-start_st | -0.39 | CGGACCCACAGACACGAGCTTG | (SEQ ID NO: 569) |
| [37,] | hsa-miR-99b_st | -0.4 | CGCAAGGTCGGTTCTACGGGTG | (SEQ ID NO: 559) |

TABLE 103

Oxaliplatin microRNA biomarkers.

| | Medianprobe | Corr | Sequence | |
|---|---|---|---|---|
| [1,] | hsa-let-7e_st | -0.35 | AACTATACAACCTCCTACCTCA | (SEQ ID NO: 549) |
| [2,] | hsa-miR-100_st | -0.36 | CACAAGTTCGGATCTACGGGTT | (SEQ ID NO: 17) |
| [3,] | hsa-miR-125a-5p_st | -0.35 | TCACAGGTTAAAGGGTCTCAGGGA | (SEQ ID NO: 551) |
| [4,] | hsa-miR-125b-1-star_st | -0.41 | AGCTCCCAAGAGCCTAACCCGT | (SEQ ID NO: 163) |
| [5,] | hsa-miR-125b_st | -0.39 | TCACAAGTTAGGGTCTCAGGGA | (SEQ ID NO: 602) |
| [6,] | hsa-miR-1269_st | -0.36 | CCAGTAGCACGGCTCAGTCCAG | (SEQ ID NO: 667) |
| [7,] | hsa-miR-1270_st | -0.31 | ACACAGCTCTTCCATATCTCCAG | (SEQ ID NO: 668) |
| [8,] | hsa-miR-130a_st | -0.33 | ATGCCCTTTTAACATTGCACTG | (SEQ ID NO: 313) |
| [9,] | hsa-miR-134_st | -0.26 | CCCCTCTGGTCAACCAGTCACA | (SEQ ID NO: 164) |

TABLE 103-continued

Oxaliplatin microRNA biomarkers.

| | Medianprobe | Corr | Sequence | |
|---|---|---|---|---|
| [10,] | hsa-miR-143_st | -0.3 | GAGCTACAGTGCTTCATCTCA | (SEQ ID NO: 31) |
| [11,] | hsa-miR-145_st | -0.25 | AGGGATTCCTGGGAAAACTGGAC | (SEQ ID NO: 669) |
| [12,] | hsa-miR-151-3p_st | -0.31 | CCTCAAGGAGCTTCAGTCTAG | (SEQ ID NO: 539) |
| [13,] | hsa-miR-151-5p_st | -0.31 | ACTAGACTGTGAGCTCCTCGA | (SEQ ID NO: 540) |
| [14,] | hsa-miR-181a-2-star_st | -0.35 | GGTACAGTCAACGGTCAGTGGT | (SEQ ID NO: 612) |
| [15,] | hsa-miR-193a-3p_st | -0.26 | ACTGGGACTTTGTAGGCCAGTT | (SEQ ID NO: 366) |
| [16,] | hsa-miR-193a-5p_st | -0.39 | TCATCTCGCCCGCAAAGACCCA | (SEQ ID NO: 165) |
| [17,] | hsa-miR-217_st | -0.32 | TCCAATCAGTTCCTGATGCAGTA | (SEQ ID NO: 670) |
| [18,] | hsa-miR-21_st | -0.26 | TCAACATCAGTCTGATAAGCTA | (SEQ ID NO: 592) |
| [19,] | hsa-miR-221-star_st | -0.29 | AAATCTACATTGTATGCCAGGT | (SEQ ID NO: 613) |
| [20,] | hsa-miR-22_st | -0.38 | ACAGTTCTTCAACTGGCAGCTT | (SEQ ID NO: 167) |
| [21,] | hsa-miR-23a-star_st | -0.34 | AAATCCCATCCCCAGGAACCCC | (SEQ ID NO: 604) |
| [22,] | hsa-miR-23a_st | -0.37 | GGAAATCCCTGGCAATGTGAT | (SEQ ID NO: 571) |
| [23,] | hsa-miR-23b-star_st | -0.3 | AAATCAGCATGCCAGGAACCCA | (SEQ ID NO: 591) |
| [24,] | hsa-miR-23b_st | -0.39 | GGTAATCCCTGGCAATGTGAT | (SEQ ID NO: 590) |
| [25,] | hsa-miR-24-2-star_st | -0.37 | CTGTGTTTCAGCTCAGTAGGCA | (SEQ ID NO: 579) |
| [26,] | hsa-miR-24_st | -0.39 | CTGTTCCTGCTGAACTGAGCCA | (SEQ ID NO: 580) |
| [27,] | hsa-miR-27a-star_st | -0.29 | TGCTCACAAGCAGCTAAGCCCT | (SEQ ID NO: 593) |
| [28,] | hsa-miR-27a_st | -0.27 | GCGGAACTTAGCCACTGTGAA | (SEQ ID NO: 501) |
| [29,] | hsa-miR-27b-star_st | -0.37 | GTTCACCAATCAGCTAAGCTCT | (SEQ ID NO: 654) |
| [30,] | hsa-miR-27b_st | -0.35 | GCAGAACTTAGCCACTGTGAA | (SEQ ID NO: 567) |
| [31,] | hsa-miR-28-3p_st | -0.42 | TCCAGGAGCTCACAATCTAGTG | (SEQ ID NO: 605) |
| [32,] | hsa-miR-28-5p_st | -0.42 | CTCAATAGACTGTGAGCTCCTT | (SEQ ID NO: 594) |
| [33,] | hsa-miR-30a-star_st | -0.39 | GCTGCAAACATCCGACTGAAAG | (SEQ ID NO: 502) |
| [34,] | hsa-miR-30a_st | -0.38 | CTTCCAGTCGAGGATGTTTACA | (SEQ ID NO: 503) |
| [35,] | hsa-miR-30c-2-star_st | -0.39 | AGAGTAAACAGCCTTCTCCCAG | (SEQ ID NO: 504) |
| [36,] | hsa-miR-34c-5p_st | -0.28 | GCAATCAGCTAACTACACTGCCT | (SEQ ID NO: 506) |
| [37,] | hsa-miR-376a_st | -0.28 | ACGTGGATTTTCCTCTATGAT | (SEQ ID NO: 607) |
| [38,] | hsa-miR-455-3p_st | -0.27 | GTGTATATGCCCATGGACTGC | (SEQ ID NO: 178) |
| [39,] | hsa-miR-543_st | -0.26 | AAGAAGTGCACCGCGAATGTTT | (SEQ ID NO: 182) |
| [40,] | hsa-miR-574-3p_st | -0.4 | TGTGGGTGTGTGCATGAGCGTG | (SEQ ID NO: 671) |
| [41,] | hsa-miR-99b-star_st | -0.27 | CGGACCCACAGACACGAGCTTG | (SEQ ID NO: 569) |
| [42,] | hsa-miR-99b_st | -0.31 | CGCAAGGTCGGTTCTACGGGTG | (SEQ ID NO: 559) |

TABLE 104

Hydroxyurea microRNA biomarkers.

| | Medianprobe | Corr | Sequence | |
|---|---|---|---|---|
| [1,] | hsa-let-7e_st | -0.43 | AACTATACAACCTCCTACCTCA | (SEQ ID NO: 549) |
| [2,] | hsa-miR-103_st | -0.26 | TCATAGCCCTGTACAATGCTGCT | (SEQ ID NO: 660) |
| [3,] | hsa-miR-107_st | -0.27 | TGATAGCCCTGTACAATGCTGCT | (SEQ ID NO: 661) |
| [4,] | hsa-miR-10a_st | -0.35 | CACAAATTCGGATCTACAGGGTA | (SEQ ID NO: 538) |
| [5,] | hsa-miR-1180_st | -0.26 | ACACACCCACGCGAGCCGGAAA | (SEQ ID NO: 662) |
| [6,] | hsa-miR-125a-3p_st | -0.29 | GGCTCCCAAGAACCTCACCTGT | (SEQ ID NO: 601) |
| [7,] | hsa-miR-125a-5p_st | -0.44 | TCACAGGTTAAAGGGTCTCAGGGA | (SEQ ID NO: 551) |
| [8,] | hsa-miR-1287_st | -0.31 | GACTCGAACCACTGATCCAGCA | (SEQ ID NO: 603) |
| [9,] | hsa-miR-132_st | -0.39 | CGACCATGGCTGTAGACTGTTA | (SEQ ID NO: 664) |
| [10,] | hsa-miR-149_st | -0.28 | GGGAGTGAAGACACGGAGCCAGA | (SEQ ID NO: 500) |
| [11,] | hsa-miR-151-3p_st | -0.57 | CCTCAAGGAGCTTCAGTCTAG | (SEQ ID NO: 539) |
| [12,] | hsa-miR-151-5p_st | -0.64 | ACTAGACTGTGAGCTCCTCGA | (SEQ ID NO: 540) |
| [13,] | hsa-miR-182_st | -0.35 | AGTGTGAGTTCTACCATTGCCAAA | (SEQ ID NO: 563) |
| [14,] | hsa-miR-183_st | -0.35 | AGTGAATTCTACCAGTGCCATA | (SEQ ID NO: 565) |
| [15,] | hsa-miR-193b_st | -0.33 | AGCGGGACTTTGAGGGCCAGTT | (SEQ ID NO: 583) |
| [16,] | hsa-miR-195_st | -0.27 | GCCAATATTTCTGTGCTGCTA | (SEQ ID NO: 672) |
| [17,] | hsa-miR-21_st | -0.28 | TCAACATCAGTCTGATAAGCTA | (SEQ ID NO: 592) |
| [18,] | hsa-miR-221-star_st | -0.31 | AAATCTACATTGTATGCCAGGT | (SEQ ID NO: 613) |
| [19,] | hsa-miR-22_st | -0.41 | ACAGTTCTTCAACTGGCAGCTT | (SEQ ID NO: 167) |
| [20,] | hsa-miR-23a_st | -0.29 | GGAAATCCCTGGCAATGTGAT | (SEQ ID NO: 571) |
| [21,] | hsa-miR-23b_st | -0.36 | GGTAATCCCTGGCAATGTGAT | (SEQ ID NO: 590) |
| [22,] | hsa-miR-24_st | -0.36 | CTGTTCCTGCTGAACTGAGCCA | (SEQ ID NO: 580) |
| [23,] | hsa-miR-26a_st | -0.3 | AGCCTATCCTGGATTACTTGAA | (SEQ ID NO: 537) |
| [24,] | hsa-miR-27b_st | -0.29 | GCAGAACTTAGCCACTGTGAA | (SEQ ID NO: 567) |
| [25,] | hsa-miR-28-3p_st | -0.29 | TCCAGGAGCTCACAATCTAGTG | (SEQ ID NO: 605) |
| [26,] | hsa-miR-28-5p_st | -0.32 | CTCAATAGACTGTGAGCTCCTT | (SEQ ID NO: 594) |
| [27,] | hsa-miR-30a-star_st | -0.26 | GCTGCAAACATCCGACTGAAAG | (SEQ ID NO: 502) |
| [28,] | hsa-miR-30a_st | -0.34 | CTTCCAGTCGAGGATGTTTACA | (SEQ ID NO: 503) |
| [29,] | hsa-miR-30b-star_st | -0.27 | GAAGTAAACATCCACCTCCCAG | (SEQ ID NO: 673) |
| [30,] | hsa-miR-30b_st | -0.29 | AGCTGAGTGTAGGATGTTTACA | (SEQ ID NO: 546) |
| [31,] | hsa-miR-30d_st | -0.4 | CTTCCAGTCGGGGATGTTTACA | (SEQ ID NO: 547) |
| [32,] | hsa-miR-320d_st | -0.33 | TCCTCTCAACCCAGCTTTT | (SEQ ID NO: 91) |
| [33,] | hsa-miR-34a_st | -0.25 | ACAACCAGCTAAGACACTGCCA | (SEQ ID NO: 234) |

TABLE 104-continued

Hydroxyurea microRNA biomarkers.

| | Medianprobe | Corr | Sequence | |
|---|---|---|---|---|
| [34,] | hsa-miR-501-3p_st | -0.26 | AGAATCCTTGCCCGGGTGCATT | (SEQ ID NO: 95) |
| [35,] | hsa-miR-532-3p_st | -0.27 | TGCAAGCCTTGGGTGTGGGAGG | (SEQ ID NO: 97) |
| [36,] | hsa-miR-584_st | -0.35 | CTCAGTCCCAGGCAAACCATAA | (SEQ ID NO: 581) |
| [37,] | hsa-miR-99b-star_st | -0.35 | CGGACCCACAGACACGAGCTTG | (SEQ ID NO: 569) |
| [38,] | hsa-miR-99b_st | -0.46 | CGCAAGGTCGGTTCTACGGGTG | (SEQ ID NO: 559) |

TABLE 105

Tegafur microRNA biomarkers.

| | Medianprobe | Corr | Sequence | |
|---|---|---|---|---|
| [1,] | 14qII-14_st | -0.26 | ACACTCATACGCCGGCAGTTGTCAT | (SEQ ID NO: 674) |
| [2,] | 14qII-14_x_st | -0.26 | ATCACCCAACACTCATACGCCGGCA | (SEQ ID NO: 627) |
| [3,] | 14qII-1_st | -0.26 | ACTTCCAGACCTGTATTCACCGTCA | (SEQ ID NO: 675) |
| [4,] | 14qII-1_x_st | -0.26 | GGACCTCAGACTTCCAGACCTGTAT | (SEQ ID NO: 599) |
| [5,] | 14qII-26_st | -0.26 | CGTATGTGACTCATACTCCACCAGT | (SEQ ID NO: 676) |
| [6,] | hsa-let-7a_st | -0.27 | AACTATACAACCTACTACCTCA | (SEQ ID NO: 575) |
| [7,] | hsa-let-7e_st | -0.44 | AACTATACAACCTCCTACCTCA | (SEQ ID NO: 549) |
| [8,] | hsa-let-7f_st | -0.32 | AACTATACAATCTACTACCTCA | (SEQ ID NO: 577) |
| [9,] | hsa-miR-100_st | -0.3 | CACAAGTTCGGATCTACGGGTT | (SEQ ID NO: 17) |
| [10,] | hsa-miR-10b_st | -0.26 | CACAAATTCGGTTCTACAGGGTA | (SEQ ID NO: 550) |
| [11,] | hsa-miR-125a-3p_st | -0.26 | GGCTCCCAAGAACCTCACCTGT | (SEQ ID NO: 601) |
| [12,] | hsa-miR-125a-5p_st | -0.4 | TCACAGGTTAAAGGGTCTCAGGGA | (SEQ ID NO: 551) |
| [13,] | hsa-miR-125b-1-star_st | -0.36 | AGCTCCCAAGAGCCTAACCCGT | (SEQ ID NO: 163) |
| [14,] | hsa-miR-125b_st | -0.33 | TCACAAGTTAGGGTCTCAGGGA | (SEQ ID NO: 602) |
| [15,] | hsa-miR-130a_st | -0.35 | ATGCCCTTTTAACATTGCACTG | (SEQ ID NO: 313) |
| [16,] | hsa-miR-134_st | -0.3 | CCCCTCTGGTCAACCAGTCACA | (SEQ ID NO: 164) |
| [17,] | hsa-miR-149_st | -0.41 | GGGAGTGAAGACACGGAGCCAGA | (SEQ ID NO: 500) |
| [18,] | hsa-miR-151-3p_st | -0.33 | CCTCAAGGAGCTTCAGTCTAG | (SEQ ID NO: 539) |
| [19,] | hsa-miR-151-5p_st | -0.33 | ACTAGACTGTGAGCTCCTCGA | (SEQ ID NO: 540) |
| [20,] | hsa-miR-181a-2-star_st | -0.35 | GGTACAGTCAACGGTCAGTGGT | (SEQ ID NO: 612) |
| [21,] | hsa-miR-217_st | -0.27 | TCCAATCAGTTCCTGATGCAGTA | (SEQ ID NO: 670) |
| [22,] | hsa-miR-21_st | -0.31 | TCAACATCAGTCTGATAAGCTA | (SEQ ID NO: 592) |
| [23,] | hsa-miR-22-star_st | -0.26 | TAAAGCTTGCCACTGAAGAACT | (SEQ ID NO: 578) |
| [24,] | hsa-miR-221-star_st | -0.37 | AAATCTACATTGTATGCCAGGT | (SEQ ID NO: 613) |
| [25,] | hsa-miR-221st | -0.3 | GAAACCCAGCAGACAATGTAGCT | (SEQ ID NO: 620) |
| [26,] | hsa-miR-222-star_st | -0.29 | AGGATCTACACTGGCTACTGAG | (SEQ ID NO: 677) |
| [27,] | hsa-miR-27b_st | -0.31 | GCAGAACTTAGCCACTGTGAA | (SEQ ID NO: 567) |
| [28,] | hsa-miR-299-3p_st | -0.27 | AAGCGGTTTACCATCCCACATA | (SEQ ID NO: 168) |
| [29,] | hsa-miR-299-5p_st | -0.28 | ATGTATGTGGGACGGTAAACCA | (SEQ ID NO: 606) |
| [30,] | hsa-miR-30a-star_st | -0.47 | GCTGCAAACATCCGACTGAAAG | (SEQ ID NO: 502) |
| [31,] | hsa-miR-30a_st | -0.42 | CTTCCAGTCGAGGATGTTTACA | (SEQ ID NO: 503) |
| [32,] | hsa-miR-30c-2-star_st | -0.45 | AGAGTAAACAGCCTTCTCCCAG | (SEQ ID NO: 504) |
| [33,] | hsa-miR-30c_st | -0.37 | GCTGAGAGTGTAGGATGTTTACA | (SEQ ID NO: 301) |
| [34,] | hsa-miR-30e-star_st | -0.28 | GCTGTAAACATCCGACTGAAAG | (SEQ ID NO: 505) |
| [35,] | hsa-miR-337-5p_st | -0.36 | AACTCCTGTATGAGCCGTTC | (SEQ ID NO: 169) |
| [36,] | hsa-miR-376a_st | -0.32 | ACGTGGATTTTCCTCTATGAT | (SEQ ID NO: 607) |
| [37,] | hsa-miR-376c_st | -0.36 | ACGTGGAATTTCCTCTATGTT | (SEQ ID NO: 170) |
| [38,] | hsa-miR-377-star_st | -0.27 | GAATTCACCAAGGGCAACCTCT | (SEQ ID NO: 171) |
| [39,] | hsa-miR-379_st | -0.32 | CCTACGTTCCATAGTCTACCA | (SEQ ID NO: 172) |
| [40,] | hsa-miR-382_st | -0.33 | CGAATCCACCACGAACAACTTC | (SEQ ID NO: 174) |
| [41,] | hsa-miR-409-3p_st | -0.28 | AGGGGTTCACCGAGCAACATTC | (SEQ ID NO: 81) |
| [42,] | hsa-miR-409-5p_st | -0.3 | ATGCAAAGTTGCTCGGGTAACCT | (SEQ ID NO: 175) |
| [43,] | hsa-miR-411_st | -0.34 | CGTACGGTATACGGTCTACTA | (SEQ ID NO: 176) |
| [44,] | hsa-miR-485-5p_st | -0.27 | GAATTCATCACGGCCAGCCTCT | (SEQ ID NO: 179) |
| [45,] | hsa-miR-487a_st | -0.26 | AACTGGATGTCCCTGTATGATT | (SEQ ID NO: 609) |
| [46,] | hsa-miR-487b_st | -0.28 | AAGTGGATGACCCTGTACGATT | (SEQ ID NO: 82) |
| [47,] | hsa-miR-495_st | -0.25 | AAGAAGTGCACCATGTTTGTTT | (SEQ ID NO: 610) |
| [48,] | hsa-miR-543_st | -0.35 | AAGAAGTGCACCGCGAATGTTT | (SEQ ID NO: 182) |
| [49,] | hsa-miR-654-5p_st | -0.31 | GCACATGTTCTGCGGCCCACCA | (SEQ ID NO: 611) |
| [50,] | hsa-miR-758_st | -0.28 | GGTTAGTGGACCAGGTCACAAA | (SEQ ID NO: 35) |
| [51,] | hsa-miR-9-star_st | -0.34 | ACTTTCGGTTATCTAGCTTTAT | (SEQ ID NO: 651) |
| [52,] | hsa-miR-98_st | -0.34 | AACAATACAACTTACTACCTCA | (SEQ ID NO: 652) |
| [53,] | hsa-miR-99b-star_st | -0.29 | CGGACCCACAGACACGAGCTTG | (SEQ ID NO: 569) |
| [54,] | hsa-miR-99b_st | -0.37 | CGCAAGGTCGGTTCTACGGGTG | (SEQ ID NO: 559) |

TABLE 106

Daunorubicin microRNA biomarkers.

| | Medianprobe | Corr | Sequence | |
|---|---|---|---|---|
| [1,] | hsa-let-7e_st | -0.42 | AACTATACAACCTCCTACCTCA | (SEQ ID NO: 549) |
| [2,] | hsa-miR-10a_st | -0.28 | CACAAATTCGGATCTACAGGGTA | (SEQ ID NO: 538) |
| [3,] | hsa-miR-125a-5p_st | -0.41 | TCACAGGTTAAAGGGTCTCAGGGA | (SEQ ID NO: 551) |
| [4,] | hsa-miR-146a_st | -0.26 | AACCCATGGAATTCAGTTCTCA | (SEQ ID NO: 19) |
| [5,] | hsa-miR-151-3p_st | -0.43 | CCTCAAGGAGCTTCAGTCTAG | (SEQ ID NO: 539) |
| [6,] | hsa-miR-151-5p_st | -0.49 | ACTAGACTGTGAGCTCCTCGA | (SEQ ID NO: 540) |
| [7,] | hsa-miR-193b_st | -0.36 | AGCGGGACTTTGAGGGCCAGTT | (SEQ ID NO: 583) |
| [8,] | hsa-miR-200b-star_st | -0.26 | TCCAATGCTGCCCAGTAAGATG | (SEQ ID NO: 555) |
| [9,] | hsa-miR-200b_st | -0.27 | TCATCATTACCAGGCAGTATTA | (SEQ ID NO: 544) |
| [10,] | hsa-miR-203_st | -0.29 | CTAGTGGTCCTAAACATTTCAC | (SEQ ID NO: 511) |
| [11,] | hsa-miR-221-star_st | -0.26 | AAATCTACATTGTATGCCAGGT | (SEQ ID NO: 613) |
| [12,] | hsa-miR-22_st | -0.35 | ACAGTTCTTCAACTGGCAGCTT | (SEQ ID NO: 167) |
| [13,] | hsa-miR-23a_st | -0.41 | GGAAATCCCTGGCAATGTGAT | (SEQ ID NO: 571) |
| [14,] | hsa-miR-24-2-star_st | -0.31 | CTGTGTTTCAGCTCAGTAGGCA | (SEQ ID NO: 579) |
| [15,] | hsa-miR-24_st | -0.34 | CTGTTCCTGCTGAACTGAGCCA | (SEQ ID NO: 580) |
| [16,] | hsa-miR-27a_st | -0.27 | GCGGAACTTAGCCACTGTGAA | (SEQ ID NO: 501) |
| [17,] | hsa-miR-29a_st | -0.28 | TAACCGATTTCAGATGGTGCTA | (SEQ ID NO: 584) |
| [18,] | hsa-miR-29b-1-star_st | -0.28 | TCTAAACCACCATATGAAACCAGC | (SEQ ID NO: 622) |
| [19,] | hsa-miR-29b_st | -0.34 | AACACTGATTTCAAATGGTGCTA | (SEQ ID NO: 545) |
| [20,] | hsa-miR-30a-star_st | -0.35 | GCTGCAAACATCCGACTGAAAG | (SEQ ID NO: 502) |
| [21,] | hsa-miR-30a_st | -0.4 | CTTCCAGTCGAGGATGTTTACA | (SEQ ID NO: 503) |
| [22,] | hsa-miR-30b_st | -0.32 | AGCTGAGTGTAGGATGTTTACA | (SEQ ID NO: 546) |
| [23,] | hsa-miR-30c-2-star_st | -0.31 | AGAGTAAACAGCCTTCTCCCAG | (SEQ ID NO: 504) |
| [24,] | hsa-miR-30c_st | -0.32 | GCTGAGAGTGTAGGATGTTTACA | (SEQ ID NO: 301) |
| [25,] | hsa-miR-30d_st | -0.36 | CTTCCAGTCGGGGATGTTTACA | (SEQ ID NO: 547) |
| [26,] | hsa-miR-30e-star_st | -0.27 | GCTGTAAACATCCGACTGAAAG | (SEQ ID NO: 505) |
| [27,] | hsa-miR-372_st | -0.29 | ACGCTCAAATGTCGCAGCACTTT | (SEQ ID NO: 646) |
| [28,] | hsa-miR-373_st | -0.28 | ACACCCCAAAATCGAAGCACTTC | (SEQ ID NO: 408) |
| [29,] | hsa-miR-516a-5p_st | -0.44 | GAAAGTGCTTCTTTCCTCGAGAA | (SEQ ID NO: 558) |
| [30,] | hsa-miR-518e-star_st | -0.27 | CAGAAAGCGCTTCCCTCTAGAG | (SEQ ID NO: 573) |
| [31,] | hsa-miR-519a-star_st | -0.31 | CAGAAAGCGCTTCCCTCTAGAG | (SEQ ID NO: 573) |
| [32,] | hsa-miR-519a_st | -0.33 | ACACTCTAAAAGGATGCACTTT | (SEQ ID NO: 574) |
| [33,] | hsa-miR-519b-5p_st | -0.29 | CAGAAAGCGCTTCCCTCTAGAG | (SEQ ID NO: 573) |
| [34,] | hsa-miR-5190-5p_st | -0.31 | CAGAAAGCGCTTCCCTCTAGAG | (SEQ ID NO: 573) |
| [35,] | hsa-miR-522-star_st | -0.28 | CAGAAAGCGCTTCCCTCTAGAG | (SEQ ID NO: 573) |
| [36,] | hsa-miR-523-star_st | -0.26 | CAGAAAGCGCTTCCCTCTAGAG | (SEQ ID NO: 573) |
| [37,] | hsa-miR-526a_st | -0.3 | CAGAAAGTGCTTCCCTCTAGAG | (SEQ ID NO: 572) |
| [38,] | hsa-miR-584_st | -0.31 | CTCAGTCCCAGGCAAACCATAA | (SEQ ID NO: 581) |
| [39,] | hsa-miR-675_st | -0.28 | CACTGTGGGCCCTCTCCGCACCA | (SEQ ID NO: 516) |
| [40,] | hsa-miR-99b_st | -0.37 | CGCAAGGTCGGTTCTACGGGTG | (SEQ ID NO: 559) |

Table 107

Bleomycin microRNA biomarkers.

| | Medianprobe | Corr | Sequence | |
|---|---|---|---|---|
| [1,] | HETT-1800_st | -0.29 | GTGCACTGTGTCCTCAGGGGTGATC | (SEQ ID NO: 678) |
| [2,] | HETT-1800_x_st | -0.25 | TCAGGGGTGATCAGAGCCCAGTGCT | (SEQ ID NO: 491) |
| [3,] | hsa-miR-106a_st | -0.29 | CTACCTGCACTGTAAGCACTTTT | (SEQ ID NO: 150) |
| [4,] | hsa-miR-106b-star_st | -0.26 | GCAGCAAGTACCCACAGTGCGG | (SEQ ID NO: 2) |
| [5,] | hsa-miR-106b_st | -0.29 | ATCTGCACTGTCAGCACTTTA | (SEQ ID NO: 37) |
| [6,] | hsa-miR-107_st | -0.3 | TGATAGCCCTGTACAATGCTGCT | (SEQ ID NO: 661) |
| [7,] | hsa-miR-1207-5p_st | -0.29 | CCCCTCCCAGCCTCCCTGCCA | (SEQ ID NO: 109) |
| [8,] | hsa-miR-1244_st | -0.31 | AACCATCTCATACAAACCAACTACT | (SEQ ID NO: 560) |
| [9,] | hsa-miR-128_st | -0.32 | AAAGAGACCGGTTCACTGTGA | (SEQ ID NO: 110) |
| [10,] | hsa-miR-1292_st | -0.32 | CAGCGTCTGCCGGAACCCGTTCCCA | (SEQ ID NO: 499) |
| [11,] | hsa-miR-1306_st | -0.28 | CACCACCAGAGCCAACGT | (SEQ ID NO: 679) |
| [12,] | hsa-miR-1307_st | -0.29 | CACGACCGACGCCACGCCGAGT | (SEQ ID NO: 102) |
| [13,] | hsa-miR-130b_st | -0.27 | ATGCCCTTTCATCATTGCACTG | (SEQ ID NO: 403) |
| [14,] | hsa-miR-141_st | -0.34 | CCATCTTTACCAGACAGTGTTA | (SEQ ID NO: 552) |
| [15,] | hsa-miR-15b_st | -0.33 | TGTAAACCATGATGTGCTGCTA | (SEQ ID NO: 510) |
| [16,] | hsa-miR-17_st | -0.26 | CTACCTGCACTGTAAGCACTTTG | (SEQ ID NO: 152) |
| [17,] | hsa-miR-183_st | -0.26 | AGTGAATTCTACCAGTGCCATA | (SEQ ID NO: 565) |
| [18,] | hsa-miR-185-star_st | -0.32 | GACCAGAGGAAAGCCAGCCCT | (SEQ ID NO: 406) |
| [19,] | hsa-miR-185_st | -0.27 | TCAGGAACTGCCTTTCTCTCCA | (SEQ ID NO: 85) |
| [20,] | hsa-miR-188-5p_st | -0.32 | CCCTCCACCATGCAAGGGATG | (SEQ ID NO: 86) |
| [21,] | hsa-miR-18a-star_st | -0.25 | CCAGAAGGAGCACTTAGGGCAGT | (SEQ ID NO: 71) |
| [22,] | hsa-miR-18a_st | -0.26 | CTATCTGCACTAGATGCACCTTA | (SEQ ID NO: 72) |
| [23,] | hsa-miR-18b_st | -0.37 | CTAACTGCACTAGATGCACCTTA | (SEQ ID NO: 87) |
| [24,] | hsa-miR-192_st | -0.25 | GGCTGTCAATTCATAGGTCAG | (SEQ ID NO: 542) |
| [25,] | hsa-miR-19b_st | -0.27 | TCAGTTTTGCATGGATTTGCACA | (SEQ ID NO: 153) |
| [26,] | hsa-miR-200c-star_st | -0.28 | CCAAACACTGCTGGGTAAGACG | (SEQ ID NO: 231) |

Table 107-continued

Bleomycin microRNA biomarkers.

| Medianprobe | Corr | Sequence | |
|---|---|---|---|
| [27,] hsa-miR-200c_st | -0.33 | TCCATCATTACCCGGCAGTATTA | (SEQ ID NO: 556) |
| [28,] hsa-miR-203_st | -0.3 | CTAGTGGTCCTAAACATTTCAC | (SEQ ID NO: 511) |
| [29,] hsa-miR-205_st | -0.27 | CAGACTCCGGTGGAATGAAGGA | (SEQ ID NO: 295) |
| [30,] hsa-miR-20a_st | -0.25 | CTACCTGCACTATAAGCACTTTA | (SEQ ID NO: 218) |
| [31,] hsa-miR-20b_st | -0.31 | CTACCTGCACTATGAGCACTTTG | (SEQ ID NO: 88) |
| [32,] hsa-miR-215_st | -0.3 | GTCTGTCAATTCATAGGTCAT | (SEQ ID NO: 566) |
| [33,] hsa-miR-25-star_st | -0.25 | CAATTGCCCAAGTCTCCGCCT | (SEQ ID NO: 3) |
| [34,] hsa-miR-25_st | -0.39 | TCAGACCGAGACAAGTGCAATG | (SEQ ID NO: 89) |
| [35,] hsa-miR-30b_st | -0.32 | AGCTGAGTGTAGGATGTTTACA | (SEQ ID NO: 546) |
| [36,] hsa-miR-30d_st | -0.36 | CTTCCAGTCGGGGATGTTTACA | (SEQ ID NO: 547) |
| [37,] hsa-miR-320d_st | -0.25 | TCCTCTCAACCCAGCTTTT | (SEQ ID NO: 91) |
| [38,] hsa-miR-324-5p_st | -0.26 | ACACCAATGCCCTAGGGGATGCG | (SEQ ID NO: 665) |
| [39,] hsa-miR-362-5p_st | -0.36 | ACTCACACCTAGGTTCCAAGGATT | (SEQ ID NO: 92) |
| [40,] hsa-miR-378-star_st | -0.31 | ACACAGGACCTGGAGTCAGGAG | (SEQ ID NO: 409) |
| [41,] hsa-miR-421st | -0.32 | GCGCCCAATTAATGTCTGTTGAT | (SEQ ID NO: 512) |
| [42,] hsa-miR-422a_st | -0.27 | GCCTTCTGACCCTAAGTCCAGT | (SEQ ID NO: 410) |
| [43,] hsa-miR-425_st | -0.35 | TCAACGGGAGTGATCGTGTCATT | (SEQ ID NO: 286) |
| [44,] hsa-miR-500-star_st | -0.28 | CAGAATCCTTGCCCAGGTGCAT | (SEQ ID NO: 93) |
| [45,] hsa-miR-500_st | -0.26 | TCTCACCCAGGTAGCAAGGATTA | (SEQ ID NO: 94) |
| [46,] hsa-miR-501-3p_5t | -0.26 | AGAATCCTTGCCCGGGTGCATT | (SEQ ID NO: 95) |
| [47,] hsa-miR-532-3p_5t | -0.27 | TGCAAGCCTTGGGTGTGGGAGG | (SEQ ID NO: 97) |
| [48,] hsa-miR-532-5p_5t | -0.33 | ACGGTCCTACACTCAAGGCATG | (SEQ ID NO: 98) |
| [49,] hsa-miR-584_st | -0.26 | CTCAGTCCCAGGCAAACCATAA | (SEQ ID NO: 581) |
| [50,] hsa-miR-625_st | -0.3 | GGACTATAGAACTTTCCCCCT | (SEQ ID NO: 548) |
| [51,] hsa-miR-660_st | -0.3 | CAACTCCGATATGCAATGGGTA | (SEQ ID NO: 305) |
| [52,] hsa-miR-720_st | -0.27 | TGGAGGCCCCAGCGAGA | (SEQ ID NO: 680) |
| [53,] hsa-miR-93-star_st | -0.25 | CGGGAAGTGCTAGCTCAGCAGT | (SEQ ID NO: 45) |
| [54,] hsa-miR-934_st | -0.25 | CCAGTGTCTCCAGTAGTAGACA | (SEQ ID NO: 517) |
| [55,] hsa-miR-93_st | -0.34 | CTACCTGCACGAACAGCACTTTG | (SEQ ID NO: 46) |
| [56,] hsa-miR-941st | -0.34 | GCACATGTGCACACAGCCGGGTG | (SEQ ID NO: 595) |

TABLE 108

Estramustine microRNA biomarkers.

| Medianprobe | Corr | Sequence | |
|---|---|---|---|
| [1,] hsa-miR-135b-star_st | -0.38 | CCCATGGCTTTTAGCCCTACAT | (SEQ ID NO: 681) |
| [2,] hsa-miR-192-star_st | -0.27 | CTGTGACCTATGGAATTGGCAG | (SEQ ID NO: 541) |
| [3,] hsa-miR-194-star_st | -0.25 | CAGATAACAGCAGCCCCACTGG | (SEQ ID NO: 230) |
| [4,] hsa-miR-21-star_st | -0.25 | ACAGCCCATCGACTGGTGTTG | (SEQ ID NO: 166) |
| [5,] hsa-miR-23b_st | -0.26 | GGTAATCCCTGGCAATGTGAT | (SEQ ID NO: 590) |
| [6,] hsa-miR-27b-star_st | -0.27 | GTTCACCAATCAGCTAAGCTCT | (SEQ ID NO: 654) |
| [7,] hsa-miR-552_st | -0.52 | TTGTCTAACCAGTCACCTGTT | (SEQ ID NO: 682) |
| [8,] hsa-miR-592_st | -0.46 | ACATCATCGCATATTGACACAA | (SEQ ID NO: 683) |
| [9,] hsa-miR-7_st | -0.26 | ACAACAAAATCACTAGTCTTCCA | (SEQ ID NO: 570) |
| [10,] hsa-miR-874_st | -0.36 | TCGGTCCCTCGGGCCAGGGCAG | (SEQ ID NO: 310) |

TABLE 109

Mechlorethamine microRNA biomarkers.

| Medianprobe | Corr | Sequence | |
|---|---|---|---|
| [1,] hsa-let-7e_st | -0.44 | AACTATACAACCTCCTACCTCA | (SEQ ID NO: 549) |
| [2,] hsa-miR-100_st | -0.33 | CACAAGTTCGGATCTACGGGTT | (SEQ ID NO: 17) |
| [3,] hsa-miR-125a-5p_st | -0.42 | TCACAGGTTAAAGGGTCTCAGGGA | (SEQ ID NO: 551) |
| [4,] hsa-miR-151-3p_st | -0.5 | CCTCAAGGAGCTTCAGTCTAG | (SEQ ID NO: 539) |
| [5,] hsa-miR-151-5p_st | -0.53 | ACTAGACTGTGAGCTCCTCGA | (SEQ ID NO: 540) |
| [6,] hsa-miR-217_st | -0.32 | TCCAATCAGTTCCTGATGCAGTA | (SEQ ID NO: 670) |
| [7,] hsa-miR-221-star_st | -0.31 | AAATCTACATTGTATGCCAGGT | (SEQ ID NO: 613) |
| [8,] hsa-miR-22_st | -0.31 | ACAGTTCTTCAACTGGCAGCTT | (SEQ ID NO: 167) |
| [9,] hsa-miR-23a_st | -0.35 | GGAAATCCCTGGCAATGTGAT | (SEQ ID NO: 571) |
| [10,] hsa-miR-23b_st | -0.32 | GGTAATCCCTGGCAATGTGAT | (SEQ ID NO: 590) |
| [11,] hsa-miR-24-2-star_st | -0.33 | CTGTGTTTCAGCTCAGTAGGCA | (SEQ ID NO: 579) |
| [12,] hsa-miR-24_st | -0.32 | CTGTTCCTGCTGAACTGAGCCA | (SEQ ID NO: 580) |
| [13,] hsa-miR-30d_st | -0.35 | CTTCCAGTCGGGGATGTTTACA | (SEQ ID NO: 547) |
| [14,] hsa-miR-320d_st | -0.35 | TCCTCTCAACCCAGCTTTT | (SEQ ID NO: 91) |
| [15,] hsa-miR-512-3p_st | -0.32 | GACCTCAGCTATGACAGCACTT | (SEQ ID NO: 523) |
| [16,] hsa-miR-519b-5p_st | -0.3 | CAGAAAGCGCTTCCCTCTAGAG | (SEQ ID NO: 573) |
| [17,] hsa-miR-519c-5p_st | -0.31 | CAGAAAGCGCTTCCCTCTAGAG | (SEQ ID NO: 573) |

TABLE 109-continued

Mechlorethamine microRNA biomarkers.

| | Medianprobe | Corr | Sequence | |
|---|---|---|---|---|
| [18,] | hsa-miR-526a_st | −0.36 | CAGAAAGTGCTTCCCTCTAGAG | (SEQ ID NO: 572) |
| [19,] | hsa-miR-584_st | −0.39 | CTCAGTCCCAGGCAAACCATAA | (SEQ ID NO: 581) |
| [20,] | hsa-miR-99b-star_st | −0.31 | CGGACCCACAGACACGAGCTTG | (SEQ ID NO: 569) |
| [21,] | hsa-miR-99b_st | −0.39 | CGCAAGGTCGGTTCTACGGGTG | (SEQ ID NO: 559) |

TABLE 110

Streptozocin microRNA biomarkers.

| | Medianprobe | Corr | Sequence | |
|---|---|---|---|---|
| [1,] | hsa-miR-26a_st | −0.3 | AGCCTATCCTGGATTACTTGAA | (SEQ ID NO: 537) |
| [2,] | hsa-miR-34b-star_st | −0.27 | CAATCAGCTAATGACACTGCCTA | (SEQ ID NO: 534) |
| [3,] | hsa-miR-34c-5p_st | −0.29 | GCAATCAGCTAACTACACTGCCT | (SEQ ID NO: 506) |
| [4,] | hsa-miR-516a-5p_st | −0.27 | GAAAGTGCTTCTTTCCTCGAGAA | (SEQ ID NO: 558) |
| [5,] | hsa-miR-518e-star_st | −0.29 | CAGAAAGCGCTTCCCTCTAGAG | (SEQ ID NO: 573) |
| [6,] | hsa-miR-519a_st | −0.27 | ACACTCTAAAAGGATGCACTTT | (SEQ ID NO: 574) |
| [7,] | hsa-miR-519c-5p_st | −0.28 | CAGAAAGCGCTTCCCTCTAGAG | (SEQ ID NO: 573) |
| [8,] | hsa-miR-526a_st | −0.26 | CAGAAAGTGCTTCCCTCTAGAG | (SEQ ID NO: 572) |

TABLE 111

Carmustine microRNA biomarkers.

| | Medianprobe | Corr | Sequence | |
|---|---|---|---|---|
| [1,] | hsa-let-7b_st | −0.59 | AACCACACAACCTACTACCTCA | (SEQ ID NO: 600) |
| [2,] | hsa-let-7c_st | −0.5 | AACCATACAACCTACTACCTCA | (SEQ ID NO: 576) |
| [3,] | hsa-let-7d_st | −0.57 | AACTATGCAACCTACTACCTCT | (SEQ ID NO: 623) |
| [4,] | hsa-let-7f_st | −0.3 | AACTATACAATCTACTACCTCA | (SEQ ID NO: 577) |
| [5,] | hsa-let-7g_st | −0.38 | AACTGTACAAACTACTACCTCA | (SEQ ID NO: 624) |
| [6,] | hsa-let-7i_st | −0.55 | AACAGCACAAACTACTACCTCA | (SEQ ID NO: 596) |
| [7,] | hsa-miR-130a_st | −0.3 | ATGCCCTTTTAACATTGCACTG | (SEQ ID NO: 313) |
| [8,] | hsa-miR-181a_st | −0.46 | ACTCACCGACAGCGTTGAATGTT | (SEQ ID NO: 78) |
| [9,] | hsa-miR-193a-3p_st | −0.37 | ACTGGGACTTTGTAGGCCAGTT | (SEQ ID NO: 366) |
| [10,] | hsa-miR-24-2-star_st | −0.41 | CTGTGTTTCAGCTCAGTAGGCA | (SEQ ID NO: 579) |
| [11,] | hsa-miR-24_st | −0.32 | CTGTTCCTGCTGAACTGAGCCA | (SEQ ID NO: 580) |
| [12,] | hsa-miR-28-3p_st | −0.48 | TCCAGGAGCTCACAATCTAGTG | (SEQ ID NO: 605) |
| [13,] | hsa-miR-28-5p_st | −0.53 | CTCAATAGACTGTGAGCTCCTT | (SEQ ID NO: 594) |
| [14,] | hsa-miR-29b_st | −0.32 | AACACTGATTTCAAATGGTGCTA | (SEQ ID NO: 545) |
| [15,] | hsa-miR-30a_st | −0.37 | CTTCCAGTCGAGGATGTTTACA | (SEQ ID NO: 503) |
| [16,] | hsa-miR-331-3p_st | −0.3 | TTCTAGGATAGGCCCAGGGGC | (SEQ ID NO: 568) |
| [17,] | hsa-miR-98_st | −0.31 | AACAATACAACTTACTACCTCA | (SEQ ID NO: 652) |

TABLE 112

Lomustine microRNA biomarkers.

| | Medianprobe | Corr | Sequence | |
|---|---|---|---|---|
| [1,] | hsa-let-7e_st | −0.45 | AACTATACAACCTCCTACCTCA | (SEQ ID NO: 549) |
| [2,] | hsa-miR-125a-3p_st | −0.35 | GGCTCCCAAGAACCTCACCTGT | (SEQ ID NO: 601) |
| [3,] | hsa-miR-125a-5p_st | −0.47 | TCACAGGTTAAAGGGTCTCAGGGA | (SEQ ID NO: 551) |
| [4,] | hsa-miR-151-3p_st | −0.37 | CCTCAAGGAGCTTCAGTCTAG | (SEQ ID NO: 539) |
| [5,] | hsa-miR-151-5p_st | −0.43 | ACTAGACTGTGAGCTCCTCGA | (SEQ ID NO: 540) |
| [6,] | hsa-miR-193b_st | −0.41 | AGCGGGACTTTGAGGGCCAGTT | (SEQ ID NO: 583) |
| [7,] | hsa-miR-200a_st | −0.33 | ACATCGTTACCAGACAGTGTTA | (SEQ ID NO: 554) |
| [8,] | hsa-miR-200b-star_st | −0.33 | TCCAATGCTGCCCAGTAAGATG | (SEQ ID NO: 555) |
| [9,] | hsa-miR-200b_st | −0.32 | TCATCATTACCAGGCAGTATTA | (SEQ ID NO: 544) |
| [10,] | hsa-miR-200c_st | −0.31 | TCCATCATTACCCGGCAGTATTA | (SEQ ID NO: 556) |
| [11,] | hsa-miR-21_st | −0.43 | TCAACATCAGTCTGATAAGCTA | (SEQ ID NO: 592) |
| [12,] | hsa-miR-22_st | −0.38 | ACAGTTCTTCAACTGGCAGCTT | (SEQ ID NO: 167) |
| [13,] | hsa-miR-30a_st | −0.38 | CTTCCAGTCGAGGATGTTTACA | (SEQ ID NO: 503) |
| [14,] | hsa-miR-31-star_st | −0.32 | ATGGCAATATGTTGGCATAGCA | (SEQ ID NO: 614) |
| [15,] | hsa-miR-331-3p_st | −0.31 | TTCTAGGATAGGCCCAGGGGC | (SEQ ID NO: 568) |
| [16,] | hsa-miR-34a_st | −0.35 | ACAACCAGCTAAGACACTGCCA | (SEQ ID NO: 234) |
| [17,] | hsa-miR-34c-5p_st | −0.33 | GCAATCAGCTAACTACACTGCCT | (SEQ ID NO: 506) |
| [18,] | hsa-miR-935_st | −0.33 | GCGGTAGCGGAAGCGGTAACTGG | (SEQ ID NO: 639) |

TABLE 112-continued

Lomustine microRNA biomarkers.

| | Medianprobe | Corr | Sequence | |
|---|---|---|---|---|
| [19,] | hsa-miR-99b-star_st | -0.36 | CGGACCCACAGACACGAGCTTG | (SEQ ID NO: 569) |
| [20,] | hsa-miR-99b_st | -0.48 | CGCAAGGTCGGTTCTACGGGTG | (SEQ ID NO: 559) |

TABLE 113

Mercaptopurine microRNA biomarkers.

| | Medianprobe | Corr | Sequence | |
|---|---|---|---|---|
| [1,] | hsa-let-7e_st | -0.37 | AACTATACAACCTCCTACCTCA | (SEQ ID NO: 549) |
| [2,] | hsa-let-7l_st | -0.35 | AACAGCACAAACTACTACCTCA | (SEQ ID NO: 596) |
| [3,] | hsa-miR-125a-5p_st | -0.38 | TCACAGGTTAAAGGGTCTCAGGGA | (SEQ ID NO: 551) |
| [4,] | hsa-miR-22-star_st | -0.3 | TAAAGCTTGCCACTGAAGAACT | (SEQ ID NO: 578) |
| [5,] | hsa-miR-22_st | -0.43 | ACAGTTCTTCAACTGGCAGCTT | (SEQ ID NO: 167) |
| [6,] | hsa-miR-23a_st | -0.3 | GGAAATCCCTGGCAATGTGAT | (SEQ ID NO: 571) |
| [7,] | hsa-miR-23b_st | -0.39 | GGTAATCCCTGGCAATGTGAT | (SEQ ID NO: 590) |
| [8,] | hsa-miR-27b_st | -0.38 | GCAGAACTTAGCCACTGTGAA | (SEQ ID NO: 567) |
| [9,] | hsa-miR-28-3p_st | -0.32 | TCCAGGAGCTCACAATCTAGTG | (SEQ ID NO: 605) |
| [10,] | hsa-miR-28-5p_st | -0.32 | CTCAATAGACTGTGAGCTCCTT | (SEQ ID NO: 594) |
| [11,] | hsa-miR-494_st | -0.31 | GAGGTTTCCCGTGTATGTTTCA | (SEQ ID NO: 181) |
| [12,] | hsa-miR-99b_st | -0.34 | CGCAAGGTCGGTTCTACGGGTG | (SEQ ID NO: 559) |

TABLE 114

Teniposide microRNA biomarkers.

| | Medianprobe | Corr | Sequence | |
|---|---|---|---|---|
| [1,] | hsa-let-7e_st | -0.44 | AACTATACAACCTCCTACCTCA | (SEQ ID NO: 549) |
| [2,] | hsa-miR-10a_st | -0.32 | CACAAATTCGGATCTACAGGGTA | (SEQ ID NO: 538) |
| [3,] | hsa-miR-125a-5p_st | -0.42 | TCACAGGTTAAAGGGTCTCAGGGA | (SEQ ID NO: 551) |
| [4,] | hsa-miR-151-3p_st | -0.55 | CCTCAAGGAGCTTCAGTCTAG | (SEQ ID NO: 539) |
| [5,] | hsa-miR-151-5p_st | -0.58 | ACTAGACTGTGAGCTCCTCGA | (SEQ ID NO: 540) |
| [6,] | hsa-miR-193b_st | -0.31 | AGCGGGACTTTGAGGGCAGTT | (SEQ ID NO: 583) |
| [7,] | hsa-miR-221-star_st | -0.33 | AAATCTACATTGTATGCCAGGT | (SEQ ID NO: 613) |
| [8,] | hsa-miR-23a_st | -0.35 | GGAAATCCCTGGCAATGTGAT | (SEQ ID NO: 571) |
| [9,] | hsa-miR-30a-star_st | -0.33 | GCTGCAAACATCCGACTGAAAG | (SEQ ID NO: 502) |
| [10,] | hsa-miR-30a_st | -0.36 | CTTCCAGTCGAGGATGTTTACA | (SEQ ID NO: 503) |
| [11,] | hsa-miR-30b_st | -0.32 | AGCTGAGTGTAGGATGTTTACA | (SEQ ID NO: 546) |
| [12,] | hsa-miR-30c-2-star_st | -0.3 | AGAGTAAACAGCCTTCTCCCAG | (SEQ ID NO: 504) |
| [13,] | hsa-miR-30c_st | -0.31 | GCTGAGAGTGTAGGATGTTTACA | (SEQ ID NO: 301) |
| [14,] | hsa-miR-30d_st | -0.4 | CTTCCAGTCGGGGATGTTTACA | (SEQ ID NO: 547) |
| [15,] | hsa-miR-516a-5p_st | -0.44 | GAAAGTGCTTCTTTCCTCGAGAA | (SEQ ID NO: 558) |
| [16,] | hsa-miR-518e-star_st | -0.3 | CAGAAAGCGCTTCCCTCTAGAG | (SEQ ID NO: 573) |
| [17,] | hsa-miR-519a_st | -0.35 | ACACTCTAAAAGGATGCACTTT | (SEQ ID NO: 574) |
| [18,] | hsa-miR-5190-5p_st | -0.31 | CAGAAAGCGCTTCCCTCTAGAG | (SEQ ID NO: 573) |
| [19,] | hsa-miR-526a_st | -0.31 | CAGAAAGTGCTTCCCTCTAGAG | (SEQ ID NO: 572) |
| [20,] | hsa-miR-584_st | -0.35 | CTCAGTCCCAGGCAAACCATAA | (SEQ ID NO: 581) |
| [21,] | hsa-miR-99b-star_st | -0.32 | CGGACCCACAGACACGAGCTTG | (SEQ ID NO: 569) |
| [22,] | hsa-miR-99b_st | -0.42 | CGCAAGGTCGGTTCTACGGGTG | (SEQ ID NO: 559) |

TABLE 115

Dactinomycin microRNA biomarkers.

| | Medianprobe | Corr | Sequence | |
|---|---|---|---|---|
| [1,] | hsa-let-7e_st | -0.37 | AACTATACAACCTCCTACCTCA | (SEQ ID NO: 549) |
| [2,] | hsa-miR-125a-5p_st | -0.37 | TCACAGGTTAAAGGGTCTCAGGGA | (SEQ ID NO: 551) |
| [3,] | hsa-miR-130a_st | -0.31 | ATGCCCTTTTAACATTGCACTG | (SEQ ID NO: 313) |
| [4,] | hsa-miR-193b_st | -0.31 | AGCGGGACTTTGAGGGCCAGTT | (SEQ ID NO: 583) |
| [5,] | hsa-miR-22_st | -0.36 | ACAGTTCTTCAACTGGCAGCTT | (SEQ ID NO: 167) |
| [6,] | hsa-miR-23a_st | -0.33 | GGAAATCCCTGGCAATGTGAT | (SEQ ID NO: 571) |
| [7,] | hsa-miR-24-2-star_st | -0.32 | CTGTGTTTCAGCTCAGTAGGCA | (SEQ ID NO: 579) |
| [8,] | hsa-miR-27a-star_st | -0.3 | TGCTCACAAGCAGCTAAGCCCT | (SEQ ID NO: 593) |

TABLE 115-continued

Dactinomycin microRNA biomarkers.

| | Medianprobe | Corr | Sequence |
|---|---|---|---|
| [9,] | hsa-miR-27a_st | -0.36 | GCGGAACTTAGCCACTGTGAA (SEQ ID NO: 501) |
| [10,] | hsa-miR-29b_st | -0.34 | AACACTGATTTCAAATGGTGCTA (SEQ ID NO: 545) |
| [11,] | hsa-miR-30a-star_st | -0.45 | GCTGCAAACATCCGACTGAAAG (SEQ ID NO: 502) |
| [12,] | hsa-miR-30a_st | -0.5 | CTTCCAGTCGAGGATGTTTACA (SEQ ID NO: 503) |
| [13,] | hsa-miR-30c-2-star_st | -0.46 | AGAGTAAACAGCCTTCTCCCAG (SEQ ID NO: 504) |
| [14,] | hsa-miR-30c_st | -0.44 | GCTGAGAGTGTAGGATGTTTACA (SEQ ID NO: 301) |
| [15,] | hsa-miR-34c-5p_st | -0.33 | GCAATCAGCTAACTACACTGCCT (SEQ ID NO: 506) |
| [16,] | hsa-miR-372_st | -0.3 | ACGCTCAAATGTCGCAGCACTTT (SEQ ID NO: 646) |
| [17,] | hsa-miR-516a-5p_st | -0.43 | GAAAGTGCTTCTTTCCTCGAGAA (SEQ ID NO: 558) |
| [18,] | hsa-miR-99b_st | -0.32 | CGCAAGGTCGGTTCTACGGGTG (SEQ ID NO: 559) |

TABLE 116

Tretinoin microRNA biomarkers.

| | Medianprobe | Corr | Sequence |
|---|---|---|---|
| [1,] | hsa-let-7e_st | -0.34 | AACTATACAACCTCCTACCTCA (SEQ ID NO: 549) |
| [2,] | hsa-let-7i_st | -0.32 | AACAGCACAAACTACTACCTCA (SEQ ID NO: 596) |
| [3,] | hsa-miR-125a-5p_st | -0.31 | TCACAGGTTAAAGGGTCTCAGGGA (SEQ ID NO: 551) |
| [4,] | hsa-miR-151-3p_st | -0.37 | CCTCAAGGAGCTTCAGTCTAG (SEQ ID NO: 539) |
| [5,] | hsa-miR-151-5p_st | -0.39 | ACTAGACTGTGAGCTCCTCGA (SEQ ID NO: 540) |
| [6,] | hsa-miR-181a-2-star_st | -0.33 | GGTACAGTCAACGGTCAGTGGT (SEQ ID NO: 612) |
| [7,] | hsa-miR-21-star_st | -0.33 | ACAGCCCATCGACTGGTGTTG (SEQ ID NO: 166) |
| [8,] | hsa-miR-21_st | -0.38 | TCAACATCAGTCTGATAAGCTA (SEQ ID NO: 592) |
| [9,] | hsa-miR-221_st | -0.6 | GAAACCCAGCAGACAATGTAGCT (SEQ ID NO: 620) |
| [10,] | hsa-miR-222_st | -0.56 | ACCCAGTAGCCAGATGTAGCT (SEQ ID NO: 621) |
| [11,] | hsa-miR-22_st | -0.37 | ACAGTTCTTCAACTGGCAGCTT (SEQ ID NO: 167) |
| [12,] | hsa-miR-28-3p_st | -0.46 | TCCAGGAGCTCACAATCTAGTG (SEQ ID NO: 605) |

TABLE 116-continued

Tretinoin microRNA biomarkers.

| | Medianprobe | Corr | Sequence |
|---|---|---|---|
| [13,] | hsa-miR-28-5p_st | -0.43 | CTCAATAGACTGTGAGCTCCTT (SEQ ID NO: 594) |
| [14,] | hsa-miR-30a-star_st | -0.32 | GCTGCAAACATCCGACTGAAAG (SEQ ID NO: 502) |
| [15,] | hsa-miR-30a_st | -0.36 | CTTCCAGTCGAGGATGTTTACA (SEQ ID NO: 503) |
| [16,] | hsa-miR-30c-2-star_st | -0.33 | AGAGTAAACAGCCTTCTCCCAG (SEQ ID NO: 504) |
| [17,] | hsa-miR-455-3p_st | -0.32 | GTGTATATGCCCATGGACTGC (SEQ ID NO: 178) |
| [18,] | hsa-miR-99b-star_st | -0.32 | CGGACCCACAGACACGAGCTTG (SEQ ID NO: 569) |

TABLE 117

Ifosfamide microRNA biomarkers.

| | Medianprobe | Corr | Sequence |
|---|---|---|---|
| [1,] | hsa-let-7e_st | -0.34 | AACTATACAACCTCCTACCTCA (SEQ ID NO: 549) |
| [2,] | hsa-miR-125a-5p_st | -0.35 | TCACAGGTTAAAGGGTCTCAGGGA (SEQ ID NO: 551) |
| [3,] | hsa-miR-151-3p_st | -0.39 | CCTCAAGGAGCTTCAGTCTAG (SEQ ID NO: 539) |
| [4,] | hsa-miR-151-5p_st | -0.39 | ACTAGACTGTGAGCTCCTCGA (SEQ ID NO: 540) |
| [5,] | hsa-miR-182_st | -0.36 | AGTGTGAGTTCTACCATTGCCAAA (SEQ ID NO: 563) |
| [6,] | hsa-miR-183_st | -0.35 | AGTGAATTCTACCAGTGCCATA (SEQ ID NO: 565) |
| [7,] | hsa-miR-193b_st | -0.42 | AGCGGGACTTTGAGGGCCAGTT (SEQ ID NO: 583) |
| [8,] | hsa-miR-195_st | -0.39 | GCCAATATTTCTGTGCTGCTA (SEQ ID NO: 672) |
| [9,] | hsa-miR-22_st | -0.41 | ACAGTTCTTCAACTGGCAGCTT (SEQ ID NO: 167) |
| [10,] | hsa-miR-23a_st | -0.52 | GGAAATCCCTGGCAATGTGAT (SEQ ID NO: 571) |
| [11,] | hsa-miR-23b_st | -0.38 | GGTAATCCCTGGCAATGTGAT (SEQ ID NO: 590) |
| [12,] | hsa-miR-24_st | -0.53 | CTGTTCCTGCTGAACTGAGCCA (SEQ ID NO: 580) |
| [13,] | hsa-miR-27a-star_st | -0.34 | TGCTCACAAGCAGCTAAGCCCT (SEQ ID NO: 593) |
| [14,] | hsa-miR-27a_st | -0.4 | GCGGAACTTAGCCACTGTGAA (SEQ ID NO: 501) |
| [15,] | hsa-miR-27b_st | -0.3 | GCAGAACTTAGCCACTGTGAA (SEQ ID NO: 567) |
| [16,] | hsa-miR-34b-star_st | -0.37 | CAATCAGCTAATGACACTGCCTA (SEQ ID NO: 534) |

TABLE 117-continued

Ifosfamide microRNA biomarkers.

| | Medianprobe | Corr | Sequence |
|---|---|---|---|
| [17,] | hsa-miR-497_st | -0.36 | ACAAACCACAGTGTGCTGCTG (SEQ ID NO: 684) |
| [18,] | hsa-miR-99b_st | -0.33 | CGCAAGGTCGGTTCTACGGGTG (SEQ ID NO: 559) |

TABLE 118

Tamoxifen microRNA biomarkers.

| | Medianprobe | Corr | Sequence |
|---|---|---|---|
| [1,] | hsa-let-7a_st | -0.3 | AACTATACAACCTACTACCTCA (SEQ ID NO: 575) |
| [2,] | hsa-let-7b_st | -0.35 | AACCACACAACCTACTACCTCA (SEQ ID NO: 600) |
| [3,] | hsa-let-7c_st | -0.37 | AACCATACAACCTACTACCTCA (SEQ ID NO: 576) |
| [4,] | hsa-let-7e_st | -0.47 | AACTATACAACCTCCTACCTCA (SEQ ID NO: 549) |
| [5,] | hsa-let-7g_st | -0.31 | AACTGTACAAACTACTACCTCA (SEQ ID NO: 624) |
| [6,] | hsa-let-7i_st | -0.34 | AACAGCACAAACTACTACCTCA (SEQ ID NO: 596) |
| [7,] | hsa-miR-100_st | -0.44 | CACAAGTTCGGATCTACGGGTT (SEQ ID NO: 17) |
| [8,] | hsa-miR-10a_st | -0.32 | CACAAATTCGGATCTACAGGGTA (SEQ ID NO: 538) |
| [9,] | hsa-miR-125a-5p_st | -0.42 | TCACAGGTTAAAGGGTCTCAGGGA (SEQ ID NO: 551) |
| [10,] | hsa-miR-125b_st | -0.45 | TCACAAGTTAGGGTCTCAGGGA (SEQ ID NO: 602) |
| [11,] | hsa-miR-130a_st | -0.52 | ATGCCCTTTTAACATTGCACTG (SEQ ID NO: 313) |
| [12,] | hsa-miR-138_st | -0.34 | CGGCCTGATTCACAACACCAGCT (SEQ ID NO: 625) |
| [13,] | hsa-miR-149_st | -0.45 | GGGAGTGAAGACACGGAGCCAGA (SEQ ID NO: 500) |
| [14,] | hsa-miR-151-3p_st | -0.45 | CCTCAAGGAGCTTCAGTCTAG (SEQ ID NO: 539) |
| [15,] | hsa-miR-151-5p_st | -0.4 | ACTAGACTGTGAGCTCCTCGA (SEQ ID NO: 540) |
| [16,] | hsa-miR-181a-2-star_st | -0.33 | GGTACAGTCAACGGTCAGTGGT (SEQ ID NO: 612) |
| [17,] | hsa-miR-193b-star_st | -0.34 | TCATCTCGCCCTCAAAACCCCG (SEQ ID NO: 633) |
| [18,] | hsa-miR-193b_st | -0.35 | AGCGGGACTTTGAGGGCCAGTT (SEQ ID NO: 583) |
| [19,] | hsa-miR-21_st | -0.37 | TCAACATCAGTCTGATAAGCTA (SEQ ID NO: 592) |
| [20,] | hsa-miR-22-star_st | -0.33 | TAAAGCTTGCCACTGAAGAACT (SEQ ID NO: 578) |

TABLE 118-continued

Tamoxifen microRNA biomarkers.

| | Medianprobe | Corr | Sequence |
|---|---|---|---|
| [21,] | hsa-miR-221st | -0.34 | GAAACCCAGCAGACAATGTAGCT (SEQ ID NO: 620) |
| [22,] | hsa-miR-22_st | -0.37 | ACAGTTCTTCAACTGGCAGCTT (SEQ ID NO: 167) |
| [23,] | hsa-miR-23a_st | -0.35 | GGAAATCCCTGGCAATGTGAT (SEQ ID NO: 571) |
| [24,] | hsa-miR-23b_st | -0.3 | GGTAATCCCTGGCAATGTGAT (SEQ ID NO: 590) |
| [25,] | hsa-miR-24-2-star_st | -0.4 | CTGTGTTTCAGCTCAGTAGGCA (SEQ ID NO: 579) |
| [26,] | hsa-miR-24_st | -0.34 | CTGTTCCTGCTGAACTGAGCCA (SEQ ID NO: 580) |
| [27,] | hsa-miR-28-3p_st | -0.37 | TCCAGGAGCTCACAATCTAGTG (SEQ ID NO: 605) |
| [28,] | hsa-miR-28-5p_st | -0.36 | CTCAATAGACTGTGAGCTCCTT (SEQ ID NO: 594) |
| [29,] | hsa-miR-30a-star_st | -0.64 | GCTGCAAACATCCGACTGAAAG (SEQ ID NO: 502) |
| [30,] | hsa-miR-30a_st | -0.6 | CTTCCAGTCGAGGATGTTTACA (SEQ ID NO: 503) |
| [31,] | hsa-miR-30c-2-star_st | -0.63 | AGAGTAAACAGCCTTCTCCCAG (SEQ ID NO: 504) |
| [32,] | hsa-miR-30c_st | -0.49 | GCTGAGAGTGTAGGATGTTTACA (SEQ ID NO: 301) |
| [33,] | hsa-miR-30e-star_st | -0.3 | GCTGTAAACATCCGACTGAAAG (SEQ ID NO: 505) |
| [34,] | hsa-miR-34c-5p_st | -0.32 | GCAATCAGCTAACTACACTGCCT (SEQ ID NO: 506) |
| [35,] | hsa-miR-424-star_st | -0.31 | ATAGCAGCGCCTCACGTTTTG (SEQ ID NO: 100) |
| [36,] | hsa-miR-455-3p_st | -0.32 | GTGTATATGCCCATGGACTGC (SEQ ID NO: 178) |
| [37,] | hsa-miR-503_st | -0.31 | CTGCAGAACTGTTCCCGCTGCTA (SEQ ID NO: 101) |
| [38,] | hsa-miR-935_st | -0.32 | GCGGTAGCGGAAGCGGTAACTGG (SEQ ID NO: 639) |
| [39,] | hsa-miR-99b-star_st | -0.34 | CGGACCCACAGACACGAGCTTG (SEQ ID NO: 569) |
| [40,] | hsa-miR-99b_st | -0.42 | CGCAAGGTCGGTTCTACGGGTG (SEQ ID NO: 559) |

TABLE 119

Irinotecan microRNA biomarkers.

| | Medianprobe | Corr | Sequence |
|---|---|---|---|
| [1,] | hsa-let-7e_st | -0.44 | AACTATACAACCTCCTACCTCA (SEQ ID NO: 549) |
| [2,] | hsa-miR-125a-5p_st | -0.45 | TCACAGGTTAAAGGGTCTCAGGGA (SEQ ID NO: 551) |

TABLE 119-continued

Irinotecan microRNA biomarkers.

| | Medianprobe | Corr | Sequence |
|---|---|---|---|
| [3,] | hsa-miR-151-3p_st | -0.36 | CCTCAAGGAGCTTCAGTCTAG (SEQ ID NO: 539) |
| [4,] | hsa-miR-151-5p_st | -0.41 | ACTAGACTGTGAGCTCCTCGA (SEQ ID NO: 540) |
| [5,] | hsa-miR-193b_st | -0.33 | AGCGGGACTTTGAGGGCCAGTT (SEQ ID NO: 583) |
| [6,] | hsa-miR-30b_st | -0.33 | AGCTGAGTGTAGGATGTTTACA (SEQ ID NO: 546) |
| [7,] | hsa-miR-30d_st | -0.44 | CTTCCAGTCGGGGATGTTTACA (SEQ ID NO: 547) |
| [8,] | hsa-miR-320d_st | -0.32 | TCCTCTCAACCCAGCTTTT (SEQ ID NO: 91) |
| [9,] | hsa-miR-584_st | -0.32 | CTCAGTCCCAGGCAAACCATAA (SEQ ID NO: 581) |
| [10,] | hsa-miR-99b_st | -0.42 | CGCAAGGTCGGTTCTACGGGTG (SEQ ID NO: 559) |

TABLE 120

Floxuridine microRNA biomarkers.

| | Medianprobe | Corr | Sequence |
|---|---|---|---|
| [1,] | hsa-miR-30b_st | -0.38 | AGCTGAGTGTAGGATGTTTACA (SEQ ID NO: 546) |
| [2,] | hsa-miR-30d_st | -0.4 | CTTCCAGTCGGGGATGTTTACA (SEQ ID NO: 547) |
| [3,] | hsa-miR-584_st | -0.3 | CTCAGTCCCAGGCAAACCATAA (SEQ ID NO: 581) |

TABLE 121

Thioguanine microRNA biomarkers.

| | Medianprobe | Corr | Sequence |
|---|---|---|---|
| [1,] | hsa-let-7b_st | -0.3 | AACCACACAACCTACTACCTCA (SEQ ID NO: 600) |
| [2,] | hsa-let-7c_st | -0.31 | AACCATACAACCTACTACCTCA (SEQ ID NO: 576) |
| [3,] | hsa-let-7e_st | -0.48 | AACTATACAACCTCCTACCTCA (SEQ ID NO: 549) |
| [4,] | hsa-miR-125a-5p_st | -0.48 | TCACAGGTTAAAGGGTCTCAGGGA (SEQ ID NO: 551) |
| [5,] | hsa-miR-151-3p_st | -0.33 | CCTCAAGGAGCTTCAGTCTAG (SEQ ID NO: 539) |
| [6,] | hsa-miR-151-5p_st | -0.37 | ACTAGACTGTGAGCTCCTCGA (SEQ ID NO: 540) |
| [7,] | hsa-miR-217_st | -0.4 | TCCAATCAGTTCCTGATGCAGTA (SEQ ID NO: 670) |
| [8,] | hsa-miR-21_st | -0.31 | TCAACATCAGTCTGATAAGCTA (SEQ ID NO: 592) |
| [9,] | hsa-miR-22_st | -0.4 | ACAGTTCTTCAACTGGCAGCTT (SEQ ID NO: 167) |

TABLE 121-continued

Thioguanine microRNA biomarkers.

| | Medianprobe | Corr | Sequence |
|---|---|---|---|
| [10,] | hsa-miR-23a_st | -0.36 | GGAAATCCCTGGCAATGTGAT (SEQ ID NO: 571) |
| [11,] | hsa-miR-23b-star_st | -0.4 | AAATCAGCATGCCAGGAACCCA (SEQ ID NO: 591) |
| [12,] | hsa-miR-23b_st | -0.54 | GGTAATCCCTGGCAATGTGAT (SEQ ID NO: 590) |
| [13,] | hsa-miR-24_st | -0.39 | CTGTTCCTGCTGAACTGAGCCA (SEQ ID NO: 580) |
| [14,] | hsa-miR-27b-star_st | -0.34 | GTTCACCAATCAGCTAAGCTCT (SEQ ID NO: 654) |
| [15,] | hsa-miR-27b_st | -0.57 | GCAGAACTTAGCCACTGTGAA (SEQ ID NO: 567) |
| [16,] | hsa-miR-30a_st | -0.3 | CTTCCAGTCGAGGATGTTTACA (SEQ ID NO: 503) |
| [17,] | hsa-miR-494_st | -0.33 | GAGGTTTCCCGTGTATGTTTCA (SEQ ID NO: 181) |
| [18,] | hsa-miR-9-star_st | -0.42 | ACTTTCGGTTATCTAGCTTTAT (SEQ ID NO: 651) |
| [19,] | hsa-miR-99b-star_st | -0.37 | CGGACCCACAGACACGAGCTTG (SEQ ID NO: 569) |
| [20,] | hsa-miR-99b_st | -0.44 | CGCAAGGTCGGTTCTACGGGTG (SEQ ID NO: 559) |
| [21,] | hsa-miR-9_st | -0.45 | TCATACAGCTAGATAACCAAAGA (SEQ ID NO: 685) |

TABLE 122

PSC 833 microRNA biomarkers.

| | Medianprobe | Corr | Sequence |
|---|---|---|---|
| [1,] | hsa-let-7e_st | -0.31 | AACTATACAACCTCCTACCTCA (SEQ ID NO: 549) |
| [2,] | hsa-miR-125a-5p_st | -0.32 | TCACAGGTTAAAGGGTCTCAGGGA (SEQ ID NO: 551) |
| [3,] | hsa-miR-138_st | -0.42 | CGGCCTGATTCACAACACCAGCT (SEQ ID NO: 625) |
| [4,] | hsa-miR-149_st | -0.31 | GGGAGTGAAGACACGGAGCCAGA (SEQ ID NO: 500) |
| [5,] | hsa-miR-193b-star_st | -0.3 | TCATCTCGCCCTCAAAACCCCG (SEQ ID NO: 633) |
| [6,] | hsa-miR-193b_st | -0.31 | AGCGGGACTTTGAGGGCCAGTT (SEQ ID NO: 583) |
| [7,] | hsa-miR-21_st | -0.39 | TCAACATCAGTCTGATAAGCTA (SEQ ID NO: 592) |
| [8,] | hsa-miR-22-star_st | -0.3 | TAAAGCTTGCCACTGAAGAACT (SEQ ID NO: 578) |
| [9,] | hsa-miR-22_st | -0.41 | ACAGTTCTTCAACTGGCAGCTT (SEQ ID NO: 167) |
| [10,] | hsa-miR-23a_st | -0.32 | GGAAATCCCTGGCAATGTGAT (SEQ ID NO: 571) |

TABLE 122-continued

PSC 833 microRNA biomarkers.

| | Medianprobe | Corr | Sequence |
|---|---|---|---|
| [11,] | hsa-miR-23b_st | -0.36 | GGTAATCCCTGGCAATGTGAT (SEQ ID NO: 590) |
| [12,] | hsa-miR-24-2-star_st | -0.35 | CTGTGTTTCAGCTCAGTAGGCA (SEQ ID NO: 579) |
| [13,] | hsa-miR-24_st | -0.32 | CTGTTCCTGCTGAACTGAGCCA (SEQ ID NO: 580) |
| [14,] | hsa-miR-27a_st | -0.36 | GCGGAACTTAGCCACTGTGAA (SEQ ID NO: 501) |
| [15,] | hsa-miR-27b_st | -0.35 | GCAGAACTTAGCCACTGTGAA (SEQ ID NO: 567) |
| [16,] | hsa-miR-30a-star_st | -0.46 | GCTGCAAACATCCGACTGAAAG (SEQ ID NO: 502) |
| [17,] | hsa-miR-30a_st | -0.46 | CTTCCAGTCGAGGATGTTTACA (SEQ ID NO: 503) |
| [18,] | hsa-miR-30c-2-star_st | -0.44 | AGAGTAAACAGCCTTCTCCCAG (SEQ ID NO: 504) |
| [19,] | hsa-miR-30c_st | -0.36 | GCTGAGAGTGTAGGATGTTTACA (SEQ ID NO: 301) |
| [20,] | hsa-miR-543_st | -0.31 | AAGAAGTGCACCGCGAATGTTT (SEQ ID NO: 182) |
| [21,] | hsa-miR-9_st | -0.32 | TCATACAGCTAGATAACCAAAGA (SEQ ID NO: 685) |

TABLE 123

Erlotinib (tarceva) microRNA biomarkers.

| | Medianprobe | Corr | Sequence |
|---|---|---|---|
| [1,] | hsa-miR-320a_st | -0.32 | TCGCCCTCTCAACCCAGCTTTT (SEQ ID NO: 655) |
| [2,] | hsa-miR-320b_st | -0.32 | TTGCCCTCTCAACCCAGCTTTT (SEQ ID NO: 656) |
| [3,] | hsa-miR-320c_st | -0.32 | ACCCTCTCAACCCAGCTTTT (SEQ ID NO: 90) |
| [4,] | hsa-miR-362-5p_st | -0.32 | ACTCACACCTAGGTTCCAAGGATT (SEQ ID NO: 92) |
| [5,] | hsa-miR-500-star_st | -0.33 | CAGAATCCTTGCCCAGGTGCAT (SEQ ID NO: 93) |
| [6,] | hsa-miR-500_st | -0.31 | TCTCACCCAGGTAGCAAGGATTA (SEQ ID NO: 94) |
| [7,] | hsa-miR-502-3p_st | -0.34 | TGAATCCTTGCCCAGGTGCATT (SEQ ID NO: 96) |
| [8,] | hsa-miR-532-3p_st | -0.31 | TGCAAGCCTTGGGTGTGGGAGG (SEQ ID NO: 97) |
| [9,] | hsa-miR-532-5p_st | -0.35 | ACGGTCCTACACTCAAGGCATG (SEQ ID NO: 98) |
| [10,] | hsa-miR-652_st | -0.34 | CACAACCCTAGTGGCGCCATT (SEQ ID NO: 42) |
| [11,] | hsa-miR-671-5p_st | -0.36 | CTCCAGCCCCTCCAGGGCTTCCT (SEQ ID NO: 43) |

TABLE 124

Herceptin microRNA biomarkers.

| | Medianprobe | Corr | Sequence |
|---|---|---|---|
| [1,] | hsa-let-7d_st | -0.32 | AACTATGCAACCTACTACCTCT (SEQ ID NO: 623) |
| [2,] | hsa-miR-103_st | -0.3 | TCATAGCCCTGTACAATGCTGCT (SEQ ID NO: 660) |
| [3,] | hsa-miR-107_st | -0.35 | TGATAGCCCTGTACAATGCTGCT (SEQ ID NO: 661) |

TABLE 125

Celecoxib microRNA biomarkers.

| | Medianprobe | Corr | Sequence |
|---|---|---|---|
| [1,] | hsa-miR-1287_st | -0.39 | GACTCGAACCACTGATCCAGCA (SEQ ID NO: 603) |
| [2,] | hsa-miR-130a_st | -0.32 | ATGCCCTTTTAACATTGCACTG (SEQ ID NO: 313) |
| [3,] | hsa-miR-151-3p_st | -0.3 | CCTCAAGGAGCTTCAGTCTAG (SEQ ID NO: 539) |
| [4,] | hsa-miR-28-3p_st | -0.42 | TCCAGGAGCTCACAATCTAGTG (SEQ ID NO: 605) |
| [5,] | hsa-miR-28-5p_st | -0.43 | CTCAATAGACTGTGAGCTCCTT (SEQ ID NO: 594) |
| [6,] | hsa-miR-31-star_st | -0.3 | ATGGCAATATGTTGGCATAGCA (SEQ ID NO: 614) |
| [7,] | hsa-miR-455-3p_st | -0.35 | GTGTATATGCCCATGGACTGC (SEQ ID NO: 178) |

TABLE 126

Fulvestrant microRNA biomarkers.

| | Medianprobe | Corr | Sequence |
|---|---|---|---|
| [1,] | hsa-let-7b_st | -0.31 | AACCACACAACCTACTACCTCA (SEQ ID NO: 600) |
| [2,] | hsa-miR-181a-2-star_st | -0.46 | GGTACAGTCAACGGTCAGTGGT (SEQ ID NO: 612) |
| [3,] | hsa-miR-221_st | -0.6 | GAAACCCAGCAGACAATGTAGCT (SEQ ID NO: 620) |
| [4,] | hsa-miR-222_st | -0.65 | ACCCAGTAGCCAGATGTAGCT (SEQ ID NO: 621) |
| [5,] | hsa-miR-28-5p_st | -0.3 | CTCAATAGACTGTGAGCTCCTT (SEQ ID NO: 594) |
| [6,] | hsa-miR-29a_st | -0.36 | TAACCGATTTCAGATGGTGCTA (SEQ ID NO: 584) |
| [7,] | hsa-miR-31_st | -0.31 | AGCTATGCCAGCATCTTGCCT (SEQ ID NO: 615) |

TABLE 127

Iressa microRNA biomarkers.

| | Medianprobe | Corr | Sequence |
|---|---|---|---|
| [1,] | hsa-miR-505-star_st | -0.34 | ACATCAATACTTCCTGGCTCCC (SEQ ID NO: 686) |
| [2,] | hsa-miR-671-5p_st | -0.34 | CTCCAGCCCCTCCAGGGCTTCCT (SEQ ID NO: 43) |

TABLE 128

Letrozole microRNA biomarkers.

| | Medianprobe | Corr | Sequence |
|---|---|---|---|
| [1,] | U27_st | -0.36 | GAAAGTTCAGCCATATGCTTGTCAT (SEQ ID NO: 687) |
| [2,] | U29_st | -0.33 | GAGCTAGTTTGATTCATCATAGAAA (SEQ ID NO: 203) |

TABLE 129

Cetuximab (erbitux) microRNA biomarkers.

| | Medianprobe | Corr | Sequence |
|---|---|---|---|
| [1,] | hsa-miR-191_st | -0.33 | CAGCTGCTTTTGGGATTCCGTTG (SEQ ID NO: 284) |
| [2,] | hsa-miR-491-5p_st | -0.36 | CCTCATGGAAGGGTTCCCCACT (SEQ ID NO: 617) |

The invention claimed is:

1. A method of predicting the responsiveness of a patient diagnosed with brain cancer, lung cancer, or lymphoma to at least one treatment for cancer comprising:
   i) contacting a tumor sample comprising one or more nucleic acid molecules from said patient with a device comprising at least one first single-stranded nucleic acid molecule having at least 85% sequence identity to a nucleic acid sequence that is complementary or identical to at least 15 consecutive nucleotides of hsa-miR-766_st (SEQ ID NO: 1); and
   ii) measuring hybridization between said one or more nucleic acid molecules from said patient and said at least one first single-stranded nucleic acid molecule of said device to detect a level of expression of hsa-miR-766_st;
   wherein said patient is predicted to be responsive to said least one treatment for cancer if the level of expression of hsa-miR-766_st is substantially similar to the level of expression of hsa-miR-766_st in a cell or tissue known to be responsive to said at least one treatment for cancer.

2. The method of claim 1, wherein said device further comprises: i) at least one second single-stranded nucleic acid molecule having at least 85% sequence identity to a target nucleic acid molecule having a sequence that is complementary or identical to at least 15 consecutive nucleotides of at least one biomarker of sensitivity selected from the group consisting of SEQ ID NOs: 2-534, or ii) at least one second single-stranded nucleic acid molecule having at least 85% sequence identity to a target nucleic acid molecule having a sequence that is complementary or identical to at least 15 consecutive nucleotides of at least one biomarker of resistance selected from the group consisting of SEQ ID NOs: 2, 3, 17-26, 31, 32, 35, 37, 42, 43, 45, 46, 71-78, 81, 82, 85-102, 109, 110, 114, 115, 150, 152, 153, 157-161, 163-182, 189, 202, 203, 218, 230, 231, 234, 236, 247, 249-251, 253, 272-274, 277, 283, 284, 286-288, 295, 297, 301, 305, 310, 312, 313, 314, 330, 331, 360-362, 366, 403, 406, 408-410, 430, 439, 451, 452, 470, 490, 491, 499-506, 510, 511, 512, 514, 516, 517, 520, 522-526, 528, and 534-687,
  wherein said device allows specific hybridization between said at least one second single stranded nucleic acid molecule and said target nucleic acid molecule and is sufficient for detecting the level of expression of said at least one biomarker of sensitivity or said at least one biomarker of resistance,
  wherein said patient is predicted to be sensitive to said at least one treatment for cancer if the level of expression of said at least one biomarker of sensitivity is substantially similar to the level of expression of said at least one biomarker of sensitivity in a cell or tissue known to be sensitive to said at least one treatment, and
  wherein said patient is predicted to be resistant to said at least one treatment for cancer if the level of expression of said at least one biomarker of resistance is substantially similar to the level of expression of said at least one biomarker of resistance in a cell or tissue known to be sensitive to said at least one treatment.

3. The method of claim 2, wherein said at least one second single-stranded nucleic acid molecule of said device has 100% sequence identity to said target nucleic acid molecule.

4. The method of claim 2, wherein said method comprises detecting the level of expression of said at least one biomarker of sensitivity or said at least one biomarker of resistance in a biological sample from said patient.

5. The method of claim 2, wherein said device allows the determination of the level of expression of said at least one biomarker of sensitivity having a nucleic acid sequence selected from the group consisting of SEQ ID NOs: 4-12, 36, 118, 146, 209, 241, 252, 260, 280, 308, 395, and 441 or a level of expression of said at least one biomarker of resistance having a nucleic acid sequence selected from the group consisting of SEQ ID NOs: 511 and 538-548.

6. The method of claim 1, wherein said at least one first single-stranded nucleic acid molecule of said device has 100% sequence identity to hsa-miR-766_st (SEQ ID NO: 1).

7. The method of claim 2, wherein said device comprises:
  i) one or more single-stranded nucleic acid molecules having at least 85% sequence identity to a target nucleic acid molecule having a sequence that is complementary to or identical to at least 15 consecutive nucleotides of one or more biomarkers selected from hsa-miR-106b-star_st (SEQ ID NO: 2) and hsa-miR-25-star_st (SEQ ID NO: 3), wherein said device allows a determination of the sensitivity of said patient to vincristine; or
  ii) one or more single-stranded nucleic acid molecules having at least 85% sequence identity to a target nucleic acid molecule having a sequence that is complementary to or identical to at least 15 consecutive nucleotides of one or more biomarkers selected from HBII-85-2_x_st (SEQ ID NO: 4), U48_st (SEQ ID NO: 5), U55_x_st (SEQ ID NO: 6), hsa-miR-124_st (SEQ ID NO: 7), hsa-miR-1281_st (SEQ ID NOL: 8), hsa-miR-181a-star_st (SEQ ID NO: 9), hsa-miR-181b_st (SEQ ID NO: 10), hsa-miR-342-3p_st (SEQ ID NO: 11), and hsa-miR-432_st (SEQ ID NO: 12), wherein said device allows a determination of the sensitivity of said patient to cisplatin; or
  iii) one or more single-stranded nucleic acid molecules having at least 85% sequence identity to a target nucleic acid molecule having a sequence that is complementary to or identical to at least 15 consecutive nucleotides of one or more biomarkers selected from hsa-miR-124_st (SEQ ID NO: 7), hsa-miR-1281_st (SEQ ID NO: 8), hsa-miR-140-3p_st (SEQ ID NO: 13), hsa-miR-181a-star_st (SEQ ID NO: 9), hsa-miR-181b_st (SEQ ID NO: 10), hsa-miR-195-star_st (SEQ ID NO: 14), hsa-miR-342-3p_st (SEQ ID NO: 11), hsa-miR-766_st (SEQ ID NO: 1), hsa-miR-92b_st (SEQ ID NO: 15), and hsa-miR-938_st (SEQ ID NO: 16), wherein said device allows a determination of the sensitivity of said patient to etoposide; or
  iv) one or more single-stranded nucleic acid molecules having at least 85% sequence identity to a target nucleic acid molecule having a sequence that is complementary to or identical to at least 15 consecutive nucleotides of one or more biomarkers selected from hsa-miR-100_st (SEQ ID NO: 17), hsa-miR-140-3p_st (SEQ ID NO: 13), hsa-miR-140-5p_st (SEQ ID NO: 18), hsa-miR-146a_st (SEQ ID NO: 19), hsa-miR-155_st (SEQ ID NO: 20), hsa-miR-506_st (SEQ ID NO: 21), hsa-miR-508-5p_st (SEQ ID NO: 22), hsa-miR-509-3-5p_st (SEQ ID NO: 23), hsa-miR-509-3p_st (SEQ ID NO: 24), hsa-miR-510_st (SEQ ID NO: 25), hsa-miR-513a-5p_st (SEQ ID NO: 26), hsa-miR-513b_st (SEQ ID NO: 27), hsa-miR-663_st (SEQ ID NO: 28), and hsa-miR-923_st (SEQ ID NO: 29), wherein said device allows a determination of the sensitivity of said patient to azaguanine; or
  v) one or more single-stranded nucleic acid molecules having at least 85% sequence identity to a target nucleic acid molecule having a sequence that is complementary to or identical to at least 15 consecutive nucleotides of one or more biomarkers selected from U55_x_st (SEQ ID NO: 6), hsa-miR-124_st (SEQ ID NO: 7), hsa-miR-1271_st (SEQ ID NO: 30), hsa-miR-143_st (SEQ ID NO: 31), hsa-miR-342-3p_st (SEQ ID NO: 11), hsa-miR-370_st (SEQ ID NO: 32), hsa-miR-433_st (SEQ ID NO: 33), hsa-miR-654-3p_st (SEQ ID NO: 34), and hsa-miR-758_st (SEQ ID NO: 35), wherein said device allows a determination of the sensitivity of said patient to carboplatin; or
  vi) one or more single-stranded nucleic acid molecules having at least 85% sequence identity to a target nucleic acid molecule having a sequence that is complementary to or identical to at least 15 consecutive nucleotides of one or more biomarkers selected from U55_st (SEQ ID NO: 36), U55_x_st (SEQ ID NO: 6), hsa-miR-106b-star_st (SEQ ID NO: 2), hsa-miR-106b_st (SEQ ID NO: 37), hsa-miR-124_st (SEQ ID NO: 7), hsa-miR-1299_st (SEQ ID NO: 38), hsa-miR-29b-2-star_st (SEQ ID NO: 39), hsa-miR-33b-star_st (SEQ ID NO: 40), hsa-miR-629-star_st (SEQ ID NO: 41), hsa-miR-652_st (SEQ ID NO: 42), hsa-miR-671-5p_st (SEQ ID NO: 43), hsa-miR-766_st (SEQ ID NO: 1), hsa-miR-768-3p_st (SEQ ID NO: 44), hsa-miR-93-star_st (SEQ ID NO: 45), and hsa-miR-93_st (SEQ ID NO: 46), wherein said device allows a determination of the sensitivity of said patient to adriamycin; or
  vii) one or more single-stranded nucleic acid molecules having at least 85% sequence identity to a target nucleic acid molecule having a sequence that is complementary to or identical to at least 15 consecutive nucleotides of one or more biomarkers selected from ACA10_s_st (SEQ ID NO: 47), ACA18_x_st (SEQ ID NO: 48), ACA44_st (SEQ ID NO: 49), ACA51_x_st (SEQ ID NO: 50), ACA61_st (SEQ ID NO: 51) ENSG00000200394_st (SEQ ID NO: 52), ENSG00000202252_st (SEQ ID NO: 53), HBII-180A_x_st (SEQ ID NO: 54), HBII-429_st (SEQ ID NO: 55) U104_st (SEQ ID NO: 56), U13_st (SEQ ID NO: 57), U17b_st (SEQ ID NO: 58), U17b_x_st (SEQ ID NO: 59), U26_st (SEQ ID NO: 60), U3-2_s_st (SEQ ID NO: 61), U35A_st (SEQ ID NO: 62), U49A_st (SEQ ID NO: 63), U49A_x_st (SEQ ID NO: 64), U49B_s_st (SEQ ID NO: 65), U67_st (SEQ ID NO: 66), U68_st (SEQ ID NO: 67), U68_x_st (SEQ ID NO: 68), U74_x_st (SEQ ID NO: 69), hsa-miR-1275_st (SEQ ID NO: 70), hsa-miR-1281_st (SEQ ID NO: 8), hsa-miR-18a-star_st (SEQ ID NO: 71), hsa-miR-18a_st (SEQ ID NO: 72), hsa-miR-25-star_st (SEQ ID NO: 3), and hsa-miR-33b-star_st (SEQ ID NO: 40), wherein said device allows a determination of the sensitivity of said patient to aclarubicin; or viii) one or more single-stranded nucleic acid molecules having at least 85% sequence identity to a target nucleic acid molecule having a sequence that is complementary to or identical to at least 15 consecutive nucleotides of one or more biomarkers selected from 14qII-14_st (SEQ ID NO: 73), 14qII-1_st (SEQ ID NO: 74), 14qII-26_st (SEQ ID NO: 75), 14qII-26_x_st (SEQ ID NO: 76), hsa-miR-127-3p_st (SEQ ID NO: 77), hsa-miR-181a-star_st (SEQ ID NO: 9), hsa-miR-181a_st (SEQ ID NO: 78), hsa-miR-181b_st (SEQ ID NO: 10), hsa-miR-181c_st (SEQ ID NO: 79), hsa-miR-342-3p_st (SEQ ID NO: 11), hsa-miR-342-5p_st (SEQ ID NO: 80), hsa-miR-409-3p_st (SEQ ID NO: 81), hsa-miR-432_st (SEQ ID NO: 12), hsa-miR-487b_st (SEQ ID NO: 82), hsa-miR-654-3p_st (SEQ ID NO: 34), hsa-miR-768-5p_st (SEQ ID NO: 83), and hsa-miR-92b_st (SEQ ID NO: 15), wherein said device allows a determination of the sensitivity of said patient to mitoxantrone; or ix) one or more single-stranded nucleic acid molecules having at least 85% sequence identity to a target nucleic acid molecule having a sequence that is complementary to or identical to at least 15 consecutive nucleotides of one or more biomarkers selected from hsa-miR-124_st (SEQ ID NO: 7), hsa-miR-181a-star_st (SEQ ID NO: 9), and hsa-miR-181b_st (SEQ ID NO: 10), wherein said device allows a determination of the sensitivity of said patient to mitomycin; or x) one or more single-stranded nucleic acid molecules having at least 85% sequence identity to a target nucleic acid molecule having a sequence that is complementary to or identical to at least 15 consecutive nucleotides of one or more biomarkers selected from hsa-miR-106b-star_st (SEQ ID NO: 2), hsa-miR-1228_st (SEQ ID NO: 84), hsa-miR-185_st (SEQ ID NO: 85), hsa-miR-188-5p_st (SEQ ID NO: 86), hsa-miR-18b_st (SEQ ID NO: 87), hsa-miR-20b_st (SEQ ID NO: 88), hsa-miR-25_st (SEQ ID NO: 89), hsa-miR-320c_st (SEQ ID NO: 90), hsa-miR-320d_st (SEQ ID NO: 91), hsa-miR-362-5p_st (SEQ ID NO: 92), hsa-miR-500-star_st (SEQ ID NO: 93), hsa-miR-500_st (SEQ ID NO: 94), hsa-miR-501-3p_st (SEQ ID NO: 95), hsa-miR-502-3p_st (SEQ ID NO: 96), hsa-miR-532-3p_st (SEQ ID NO: 97), hsa-miR-532-5p_st (SEQ ID NO: 98), hsa-miR-652_st (SEQ ID NO: 42), and hsa-miR-766_st (SEQ ID NO: 1), wherein said device allow a determination of the sensitivity of said patient to paclitaxel; or xi) one or more single-stranded nucleic acid molecules having at least 85% sequence identity to a target nucleic acid molecule having a sequence that is complementary to or identical to at least 15 consecutive nucleotides of one or more biomarkers selected from HBII-438A_s_st (SEQ ID NO: 99), hsa-miR-155_st (SEQ ID NO: 20), hsa-miR-181a-star_st (SEQ ID NO: 9), hsa-miR-181b_st (SEQ ID NO: 10), hsa-miR-342-3p_st (SEQ ID NO: 11), hsa-miR-424-star_st (SEQ ID NO: 100), and hsa-miR-503_st (SEQ ID NO: 101), wherein said device allows a determination of the sensitivity of said patient to gemcitabine; or xii) one or more single-stranded nucleic acid molecules having at least 85% sequence identity to a target nucleic acid molecule having a sequence that is complementary to or identical to at least 15 consecutive nucleotides of one or more biomarkers selected from hsa-miR-1307_st (SEQ ID NO: 102), hsa-miR-505_st (SEQ ID NO: 103), hsa-miR-769-3p_st (SEQ ID NO: 104), and hsa-miR-769-5p_st (SEQ ID NO: 105), wherein said device allows a determination of the sensitivity of said patient to docetaxel; or xiii) one or more single-stranded nucleic acid molecules having at least 85% sequence identity to a target nucleic acid molecule having a sequence that is complementary to or identical to at least 15 consecutive nucleotides of one or more biomarkers selected from U49A_st (SEQ ID NO: 64), U49A_x_st (SEQ ID NO: 106), U49B_s_st (SEQ ID NO: 65), U49B_x_st (SEQ ID NO: 107), hsa-miR-10a-star_st (SEQ ID NO: 108), hsa-miR-1207-5p_st (SEQ ID NO: 109), hsa-miR-128_st (SEQ ID NO: 110), hsa-miR-150_st (SEQ ID NO: 111), hsa-miR-424-star_st (SEQ ID NO: 100), hsa-miR-424_st (SEQ ID NO: 112), hsa-miR-503_st (SEQ ID NO: 101), hsa-miR-766_st (SEQ ID NO: 1), and hsa-miR-768-5p_st (SEQ ID NO: 83), wherein said device allows a determination of the sensitivity of said patient to dexamethasone; or xiv) one or more single-stranded nucleic acid molecules having at least 85% sequence identity to a target nucleic acid molecule having a sequence that is complementary to or identical to at least 15 consecutive nucleotides of one or more biomarkers selected from HBII-202_st (SEQ ID NO: 113), HBII-438A_s_st (SEQ ID NO: 114), HBII-85-11_st (SEQ ID NO: 115), U104_st (SEQ ID NO: 116), U17b_st (SEQ ID NO: 117), U17b_x_st (SEQ ID NO: 59), U48_st (SEQ ID NOs: 118), U78_s_st (SEQ ID NO: 119), U78_x_st (SEQ ID NO: 120), hsa-miR-181a-star_st (SEQ ID NO: 9), hsa-miR-181 b_st (SEQ ID NO: 10), hsa-miR-342-3p_st (SEQ ID NO: 11), and hsa-miR-424-star_st (SEQ ID NO: 100), wherein said device allows a determination of the sensitivity of said patient to Ara-C (cytarabine hydrochloride); or xv) one or more single-stranded nucleic acid molecules having at least 85% sequence identity to a target nucleic acid molecule having a sequence that is complementary to or identical to at least 15 consecutive nucleotides of one or more biomarkers selected from ACA23_st (SEQ ID NO: 121), ACA24_x_st (SEQ ID NO: 122), ACA54_st (SEQ ID NO: 123), U31_st (SEQ ID NO: 124), hsa-let-7d-star_st (SEQ ID NO: 125), hsa-miR-106b-star_st (SEQ ID NO: 2), hsa-miR-1183_st (SEQ ID NO: 126), hsa-miR-1207-5p_st (SEQ ID NO: 109), hsa-miR-1268_st (SEQ ID NO: 127), hsa-miR-1281_st (SEQ ID NO: 8), hsa-miR-128_st (SEQ ID NO: 110), hsa-miR-150_st (SEQ ID NO: 111), hsa-miR-15a_st (SEQ ID NO: 128), hsa-miR-181a-star_st (SEQ ID NO: 9), hsa-miR-181c_st (SEQ ID NO: 79), hsa-miR-18b_st (SEQ ID NO: 87), hsa-miR-198_st (SEQ ID NO: 129), hsa-miR-20b-star_st (SEQ ID NO: 130), hsa-miR-223_st (SEQ ID NO: 131), hsa-miR-297_st (SEQ ID NO: 132), hsa-miR-342-5p_st (SEQ ID NO: 80), hsa-miR-363_st (SEQ ID NO: 133), hsa-miR-588_st (SEQ ID NO: 134), hsa-miR-631_st (SEQ ID NO: 135), hsa-miR-766_st (SEQ ID NO: 1), hsa-miR-768-5p_st (SEQ ID NO: 83), hsa-miR-92a-2-star_st (SEQ ID NO: 136), and hsa-miR-940_st (SEQ ID NO: 137), wherein said device allows a determination of the sensitivity of said patient to methylprednisolone; or xvi) one or more single-stranded nucleic acid molecules having at least 85% sequence identity to a target nucleic acid molecule having a sequence that is complementary to or identical to at least 15 consecutive nucleotides of one or more biomarkers selected from ACA10_s_st (SEQ ID NO: 138), ACA18_x_st (SEQ ID NO: 139), HBII-202_st (SEQ ID NO: 113), U104_st (SEQ ID NO: 140), U17b_st (SEQ ID NO: 117), U30_st (SEQ ID NO: 141), U31_x_st (SEQ ID NO: 142), U49A_st (SEQ ID NO: 143), U49A_x_st (SEQ ID NO: 144), U49B_s_st (SEQ ID NO: 145), U55_st (SEQ ID NO: 146), U55_x_st (SEQ ID NO: 146), U56_st (SEQ ID NO: 147), U67_st (SEQ ID NOs:148), U67_x_st (SEQ ID NO: 149), hsa-miR-106a_st (SEQ ID NO: 150), hsa-miR-1254_st (SEQ ID NO: 151), hsa-miR-1275_st (SEQ ID NO: 70), hsa-miR-17_st (SEQ ID NO: 152), hsa-miR-18a-star_st (SEQ ID NO: 71), hsa-miR-18a_st (SEQ ID NO: 72), hsa-miR-19b_st (SEQ ID NO: 153), hsa-miR-25-star_st (SEQ ID NO: 3), hsa-miR-297_st (SEQ ID NO: 132), hsa-miR-34b_st (SEQ ID NO: 154), hsa-miR-663b_st (SEQ ID NO: 155), and hsa-miR-92a_st (SEQ ID NO: 156), wherein said device allows a determination of the sensitivity of said patient to methotrexate; or xvii) one or more single-stranded nucleic acid molecules having at least 85% sequence identity to a target nucleic acid molecule having a sequence that is complementary to or identical to at least 15 consecutive nucleotides of one or more biomarkers selected from 14qII-14_st (SEQ ID NO: 157), 14qII-14_x_st (SEQ ID NO: 158), 14qII-1_st (SEQ ID NO: 159), 14qII-1_x_st (SEQ ID NO: 74), 14qII-26_st (SEQ ID NOs: 160), 14qII-26_x_st (SEQ ID NO: 161), 14qII-3_st (SEQ ID NO: 162), hsa-miR-125b-1-star_st (SEQ ID No: 163), hsa-miR-127-3p_st (SEQ ID NO: 77), hsa-miR-1271_st (SEQ ID NO: 30), hsa-miR-134_st (SEQ ID NO: 164), hsa-miR-155_st (SEQ ID NO: 20), hsa-miR-193a-5p_st (SEQ ID NO: 165), hsa-miR-21-star_st (SEQ ID NO: 166), hsa-miR-22_st (SEQ ID NO: 167), hsa-miR-299-3p_st (SEQ ID NO: 168), hsa-miR-337-5p_st (SEQ ID NO: 169), hsa-miR-370_st (SEQ ID NO: 32), hsa-miR-376c_st (SEQ ID NO: 170), hsa-miR-377-star_st (SEQ ID NO: 171), hsa-miR-379_st (SEQ ID NO: 172), hsa-miR-381_st (SEQ ID NO: 173), hsa-miR-382_st (SEQ ID NO: 174), hsa-miR-409-3p_st (SEQ ID NO: 81), hsa-miR-409-5p_st (SEQ ID NO: 175), hsa-miR-411_st (SEQ ID NO: 176), hsa-miR-431_st (SEQ ID NO: 177), hsa-miR-455-3p_st (SEQ ID NO: 178), hsa-miR-485-5p_st (SEQ ID NO: 179), hsa-miR-487b_st (SEQ ID NO: 82), hsa-miR-493_st (SEQ ID NO: 180), hsa-miR-494_st (SEQ ID NO: 181), hsa-miR-543_st (SEQ ID NO: 182), hsa-miR-663_st (SEQ ID NO: 28), hsa-miR-671-5p_st (SEQ ID NO: 43), and hsa-miR-758_st (SEQ ID NO: 35), wherein said device allows a determination of the sensitivity of said patient to bleomycin; or xviii) one or more single-stranded nucleic acid molecules having at least 85% identity to a target nucleic acid molecule having a sequence that is complementary to or identical to at least 15 consecutive nucleotides of one or more biomarkers selected from ENSG00000200879_st (SEQ ID NO: 183), ENSG00000202252_st (SEQ ID NO: 184), HBII-202_st (SEQ ID NO: 185), U25_st (SEQ ID NO: 186), U26_st (SEQ ID NO: 187), U28_x_st (SEQ ID NO: 188), U29_st (SEQ ID NO: 189), U30_st (SEQ ID NO: 141), U31_x_st (SEQ ID NO: 190), U74_x_st (SEQ ID NO: 191), hsa-miR-181a-star_st (SEQ ID NO: 9), hsa-miR-297_st (SEQ ID NO: 132), hsa-miR-34b_st (SEQ ID NO: 154), and hsa-miR-92a-1-star_st (SEQ ID NO: 192), wherein said device allows a determination of the sensitivity of said patient to methyl-GAG (methyl glyoxal bis amidinohydrazone dihydrochloride); or xix) one or more single-stranded nucleic acid molecules having at least 85% identity to a target nucleic acid molecule having a sequence that is complementary to or identical to at least 15 consecutive nucleotides of one or more biomarkers selected from ACA18_x_st (SEQ ID NO: 193), ACA51_x_st (SEQ ID NO: 194), ACA9_st (SEQ ID NO: 195), ACA9_x_st (SEQ ID NO: 196), HBII-180A_x_st (SEQ ID NO: 197), HBII-202_st (SEQ ID NO: 198), HBII-336_st (SEQ ID NO: 199), HBII-55_st (SEQ ID NO: 200), U104_st (SEQ ID NO: 201), U27_st (SEQ ID NO: 202), U29_st (SEQ ID NO: 203), U30_st (SEQ ID NO: 204), U31_st (SEQ ID NO: 205), U31_x_st (SEQ ID NO: 206), U38A_st (SEQ ID NO: 207), U55_st (SEQ ID NO: 208), U55_x_st (SEQ ID NO: 209), U56_st (SEQ ID NO: 210), U56_x_st (SEQ ID NO: 211), U57_st (SEQ ID NO: 212), U60_st (SEQ ID NO: 213), U74_x_st (SEQ ID NO: 191), hsa-miR-106a_st (SEQ ID NO: 150), hsa-miR-1183_st (SEQ ID NO: 126), hsa-miR-1207-5p_st (SEQ ID NO: 109), hsa-miR-1246_st (SEQ ID NO: 214), hsa-miR-1268_st (SEQ ID NO: 127), hsa-miR-1299_st (SEQ ID NO: 38), hsa-miR-1307_st (SEQ ID NO: 102), hsa-miR-142-5p_st (SEQ ID NO: 215), hsa-miR-17-star_st (SEQ ID NO: 216), hsa-miR-17_st (SEQ ID NO: 152), hsa-miR-18a-star_st (SEQ ID NO: 71), hsa-miR-18a_st (SEQ ID NO: 72), hsa-miR-18b_st (SEQ ID NO: 87), hsa-miR-195-star_st (SEQ ID. NO: 14), hsa-miR-19a_st (SEQ ID NO: 217), hsa-miR-19b_st (SEQ ID No: 153), hsa-miR-20a_st (SEQ ID NO: 218), hsa-miR-20b_st (SEQ ID NO: 88), hsa-miR-297_st (SEQ ID NO: 132), hsa-miR-330-3p_st (SEQ ID NO: 219), hsa-miR-346_st (SEQ ID NO: 220), hsa-miR-34b_st (SEQ ID NO: 154), hsa-miR-595_st (SEQ ID NO: 221), hsa-miR-629-star_st (SEQ ID NO: 41), hsa-miR-647_st (SEQ ID NO: 222), hsa-miR-766_st (SEQ ID NO: 1), hsa-miR-768-5p_st (SEQ ID NO: 83), and hsa-miR-92a_st (SEQ ID NO: 156), wherein said device allows a determination of the sensitivity of said patient to belinostat (PXD101); or xx) one or more single-stranded nucleic acid molecules having at least 85% identity to a target nucleic acid molecule having a sequence that is complementary to or identical to at least 15 consecutive nucleotides of one or more biomarkers selected from ACA10_s_st (SEQ ID NO: 223), ENSG00000199411_s_st (SEQ ID NO: 224), U104_st (SEQ ID NO: 201), U13_st (SEQ ID NO: 225), U36A_x_st (SEQ ID NO: 226), U36C_st (SEQ ID NO: 227), U74_x_st (SEQ ID NO: 69), U78_x_st (SEQ ID NO: 228), U8_x_st (SEQ ID NO: 229), hsa-miR-1246_st (SEQ ID NO: 214), hsa-miR-194-star_st (SEQ ID NO: 230), hsa-miR-200c-star_st (SEQ ID NO: 231), hsa-miR-34b_st (SEQ ID NO: 154), and hsa-miR-768-3p_st (SEQ ID NO: 44), wherein said device allows a determination of the sensitivity of said patient to 5-fluorouracil; or xxi) one or more single-stranded nucleic acid molecules having at least 85% identity to a target nucleic acid molecule having a sequence that is complementary to or identical to at least 15 consecutive nucleotides of one or more biomarkers selected from hsa-miR-106a_st (SEQ ID NO: 150), hsa-miR-106b-star_st (SEQ ID NO: 2), hsa-miR-1183_st (SEQ ID NO: 126), hsa-miR-195-star_st (SEQ ID NO: 14), hsa-miR-297_st (SEQ ID NO: 132), hsa-miR-324-3p_st (SEQ ID NO: 235), hsa-miR-34b_st (SEQ ID NO: 154), hsa-miR-371-5p_st (SEQ ID NO: 236), hsa-miR-766_st (SEQ ID NO:1), hsa-miR-92a_st (SEQ ID NO: 156), and hsa-miR-93-star_st (SEQ ID NO: 45), wherein said device allows a determination of the sensitivity of said patient to 5-Aza-2'-deoxycytidine (decitabine); or xxii) one or more single-stranded nucleic acid molecules having at least 85% identity to a target nucleic acid molecule having a sequence that is complementary to or identical to at least 15 consecutive nucleotides of one or more biomarkers selected from ACA41_x_st (SEQ ID NO: 237), ACA48_x_st (SEQ ID NO: 238), HBII-202_st (SEQ ID NO: 239), HBII-429_st (SEQ ID NO: 240), U104_st (SEQ ID NO: 140), U49A_st (SEQ ID NO: 63), U49B_s_st (SEQ ID NO: 145), U55_st (SEQ ID NO: 6), U55_x_st (SEQ ID NO: 241), U74_x_st (SEQ ID NO: 242), hsa-miR-124_st (SEQ ID NO: 7), hsa-miR-1299_st (SEQ ID NO: 38), hsa-miR-181a-star_st (SEQ ID NO: 9), hsa-miR-297_st (SEQ ID NO: 132), hsa-miR-342-5p_st (SEQ ID NO: 80), hsa-miR-34b_st (SEQ ID NO: 154), hsa-miR-631_st (SEQ ID NO: 135), hsa-miR-768-3p_st (SEQ ID NO: 44), and hsa-miR-768-5p_st (SEQ ID NO: 83), wherein said device allows a determination of the sensitivity of said patient to idarubicin; or xxiii) one or more single-stranded nucleic acid molecules having at least 85% identity to a target nucleic acid molecule having a sequence that is complementary to or identical to at least 15 consecutive nucleotides of one or more biomarkers selected from ACA7_s_st (SEQ ID NOs: 243), ENSG00000202252_st (SEQ ID NO: 244), ENSG00000207002_x_st (SEQ ID NO: 245), HBII-202_st (SEQ ID NO: 113), HBII-429_st (SEQ ID NO: 246), HBII-438A_s_st (SEQ ID NO: 247), HBII-55_st (SEQ ID NO: 248), HBII-85-11_st (SEQ ID NO: 249), HBII-85-23_x_st (SEQ ID NO: 250), HBII-85-26_st (SEQ ID NO: 251), HBII-85-2_x_st (SEQ ID NO: 252), HBII-85-6_x_st (SEQ ID NO: 253), U104_st (SEQ ID NO: 140), U13_st (SEQ ID NO: 225), U17b_st (SEQ ID NO: 254), U17b_x_st (SEQ ID NO: 59), U33_st (SEQ ID NO: 255), U34_st (SEQ ID NO: 256), U41_st (SEQ ID NO: 257), U52_st (SEQ ID NO: 258), U55_st (SEQ ID NO: 259), U55_x_st (SEQ ID NOs: 260), U56_st (SEQ ID NO: 261), U57_st (SEQ ID NO: 262), U68_st (SEQ ID NO: 263), U74_x_st (SEQ ID NO: 264), U78_s_st (SEQ ID NO: 265), U78_x_st (SEQ ID NO: 266), U83_st (SEQ ID NO: 267), U95_st (SEQ ID NO: 268), hsa-miR-1183_st (SEQ ID NO: 126), hsa-miR-1207-5p_st (SEQ ID NO: 109), hsa-miR-1228_st (SEQ ID NO: 84), hsa-miR-124_st (SEQ ID NO: 7), hsa-miR-1281_st (SEQ ID NO: 8), hsa-miR-1299_st (SEQ ID NO: 38), hsa-miR-140-3p_st (SEQ ID NO: 13), hsa-miR-142-5p_st (SEQ ID NO: 215), hsa-miR-181a-star_st (SEQ ID NO: 9), hsa-miR-181a_st (SEQ ID NO: 78), hsa-miR-181b_st (SEQ ID NO: 10), hsa-miR-181c_st (SEQ ID NO: 79), hsa-miR-195-star_st (SEQ ID NO: 14), hsa-miR-223_st (SEQ ID NO: 131), hsa-miR-297_st (SEQ ID NO: 132), hsa-miR-29b-2-star_st (SEQ ID NO: 39), hsa-miR-342-3p_st (SEQ ID NO: 11), hsa-miR-342-5p_st (SEQ ID NO: 80), hsa-miR-34b_st (SEQ ID NO: 154), hsa-miR-541-star_st (SEQ ID NO: 269), hsa-miR-610_st (SEQ ID NO: 270), hsa-miR-647_st (SEQ ID NO: 222), hsa-miR-766_st (SEQ ID NO: 1), hsa-miR-768-3p_st (SEQ ID NO: 44), hsa-miR-768-5p_st (SEQ ID NO: 83), and hsa-miR-885-5p_st (SEQ ID NO: 271), wherein said device allows a determination of the sensitivity of said patient to melphalan; or xxiv) one or more single-stranded nucleic acid molecules having at least 85% identity to a target nucleic acid molecule having a sequence that is complementary to or identical to at least 15 consecutive nucleotides of one or more biomarkers selected from hsa-miR-1246_st (SEQ ID NO: 214), hsa-miR-150_st (SEQ ID NO: 111), hsa-miR-339-3p_st (SEQ ID NO: 272), hsa-miR-339-5p_st (SEQ ID NO: 273), and hsa-miR-768-3p_st (SEQ ID NO: 44), wherein said device allows a determination of the sensitivity of said patient to IL4-PR38 fusion protein; or xxv) one or more single-stranded nucleic acid molecules having at least 85% identity to a target nucleic acid molecule having a sequence that is complementary to or identical to at least 15 consecutive nucleotides of one or more biomarkers selected from hsa-miR-1308_st (SEQ ID NO: 274), hsa-miR-148a_st (SEQ ID NO: 275), hsa-miR-152_st (SEQ ID NO: 276), hsa-miR-34a-star_st (SEQ ID NO: 277), and hsa-miR-34a_st (SEQ ID NO: 234), wherein said device allows a determination of the sensitivity of said patient to valproic acid; or xxvi) one or more single-stranded nucleic acid molecules having at least 85% identity to a target nucleic acid molecule having a sequence that is complementary to or identical to at least 15 consecutive nucleotides of one or more biomarkers selected from HBII-142_st (SEQ ID NO: 278), HBII-142_x_st (SEQ ID NO: 279), U55_st (SEQ ID NO: 6), U55_x_st (SEQ ID NO: 280), hsa-miR-1202_st (SEQ ID NO: 281), hsa-miR-124_st (SEQ ID NO: 7), hsa-miR-148a-star_st (SEQ ID NO: 282), hsa-miR-148a_st (SEQ ID NO: 275), hsa-miR-184_st (SEQ ID NO: 283), hsa-miR-191_st (SEQ ID NO: 284), hsa-miR-195-star_st (SEQ ID NO: 14), hsa-miR-29b-2-star_st (SEQ ID NO: 39), hsa-miR-425-star_st (SEQ ID NO: 285), hsa-miR-425_st (SEQ ID NO: 286), hsa-miR-449a_st (SEQ ID NO: 287), hsa-miR-449b_st (SEQ ID NO: 288), hsa-miR-551 b_st (SEQ ID NO: 289), hsa-miR-593-star_st (SEQ ID NO: 290), hsa-miR-768-3p_st (SEQ ID NO: 44), hsa-miR-768-5p_st (SEQ ID NO: 83), and hsa-miR-877_st (SEQ ID NO: 291), wherein said device allows a determination of the sensitivity of said patient to all-trans retinoic acid (ATRA); or xxvii) one or more single-stranded nucleic acid molecules having at least 85% identity to a target nucleic acid molecule having a sequence that is complementary to or identical to at least 15 consecutive nucleotides of one or more biomarkers selected from ENSG00000200879_st (SEQ ID NO: 292), ENSG00000202252_st (SEQ ID NO: 244), HBII-142_st (SEQ ID NO: 293), hsa-miR-1202_st (SEQ ID NO: 281), hsa-miR-184_st (SEQ ID NO: 283), hsa-miR-196a_st (SEQ ID NO: 294), hsa-miR-205_st (SEQ ID NO: 295), hsa-miR-29b-2-star_st (SEQ ID NO: 39), hsa-miR-29c-star_st (SEQ ID NO: 296), hsa-miR-375_st (SEQ ID NO: 297), hsa-miR-449a_st (SEQ ID NO: 287), hsa-miR-449b_st (SEQ ID NO: 288), hsa-miR-489_st (SEQ ID NO: 298), and hsa-miR-768-3p_st (SEQ ID NO: 44), wherein said device allows a determination of the sensitivity of said patient to cytoxan; or xxviii) one or more single-stranded nucleic acid molecules having at least 85% identity to a target nucleic acid molecule having a sequence that is complementary to or identical to at least 15 consecutive nucleotides of one or more biomarkers selected from hsa-miR-155_st (SEQ ID NO: 20), hsa-miR-181b_st (SEQ ID NO: 10), hsa-miR-342-3p_st (SEQ ID NO: 11), hsa-miR-342-5p_st (SEQ ID NO: 80), hsa-miR-424-star_st (SEQ ID NO: 100), and hsa-miR-503_st (SEQ ID NO: 101), wherein said device allows a determination of the sensitivity of said patient to topotecan; or xxix) one or more single-stranded nucleic acid molecules having at least 85% identity to a target nucleic acid molecule having a sequence that is complementary to or identical to at least 15 consecutive nucleotides of one or more biomarkers selected from U56_x_st (SEQ ID NO: 211), hsa-miR-106a_st (SEQ ID NO: 150), hsa-miR-126_st (SEQ ID NO: 299), hsa-miR-128_st (SEQ ID NO: 110), hsa-miR-148a-star_st (SEQ ID NO: 282), hsa-miR-148a_st (SEQ ID NO: 275), hsa-miR-153_st (SEQ ID NO: 300), hsa-miR-17_st (SEQ ID NO: 152), hsa-miR-18a-star_st (SEQ ID NO: 71), hsa-miR-18a_st (SEQ ID NO: 72), hsa-miR-18b_st (SEQ ID NO: 87), hsa-miR-19a_st (SEQ ID NO: 217), hsa-miR-19b_st (SEQ ID NO: 153), hsa-miR-20a_st (SEQ ID NO: 218), hsa-miR-20b_st (SEQ ID NO: 88), hsa-miR-25_st (SEQ ID NO: 89), hsa-miR-30c_st (SEQ ID NO: 301), hsa-miR-30e_st (SEQ ID NO: 302), hsa-miR-363-star_st (SEQ ID NO: 303), hsa-miR-363_st (SEQ ID NO: 133), hsa-miR-766_st (SEQ ID NO: 1), and hsa-miR-92a_st (SEQ ID NO: 156), wherein said device allows a determination of the sensitivity of said patient to suberoylanilide hydroxamic acid (SAHA, vorinostat); or xxx) one or more single-stranded nucleic acid molecules having at least 85% identity to a target nucleic acid molecule having a sequence that is complementary to or identical to at least 15 consecutive nucleotides of one or more biomarkers selected from hsa-miR-185_st (SEQ ID NO: 85), hsa-miR-188-5p_st (SEQ ID NO: 86), hsa-miR-362-5p_st (SEQ ID NO: 92), hsa-miR-500-star_st (SEQ ID NO: 93), hsa-miR-500_st (SEQ ID NO: 94), hsa-miR-501-3p_st (SEQ ID NO: 95), hsa-miR-501-5p_st (SEQ ID NO: 304), hsa-miR-502-3p_st (SEQ ID NO: 96), hsa-miR-532-3p_st (SEQ ID NO: 97), hsa-miR-532-5p_st (SEQ ID NO: 98), hsa-miR-652_st (SEQ ID NO: 42), hsa-miR-660_st (SEQ ID NO: 305), and hsa-miR-93_st (SEQ ID NO: 46), wherein said device allows allowing a determination of the sensitivity of said patient to depsipeptide (FR901228); or xxxi) one or more single-stranded nucleic acid molecules having at least 85% identity to a target nucleic acid molecule having a sequence that is complementary to or identical to at least 15 consecutive nucleotides of one or more biomarkers selected from hsa-miR-106b-star_st (SEQ ID NO: 2), hsa-miR-106b_st (SEQ ID NO: 37), hsa-miR-1307_st (SEQ ID NO: 102), hsa-miR-188-5p_st (SEQ ID NO: 86), hsa-miR-25-star_st (SEQ ID NO: 3), hsa-miR-25_st (SEQ ID NO: 89), hsa-miR-320c_st (SEQ ID NO: 90), hsa-miR-324-3p_st (SEQ ID NO: 235), hsa-miR-500_st (SEQ ID NO: 94), hsa-miR-501-5p_st (SEQ ID NO: 304), hsa-miR-638_st (SEQ ID NO: 306), hsa-miR-652_st (SEQ ID NO: 42), hsa-miR-93-star_st (SEQ ID NO: 45), and hsa-miR-93_st (SEQ ID NO: 46), wherein said device allows a determination of the sensitivity of said patient to bortezomib; or xxxii) one or more single-stranded nucleic acid molecules having at least 85% identity to a target nucleic acid molecule having a sequence that is complementary to or identical to at least 15 consecutive nucleotides of one or more biomarkers selected from HBII-85-2_x_st (SEQ ID NO: 252), U104_st (SEQ ID NO: 201), U41_st (SEQ ID NO: 307), U52_st (SEQ ID NO: 258), U55_st (SEQ ID NO: 6), U55_x_st (SEQ ID NO: 308), U57_st (SEQ ID NO: 262), U74_x_st (SEQ ID NO: 309), hsa-miR-124_st (SEQ ID NO: 7), hsa-miR-1281_st (SEQ ID NO: 8), hsa-miR-1299_st (SEQ ID NO: 38), hsa-miR-140-3p_st (SEQ ID NO: 13), hsa-miR-142-5p_st (SEQ ID NO: 215), hsa-miR-181a-star_st (SEQ ID NO: 9), hsa-miR-181a_st (SEQ ID NO: 78), hsa-miR-181b_st (SEQ ID NO: 10), hsa-miR-181c_st (SEQ ID NO: 79), hsa-miR-195-star_st (SEQ ID NO: 14), hsa-miR-223_st (SEQ ID NO: 131), hsa-miR-297_st (SEQ ID NO: 132), hsa-miR-342-3p_st (SEQ ID NO: 11), hsa-miR-342-5p_st (SEQ ID NO: 80), hsa-miR-34b_st (SEQ ID NO: 154), hsa-miR-766_st (SEQ ID NO: 1), hsa-miR-768-5p_st (SEQ ID NO: 83), and hsa-miR-874_st (SEQ ID NO: 310), wherein said device allows a determination of the sensitivity of said patient to leukeran; or xxxiii) one or more single-stranded nucleic acid molecules having at least 85% identity to a target nucleic acid molecule having a sequence that is complementary to or identical to at least 15 consecutive nucleotides of one or more biomarkers selected from HBII-276_st (SEQ ID NO: 311), HBII-438A_s_st (SEQ ID NO: 247), HBII-52-32_x_st (SEQ ID NO: 312), HBII-85-11_st (SEQ ID NO: 115), hsa-miR-130a_st (SEQ ID NO: 313), hsa-miR-155_st (SEQ ID NO: 20), hsa-miR-181a-star_st (SEQ ID NO: 9), hsa-miR-181a_st (SEQ ID NO: 78), hsa-miR-181b_st (SEQ ID NO: 10), hsa-miR-20b-star_st (SEQ ID NO: 130), hsa-miR-20b_st (SEQ ID NO: 88), hsa-miR-34c-3p_st (SEQ ID NO: 314), hsa-miR-363_st (SEQ ID NO: 133), hsa-miR-424-star_st (SEQ ID NO: 100), hsa-miR-503_st (SEQ ID NO: 101), hsa-miR-554_st (SEQ ID NO: 315), and hsa-miR-766_st (SEQ ID NO: 1), wherein said device allows a determination of the sensitivity of said patient to fludarabine; or xxxiv) one or more single-stranded nucleic acid molecules having at least 85% identity to a target nucleic acid molecule having a sequence that is complementary to or identical to at least 15 consecutive nucleotides of one or more biomarkers selected from hsa-miR-106b-star_st (SEQ ID NO: 2), hsa-miR-25-star_st (SEQ ID NO: 3), hsa-miR-362-5p_st (SEQ ID NO: 92), hsa-miR-500-star_st (SEQ ID NO: 93), hsa-miR-500_st (SEQ ID NO: 94), hsa-miR-502-3p_st (SEQ ID NO: 96), hsa-miR-532-5p_st (SEQ ID NO: 98), hsa-miR- 652_st (SEQ ID NO: 42), and hsa-miR-671-5p_st (SEQ ID NO: 43), wherein said device allows a determination of the sensitivity of said patient to vinblastine; or xxxv) one or more single-stranded nucleic acid molecules having at least 85% identity to a target nucleic acid molecule having a sequence that is complementary to or identical to at least 15 consecutive nucleotides of one or more biomarkers selected from U55_st (SEQ ID NO: 308), U55_x_st (SEQ ID NO: 6), hsa-miR-1207-5p_st (SEQ ID NO: 109), hsa-miR-1246_st (SEQ ID NO: 214), hsa-miR-1281_st (SEQ ID NO: 8), hsa-miR-181a-star_st (SEQ ID NO: 9), hsa-miR-181b_st (SEQ ID NO: 10), hsa-miR-181c_st (SEQ ID NO: 79), hsa-miR-297_st (SEQ ID NO: 132), hsa-miR-766_st (SEQ ID NO: 1), and hsa-miR-923_st (SEQ ID NO: 29), wherein said device allows a determination of the sensitivity of said patient to busulfan; or xxxvi) one or more single-stranded nucleic acid molecules having at least 85% identity to a target nucleic acid molecule having a sequence that is complementary to or identical to at least 15 consecutive nucleotides of one or more biomarkers selected from U13_st (SEQ ID NO: 316), U17a_st (SEQ ID NO: 317), U25_st (SEQ ID NO: 318), U29_st (SEQ ID NO: 203), U3-2_s_st (SEQ ID NO: 319), U41_st (SEQ ID NO: 307), U52_st (SEQ ID NO: 320), U55_st (SEQ ID NO: 241), hsa-miR-1207-5p_st (SEQ ID NO: 109), hsa-miR-1299_st (SEQ ID NO: 38), hsa-miR-140-3p_st (SEQ ID NO: 13), hsa-miR-140-5p_st (SEQ ID NO: 18), hsa-miR-17-star_st (SEQ ID NO: 216), hsa-miR-181d_st (SEQ ID NO: 321), hsa-miR-223_st (SEQ ID NO: 131), hsa-miR-297_st (SEQ ID NO: 132), hsa-miR-34b_st (SEQ ID NO: 154), hsa-miR-766_st (SEQ ID NO: 1), hsa-miR-92a-1-star_st (SEQ ID NO: 192), and hsa-miR-92a_st (SEQ ID NO: 156), wherein said device allows a determination of the sensitivity of said patient to dacarbazine; or xxxvii) one or more single-stranded nucleic acid molecules having at least 85% identity to a target nucleic acid molecule having a sequence that is complementary to or identical to at least 15 consecutive nucleotides of one or more biomarkers selected from ACA10_s_st (SEQ ID NO: 138), ACA15_s_st (SEQ ID NO: 322), ACA18_x_st (SEQ ID NO: 139), ACA21_st (SEQ ID NO: 323), ACA51_x_st (SEQ ID NO: 324), HBII-180A_x_st (SEQ ID NO: 54), HBII-202_st (SEQ ID NO: 113), HBII-429_st (SEQ ID NO: 55), HBII-55_st (SEQ ID NO: 248), HBII-99_st (SEQ ID NO: 325), U104_st (SEQ ID NO: 326), U17b_st (SEQ ID NO: 327), U17b_x_st (SEQ ID NO: 328), U25_st (SEQ ID NO: 329), U27_st (SEQ ID NO: 330), U29_st (SEQ ID NO: 331), U30_st (SEQ ID NO: 332), U31_st (SEQ ID NO: 124), U31_x_st (SEQ ID NO: 333), U33_st (SEQ ID NO: 334), U36C_st (SEQ ID NO: 335), U50B_st (SEQ ID NO: 336), U55_st (SEQ ID NO: 241), U55_x_st (SEQ ID NO: 260), U56_st (SEQ ID NO: 337), U56_x_st (SEQ ID NO: 338), U57_st (SEQ ID NO: 339), U71d_x_st (SEQ ID NO: 340), U73a_st (SEQ ID NO: 341), U74_x_st (SEQ ID NO: 69), U78_s_st (SEQ ID NO: 265), U78_x_st (SEQ ID NO: 266), U95_st (SEQ ID NO: 268), hsa-miR-106a_st (SEQ ID NO: 150), hsa-miR-106b_st (SEQ ID NO: 37), hsa-miR-1246_st (SEQ ID NO: 214), hsa-miR-1275_st (SEQ ID NO: 70), hsa-miR-1307_st (SEQ ID NO: 102), hsa-miR-142-5p_st (SEQ ID NO: 215), hsa-miR-148a-star_st (SEQ ID NO: 282), hsa-miR-153_st (SEQ ID NO: 300), hsa-miR-17-star_st (SEQ ID NO: 216), hsa-miR-17_st (SEQ ID NO: 152), hsa-miR-18a-star_st (SEQ ID NO: 71), hsa-miR-18a_st (SEQ ID NO: 72), hsa-miR-18b_st (SEQ ID NO: 87), hsa-miR-19a_st (SEQ ID NO: 217), hsa-miR-19b_st (SEQ ID NO: 153), hsa-miR-20a_st (SEQ ID NO: 218), hsa-miR-297_st (SEQ ID NO: 132), hsa-miR-301a_st (SEQ ID NO: 342), and hsa-miR-34b_st (SEQ ID NO: 154), wherein said device allows a determination of the sensitivity of said patient to oxaliplatin; or xxxviii) one or more single-stranded nucleic acid molecules having at least 85% identity to a target nucleic acid molecule having a sequence that is complementary to or identical to at least 15 consecutive nucleotides of one or more biomarkers selected from ACA7_s_st (SEQ ID NO: 243), ENSG00000199282_st (SEQ ID NO: 343), ENSG00000201859_x_st (SEQ ID NO: 344), HBII-202_st (SEQ ID NO: 239), HBII-336_st (SEQ ID NO: 345), HBII-429_st (SEQ ID NO: 246), U104_st (SEQ ID NO: 140), U25_st (SEQ ID NO: 329), U33_st (SEQ ID NO: 346), U34_st (SEQ ID NO: 347), U38A_st (SEQ ID NO: 348), U41_st (SEQ ID NO: 307), U49B_s_st (SEQ ID NO: 107), U52_st (SEQ ID NO: 349), U55_st (SEQ ID NO: 6), U55_x_st (SEQ ID NO: 260), U74_x_st (SEQ ID NO: 350), hsa-miR-1207-5p_st (SEQ ID NO: 109), hsa-miR-124_st (SEQ ID NO: 7), hsa-miR-1281_st (SEQ ID NO: 8), hsa-miR-1299_st (SEQ ID NO: 38), hsa-miR-140-3p_st (SEQ ID NO: 13), hsa-miR-155_st (SEQ ID NO: 20), hsa-miR-181a-star_st (SEQ ID NO: 9), hsa-miR-181b_st (SEQ ID NO: 10), hsa-miR-181c_st (SEQ ID NO: 79), hsa-miR-195-star_st (SEQ ID NO: 14), hsa-miR-223_st (SEQ ID NO: 131), hsa-miR-297_st (SEQ ID NO: 132), hsa-miR-34b_st (SEQ ID NO: 154), hsa-miR-491-3p_st (SEQ ID NO: 351), hsa-miR-595_st (SEQ ID NO: 221), hsa-miR-631_st (SEQ ID NO: 135), hsa-miR-766_st (SEQ ID NO: 1), and hsa-miR-768-5p_st (SEQ ID NO: 83), wherein said device allows a determination of the sensitivity of said patient to hydroxyurea; or xxxix) one or more single-stranded nucleic acid molecules having at least 85% identity to a target nucleic acid molecule having a sequence that is complementary to or identical to at least 15 consecutive nucleotides of one or more biomarkers selected from HBII-180A_x_st (SEQ ID NO: 352), U104_st (SEQ ID NO: 353), U33_st (SEQ ID NO: 354), U34_st (SEQ ID NO: 355), U43_x_st (SEQ ID NO: 356), U51_st (SEQ ID NO: 357), U55_x_st (SEQ ID NO: 36), U74_x_st (SEQ ID NO: 191), U78_s_st (SEQ ID NO: 119), U78_x_st (SEQ ID NO: 228), hsa-miR-1228-star_st (SEQ ID NO: 358), hsa-miR-1246_st (SEQ ID NO: 214), hsa-miR-124_st (SEQ ID NO: 7), hsa-miR-1299_st (SEQ ID NO: 38), hsa-miR-1307_st (SEQ ID NO: 102), hsa-miR-149-star_st (SEQ ID NO: 359), hsa-miR-16_st (SEQ ID NO: 360), hsa-miR-18a_st (SEQ ID NO: 72), hsa-miR-195-star_st (SEQ ID NO: 14), hsa-miR-297_st (SEQ ID NO: 132), hsa-miR-330-3p_st (SEQ ID NO: 219), hsa-miR-346_st (SEQ ID NO: 220), hsa-miR-34b_st (SEQ ID NO: 154), hsa-miR-638_st (SEQ ID NO: 306), hsa-miR-923_st (SEQ ID NO: 29), and hsa-miR-92a_st (SEQ ID NO: 156), wherein said device allows a determination of the sensitivity of said patient to tegafur; or xl) one or more single-stranded nucleic acid molecules having at least 85% identity to a target nucleic acid molecule having a sequence that is complementary to or identical to at least 15 consecutive nucleotides of one or more biomarkers selected from ACA48_x_st (SEQ ID NO: 238), HBII-85-26_st (SEQ ID NO: 361), HBII-85-6_x_st (SEQ ID NO: 362), U104_st (SEQ ID NO: 140), U55_st (SEQ ID NO: 280), U55_x_st (SEQ ID NO: 308), U74_x_st (SEQ ID NO: 264), hsa-miR-106a-star_st (SEQ ID NO: 363), hsa-miR-106bstar_st (SEQ ID NO: 2), hsa-miR-106b_st (SEQ ID NO: 37), hsa-miR-124_st (SEQ ID NO: 7), hsa-miR-1281_st (SEQ ID NO: 8), hsa-miR-1299_st (SEQ ID NO: 38), hsa-miR-181a-star_st (SEQ ID NO: 9), hsa-miR-195-star_st (SEQ ID NO: 14), hsa-miR-297_st (SEQ ID NO: 132), hsa-miR-29b-2-star_st (SEQ ID NO: 39), hsa-miR-33b-star_st (SEQ ID NO: 40), hsa-miR-342-5p_st (SEQ ID NO: 80), hsa-miR-34b_st (SEQ ID NO: 154), hsa-miR-629-star_st (SEQ ID NO: 41), hsa-miR-652_st (SEQ ID NO: 42), hsa-miR-671-5p_st (SEQ ID NO: 43), hsa-miR-766_st (SEQ ID NO: 1), hsa-miR-768-3p_st (SEQ ID NO: 44), hsa-miR-768-5p_st (SEQ ID NO: 83), hsa-miR-877-star_st (SEQ ID NO: 364), hsa-miR-93-star_st (SEQ ID NO: 45), and hsa-miR-93_st (SEQ ID NO: 46), wherein said device allows a determination of the sensitivity of said patient to daunorubicin; or xli) one or more single-stranded nucleic acid molecules having at least 85% identity to a target nucleic acid molecule having a sequence that is complementary to or identical to at least 15 consecutive nucleotides of one or more biomarkers selected from 14qII-14_st (SEQ ID NO: 157), 14qII-14_x_st (SEQ ID NO: 158), 14qII-1_st (SEQ ID NO: 159), 14qII-1_x_st (SEQ ID NO: 74), 14qII-26_st (SEQ ID NO: 160), 14qII-26_x_st (SEQ ID NO: 161), 14qII-3_st (SEQ ID NO: 162), hsa-miR-125b-1-star_st (SEQ ID NO: 163), hsa-miR-127-3p_st (SEQ ID NO: 77), hsa-miR-1271_st (SEQ ID NO: 30), hsa-miR-134_st (SEQ ID NO: 164), hsa-miR-155_st (SEQ ID NO: 20), hsa-miR-193a-5p_st (SEQ ID NO: 165), hsa-miR-21-star_st (SEQ ID NO: 166), hsa-miR-22_st (SEQ ID NO: 167), hsa-miR-299-3p_st (SEQ ID NO: 168), hsa-miR-337-5p_st (SEQ ID NO: 169), hsa-miR-370_st (SEQ ID NO: 32), hsa-miR-376c_st (SEQ ID NO: 170), hsa-miR-377-star_st (SEQ ID NO: 171), hsa-miR-379_st (SEQ ID NO: 172), hsa-miR-381_st (SEQ ID NO: 173), hsa-miR-382_st (SEQ ID NO: 174), hsa-miR-409-3p_st (SEQ ID NO: 81), hsa-miR-409-5p_st (SEQ ID NO: 175), hsa-miR-411_st (SEQ ID NO: 176), hsa-miR-431_st (SEQ ID NO: 177), hsa-miR-455-3p_st (SEQ ID NO: 178), hsa-miR-485-5p_st (SEQ ID NO: 179), hsa-miR-487b_st (SEQ ID NO: 82), hsa-miR-493_st (SEQ ID NO:180), hsa-miR-494_st (SEQ ID NO: 181), hsa-miR-543_st (SEQ ID NO: 182), hsa-miR-663_st (SEQ ID NO: 28), hsa-miR-671-5p_st (SEQ ID NO: 43), and hsa-miR-758_st (SEQ ID NO: 35), wherein said device allows a determination of the sensitivity of said patient to bleomycin; or xlii) one or more single-stranded nucleic acid molecules having at least 85% identity to a target nucleic acid molecule having a sequence that is complementary to or identical to at least 15 consecutive nucleotides of one or more biomarkers selected from hsa-miR-1226_st (SEQ ID NO: 365), hsa-miR-193a-3p_st (SEQ ID NO: 366), hsa-miR-193a-5p_st (SEQ ID NO: 165), hsa-miR-330-3p_st (SEQ ID NO: 219), hsa-miR-330-5p_st (SEQ ID NO: 367), hsa-miR-378_st (SEQ ID NO: 368), and hsa-miR-586_st (SEQ ID NO: 369), wherein said device allows a determination of the sensitivity of said patient to estramustine; or xliii) one or more single-stranded nucleic acid molecules having at least 85% identity to a target nucleic acid molecule having a sequence that is complementary to or identical to at least 15 consecutive nucleotides of one or more biomarkers selected from ACA13_st (SEQ ID NO: 370), ACA21_st (SEQ ID NO: 323), ACA48_x_st (SEQ ID NO: 371), ACA7_s_st (SEQ ID NO: 372), ACA9_st (SEQ ID NO: 373), ENSG00000202252_st (SEQ ID NO: 184), HBII-202_st (SEQ ID NO: 198), HBII-239_st (SEQ ID NO: 374), HBII-336_st (SEQ ID NO: 345), HBII-429_st (SEQ ID NO: 240), U104_st (SEQ ID NO: 140), U33_st (SEQ ID NO: 375), U34_st (SEQ ID NO: 376), U52_st (SEQ ID NO: 258), U55_st (SEQ ID NO: 308), U55_x_st (SEQ ID NO: 260), U74_x_st (SEQ ID NO: 377), U75_st (SEQ ID NO: 378), U78_s_st (SEQ ID NO: 265), U78_x_st (SEQ ID NO: 120), U95_st (SEQ ID NO: 379), hsa-miR-124_st (SEQ ID NO: 7), hsa-miR-1281_st (SEQ ID NO: 8), hsa-miR-1299_st (SEQ ID NO: 38), hsa-miR-142-5p_st (SEQ ID NO: 215), hsa-miR-181a-star_st (SEQ ID NO: 9), hsa-miR-181a_st (SEQ ID NO: 78), hsa-miR-181b_st (SEQ ID NO: 10), hsa-miR-195-star_st (SEQ ID NO: 14), hsa-miR-297_st (SEQ ID NO: 132), hsa-miR-29b-2-star_st (SEQ ID NO: 39), hsa-miR-331-5p_st (SEQ ID NO: 380), hsa-miR-34b_st (SEQ ID NO: 154), hsa-miR-425_st (SEQ ID NO: 286), hsa-miR-766_st (SEQ ID NO: 1), hsa-miR-768-3p_st (SEQ ID NO: 44), and hsa-miR-768-5p_st (SEQ ID NO: 83), wherein said device allows a determination of the sensitivity of said patient to mechlorethamine; or xliv) one or more single-stranded nucleic acid molecules having at least 85% identity to a target nucleic acid molecule having a sequence that is complementary to or identical to at least 15 consecutive nucleotides of one or more biomarkers selected from hsa-miR-296-3p_st (SEQ ID NO: 381) and hsa-miR-923_st (SEQ ID NO: 29), wherein said device allows a determination of the sensitivity of said patient to streptozocin; or xlv) one or more single-stranded nucleic acid molecules having at least 85% identity to a target nucleic acid molecule having a sequence that is complementary to or identical to at least 15 consecutive nucleotides of one or more biomarkers selected from ACA10_s_st (SEQ ID NO: 382), ACA44_st (SEQ ID NO: 383), ACA52_st (SEQ ID NO: 384), ACA61_st (SEQ ID NO: 385), HBII-142_st (SEQ ID NO: 278), HBII-180A_x_st (SEQ ID NO: 386), HBII-382_s_st (SEQ ID NO: 387), HBII-429_st (SEQ ID NO: 388), U13_st (SEQ ID NO: 389), U17a_st (SEQ ID NO: 390), U17a_x_st (SEQ ID NO: 391), U17b_st (SEQ ID NO: 58), U17b_x_st (SEQ ID NO: 392), U38A_st (SEQ ID NO: 393), U41_st (SEQ ID NO: 394), U48_st (SEQ ID NO: 395), U52_st (SEQ ID NO: 396), U55_st (SEQ ID NO: 146), U55_x_st (SEQ ID NO: 280), U67_st (SEQ ID NO: 66), U67_x_st (SEQ ID NO: 397), U70_x_st (SEQ ID NO: 398), U74_x_st (SEQ ID NO: 399), U83B_st (SEQ ID NO: 400), hsa-miR-106a_st (SEQ ID NO: 150), hsa-miR-1274a_st (SEQ ID NO: 401), hsa-miR-1275_st (SEQ ID NO: 70), hsa-miR-1280_st (SEQ ID NO: 402), hsa-miR-130b_st (SEQ ID NO: 403), hsa-miR-146b-3p_st (SEQ ID NO: 404), hsa-miR-146b-5p_st (SEQ ID NO: 405), hsa-miR-17-star_st (SEQ ID NO: 216), hsa-miR-185-star_st (SEQ ID NO: 406), hsa-miR-18a-star_st (SEQ ID NO: 71), hsa-miR-18a_st (SEQ ID NO: 72), hsa-miR-18b_st (SEQ ID NO: 87), hsa-miR-19a_st (SEQ ID NO: 217), hsa-miR-19b_st (SEQ ID NO: 153), hsa-miR-202_st (SEQ ID NO: 407), hsa-miR-20a_st (SEQ ID NO: 218), hsa-miR-20b_st (SEQ ID NO: 88), hsa-miR-223_st (SEQ ID NO: 131), hsa-miR-25-star_st (SEQ ID NO: 3), hsa-miR-373_st (SEQ ID NO: 408), hsa-miR-378-star_st (SEQ ID NO: 409), hsa-miR-422a_st (SEQ ID NO: 410), hsa-miR-423-5p_st (SEQ ID NO: 411), hsa-miR-451_st (SEQ ID NO: 412), hsa-miR-486-3p_st (SEQ ID NO: 413), hsa-miR-486-5p_st (SEQ ID NO: 414), hsa-miR-504_st (SEQ ID NO: 415), hsa-miR-550_st (SEQ ID NO: 416), hsa-miR-616_st (SEQ ID NO: 417), hsa-miR-671-3p_st (SEQ ID NO: 418), hsa-miR-671-5p_st (SEQ ID NO: 43), hsa-miR-766_st (SEQ ID NO: 1), hsa-miR-92a-1-star_st (SEQ ID NO: 192), hsa-miR-92a_st (SEQ ID NO: 156), and hsa-miR-93-star_st (SEQ ID NO: 45), wherein said device allows a determination of the sensitivity of said patient to carmustine; or xlvi) one or more single-stranded nucleic acid molecules having at least 85% identity to a target nucleic acid molecule having a sequence that is complementary to or identical to at least 15 consecutive nucleotides of one or more biomarkers selected from U41_st (SEQ ID NO: 394), hsa-miR-106b-star_st (SEQ ID NO: 2), hsa-miR-1183_st (SEQ ID NO: 126), hsa-miR-1207-5p_st (SEQ ID NO: 109), hsa-miR-1281_st (SEQ ID NO: 8), hsa-miR-18b_st (SEQ ID NO: 87), hsa-miR-195-star_st (SEQ ID NO: 14), hsa-miR-615-3p_st (SEQ ID NO: 419), hsa-miR-631_st (SEQ ID NO: 135), hsa-miR-766_st (SEQ ID NO: 1), and hsa-miR-92a-2-star_st (SEQ ID NO: 136), wherein said device allows a determination of the sensitivity of said patient to lomustine; or xlvii) one or more single-stranded nucleic acid molecules having at least 85% identity to a target nucleic acid molecule having a sequence that is complementary to or identical to at least 15 consecutive nucleotides of one or more biomarkers selected from ACA43_st (SEQ ID NO: 420), ACA57_st (SEQ ID NO: 421), ENSG00000199411_s_st (SEQ ID NO: 422), ENSG00000200879_st (SEQ ID NO: 423), ENSG00000202252_st (SEQ ID NO: 424), HBII-142_st (SEQ ID NO: 293), HBII-142_x_st (SEQ ID NO: 425), HBII-202_st (SEQ ID NO: 426), HBII-429_st (SEQ ID NO: 427), U13_st (SEQ ID NO: 428), U25_st (SEQ ID NO: 429), U27_st (SEQ ID NO: 330), U29_st (SEQ ID NO: 430), U30_st (SEQ ID NO: 431), U31_x_st (SEQ ID NO: 190), U36C_st (SEQ ID NO: 335), U38A_st (SEQ ID NO: 432), U52_st (SEQ ID NO: 349), U55_st (SEQ ID NO: 433), U55_x_st (SEQ ID NO: 146), U59B_st (SEQ ID NO: 434), U74_x_st (SEQ ID NO: 377), U83B_st (SEQ ID NO: 400), U83_st (SEQ ID NO: 435), hsa-miR-106a_st (SEQ ID NO: 150), hsa-miR-1275_st (SEQ ID NO: 70), hsa-miR-17-star_st (SEQ ID NO: 216), hsa-miR-17_st (SEQ ID NO: 152), hsa-miR-18a-star_st (SEQ ID NO: 71), hsa-miR-18a_st (SEQ ID NO: 72), hsa-miR-18b_st (SEQ ID NO: 87), hsa-miR-19a_st (SEQ ID NO: 217), hsa-miR-19b_st (SEQ ID NO: 153), hsa-miR-20a_st (SEQ ID NO: 218), hsa-miR-20b_st (SEQ ID NO: 88), hsa-miR25-star_st (SEQ ID NO: 3), hsa-miR-378-star_st (SEQ ID NO: 409), hsa-miR-378_st (SEQ ID NO: 368), hsa-miR-422a_st (SEQ ID NO: 410), hsa-miR-423-5p_st (SEQ ID NO: 411), hsa-miR-663b_st (SEQ ID NO: 155), hsa-miR-766_st (SEQ ID NO: 1), hsa-miR-92a-1-star_st (SEQ ID NO: 192), and hsa-miR-92a_st (SEQ ID NO: 156), wherein said device allows a determination of the sensitivity of said patient to mercaptopurine; or xlviii) one or more single-stranded nucleic acid molecules having at least 85% identity to a target nucleic acid molecule having a sequence that is complementary to or identical to at least 15 consecutive nucleotides of one or more biomarkers selected from ACA48_x_st (SEQ ID NO: 436), ACA7_s_st (SEQ ID NO: 437), HBII-239_st (SEQ ID NO: 438), HBII-429_st (SEQ ID NO: 55), HBII-85-26_st (SEQ ID NO: 439), U104_st (SEQ ID NO: 140), U17b_st (SEQ ID NO: 58), U17b_x_st (SEQ ID NO: 328), U55_st (SEQ ID NO: 308), U55_x_st (SEQ ID NO: 280), hsa-miR-106b-star_st (SEQ ID NO: 2), hsa-miR-124_st (SEQ ID NO: 7), hsa-miR-1281_st (SEQ ID NO: 8), hsa-miR-1299_st (SEQ ID NO: 38), hsa-miR-140-3p_st (SEQ ID NO: 13), hsa-miR-142-5p_st (SEQ ID NO: 215), hsa-miR-181a-star_st (SEQ ID NO: 9), hsa-miR-181a_st (SEQ ID NO: 78), hsa-miR-181b_st (SEQ ID NO: 10), hsa-miR-181c_st (SEQ ID NO: 79), hsa-miR-195-star_st (SEQ ID NO: 14), hsa-miR-297_st (SEQ ID NO: 132), hsa-miR-29b-2-star_st (SEQ ID NO: 39), hsa-miR-33b-star_st (SEQ ID NO: 40), hsa-miR-34b_st (SEQ ID NO: 154), hsa-miR-629-star_st (SEQ ID NO: 41), hsa-miR-766_st (SEQ ID NO: 1), hsa-miR-768-3p_st (SEQ ID NO: 44), hsa-miR-768-5p_st (SEQ ID NO: 83), and hsa-miR-92b_st (SEQ ID NO: 15), wherein said device allows a determination of the sensitivity of said patient to teniposide; or xlix) one or more single-stranded nucleic acid molecules having at least 85% identity to a target nucleic acid molecule having a sequence that is complementary to or identical to at least 15 consecutive nucleotides of one or more biomarkers selected from hsa-miR-106b-star_st (SEQ ID NO: 2), hsa-miR-106b_st (SEQ ID NO: 37), hsa-miR-1275_st (SEQ ID NO: 70), hsa-miR-25-star_st (SEQ ID NO: 3), hsa-miR-25_st (SEQ ID NO: 89), hsa-miR-33b-star_st (SEQ ID NO: 40), hsa-miR-362-5p_st (SEQ ID NO: 92), hsa-miR-500-star_st (SEQ ID NO: 93), hsa-miR-500_st (SEQ ID NO: 94), hsa-miR-501-5p_st (SEQ ID NO: 304), hsa-miR-502-3p_st (SEQ ID NO: 96), hsa-miR-532-5p_st (SEQ ID NO: 98), hsa-miR-629-star_st (SEQ ID NO: 41), hsa-miR-629_st (SEQ ID NO: 440), hsa-miR-652_st (SEQ ID NO: 42), hsa-miR-671-5p_st (SEQ ID NO: 43), hsa-miR-766_st (SEQ ID NO: 1), hsa-miR-93-star_st (SEQ ID NO: 45), and hsa-miR-93_st (SEQ ID NO: 46), wherein said device allows a determination of the sensitivity of said patient to dactinomycin; or l) one or more single-stranded nucleic acid molecules having at least 85% identity to a target nucleic acid molecule having a sequence that is complementary to or identical to at least 15 consecutive nucleotides of one or more biomarkers selected from HBII-142_st (SEQ ID NO: 278), HBII-142_x_st (SEQ ID NO: 279), U55_st (SEQ ID NO: 6), U55_x_st (SEQ ID NO: 280), hsa-miR-1202_st (SEQ ID NO: 281), hsa-miR-124_st (SEQ ID NO: 7), hsa-miR-148a-star_st (SEQ ID NO: 282), hsa-miR-148a_st (SEQ ID NO: 275), hsa-miR-184_st (SEQ ID NO: 283), hsa-miR-191_st (SEQ ID NO: 284), hsa-miR-195-star_st (SEQ ID NO: 14), hsa-miR-29b-2-star_st (SEQ ID NO: 39), hsa-miR-425-star_st (SEQ ID NO: 285), hsa-miR-425_st (SEQ ID NO: 286), hsa-miR-449a_st (SEQ ID NO: 287), hsa-miR-449b_st (SEQ ID NO: 288), hsa-miR-551b_st (SEQ ID NO: 289), hsa-miR-593-star_st (SEQ ID NO:

290), hsa-miR-768-3p_st (SEQ ID NO: 44), hsa-miR-768-5p_st (SEQ ID NO: 83), and hsa-miR-877_st (SEQ ID NO: 291), wherein said device allows a determination of the sensitivity of said patient to tretinoin; or
li) one or more single-stranded nucleic acid molecules having at least 85% identity to a target nucleic acid molecule having a sequence that is complementary to or identical to at least 15 consecutive nucleotides of one or more biomarkers selected from U17b_st (SEQ ID NO: 254), U48_st (SEQ ID NO: 441), U49B_s_st (SEQ ID NO: 442), U55_st (SEQ ID NO: 209), hsa-miR-1207-5p_st (SEQ ID NO: 109), hsa-miR-128_st (SEQ ID NO: 110), hsa-miR-181a-star_st (SEQ ID NO: 9), hsa-miR-181c-star_st (SEQ ID NO: 443), hsa-miR-181d_st (SEQ ID NO: 321), hsa-miR-20b-star_st (SEQ ID NO: 130), hsa-miR-20b_st (SEQ ID NO: 88), hsa-miR-223_st (SEQ ID NO: 131), hsa-miR-363_st (SEQ ID NO: 133), and hsa-miR-766_st (SEQ ID NO: 1), wherein said device allows a determination of the sensitivity of said patient to ifosfamide; or
lii) one or more single-stranded nucleic acid molecules having at least 85% identity to a target nucleic acid molecule having a sequence that is complementary to or identical to at least 15 consecutive nucleotides of one or more biomarkers selected from ACA10_s_st (SEQ ID NO: 444), ACA15_s_st (SEQ ID NO: 445), ACA43_st (SEQ ID NO: 446), ACA44_st (SEQ ID NO: 447), ACA51_x_st (SEQ ID NO: 324), ACA57_st (SEQ ID NO: 448), ENSG00000202252_st (SEQ ID NO: 449), HBII-142_st (SEQ ID NO: 450), HBII-142_x_st (SEQ ID NO: 425), HBII-180A_x_st (SEQ ID NO: 54), HBII-180C_st (SEQ ID NO: 451), HBII-180C_x_st (SEQ ID NO: 452), HBII-202_st (SEQ ID NO: 198), HBII-429_st (SEQ ID NO: 388), HBII-55_st (SEQ ID NO: 453), U104_st (SEQ ID NO: 56), U17a_st (SEQ ID NO: 454), U17a_x_st (SEQ ID NO: 455), U17b_st (SEQ ID NO: 456), U17b_x_st (SEQ ID NO: 457), U32A_x_st (SEQ ID NO: 458), U33_st (SEQ ID NO: 459), U34_st (SEQ ID NO: 256), U35A_st (SEQ ID NO: 460), U38A_st (SEQ ID NO: 461), U43_st (SEQ ID NO: 462), U43_x_st (SEQ ID NO: 462), U46_x_st (SEQ ID NO: 463), U52_st (SEQ ID NO: 258), U55_st (SEQ ID NO: 209), U55_x_st (SEQ ID NO: 146), U56_st (SEQ ID NO: 464), U56_x_st (SEQ ID NO: 211), U59B_st (SEQ ID NO: 465), U68_st (SEQ ID NO: 466), U70_x_st (SEQ ID NO: 398), U71d_st (SEQ ID NO: 467), U71d_x_st (SEQ ID NO: 468), U74_x_st (SEQ ID NO: 191), U83B_st (SEQ ID NO: 469), hsa-miR-106a_st (SEQ ID NO: 150), hsa-miR-106b-star_st (SEQ ID NO: 2), hsa-miR-106b_st (SEQ ID NO: 37), hsa-miR-1183_st (SEQ ID NO: 126), hsa-miR-1228_st (SEQ ID NO: 84), hsa-miR-1246_st (SEQ ID NO: 214), hsa-miR-1281_st (SEQ ID NO: 8), hsa-miR-149-star_st (SEQ ID NO: 359), hsa-miR-17-star_st (SEQ ID NO: 216), hsa-miR-17_st (SEQ ID NO: 152), hsa-miR-18a-star_st (SEQ ID NO: 71), hsa-miR-18a_st (SEQ ID NO: 72), hsa-miR-195-star_st (SEQ ID NO: 14), hsa-miR-19a_st (SEQ ID NO: 217), hsa-miR-19b_st (SEQ ID NO: 153), hsa-miR-20a_st (SEQ ID NO: 218), hsa-miR-25-star_st (SEQ ID NO: 3), hsa-miR-297_st (SEQ ID NO: 132), hsa-miR-34b_st (SEQ ID NO: 154), hsa-miR-593-star_st (SEQ ID NO: 290), hsa-miR-629-star_st (SEQ ID NO: 41), hsa-miR-652_st (SEQ ID NO: 42), hsa-miR-671-5p_st (SEQ ID NO: 43), hsa-miR-769-5p_st (SEQ ID NO: 105), hsa-miR-92a_st (SEQ ID NO: 156), hsa-miR-93-star_st (SEQ ID NO: 45), and hsa-miR-93_st (SEQ ID NO: 46), wherein said device allows a determination of the sensitivity of said patient to tamoxifen; or
liii) one or more single-stranded nucleic acid molecules having at least 85% identity to a target nucleic acid molecule having a sequence that is complementary to or identical to at least 15 consecutive nucleotides of one or more biomarkers selected from hsa-miR-181a-star_st (SEQ ID NO: 9), hsa-miR-297_st (SEQ ID NO: 132), hsa-miR-432_st (SEQ ID NO: 12), hsa-miR-766_st (SEQ ID NO: 1), and hsa-miR-874_st (SEQ ID NO: 310), wherein said device allows a determination of the sensitivity of said patient to irinotecan; or
liv) one or more single-stranded nucleic acid molecules having at least 85% identity to a target nucleic acid molecule having a sequence that is complementary to or identical to at least 15 consecutive nucleotides of one or more biomarkers selected from HBII-202_st (SEQ ID NO: 239), HBII-85-11_st (SEQ ID NO: 470), U104_st (SEQ ID NO: 471), and U13_st (SEQ ID NO: 472), wherein said device allows a determination of the sensitivity of said patient to floxuridine; or
lv) one or more single-stranded nucleic acid molecules having at least 85% identity to a target nucleic acid molecule having a sequence that is complementary to or identical to at least 15 consecutive nucleotides of one or more biomarkers selected from ACA13_st (SEQ ID NO: 473), ENSG00000202093_x_st (SEQ ID NO: 474), ENSG00000202252_st (SEQ ID NO: 244), HBII-202_st (SEQ ID NO: 198), HBII-429_st (SEQ ID NO: 475), HBII-55_st (SEQ ID NO: 476), U104_st (SEQ ID NO: 116), U13_st (SEQ ID NO: 477), U17b_st (SEQ ID NO: 456), U17b_x_st (SEQ ID NO: 59), U25_st (SEQ ID NO: 478), U27_st (SEQ ID NO: 330), U29_st (SEQ ID NO: 203), U30_st (SEQ ID NO: 479), U31_st (SEQ ID NO: 142), U31_x_st (SEQ ID NO: 205), U36A_st (SEQ ID NO: 480), U36C_st (SEQ ID NO: 481), U38A_st (SEQ ID NO: 348), U52_st (SEQ ID NO: 258), U54_st (SEQ ID NO: 482), U55_st (SEQ ID NO: 208), U55_x_st (SEQ ID NO: 280), U56_x_st (SEQ ID NO: 210), U74_x_st (SEQ ID NO: 264), U75_st (SEQ ID NO: 483), U78_s_st (SEQ ID NO: 484), U78_x_st (SEQ ID NO: 228), U83B_st (SEQ ID NO: 485), U83_st (SEQ ID NO: 486), U95_st (SEQ ID NO: 487), hsa-miR-106a_st (SEQ ID NO: 150), hsa-miR-1183_st (SEQ ID NO: 126), hsa-miR-1246_st (SEQ ID NO: 214), hsa-miR-1281_st (SEQ ID NO: 8), hsa-miR-142-5p_st (SEQ ID NO: 215), hsa-miR-17-star_st (SEQ ID NO: 216), hsa-miR-17_st (SEQ ID NO: 152), hsa-miR-18a-star_st (SEQ ID NO: 71), hsa-miR-18a_st (SEQ ID NO: 72), hsa-miR-18b_st (SEQ ID NO: 87), hsa-miR-19a_st (SEQ ID NO: 217), hsa-miR-19b_st (SEQ ID NO: 153), hsa-miR-20a_st (SEQ ID NO: 218), hsa-miR-297_st (SEQ ID NO: 132), hsa-miR-34b_st (SEQ ID NO: 154), hsa-miR-378-star_st (SEQ ID NO: 409), hsa-miR-378_st (SEQ ID NO: 368), hsa-miR-491-3p_st (SEQ ID NO: 351), hsa-miR-766_st (SEQ ID NO: 1), hsa-miR-92a-1-star_st (SEQ ID NO: 192), and hsa-miR-92a_st (SEQ ID NO: 156), wherein said device allows a determination of the sensitivity of said patient to thioguanine; or
lvi) one or more single-stranded nucleic acid molecules having at least 85% identity to a target nucleic acid molecule having a sequence that is complementary to or identical to at least 15 consecutive nucleotides of one or more biomarkers selected from ACA18_x_st (SEQ ID NO: 48), ACA9_st (SEQ ID NO: 373), ENSG00000202252_st (SEQ ID NO: 488), HBII-180A_x_st (SEQ ID NO: 54), HBII-180B_x_st (SEQ ID NO: 489), HBII-180C_st (SEQ ID NO: 490), HBII-180C_x_st (SEQ ID NO: 491), HBII-382_s_st (SEQ ID NO: 492), U3-2_s_st (SEQ ID NO: 493), U34_st (SEQ ID NO: 355), U38B_st (SEQ ID NO: 494), U50B_x_st (SEQ ID NO: 495), U56_st (SEQ ID NO: 496), U59B_st (SEQ ID NO: 497), U68_x_st (SEQ ID NO: 498), hsa-miR-106a_st (SEQ ID NO: 150), hsa-miR-1281_st (SEQ ID NO: 8), hsa-miR-1292_st (SEQ ID NO: 499), hsa-miR-1307_st (SEQ ID NO: 102), hsa-miR-17-star_st (SEQ ID NO: 216), hsa-miR-17_st (SEQ ID NO: 152), hsa-miR-18a-star_st (SEQ ID NO: 71), hsa-miR-18a_st (SEQ ID NO: 72), hsa-miR-18b_st (SEQ ID NO: 87), hsa-miR-19b_st (SEQ ID NO: 153), hsa-miR-20a_st (SEQ ID NO: 218), hsa-miR-25-star_st (SEQ ID NO: 3), hsa-miR-378-star_st (SEQ ID NO: 409), hsa-miR-378_st (SEQ ID NO: 368), hsa-miR-422a_st (SEQ ID NO: 410), hsa-miR-92a-1-star_st (SEQ ID NO: 192), hsa-miR-92a_st (SEQ ID NO: 156), and hsa-miR-93-star_st (SEQ ID NO: 45), wherein said device allows a determination of the sensitivity of said patient to PSC 833; or lvii) one or more single-stranded nucleic acid molecules having at least 85% identity to a target nucleic acid molecule having a sequence that is complementary to or identical to at least 15 consecutive nucleotides of one or more biomarkers selected from hsa-miR-130a_st (SEQ ID NO: 313), hsa-miR-149_st (SEQ ID NO: 500), hsa-miR-193a-3p_st (SEQ ID NO: 366), hsa-miR-27a_st (SEQ ID NO: 501), hsa-miR-30a-star_st (SEQ ID NO: 502), hsa-miR-30a_st (SEQ ID NO: 503), hsa-miR-30c-2-star_st (SEQ ID NO: 504), hsa-miR-30c_st (SEQ ID NO: 301), and hsa-miR-30e-star_st (SEQ ID NO: 505), wherein said device allows a determination of the sensitivity of said patient to erlotinib; or lviii) one or more single-stranded nucleic acid molecules having at least 85% identity to a target nucleic acid molecule having a sequence that is complementary to or identical to at least 15 consecutive nucleotides of one or more biomarkers selected from hsa-miR-34c-3p_st (SEQ ID NO: 314), hsa-miR-34c-5p_st (SEQ ID NO: 506), and hsa-miR-489_st (SEQ ID NO: 298), wherein said device allows a determination of the sensitivity of said patient to herceptin; or lix) one or more single-stranded nucleic acid molecules having at least 85% identity to a target nucleic acid molecule having a sequence that is complementary to or identical to at least 15 consecutive nucleotides of one or more biomarkers selected from ACA18_x_st (SEQ ID NO: 139), ACA51_x_st (SEQ ID NO: 507), HBII-142_st (SEQ ID NOs: 293), HBII-142_x_st (SEQ ID NO: 508), HBII-180A_x_st (SEQ ID NO: 386), HBII-180C_x_st (SEQ ID NO: 451), U68_x_st (SEQ ID NO: 67), U70_x_st (SEQ ID NO: 509), hsa-miR-1207-5p_st (SEQ ID NO: 109), hsa-miR-1268_st (SEQ ID NO: 127), and hsa-miR-768-3p_st (SEQ ID NO: 44), wherein said device allows a determination of the sensitivity of said patient to celecoxib; or lx) one or more single-stranded nucleic acid molecules having at least 85% identity to a target nucleic acid molecule having a sequence that is complementary to or identical to at least 15 consecutive nucleotides of one or more biomarkers selected from U104_st (SEQ ID NO: 116), hsa-miR-1202_st (SEQ ID NO: 281), hsa-miR-1226_st (SEQ ID NO: 365), hsa-miR-15b_st (SEQ ID NO: 510), hsa-miR-191_st (SEQ ID NO: 284), hsa-miR-203_st (SEQ ID NO: 511), hsa-miR-25_st (SEQ ID NO: 89), hsa-miR-29b-2-star_st (SEQ ID NO: 39), hsa-miR-301a_st (SEQ ID NO: 342), hsa-miR-339-5p_st (SEQ ID NO: 273), hsa-miR-342-5p_st (SEQ ID NO: 80), hsa-miR-421_st (SEQ ID NO: 512), hsa-miR-425-star_st (SEQ ID NO: 285), hsa-miR-425_st (SEQ ID NO: 286), hsa-miR-449b_st (SEQ ID NO: 288), hsa-miR-489_st (SEQ ID NO: 298), hsa-miR-492_st (SEQ ID NO: 513), hsa-miR-622_st (SEQ ID NO: 514), hsa-miR-768-3p_st (SEQ ID NO: 44), and hsa-miR-768-5p_st (SEQ ID NO: 83), wherein said device allows a determination of the sensitivity of said patient to fulvestrant; or lxi) one or more single-stranded nucleic acid molecules having at least 85% identity to a target nucleic acid molecule having a sequence that is complementary to or identical to at least 15 consecutive nucleotides of one or more biomarkers selected from hsa-miR-1826_st (SEQ ID NO: 515), hsa-miR-205_st (SEQ ID NO: 295), hsa-miR-30c_st (SEQ ID NO: 301), hsa-miR-675_st (SEQ ID NO: 516), and hsa-miR-934_st (SEQ ID NO: 517), wherein said device allows a determination of the sensitivity of said patient to iressa; or lxii) one or more single-stranded nucleic acid molecules having at least 85% identity to a target nucleic acid molecule having a sequence that is complementary to or identical to at least 15 consecutive nucleotides of one or more biomarkers selected from hsa-miR-1323_st (SEQ ID NO: 518), hsa-miR-184_st (SEQ ID NO: 283), hsa-miR-187_st (SEQ ID NO: 519), hsa-miR-197_st (SEQ ID NO: 520), hsa-miR-498_st (SEQ ID NO: 521), hsa-miR-504_st (SEQ ID NO: 415), hsa-miR-506_st (SEQ ID NO: 21), hsa-miR-508-5p_st (SEQ ID NO: 22), hsa-miR-509-3-5p_st (SEQ ID NO: 23), hsa-miR-509-3p_st (SEQ ID NO: 24), hsa-miR-509-5p_st (SEQ ID NO: 522), hsa-miR-510_st (SEQ ID NO: 25), hsa-miR-512-3p_st (SEQ ID NO: 523), hsa-miR-513a-5p_st (SEQ ID NO: 26), hsa-miR-513b_st (SEQ ID NO: 27), hsa-miR-513c_st (SEQ ID NO: 524), hsa-miR-516b_st (SEQ ID NO: 525), hsa-miR-517a_st (SEQ ID NO: 526), hsa-miR-517b_st (SEQ ID NO: 527), hsa-miR-525-5p_st (SEQ ID NO: 528), hsa-miR-526b_st (SEQ ID NO: 529), hsa-miR-551a_st (SEQ ID NO: 530), hsa-miR-873_st (SEQ ID NO: 531), and hsa-miR-891a_st (SEQ ID NO: 532), wherein said device allows a determination of the sensitivity of said patient to anastrozole; or lxiii) one or more single-stranded nucleic acid molecules having at least 85% identity to a target nucleic acid molecule having a sequence that is complementary to or identical to at least 15 consecutive nucleotides of one or more biomarkers selected from hsa-miR-1323_st (SEQ ID NO: 518), hsa-miR-361-5p_st (SEQ ID NO: 533), hsa-miR-498_st (SEQ ID NO: 521), hsa-miR-512-3p_st (SEQ ID NO: 523), hsa-miR-516b_st (SEQ ID NO: 525), hsa-miR-517a_st (SEQ ID NO: 526), hsa-miR-525-5p_st (SEQ ID NO: 528), hsa-miR-551a_st (SEQ ID NO: 530), and hsa-miR-873_st (SEQ ID NO: 531), wherein said device allows a determination of the sensitivity of said patient to letrozole; or lxiv) one or more single-stranded nucleic acid molecules having at least 85% identity to a target nucleic acid molecule having a sequence that is complementary to or identical to at least 15 consecutive nucleotides of one or more biomarkers selected from hsa-let-7i-star_st (SEQ ID NO: 232), hsa-miR-338-3p_st (SEQ ID NO: 233), and hsa-miR-34a_st (SEQ ID NO: 234), wherein said device allows a determination of the sensitivity of said patient to radiation; or lxv) one or more single-stranded nucleic acid molecules having at least 85% identity to a target nucleic acid molecule having a sequence that is complementary to or identical to at least 15 consecutive nucleotides of one or more biomarkers selected from hsa-miR-1826_st (SEQ ID NO: 515), hsa-miR-30c-2-star_st (SEQ ID NO: 504), hsa-miR-34b-star_st (SEQ ID NO: 534), hsa-miR-34c-3p_st (SEQ ID NO: 314), hsa-miR-34c-5p_st (SEQ ID NO: 506), and hsa-miR-489_st (SEQ ID NO: 298), wherein said device allows a determination of the sensitivity of said patient to cetuximab.

8. The method of claim 5, wherein said device comprises two or more of said single-stranded nucleic acid molecules of i) to lxv).

9. The method of claim 2, wherein said device comprises:

i) one or more single-stranded nucleic acid molecules having at least 85% identity to a target nucleic acid molecule having a sequence that is complementary to or identical to at least 15 consecutive nucleotides of one or more biomarkers selected from HBII-85-29_st (SEQ ID NO: 535), hsa-miR-130a_st (SEQ ID NO: 313), hsa-miR-148b_st (SEQ ID NO: 536), hsa-miR-184_st (SEQ ID NO: 283), hsa-miR-26a_st (SEQ ID NO: 537), hsa-miR-30a-star_st (SEQ ID NO: 502), hsa-miR-30a_st (SEQ ID NO: 503), hsa-miR-30c-2-star_st (SEQ ID NO: 504), hsa-miR-30c_st (SEQ ID NO: 301), hsa-miR-34a-star_st (SEQ ID NO: 277), hsa-miR-34a_st (SEQ ID NO: 234), hsa-miR-34c-5p_st (SEQ ID NO: 506), hsa-miR-449a_st (SEQ ID NO: 287), and hsa-miR-449b_st (SEQ ID NO: 288), wherein said device allows a determination of the resistance of said patient to vincristine; or ii) one or more single-stranded nucleic acid molecules having at least 85% identity to a target nucleic acid molecule having a sequence that is complementary to or identical to at least 15 consecutive nucleotides of one or more biomarkers selected from hsa-miR-10a_st (SEQ ID NO: 538), hsa-miR-151-3p_st (SEQ ID NO: 539), hsa-miR-151-5p_st (SEQ ID NO: 540), hsa-miR-192-star_st (SEQ ID NO: 541), hsa-miR-192_st (SEQ ID NO: 542), hsa-miR-194_st (SEQ ID NO: 543), hsa-miR-200b_st (SEQ ID NO: 544), hsa-miR-203_st (SEQ ID NO: 511), hsa-miR-29b_st (SEQ ID NO: 545), hsa-miR-30b_st (SEQ ID NO: 546), hsa-miR-30d_st (SEQ ID NO: 547), and hsa-miR-625_st (SEQ ID NO: 548), wherein said device allows a determination of the resistance of said patient to cisplatin; or iii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-10b_st (SEQ ID NO: 550), hsa-miR-125a-5p_st (SEQ ID NO: 551), hsa-miR-141_st (SEQ ID NO: 552), hsa-miR-151-3p_st (SEQ ID NO: 539), hsa-miR-151-5p_st (SEQ ID NO: 540), hsa-miR-200a-star_st (SEQ ID NO: 553), hsa-miR-200a_st (SEQ ID NO: 554), hsa-miR-200b-star_st (SEQ ID NO: 555), hsa-miR-200c_st (SEQ ID NO: 556), hsa-miR-203_st (SEQ ID NO: 511), hsa-miR-30a_st (SEQ ID NO: 503), hsa-miR-30b_st (SEQ ID NO: 546), hsa-miR-30c_st (SEQ ID NO: 301), hsa-miR-30d_st (SEQ ID NO: 547), hsa-miR-429_st (SEQ ID NO: 557), hsa-miR-516a-5p_st (SEQ ID NO: 558), hsa-miR-934_st (SEQ ID NO: 517), and hsa-miR-99b_st (SEQ ID NO: 559), wherein said device allows a determination of the resistance of said patient to etoposide; or iv) one or more single-stranded nucleic acid molecules having at least 85% identity to a target nucleic acid molecule having a sequence that is complementary to or identical to at least 15 consecutive nucleotides of one or more biomarkers selected from hsa-miR-1244_st (SEQ ID NO: 560), hsa-miR-1303_st (SEQ ID NO: 561), hsa-miR-141-star_st (SEQ ID NO: 562), hsa-miR-141_st (SEQ ID NO: 552), hsa-miR-182_st (SEQ ID NO: 563), hsa-miR-183-star_st (SEQ ID NO: 564), hsa-miR-183_st (SEQ ID NO: 565), hsa-miR-192-star_st (SEQ ID NO: 541), hsa-miR-192_st (SEQ ID NO: 542), hsa-miR-194_st (SEQ ID NO: 543), hsa-miR-200a-star_st (SEQ ID NO:553), hsa-miR-200a_st (SEQ ID NO: 554), hsa-miR-200b-star_st (SEQ ID NO:555), hsa-miR-200b_st (SEQ ID NO:544), hsa-miR-200c-star_st (SEQ ID NO: 231), hsa-miR-200c_st (SEQ ID NO: 556), hsa-miR-203_st (SEQ ID NO: 511), hsa-miR-205_st (SEQ ID NO:295), hsa-miR-215_st (SEQ ID NO: 566), hsa-miR-27b_st (SEQ ID NO: 567), hsa-miR-331-3p_st (SEQ ID NO: 568), hsa-miR-375_st (SEQ ID NO: 297), hsa-miR-429_st (SEQ ID NO: 557), hsa-miR-622_st (SEQ ID NO: 514), hsa-miR-934_st (SEQ ID NO: 517), and hsa-miR-99b-star_st (SEQ ID NO: 569), wherein said device allows a determination of the resistance of said patient to azaguanine; or v) one or more single-stranded nucleic acid molecules having at least 85% identity to a target nucleic acid molecule having a sequence that is complementary to or identical to at least 15 consecutive nucleotides of one or more biomarkers selected from hsa-miR-10a_st (SEQ ID NO: 538), hsa-miR-183_st (SEQ ID NO: 565), hsa-miR-192-star_st (SEQ ID NO: 541), hsa-miR-192_st (SEQ ID NO: 542), hsa-miR-194_st (SEQ ID NO: 543), hsa-miR-200a-star_st (SEQ ID NO: 553), hsa-miR-200a_st (SEQ ID NO: 554), hsa-miR-200b-star_st (SEQ ID NO:555), hsa-miR-200b_st (SEQ ID NO: 544), hsa-miR-200c-star_st (SEQ ID NO: 231), hsa-miR-203_st (SEQ ID NO: 511), hsa-miR-29b_st (SEQ ID NO: 545), hsa-miR-30b_st (SEQ ID NO: 546), hsa-miR-30d_st (SEQ ID NO: 547), hsa-miR-429_st (SEQ ID NO: 557), hsa-miR-625_st (SEQ ID NO: 548), and hsa-miR-7_st (SEQ ID NO: 570), wherein said device allows a determination of the resistance of said patient to carboplatin; or vi) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-125a-5p_st (SEQ ID NO: 551), hsa-miR-151-3p_st (SEQ ID NO: 539), hsa-miR-151-5p_st (SEQ ID NO: 540), hsa-miR-203_st (SEQ ID NO: 511), hsa-miR-23a_st (SEQ ID NO: 571), hsa-miR-29b_st (SEQ ID NO: 545), hsa-miR-30a_st (SEQ ID NO:503), hsa-miR-30c_st (SEQ ID NO: 301), hsa-miR-516a-5p_st (SEQ ID NO: 558), hsa-miR-518d-5p_st (SEQ ID NO: 572), hsa-miR-518e-star_st (SEQ ID NO: 573), hsa-miR-519a-star_st (SEQ ID NO: 573), hsa-miR-519a_st (SEQ ID NO: 574), hsa-miR-519b-5p_st (SEQ ID NO: 573), hsa-miR-519c-5p_st (SEQ ID NO: 573), hsa-miR-522-star_st (SEQ ID NO: 573), hsa-miR-523-star_st (SEQ ID NO: 573), hsa-miR-526a_st (SEQ ID NO: 572), and hsa-miR-99b_st (SEQ ID NO: 559), wherein said device allows a determination of the resistance of said patient to adriamycin; or vii) one or more single-stranded nucleic acid molecules having at least 85% identity to a target nucleic acid molecule having a sequence that is complementary to or identical to at least 15 consecutive nucleotides of one or more biomarkers selected from hsa-let-7a_st (SEQ ID NO: 575), hsa-let-7c_st (SEQ ID NO: 576), hsa-let-7e_st (SEQ ID NO: 549), hsa-let-7f_st (SEQ ID NO: 577), hsa-miR-125a-5p_st (SEQ ID NO: 551), hsa-miR-193a-5p_st (SEQ ID NO: 165), hsa-miR-22-star_st (SEQ ID NO: 578), hsa-miR-22_st (SEQ ID NO: 167), hsa-miR-23a_st (SEQ ID NO: 571), hsa-miR-24-2-star_st (SEQ ID NO: 579), hsa-miR-24_st (SEQ ID NO: 580), hsa-miR-30a_st (SEQ ID NO: 503), and hsa-miR-99b_st (SEQ ID NO: 559), wherein said device allows a determination of the resistance of said patient to aclarubicin; or viii) one or more single-stranded nucleic acid molecules having at least 85% identity to a target nucleic acid molecule having a sequence that is complementary to or identical to at least 15 consecutive nucleotides of one or more biomarkers selected from hsa-miR-151-5p_st (SEQ ID NO: 540), hsa-miR-29b_st (SEQ ID NO: 545), hsa-miR-30b_st (SEQ ID NO: 546), hsa-miR-30d_st (SEQ ID NO: 547), hsa-miR-506_st (SEQ ID NO: 21), hsa-miR-508-5p_st (SEQ ID NO: 22), hsa-miR-509-3-5p_st (SEQ ID NO: 23), hsa-miR-509-3p_st (SEQ ID NO: 24), hsa-miR-509-5p_st (SEQ ID NO: 522), hsa-miR-510_st (SEQ ID NO: 25), hsa-miR-513a-5p_st (SEQ ID NO: 26), hsa-miR-513c_st (SEQ ID NO: 524), hsa-miR-516a-5p_st (SEQ ID NO: 558), hsa-miR-584_st (SEQ ID NO: 581), and hsa-miR-885-3p_st (SEQ ID NO: 582), wherein said device allows a determination of the resistance of said patient to mitoxantrone; or ix) one or more single-stranded nucleic acid molecules having at least 85% identity to a target nucleic acid molecule having a sequence that is complementary to or identical to at least 15 consecutive nucleotides of one or more biomarkers selected from hsa-miR-516a-5p_st (SEQ ID NO: 558) and hsa-miR-526a_st (SEQ ID NO: 572), wherein said device allows a determination of the resistance of said patient to mitomycin; or x) one or more single-stranded nucleic acid molecules having at least 85% identity to a target nucleic acid molecule having a sequence that is complementary to or identical to at least 15 consecutive nucleotides of one or more biomarkers selected from HBII-85-29_st (SEQ ID NO: 535), hsa-let-7e_st (SEQ ID NO: 549), hsa-miR-125a-5p_st (SEQ ID NO: 551), hsa-miR-130a_st (SEQ ID NO: 313), hsa-miR-193b_st (SEQ ID NO: 583), hsa-miR-22_st (SEQ ID NO: 167), hsa-miR-27a_st (SEQ ID NO: 501), hsa-miR-29a_st (SEQ ID NO: 584), hsa-miR-29b_st (SEQ ID NO: 545), hsa-miR-30a-star_st (SEQ ID NO: 502), hsa-miR-30a_st (SEQ ID NO: 503), hsa-miR-30c-2-star_st (SEQ ID NO: 504), hsa-miR-30c_st (SEQ ID NO: 301), hsa-miR-34a_st (SEQ ID NO: 234), hsa-miR-34b-star_st (SEQ ID NO 534), hsa-miR-34c-3p_st (SEQ ID NO: 314), and hsa-miR-34c-5p_st (SEQ ID NO: 506), wherein said device allows a determination of the resistance of said patient to paclitaxel; or xi) one or more single-stranded nucleic acid molecules having at least 85% identity to a target nucleic acid molecule having a sequence that is complementary to or identical to at least 15 consecutive nucleotides of one or more biomarkers selected from hsa-miR-141_st (SEQ ID NO: 552), hsa-miR-584_st (SEQ ID NO: 581), and hsa-miR-934_st (SEQ ID NO: 517), wherein said device allows a determination of the resistance of said patient to gemcitabine; or xii) one or more single-stranded nucleic acid molecules having at least 85% identity to a target nucleic acid molecule having a sequence that is complementary to or identical to at least 15 consecutive nucleotides of one or more biomarkers selected from HBII-438A_s_st (SEQ ID NO: 585), HBII-85-11_st (SEQ ID NO: 249), HBII-85-15_x_st (SEQ ID NO: 586), HBII-85-23_x_st (SEQ ID NO: 587), HBII-85-29_st (SEQ ID NO: 588), HBII-85-29_x_st (SEQ ID NO: 589), hsa-miR-184_st (SEQ ID NO: 283), hsa-miR-29a_st (SEQ ID NO: 584), hsa-miR-29b_st (SEQ ID NO: 545), hsa-miR-34a_st (SEQ ID NO: 234), hsa-miR-34c-3p_st (SEQ ID NO: 314), hsa-miR-34c-5p_st (SEQ ID NO: 506), and hsa-miR-424-star_st (SEQ ID NO: 100), wherein said device allows a determination of the resistance of said patient to docetaxel; or xiii) one or more single-stranded nucleic acid molecules having at least 85% identity to a target nucleic acid molecule having a sequence that is complementary to or identical to at least 15 consecutive nucleotides of one or more biomarkers selected from hsa-miR-99b_st (SEQ ID NO: 559), hsa-let-7e_st (SEQ ID NO: 549), hsa-miR-151-5p_st (SEQ ID NO: 540), hsa-miR-182_st (SEQ ID NO: 563), hsa-miR-23b_st (SEQ ID NO: 590), hsa-miR-24_st (SEQ ID NO: 580), and hsa-miR-34a_st (SEQ ID NO: 234), wherein said device allows a determination of the resistance of said patient to dexamethasone; or xiv) one or more single-stranded nucleic acid molecules having at least 85% identity to a target nucleic acid molecule having a sequence that is complementary to or identical to at least 15 consecutive nucleotides of one or more biomarkers selected from hsa-miR-151-5p_st (SEQ ID NO: 540), hsa-miR-23b-star_st (SEQ ID NO: 591), hsa-miR-23b_st (SEQ ID NO: 590), hsa-miR-27b_st (SEQ ID NO: 567), and hsa-miR-99b_st (SEQ ID NO: 559), wherein said device allows a determination of the resistance of said patient to Ara-C (cytarabine hydrochloride); or xv) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-125a-5p_st (SEQ ID NO: 551), hsa-miR-1308_st (SEQ ID NO: 274), hsa-miR-151-3p_st (SEQ ID NO: 539), hsa-miR-151-5p_st (SEQ ID NO: 540), hsa-miR-182_st (SEQ ID NO: 563), hsa-miR-193b_st (SEQ ID NO: 583), hsa-miR-21-star_st (SEQ ID NO: 166), hsa-miR-21_st (SEQ ID NO: 592), hsa-miR-22_st (SEQ ID NO: 167), hsa-miR-23a_st (SEQ ID NO: 571), hsa-miR-23b_st (SEQ ID NO: 590), hsa-miR-24-2-star_st (SEQ ID NO: 579), hsa-miR-24_st (SEQ ID NO: 580), hsa-miR-27a-star_st (SEQ ID NO: 593), hsa-miR-27a_st (SEQ ID NO: 501), hsa-miR-27b_st (SEQ ID NO: 567), hsa-miR-339-3p_st (SEQ ID NO: 272), hsa-miR-34a_st (SEQ ID NO: 234), and hsa-miR-99b_st (SEQ ID NO: 559), wherein said device allows a determination of the resistance of said patient to methylprednisolone; or xvi) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-125a-5p_st (SEQ ID NO: 551), hsa-miR-22_st (SEQ ID NO: 167), hsa-miR-23b_st (SEQ ID NO: 590), hsa-miR-27b_st (SEQ ID NO: 567), hsa-miR-28-5p_st (SEQ ID NO: 594), hsa-miR-30a-star_st (SEQ ID NO: 502), hsa-miR-30a_st (SEQ ID NO: 503), hsa-miR-34c-5p_st (SEQ ID NO: 506), hsa-miR-516b_st (SEQ ID NO: 525), hsa-miR-517a_st (SEQ ID NO: 526), and hsa-miR-525-5p_st (SEQ ID NO: 528), wherein said device allows a determination of the resistance of said patient to methotrexate; or xvii) one or more single-stranded nucleic acid molecules having at least 85% identity to a target nucleic acid molecule having a sequence that is complementary to or identical to at least 15 consecutive nucleotides of one or more biomarkers selected from hsa-miR-1244_st (SEQ ID NO: 560), hsa-miR-128_st (SEQ ID NO: 110), hsa-miR-1292_st (SEQ ID NO: 499), hsa-miR-141_st (SEQ ID NO: 552), hsa-miR-15b_st (SEQ ID NO: 510), hsa-miR-185-star_st (SEQ ID NO: 406), hsa-miR-188-5p_st (SEQ ID NO: 86), hsa-miR-18b_st (SEQ ID NO: 87), hsa-miR-200c_st (SEQ ID NO: 556), hsa-miR-203_st (SEQ ID NO: 511), hsa-miR-20b_st (SEQ ID NO: 88), hsa-miR-215_st (SEQ ID NO: 566), hsa-miR-25_st (SEQ ID NO: 89), hsa-miR-30b_st (SEQ ID NO: 546), hsa-miR-30d_st (SEQ ID NO: 547), hsa-miR-362-5p_st (SEQ ID NO: 92), hsa-miR-378-star_st (SEQ ID NO: 409), hsa-miR-421_st (SEQ ID NO: 512), hsa-miR-425_st (SEQ ID NO: 286), hsa-miR-532-5p_st (SEQ ID NO: 98), hsa-miR-93_st (SEQ ID NO: 46), and hsa-miR-941_st (SEQ ID NO: 595), wherein said device allows a determination of the resistance of said patient to bleomycin; or xviii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-let-7i_st (SEQ ID No: 596), hsa-miR-10a_it (SEQ ID NO: 538), hsa-miR-10b_st (SEQ ID NO: 550), hsa-miR-125a-5p_st (SEQ ID NO: 551), hsa-miR-1301_st (SEQ ID NO: 597), hsa-miR-140-5p_st (SEQ ID NO: 18), and hsa-miR-99b_st (SEQ ID NO: 559), wherein said device allows a determination of the resistance of said patient to methyl-GAG (methyl glyoxal bis amidinohydrazone dihydrochloride); or xix) one or more single-stranded nucleic acid molecules having at least 85% identity to a target nucleic acid molecule having a sequence that is complementary to or identical to at least 15 consecutive nucleotides of one or more biomarkers selected from 14qII-14_st (SEQ ID NO: 598), 14qII-1_x_st (SEQ ID NO: 599), hsa-let-7b_st (SEQ ID NO: 600), hsa-let-7c_st (SEQ ID NO: 576), hsa-let-7e_st (SEQ ID NO: 549), hsa-miR-10a_st (SEQ ID NO: 538), hsa-miR-10b_st (SEQ ID NO: 550), hsa-miR-125a-3p_st (SEQ ID NO: 601), hsa-miR-125a-5p_st (SEQ ID NO: 551), hsa-miR-125b-1-star_st (SEQ ID NO: 163), hsa-miR-125b_st (SEQ ID NO: 602), hsa-miR-1287_st (SEQ ID NO: 603), hsa-miR-134_st (SEQ ID NO: 164), hsa-miR-151-3p_st (SEQ ID NO: 539), hsa-miR-151-5p_st (SEQ ID NO: 540), hsa-miR-22_st (SEQ ID NO: 167), hsa-miR-23a-star_st (SEQ ID NO: 604), hsa-miR-23a_st (SEQ ID NO: 571), hsa-miR-23b_st (SEQ ID NO: 590), hsa-miR-24-2-star_st (SEQ ID NO: 579), hsa-miR-24_st (SEQ ID NO: 580), hsa-miR-27a_st (SEQ ID NO: 501), hsa-miR-27b_st (SEQ ID NO: 567), hsa-miR-28-3p_st (SEQ ID NO: 605), hsa-miR-28-5p_st (SEQ ID NO: 594), hsa-miR-299-5p_st (SEQ ID NO: 606), hsa-miR-337-5p_st (SEQ ID NO: 169), hsa-miR-370_st (SEQ ID NO: 32), hsa-miR-376a_st (SEQ ID No: 607), hsa-miR-376c_st (SEQ ID NO: 170), hsa-miR-379_st (SEQ ID NO: 172), hsa-miR-381_st (SEQ ID NO: 173), hsa-miR-382_st (SEQ ID NO: 174), hsa-miR-409-3p_st (SEQ ID NO: 81), hsa-miR-409-5p_st (SEQ ID NO: 175), hsa-miR-411_st (SEQ ID NO: 176), hsa-miR-431_st (SEQ ID NO: 177), hsa-miR-452_st (SEQ ID NO: 608), hsa-miR-485-5p_st (SEQ ID NO: 179), hsa-miR-487a_st (SEQ ID NO: 609), hsa-miR-487b_st (SEQ ID NO: 82), hsa-miR-494_st (SEQ ID NO: 181), hsa-miR-495_st (SEQ ID NO: 610), hsa-miR-543_st (SEQ ID NO: 182), hsa-miR-654-5p_st (SEQ ID NO: 611), hsa-miR-99b-star_st (SEQ ID NO: 569), and hsa-miR-99b_st (SEQ ID NO: 559), wherein said device allows a determination of the resistance of said patient to belinostat (PXD101); or xx) one or more single-stranded nucleic acid molecules having at least 85% identity to a target nucleic acid molecule having a sequence that is complementary to or identical to at least 15 consecutive nucleotides of one or more biomarkers selected from hsa-miR-100_st (SEQ ID NO: 17), hsa-miR-125b_st (SEQ ID NO: 602), hsa-miR-130a_st (SEQ ID NO: 313), hsa-miR-181a-2-star_st (SEQ ID NO: 612), hsa-miR-184_st (SEQ ID NO: 283), hsa-miR-197_st (SEQ ID NO: 520), hsa-miR-221-star_st (SEQ ID NO: 613), hsa-miR-30a-star_st (SEQ ID NO: 502), hsa-miR-30a_st (SEQ ID NO: 503), hsa-miR-30c-2-star_st (SEQ ID NO: 504), hsa-miR-525-5p_st (SEQ ID NO: 528), and hsa-miR-584_st (SEQ ID NO: 581), wherein said device allows a determination of the resistance of said patient to 5-fluorouracil; or xxi) one or more single-stranded nucleic acid molecules having at least 85% identity to a target nucleic acid molecule having a sequence that is complementary to or identical to at least 15 consecutive nucleotides of one or more biomarkers selected from hsa-miR-1207-5p_st (SEQ ID NO: 109), hsa-miR-625_st (SEQ ID NO: 548), and hsa-miR-766_st (SEQ ID NO: 1), wherein said device allows a determination of the resistance of said patient to; or xxii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-151-3p_st (SEQ ID NO: 539), hsa-miR-151-5p_st (SEQ ID NO: 540), hsa-miR-21_st (SEQ ID NO: 592), hsa-miR-22_st (SEQ ID NO: 167), hsa-miR-30a-star_st (SEQ ID NO: 502), hsa-miR-30a_st (SEQ ID NO: 503), hsa-miR-30c-2-star_st (SEQ ID NO: 504), and hsa-miR-99b_st (SEQ ID NO: 559), wherein said device allows a determination of the resistance of said patient to 5-Aza-2'-deoxycytidine (decitabine); or xxiii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-125a-5p_st (SEQ ID NO: 551), hsa-miR-151-3p_st (SEQ ID NO: 539), hsa-miR-151-5p_st (SEQ ID NO: 540), hsa-miR-221-star_st (SEQ ID NO: 613), hsa-miR-23a_st (SEQ ID NO: 571), hsa-miR-24-2-star_st (SEQ ID NO: 579), hsa-miR-24_st (SEQ ID NO: 580), hsa-miR-30b_st (SEQ ID NO: 546), hsa-miR-30d_st (SEQ ID NO: 547), hsa-miR-526a_st (SEQ ID NO: 572), hsa-miR-584_st (SEQ ID NO: 581), and hsa-miR-99b_st (SEQ ID NO: 559), wherein said device allows a determination of the resistance of said patient to idarubicin; or xxiv) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-10a_st (SEQ ID NO: 538), hsa-miR-125a-3p_st (SEQ ID NO: 601), hsa-miR-125a-5p_st (SEQ ID NO: 551), hsa-miR-151-3p_st (SEQ ID NO: 539), hsa-miR-151-5p_st (SEQ ID NO: 540), hsa-miR-182_st (SEQ ID NO: 563), hsa-miR-183-star_st (SEQ ID NO: 564), hsa-miR-183_st (SEQ ID NO: 565), hsa-miR-193b_st (SEQ ID NO: 583), hsa-miR-200b-star_st (SEQ ID NO: 555), hsa-miR-200b_st (SEQ ID NO: 544), hsa-miR-21_st (SEQ ID NO: 592), hsa-miR-221-star_st (SEQ ID NO: 613), hsa-miR-22_st (SEQ ID NO: 167), hsa-miR-23a_st (SEQ ID NO: 571), hsa-miR-23b_st (SEQ ID NO: 590), hsa-miR-24_st (SEQ ID NO: 580), hsa-miR-27b_st (SEQ ID NO: 567), hsa-miR-29b_st (SEQ ID NO: 545), hsa-miR-30a_st (SEQ ID NO: 503), hsa-miR-30d_st (SEQ ID NO: 547), hsa-miR-31-star_st (SEQ ID NO: 614), hsa-miR-31_st (SEQ ID NO: 615), hsa-miR-320d_st (SEQ ID NO: 91), hsa-miR-584_st (SEQ ID NO: 581), and hsa-miR-99b_st (SEQ ID NO: 559), wherein said device allows a determination of the resistance of said patient to melphalan; or xxv) one or more single-stranded nucleic acid molecules having at least 85% identity to a target nucleic acid molecule having a sequence that is complementary to or identical to at least 15 consecutive nucleotides of one or more biomarkers selected from hsa-let-7a_st (SEQ ID NO: 575), hsa-miR-100_st (SEQ ID NO: 17), and hsa-miR-146a_st (SEQ ID NO: 19), wherein said device allows a determination of the resistance of said patient to IL4-PR38 fusion protein; or xxvi) one or more single-stranded nucleic acid molecules having at least 85% identity to a target nucleic acid molecule having a sequence that is complementary to or identical to at least 15 consecutive nucleotides of one or more biomarkers selected from HBII-85-26_st (SEQ ID NO: 439), HBII-85-6_x_st (SEQ ID NO: 616), hsa-miR-491-5p_st (SEQ ID NO: 617), hsa-miR-589-star_st (SEQ ID NO: 618), hsa-miR-625_st (SEQ ID NO: 548), and hsa-miR-744_st (SEQ ID NO: 619), wherein said device allows a determination of the resistance of said patient to valproic acid; or xxvii) one or more single-stranded nucleic acid molecules having at least 85% identity to a target nucleic acid molecule having a sequence that is complementary to or identical to at least 15 consecutive nucleotides of one or more biomarkers selected from hsa-let-7b_st (SEQ ID NO: 600), hsa-let-7e_st (SEQ ID NO: 549), hsa-let-7i_st (SEQ ID NO: 596), hsa-miR-10a_st (SEQ ID NO: 538), hsa-miR-10b_st (SEQ ID NO: 550), hsa-miR-125a-3p_st (SEQ ID NO: 601), hsa-miR-125a-5p_st (SEQ ID NO: 551), hsa-miR-151-3p_st (SEQ ID NO: 539), hsa-miR-151-5p_st (SEQ ID NO: 540), hsa-miR-181a-2-star_st (SEQ ID NO: 612), hsa-miR-21-star_st (SEQ ID NO: 166), hsa-miR-21_st (SEQ ID NO: 592), hsa-miR-221_st (SEQ ID NO: 620), hsa-miR-222_st (SEQ ID NO: 621), hsa-miR-22_st (SEQ ID NO: 167), hsa-miR-28-3p_st (SEQ ID NO: 605), hsa-miR-28-5p_st (SEQ ID NO: 594), hsa-miR-29b-1-star_st (SEQ ID NO: 622), hsa-miR-30a-star_st (SEQ ID NO: 502), hsa-miR-30a_st (SEQ ID NO: 503), hsa-miR-30c-2-star_st (SEQ ID NO: 504), hsa-miR-455-3p_st (SEQ ID NO: 178), hsa-miR-99b-star_st (SEQ ID NO: 569), and hsa-miR-99b_st (SEQ ID NO: 559), wherein said device allows a determination of the resistance of said patient to all-trans retinoic acid (ATRA); or xxviii) one or more single-stranded nucleic acid molecules having at least 85% identity to a target nucleic acid molecule having a sequence that is complementary to or identical to at least 15 consecutive nucleotides of one or more biomarkers selected from hsa-let-7b_st (SEQ ID NO: 600), hsa-let-7d_st (SEQ ID NO: 623), hsa-let-7g_st (SEQ ID NO: 624), hsa-let-7i_st (SEQ ID NO: 596), hsa-miR-100_st (SEQ ID NO: 17), hsa-miR-138_st (SEQ ID NO: 625), hsa-miR-221_st (SEQ ID NO: 620), hsa-miR-222_st (SEQ ID NO: 621), hsa-miR-27a-star_st (SEQ ID NO: 593), hsa-miR-29a_st (SEQ ID NO: 584), hsa-miR-31_st (SEQ ID NO: 615), hsa-miR-503_st (SEQ ID NO: 101), and hsa-miR-625_st (SEQ ID NO: 548), wherein said device allows a determination of the resistance of said patient to cytoxan; or xxix) one or more single-stranded nucleic acid molecules having at least 85% identity to a target nucleic acid molecule having a sequence that is complementary to or identical to at least 15 consecutive nucleotides of one or more biomarkers selected from HBII-289_st (SEQ ID NO: 626), hsa-miR-141_st (SEQ ID NO: 552), hsa-miR-373_st (SEQ ID NO: 408), hsa-miR-512-3p_st (SEQ ID NO: 523), hsa-miR-517a_st (SEQ ID NO: 526), hsa-miR-525-5p_st (SEQ ID NO: 528), hsa-miR-584_st (SEQ ID NO: 581), and hsa-miR-934_st (SEQ ID NO: 517), wherein said device allows a determination of the resistance of said patient to topotecan; or xxx) one or more single-stranded nucleic acid molecules having at least 85% identity to a target nucleic acid molecule having a sequence that is complementary to or identical to at least 15 consecutive nucleotides of one or more biomarkers selected from 14qII-14_st (SEQ ID NO: 627), 14qII-14_x_st (SEQ ID NO: 73), 14qII-1_x_st (SEQ ID NO: 628), 14qII-26_st (SEQ ID No: 629), 14qII-26_x_st (SEQ ID NO: 630), hsa-let-7e_st (SEQ ID NO: 549), hsa-miR-125a-3p_st (SEQ ID NO: 601), hsa-miR-125a-5p_st (SEQ ID NO: 551), hsa-miR-125b-1-star_st (SEQ ID NO: 163), hsa-miR-127-3p_st (SEQ ID NO: 77), hsa-miR-127-5p_st (SEQ ID NO: 631), hsa-miR-134_st (SEQ ID NO: 164), hsa-miR-143-star_st (SEQ ID NO: 632), hsa-miR-143_st (SEQ ID NO: 31), hsa-miR-193a-3p_st (SEQ ID NO: 366), hsa-miR-193a-5p_st (SEQ ID NO: 165), hsa-miR-193b-star_st (SEQ ID NO: 633), hsa-miR-199a-5p_st (SEQ ID NO: 634), hsa-miR-21-star_st (SEQ ID NO: 166), hsa-miR-210_st (SEQ ID NO: 635), hsa-miR-214_st (SEQ ID NO: 636), hsa-miR-22_st (SEQ ID NO: 167), hsa-miR-23a-star_st (SEQ ID NO: 604), hsa-miR-23b-star_st (SEQ ID NO: 591), hsa-miR-23b_st (SEQ ID NO: 590), hsa-miR-24-2-star_st (SEQ ID NO: 579), hsa-miR-24_st (SEQ ID NO: 580), hsa-miR-27a-star_st (SEQ ID NO: 593), hsa-miR-27a_st (SEQ ID NO: 501), hsa-miR-27b_st (SEQ ID NO: 567), hsa-miR-28-3p_st (SEQ ID NO: 605), hsa-miR-299-3p_st (SEQ ID NO: 168), hsa-miR-337-5p_st (SEQ ID NO: 169), hsa-miR-339-3p_st (SEQ ID NO: 272), hsa-miR-339-5p_st (SEQ ID NO: 273), hsa-miR-370_st (SEQ ID NO: 32), hsa-miR-376c_st (SEQ ID NO: 170), hsa-miR-377-star_st (SEQ ID NO: 171), hsa-miR-379_st (SEQ ID NO: 172), hsa-miR-381_st (SEQ ID NO: 173), hsa-miR-409-3p_st (SEQ ID NO: 81), hsa-miR-409-5p_st (SEQ ID NO: 175), hsa-miR-410_st (SEQ ID NO: 637), hsa-miR-411_st (SEQ ID NO: 176), hsa-miR-431_st (SEQ ID NO: 177), hsa-miR-455-3p_st (SEQ ID NO: 178), hsa-miR-485-5p_st (SEQ ID NO: 179), hsa-miR-487a_st (SEQ ID NO: 609), hsa-miR-487b_st (SEQ ID NO: 82), hsa-miR-491-5p_st (SEQ ID NO: 617), hsa-miR-493_st (SEQ ID NO: 180), hsa-miR-494_st (SEQ ID NO: 181), hsa-miR-542-5p_st (SEQ ID NO: 638), hsa-miR-744_st (SEQ ID NO: 619), hsa-miR-758_st (SEQ ID NO: 35), hsa-miR-935_st (SEQ ID NO: 639), hsa-miR-99b-star_st (SEQ ID NO: 569), and hsa-miR-99b_st (SEQ ID NO: 559), wherein said device allows a determination of the resistance of said patient to suberoylanilide hydroxamic acid (SAHA, vorinostat); or xxxi) one or more single-stranded nucleic acid molecules having at least 85% identity to a target nucleic acid molecule having a sequence that is complementary to or identical to at least 15 consecutive nucleotides of one or more biomarkers selected from HBII-85-11_st (SEQ ID NO: 470), HBII-85-1_x_st (SEQ ID NO: 640), HBII-85-23_x_st (SEQ ID NO: 641), HBII-85-29_st (SEQ ID NO: 642), HBII-85-29_x_st (SEQ ID NO: 642), U28_st (SEQ ID NO: 643), hsa-miR-155_st (SEQ ID NO: 20), hsa-miR-196b_st (SEQ ID NO: 644), hsa-miR-200a-star_st (SEQ ID NO: 553), hsa-miR-200a_st (SEQ ID NO: 554), hsa-miR-200b-star_st (SEQ ID NO: 555), hsa-miR-200b_st (SEQ ID NO: 544), hsa-miR-203_st (SEQ ID NO: 511), hsa-miR-29b_st (SEQ ID NO: 545), hsa-miR-30c_st (SEQ ID NO: 301), hsa-miR-371-3p_st (SEQ ID NO: 645), hsa-miR-371-5p_st (SEQ ID NO: 236), hsa-miR-372_st (SEQ ID NO: 646), hsa-miR-373_st (SEQ ID NO: 408), hsa-miR-516a-5p_st (SEQ ID NO: 558), hsa-miR-518d-5p_st (SEQ ID NO: 572), hsa-miR-518e-star_st (SEQ ID NO: 573), hsa-miR-519a-star_st (SEQ ID NO: 573), hsa-miR-519a_st (SEQ ID NO: 574), hsa-miR-519b-5p_st (SEQ ID NO: 573), hsa-miR-519c-5p_st (SEQ ID NO: 573), hsa-miR-523-star_st (SEQ ID NO: 573), and hsa-miR-886-3p_st (SEQ ID NO: 647), wherein said device allows a determination of the resistance of said patient to depsipeptide (FR901228); or xxxii) one or more single-stranded nucleic acid molecules having at least 85% identity to a target nucleic acid molecule having a sequence that is complementary to or identical to at least 15 consecutive nucleotides of one or more biomarkers selected from HBII-438A_s_st (SEQ ID NO: 648), HBII-52-32_x_st (SEQ ID NO: 649), HBII-85-1_x_st (SEQ ID NO: 640), HBII-85-23_x_st (SEQ ID NO: 650), hsa-let-7e_st (SEQ ID NO: 549), hsa-miR-125a-3p_st (SEQ ID NO: 601), hsa-miR-125a-5p_st (SEQ ID NO: 551), hsa-miR-149_st (SEQ ID NO: 500), hsa-miR-151-3p_st (SEQ ID NO: 539), hsa-miR-151-5p_st (SEQ ID NO: 540), hsa-miR-193b_st (SEQ ID NO: 583), hsa-miR-21-star_st (SEQ ID NO: 166), hsa-miR-21_st (SEQ ID NO: 592), hsa-miR-22_st (SEQ ID NO: 167), hsa-miR-23a-star_st (SEQ ID NO: 604), hsa-miR-23a_st (SEQ ID NO: 571), hsa-miR-24-2-star_st (SEQ ID NO: 579), hsa-miR-24_st (SEQ ID NO: 580), hsa-miR-27a-star_st (SEQ ID NO: 593), hsa-miR-27a_st (SEQ ID NO: 501), hsa-miR-30a-star_st (SEQ ID NO: 502), hsa-miR-30a_st (SEQ ID NO: 503), hsa-miR-30c-2-star_st (SEQ ID NO: 504), hsa-miR-30c_st (SEQ ID NO: 301), hsa-miR-31-star_st (SEQ ID NO: 614), hsa-miR-516a-5p_st (SEQ ID NO: 558), hsa-miR-518d-5p_st (SEQ ID NO: 572), hsa-miR-518e-star_st (SEQ ID NO: 573), hsa-miR-519a-star_st (SEQ ID NO: 573), hsa-miR-519c-5p_st (SEQ ID NO: 573), hsa-miR-522-star_st (SEQ ID NO: 573), hsa-miR-9-star_st (SEQ ID NO: 651), hsa-miR-935_st (SEQ ID NO: 639), hsa-miR-98_st (SEQ ID NO: 652), hsa-miR-99b-star_st (SEQ ID NO: 569), and hsa-miR-99b_st (SEQ ID NO: 559), wherein said device allows a determination of the resistance of said patient to bortezomib; or xxxiii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-10a_st (SEQ ID NO: 538), hsa-miR-125a-3p_st (SEQ ID NO: 601), hsa-miR-125a-5p_st (SEQ ID NO: 551), hsa-miR-1287_st (SEQ ID NO: 603), hsa-miR-141_st (SEQ ID NO: 552), hsa-miR-151-3p_st (SEQ ID NO: 539), hsa-miR-151-5p_st (SEQ ID NO: 540), hsa-miR-182_st (SEQ ID NO: 563), hsa-miR-183-star_st (SEQ ID NO: 564), hsa-miR-183_st (SEQ ID NO: 565), hsa-miR-192_st (SEQ ID NO: 542), hsa-miR-193b_st (SEQ ID NO: 583), hsa-miR-194_st (SEQ ID NO: 543), hsa-miR-200b-star_st (SEQ ID NO: 555), hsa-miR-200b_st (SEQ ID NO: 544), hsa-miR-200c_st (SEQ ID NO: 556), hsa-miR-203_st (SEQ ID NO: 511), hsa-miR-21_st (SEQ ID NO: 592), hsa-miR-221-star_st (SEQ ID NO: 613), hsa-miR-22_st (SEQ ID NO: 167), hsa-miR-23a_st (SEQ ID NO: 571), hsa-miR-23b-star_st (SEQ ID NO: 591), hsa-miR-23b_st (SEQ ID NO: 590), hsa-miR-24_st (SEQ ID NO: 580), hsa-miR-27b_st (SEQ ID NO: 567), hsa-miR-29b_st (SEQ ID NO: 545), hsa-miR-30b_st (SEQ ID NO: 546), hsa-miR-30d_st (SEQ ID NO: 547), hsa-miR-320d_st (SEQ ID NO: 91), hsa-miR-584_st (SEQ ID NO: 581), hsa-miR-99b-star_st (SEQ ID NO: 569), and hsa-miR-99b_st (SEQ ID NO: 559), wherein said device allows a determination of the resistance of said patient to leukeran; or xxxiv) one or more single-stranded nucleic acid molecules having at least 85% identity to a target nucleic acid molecule having a sequence that is complementary to or identical to at least 15 consecutive nucleotides of one or more biomarkers selected from U91_s_st (SEQ ID NO: 653), hsa-miR-10a_st (SEQ ID NO: 538), hsa-miR-125a-5p_st (SEQ ID NO: 551), hsa-miR-134_st (SEQ ID NO: 164), hsa-miR-141-star_st (SEQ ID NO: 562), hsa-miR-141_st (SEQ ID NO: 552), hsa-miR-151-5p_st (SEQ ID NO: 540), hsa-miR-192_st (SEQ ID NO: 542), hsa-miR-193b_st (SEQ ID NO: 583), hsa-miR-194_st (SEQ ID NO: 543), hsamiR-200a-star_st (SEQ ID NO: 553), hsa-miR-200a_st (SEQ ID NO: 554), hsa-miR-200b-star_st (SEQ ID NO: 555), hsa-miR-200b_st (SEQ ID NO: 544), hsa-miR-200c_st (SEQ ID NO: 556), hsa-miR-203_st (SEQ ID NO: 511), hsa-miR-205_st (SEQ ID NO: 295), hsa-miR-210_st (SEQ ID NO: 635), hsa-miR-215_st (SEQ ID NO: 566), hsa-miR-23b-star_st (SEQ ID NO: 591), hsa-miR-23b_st (SEQ ID NO: 590), hsa-miR-24_st (SEQ ID NO: 580), hsa-miR-27b-star_st (SEQ ID NO: 654), hsa-miR-27b_st (SEQ ID NO: 567), hsa-miR-299-5p_st (SEQ ID NO: 606), hsa-miR-320a_st (SEQ ID NO: 655), hsa-miR-320b_st (SEQ ID NO: 656), hsa-miR-320c_st (SEQ ID NO: 90), hsa-miR-320d_st (SEQ ID NO: 91), hsa-miR-337-5p_st (SEQ ID NO: 169), hsa-miR-339-3p_st (SEQ ID NO: 272), hsa-miR-339-5p_st (SEQ ID NO: 273), hsa-miR-370_st (SEQ ID NO: 32), hsa-miR-375_st (SEQ ID NO: 297), hsa-miR-382_st (SEQ ID NO: 174), hsa-miR-429_st (SEQ ID NO: 557), hsa-miR-485-5p_st (SEQ ID NO: 179), hsa-miR-487a_st (SEQ ID NO: 609), hsa-miR-494_st (SEQ ID NO: 181), hsa-miR-99b-star_st (SEQ ID NO: 569), and hsa-miR-99b_st (SEQ ID NO: 559), wherein said device allows a determination of the resistance of said patient to fludarabine; or xxxv) one or more single-stranded nucleic acid molecules having at least 85% identity to a target nucleic acid molecule having a sequence that is complementary to or identical to at least 15 consecutive nucleotides of one or more biomarkers selected from HBII-85-1_x_st (SEQ ID NO: 657), HBII-85-29_st (SEQ ID NO: 535), hsa-miR-125a-5p_st (SEQ ID NO: 551), hsa-miR-130a_st (SEQ ID NO: 313), hsa-miR-139-5p_st (SEQ ID NO: 658), hsa-miR-149_st (SEQ ID NO: 500), hsa-miR-16_st (SEQ ID NO: 360), hsa-miR-193b_st (SEQ ID NO: 583), hsa-miR-196b_st (SEQ ID NO: 644), hsa-miR-200a_st (SEQ ID NO: 554), hsa-miR-200b-star_st (SEQ ID NO: 555), hsa-miR-200b_st (SEQ ID NO: 544), hsa-miR-203_st (SEQ ID NO: 511), hsa-miR-22_st (SEQ ID NO: 167), hsa-miR-26a_st (SEQ ID NO: 537), hsa-miR-29b_st (SEQ ID NO: 545), hsa-miR-30a-star_st (SEQ ID NO: 502), hsa-miR-30a_st (SEQ ID NO:503), hsa-miR-30c-2-star_st (SEQ ID NO: 504), hsa-miR-30c_st (SEQ ID NO: 301), hsa-miR-331-3p_st (SEQ ID NO: 568), hsa-miR-34a_st (SEQ ID NO: 234), hsa-miR-34b-star_st (SEQ ID NO: 534), hsa-miR-34c-3p_st (SEQ ID NO: 314), hsa-miR-34c-5p_st (SEQ ID NO: 506), hsa-miR-449a_st (SEQ ID NO: 287), hsa-miR-449b_st (SEQ ID NO: 288), hsa-miR-516a-5p_st (SEQ ID NO: 558), and hsa-miR-675_st (SEQ ID NO: 516), wherein said device allows a determination of the resistance of said patient to vinblastine; or xxxvi) one or more single-stranded nucleic acid molecules having at least 85% identity to a target nucleic acid molecule having a sequence that is complementary to or identical to at least 15 consecutive nucleotides of one or more biomarkers selected from hsa-let-7b_st (SEQ ID NO: 600), hsa-let-7e_st (SEQ ID NO: 549), hsa-miR-10a_st (SEQ ID NO: 538), hsa-miR-125a-3p_st (SEQ ID NO: 601), hsa-miR-125a-5p_st (SEQ ID NO: 551), hsa-miR-149_st (SEQ ID NO: 500), hsa-miR-151-3p_st (SEQ ID NO: 539), hsa-miR-151-5p_st (SEQ ID NO: 540), hsa-miR-182_st (SEQ ID NO: 563), hsa-miR-183-star_st (SEQ ID NO: 564), hsa-miR-183_st (SEQ ID NO: 565), hsa-miR-193b_st (SEQ ID NO: 583), hsa-miR-203_st (SEQ ID NO: 511), hsa-miR-22_st (SEQ ID NO: 167), hsa-miR-23a_st (SEQ ID NO: 571), hsa-miR-23b_st (SEQ ID NO: 590), hsa-miR-24-1-star_st (SEQ ID NO: 659), hsa-miR-24_st (SEQ ID NO: 580), hsa-miR-27b_st (SEQ ID NO: 567), hsa-miR-30b_st (SEQ ID NO: 546), hsa-miR-30d_st (SEQ ID NO: 547), hsa-miR-320d_st (SEQ ID NO: 91), hsa-miR-532-3p_st (SEQ ID NO: 97), hsa-miR-99b-star_st (SEQ ID NO: 569), and hsa-miR-99b_st (SEQ ID NO: 559), wherein said device allows a determination of the resistance of said patient to busulfan; or xxxvii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-103_st (SEQ ID NO: 660), hsa-miR-107_st (SEQ ID NO: 661), hsa-miR-1180_st (SEQ ID NO: 662), hsa-miR-1231_st (SEQ ID NO: 663), hsa-miR-125a-3p_st (SEQ ID NO: 601), hsa-miR-125a-5p_st (SEQ ID NO: 551), hsa-miR-1301_st (SEQ ID NO: 597), hsa-miR-1303_st (SEQ ID NO: 561), hsa-miR-132_st (SEQ ID NO: 664), hsa-miR-141_st (SEQ ID NO: 552), hsa-miR-151-3p_st (SEQ ID NO: 539), hsa-miR-151-5p_st (SEQ ID NO: 540), hsa-miR-182_st (SEQ ID NO: 563), hsa-miR-183_st (SEQ ID NO: 565), hsa-miR-192_st (SEQ ID NO: 542), hsa-miR-194_st (SEQ ID NO: 543), hsa-miR-200b_st (SEQ ID NO: 544), hsa-miR-200c_st (SEQ ID NO: 556), hsa-miR-215_st (SEQ ID NO: 566), hsa-miR-22_st (SEQ ID NO: 167), hsa-miR-24_st (SEQ ID NO: 580), hsa-miR-28-3p_st (SEQ ID NO: 605), hsa-miR-28-5p_st (SEQ ID NO: 594), hsa-miR-30a_st (SEQ ID NO: 503), hsa-miR-30b_st (SEQ ID NO: 546), hsa-miR-30d_st (SEQ ID NO: 547), hsa-miR-324-5p_st (SEQ ID NO: 665), hsa-miR-339-3p_st (SEQ ID NO: 272), hsa-miR-34a-star_st (SEQ ID NO: 277), hsa-miR-34a_st (SEQ ID NO: 234), hsa-miR-429_st (SEQ ID No: 557), hsa-miR-589_st (SEQ ID NO: 666), hsa-miR-934_st (SEQ ID NO: 517), hsa-miR-935_st (SEQ ID NO: 639), hsa-miR-99b-star_st (SEQ ID NO: 569), and hsa-miR-99b_st (SEQ ID NO: 559), wherein said device allows a determination of the resistance of said patient to dacarbazine; or xxxviii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-100_st (SEQ ID NO: 17), hsa-miR-125a-5p_st (SEQ ID NO: 551), hsa-miR-125b-1-star_st (SEQ ID NO: 163), hsa-miR-125b_st (SEQ ID NO: 602), hsa-miR-1269_st (SEQ ID NO: 667), hsa-miR-1270_st (SEQ ID NO: 668), hsa-miR-130a_st (SEQ ID NO: 313), hsa-miR-134_st (SEQ ID NO: 164), hsa-miR-143_st (SEQ ID NO: 31), hsa-miR-145_st (SEQ ID NO: 669), hsa-miR-151-3p_st (SEQ ID NO: 539), hsa-miR-151-5p_st (SEQ ID NO: 540), hsa-miR-181a-2-star_st (SEQ ID NO: 612), hsa-miR-193a-3p_st (SEQ ID NO: 366), hsa-miR-193a-5p_st (SEQ ID NO: 165), hsa-miR-217_st (SEQ ID NO: 670), hsa-miR-21_st (SEQ ID NO: 592), hsa-miR-221-star_st (SEQ ID NO: 613), hsa-miR-22_st (SEQ ID NO: 167), hsa-miR-23a-star_st (SEQ ID NO: 604), hsa-miR-23a_st (SEQ ID NO: 571), hsa-miR-23b-star_st (SEQ ID NO: 591), hsa-miR-23b_st (SEQ ID NO: 590), hsa-miR-24-2-star_st (SEQ ID NO: 579), hsa-miR-24_st (SEQ ID NO: 580), hsa-miR-27a-star_st (SEQ ID NO: 593), hsa-miR-27a_st (SEQ ID NO: 501), hsa-miR-27b-star_st (SEQ ID NO: 654), hsa-miR-27b_st (SEQ ID NO: 567), hsa-miR-28-3p_st (SEQ ID NO: 605), hsa-miR-28-5p_st (SEQ ID NO: 594), hsa-miR-30a-star_st (SEQ ID NO: 502), hsa-miR-30a_st (SEQ ID NO: 503), hsa-miR-30c-2-star_st (SEQ ID NO: 504), hsa-miR-34c-5p_st (SEQ ID NO: 506), hsa-miR-376a_st (SEQ ID NO: 607), hsa-miR-455-3p_st (SEQ ID NO: 178), hsa-miR-543_st (SEQ ID NO: 182), hsa-miR-574-3p_st (SEQ ID NO: 671), hsa-miR-99b-star_st (SEQ ID NO: 569), and hsa-miR-99b_st (SEQ ID NO: 559), wherein said device allows a determination of the resistance of said patient to oxaliplatin; or xxxix) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-103_st (SEQ ID NO: 660), hsa-miR-107_st (SEQ ID NO: 661), hsa-miR-10a_st (SEQ ID NO: 538), hsa-miR-1180_st (SEQ ID NO: 662), hsa-miR-125a-3p_st (SEQ ID NO: 601), hsa-miR-125a-5p_st (SEQ ID NO: 551), hsa-miR-1287_st (SEQ ID NO: 603), hsa-miR-132_st (SEQ ID NO: 664), hsa-miR-149_st (SEQ ID NO: 500), hsa-miR-151-3p_st (SEQ ID NO: 539), hsa-miR-151-5p_st (SEQ ID NO: 540), hsa-miR-182_st (SEQ ID NO: 563), hsa-miR-183_st (SEQ ID NO: 565), hsa-miR-193b_st (SEQ ID NO: 583), hsa-miR-195_st (SEQ ID NO: 672), hsa-miR-21_st (SEQ ID NO: 592), hsa-miR-221-star_st (SEQ ID NO: 613), hsa-miR-22_st (SEQ ID NO: 167), hsa-miR-23a_st (SEQ ID NO: 571), hsa-miR-23b_st (SEQ ID NO: 590), hsa-miR-24_st (SEQ ID NO: 580), hsa-miR-26a_st (SEQ ID NO: 537), hsa-miR-27b_st (SEQ ID NO: 567), hsa-miR-28-3p_st (SEQ ID NO: 605), hsa-miR-28-5p_st (SEQ ID NO: 594), hsa-miR-30a-star_st (SEQ ID NO: 502), hsa-miR-30a_st (SEQ ID NO: 503), hsa-miR-30b-star_st (SEQ ID NO: 673), hsa-miR-30b_st (SEQ ID NO: 546), hsa-miR-30d_st (SEQ ID NO: 547), hsa-miR-320d_st (SEQ ID NO: 91), hsa-miR-34a_st (SEQ ID NO: 234), hsa-miR-501-3p_st (SEQ ID NO: 95), hsa-miR-532-3p_st (SEQ ID NO: 97), hsa-miR-584_st (SEQ ID NO: 581), hsa-miR-99b-star_st (SEQ ID NO: 569), and hsa-miR-99b_st (SEQ ID NO: 559), wherein said device allows a determination of the resistance of said patient to hydroxyurea; or xl) one or more single-stranded nucleic acid molecules having at least 85% identity to a target nucleic acid molecule having a sequence that is complementary to or identical to at least 15 consecutive nucleotides of one or more biomarkers selected from 14qII-14_st (SEQ ID NO: 674), 14qII-14_x_st (SEQ ID NO: 627), 14qII-1_st (SEQ ID NO: 675), 14qII-1_x_st (SEQ ID NO: 599), 14qII-26_st (SEQ ID NO: 676), hsa-let-7a_st (SEQ ID NO: 575), hsa-let-7e_st (SEQ ID NO: 549), hsa-let-7f_st (SEQ ID NO: 577), hsa-miR-100_st (SEQ ID NO: 17), hsa-miR-10b_st (SEQ ID NO: 550), hsa-miR-125a-3p_st (SEQ ID NO: 601), hsa-miR-125a-5p_st (SEQ ID NO: 551), hsa-miR-125b-1-star_st (SEQ ID NO: 163), hsa-miR-125b_st (SEQ ID NO: 602), hsa-miR-130a_st (SEQ ID NO: 313), hsa-miR-134_st (SEQ ID NO: 164), hsa-miR-149_st (SEQ ID NO: 500), hsa-miR-151-3p_st (SEQ ID NO: 539), hsa-miR-151-5p_st (SEQ ID NO: 540), hsa-miR-181a-2-star_st (SEQ ID NO: 612), hsa-miR-217_st (SEQ ID NO: 670), hsa-miR-21_st (SEQ ID NO: 592), hsa-miR-22_st (SEQ ID NO: 578), hsa-miR-221-star_st (SEQ ID NO: 613), hsa-miR-221_st (SEQ ID NO: 620), hsa-miR-222-star_st (SEQ ID NO: 677), hsa-miR-27b_st (SEQ ID NO: 567), hsa-miR-299-3p_st (SEQ ID NO: 168), hsa-miR-299-5p_st (SEQ ID NO: 606), hsa-miR-30a-star_st (SEQ ID NO: 502), hsa-miR-30a_st (SEQ ID NO: 503), hsa-miR-30c-2-star_st (SEQ ID NO: 504), hsa-miR-30c_st (SEQ ID NO: 301), hsa-miR-30e-star_st (SEQ ID NO: 505), hsa-miR-337-5p_st (SEQ ID NO: 169), hsa-miR-376a_st (SEQ ID NO: 607), hsa-miR-376c_st (SEQ ID NO: 170), hsa-miR-377-star_st (SEQ ID NO: 171), hsa-miR-379_st (SEQ ID NO: 172), hsa-miR-382_st (SEQ ID NO: 174), hsa-miR-409-3p_st (SEQ ID NO: 81), hsa-miR-409-5p_st (SEQ ID NO: 175), hsa-miR-411_st (SEQ ID NO: 176), hsa-miR-485-5p_st (SEQ ID NO: 179), hsa-miR-487a_st (SEQ ID NO: 609), hsa-miR-487b_st (SEQ ID NO: 82), hsa-miR-495_st (SEQ ID NO: 610), hsa-miR-543_st (SEQ ID NO: 182), hsa-miR-654-5p_st (SEQ ID NO: 611), hsa-miR-758_st (SEQ ID NO: 35), hsa-miR-9-star_st (SEQ ID NO: 651), hsa-miR-98_st (SEQ ID NO: 652), hsa-miR-99b-star_st (SEQ ID NO: 569), and hsa-miR-99b_st (SEQ ID NO: 559), wherein said device allows a determination of the resistance of said patient to tegafur; or xli) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-10a_st (SEQ ID NO: 538), hsa-miR-125a-5p_st (SEQ ID NO: 551), hsa-miR-146a_st (SEQ ID NO: 19), hsa-miR-151-3p_st (SEQ ID NO: 539), hsa-miR-151-5p_st (SEQ ID NO: 540), hsa-miR-193b_st (SEQ ID NO: 583), hsa-miR-200b-star_st (SEQ ID NO: 555), hsa-miR-200b_st (SEQ ID NO: 544), hsa-miR-203_st (SEQ ID NO: 511), hsa-miR-221-star_st (SEQ ID NO: 613), hsa-miR-22_st (SEQ ID NO: 167), hsa-miR-23a_st (SEQ ID NO: 571), hsa-miR-24-2-star_st (SEQ ID NO: 579), hsa-miR-24_st (SEQ ID NO: 580), hsa-miR-27a_st (SEQ ID NO: 501), hsa-miR-29a_st (SEQ ID NO: 584), hsa-miR-29b-1-star_st (SEQ ID NO: 622), hsa-miR-29b_st (SEQ ID NO: 545), hsa-miR-30a-star_st (SEQ ID NO: 502), hsa-miR-30a_st (SEQ ID NO: 503), hsa-miR-30b_st (SEQ ID NO: 546), hsa-miR-30c-2-star_st (SEQ ID NO: 504), hsa-miR-30c_st (SEQ ID NO: 301), hsa-miR-30d_st (SEQ ID NO: 547), hsa-miR-30e-star_st (SEQ ID NO: 505), hsa-miR-372_st (SEQ ID NO: 646), hsa-miR-373_st (SEQ ID NO: 408), hsa-miR-516a-5p_st (SEQ ID NO: 558), hsa-miR-518e-star_st (SEQ ID NO: 573), hsa-miR-519a-star_st (SEQ ID NO: 573), hsa-miR-519a_st (SEQ ID NO: 574), hsa-miR-519b-5p_st (SEQ ID NO: 573), hsa-miR-519c-5p_st (SEQ ID NO: 573), hsa-miR-522-star_st (SEQ ID NO: 573), hsa-miR-523-star_st (SEQ ID NO: 573), hsa-miR-526a_st (SEQ ID NO: 572), hsa-miR-584_st (SEQ ID NO: 581), hsa-miR-675_st (SEQ ID NO: 516), and hsa-miR-99b_st (SEQ ID NO: 559), wherein said device allows a determination of the resistance of said patient to daunorubicin; or xlii) one or more single-stranded nucleic acid molecules having at least 85% identity to a target nucleic acid molecule having a sequence that is complementary to or identical to at least 15 consecutive nucleotides of one or more biomarkers selected from HBII-180C_st (SEQ ID NO: 678), HBII-180C_x_st (SEQ ID NO: 491), hsa-miR-106a_st (SEQ ID NO: 150), hsa-miR-106b-star_st (SEQ ID NO: 2), hsa-miR-106b_st (SEQ ID NO: 37), hsa-miR-107_st (SEQ ID NO: 661), hsa-miR-1207-5p_st (SEQ ID NO: 109), hsa-miR-1244_st (SEQ ID NO: 560), hsa-miR-128_st (SEQ ID NO: 110), hsa-miR-1292_st (SEQ ID NO: 499), hsa-miR-1306_st (SEQ ID NO: 679), hsa-miR-1307_st (SEQ ID NO: 102), hsa-miR-130b_st (SEQ ID NO: 403), hsa-miR-141_st (SEQ ID NO: 552), hsa-miR-15b_st (SEQ ID NO: 510), hsa-miR-17_st (SEQ ID NO: 152), hsa-miR-183_st (SEQ ID NO: 565), hsa-miR-185-star_st (SEQ ID NO: 406), hsa-miR-185_st (SEQ ID NO: 85), hsa-miR-188-5p_st (SEQ ID NO: 86), hsa-miR-18a-star_st (SEQ ID NO: 71), hsa-miR-18a_st (SEQ ID NO: 72), hsa-miR-18b_st (SEQ ID NO: 87), hsa-miR-192_st (SEQ ID NO: 542), hsa-miR-19b_st (SEQ ID NO: 153), hsa-miR-200c-star_st (SEQ ID NO: 231), hsa-miR-200c_st (SEQ ID NO: 556), hsa-miR-203_st (SEQ ID NO: 511), hsa-miR-205_st (SEQ ID NO: 295), hsa-miR-20a_st (SEQ ID NO: 218), hsa-miR-20b_st (SEQ ID NO: 88), hsa-miR-215_st (SEQ ID NO: 566), hsa-miR-25-star_st (SEQ ID NO: 3), hsa-miR-25_st (SEQ ID NO: 89), hsa-miR-30b_st (SEQ ID NO: 546), hsa-miR-30d_st (SEQ ID NO: 547), hsa-miR-320d_st (SEQ ID NO: 91), hsa-miR-324-5p_st (SEQ ID NO: 665), hsa-miR-362-5p_st (SEQ ID NO: 92), hsa-miR-378-star_st (SEQ ID NO: 409), hsa-miR-421_st (SEQ ID NO: 512), hsa-miR-422a_st (SEQ ID NO: 410), hsa-miR-425_st (SEQ ID NO: 286), hsa-miR-500-star_st (SEQ ID NO: 93), hsa-miR-500_st (SEQ ID NO: 94), hsa-miR-501-3p_st (SEQ ID NO: 95), hsa-miR-532-3p_st (SEQ ID NO: 97), hsa-miR-532-5p_st (SEQ ID NO: 98), hsa-miR-584_st (SEQ ID NO: 581), hsa-miR-625_st (SEQ ID NO: 548), hsa-miR-660_st (SEQ ID NO: 305), hsa-miR-720_st (SEQ ID NO: 680), hsa-miR-93-star_st (SEQ ID NO: 45), hsa-miR-934_st (SEQ ID NO: 517), hsa-miR-93_st (SEQ ID NO: 46), and hsa-miR-941_st (SEQ ID NO: 595), wherein said device allows a determination of the resistance of said patient to bleomycin; or xliii) one or more single-stranded nucleic acid molecules having at least 85% identity to a target nucleic acid molecule having a sequence that is complementary to or identical to at least 15 consecutive nucleotides of one or more biomarkers selected from hsa-miR-135b-star_st (SEQ ID NO: 681), hsa-miR-192-star_st (SEQ ID NO: 541), hsa-miR-194-star_st (SEQ ID NO: 230), hsa-miR-21-star_st (SEQ ID NO: 166), hsa-miR-23b_st (SEQ ID NO: 590), hsa-miR-27b-star_st (SEQ ID NO: 654), hsa-miR-552_st (SEQ ID NO: 682), hsa-miR-592_st (SEQ ID NO: 683), hsa-miR-7_st (SEQ ID NO: 570), and hsa-miR-874_st (SEQ ID NO: 310), wherein said device allows a determination of the sensitivity of said patient to estramustine; or xliv) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-100_st (SEQ ID NO: 17), hsa-miR-125a-5p_st (SEQ ID NO: 551), hsa-miR-151-3p_st (SEQ ID NO: 539), hsa-miR-151-5p_st (SEQ ID NO: 540), hsa-miR-217_st (SEQ ID NO: 670), hsa-miR-221-star_st (SEQ ID NO: 613), hsa-miR-22_st (SEQ ID NO: 167), hsa-miR-23a_st (SEQ ID NO: 571), hsa-miR-23b_st (SEQ ID NO: 590), hsa-miR-24-2-star_st (SEQ ID NO: 579), hsa-miR-24_st (SEQ ID NO: 580), hsa-miR-30d_st (SEQ ID NO: 547), hsa-miR-320d_st (SEQ ID NO: 91), hsa-miR-512-3p_st (SEQ ID NO: 523), hsa-miR-519b-5p_st (SEQ ID NO: 573), hsa-miR-519c-5p_st (SEQ ID NO: 573), hsa-miR-526a_st (SEQ ID NO: 572), hsa-miR-584_st (SEQ ID NO: 581), hsa-miR-99b-star_st (SEQ ID NO: 569), and hsa-miR-99b_st (SEQ ID NO: 559), wherein said device allows a determination of the resistance of said patient to mechlorethamine; or xlv) one or more single-stranded nucleic acid molecules having at least 85% identity to a target nucleic acid molecule having a sequence that is complementary to or identical to at least 15 consecutive nucleotides of one or more biomarkers selected from hsa-miR-26a_st (SEQ ID NO: 537), hsa-miR-34b-star_st (SEQ ID NO: 534), hsa-miR-34c-5p_st (SEQ ID NO: 506), hsa-miR-516a-5p_st (SEQ ID NO: 558), hsa-miR-518e-star_st (SEQ ID NO: 573), hsa-miR-519a_st (SEQ ID NO: 574), hsa-miR-519c-5p_st (SEQ ID NO: 573), and hsa-miR-526a_st (SEQ ID NO: 572), wherein said device allows a determination of the resistance of said patient to streptozocin; or xlvi) one or more single-stranded nucleic acid molecules having at least 85% identity to a target nucleic acid molecule having a sequence that is complementary to or identical to at least 15 consecutive nucleotides of one or more biomarkers selected from hsa-let-7b_st (SEQ ID NO: 600), hsa-let-7c_st (SEQ ID NO: 576), hsa-let-7d_st (SEQ ID NO: 623), hsa-let-7f_st (SEQ ID NO: 577), hsa-let-7g_st (SEQ ID NO: 624), hsa-let-7i_st (SEQ ID NO: 596), hsa-miR-130a_st (SEQ ID NO: 313), hsa-miR-181a_st (SEQ ID NO: 78), hsa-miR-193a-3p_st (SEQ ID NO: 366), hsa-miR-24-2-star_st (SEQ ID NO: 579), hsa-miR-24_st (SEQ ID NO: 580), hsa-miR-28-3p_st (SEQ ID NO: 605), hsa-miR-28-5p_st (SEQ ID NO: 594), hsa-miR-29b_st (SEQ ID NO: 545), hsa-miR-30a_st (SEQ ID NO: 503), hsa-miR-331-3p_st (SEQ ID NO: 568), and hsa-miR-98_st (SEQ ID NO: 652), wherein said device allows a determination of the sensitivity of said patient to carmustine; or xlvii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-125a-3p_st (SEQ ID NO: 601), hsa-miR-125a-5p_st (SEQ ID NO: 551), hsa-miR-151-3p_st (SEQ ID NO: 539), hsa-miR-151-5p_st (SEQ ID NO: 540), hsa-miR-193b_st (SEQ ID NO: 583), hsa-miR-200a_st (SEQ ID NO: 554), hsa-miR-200b-star_st (SEQ ID NO: 555), hsa-miR-200b_st (SEQ ID NO: 544), hsa-miR-200c_st (SEQ ID NO: 556), hsa-miR-21_st (SEQ ID NO: 592), hsa-miR-22_st (SEQ ID NO: 167), hsa-miR-30a_st (SEQ ID NO: 503), hsa-miR-31-star_st (SEQ ID NO: 614), hsa-miR-331-3p_st (SEQ ID NO: 568), hsa-miR-34a_st (SEQ ID NO: 234), hsa-miR-34c-5p_st (SEQ ID NO: 506), hsa-miR-935_st (SEQ ID NO: 639), hsa-miR-99b-star_st (SEQ ID NO: 569), and hsa-miR-99b_st (SEQ ID NO: 559), wherein said device allows a determination of the sensitivity of said patient to lomustine; or xlviii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-let-7i_st (SEQ ID NO: 596), hsa-miR-125a-5p_st (SEQ ID NO: 551), hsa-miR-22-star_st (SEQ ID NO: 578), hsa-miR-22_st (SEQ ID NO: 167), hsa-miR-23a_st (SEQ ID NO: 571), hsa-miR-23b_st (SEQ ID NO: 590), hsa-miR-27b_st (SEQ ID NO: 567), hsa-miR-28-3p_st (SEQ ID NO: 605), hsa-miR-28-5p_st (SEQ ID NO: 594), hsa-miR-494_st (SEQ ID NO: 181), and hsa-miR-99b_st (SEQ ID NO: 559), wherein said device allows a determination of the resistance of said patient to mercaptopurine; or xlix) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-10a_st (SEQ ID NO: 538), hsa-miR-125a-5p_st (SEQ ID NO: 551), hsa-miR-151-3p_st (SEQ ID NO: 539), hsa-miR-151-5p_st (SEQ ID NO: 540), hsa-miR-193b_st (SEQ ID NO: 583), hsa-miR-221-star_st (SEQ ID NO: 613), hsa-miR-23a_st (SEQ ID NO: 571), hsa-miR-30a-star_st (SEQ ID NO: 502), hsa-miR-30a_st (SEQ ID NO: 503), hsa-miR-30b_st (SEQ ID NO: 546), hsa-miR-30c-2-star_st (SEQ ID NO: 504), hsa-miR-30c_st (SEQ ID NO: 301), hsa-miR-30d_st (SEQ ID NO: 547), hsa-miR-516a-5p_st (SEQ ID NO: 558), hsa-miR-518e-star_st (SEQ ID NO: 573), hsa-miR-519a_st (SEQ ID NO: 574), hsa-miR-519c-5p_st (SEQ ID NO: 573), hsa-miR-526a_st (SEQ ID NO: 572), hsa-miR-584_st (SEQ ID NO: 581), hsa-miR-99b-star_st (SEQ ID NO: 569), and hsa-miR-99b_st (SEQ ID NO: 559), wherein said device allows a determination of the resistance of said patient to teniposide; or l) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-125a-5p_st (SEQ ID NO: 551), hsa-miR-130a_st (SEQ ID NO: 313), hsa-miR-193b_st (SEQ ID NO: 583), hsa-miR-22_st (SEQ ID NO: 167), hsa-miR-23a_st (SEQ ID NO: 571), hsa-miR-24-2-star_st (SEQ ID NO: 579), hsa-miR-27a-star_st (SEQ ID NO: 593), hsa-miR-27a_st (SEQ ID NO: 501), hsa-miR-29b_st (SEQ ID NO: 545), hsa-miR-30a-star_st (SEQ ID NO: 502), hsa-miR-30a_st (SEQ ID NO: 503), hsa-miR-30c-2-star_st (SEQ ID NO: 504), hsa-miR-30c_st (SEQ ID NO: 301), hsa-miR-34c-5p_st (SEQ ID NO: 506), hsa-miR-372_st (SEQ ID NO: 646), hsa-miR-516a-5p_st (SEQ ID NO: 558), and hsa-miR-99b_st (SEQ ID NO: 559), wherein said device allows a determination of the resistance of said patient to dactinomycin; or li) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-let-7i_st (SEQ ID NO: 596), hsa-miR-125a-5p_st (SEQ ID NO: 551), hsa-miR-151-3p_st (SEQ ID NO: 539), hsa-miR-151-5p_st (SEQ ID NO: 540), hsa-miR-181a-2-star_st (SEQ ID NO: 612), hsa-miR-21-star_st (SEQ ID NO: 166), hsa-miR-21_st (SEQ ID NO: 592), hsa-miR-221_st (SEQ ID NO: 620), hsa-miR-222_st (SEQ ID NO: 621), hsa-miR-22_st (SEQ ID NO: 167), hsa-miR-28-3p_st (SEQ ID NO: 605), hsa-miR-28-5p_st (SEQ ID NO: 594), hsa-miR-30a-star_st (SEQ ID NO: 502), hsa-miR-30a_st (SEQ ID NO: 503), hsa-miR-30c-2-star_st (SEQ ID NO: 504), hsa-miR-455-3p_st (SEQ ID NO: 178), and hsa-miR-99b-star_st (SEQ ID NO: 569), wherein said device allows a determination of the resistance of said patient to tretinoin; or lii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-125a-5p_st (SEQ ID NO: 551), hsa-miR-151-3p_st (SEQ ID NO: 539), hsa-miR-151-5p_st (SEQ ID NO: 540), hsa-miR-182_st (SEQ ID NO: 563), hsa-miR-183_st (SEQ ID NO: 565), hsa-miR-193b_st (SEQ ID NO: 583), hsa-miR-195_st (SEQ ID NO: 672), hsa-miR-22_st (SEQ ID NO: 167), hsa-miR-23a_st (SEQ ID NO: 571), hsa-miR-23b_st (SEQ ID NO: 590), hsa-miR-24_st (SEQ ID NO: 580), hsa-miR-27a-star_st (SEQ ID NO: 593), hsa-miR-27a_st (SEQ ID NO: 501), hsa-miR-27b_st (SEQ ID NO: 567), hsa-miR-34b-star_st (SEQ ID NO: 534), hsa-miR-497_st (SEQ ID NO: 684), and hsa-miR-99b_st (SEQ ID NO: 559), wherein said device allows a determination of the resistance of said patient to ifosfamide; or liii) one or more single-stranded nucleic acid molecules having at least 85% identity to a target nucleic acid molecule having a sequence that is complementary to or identical to at least 15 consecutive nucleotides of one or more biomarkers selected from hsa-let-7a_st (SEQ ID NO: 575), hsa-let-7b_st (SEQ ID NO: 600), hsa-let-7c_st (SEQ ID NO: 576), hsa-let-7e_st (SEQ ID NO: 549), hsa-let-7g_st (SEQ ID NO: 624), hsa-let-7i_st (SEQ ID NO: 596), hsa-miR-100_st (SEQ ID NO: 17), hsa-miR-10a_st (SEQ ID NO: 538), hsa-miR-125a-5p_st (SEQ ID NO: 551), hsa-miR-125b_st (SEQ ID NO: 602), hsa-miR-130a_st (SEQ ID NO: 313), hsa-miR-138_st (SEQ ID NO: 625), hsa-miR-149_st (SEQ ID NO: 500), hsa-miR-151-3p_st (SEQ ID NO: 539), hsa-miR-151-5p_st (SEQ ID NO: 540), hsa-miR-181a-2-star_st (SEQ ID NO: 612), hsa-miR-193b-star_st (SEQ ID NO: 633), hsa-miR-193b_st (SEQ ID NO: 583), hsa-miR-21_st (SEQ ID NO: 592), hsa-miR-22-star_st (SEQ ID NO: 578), hsa-miR-221_st (SEQ ID NO: 620), hsa-miR-22_st (SEQ ID NO: 167), hsa-miR-23a_st (SEQ ID NO: 571), hsa-miR-23b_st (SEQ ID NO: 590), hsa-miR-24-2-star_st (SEQ ID NO: 579), hsa-miR-24_st (SEQ ID NO: 580), hsa-miR-28-3p_st (SEQ ID NO: 605), hsa-miR-28-5p_st (SEQ ID NO: 594), hsa-miR-30a-star_st (SEQ ID NO: 502), hsa-miR-30a_st (SEQ ID NO: 503), hsa-miR-30c-2-star_st (SEQ ID NO: 504), hsa-miR-30c_st (SEQ ID NO: 301), hsa-miR-30e-star_st (SEQ ID NO: 505), hsa-miR-34c-5p_st (SEQ ID NO: 506), hsa-miR-424-star_st (SEQ ID NO: 100), hsa-miR-455-3p_st (SEQ ID NO: 178), hsa-miR-503_st (SEQ ID NO: 101), hsa-miR-935_st (SEQ ID NO: 639), hsa-miR-99b-star_st (SEQ ID NO: 569), and hsa-miR-99b_st (SEQ ID NO: 559), wherein said device allows a determination of the resistance of said patient to tamoxifen; or liv) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-125a-5p_st (SEQ ID NO: 551), hsa-miR-151-3p_st (SEQ ID NO: 539), hsa-miR-151-5p_st (SEQ ID NO: 540), hsa-miR-193b_st (SEQ ID NO: 583), hsa-miR-30b_st (SEQ ID NO: 546), hsa-miR-30d_st (SEQ ID NO: 547), hsa-miR-320d_st (SEQ ID NO: 91), hsa-miR-584_st (SEQ ID NO: 581), and hsa-miR-99b_st (SEQ ID NO: 559), wherein said device allows a determination of the resistance of said patient to irinotecan; or lv) one or more single-stranded nucleic acid molecules having at least 85% identity to a target nucleic acid molecule having a sequence that is complementary to or identical to at least 15 consecutive nucleotides of one or more biomarkers selected from hsa-miR-30b_st (SEQ ID NO: 546), hsa-miR-30d_st (SEQ ID NO: 547), and hsa-miR-584_st (SEQ ID NO: 581), wherein said device allows a determination of the resistance of said patient to floxuridine; and/or lvi) one or more single-stranded nucleic acid molecules having at least 85% identity to a target nucleic acid molecule having a sequence that is complementary to or identical to at least 15 consecutive nucleotides of one or more biomarkers selected from hsa-let-7b_st (SEQ ID NO: 600), hsa-let-7c_st (SEQ ID No: 576), hsa-let-7e_st (SEQ ID NO: 549), hsa-miR-125a-5p_st (SEQ ID NO: 551), hsa-miR-151-3p_st (SEQ ID NO: 539), hsa-miR-151-5p_st (SEQ ID NO: 540), hsa-miR-217_st (SEQ ID NO: 670), hsa-miR-21_st (SEQ ID NO: 592), hsa-miR-22_st (SEQ ID NO: 167), hsa-miR-23a_st (SEQ ID NO: 571), hsa-miR-23b-star_st (SEQ ID NO: 591), hsa-miR-23b_st (SEQ ID NO: 590), hsa-miR-24_st (SEQ ID NO: 580), hsa-miR-27b-star_st (SEQ ID NO: 654), hsa-miR-27b_st (SEQ ID NO: 567), hsa-miR-30a_st (SEQ ID NO: 503), hsa-miR-494_st (SEQ ID NO: 181), hsa-miR-9-star_st (SEQ ID NO: 651), hsa-miR-99b-star_st (SEQ ID NO: 569), hsa-miR-99b_st (SEQ ID NO: 559), and hsa-miR-9_st (SEQ ID NO: 685), wherein said device allows a determination of the resistance of said patient to thioguanine; or lvii) one or more single-stranded nucleic acid molecules having at least 85% identity to a target nucleic acid molecule having a sequence that is complementary to or identical to at least 15 consecutive nucleotides of one or more biomarkers selected from hsa-let-7e_st (SEQ ID NO: 549), hsa-miR-125a-5p_st (SEQ ID NO: 551), hsa-miR-138_st (SEQ ID NO: 625), hsa-miR-149_st (SEQ ID NO: 500), hsa-miR-193b-star_st (SEQ ID NO: 633), hsa-miR-193b_st (SEQ ID NO: 583), hsa-miR-21_st (SEQ ID NO: 592), hsa-miR-22-star_st (SEQ ID NO: 578), hsa-miR-22_st (SEQ ID NO: 167), hsa-miR-23a_st (SEQ ID NO: 571), hsa-miR-23b_st (SEQ ID NO: 590), hsa-miR-24-2-star_st (SEQ ID NO: 579), hsa-miR-24_st (SEQ ID NO: 580), hsa-miR-27a_st (SEQ ID NO: 501), hsa-miR-27b_st (SEQ ID NO: 567), hsa-miR-30a-star_st (SEQ ID NO: 502), hsa-miR-30a_st (SEQ ID NO: 503), hsa-miR-30c-2-star_st (SEQ ID NO: 504), hsa-miR-30c_st (SEQ ID NO: 301), hsa-miR-543_st (SEQ ID NO: 182), and hsa-miR-9_st (SEQ ID NO: 685), wherein said device allows a determination of the resistance of said patient to PSC 833; or lviii) one or more single-stranded nucleic acid molecules having at least 85% identity to a target nucleic acid molecule having a sequence that is complementary to or identical to at least 15 consecutive nucleotides of one or more biomarkers selected from hsa-miR-320a_st (SEQ ID NO: 655), hsa-miR-320b_st (SEQ ID NO: 656), hsa-miR-320c_st (SEQ ID NO: 90), hsa-miR-362-5p_st (SEQ ID NO: 92), hsa-miR-500-star_st (SEQ ID NO: 93), hsa-miR-500_st (SEQ ID NO: 94), hsa-miR-502-3p_st (SEQ ID NO: 96), hsa-miR-532-3p_st (SEQ ID NO: 97), hsa-miR-532-5p_st (SEQ ID NO: 98), hsa-miR-652_st (SEQ ID NO: 42), and hsa-miR-671-5p_st (SEQ ID NO: 43), wherein said device allows a determination of the resistance of said patient to erlotinib; or lix) one or more single-stranded nucleic acid molecules having at least 85% identity to a target nucleic acid molecule having a sequence that is complementary to or identical to at least 15 consecutive nucleotides of one or more biomarkers selected from hsa-let-7d_st (SEQ ID NO: 623), hsa-miR-103_st (SEQ ID NO: 660), and hsa-miR-107_st (SEQ ID NO: 661), wherein said device allows a determination of the sensitivity of said patient to herceptin; or lx) one or more single-stranded nucleic acid molecules having at least 85% identity to a target nucleic acid molecule having a sequence that is complementary to or identical to at least 15 consecutive nucleotides of one or more biomarkers selected from hsa-miR-1287_st (SEQ ID NO: 603), hsa-miR-130a_st (SEQ ID NO: 313), hsa-miR-151-3p_st (SEQ ID NO: 539), hsa-miR-28-3p_st (SEQ ID NO: 605), hsa-miR-28-5p_st (SEQ ID NO: 594), hsa-miR-31-star_st (SEQ ID NO: 614), and hsa-miR-455-3p_st (SEQ ID NO: 178), wherein said device allows a determination of the resistance of said patient to celecoxib; or lxi) one or more single-stranded nucleic acid molecules having at least 85% identity to a target nucleic acid molecule having a sequence that is complementary to or identical to at least 15 consecutive nucleotides of one or more biomarkers selected from hsa-let-7b_st (SEQ ID NO: 600), hsa-miR-181a-2-star_st (SEQ ID NO: 612), hsa-miR-221_st (SEQ ID NO: 620), hsa-miR-222_st (SEQ ID NO: 621), hsa-miR-28-5p_st (SEQ ID NO: 594), hsa-miR-29a_st (SEQ ID NO: 584), and hsa-miR-31_st (SEQ ID NO: 615), wherein said device allows a determination of the resistance of said patient to fulvestrant; or lxii) one or more single-stranded nucleic acid molecules having at least 85% identity to a target nucleic acid molecule having a sequence that is complementary to or identical to at least 15 consecutive nucleotides of one or more biomarkers selected from hsa-miR-505-star_st (SEQ ID NO: 686), and hsa-miR-671-5p_st (SEQ ID NO: 43), wherein said device allows a determination of the resistance of said patient to iressa; or lxiii) one or more single-stranded nucleic acid molecules having at least 85% identity to a target nucleic acid molecule having a sequence that is complementary to or identical to at least 15 consecutive nucleotides of one or more biomarkers selected from U27_st (SEQ ID NO: 687) and U29_st (SEQ ID NO: 203), wherein said device allows a determination of the resistance of said patient to letrozole; or lxiv) one or more single-stranded nucleic acid molecules having at least 85% identity to a target nucleic acid molecule having a sequence that is complementary to or identical to at least 15 consecutive nucleotides of one or more biomarkers selected from hsa-miR-191_st (SEQ ID NO: 284) and hsa-miR-491-5p_st (SEQ ID NO: 617), wherein said device allows a determination of the resistance of said patient to cetuximab.

10. The method of claim 9, wherein said device comprises two or more of said single-stranded nucleic acid molecules of i) to lxiv).

11. The method of claim 1, wherein said treatment is selected from vincristine, cisplatin, etoposide, azaguanine, carboplatin, adriamycin, aclarubicin, mitoxantrone, mitoxantrone, mitomycin, paclitaxel, gemcitabine, docetaxel, dexamethasone, ara-c, methylprednisolone, methotrexate, bleomycin, methyl-gag, belinostat, carboplatin, 5-fu (5-fluorouracil), idarubicin, melphalan, IL4-PR38, valproic acid, all-trans retinoic acid (ATRA), cytoxan, topotecan, suberoylanilide hydroxamic acid (SAHA, vorinostat), depsipeptide (FR901228), bortezomib, leukeran, fludarabine, vinblastine, busulfan, dacarbazine, oxaliplatin, hydroxyurea, tegafur, daunorubicin, estramustine, mechlorethamine, streptozocin, carmustine, lomustine, mercaptopurine, teniposide, dactinomycin, tretinoin, ifosfamide, tamoxifen, irinotecan, floxuridine, thioguanine, PSC 833, erlotinib, herceptin, celecoxib, fulvestrant, iressa, anastrozole, letrozole, cetuximab, rituximab, radiation, histone deacetylase (HDAC) inhibitors, and 5-Aza-2'-deoxycytidine (decitabine).

12. The method of claim 2, wherein said at least one first single-stranded nucleic acid molecule or said at least one second single-stranded nucleic acid molecule of said device has a length in the range of 15 to 100 nucleotides.

13. The method of claim 12, wherein said at least one first single-stranded nucleic acid molecule or said at least one second single-stranded nucleic acid molecule of said device has a length in the range of 20 to 60 nucleotides.

14. The method of claim 2, wherein said method comprises converting the level of expression of said at least one biomarker of sensitivity and/or said at least one biomarker of resistance into a mean score correlation coefficient for said treatment for cancer,
wherein said mean score correlation coefficient identifies the sensitivity of said patient to said treatments for cancer.

15. The method of claim 14, wherein said method further comprises subtracting the mean correlation coefficient for said at least one biomarker of resistance from the mean correlation coefficient for said at least one biomarker of sensitivity to obtain a difference score correlation coefficient for said treatment,
wherein the difference score correlation coefficient identifies the sensitivity of said patient to said treatment for cancer.

16. The method of claim 15, wherein said mean score correlation coefficient and/or said difference score correlation coefficient above 0.3 indicates said patient is sensitive to said treatment for cancer.

17. The method of claim 2, wherein the level of expression of said at least one biomarker of sensitivity or said at least one biomarker of resistance is determined using a quantitative reverse transcription-polymerase chain reaction (qRT-PCR), by detecting the level of mRNA transcribed from one or more genes, by detecting the level of a protein product of one or more genes, or by detecting the level of the biological activity of a protein product of one or more genes.

18. The method of claim 2, wherein the level of expression of said at least one biomarker of sensitivity or said at least one biomarker of resistance is determined in a cancer cell of said patient.

19. A method of treating a patient having cancer, said method comprising:
(a) administering a first cancer treatment to the patient, wherein the patient was previously determined to be responsive to the first cancer treatment according to the method of claim 1; or
(b) administering a second cancer treatment that is different from the first cancer treatment to the patient, wherein the patient was previously determined to be non-responsive to the first cancer treatment as a monotherapy according to the method of claim 1.

20. The method of claim 19, wherein the patient in (b) is administered both the first cancer treatment and the second cancer treatment.

21. The method of claim 2, wherein:
(a) if the level of expression of the at least one biomarker of sensitivity indicates that the cancer patient is sensitive to the at least one treatment for cancer, said method further comprises administering the at least one treatment for cancer to the cancer patient as a first cancer treatment; or
(b) if the level of expression of the at least one biomarker of sensitivity indicates that the cancer patient is not sensitive to the at least one treatment for cancer, said method further comprises administering a second cancer treatment that is different from the first cancer treatment.

22. The method of claim 21, wherein the patient in (b) is administered both the first cancer treatment and the second cancer treatment.

23. The method of claim 2, wherein said device comprises i) and ii), and wherein said device is sufficient for detecting the level of expression of a least one said biomarker of sensitivity and at least one said biomarker of resistance.

24. The method of claim 23, wherein said method comprises detecting the level of expression of said at least one biomarker of sensitivity and said at least one biomarker of resistance in a biological sample from said patient.

25. The method of claim 23, wherein said device allows the determination of the level of expression of said at least one biomarker of sensitivity having a nucleic acid sequence selected from the group consisting of SEQ ID NOs: 4-12, 36, 118, 146, 209, 241, 252, 260, 280, 308, 395, and 441 and a level of expression of said at least one biomarker of resistance having a nucleic acid sequence selected from the group consisting of SEQ ID NOs: 511 and 538-548.

26. The method of claim 1, wherein:
(a) if the level of expression of hsa-miR-766_st (SEQ ID NO: 1) indicates that the patient is responsive to the at least one treatment for cancer, said method further comprises administering the at least one treatment for cancer to the patient as a first cancer treatment; or
(b) if the level of expression of hsa-miR-766_st (SEQ ID NO: 1) indicates that the patient is non-responsive to the at least one treatment for cancer, said method further comprises administering a second cancer treatment that is different from the first cancer treatment.

27. The method of claim 2, wherein:
(a) if the level of expression of the at least one biomarker of resistance indicates that the patient is not resistant to the at least one treatment for cancer, said method further comprises administering the at least one treatment for cancer to the patient as a first cancer treatment; or (b) if the level of expression of the at least one biomarker of resistance indicates that the patient is resistant to the at least one treatment for cancer, said method further comprises administering a second cancer treatment that is different from the first cancer treatment.

28. A method of detecting a level of expression of hsa-miR-766 in a tumor sample from a patient diagnosed with brain cancer, lung cancer, or lymphoma comprising:
   i) contacting the tumor sample comprising one or more nucleic acid molecules from said patient to one or more probes comprising at least one first single-stranded nucleic acid molecule having at least 85% sequence identity to a nucleic acid sequence that is complementary or identical to at least 15 consecutive nucleotides of hsa-miR-766_st (SEQ ID NO: 1); and
   ii) detecting the level of expression of hsa-miR-766_st by performing microarray analysis or quantitative reverse transcriptase polymerase chain reaction (qRT-PCR).

* * * * *

UNITED STATES PATENT AND TRADEMARK OFFICE
CERTIFICATE OF CORRECTION

PATENT NO. : 9,598,734 B2
APPLICATION NO. : 13/695102
DATED : March 21, 2017
INVENTOR(S) : Steen Knudsen It is certified that error appears in the above-identified patent and that said Letters Patent is hereby corrected as shown below:

In the Claims

Column 388, Claim 1, Lines 52-53, replace "be responsive to said least one treatment of" with --be responsive to said at least one treatment of--.

Column 389, Claim 7, Line 62, replace "(SEQ ID NOL: 8)" with --(SEQ ID NO: 8)--.

Column 391, Claim 7, Line 65, replace "said device allow a" with --said device allows a--.

Column 392, Claim 7, Lines 49-50, replace "hsa-miR-181 b_st" with --hsa-miR-181b_st--.

Column 397, Claim 7, Line 19, replace "hsa-miR-181 b_st" with --hsa-miR-181b_st--;
Line 62, replace "wherein said device allows allowing a determination of" with --wherein said device allows a determination of--.

Column 401, Claim 7, Line 8, replace "hsa-miR-106bstar_st" with --hsa-miR-106b-star_st--.

Column 409, Claim 9, Line 44, replace "hsa-miR-151-5p st" with --hsa-miR-151-5p_st--.

Column 413, Claim 9, Lines 45-46, replace "hsa-miR-10a_it" with --hsa-miR-10a_st--.

Column 414, Claim 9, Lines 50-51, replace "determination of the resistance of said patient to; or" with --determination of the resistance of said patient to radiation; or--.

Column 426, Claim 9, Lines 48-49, replace "hsa_miR-193b-star st" with --hsa_miR-193b-star_st--.

Column 429, Claim 11, Lines 11-12, replace "aclarubicin, mitoxantrone, mitoxantrone, mitomycin" with --aclarubicin, mitoxantrone, mitomycin--.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*

Column 430, Claim 21, Line 21, replace "that the cancer patient is" with --that the patient is--;
            Line 24, replace "to the cancer patient is" with --to the patient is--;
            Line 27, replace "that the cancer patient is" with --that the patient is--;
     Claim 23, Line 37, replace "of a least one" with --of at least one--.

Column 431, Claim 28, Lines 20-21, replace "quantitative reverse transcriptase polymerase chain reaction (qRT-PCR)" with --quantitative reverse transcription-polymerase chain reaction (qRT-PCR)--.